US006872546B1

(12) United States Patent
Hastings et al.

(10) Patent No.: US 6,872,546 B1
(45) Date of Patent: Mar. 29, 2005

(54) HYALURONAN-BINDING PROTEINS AND ENCODING GENES

(75) Inventors: Gregg A. Hastings, Westlake Village, CA (US); Gene Liau, Darnestown, MD (US); Elena Tsifrina, Owings Mills, MD (US)

(73) Assignees: Human Genome Sciences, Inc., Rockville, MD (US); The American Red Cross, Falls Church, VA (US)

( * ) Notice: Subject to any disclaimer, the term of this patent is extended or adjusted under 35 U.S.C. 154(b) by 0 days.

(21) Appl. No.: 09/466,778

(22) Filed: Dec. 20, 1999

Related U.S. Application Data

(60) Provisional application No. 60/113,871, filed on Dec. 23, 1998.

(51) Int. Cl.[7] .......................... C12P 21/06; C07K 14/00; A61K 38/04; A61K 38/00
(52) U.S. Cl. .................. 435/69.1; 435/69.7; 435/252.3; 435/320.1; 530/350; 530/324; 530/326; 530/328; 514/12
(58) Field of Search ................................. 530/350, 300, 530/324, 326, 328; 435/69.1, 69.7, 252.3, 320.1; 514/12

(56) References Cited

U.S. PATENT DOCUMENTS 5,635,370 A 6/1997 Hockfield et al.
5,846,763 A * 12/1998 Lee et al. .................. 435/69.1

FOREIGN PATENT DOCUMENTS

WO     WO01/81544 A2    11/2001
WO     WO02/086093 A2    10/2002

OTHER PUBLICATIONS

Lee et al., GenBank Accession No: W84087 (A_Geneseq_36 Database); Dec. 8, 1998.*
Tao et al., GenBank Accession No: Q9NRY3 (SPTREMBL_15 Database); Oct. 1, 2000.*
Blum et al., GenBank Accession No: Q9UF98 (SPTREMBL_15 Database); May 1, 2000.*
Lee et al. "A novel secretory Tumor Necrosis Factor–inducible Protein (TSG–6) is a mamber of the family of Hyaluronate Binding Proteins, closely related to the Adhesion Receptor CD44" Jan. 1992, vol. 116, No. 2, pp. 545–557.*
Politz et al., "Stabillin–1 and –2 constitute a novel family of fasciclin–like hyaluronan receptor homologues," Biochem. J. 362:155–164 (2002).
Zhou et al., "Purification and molecular identification of the human hyaluronan receptor for endocytosis," Glycobiology 13(5):339–349 (2003).
Oertli et al., "Mechanisms of hyaluronan–induced up–regulation of ICAM–1 and VCAM–1 expression by murine kidney tubular epithelial cells: hyaluronan triggers cell adhesion molecules expression through a mechanism involving activation of nuclear factor–KB and activating protein–1," J of Immunology 161:3431–7 (1998).
Tsifrina et al., "Identification and characterization of three cDNAs that encode putative novel hyaluronan–binding proteins, including an endothelial cell–specific hyaluronan receptor," Am J Pathol 155(5):1625–33 (1999).
McCarty et al., "Enhanced synovial production of hyaluronic acid may explain rapid clinical response to high–dose glucosamine in osteoarthritis," Med Hypothesis. 50(6):507–10 (1998).
Uebelhart et al., "Effects of hyaluronic acid on cartilage degradation," Curr Opin Rheumatol. 11(5):427–35 (1999).
Naor et al., "CD44: structure, function, and association with the Malignant process," Adv Cancer Res. 71:241–319 (1997).
Wisniewski et al., TSG–6: an IL–1/TNF–inducible protein with anti–inflammatory activity, Cytokine Growth Factor Rev. 8(2):143–156 (1997).
Day, "The structure and regulation of hyaluronan–binding proteins," Biochemical Society Transactions, 27(2):115–121 (1999).
Knudson, et al., "Hyaluronan–binding protein in development, tissue homeostasis, and disease," The FASEB Journal, 7(13):1233–1241 (1993).
Genbank Accession No. NM_017564, Tao et al., "*Homo sapiens* hypothetical protein DKFZp434E0321 (FELL), mRNA," Mar. 14, 2001.
Genbank Accession No. T47504, Hillier et al., "yb14f01.r1 Stratagene placenta (#937225) *Homo sapiens* cDNA clone IMAGE:71171 5' similar to similar to SP:A41735 A41735 Hyaluronate–Binding Protein TSG–6 Precursor, mRNA sequence," Feb. 1, 1995.
Genbank Accession No. T47504, Hillier et al., "zr82b05.r1 Soares_NhHMPu_S1 *Homo sapiens* cDNA clone IMAGE:682161 5', mRNA sequence," Mar. 17, 1997.

* cited by examiner

Primary Examiner—Christopher S. F. Low
Assistant Examiner—Rita Mitra
(74) Attorney, Agent, or Firm—Human Genome Sciences, Inc.

(57) ABSTRACT

The present invention relates to full-length WF-HABP, WF-HABP, OE-HABP, and BM-HABP, novel members of the hyaluronan receptor family. The invention provides isolated nucleic acid molecules encoding human to full-length WF-HABP, WF-HABP, OE-HABP, and BM-HABP receptors. Full-length WF-HABP, WF-HABP, OE-HABP, and BM-HABP polypeptides are also provided, as are vectors, host cells and recombinant methods for producing the same. The invention further relates to screening methods for identifying agonists and antagonists of full-length WF-HABP, WF-HABP, OE-HABP, and BM-HABP receptor activity. Also provided are diagnostic methods for detecting disease states related to the aberrant expression of full-length WF-HABP, WF-HABP, OE-HABP, and BM-HABP receptors. Further provided are therapeutic methods for treating disease states including, but not limited to, proliferative conditions, metastasis, inflammation, ischemia, host defense dysfunction, immune surveillance dysfunction, arthritis, multiple sclerosis, autoimmunity, immune dysfunction, and allergy.

56 Claims, 66 Drawing Sheets

FIGURE 1A

```
  1  CTGCGGACCGGTCTGCCACTTGCCAGGTGAGACCGCTGATGGGAAGACCAGCTGTGTGCAG     60

61  GGAAAGCGAGGTGGGGGATGGGCCGTGCCTGCTGCCTGCTCCCACGAGGTGCAGAA         120

121  GGCCACGCAGACAGGCCGGGGTGTTCCTGCAGCTGAGGGTCGCCGTGGCCATGATGGACCA    180
  1                                                        M  M  D  Q    4

181  GGGCTGCCGGGAAATCCTTACCACAGCGGGCCCTTTCACCGTGCTGGTGCCATCCGTCTC    240
  5   G  C  R  E  I  L  T  T  A  G  P  F  T  V  L  V  P  S  V  S    24

241  CTCCTTCTCCTCCAGGACCATGAATGCATCCCTTGCCCAGCAGCTCTGTAGACAGCACAT    300
 25   S  F  S  S  R  T  M  N  A  S  L  A  Q  Q  L  C  R  Q  H  I    44

301  CATCGCAGGCCAGCACATCCTGGAGGACACAAGGACCCAACAAACACGAAGGTGGTGGAC    360
 45   I  A  G  Q  H  I  L  E  D  T  R  T  Q  Q  T  R  R  W  W  T    64

361  GCTGGGCCGGCAGGAGATCACCGTCACCTTTAACCAATTCACGAAATACTCCTACAAGTA    420
 65   L  A  G  Q  E  I  T  V  T  F  N  Q  F  T  K  Y  S  Y  K  Y    84
```

FIGURE 1B

```
421  CAAAGACCAGCCCCAGCAGAGACGTTCAACATCTACAAGGCCAACAACATAGCAGCTAATGG  480
85    K  D  Q  P  Q  Q  T  F  N  I  Y  K  A  N  N  I  A  A  N  G    104

481  CGTCTTCCACGTGGTCACTGGCCTGCGGTGGCAGGCCCCCTCTGGGGACCCCTGGGGATCC  540
105   V  F  H  V  V  T  G  L  R  W  Q  A  P  S  G  T  P  G  D  P    124

541  CAAGAGAACTATCGGACAGATCCTCGCCTCTACCGAGGCCTTCAGCCGCTTTGAAACCAT  600
125   K  R  T  I  G  Q  I  L  A  S  T  E  A  F  S  R  F  E  T  I    144

601  CCTGGAGAACTGTGGGCTGCCCTCCATCCTGGACGGACCTGGGCCCTTCACAGTCTTTGC  660
145   L  E  N  C  G  L  P  S  I  L  D  G  P  G  P  F  T  V  F  A    164

661  CCCAAGCAATGAGGCTGTGGACAGCTTGCGTGACGGCCGCCTGATCTACCTCTTCACAGC  720
165   P  S  N  E  A  V  D  S  L  R  D  G  R  L  I  Y  L  F  T  A    184

721  GGGTCTCTCTAAACTGCAGGAGTTGGTGCGGTACCACATCTACAACCACGGCCAGCTGAC  780
185   G  L  S  K  L  Q  E  L  V  R  Y  H  I  Y  N  H  G  Q  L  T    204

781  CGTTGAGAAGCTCATCTCCAAGGGTCGGATCCTCACCATGGCCAACCAGGTCCTGGCTGT  840
205   V  E  K  L  I  S  K  G  R  I  L  T  M  A  N  Q  V  L  A  V    224
```

FIGURE 1C

```
841  GAACATTTCTGAGGAGGGGCGCATCCTGCTGGGACCCGAGGGGGTCCCGCTGCAGAGGGT  900
225   N  I  S  E  E  G  R  I  L  L  G  P  E  G  V  P  L  Q  R  V   244

901  AGACGTGATGGCCGCCAATGGCGTGATCCACATGCTGGACGGCATCCTGCTGCCCCGAC   960
245   D  V  M  A  A  N  G  V  I  H  M  L  D  G  I  L  L  P  P  T   264

961  CATCCTGCCCATCCTGCCCAAGCACTGCAGCGAGGAGCAGCACAAGATTGTGGCGGGCTC  1020
265   I  L  P  I  L  P  K  H  C  S  E  E  Q  H  K  I  V  A  G  S   284

1021 CTGTGTGGACTGCCAAGCCCTGAACACCAGCACTGTCCCCCCAACAGTGTGAAGCTGGA  1080
285   C  V  D  C  Q  A  L  N  T  S  T  C  P  P  N  S  V  K  L  D   304

1081 CATCTTCCCCAAGGAGTGTGTCTACATCCATGACCCAACGGGCTCAATGTGCTAAAGAA  1140
305   I  F  P  K  E  C  V  Y  I  H  D  P  T  G  L  N  V  L  K  K   324

1141 GGGCTGTGCCAGCTACTGCAACATGGAACAAGGCTGCTGCAAAGGTTTTT  1200
325   G  C  A  S  Y  C  N  M  E  Q  G  C  C  K  G  F  F   344

1201 CGGGCCTGACTGCACGCAGTGTCCTCCAACCCCTGCTATGGCAAAGGCAA  1260
345   G  P  D  C  T  Q  C  P  G  G  F  S  N  P  C  Y  G  K  G  N   364
```

FIGURE 1D

```
1261  TTGCAGTGATGGGATCCAAGGGCAATGGGGCCTCTGCTTCCCAGACTACAAGGGCAT  1320
 365   C  S  D  G  I  Q  G  N  G  A  C  L  C  F  P  D  Y  K  G  I   384

1321  CGCCTGCCACATCTGCTCGAACCCAAACAAGCATGGAGAGCAATGCCAGGAAGACTGCGG  1380
 385   A  C  H  I  C  S  N  P  N  K  H  G  E  Q  C  Q  E  D  C  G   404

1381  CTGTGTCCATGGTCTCTGCGACAACCGCCCAGGCAGTGGGGGGGTGTGCCAGCAGGGCAC  1440
 405   C  V  H  G  L  C  D  N  R  P  G  S  G  G  V  C  Q  Q  G  T   424

1441  GTGTGCCCCTGGCTTCAGTGGCCGGTTCTGCAACGAGTCCATGGGGGACTGTGGGCCCAC  1500
 425   C  A  P  G  F  S  G  R  F  C  N  E  S  M  G  D  C  G  P  T   444

1501  AGGGCTGGCCCAGCACTGCCACCTGCATGCCCGCTGTGTTAGCCAGGAGGGTGTTGCCAG  1560
 445   G  L  A  Q  H  C  H  L  H  A  R  C  V  S  Q  E  G  V  A  R   464

1561  ATGTCGCTGTCTTGATGGCTTTGAGGGCTTCCTGCACACCTAGCAACCCCTG  1620
 465   C  R  C  L  D  G  F  E  G  D  G  F  S  C  T  P  S  N  P  C   484

1621  CTCCCACCCGGACCGTGGAGGCTGCTCAGAGAATGCTGAGTGTGTCCCTGGTCCCTGGG  1680
 485   S  H  P  D  R  G  G  C  S  E  N  A  E  C  V  P  G  S  L  G   504
```

FIGURE 1E

```
1681  CACCCCACCACTGCACATGCCACAAAGGCTGGAGTGGGGATGGCCGCGTCTGTGTGGCTAT  1740
 505   T  H  H  C  T  H  K  G  W  S  G  D  D  G  R  V  C  V  A  I    524

1741  TGACGAGTGTGTGAGCTGGACGTGAGAGGTGGCCCACACCGATGCCCTCTGCAGCTATGT  1800
 525   D  E  C  E  L  D  V  R  G  G  C  H  T  D  A  L  C  S  Y  V    544

1801  GGGCCCCGGGCAGAGCCGATGCACCTGCAAGCTGGGCTTTGCCGGGGATGGCTACCAGTG  1860
 545   G  P  G  Q  S  R  C  T  C  K  L  G  F  A  G  D  G  Y  Q  C    564

1861  CAGCCCCCATCGACCCCTGCCGGGCAATGGCGGCTGCCACGGCCTGGAGCTGGAGGC     1920
 565   S  P  I  D  P  C  R  A  G  N  G  G  C  H  G  L  E  L  E  A    584

1921  AAATGCCCACTTCTCCATCTTCTACCAATGGCTTAAGAGTGCCGGCATCACGCTTCCTGC  1980
 585   N  A  H  F  S  I  F  Y  Q  W  L  K  S  A  G  I  T  L  P  A    604

1981  CGACCGGCGAGTCACAGCCCTGGTGCCCTCCGAGGCTGCAGTCCGTCAGCTGAGCCCCGA  2040
 605   D  R  R  V  T  A  L  V  P  S  E  A  A  V  R  Q  L  S  P  E    624

2041  GGACCGAGCTTTCTGGCTGCAGCCAAGGACGCTGCCGAACCTGGTCCGAGCTCAGGGCCCCATTTCT  2100
 625   D  R  A  F  W  L  Q  P  R  T  L  P  N  L  V  R  A  H  F  L    644
```

FIGURE 1F

```
2101  CCAGGGTGCCCTCTTCGAGGAGGAGCTGGCCCGGCTGGGTGGGCAGGAAGTGGCCACCCT  2160
 645    Q  G  A  L  F  E  E  E  L  A  R  L  G  G  Q  E  V  A  T  L   664

2161  GAACCCCACCACACGCTGGGAGATTCGCAACATTAGTGGAGGGTCTGGGTGCAGAATGC  2220
 665    N  P  T  T  R  W  E  I  R  N  I  S  G  R  V  W  V  Q  N  A   684

2221  CAGCGTGGATGTGGCTGACCTCCTTGCCACCAACGGTGTCCTACACATCCTCAGCCAGGT  2280
 685    S  V  D  V  A  D  L  L  A  T  N  G  V  L  H  I  L  S  Q  V   704

2281  CTTACTGCCCCCCGAGGGGATGTGCCCGGTGGGCAGGGTTGCTGCAGCAGCTGGACTT  2340
 705    L  L  P  P  R  G  D  V  P  G  G  Q  G  L  L  Q  Q  L  D  L   724

2341  GGTGCCCTGCCTCAGCCTCTCTTCCGGGAATTGCTGCAGCACCATGGGTTGGTGCCCCAGAT  2400
 725    V  P  A  F  S  L  F  R  E  L  L  Q  H  H  G  L  V  P  Q  I   744

2401  TGAGGCTGCCACTGCCTACACCATCTTTGTGCCCACCAACCGCTCCCTGGAGGCCCAGGG  2460
 745    E  A  A  T  A  Y  T  I  F  V  P  T  N  R  S  L  E  A  Q  G   764

2461  CAACAGCAGTCACCTGGACGCAGACACAGTGCGGCACCATGTGGTCCTGGGGGAGGCCCT  2520
 765    N  S  S  H  L  D  A  D  T  V  R  H  H  V  V  L  G  E  A  L   784
```

FIGURE 1G

```
2521  CTCCATGGAAACCCTGCGGAAGGGTGGACACCGCAACTCCCTCCTGGGCCCTGCCCACTG  2580
785    S  M  E  T  L  R  K  G  G  H  R  N  S  L  L  G  P  A  H  W    804

2581  GATCGTCTTCTACAACCACAGTGGCCAGCCTGAGGTGAACCATGTGCCACTGGAAGGCCC  2640
805    I  V  F  Y  N  H  S  G  Q  P  E  V  N  H  V  P  L  E  G  P    824

2641  CATGCTGGAGGCCCCCTGGCCGTCGCGCTCGCTGATTGGTCTGTCTGGGGTCCTGACGGTGGGCTC  2700
825    M  L  E  A  P  G  R  S  L  I  G  L  S  G  V  L  T  V  G  S    844

2701  AAGTCGCTGCCTGCATAGCCACGCTGAGGCCCTGCGGGAGAAATGTGTAAACTGCACCAG  2760
845    S  R  C  L  H  S  H  A  E  A  L  R  E  K  C  V  N  C  T  R    864

2761  GAGATTCCGCTGCACTCAGGGCTTCCAGCTGCAGGACACACCAGGAAGAGCTGTGTCTA  2820
865    R  F  R  C  T  Q  G  F  Q  L  Q  D  T  P  R  K  S  C  V  Y    884

2821  CCGATCTGGCTTCTCTCCCGGGCTGTCTTACACATGTGCCAAGAAGATCCAGGT  2880
885    R  S  G  F  S  F  S  R  G  C  S  Y  T  C  A  K  K  I  Q  V    904

2881  GCCGGACTGCTGCCCTGGTTTCTTTGGCACGCTGTGTGAGCCATGCCCAGGGGGTCTAGG  2940
905    P  D  C  C  P  G  F  F  G  T  L  C  E  P  C  P  G  G  L  G    924
```

FIGURE 1H

```
2941 GGGGGTGTGCTCAGGCCATGGGCCAGTGCCAGGACAGGTTCCTGGGCAGCGGGGAGTGCCA  3000
 925  G  V  C  S  G  H  G  Q  C  Q  D  R  F  L  G  S  G  E  C  H   944

3001 CTGCCACGAGGGCTTCCATGAACGGCCTGTGAGGTGTGTGAGCTGGGCCGCTACGGGCC    3060
 945  C  H  E  G  F  H  G  T  A  C  E  V  C  E  L  G  R  Y  G  P   964

3061 CAACTGCACCGGAGTGTGTGACTGTGCCCATGGGCTGTGCCAGGAGGGGCTGCAAGGGGA   3120
 965  N  C  T  G  V  C  D  C  A  H  G  L  C  Q  E  G  L  Q  G  D   984

3121 CGGAAGCTGTGTGTGTAACGTGGGCTGGCAGGGCCTCCGTGACCAGAAAATCACCAG     3180
 985  G  S  C  V  C  N  V  G  W  Q  G  L  R  C  D  Q  K  I  T  S  1004

3181 CCCTCAGTGCCCTAGGAAGTGCGACCCCAATGCCAACTGCGTGCAGGACTCGGCCGAGC   3240
1005  P  Q  C  P  R  K  C  D  P  N  A  N  C  V  Q  D  S  A  G  A  1024

3241 CTCCACCTGCGCCTGCGCTGCGGGGATACTCCGGCAATGGCATCTTCTGTTCAGAGGTGGA  3300
1025  S  T  C  A  C  A  A  G  Y  S  G  N  G  I  F  C  S  E  V  D  1044

3301 CCCCTGCGCCCACGGCCATGGGGGCTGCTCCCCTCATGCCAACTGTACCAAGGTGGCACC  3360
1045  P  C  A  H  G  H  G  G  C  S  P  H  A  N  C  T  K  V  A  P  1064
```

FIGURE 1I

```
3361  TGGGCAGCGGACATGCACCTGCCAGGATGGCTACATGGGCGACGGGGAGCTGTGCCAGGA  3420
1065   G  Q  R  T  C  T  C  Q  D  D  G  Y  M  G  D  G  E  L  C  Q  E   1084

3421  AATTAACAGCTGTCTCTCATCCACCACGCGGGGGCTGCCACATTCACGCGCCGAGTGCATCCCCAC  3480
1085   I  N  S  C  L  I  H  H  G  G  C  H  I  H  A  E  C  I  P  Q   1104

3481  TGGCCCCCAGCAGGTCTCCTGCAGCTGCCGTGAGGGTTACAGCGGGGATGGCATCCGGAC  3540
1105   G  P  Q  Q  V  S  C  R  E  G  Y  S  G  D  G  I  R  T   1124

3541  CTGCGAGCTCCTGGACCCCTGCTCTAAGAACAATGGAGGATGCAGCCCATATGCCACCTG  3600
1125   C  E  L  L  D  P  C  S  K  N  N  G  G  C  S  P  Y  A  T  C   1144

3601  CAAAAGCACAGGGGATGGCCAGAGAGACATGTACCTGCGACACAGCCCACACCGTGGGGA  3660
1145   K  S  T  G  D  G  Q  R  T  C  T  C  D  T  A  H  T  V  G  D   1164

3661  CGGCCTCACCTGCCGTGCCCGAGTCGGCCTGGAGCTCCTGAGGGATAAGCATGCCTCATT  3720
1165   G  L  T  C  R  A  R  V  G  L  E  L  L  R  D  K  H  A  S  F   1184

3721  CTTCAGCCTCCGCCTCCTGGAATATAAGGAGCTCAAGGGCGATGGGCCTTTCACCATCTT  3780
1185   F  S  L  R  L  L  E  Y  K  E  L  K  G  D  G  P  F  T  I  F   1204
```

FIGURE 1J

```
3781  CGTGCCGCACGCAGATCTAATGAGCAACCTGTCGCAGGATGAGCTGGCCCGGATTCGTGC  3840
1205   V  P  H  A  D  L  M  S  N  L  S  Q  D  E  L  A  R  I  R  A   1224

3841  GCATCGCCAGCTGGTGTTCGCTACCACGTGGTTGGCTGTGTCGGCGGCTGCGGAGCGAGGA  3900
1225   H  R  Q  L  V  F  R  Y  H  V  V  G  C  R  R  L  R  S  E  D   1244

3901  CCTGCTGGAGCAGGGGTACGCCACGCCCTCTCAGGGCACCACTGCGCTTCAGCGAGAG  3960
1245   L  L  E  Q  G  Y  A  T  A  L  S  G  H  P  L  R  F  S  E  R   1264

3961  GGAGGGCAGCATATACCTCAATGACTTCGCGCGTGTGAGCAGGACCATGAGGCCGT  4020
1265   E  G  S  I  Y  L  N  D  F  A  R  V  V  S  S  D  H  E  A  V   1284

4021  GAACGGCATCCTGCACTTCATTGACCGTGTCCTGCTGCCCCCGAGGCGCTGCACTGGGA  4080
1285   N  G  I  L  H  F  I  D  R  V  L  L  P  P  E  A  L  H  W  E   1304

4081  GCCTGATGATGCTCCCATCCCGAGGAGAAATGTCACCGCCGCCGCCCAGGGCTTCGGTTA  4140
1305   P  D  D  A  P  I  P  R  R  N  V  T  A  A  A  Q  G  F  G  Y   1324

4141  CAAGATCTTCAGCGGCCTCCTGAAGGTGGCCGGCCTCCTGCCTCTTCGAGAGGCATC  4200
1325   K  I  F  S  G  L  L  K  V  A  G  L  L  P  L  L  R  E  A  S   1344
```

FIGURE 1K

```
4201  CCATAGGCCCTTCACAATGCTGTGGCCCACAGACGCCGCCTTTGAGCTGCCTCCGGA  4260
1345   H  R  P  F  T  M  L  W  P  T  D  A  A  F  R  A  L  P  P  D   1364

4261  TCGCCAGGCCTGGCTGTACCATGAGGACCACCGTGACAAGCTAGCAGCCATTCTGCGGGG  4320
1365   R  Q  A  W  L  Y  H  E  D  H  R  D  K  L  A  A  I  L  R  G   1384

4321  CCACATGATTCGCAATGTCGAGGCCTTGGCATCTGACCTGCCCAACCTGGGCCCCACTTCG  4380
1385   H  M  I  R  N  V  E  A  L  A  S  D  L  P  N  L  G  P  L  R   1404

4381  AACCATGCATGGGACCCCATCTCTTTCCTGCAGCCGAACGCGGCCCGGTGAGCTCAT  4440
1405   T  M  H  G  T  P  I  S  F  L  Q  S  R  T  R  P  G  E  L  M   1424

4441  GGTGGGTGAGGATGATGCTCGCATTGTGCAGCGGCACTTGCCCTTTGAGGGTGGCCTGGC  4500
1425   V  G  E  D  D  A  R  I  V  Q  R  H  L  P  F  E  G  G  L  A   1444

4501  CTATGGCATCGACCAGCTGCTGGAGCCACCTGGCCTTGGTGCTCGCTGTGACCACTTTGA  4560
1445   Y  G  I  D  Q  L  L  E  P  P  G  L  G  A  R  C  D  H  F  E   1464

4561  GACCCGGCCCCTGCGACTGAACACCTGCAGCATCTGTGGGCTGGAGCCACCCTGTCCTGA  4620
1465   T  R  P  L  R  L  N  T  C  S  I  C  G  L  E  P  P  C  P  E   1484
```

FIGURE 1L

```
4621  GGGTCACAGGAGCAGGGCAGCCCTGAGGCCTGCTGGCGCTTCTACCCGAAGTTCTGGAC  4680
1485   G  S  Q  E  Q  G  S  P  E  A  C  W  R  F  Y  P  K  F  W  T   1504

4681  GTCCCCTCCGCTGCACTCTTTGGGATTACGCAGCCTCGGGTCCACCCCAGCCTTTGGGG  4740
1505   S  P  P  L  H  S  L  G  L  R  S  V  W  V  H  P  S  L  W  G   1524

4741  TAGGCCCCAAGGCCTGGGCAGGGCTGCCACCGCAATTGTGTCACCACCTGGAAGCC    4800
1525   R  P  Q  G  L  G  R  G  C  H  R  N  C  V  T  T  W  K  P      1544

4801  CAGTCTGCTGCCCTGGTCACTATGGCAGTGAGTGCCAAGCTTGCCCTGCGGCCCCAGCAG  4860
1545   S  C  C  P  G  H  Y  G  S  E  C  Q  A  C  P  G  G  P  S  S   1564

4861  CCCTTGTAGTGACCGTGTGGTGCATGGACGGCATGAGTGGCAGTGGGCAGTGTCTGTG   4920
1565   P  C  S  D  R  G  V  C  M  D  G  M  S  G  S  G  Q  C  L  C   1584

4921  CCGTTCAGGTTTTGCTGGAACAGCCTGTGAACTCTGTGCTCCTGGTGCCTTTGGCCCCA  4980
1585   R  S  G  F  A  G  T  A  C  E  L  C  A  P  G  A  F  G  P  H   1604

4981  TTGTCAAGCCTGCCACTGTGCATGGCCGTGTGATGAGGGCCTTGGGGGCTCTGG      5040
1605   C  Q  A  C  R  C  T  V  H  G  R  C  D  E  G  L  G  G  S  G   1624
```

FIGURE 1M

```
5041  CTCCTGCTTCTCTGTGATGAAGGCTGGACTGGGCCACGCTGTGAGGTGCAACTGGAGCTGCA  5100
1625   S  C  F  C  D  E  G  W  T  G  P  R  C  E  V  Q  L  E  L  Q   1644

5101  GCCTGTGTGTACCCCACCCCTGTGCACCCGAGGCTGTGTGCCGTGCAGGCAACAGCTGTGA  5160
1645   P  V  C  T  P  P  C  A  P  E  A  V  C  R  A  G  N  S  C  E   1664

5161  GTGCAGCCTGGGCTATGAAGGGGATGGCGGTGTGTGTACAGTGGCAGACCTGTGCCAGGA  5220
1665   C  S  L  G  Y  E  G  D  G  R  V  C  T  V  A  D  L  C  Q  D   1684

5221  CGGGCATGGTGCTGCAGTGAGCTGTAGCCAGGTAGGAACAATGGTCACTTG  5280
1685   G  H  G  G  C  S  E  H  A  N  C  S  Q  V  G  T  M  V  T  C   1704

5281  TACCTGCCCTGCCCGACTACGAGGGTGCCTGAGCTGCCGCAACCCCCTGCAC  5340
1705   T  C  L  P  D  Y  E  G  D  G  W  S  C  R  A  R  N  P  C  T   1724

5341  AGATGGCCACCGCGGGGGCTGCAGCGAGCACGCCAACTGCTTGAGCACCGGCCTGAACAC  5400
1725   D  G  H  R  G  G  C  S  E  H  A  N  C  L  S  T  G  L  N  T   1744

5401  ACGGCGCTGTGAGTGCCACGCAGGCTACGTAGGCGATGGACTGCAGTGTCTGGAGGAGTC  5460
1745   R  R  C  E  C  H  A  G  Y  V  G  D  D  G  L  Q  C  L  E  E  S  1764
```

FIGURE 1N

```
5461  GGAACCACCTGTGGACCGGCTGCTTGGGGCCACCGCCCTGCCACTCAGATGCCATGTG  5520
1765   E  P  P  V  D  R  C  L  G  Q  P  P  P  C  H  S  D  A  M  C   1784

5521  CACTGACCTGCACTTCCAGGAGAAACGGGCTGGCGTTTTCCACCTCCAGGCCACCAGCGG  5580
1785   T  D  L  H  F  Q  E  K  R  A  G  V  F  H  L  Q  A  T  S  G   1804

5581  CCCTTATGGTCTCTGAACTTTTCGGAGGCGGCATGCGTGAGGCAGGAGCGTCCT        5640
1805   P  Y  G  L  N  F  S  E  A  E  A  C  E  A  Q  G  A  V  L      1824

5641  TGCTTCATTCCCTCCAGCTCTCTGCCCAGCAGCCTGGGCTTCCACCTGTGCCTCATGGG   5700
1825   A  S  F  P  Q  L  S  A  A  Q  Q  L  G  F  H  L  C  L  M  G   1844

5701  CTGGCTGGCCAATGGCTCCACCGCCCACCCTGTGGTTTTCCCTGTGGCGGACTGTGGCAA  5760
1845   W  L  A  N  G  S  T  A  H  P  V  V  F  P  V  A  D  C  G  N   1864

5761  TGGTCGGGTGGGCATAGTCAGCCTGGGTGCCCGCAAGAACCTCTCAGAACGCTGGGATGC  5820
1865   G  R  V  G  I  V  S  L  G  A  R  K  N  L  S  E  R  W  D  A   1884

5821  CTACTGCTTCCGTGTGCAAGATGTGGCCTGCCGATGCCGAAATGGCTTCGTGGGTGACGG  5880
1885   Y  C  F  R  V  Q  D  V  A  C  R  C  R  N  G  F  V  G  D  G   1904
```

FIGURE 10

```
5881  GATCAGCACGTGCAATGGGAAGCTGCTGGATGTGCTGGCTGCCACTGCCAACTTCTCCAC  5940
1905   I  S  T  C  N  G  K  L  L  D  V  L  A  A  T  A  N  F  S  T    1924

5941  CTTCTATGGGATGCTATTGGGCTATGCCAATGCCACCCAGCGGGGTCTCGACTTCCTGGA  6000
1925   F  Y  G  M  L  L  G  Y  A  N  A  T  Q  R  G  L  D  F  L  D    1944

6001  CTTCCTGGATGATGAGCTCACGTATAAGACACTCTTCGTCCCTGTCAATGAAGGCTTTGT  6060
1945   F  L  D  D  E  L  T  Y  K  T  L  F  V  P  V  N  E  G  F  V    1964

6061  GGACAACATGACGCTGAGTGGCCCAAACTTGGAGCTGCATGCCTCAACGCCACCTCCT    6120
1965   D  N  M  T  L  S  G  P  K  L  E  L  H  A  S  N  A  T  L  L    1984

6121  AAGTGCCAACGCCAGCCAGGGGAAGTTGCTTCCGGCCCACTCAGGCCTCAGCCTCATCAT  6180
1985   S  A  N  A  S  Q  G  K  L  L  P  A  H  S  G  L  S  L  I  I    2004

6181  CAGTGACGCAGGCCCCTGACAACAGTTCCTGGGCCCCTGTGGCCCCAGGGACAGTTGTGGT  6240
2005   S  D  A  G  P  D  N  S  S  W  A  P  V  A  P  G  T  V  V  V    2024

6241  TAGCCGTATCATTGTGTGGGACATCATGGCCTTCAATGGCATCATCCATGCTCTGGCCAG  6300
2025   S  R  I  I  V  W  D  I  M  A  F  N  G  I  I  H  A  L  A  S    2044
```

FIGURE 1P

```
6301 CCCCCTCCTGGCACCCCCACAGCCCCCAGGCAGTGCTGGCGCNTGAAGCCCCACCTGTGC 6360
2045  P  L  L  A  P  P  Q  P  P  Q  A  V  L  A  X  E  A  P  P  V  A  2064

6361 GGCAGGCCGTGGGGCTGTGCTTGCCGCTGGAGCACTGCTTGGCTTGGTGGCCGGAGCTCT 6420
2065  A  G  V  G  A  V  L  A  A  G  A  L  L  G  L  V  A  G  A  L  2084

6421 CTACCTCCGTGCCCGAGGCAAGCCCATGGGCTTTGGCTTCTCTGCCTTCCAGGCGGAAGA 6480
2085  Y  L  R  A  R  G  K  P  M  G  F  G  F  S  A  F  Q  A  E  D  2104

6481 TGATGCTGATGACGANTTCTCACCGTGGCAAGAAGGACCAACCCCACNTTGGTNTNTGT 6540
2105  D  A  D  D  X  F  S  P  W  Q  E  G  T  N  P  T  L  V  X  V  2124

6541 CCCCAACCCTGTCTTTGGCAGGAGCGACACCTTTTGTGAACCCTTCGATGACTCACTGCTGGA 6600
2125  P  N  P  V  F  G  S  D  T  F  C  E  P  F  D  D  S  L  L  E  2144

6601 GGAGGACTTCCCTGACACCCAGAGGATCCTCACAGTCAAGTGACGAGGCTGGGGCTGAAA 6660
2145  E  D  F  P  D  T  Q  R  I  L  T  V  K  *                    2158

6661 GCAGAAGCATGCACAGGGAGGAGACCANTTTTATTGCTCTGTCTGGGTGGATGGGGCAGGA 6720

6721 GGGNCTGAGGGCCCTGTCCCAGACAATANNNGTNCCCTCGAG 6761
```

FIGURE 2A

```
  1     GAGCACGCCAACTGTAGCCAGGTAGGAACAATGGTCACTTGTACCTGCCCGACTAC         60
  1                                    M  V  T  C  T  C  L  P  D  Y   10

61     GAGGGTGATGGCTGGAGCTGCCGGGCCCGCAACCCCTGCACAGATGGCCACCGCGGGGGC    120
 11      E  G  D  G  W  S  C  R  A  R  N  P  C  T  D  G  H  R  G  G   30

121     TGCAGCGAGCACGCCAACTGCTTGAGCACCGGCCTGAACACGCGGCGCTGTGAGTGCCAC    180
 31      C  S  E  H  A  N  C  L  S  T  G  L  N  T  R  R  C  E  C  H   50

181     GCAGGCTACGTAGGCGATGGACTGCAGTGTCTGGAGGAGTCGGAACCACCTGTGGACCGC    240
 51      A  G  Y  V  G  D  G  L  Q  C  L  E  E  S  E  P  P  V  D  R   70

241     TGCTTGGGCCAGCCACCGCCCTGCCACTCAGATGCCATGTGCACTGACCTGCACTTCCAG    300
 71      C  L  G  Q  P  P  P  C  H  S  D  A  M  C  T  D  L  H  F  Q   90

301     GAGAAACGGGCTGGCGTTTTCCACTTGCAGGCCCTTATGGTCTGAACTTT            360
 91      E  K  R  A  G  V  F  H  L  Q  A  T  S  G  P  Y  G  L  N  F  110

361     TCGGAGGCTGAGGCGGAAGCAGGGAGCCGTCCTTGCTTCATTCCCTCAGCTC            420
111      S  E  A  E  A  C  E  A  Q  G  A  V  L  A  S  F  P  L       130
```

FIGURE 2B

```
     ************************************************************
421  TCTGCTGCCCAGCAGCTGGGCTTCCACCTGTGCCTCATGGGCTGGCTGGCCAATGGCTCC  480
131  S  A  A  Q  Q  L  G  F  H  L  C  L  M  G  W  L  A  N  G  S   150
     ******************************
481  ACTGCCCACCCTGTGGTTTTCCCTGTGGCGGACTGTGGCAATGGTCGGGTGGGCATAGTC  540
151  T  A  H  P  V  V  F  P  V  A  D  C  G  N  G  R  V  G  I  V   170

541  AGCCTGGGTGCCCGCAAGAACCTCTCAGAACGCTGGGATGCCTACTGCTTCCGTGTGCAA  600
171  S  L  G  A  R  K  N  L  S  E  R  W  D  A  Y  C  F  R  V  Q   190

601  GATGTGGCCTGCCGATGCCGAAATGGCTTCGTGGGTGACGGGATCAGCACGTGCAATGGG  660
191  D  V  A  C  R  C  R  N  G  F  V  G  D  G  I  S  T  C  N  G   210

661  AAGCTGCTGGATGTGCTGGCTGCCACTGCCAACTTCTCCACCTTCTATGGGATGCTATTG  720
211  K  L  L  D  V  L  A  A  T  A  N  F  S  T  F  Y  G  M  L  L   230

721  GGCTATGCCAATGCCACCCAGCGGGTCTCTGACTTCCTGGATGATGAGCTC          780
231  G  Y  A  N  A  T  Q  R  G  L  D  F  L  D  D  E  L              250

781  ACGTATAAGACACTCTTCGTCCCTGTCAATGAAGGCTTTGTGGACAACATGACGCTGAGT  840
251  T  Y  K  T  L  F  V  P  V  N  E  G  F  V  D  N  M  T  L  S   270
```

FIGURE 2C

```
 841  GGCCCAAACTTGGAGCTGCATGCCTCCAACGCCACCCTCCTAAGTGCCAACGCCAGCCAG   900
 271   G  P  N  L  E  L  H  A  S  N  A  T  L  L  S  A  N  A  S  Q   290

901  GGGAAGTTGCTTCCGGCCCACTCAGCCTCAGCTTCATCATCAGTGACGCAGGCCCTGAC    960
 291   G  K  L  L  P  A  H  S  G  L  S  L  I  I  S  D  A  G  P  D   310

961  AACAGTTCCTGGGCCCCTGTGGCCCCAGGACAGTTGTGGTTAGCCGTATCATTGTGTGG   1020
 311   N  S  S  W  A  P  V  A  P  G  T  V  V  V  S  R  I  I  V  W   330

1021  GACATCATGGCCTTCAATGGCATCATCCATGCTCTGGCCAGCCCCCTCCTGGCACCCCCA   1080
 331   D  I  M  A  F  N  G  I  I  H  A  L  A  S  P  L  L  A  P  P   350

1081  CAGCCCCCAGGCAGTGCTGGCGCNTGAAGCCCCACCTGTGGCCGCAGGCGTGGGGCTGTG   1140
 351   Q  P  P  Q  A  V  L  A  X  E  A  P  P  V  A  A  G  V  G  A  V  370

1141  CTTGCCGCTGGAGCACTGCTTGGCTTGGTGGCCGGAGCTCTCTACCTCCGTGCCCGAGGC   1200
 371   L  A  A  G  A  L  L  G  L  V  A  G  A  L  Y  L  R  A  R  G   390

1201  AAGCCCATGGGCTTTGGCTTCTCTGCCTTCCAGGCGGAAGATGATGCTGATGACGANTTC   1260
 391   K  P  M  G  F  G  F  S  A  F  Q  A  E  D  D  A  D  D  X  F   410
```

FIGURE 2D

```
1261  TCACCGTGGCAAGAAGGGACCAACCCCACNTTGGTNTNTGTCCCAACCCTGTCTTTGGC  1320
 411   S  P  W  Q  E  G  T  N  P  T  L  V  X  V  P  N  P  V  F  G   430

1321  AGCGACACCTTTGTGAACCCTTCGATGACTCACTGCTGGAGGAGGACTTCCCTGACACC  1380
 431   S  D  T  F  C  E  P  F  D  D  S  L  L  E  E  D  F  P  D  T   450

1381  CAGAGGATCCTCACAGTCAAGTGACGAGGCTGAAAGCAGAAGCATGCACAGGA        1440
 451   Q  R  I  L  T  V  K  *                                       458

1441  GGAGACCANTTTTATTGCTTGTCTGGGTGGATGGGCAGGAGGNCTGAGGGCCTGTCCC   1500

1501  AGACAATANNNGTNCCCTCGAG  1522
```

FIGURE 3A

```
1    GCCCACGCGTCCGACCGGGACAGCTCGCGGCCCCNAGAGCTCTAGCCGTNGAGGAGCTG    60

61   CCTGGGGACGTTTGCCCTGGGGCCCCCAGCCCTGGCCCGGGTCACCCTGGCCATGAGGAGATG   120
                                                                  M    1

121  GGCCTGTGTTGCCTCCTGGTCCCCATTGCTCCTGCTGCCCGGCTCCTACGGACTGCCCTTCTAC   180
2    G  L  L  L  L  V  P  L  L  L  L  P  G  S  Y  G  L  P  F  Y         21

181  TACGGCTTCTACTACTCCAACAGCGCCAACGACCAGAACCTAGGCAACGGTCATGGCAAA   240
22   Y  G  F  Y  Y  S  N  S  A  N  D  Q  N  L  G  N  G  H  G  K         41

241  GACCTACNTAATGGAGTGAAGCTGGTGGTGGAGACACCCGAGGAGACCCTGTTCACCTAC   300
42   D  L  X  N  G  V  K  L  V  V  E  T  P  E  E  T  L  F  T  Y         61

301  CAAGGGGCCAGTGTGATCCTGCCCTGCCGCTACCGCTACGAGCCGGCCCTGGTCTCCCCG   360
62   Q  G  A  S  V  I  L  P  C  R  Y  R  Y  E  P  A  L  V  S  P         81

361  CGGCGTGTGCGTGTCAAATGGTGGAAGCTGTCGGAGAACGGGCCCCAGAGAAGGACGTG   420
82   R  R  V  R  V  K  W  W  K  L  S  E  N  G  A  P  E  K  D  V        101
```

FIGURE 3B

```
421  CTGGTGGCCATCGGGCTGAGGCACCCGCTCCTTTGGGACTACCAAGGCCGCGTGCACCTG   480
102   L  V  A  I  G  L  R  H  R  S  F  G  D  Y  Q  G  R  V  H  L   121

481  CGGCAGGACAAAGAGCATGACGTCTCGNTGGAGATCCAGAGNTCTGCGGCTGGAGGACTAT   540
122   R  Q  D  K  E  H  D  V  S  X  E  I  Q  X  L  R  L  E  D  Y   141

541  GGGCCGTTACCGCTGTGAGGTCATNGACGGGGCTGGAGGATGAAAGCGGTGTCTGGAGCTG   600
142   G  R  Y  R  C  E  V  X  D  G  L  E  D  E  S  G  L  V  E  L   161

601  GAGCTGCGGGGTGTGGTCTTTCCTTACCAGTCCCCAACGGGCGCTACCAGTTCAACTTC   660
162   E  L  R  G  V  V  F  P  Y  Q  S  P  N  G  R  Y  Q  F  N  F   181
                                ****************************

661  CACGAGGGCCAGCAGGTCTGTGCAGAGCAGGCTGCGGTGGTGGCCTCCTTTGAGCAGCTC   720
182   H  E  G  Q  Q  V  C  A  E  Q  A  A  V  V  A  S  F  E  Q  L   201
     ************************************************************

721  TTCCGGGCCTGGGAGGAGGGCCTGGACTGGTGCAACGCGGGCTGGCTGCAGGATGCCACG   780
202   F  R  A  W  E  E  G  L  D  W  C  N  A  G  W  L  Q  D  A  T   221
     ************************************************************

781  GTGCAGTACCCCATCATGTTGCCCCGGCAGCCCTGCGGTGGCCCGGACCTGGCACCTGGC   840
222   V  Q  Y  P  I  M  L  P  R  Q  P  C  G  G  P  D  L  A  P  G   241
     ************************
```

FIGURE 3C

```
841  GTGCGAAGCTACGGGCCCCCGCCTGCACCGCTATGATGTATTCTGCTTCGCT  900
242  V   R   S   Y   G   P   R   H   R   L   H   R   Y   D   V   F   C   F   A  261

901  ACTGCCCTCARGGGGCGGGTGTACTACCTGGANCACCCTGAGAANCTGACANAA  960
262  T   A   L   X   G   R   V   Y   Y   L   X   H   P   E   X   L   T   X  281

961  GCAAGGGAAGCCTGCCAAGAAAAAT  985
282  A   R   E   A   C   Q   E   K  289
```

FIGURE 4A

```
1    GGAATCACATGCACAGTTGTGGATTTYTGCAAACAGGACAACGGGGGCTGTGCAAAGGTG    60

61   GCCAGATGCTCCCAGAAGGGCACGAAGGTCTCCTGCAGCTGCCAGAAGGGATACAAAGGG   120

121  GACGGGCACACAGCTGCACAGAGATAGACCCCTGTGCAGACGGCCTTAACGGAGGGTGTCAC   180

181  GAGCACGCCACCTGTAAGATGACAGGCCCGGGCAAGCACAAGTGTGAGTGTAAAAGTCAC   240
1                     M  T  G  P  G  K  H  K  C  E  C  K  S  H    14

241  TATGTCGGAGATGGGCTGAACTGTGAGCCGGAGCAGCTGCCCATTGACCGCTGCTTACAG   300
15    Y  V  G  D  G  L  N  C  E  P  E  Q  L  P  I  D  R  C  L  Q    34

301  GACAATGGGCAGTGCCATGCAGACGCCAAATGTGTCGACCTCCACTTCCAGGATACCACT   360
35    D  N  G  Q  C  H  A  D  A  K  C  V  D  L  H  F  Q  D  T  T    54

361  GTTGGGGGTGTTCCATCTACGCTCCCCACTGGGCCAGTATAAAGCTGACCTTTGACAAAGCC   420
55    V  G  V  F  H  L  R  S  P  L  G  Q  Y  K  L  T  F  D  K  A    74

421  AGAGAGGCCTGTGCCAACGAAGCTGCCAACCATGGCAACCTACAACCAGTCTCCTATNNC   480
75    R  E  A  C  A  N  E  A  A  T  M  A  T  Y  N  Q  L  S  Y  X    94
```

FIGURE 4B

```
481  CAGAAGGCCAAGTACCACCACCTGTGCTCAGCAGGCTGGAGACCGGACGGGCGGGTTGCCTAC  540
95    Q  K  A  K  Y  H  L  C  S  A  G  W  L  E  T  G  R  V  A  Y    114

541  CCCACACAGCCTTCGCTTCGCCTCCCAGAACTGTGGCTCTGGTGTGGGGATAGTGGACTATGGA  600
115   P  T  A  F  A  S  Q  N  C  G  S  G  V  V  G  I  V  D  Y  G    134

601  CCTAGACCCAACAAGAGTGAAATGTGGGATGTCTTCTGCTATCGGATGAAAGATGTGAAC    660
135   P  R  P  N  K  S  E  M  W  D  V  F  C  Y  R  M  K  D  V  N    154

661  TGCACCTNCAAGGTGGGCTATGTGGTAGGAGATGGCTTCTCATACAGTGGAAACCTGCTGCAG  720
155   C  T  X  K  V  G  Y  V  V  G  D  G  F  S  Y  S  G  N  L  L  Q   174

721  GTCCTGATGTCCTTCCCCTCCCTCACTAACTTCCTCACAGAAGTGCTGGCCTATTCCAAC    780
175   V  L  M  S  F  P  S  L  T  N  F  L  T  E  V  L  A  Y  S  N    194

781  AGCTCAGCTCGAGGCCGTGCATTTCTAGAACACCTGACTGACCTGTCCATCCGCGGCACC    840
195   S  S  A  R  G  R  A  F  L  E  H  L  T  D  L  S  I  R  G  T    214
```

FIGURE 4C

```
841   CTCTTTGTNCCACAGAACAGTGGGCTGGGGAGAATGAGACCTTGTCTGGGCGGGACATC   900
215    L  F  V  P  Q  N  S  G  L  G  E  N  E  T  L  S  G  R  D  I   234

901   GAGCACCACCTCGCCAATGTCAGCATGTTTTTCTACAATGACCTTGTCAATGGCACCACC   960
235    E  H  H  L  A  N  V  S  M  F  F  Y  N  D  L  V  N  G  T  T   254

961   CTGCAAACGAGGCTGGGAAGCAAGCTGCTCATCACTGACAGACAGGACCCACTCCACCCG  1020
255    L  Q  T  R  L  G  S  K  L  L  I  T  D  R  Q  D  P  L  H  P   274

1021  ACGGAGACCAGGTGTGTTGATGGAAGAGACACTCTGGAGTGGGACATCTGTGCCTCCAAT  1080
275    T  E  T  R  C  V  D  G  R  D  T  L  E  W  D  I  C  A  S  N   294

1081  GGGATCACACATGTCATTTCCAGGYCTTTAAAAGCACCCCCTGCCCCCCGTGACCTTGNCC  1140
295    G  I  T  H  V  I  S  R  X  L  K  A  P  P  A  P  V  T  L  X   314

1141  CACACTGGNTTGGGAGNAGGGATCTTCTNTGNCATCATCCTGGTAGTCCTGGACTGGGCTGTTGCC  1200
315    H  T  G  L  G  X  G  I  F  X  X  I  I  L  V  T  G  A  V  A   334

1201  TTGGCTGCTTACTCCTACTTTCGGATAAACCGAAAACAATCGGCTTCCANCATTTTGA   1259
335    L  A  A  Y  S  Y  F  R  I  N  R  K  T  I  G  F  X  H  F       353
```

FIGURE 5B

```
            130         140         150
121  PGDPKRTIGQI LASTEAFSRFE ETILENCGL    WF-HABP(FL).filed.aa
  7  ----RRTKDKT ASRTE-----  ---------    Human TSG-6 (gi|339994)

160         170         180
151  PSILDGPGPFT VFAPSNEAVDS LRDGRLIY     WF-HABP(FL).filed.aa
 43  ---------- ---------- --------      Human TSG-6 (gi|339994)

190         200         210
181  LFTAGLSKLQE LVRYHIYNHGQ LTVEKLIS     WF-HABP(FL).filed.aa
 43  ---------- ---------- -------S      Human TSG-6 (gi|339994)

220         230         240
211  KGRILTMANQV LAVNISEEGRI LLGPEGVP     WF-HABP(FL).filed.aa
 46  KG-------- ---------- --------      Human TSG-6 (gi|339994)
```

FIGURE 5E

```
451 HLHARCVSQEGVARCRCLDGFEGDGFSCTP  WF-HABP(FL).filed.aa
 52 ------------------------------  Human TSG-6 (gi|339994)

481 SNPCSHPDRGGCSENAECVPGSLGTHHCTC  WF-HABP(FL).filed.aa
 52 ------------------------------  Human TSG-6 (gi|339994)

511 HKGWSGDGRVCVAIDECELDVRGGCHTDAL  WF-HABP(FL).filed.aa
 52 ------------------------------  Human TSG-6 (gi|339994)

541 CSYVGPGQSRCTCKLGFAGDGYQCSPIDPC  WF-HABP(FL).filed.aa
 52 ------------------------------  Human TSG-6 (gi|339994)
```

FIGURE 5N

```
1441 GGLAYGIDQLLEPPGLGARCDHFETRPLRL  WF-HABP(FL).filed.aa
 151 ------------------------------  Human TSG-6 (gi|339994)

1471 NTCSICGLEPPCPEGSQEQGSPEACWREYP  WF-HABP(FL).filed.aa
 151 ------------------------------  Human TSG-6 (gi|339994)

1501 KFMTSPPLHSLGLRSVWVHPSLWGRPQGLG  WF-HABP(FL).filed.aa
 151 ------------------------------  Human TSG-6 (gi|339994)

1531 RGCHRNCVTTTWKPSCCPGHYGSECQACPG  WF-HABP(FL).filed.aa
 151 ------------------------------  Human TSG-6 (gi|339994)
```

FIGURE 50

```
1570        1580         1590
1561 GPSSPCSDRGVCMDGMSGSGQCLCRSGFAG  WF-HABP(FL).filed.aa
 151 ----------------------------  Human TSG-6 (gi|339994)

1600        1610         1620
1591 TACELCAPGAFGPHCQACRCTVHGRCDEGL  WF-HABP(FL).filed.aa
 151 -------------------- KC  NIG -  Human TSG-6 (gi|339994)

1630        1640         1650
1621 GGSGSCFCDEGWTGPRCEVQLELQPVCTPP  WF-HABP(FL).filed.aa
 166 ----------------------------  Human TSG-6 (gi|339994)
```

Decoration 'Decoration #1': Shade (with solid black) residues that match the Consensus exactly.

FIGURE 6A

```
  1  M V T C T C L P D Y E G D G                         WF-HABP AA SEQUENCE*
  1  T M - - - - - - - - - - W S C R A R N P C T D G H R G G  Human TSG-6 (gi|339994)
                              R R T E D E T A S R T E S K G -

31  C S E H A N C L S T G L N T R                       WF-HABP AA SEQUENCE*
 52                            R C E C H A G Y V G D G L Q C  Human TSG-6 (gi|339994)
                              T R K - - - - - - - - - - - -

61  L E E S E P P V D R C L G Q P P P C H S D A M C T D L H F Q  WF-HABP AA SEQUENCE*
 61  - - - - - - - - - - - - - - - - - - - - - - - - - - - - -   Human TSG-6 (gi|339994)

91  E K R A G V F H L Q A T S G P Y G L N F S E A A C E A Q     WF-HABP AA SEQUENCE*
 61  - - - - - - - - - - - - - - - - - - - - - - - - - - -      Human TSG-6 (gi|339994)
```

FIGURE 6B

```
121 GAVLASFPQLSAAQQLGFHLCLHGWLANGS                    WF-HABP AA SEQUENCE*
 61 -----------------------------                    Human TSG-6 (gi|339994)

151 TAHPVVFPVADCG----------NGRVGIVSLGHRKMLSE         WF-HABP AA SEQUENCE*
 61 -------------E AGRV T-----              KQNPK    Human TSG-6 (gi|339994)

181 RWDACFRVQDVACPRNGFVGDGISTCNG                     WF-HABP AA SEQUENCE*
 94 R---------------------------                     Human TSG-6 (gi|339994)

211 KLLDVLAATANFSTFYGMLLGYANATQRGL                   WF-HABP AA SEQUENCE*
 97 -----------------------------                    Human TSG-6 (gi|339994)
```

FIGURE 6C

```
241 D F L D F L D D E L T Y K T L F V P V N E G F V D N N T L S    WF-HABP AA SEQUENCE*
 97 - - - - - - - - - - - - - - - - - - - - - - - - - - - - - -    Human TSG-6 (gi|339994)
        250              260              270

271 G P M L E L H A S M A T L L S A M A S Q G K L L P A H S G L    WF-HABP AA SEQUENCE*
 97 - - - - - - - - - - - - - - - - - - - - - - - - - - - - - -    Human TSG-6 (gi|339994)
        280              290              300

301 S L I I S D A G P D N S S W A P V A P G T V V V S R I I V W    WF-HABP AA SEQUENCE*
 97 - - - - - - - - - - - - - - - - - - - - - - - - - - - - - -    Human TSG-6 (gi|339994)
        310              320              330

331 D I M A F N G I I H A L A S P L L A P P P Q A V L A X E A       WF-HABP AA SEQUENCE*
 97 - - - - - - - - - - - - - - - - - - - - - - - - - - I   E R    Human TSG-6 (gi|339994)
        340              350              360
```

Decoration 'Decoration #1': Shade (with solid black) residues that match the Consensus exactly.

FIGURE 7B

```
              130            140            150
116  QGRVHLRQDKEHDVSXEIQXLRLEDYGRY R    OE-HABP ORF Sequence
110  QGRV FLRESSENDAS LITNIMLEDYGRYK     Cartilage Link (gi|212260).aa 160            170            180
146  CEV XDGLEDESGLVELELRGVVFPYQSPNG     OE-HABP ORF Sequence
140  CEV IEGLEDDTAVVALNLEGVVFPYSPRLG     Cartilage Link (gi|212260).aa 190            200            210
176  RYQFNFHEGQQVCAEQAAVVASFEQLFRAW      OE-HABP ORF Sequence
170  RYNLNFHEAQQACLDQDSIIASFDQLYEAW      Cartilage Link (gi|212260).aa 220            230            240
206  EGLDWCNAGWLQDATVQYPIMLPRQPCGG       OE-HABP ORF Sequence
200  RSGLDWCNAGWLSDGSVQYPITKPREPCGG      Cartilage Link (gi|212260).aa
```

FIGURE 7C

```
236 PDLAPGVRSYG PRHRR LH RYDVFCF A TAL X      OE-HABP ORF Sequence
230 KNTVPGVRNYGF WDKE RSRYDVFCF T SNFN        Cartilage Link (gi|212260).aa 266 GRVYYL XHPE X LTLT X AREAC Q ---------    OE-HABP ORF Sequence
260 GRFYYL IHPT KLTYDE AVQACLKDGAQIAK         Cartilage Link (gi|212260).aa 288 ----------------------------------        OE-HABP ORF Sequence
290 VGQIFAAWKLLGYDRCDAGWLADGSVRYPI            Cartilage Link (gi|212260).aa
```

Decoration 'Decoration #1': Shade (with solid black) residues that match the Consensus exactly.

FIGURE 8A

```
1   MTGPGKHKCECKSHYVGDGLNCEPEQLP--ID                    BM-HABP AA SEQUENCE*
1   MV-------------------------VL                       TSG-6 (GI|2062475).AA
                 10        20        30

31  RCLQDNGQCHADAKCV--DL----------                      BM-HABP AA SEQUENCE*
5   LCL-------------CVLLWEEAHGWGFKNG                    TSG-6 (GI|2062475).AA
         40        50        60

49  HFQDT----TVGVFHLRSPLGQYKLTF--DK                     BM-HABP AA SEQUENCE*
24  IFHNSIWLEQAAGVYHREARAGRYKLTYAE                      TSG-6 (GI|2062475).AA
         70        80        90

74  AREACANEAATMATYNQLSYXQKAKYHLCS                      BM-HABP AA SEQUENCE*
54  AKAVCEFEGGRLATYKQLEAARKIGFHVCA                      TSG-6 (GI|2062475).AA
        100       110       120
```

FIGURE 8B

```
104 AGWLETGRVAYPTAFASQNCGSGVVGIVDY   BM-HABP AA SEQUENCE*
 84 AGWMAKGRVGYPIVKPGPNCGFGKTGIIDY   TSG-6 (GI|2062475).AA

134 GPRPNKSEMWDVFCYRMKDVNCTX-----K   BM-HABP AA SEQUENCE*
114 GIRLNRSERWDAYCYNPHAKECGGVFTDPK   TSG-6 (GI|2062475).AA

159 VGYVGDGFS--YSGNLL----------QV   BM-HABP AA SEQUENCE*
144 RIFKSPGFPNEYDDNQVCYWHIRLKYGQRI   TSG-6 (GI|2062475).AA

176 LMSFPS------------LTNFLTEVLAYSNSS   BM-HABP AA SEQUENCE*
174 HLSFLDFDLEHDPGCLADYVEIYDSYDDVH   TSG-6 (GI|2062475).AA
```

FIGURE 8C

```
                  250              260              270
197  A R G R A F L E H L T D L S I R G T L F V   P Q - - N S G L G   BM-HABP AA SEQUENCE*
204  G - - - - - - - - - - - - - - - - - - - -   - - F V G R Y C G   D E L P   TSG-6 (GI|2062475).AA 280              290              300
225  E N E T L S G R D I E H H L A N V S M F F Y N D L V   N G T T   BM-HABP AA SEQUENCE*
216  E D I I S T G N V M T L K F - - - - - - - - - - - -   L S D A S V   TSG-6 (GI|2062475).AA 310              320              330
255  L Q T R L G S K L L I T D R Q D P L H P T   E T R C V D G R D   BM-HABP AA SEQUENCE*
236  T A G G F Q I K Y V T V D - - - - - - - -   P A S K S Q A K N   TSG-6 (GI|2062475).AA 340              350              360
285  T L E W D I C A S N G I T H V I S R X L K A P P A P V T L   X   BM-HABP AA SEQUENCE*
259  T - - - - - - - S T T G N K K F L P - - - - - - - - - - -   -   TSG-6 (GI|2062475).AA
```

FIGURE 8D

```
      370              380              390
315  H T G L G x G I F x x I L V T G A V A L A A Y S   Y F R I N   BM-HABP AA SEQUENCE*
270  - - - - - - - - - - - - - - - - - - - - - G R F S H L        TSG-6 (GI|2062475).AA

345  R K T I G F x H F                                             BM-HABP AA SEQUENCE*
276                                                                TSG-6 (GI|2062475).AA
```

Decoration 'Decoration #1': Shade (with solid black) residues that match the Consensus exactly.

US 6,872,546 B1

HYALURONAN-BINDING PROTEINS AND ENCODING GENES

CROSS REFERENCE TO RELATED APPLICATIONS

This application claims benefit under 35 U.S.C. § 119(e) of the filing date of now abandoned U.S. Provisional Application Ser. No. 60/113,871 filed on Dec. 23, 1998, which is hereby incorporated by reference in its entirety.

STATEMENT REGARDING FEDERALLY SPONSORED RESEARCH OR DEVELOPMENT

The invention described in this application was developed in part with Federal funding (grant number HL37510) from the National Institutes of Health. The Federal Government may have rights to the claimed invention.

FIELD OF THE INVENTION

The present invention relates to a novel member of the Hyaluronan-binding protein family, the full-length WF-HABP protein. More specifically, the present invention relates to the discovery, identification and characterization of nucleotides that encode full-length WF-HABP. The invention encompasses full-length WF-HABP polynucleotides; host cell expression systems; encompasses full-length WF-HABP polypeptides (including fragments, variants, derivatives and analogs thereof); encompasses full-length WF-HABP fusion proteins; antibodies encompasses full-length WF-HABP; agonists and antagonists encompasses full-length WF-HABP; and other compounds that modulate encompasses full-length WF-HABP gene expression or encompasses full-length WF-HABP activity; that can be used for diagnosis, drug screening, and treatment or prevention of disorders which include, but are not limited to, vascular disorders and conditions, congenital pain insensitivity, inflammation, ischemia, host defense dysfunction, immune surveillance dysfunction, neural disorders, arthritis, edema, multiple sclerosis, autoimmunity, immune dysfunction, cancers, metastasis, integumentary disorders, and allergy.

The present invention relates to a novel member of the Hyaluronan-binding protein family, the WF-HABP protein. More specifically, the present invention relates to the discovery, identification and characterization of nucleotides that encode WF-HABP. The invention encompasses WF-HABP polynucleotides; host cell expression systems; WF-HABP polypeptides (including fragments, variants, derivatives and analogs thereof); WF-HABP fusion proteins; antibodies to WF-HABP; agonists and antagonists of WF-HABP; and other compounds that modulate WF-HABP gene expression or WF-HABP activity; that can be used for diagnosis, drug screening, and treatment or prevention of disorders which include, but are not limited to, vascular disorders and conditions, congenital pain insensitivity, inflammation, ischemia, host defense dysfunction, immune surveillance dysfunction, neural disorders, arthritis, edema, multiple sclerosis, autoimmunity, immune dysfunction, cancers, metastasis, integumentary disorders, and allergy.

The present invention relates to a novel member of the Hyaluronan-binding protein family, the OE-HABP protein. More specifically, the present invention relates to the discovery, identification and characterization of nucleotides that encode OE-HABP. The invention encompasses OE-HABP polynucleotides; host cell expression systems; OE-HABP polypeptides (including fragments, variants, derivatives and analogs thereof); OE-HABP fusion proteins; antibodies OE-HABP; agonists and antagonists of OE-HABP; and other compounds that OE-HABP gene expression or OE-HABP activity; that can be used for diagnosis, drug screening, and treatment or prevention of disorders which include, but are not limited to, vascular disorders and conditions, congenital pain insensitivity, inflammation, ischemia, host defense dysfunction, immune surveillance dysfunction, neural disorders, arthritis, edema, multiple sclerosis, autoimmunity, immune dysfunction, cancers, metastasis, integumentary disorders, and allergy.

The present invention relates to a novel member of the Hyaluronan-binding protein family, the BM-HABP protein. More specifically, the present invention relates to the discovery, identification and characterization of nucleotides that encode BM-HABP. The invention encompasses BM-HABP polynucleotides; host cell expression systems; BM-HABP polypeptides (including fragments, variants, derivatives and analogs thereof); BM-HABP fusion proteins; antibodies BM-HABP; agonists and antagonists of BM-HABP; and other compounds that BM-HABP gene expression or BM-HABP activity; that can be used for diagnosis, drug screening, and treatment or prevention of disorders which include, but are not limited to, vascular disorders and conditions, congenital pain insensitivity, inflammation, ischemia, host defense dysfunction, immune surveillance dysfunction, neural disorders, arthritis, edema, multiple sclerosis, autoimmunity, immune dysfunction, cancers, metastasis, integumentary disorders, and allergy.

BACKGROUND OF THE INVENTION

Hyaluronan (HA, hyaluronate, hyaluronan, hyaluronic acid) is a negatively charged, high molecular weight, connective tissue polysaccharide found in the extracellular matrix of most animal tissues. HA consists of alternating N-acetyl-D-glucosamine and D-glururonic acid residues linked by B(1–4) and B(1–3) bonds which has a molecular weight ranging from 1 and $50 \times 10^6$ Da (Brimacombe, J S., et al., in Mucopolysaccarides. (Elsevier, Amsterdam, 1964)) depending upon its source. For example, its has been determined that HA averages between $3–5 \times 10^6$ Da, or $6–7 \times 10^6$ Da, when isolated from rheumatoid fluid, or normal synovial fluid, respectively (Laurent, T C, et al., Immunol Cell Biol., 74:1–7, (1996)). In addition, dilute solutions of HA (<1 mg/mL) are known to result in highly entangled networks which instill unique rheological characteristics to the solution in hand (Laurent, T C., Immuno Cell Biol., 74:1–7, (1996)). For example, solutions of hyaluronan are viscoelastic with the viscosity maintaining a pronounced dependency on shear forces (Ogston, A G., et al., J. Physiol., 199:244–52, (1953)). Therefore, considering the increased localization of HA in the body between surfaces that move against each other, combined with the mechanicauphysical characteristics ascribed above, HA has been attributed the primary role of lubrication and protection of joints and tissues, cartilage surfaces and muscle bundles. Further, HA has also been associated with the scavenging of free radicals and debris (Myint, P., et al., Biochim. Biophys. Acta, 925:194–202, (1987), and Laurent, T C, Ann. Rheum. Dis., 54:429–32, (1995), respectively), keeping the joint cavities open (Edwards, J C W., et al., J. Anat., 185:355–67, 1994), forming flow barriers in the synovium (McDonald, J N., et al., J. Physiol., 485.1:179–93, (1995)), and the prevention of capillary growth (Sattar, A., Sernin. Arthritis Rheum., 22:37–43, (1992)).

HA is synthesized ubiquitously in the plasma membrane of all vertebrate tissues and in some bacteria (Fraser, J R E, J. Intern Med., 242:27–33, (1997)). It is catabolized locally through receptor-mediated endocytosis and lysosomal degradation, in addition to, the lymph nodes and endothelial cells of the liver sinusoids. HA is commonly isolated from the vitreous body of the eye, synovial fluid, rheumatoid fluid, umbilical cord, and skin. Several physiological functions have been associated with HA, in particular water homeostasis; mitosis, cell migration, differentiation, angiogenesis (Rooney P and Kumar S (1994) EXS (Switzerland) 70:179–90); and tissue remodeling, both in normal or tumor-associated events. Its role in water homeostasis (resistance to bulk flow of solvent) is particularly important as it has been shown to prevent excessive fluid exchange between tissue compartments, during both normal conditions and injury (Day, T D., Nature, 166:785–6., (1950)). In addition, HA is thought to play an important role in the promotion of cell proliferation and migration during tissue development and regeneration (Toole, B P., in Cell Biology of Extracellular Matrix (Hay E D, ed), pp. 305–339 (Plenum Press, New York, (1991)).

The matrix-induced effects on cells are directed by a wide variety of HA-binding proteins which are classified into two groups: structural (matrix) and cell-surface-associated (HA-receptors) (Tool, B P., Curr Opin Cell Biol 2:839–844 (1990)). The widespread occurrence of HRs indicate their importance in tissue organization and control of cellular behavior. The family is known as the hyaladherins and includes those RA-binding proteins which act as part of the structural matrix and those which interact with HA at the plasma membrane as cell-surface matrix receptors. Although not comprehensive, some of the identified members of the hyaladherin family include aggrecan, link protein (Manuskiatti, W., Int J Dermatology, 35(8):539–533, (1996)), versican, hyaluronectin, neurocan (Knudson, C B et al., FASEB J, 7:1233–1241, (1993)), CD44 family of receptors (Underhill, C B., J Cell Sci,), RHAMM (Receptor for Hyaluronan-Mediated Motility), and TSG-6 (Tumor Necrosis Factor-Stimulated Gene 6). With the recognition of the Hyaluronan cell-surface receptor (HR); cell biologists, pathologists, and immunologists have begun to investigate the importance of the HA and HR for their potential diagnostic and therapeutic value.

HRs found within the cartilage matrix have been well characterized. Aggrecan is the large aggregating chondroitin sulfate proteoglycan of cartilage which has a high affinity for HA (Hardingham et al, Biochim Biophys. Acta., 279:401–405, (1972)). Link protein is a 45–48 kDa glycoprotein which also demonstrates strong specific binding affinity. HA may bind more than 100 aggrecan and link protein molecules in a supramolecular complex which confers the viscoelastic properties of cartilage. Other matrix proteins such as PG-M and type VI collagen which participate in assembly and integrity may also be involved.

HA-binding proteins are also found in noncartilaginous tissues. Versican of fibroblasts, hyaluronectin of nervous and soft connective tissues, glial hyaluronan binding protein in the central nervous system, and neurocan, a chondroitin sulfate proteoglycan of brain, also form strong structural complexes with HA. All matrix hyaloadherins contain tandem repeated B loops, a structural motif believed to contain the HA-binding domain.

HR hyaloadherins have been detected on several cell types from a wide variety of tissues based upon hyaluronans ability to aggregate such cells (Pessac, B., et al., Science, 175:898–900, (1972)). Some reports suggest that HRs are related to the CD44 family of lymphocyte homing receptors which include the isoforms, Pgp-1, Hermes antigen, H-CAM and ECMRIII. The distal extracellular domain of CD44 has sequence homology to one of the B loop motifs of link protein. The numerous isoforms suggest different cellular functions and demonstrate binding to other ligands such as collagens I and IV and mucosal vascular addressing. Further, although many roles have been attributed to the CD44-hyaluronan interaction, its roles in development, tumour progression, and in the immune response appear to be the most prevalent (Sherman, L., Curr. Opinion Cell Biol., 6:726–33, (1994).

Other non-CD44 HRs include cell-surface antigens termed IVd4 which block binding of HA, liver endothelial cell receptors (LEC) which are involved in the clearance of HA from the circulation, and fibroblast-produced HR which may be located on the cell surface where it mediates HA-induced cell locomotion. Its 58 kDA soluble form contains an HA-binding component unrelated to the B loop motif and is known as a receptor for HA mediated motility (RHAMM). The important distinctions between cell-surface and matrix hyaloadherins are 1) HA hexasaccharides represent the minimum size molecule that interacts with these cell-surface receptors, 2) binding affinity increases with increasing polymer length, and 3) binding increases with increasing buffer ionic strength.

Increased matrix presence of HA has been correlated with cell migration in embryogenesis, limb regeneration, wound healing and tumor invasion. Since the CD44 HR have been shown to associate with cytoskeletal ankyrin, proteins of the HR complex may affect re-organization of the actin cytoskeleton and other activities such as cell ruffling, detachment from the substratum, and locomotion necessary for cell migration. RHAMM, as one of the HR complex proteins, binds to HA with high affinity and is expressed only in the leading lamellae and perinuclear regions of migrating fibroblasts.

Since RHAMM does not include a transmembrane hydrophobic region, it is assumed to be a peripheral protein associated with intracellular, membrane bound tyrosine kinase. In studies of timed administration of HA and an inhibitor of tyrosine kinase, HA stimulated locomotion via a rapid tyrosine kinase signal transduction pathway.

Invasive or metastatic cancer cells have the capacity to exit from the vascular system by use of sets of molecules, at least one of which always has a receptor function. One series of such sets might include successive interactions among endothelial VLA-4 integrin and E-selectin, subendothelial collagen IV and B-4 integrin, and soft connective tissue HA and CD44 or HR interactions (Zetter B R (1993) Semin Cancer Biol 4:215–218).

Some tumor cells also have the capacity to assemble HA-enriched pericellular matrices which reduce cell adhesion to the outside of the growing tumor and protect the tumor from immune surveillance. In addition, the presence of high HA attracts endothelial cells which are active in angiogenesis. The combination of these HA functions allows the rapid establishment and growth of invasive tumor cells.

The transforming oncogene H-ras may promote cell locomotion. Hardwick et al (1992 J Cell Biol 117:1343–1350) reported that H-ras actually regulates expression of RHAMM, showed binding between HA and RHAMM, and produced an antibody to the protein which is capable of inhibiting HA/HR locomotion.

The fact that WF-HABP, OE-HABP, and BM-HABP polynucleotides and polypeptides are members of the hyaluronan receptor family suggests that: invention would play an important role in diverse human disease states ranging from inflammatory conditions to, cancer metastasis, and more generally that members of this family mediate cellular responses such as activation, survival, proliferation, migration, signalling, and differentiation; that hyaluronan receptor family members provide an important model system for the in vitro study of arthritus, angiogenesis, and hematopoietic or immune disorders; and that hyaluronan receptors would provide defined targets for the development of new anti-cancer, arthritus, and healing wound tissue agents.

SUMMARY OF THE INVENTION

The present invention provides isolated nucleic acid molecules comprising polynucleotides encoding the full-length WF-HABP having the amino acid sequence shown in FIGS. 1A–P (SEQ ID NO:2) or the amino acid sequence encoded by the cDNA clone encoding full-length WF-HABP. The present invention also relates to recombinant vectors, which include the isolated nucleic acid molecules of the present invention, and to host cells containing the recombinant vectors, as well as to methods of making such vectors and host cells and for using them or other genetically modified host cells to produce full-length WF-HABP polypeptides (including fragments, variants, derivatives, and analogs thereof) by recombinant techniques.

The present invention provides isolated nucleic acid molecules comprising polynucleotides encoding the WF-HABP having the amino acid sequence shown in FIGS. 2A–D (SEQ ID NO:5) or the amino acid sequence encoded by the cDNA clone encoding WF-HABP deposited in a vector as ATCC Deposit Number 203503 Dec. 1, 1998. The present invention also relates to recombinant vectors, which include the isolated nucleic acid molecules of the present invention, and to host cells containing the recombinant vectors, as well as to methods of making such vectors and host cells and for using them or other genetically modified host cells to WF-HABP polypeptides (including fragments, variants, derivatives, and analogs thereof) by recombinant techniques.

The present invention provides isolated nucleic acid molecules comprising polynucleotides encoding OE-HABP having the amino acid sequence shown in FIGS. 3A–C (SEQ ID NO:8) or the amino acid sequence encoded by the cDNA clone encoding OE-HABP deposited in a vector as ATCC Deposit Number 203501 on Dec. 1, 1998. The present invention also relates to recombinant vectors, which include the isolated nucleic acid molecules of the present invention, and to host cells containing the recombinant vectors, as well as to methods of making such vectors and host cells and for using them or other genetically modified host cells to produce OE-HABP polypeptides (including fragments, variants, derivatives, and analogs thereof) by recombinant techniques.

The present invention provides isolated nucleic acid molecules comprising polynucleotides encoding BM-HABP having the amino acid sequence shown in FIGS. 4A–C (SEQ ID NO:11) or the amino acid sequence encoded by the cDNA clone encoding BM-HABP deposited in a vector as ATCC Deposit Number 203502 on Dec. 1, 1998. The present invention also relates to recombinant vectors, which include the isolated nucleic acid molecules of the present invention, and to host cells containing the recombinant vectors, as well as to methods of making such vectors and host cells and for using them or other genetically modified host cells to produce BM-HABP polypeptides (including fragments, variants, derivatives, and analogs thereof) by recombinant techniques.

The invention further provides isolated full-length WF-HABP polypeptides having amino acid sequences encoded by the polynucleotides described herein.

The invention further provides isolated WF-HABP polypeptides having amino acid sequences encoded by the polynucleotides described herein.

The invention further provides isolated OE-HABP polypeptides having amino acid sequences encoded by the polynucleotides described herein.

The invention further provides isolated BM-HABP polypeptides having amino acid sequences encoded by the polynucleotides described herein.

The present invention also provides a screening method for identifying. compounds capable of eliciting a cellular response induced by the full-length WF-HABP, which involves contacting cells which express WF-HABP with the candidate compound, assaying a cellular response (e.g., ion flux, cellular proliferation, cellular migration, cell adhesion, etc.), and comparing the cellular response to a standard cellular response, the standard being assayed in absence of the candidate compound; whereby, an increased cellular response over the standard indicates that the compound is an agonist.

The present invention also provides a screening method for identifying compounds capable of eliciting a cellular response induced by WF-HABP, which involves contacting cells which express WF-HABP with the candidate compound, assaying a cellular response (e.g., ion flux, cellular proliferation, cellular migration, cell adhesion, etc.), and comparing the cellular response to a standard cellular response, the standard being assayed in absence of the candidate compound; whereby, an increased cellular response over the standard indicates that the compound is an agonist.

The present invention also provides a screening method for identifying compounds capable of eliciting a cellular response induced by OE-HABP, which involves contacting cells which express OE-HABP with the candidate compound, assaying a cellular response (e.g., ion flux, cellular proliferation, cellular migration, cell adhesion, etc.), and comparing the cellular response to a standard cellular response, the standard being assayed in absence of the candidate compound; whereby, an increased cellular response over the standard indicates that the compound is an agonist.

The present invention also provides a screening method for identifying compounds capable of eliciting a cellular response induced by BM-HABP, which involves contacting cells which express BM-HABP with the candidate compound, assaying a cellular response (e.g., ion flux, cellular proliferation, cellular migration, cell adhesion, etc.), and comparing the cellular response to a standard cellular response, the standard being assayed in absence of the candidate compound; whereby, an increased cellular response over the standard indicates that the compound is an agonist.

The present invention also provides a screening method for identifying compounds capable of enhancing or inhibiting a cellular response induced by the full-length WF-HABP receptors, which involves contacting cells which express full-length WF-HABP receptors with the candidate compound in the presence of a full-length WF-HABP agonist (e.g., hyaluronan) or other stimulus (e.g., injury, or IL-1b or TNF-a induction), assaying a cellular response (e.g., ion flux, cellular proliferation, cellular migration, cell adhesion, etc.), and comparing the cellular response to a standard cellular response, the standard being assayed when contact is made between the agonist and full-length WF-HABP or when full-length WF-HABP is exposed to the stimulus, in absence of the candidate compound; whereby, an increased cellular response over the standard indicates that the compound is an agonist and a decreased cellular response over the standard indicates that the compound is an antagonist.

The present invention also provides a screening method for identifying compounds capable of enhancing or inhibiting a cellular response induced by WF-HABP receptors, which involves contacting cells which express WF-HABP receptors with the candidate compound in the presence of a WF-HABP agonist (e.g., hyaluronan) or other stimulus (e.g., injury, or IL-1b or TNF-a induction), assaying a cellular response (e.g., ion flux, cellular proliferation, cellular migration, cell adhesion, etc.), and comparing the cellular response to a standard cellular response, the standard being assayed when contact is made between the agonist and WF-HABP or when WF-HABP is exposed to the stimulus, in absence of the candidate compound; whereby, an increased cellular response over the standard indicates that the compound is an agonist and a decreased cellular response over the standard indicates that the compound is an antagonist.

The present invention also provides a screening method for identifying compounds capable of enhancing or inhibiting a cellular response induced by OE-HABP receptors, which involves contacting cells which express OE-HABP receptors with the candidate compound in the presence of a OE-HABP agonist (e.g., hyaluronan) or other stimulus (e.g., injury, or IL-1b or TNF-a induction), assaying a cellular response (e.g., ion flux, such as, cellular proliferation, cellular migration, cell adhesion, etc.), and comparing the cellular response to a standard cellular response, the standard being assayed when contact is made between the agonist and OE-HABP or when OE-HABP is exposed to the stimulus, in absence of the candidate compound; whereby, an increased cellular response over the standard indicates that the compound is an agonist and a decreased cellular response over the standard indicates that the compound is an antagonist.

The present invention also provides a screening method for identifying compounds capable of enhancing or inhibiting a cellular response induced by BM-HABP receptors, which involves contacting cells which express BM-HABP receptors with the candidate compound in the presence of a BM-HABP agonist (e.g., hyaluronan) or other stimulus (e.g., injury, or IL-1b or TNF-a induction), assaying a cellular response (e.g., ion flux, cellular proliferation, cellular migration, cell adhesion, etc.), and comparing the cellular response to a standard cellular response, the standard being assayed when contact is made between the agonist and BM-HABP or when BM-HABP is exposed to the stimulus, in absence of the candidate compound; whereby, an increased cellular response over the standard indicates that the compound is an agonist and a decreased cellular response over the standard indicates that the compound is an antagonist.

In another embodiment, a screening assay for agonists and antagonists is provided which involves determining the effect a candidate compound has on the binding of cellular ligands (e.g., hyaluronan, chondroitin-sulfate proteoglycans, etc.) to full-length WF-HABP. In particular, the method involves contacting full-length WF-HABP with a ligand or other stimulus (e.g., injury, or IL-1b or TNF-a induction) and a candidate compound and determining whether ligand binding to full-length WF-HABPs is increased or decreased due to the presence of the candidate compound.

In another embodiment, a screening assay for agonists and antagonists is provided which involves determining the effect a candidate compound has on the binding of cellular ligands (e.g., hyaluronan, chondroitin-sulfate proteoglycans, etc.) to WF-HABP. In particular, the method involves contacting WF-HABP with a ligand or other stimulus (e.g., injury, or IL-1b or TNF-a induction) and a candidate compound and determining whether ligand binding to WF-HABPs is increased or decreased due to the presence of the candidate compound.

In another embodiment, a screening assay for agonists and antagonists is provided which involves determining the effect a candidate compound has on the binding of cellular ligands (e.g., hyaluronan, chondroitin-sulfate proteoglycans, etc.) to OE-HABP. In particular, the method involves contacting OE-HABP with a ligand or other stimulus (e.g., injury, or IL-1b or TNF-a induction) and a candidate compound and determining whether ligand binding to OE-HABPs is increased or decreased due to the presence of the candidate compound.

In another embodiment, a screening assay for agonists and antagonists is provided which involves determining the effect a candidate compound has on the binding of cellular ligands (e.g., hyaluronan, chondroitin-sulfate proteoglycans, etc.) to BM-HABP. In particular, the method involves contacting BM-HABP with a ligand or other stimulus (e.g., injury, or IL-1b or TNF-a induction) and a candidate compound and determining whether ligand binding to BM-HABPs is increased or decreased due to the presence of the candidate compound.

The invention further provides a diagnostic method useful during diagnosis or prognosis of disease states resulting from aberrant cell secretion, activation, survival, migration, differentiation and/or proliferation, due to alterations in full-length WF-HABP coding sequences and/or receptor expression.

The invention further provides a diagnostic method useful during diagnosis or prognosis of disease states resulting from aberrant cell secretion, activation, survival, migration, differentiation and/or proliferation, due to alterations in WF-HABP coding sequences and/or receptor expression.

The invention further provides a diagnostic method useful during diagnosis or prognosis of disease states resulting from aberrant cell secretion, activation, survival, migration, differentiation and/or proliferation, due to alterations in OE-HABP coding sequences and/or receptor expression.

The invention further provides a diagnostic method useful during diagnosis or prognosis of disease states resulting from aberrant cell secretion, activation, survival, migration, differentiation and/or proliferation, due to alterations in BM-HABP coding sequences and/or receptor expression.

An additional embodiment of the invention is related to a method for treating an individual in need of an increased level of full-length WF-HABP activity in the body comprising administering to such an individual a composition comprising a therapeutically effective amount of full-length WF-HABP polypeptides or polynucleotides of the invention or a full-length WF-HABP agonist.

An additional embodiment of the invention is related to a method for treating an individual in need of an increased level of WF-HABP activity in the body comprising administering to such an individual a composition comprising a therapeutically effective amount of WF-HABP-polypeptides or polynucleotides of the invention or a WF-HABP agonist.

An additional embodiment of the invention is related to a method for treating an individual in need of an increased level of OE-HABP activity in the body comprising administering to such an individual a composition comprising a therapeutically effective amount of OE-HABP polypeptides or polynucleotides of the invention or a OE-HABP agonist.

An additional embodiment of the invention is related to a method for treating an individual in need of an increased level of BM-HABP activity in the body comprising administering to such an individual a composition comprising a therapeutically effective amount of BM-HABP polypeptides or polynucleotides of the invention or a BM-HABP agonist.

A still further embodiment of the invention is related to a method for treating an individual in need of a decreased level of a full-length WF-HABP receptor activity in the body comprising, administering to such an individual a composition comprising a therapeutically effective amount of full-length WF-HABP polypeptides or polynucleotides of the invention a full-length WF-HABP antagonist.

A still further embodiment of the invention is related to a method for treating an individual in need of a decreased level of a WF-HABP receptor activity in the body comprising, administering to such an individual a composition comprising a therapeutically effective amount of WF-HABP polypeptides or polynucleotides of the invention a WF-HABP antagonist.

A still further embodiment of the invention is related to a method for treating an individual in need of a decreased level of a OE-HABP receptor activity in the body comprising, administering to such an individual a composition comprising a therapeutically effective amount of OE-HABP polypeptides or polynucleotides of the invention a OE-HABP antagonist.

A still further embodiment of the invention is related to a method for treating an individual in need of a decreased level of a BM-HABP receptor activity in the body comprising, administering to such an individual a composition comprising a therapeutically effective amount of BM-HABP polypeptides or polynucleotides of the invention a BM-HABP antagonist.

The invention additionally provides soluble forms of the polypeptides of the present invention. Soluble peptides are defined by amino acid sequences wherein the sequence comprises the polypeptide sequence lacking a transmembrane domain (e.g., full-length WF-HABP polypeptide fragments corresponding to intracellular and/or extracellular domains). Such soluble forms of full-length WF-HABP are useful as antagonists of the membrane bound forms of the receptor.

The invention additionally provides soluble forms of the polypeptides of the present invention. Soluble peptides are defined by amino acid sequences wherein the sequence comprises the polypeptide sequence lacking a transmembrane domain (e.g., WF-HABP polypeptide fragments corresponding to intracellular and/or extracellular domains). Such soluble forms of WF-HABP are useful as antagonists of the membrane bound forms of the receptor.

The invention additionally provides soluble forms of the polypeptides of the present invention. Soluble peptides are defined by amino acid sequences wherein the sequence comprises the polypeptide sequence lacking a transmembrane domain (e.g., OE-HABP polypeptide fragments corresponding to intracellular and/or extracellular domains). Such soluble forms of OE-HABP are useful as antagonists of the membrane bound forms of the receptor.

The invention additionally provides soluble forms of the polypeptides of the present invention. Soluble peptides are defined by amino acid sequences wherein the sequence comprises the polypeptide sequence lacking a transmembrane domain (e.g., BM-HABP polypeptide fragments corresponding to intracellular and/or extracellular domains). Such soluble forms of BM-HABP are useful as antagonists of the membrane bound forms of the receptor.

BRIEF DESCRIPTION OF THE FIGURES

FIGS. 1A–P show the nucleotide sequence (SEQ ID NO:1) and deduced amino acid sequence (SEQ ID NO:2) of the full-length WF-HABP. The deduced complete amino acid sequence includes 2157 amino acid residues and has a deduced molecular weight of about 231657.63 Da. The predicted domains of the WF-HABP polypeptide are: an HA binding motif (amino acid residues E-1791 to C-1894 of SEQ ID NO:2), double underlined; EGF-like Type 1 domains (amino acid residues from C-375 to C-386, amino acid residues from C-943 to C-954, amino acid residues from C-987 to C-998, amino acid residues from C-1582 to C-1593, and amino acid residues from C-1626 to C-1637 of SEQ ID NO:2), indicated by "~" above the line; EGF-like Type 2 domains (amino acid residues from C-465 to C-478, amino acid residues from C-508 to C-521, amino acid residues from C-551 to C-564, amino acid residues from C-943 to C-957, amino acid residues from C-987 to C-998, amino acid residues from C-1027 to C-1040, amino acid residues from C-1069 to C-1082, amino acid residues from C-1111 to C-1125, amino acid residues from C-1582 to C-1596, amino acid residues from C-1582 to C-1596, amino acid residues from C-1626 to C-1637, amino acid residues from C-1663 to C-1676, amino acid residues from C-1747 to C-1760, and amino acid residues from C-1894 to C-1908 of SEQ ID NO:2), dashed-underline; laminin-type EGF domain (amino acid residues from C-943 to C-977, and amino acid residues from C-1582 to C-1616 of SEQ ID NO:2), italicized; link protein domain (amino acid residues from C-1817 to C-1862 of SEQ ID NO:2), "*" above the line; cytochrome P450 cysteine heme-iron ligand binding domains (amino acid residues from F-344 to G-353, and amino acid residues from W-514 to A-523 of SEQ ID NO:2), lower case letters; prokaryotic membrane lipoprotein lipid attachment site domains (amino acid residues from P-1103 to C-1113, and amino acid residues from T-1405 to C-1415 of SEQ ID NO:2), strikethrough letters.

FIGS. 2A–D show the nucleotide sequence (SEQ ID NO:4) and deduced amino acid sequence (SEQ ID NO:5) of WF-HABP. The deduced complete amino acid sequence includes 457 amino acid residues and has a deduced molecular weight of about 48448.90 Da. The predicted domains of the WF-HABP polypeptide are: an HA binding domain (amino acid residues E-91 to C-194 of SEQ ID NO:5), double underlined; EGF-like Type 2 domain (amino acid residues C-194 to C-208, of SEQ ID NO:5), dashed-underline; and a link domain domain (amino acid residues C-117 to C-162, of SEQ ID NO:5), "*" above the line.

FIGS. 3A–C show the nucleotide sequence (SEQ ID NO:7) and deduced amino acid sequence (SEQ ID NO:8) of OE-HABP. The deduced complete amino acid sequence includes 289 amino acid residues and has a deduced molecular weight of about 33174.55 Da. The predicted domains of the OE-HABP polypeptide are: an HA binding motif domain (amino acid residues P-97 to F-168, amino acid residues L-209 to C-286, of SEQ ID NO:8), double underlined; and a link protein domain (amino acid residues C-188 to C-233 of SEQ ID NO:8), "*" above the line.

FIGS. 4A–C show the nucleotide sequence (SEQ ID NO:10) and deduced amino acid sequence (SEQ ID NO:11)

of BM-HABP. The deduced complete amino acid sequence includes 353 amino acid residues and has a deduced molecular weight of about 36063.32 Da The predicted domains of the BM-HABP polypeptide are: an HA binding motif domain (amino acid residues Q-121 to L-215 of SEQ ID NO:11), double underlined.

Figure 5A:
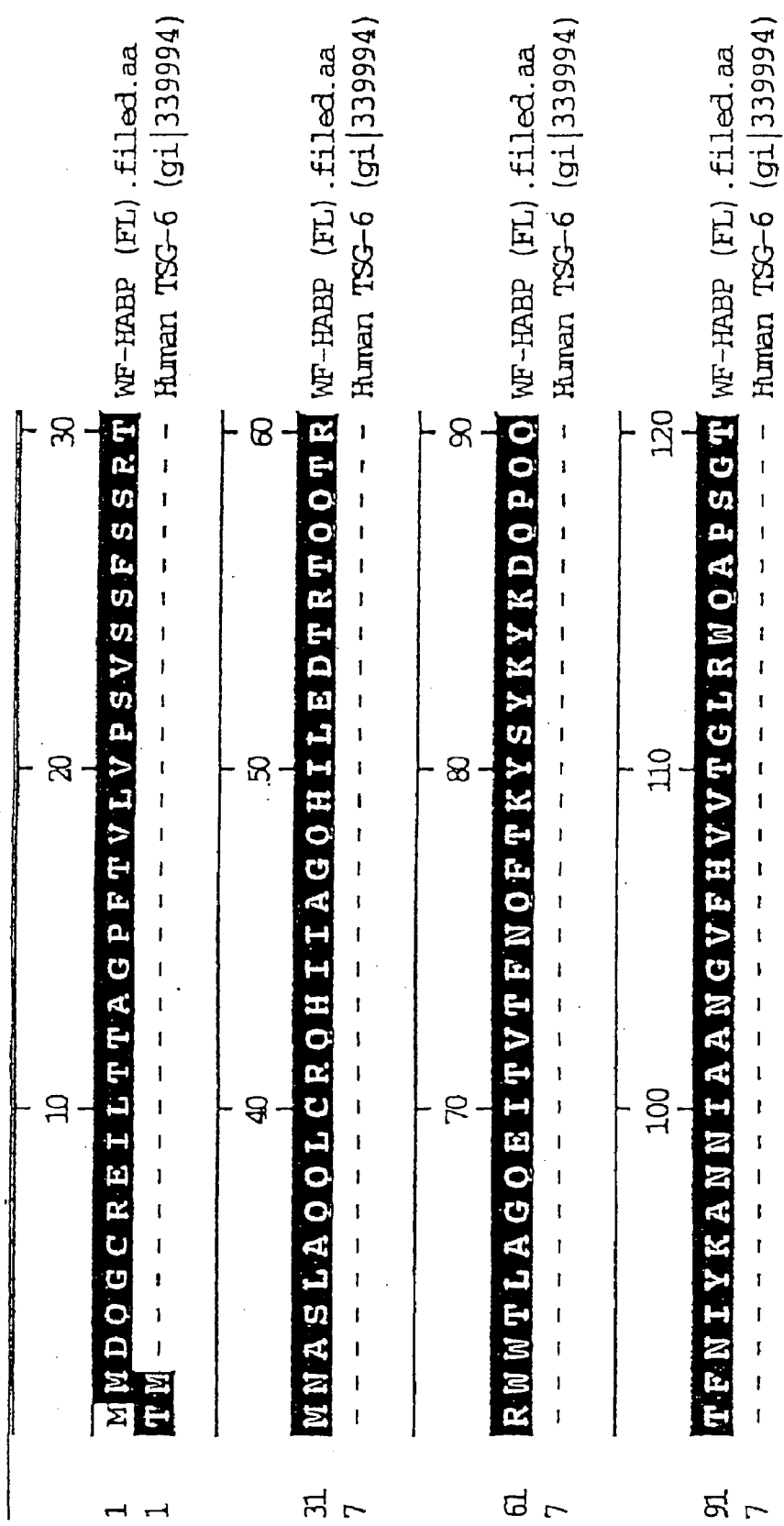
Figure 5C:
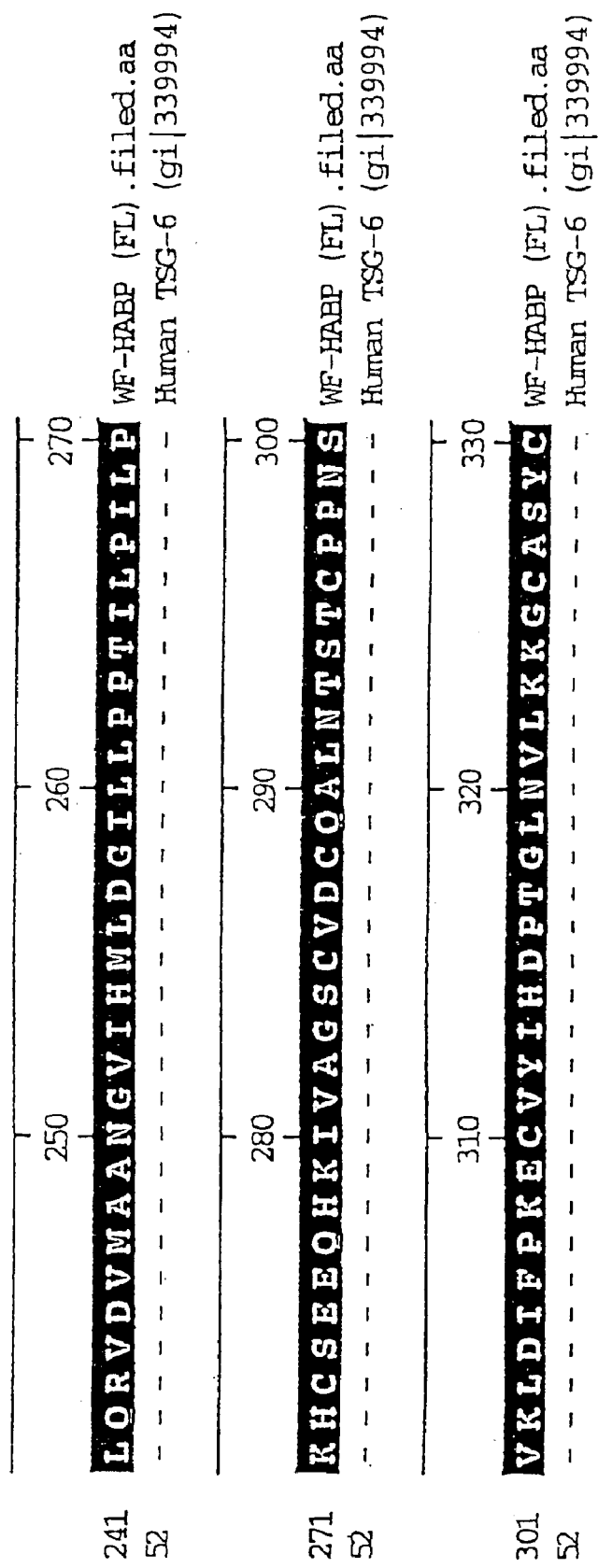
Figure 5D:
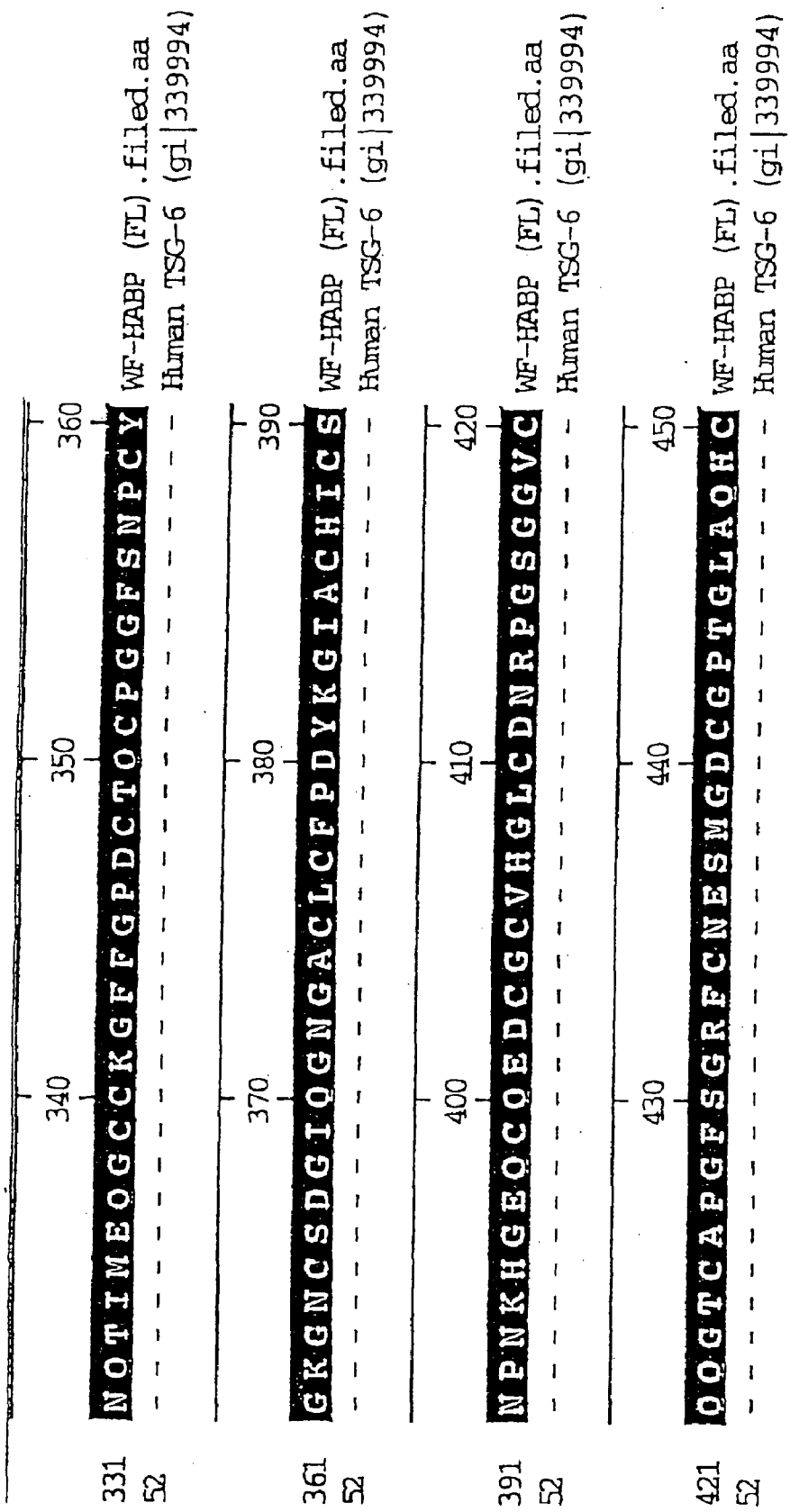
Figure 5F:
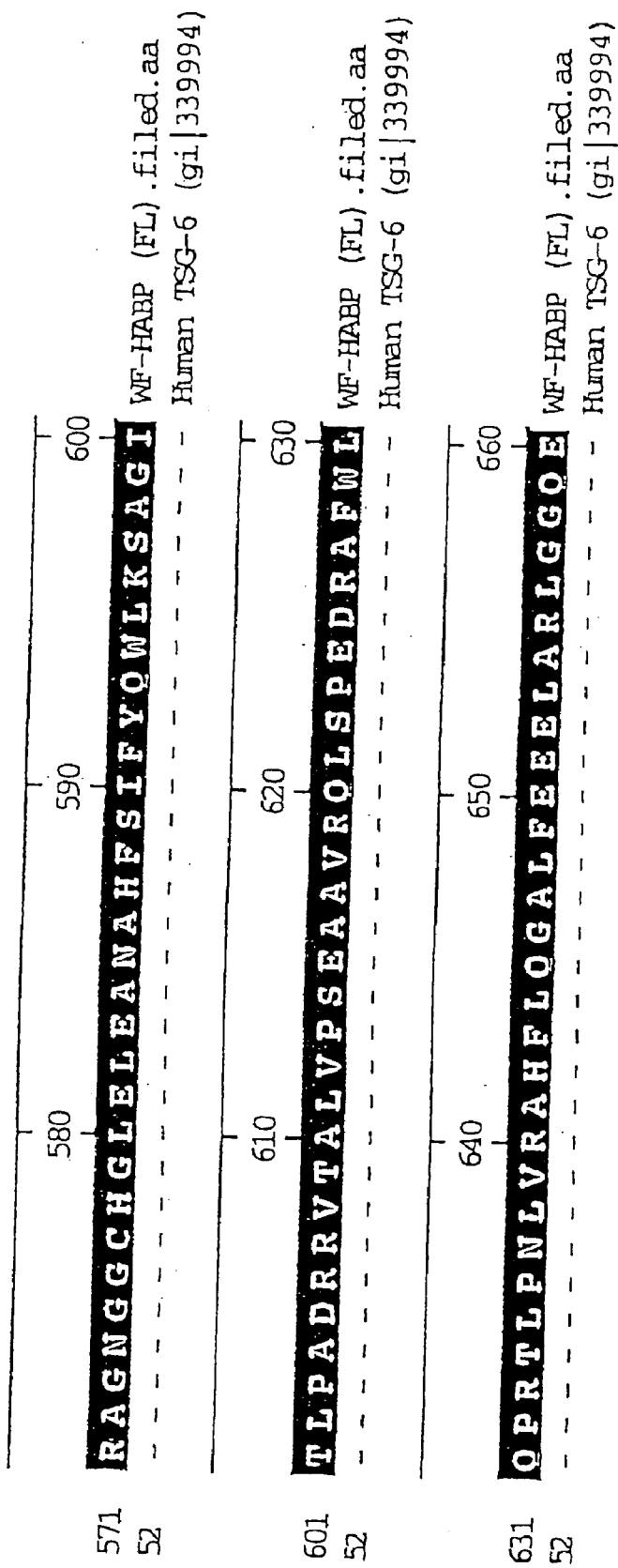
Figure 5G:
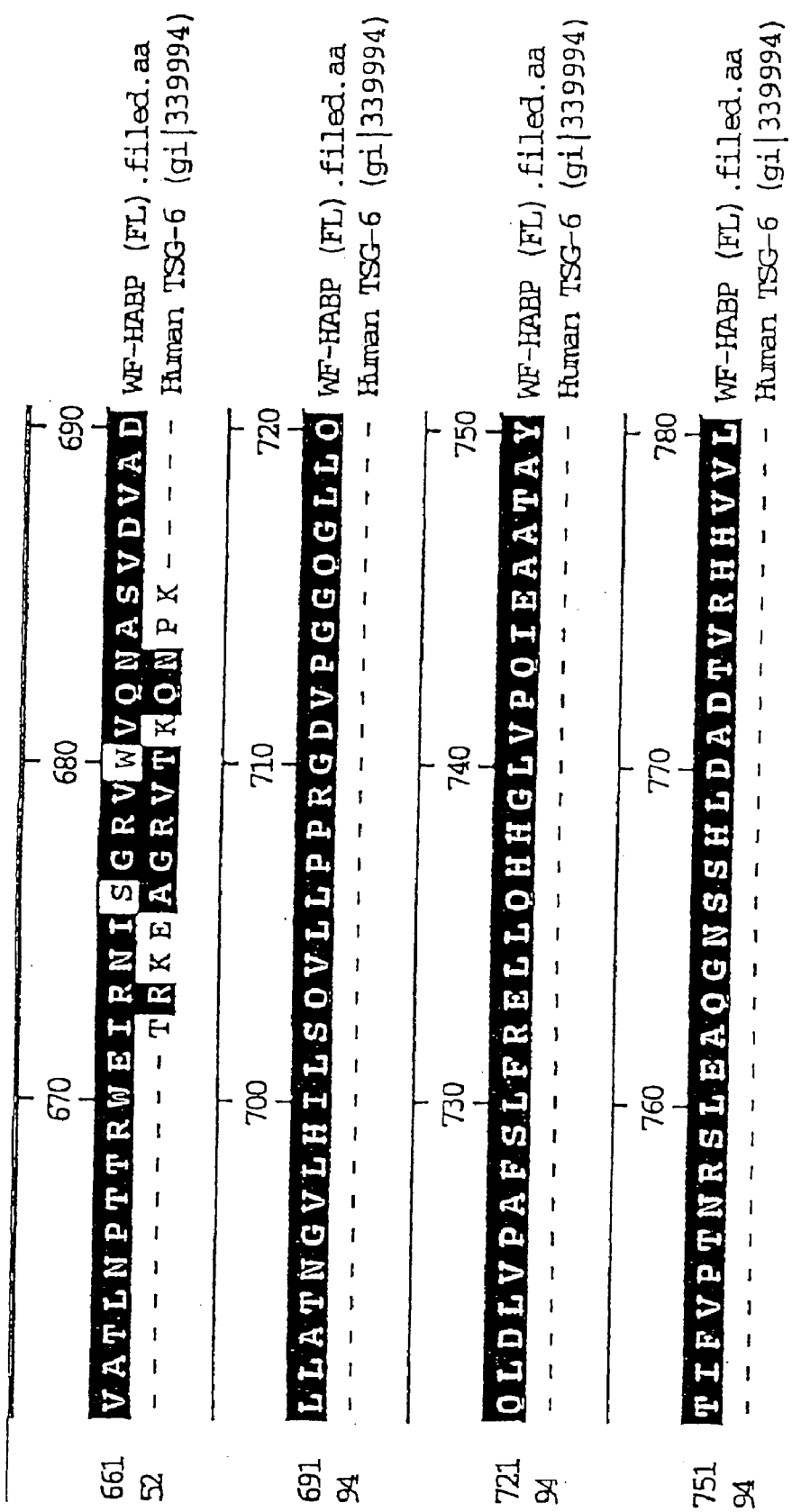
Figure 5H:
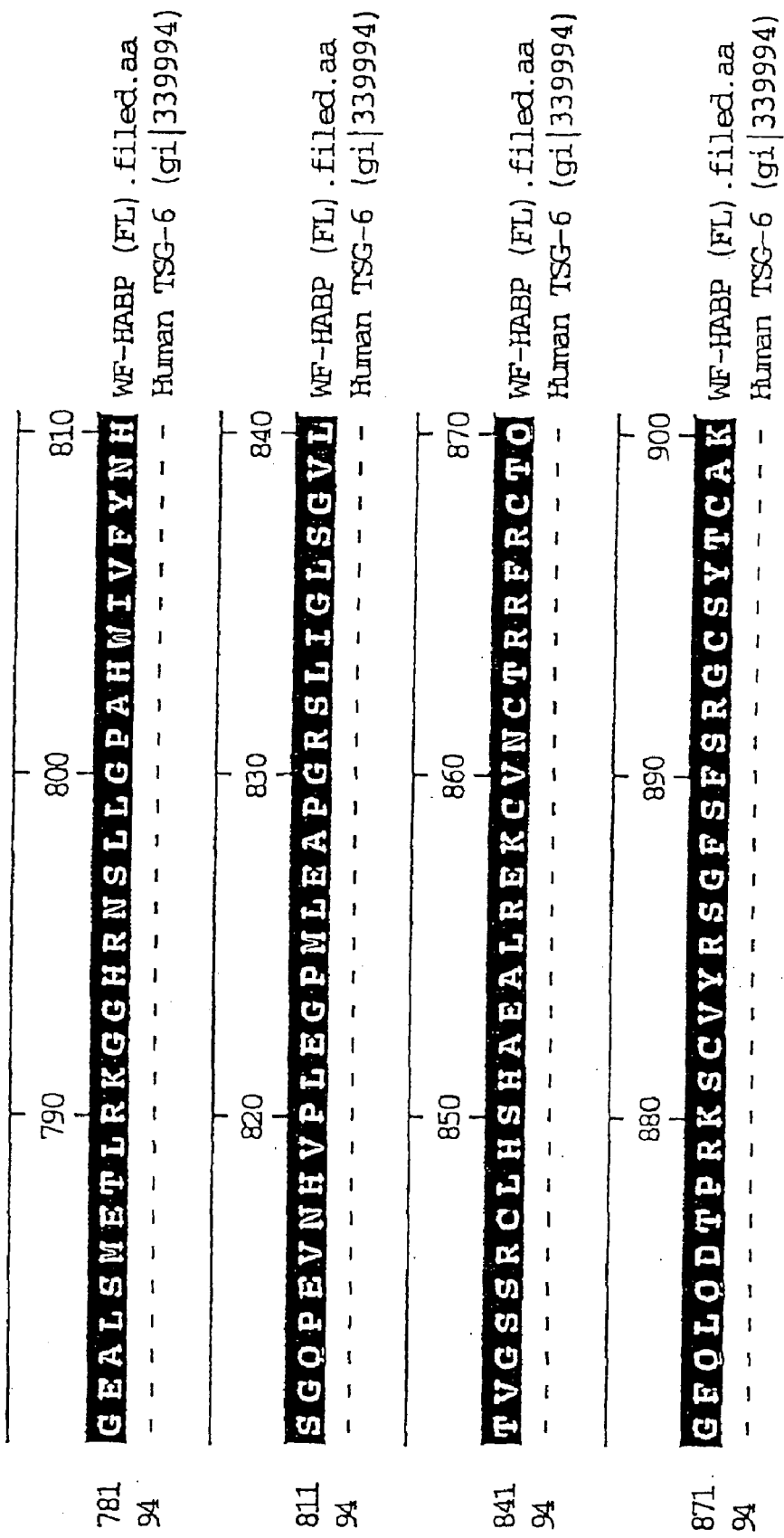
Figure 5I:
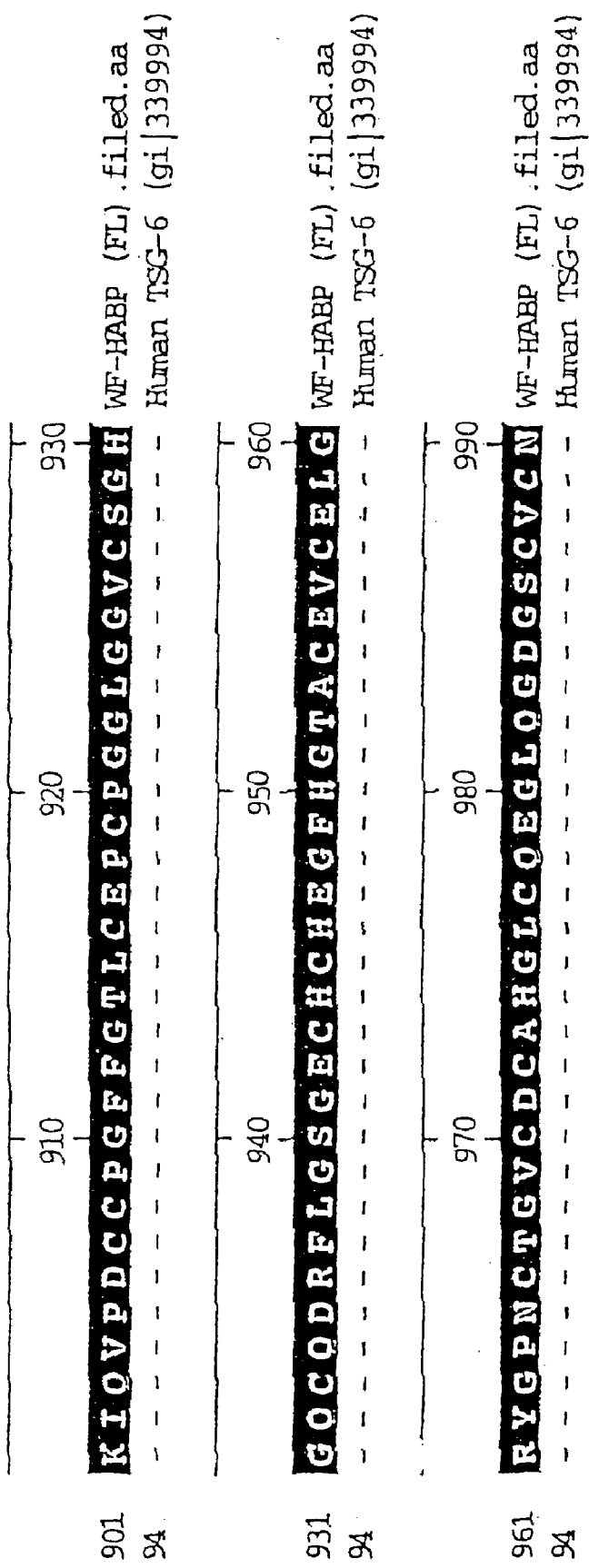
Figure 5J:
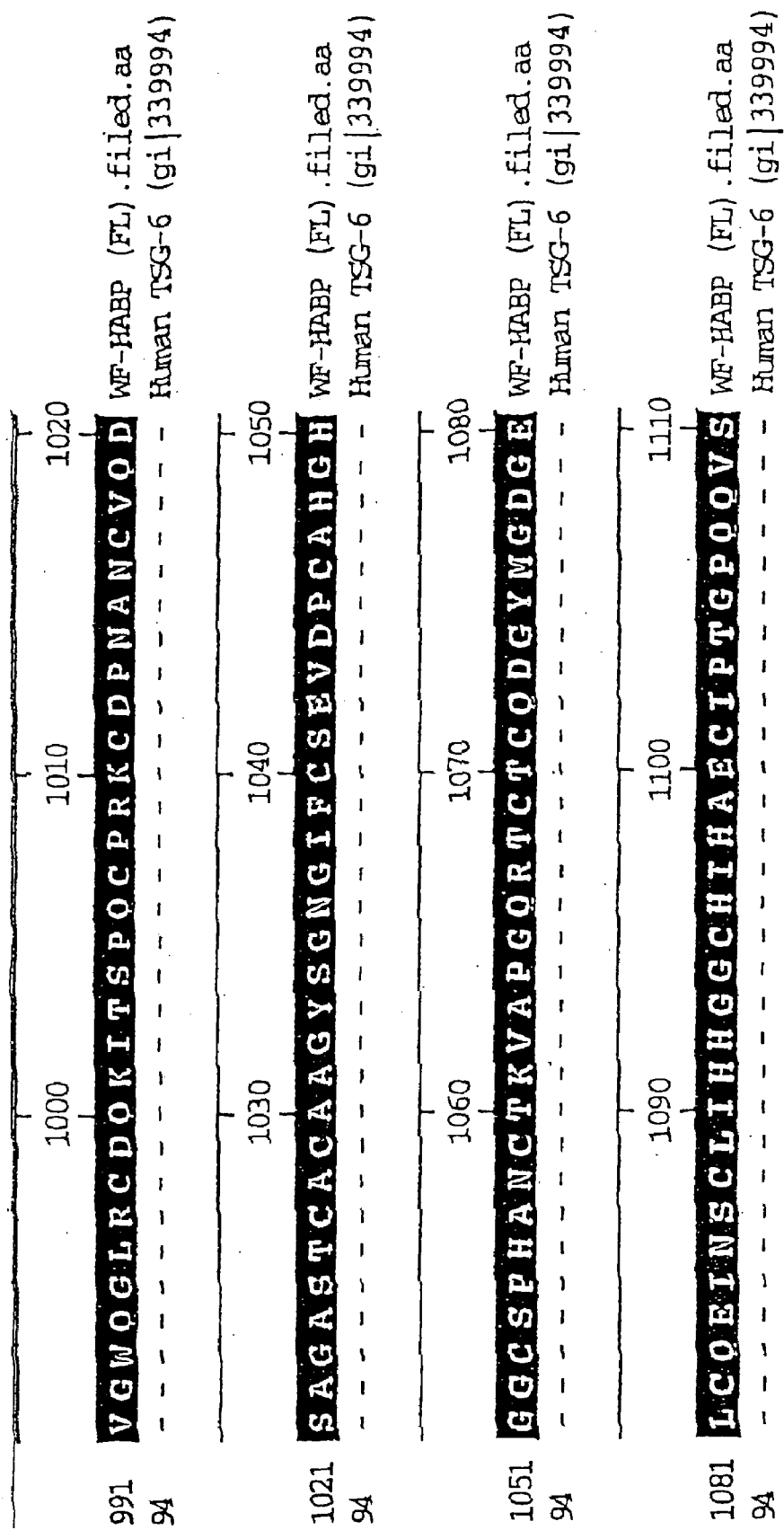
Figure 5K:
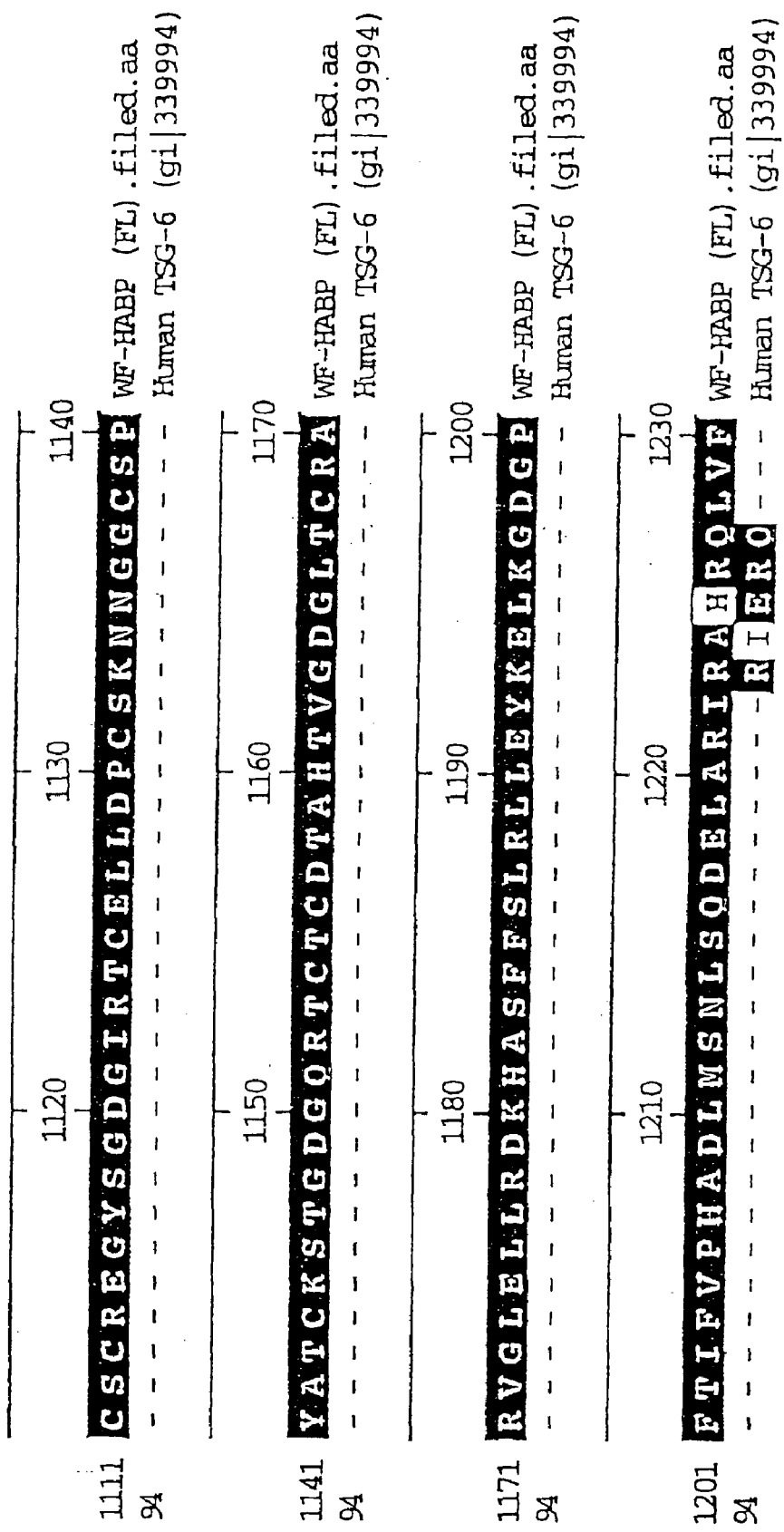
Figure 5L:
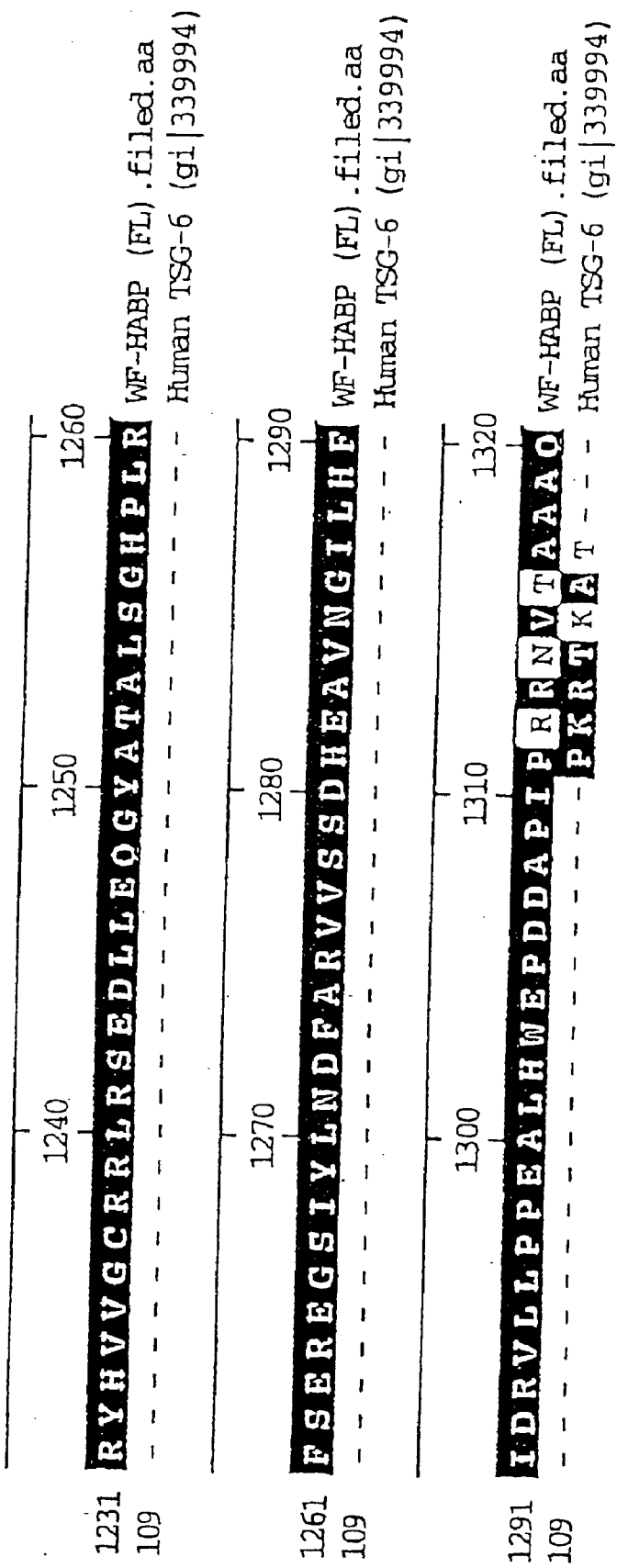
Figure 5M:
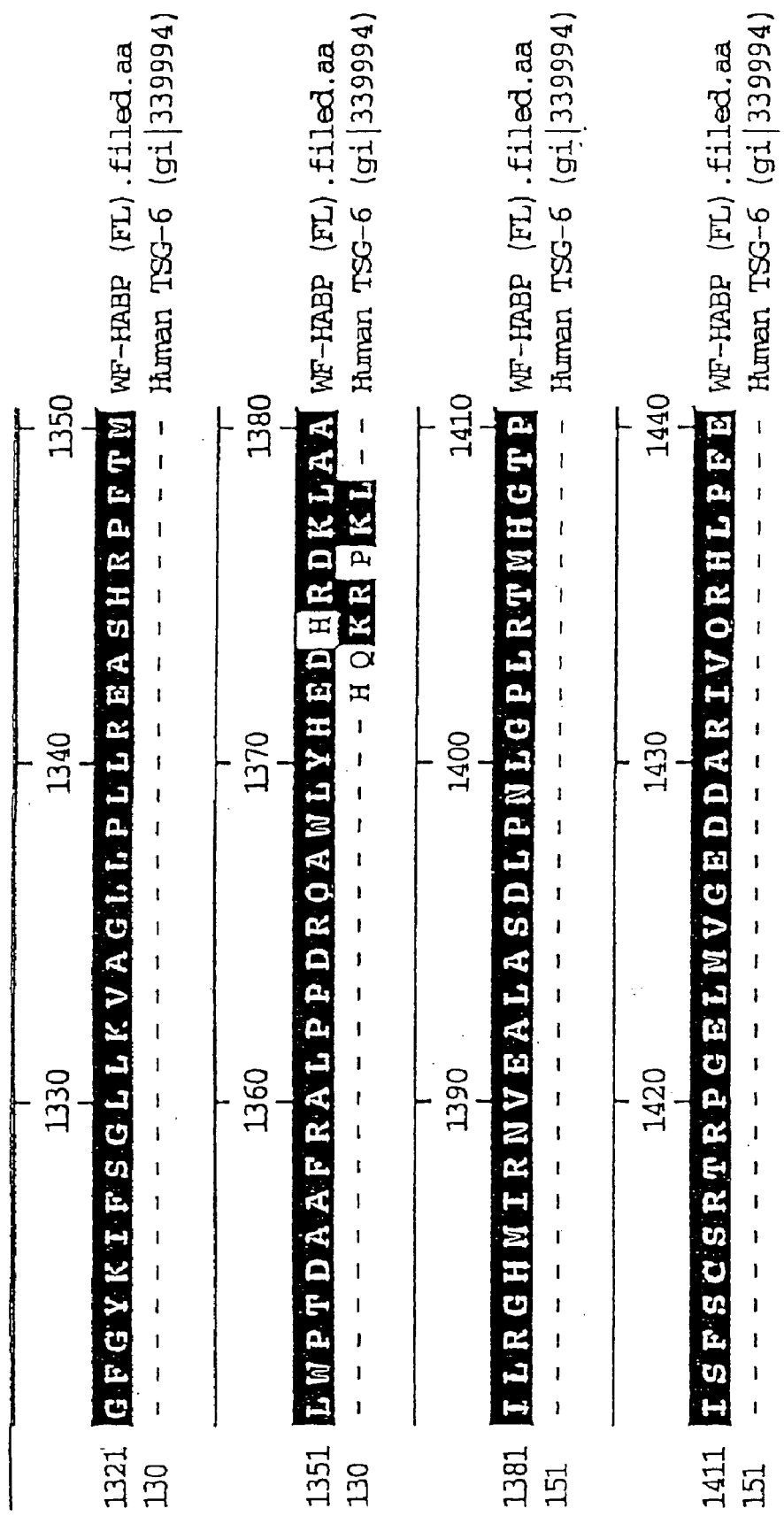
Figure 5P:
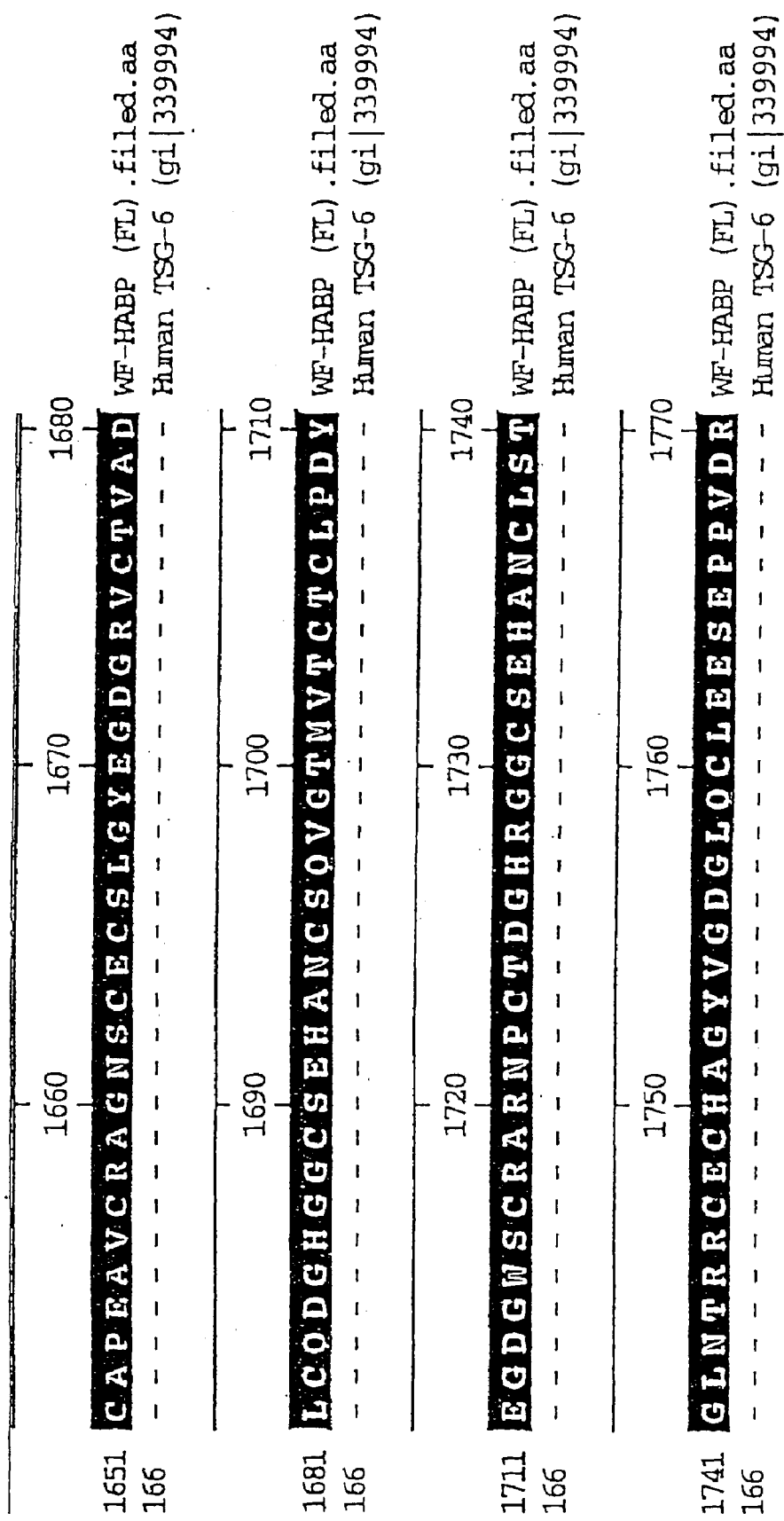
Figure 5Q:
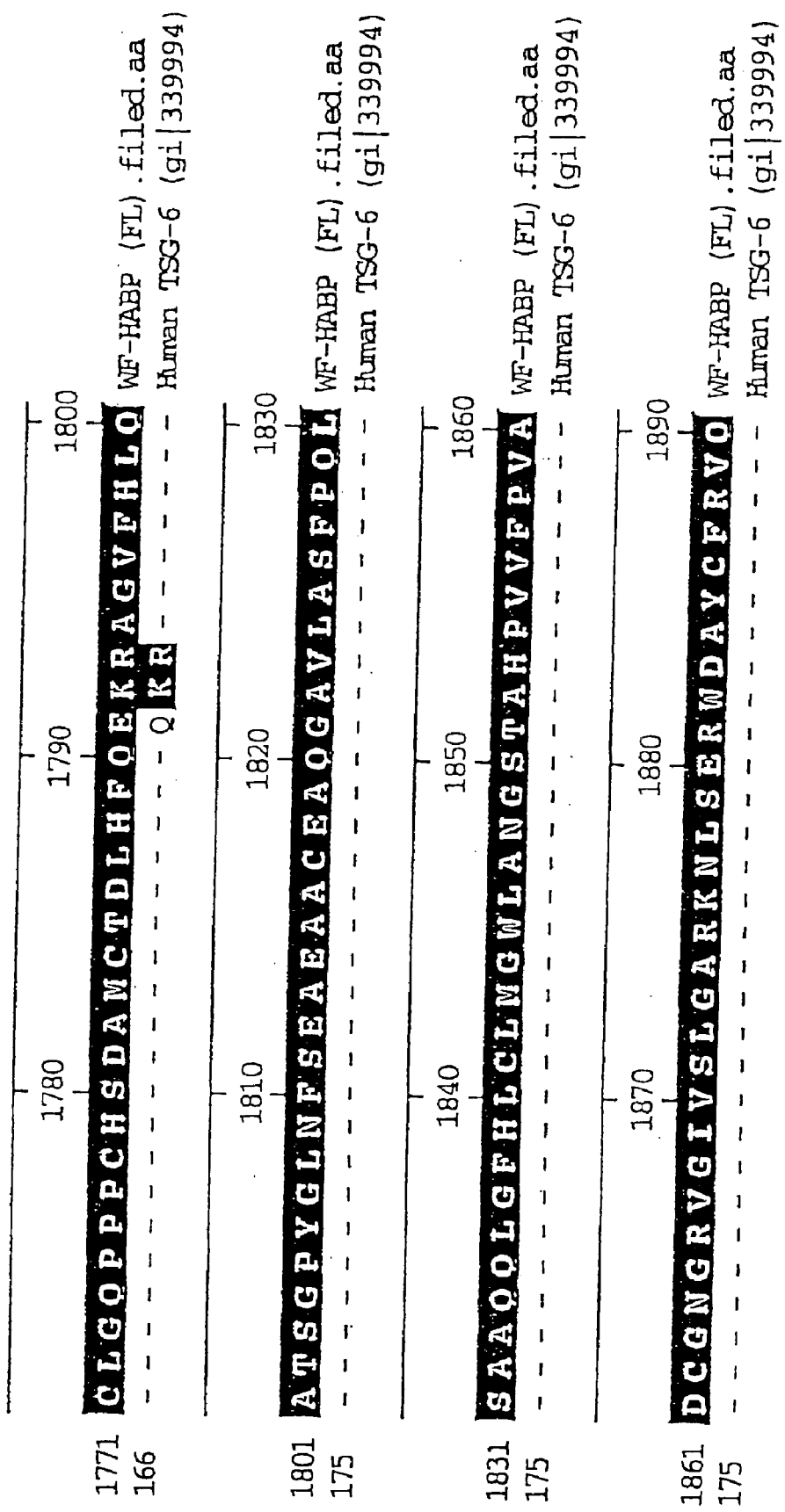
Figure 5R:
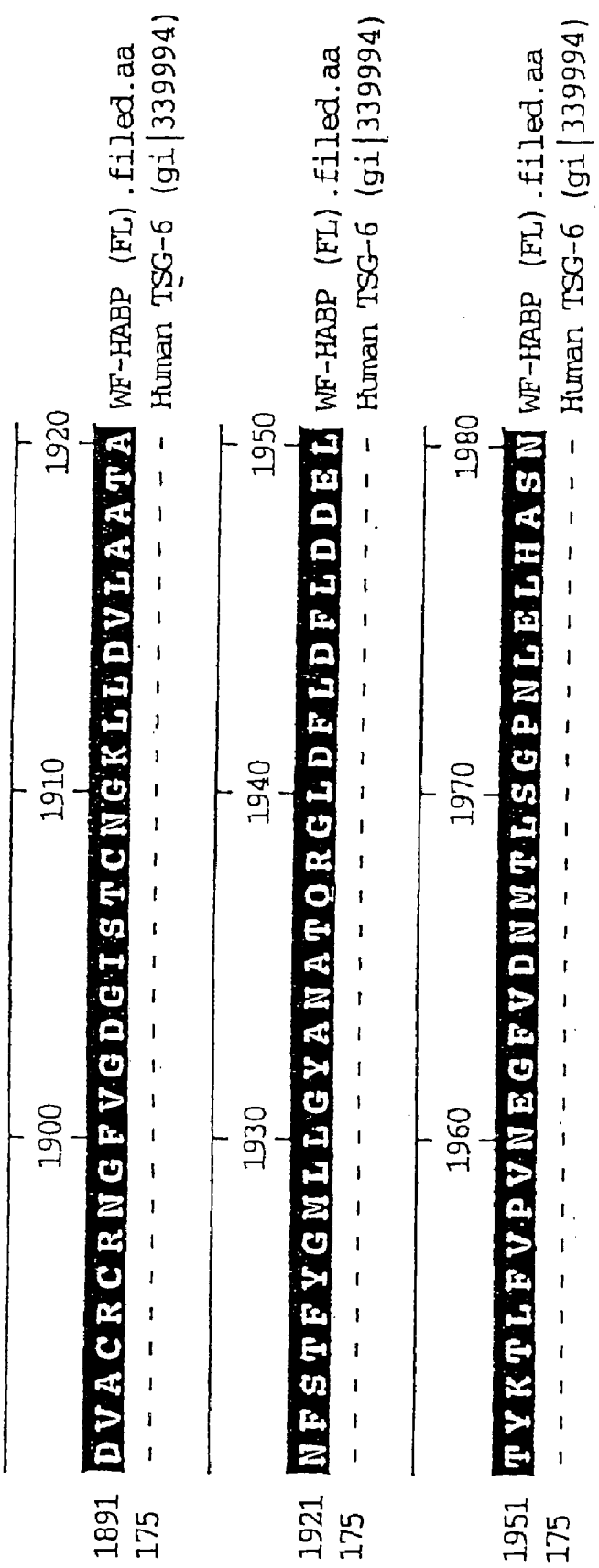
Figure 5S:
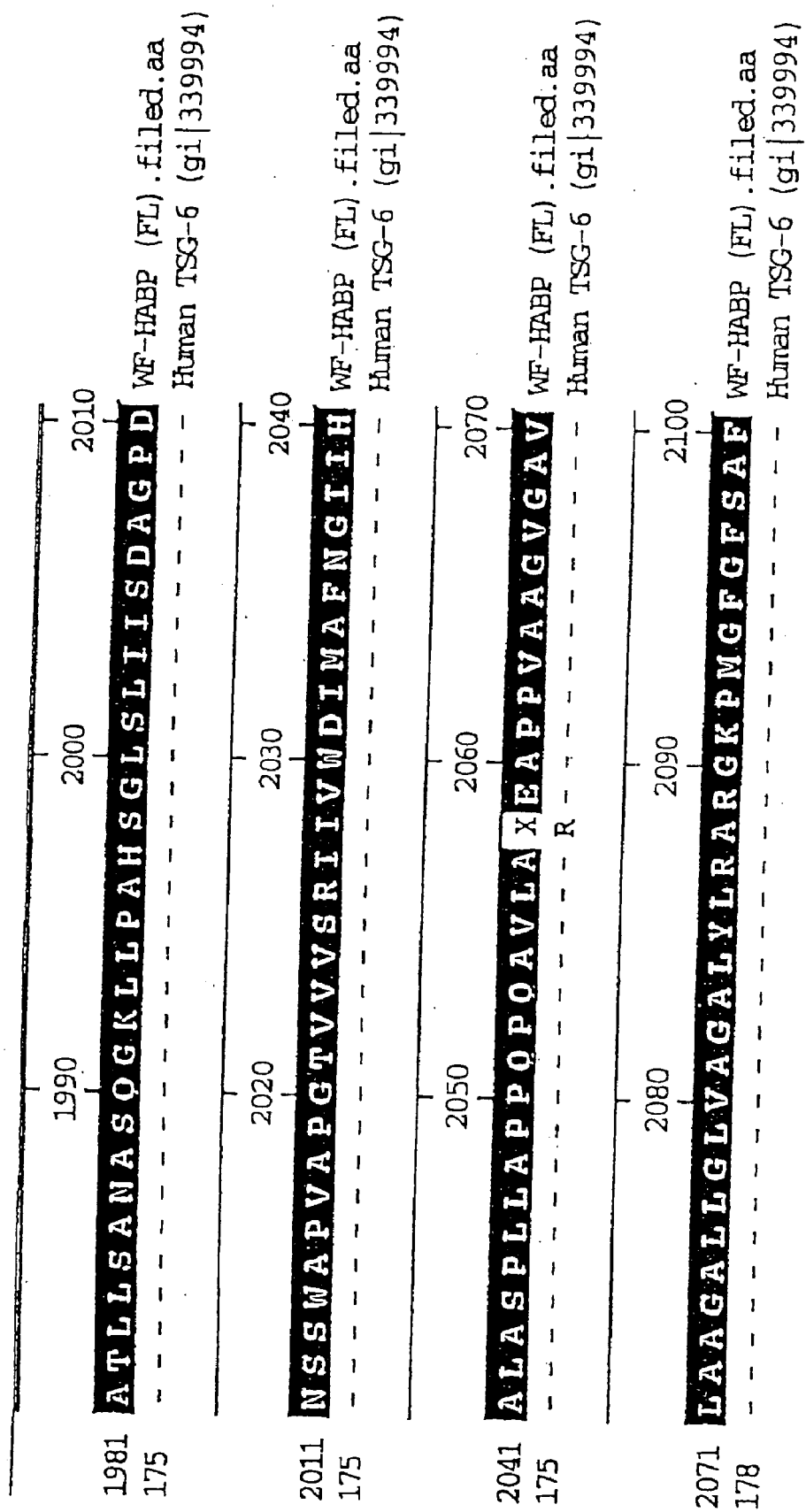
Figure 5T:
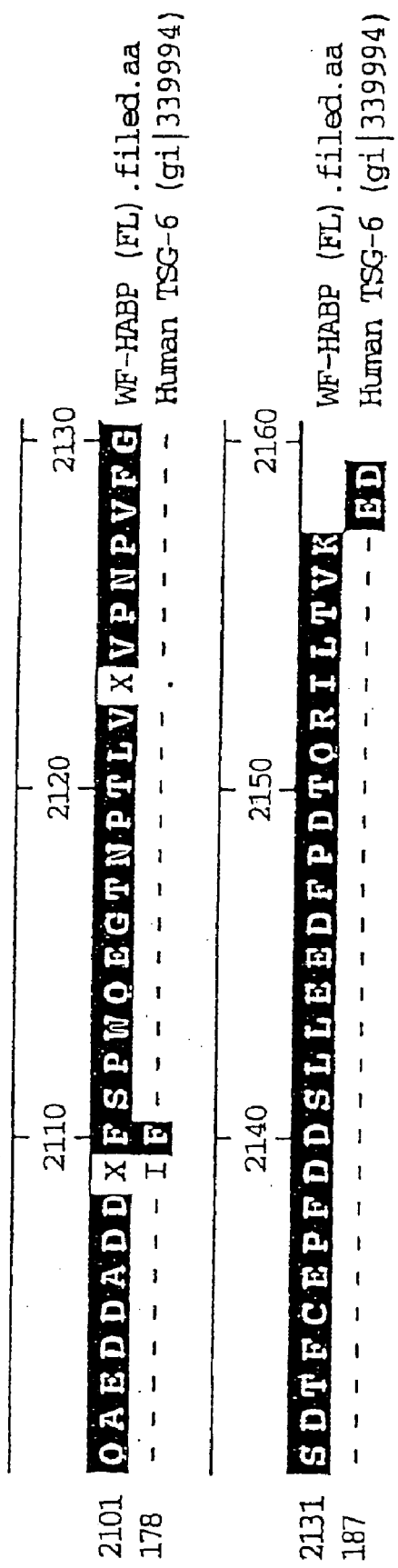
Figure 6D:
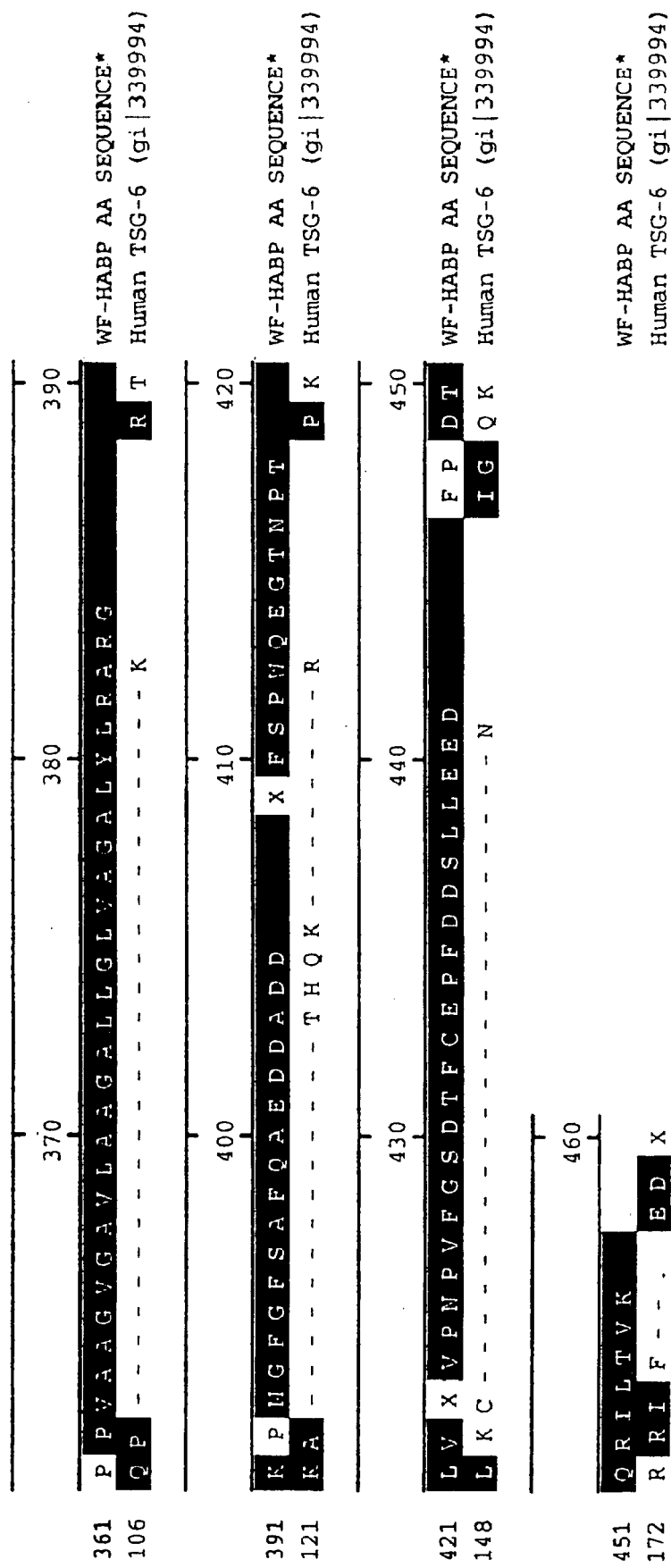
Figure 7A:
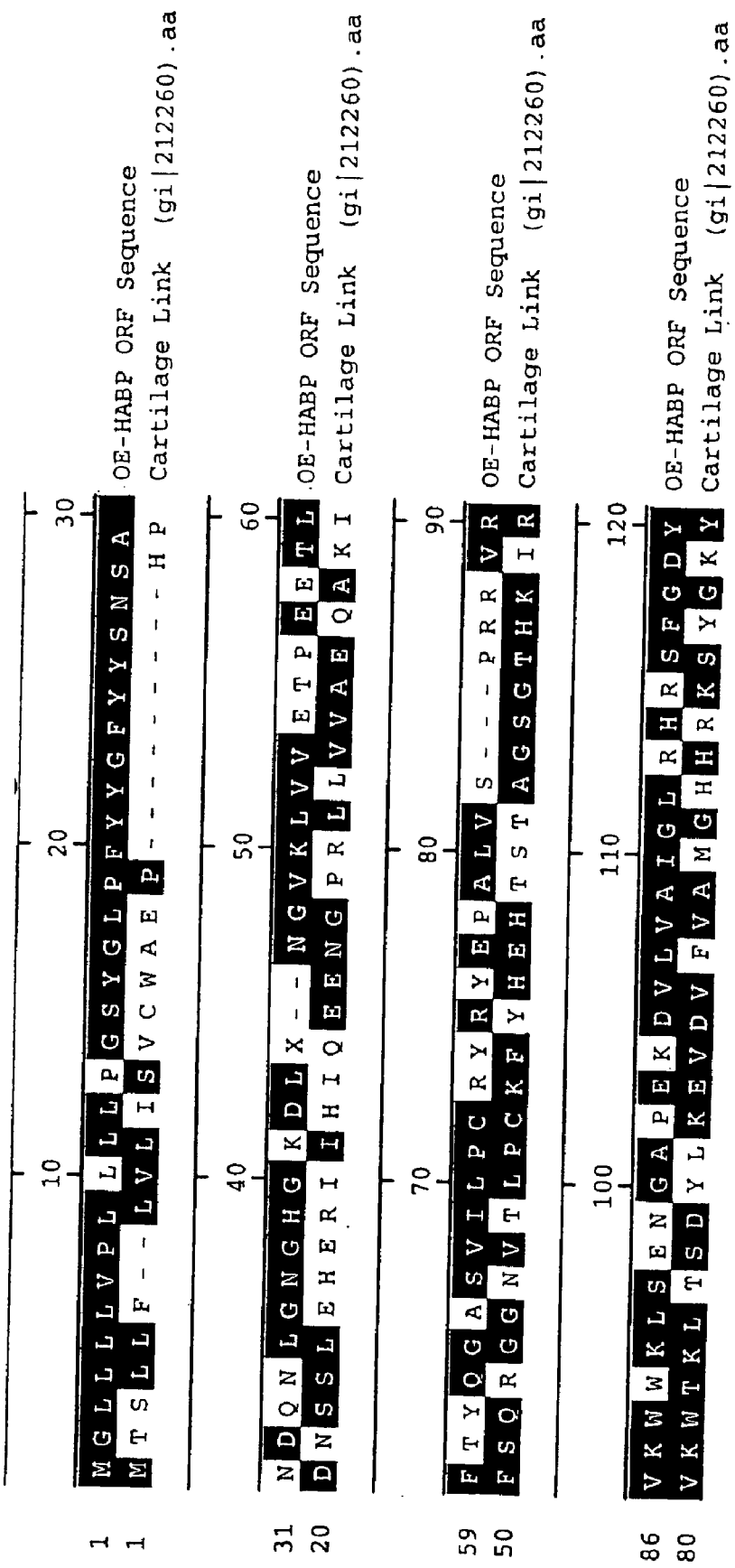
Figure 7D:
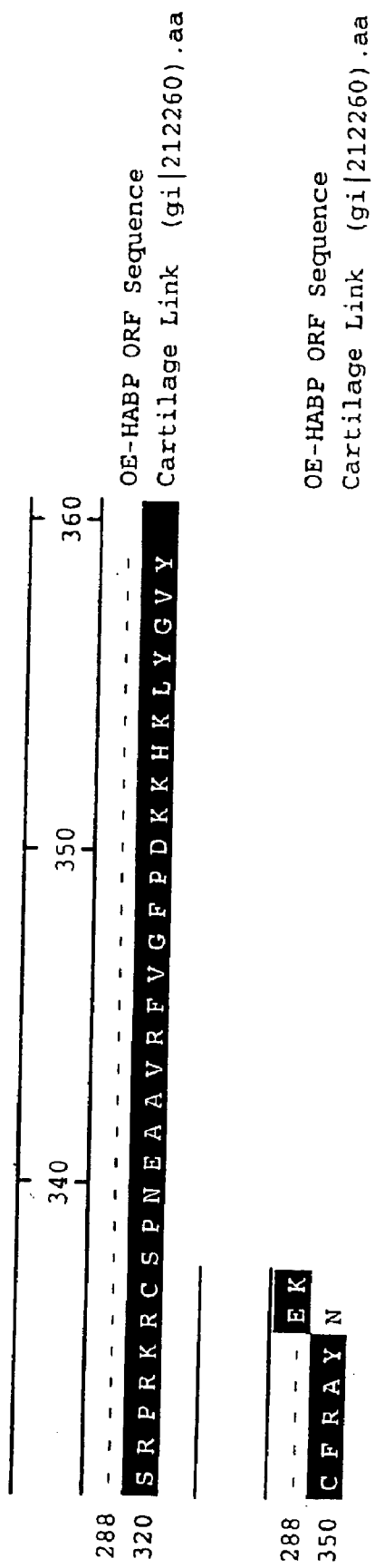

FIGS. 5A–T show the regions of identity between the amino acid sequence of the full-length WF-HABP protein (SEQ ID NO:2) and the translation product of the human TSG-6 protein (SEQ ID NO:3; See Genbank Accession No. gi|339994), as determined by Megalign (DNA Star suite of programs) analysis. Identical amino acids between the two polypeptides are shaded, while the non-identical regions remain unshaded. By examining the regions of amino acids shaded and/or unshaded, the skilled artisan can readily identify conserved domains between the two polypeptides.

FIGS. 6A–D show the regions of identity between the amino acid sequence of the WF-HABP protein (SEQ ID NO:5) and the translation product of the human TSG-6 protein (SEQ ID NO:3; See Genbank Accession No. gi|339994), as determined by Megalign (DNA Star suite of programs) analysis. Identical amino acids between the two polypeptides are shaded, while the non-identical regions remain unshaded. By examining the regions of amino acids shaded and/or unshaded, the skilled artisan can readily identify conserved domains between the two polypeptides.

FIGS. 7A–D show the regions of identity between the amino acid sequence of the OE-HABP protein (SEQ ID NO:8) and the translation product of the Cartilage Link Protein from *Gallus gallus* (SEQ ID NO:9; See Genbank Accession No. gi|212260), as determined by Megalign (DNA Star suite of programs) analysis. Identical amino acids between the two polypeptides are shaded, while the non-identical regions remain unshaded. By examining the regions of amino acids shaded and/or unshaded, the skilled artisan can readily identify conserved domains between the two polypeptides.

FIGS. 8A–D show the regions of identity between the amino acid sequence of the BM-HABP protein (SEQ ID NO:11) and the translation product of the TSG-6 protein from *Mus musculus* (SEQ ID NO:12; See Genbank Accession No. 2062475), as determined by Megalign (DNA Star suite of programs) analysis. Identical amino acids between the two polypeptides are shaded, while the non-identical regions remain unshaded. By examining the regions of amino acids shaded and/or unshaded, the skilled artisan can readily identify conserved domains between the two polypeptides.

Figure 9A:
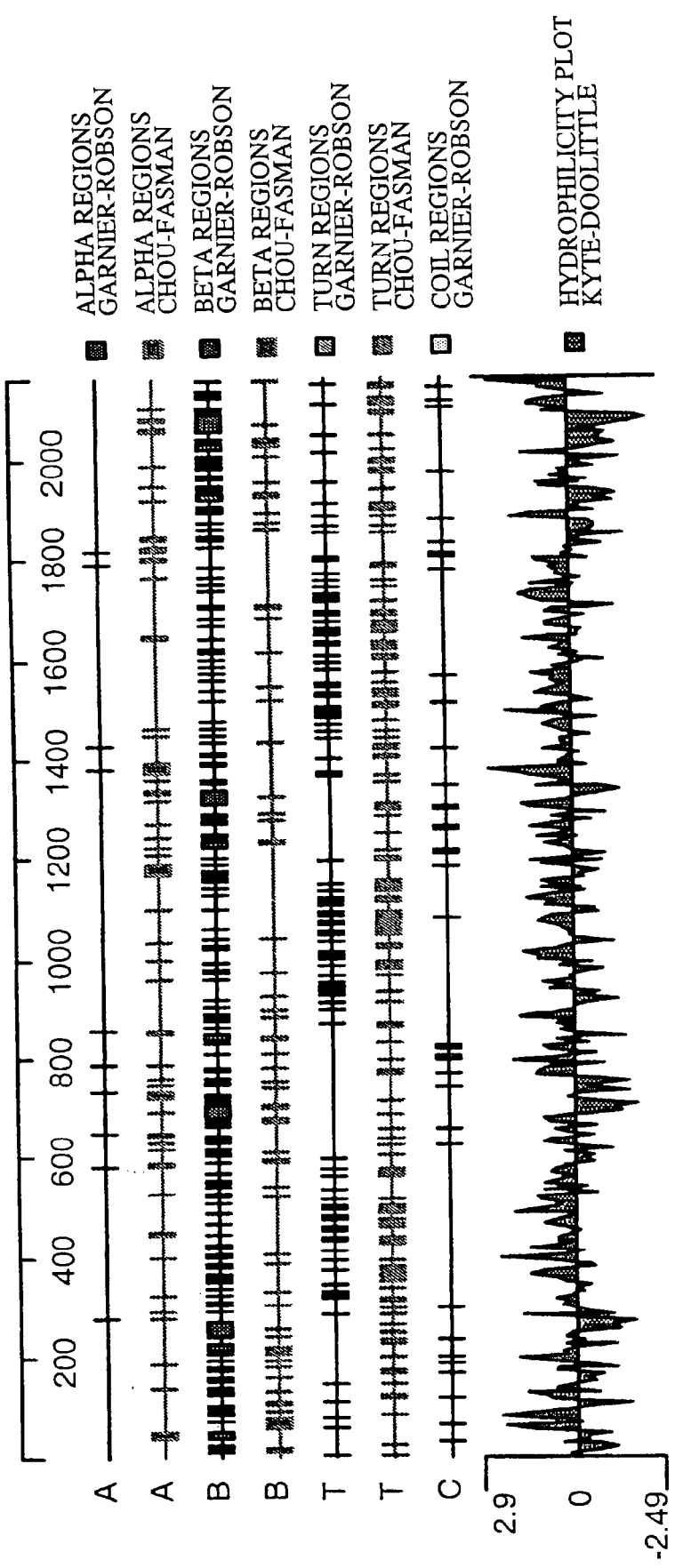
Figure 9B:
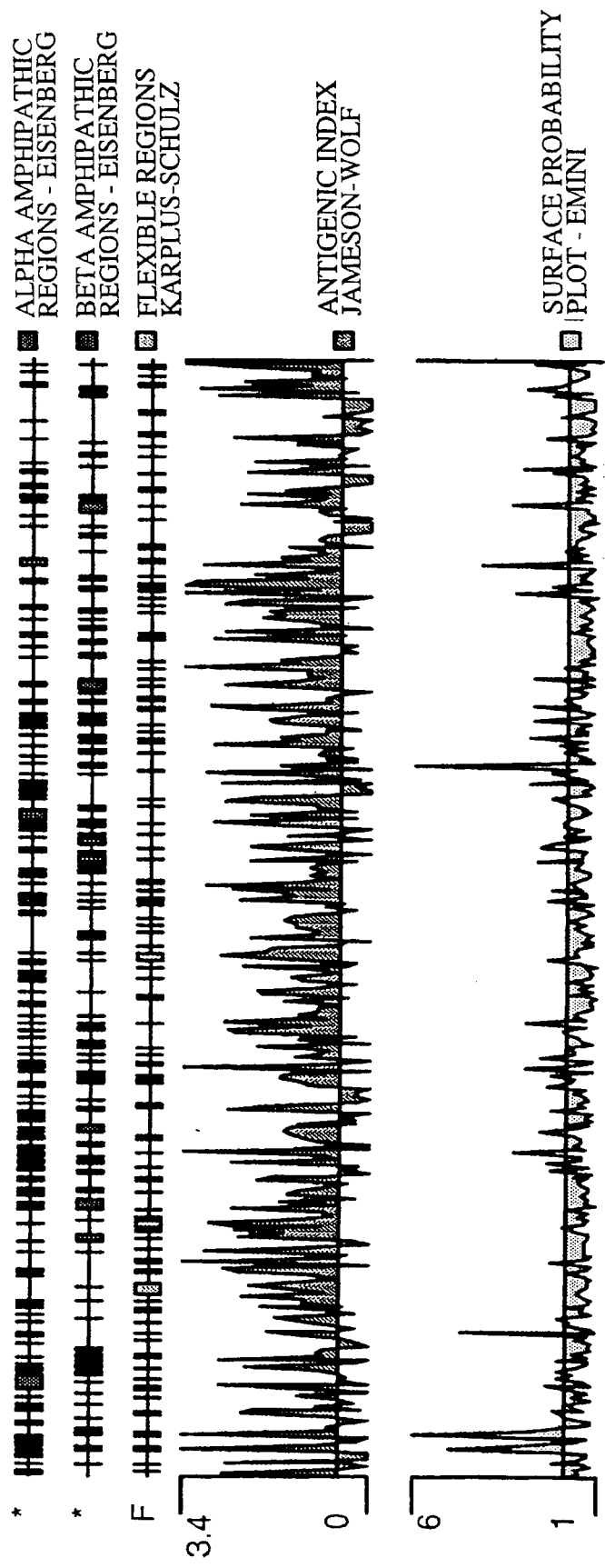

FIGS. 9A–B show a structural analysis of the full-length WF-HABP amino acid sequence of FIGS. 1A–P (SEQ ID NO:2), generated using the default parameters of the recited computer programs. Alpha, beta, turn and coil regions; hydrophilicity and hydrophobicity; amphipathic regions; flexible regions; antigenic index and surface probabilities are shown. In the "Antigenic Index—Jameson-Wolf" graph, amino acid residues: M-1 to I-9 as depicted in FIGS. 1A–P (SEQ ID NO:2) correspond to the shown highly antigenic regions of WF-HABP protein.

Figure 10A:
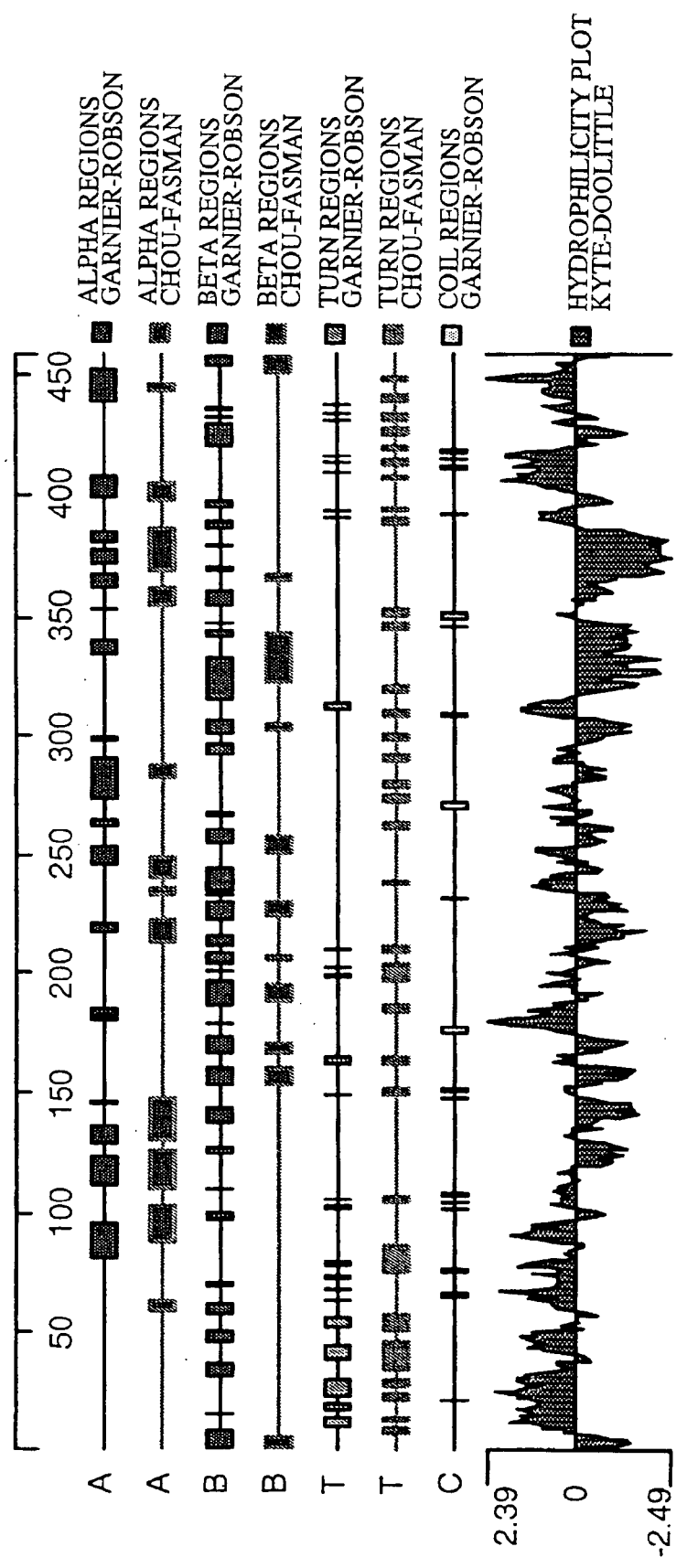
Figure 10B:
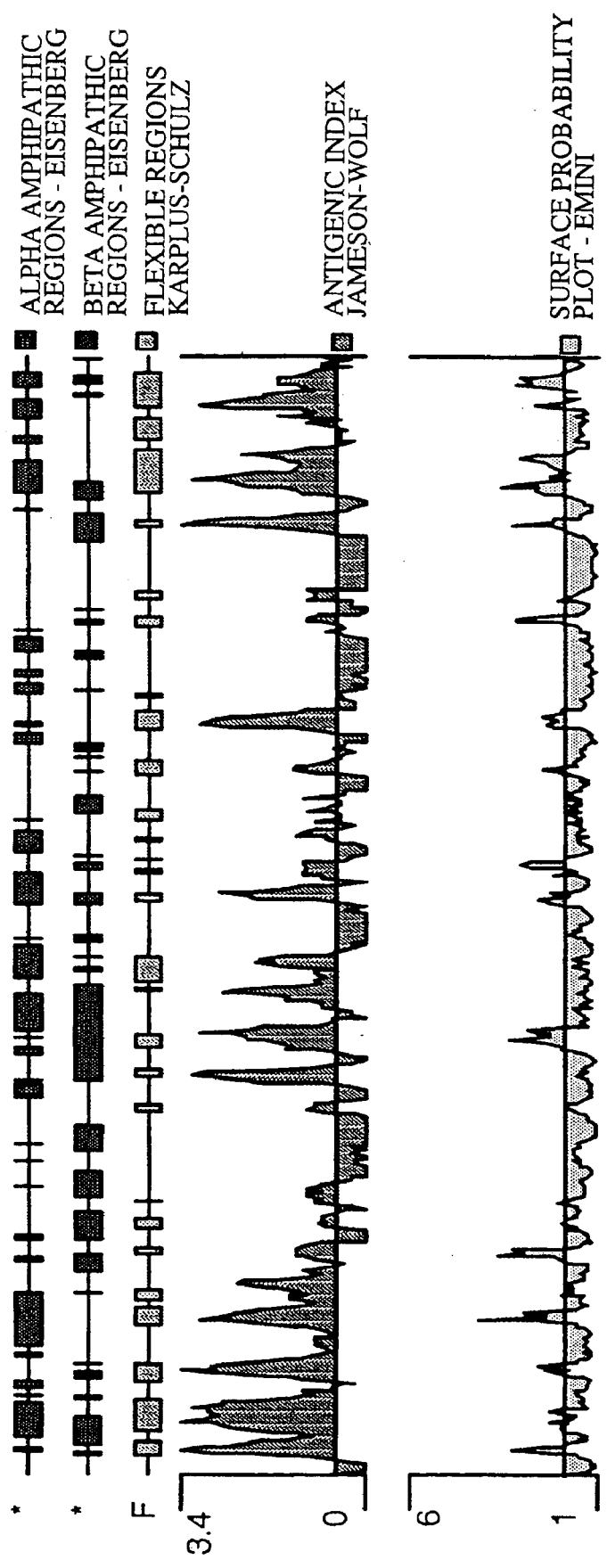

FIGS. 10A–B show a structural analysis of WF-HABP partial amino acid sequence of FIGS. 2A–D (SEQ ID NO:5), generated using the default parameters of the recited computer programs. Alpha, beta, turn and coil regions; hydrophilicity and hydrophobicity; amphipathic regions; flexible regions; antigenic index and surface probabilities are shown. In the "Antigenic Index—Jameson-Wolf" graph, amino acid residues: M-1 to I-9 as depicted in FIGS. 2A–D (SEQ ID NO:5) correspond to the shown highly antigenic regions of WF-HABP protein.

Figure 11A:
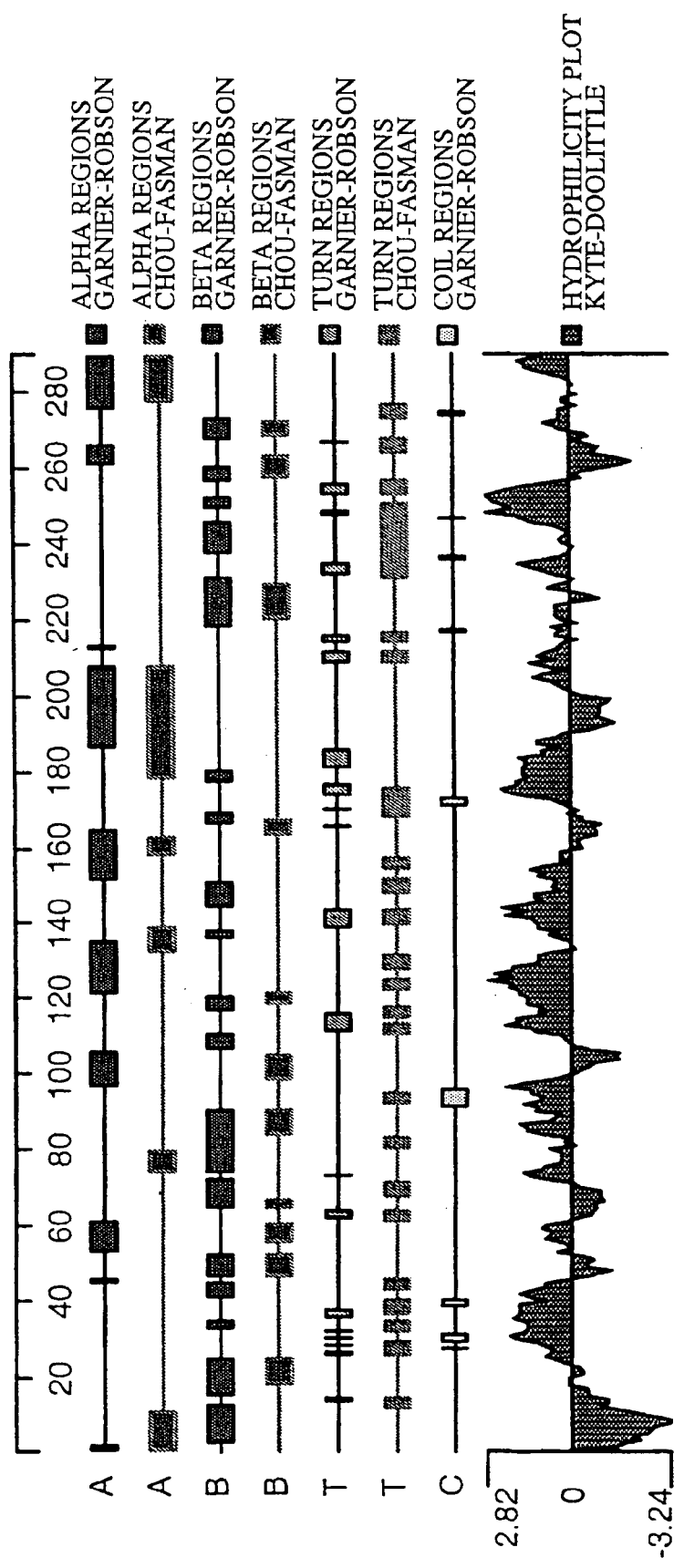
Figure 11B:
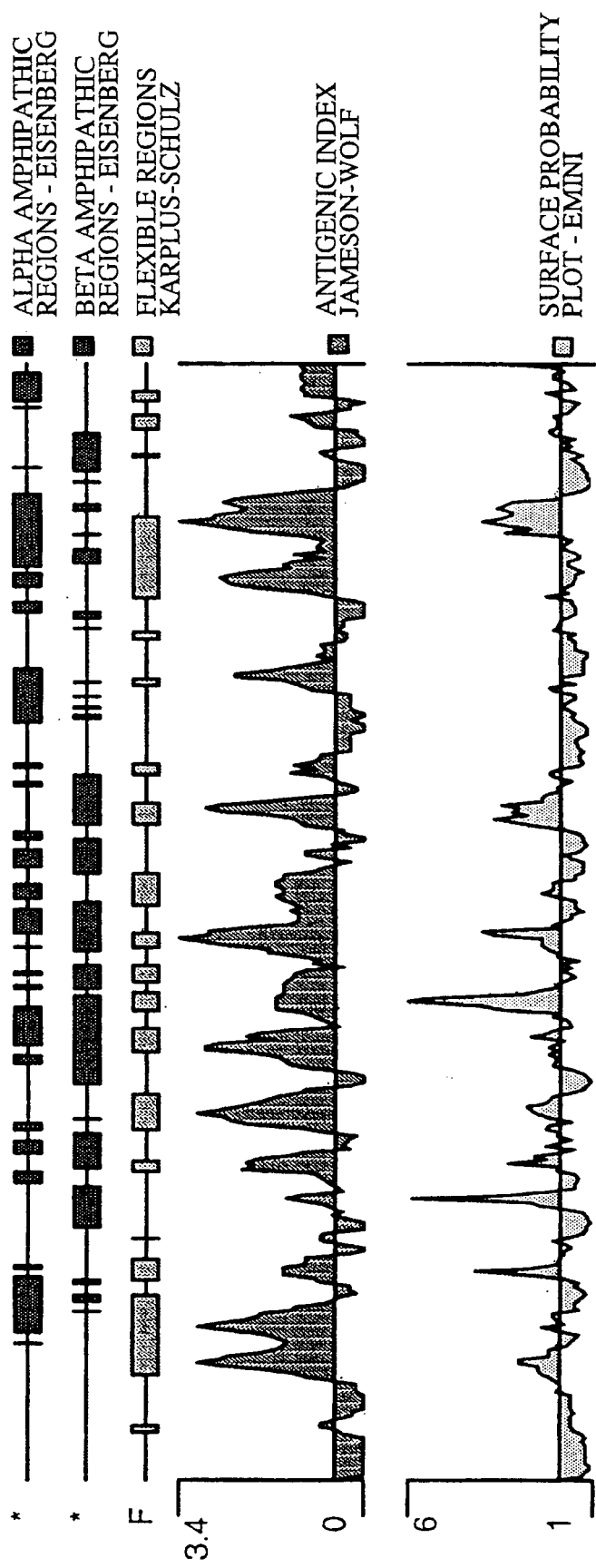

FIGS. 11A–B show a structural analysis of OE-HABP partial amino acid sequence of FIGS. 2A–D (SEQ ID NO:8), generated using the default parameters of the recited computer programs. Alpha, beta, turn and coil regions; hydrophilicity and hydrophobicity; amphipathic regions; flexible regions; antigenic index and surface probabilities are shown. In the "Antigenic Index—Jameson-Wolf" graph, amino acid residues: M-1 to I-9 as depicted in FIGS. 3A–C (SEQ ID NO:8) correspond to the shown highly antigenic regions of OE-HABP protein.

Figure 12A:
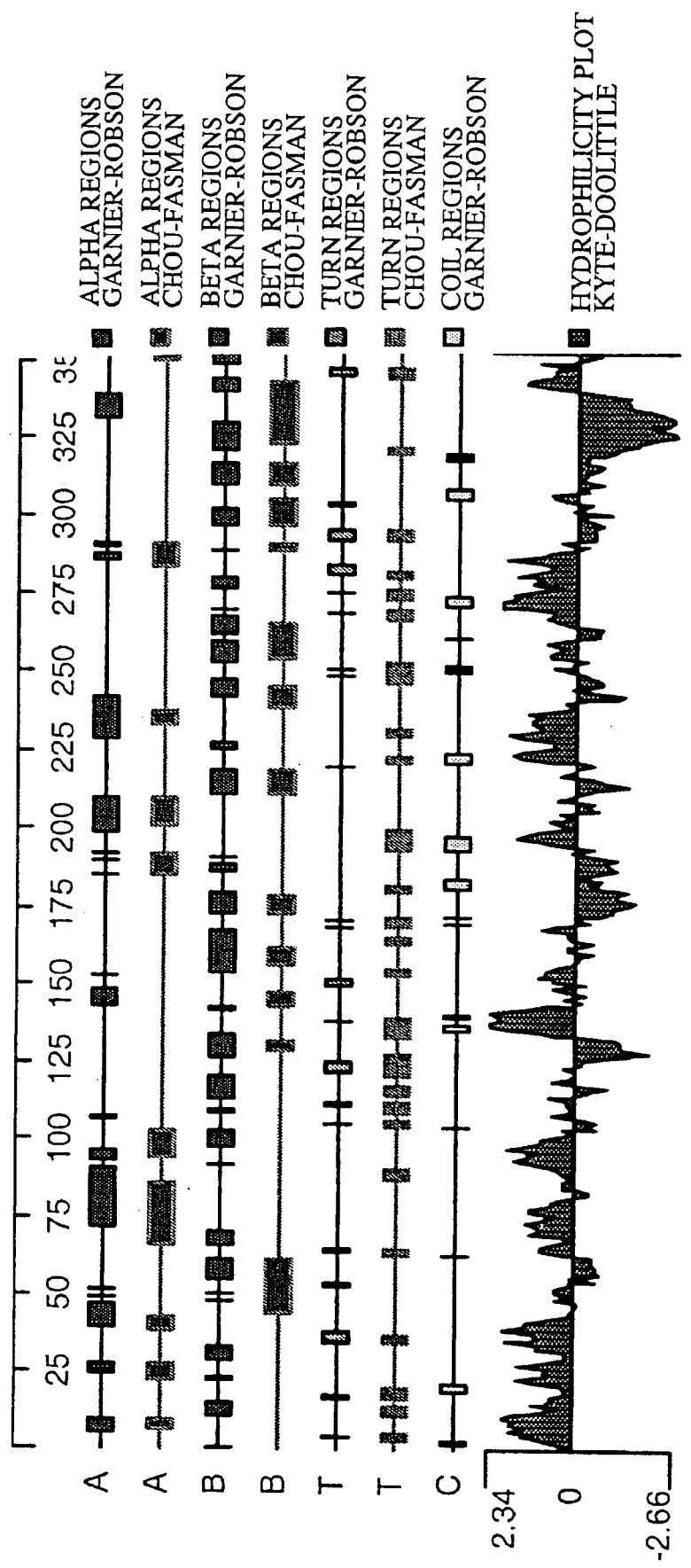
Figure 12B:
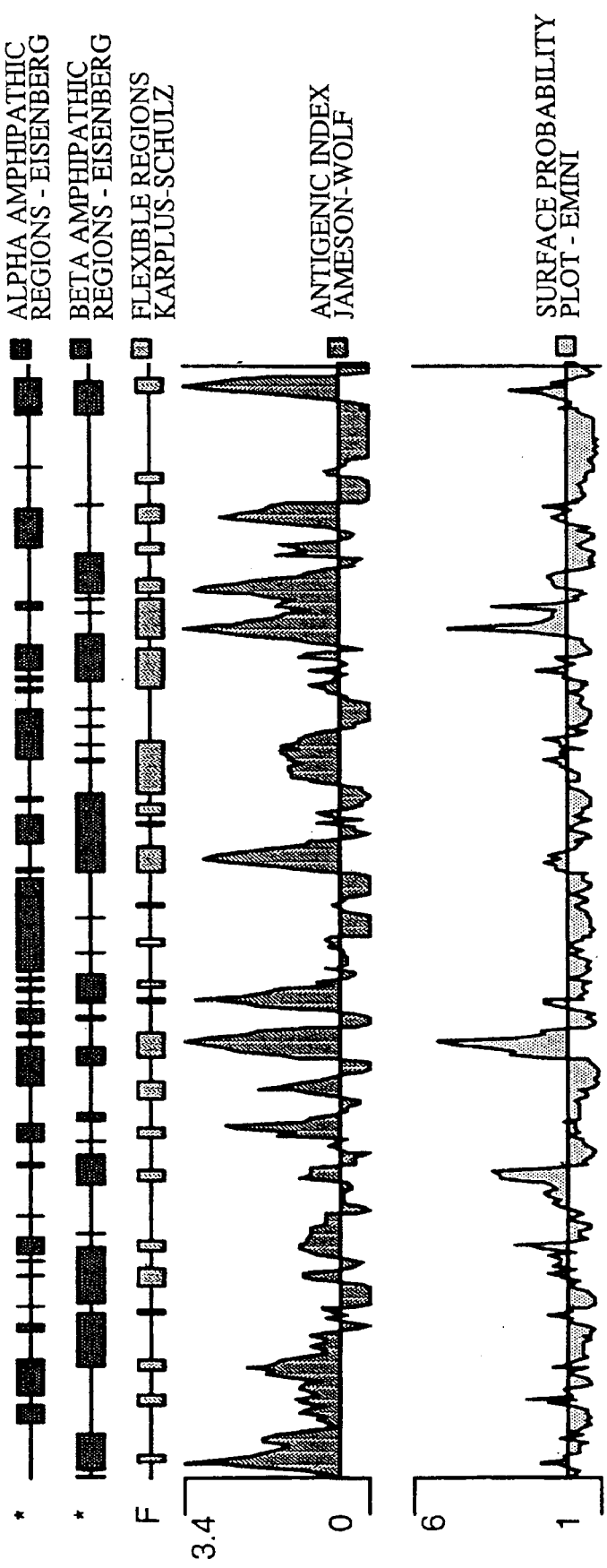

FIGS. 12A–B show a structural analysis of BM-HABP partial amino acid sequence of FIGS. 4A–C (SEQ ID NO:11), generated using the default parameters of the recited computer programs. Alpha, beta, turn and coil regions; hydrophilicity and hydrophobicity; amphipathic regions; flexible regions; antigenic index and surface probabilities are shown. In the "Antigenic Index—Jameson-Wolf" graph, amino acid residues: M-1 to I-9 as depicted in FIGS. 4A–C (SEQ ID NO:11) correspond to the shown highly antigenic regions of BM-HABP protein.

DETAILED DESCRIPTION OF THE INVENTION

The present invention provides isolated nucleic acid molecules comprising polynucleotides encoding a full-length WF-HABP polypeptide (FIGS. 1A–P (SEQ ID NO:2)). The full-length WF-HABP protein shown in FIGS. 1A–P (SEQ ID NO:2) shares sequence homology with the human TSG-6 protein (FIGS. 5A–T (SEQ ID NO:3)).

The present invention provides isolated nucleic acid molecules comprising polynucleotides encoding a WF-HABP polypeptide (FIGS. 2A–D (SEQ ID NO:5)), the amino acid sequence of which was determined by sequencing a cloned cDNA (Clone HWFBG79). The WF-HABP protein shown in FIGS. 2A–D (SEQ ID NO:5) shares sequence homology with human cartilage link protein (FIGS. 6A–D (SEQ ID NO:6)). The nucleotide sequence shown in FIGS. 2A–D (SEQ ID NO:4) was obtained by sequencing a cDNA clone (Clone HWFBG79). On Dec. 1, 1998, the plasmid corresponding to this clone was deposited with the American Type Culture Collection, 10801 University Blvd, Manassas, Va., 20110-2209, and was assigned accession number 203503. The deposited cDNA is contained in the pbluescript plasmid (Stratagene, La Jolla, Calif.).

The present invention provides isolated nucleic acid molecules comprising polynucleotides encoding a OE-HABP polypeptide (FIGS. 3A–C (SEQ ID NO:8)), the amino acid sequence of which was determined by sequencing a cloned cDNA (Clone HOEDH76). The OE-HABP protein shown in FIGS. 3A–C (SEQ ID NO:8) shares sequence homology with the Gallus gallus cartilage link protein (FIGS. 7A–D (SEQ ID NO:9)). The nucleotide sequence shown in FIGS. 3A–C (SEQ ID NO:7) was obtained by sequencing a cDNA clone (Clone HOEDH76). On Dec. 1, 1998, the plasmid corresponding to this clone was deposited with the American Type Culture Collection, 10801 University Blvd, Manassas, Va., 20110-2209, and was assigned accession number 203501. The deposited cDNA is contained in the pBluescript plasmid (Stratagene, La Jolla, Calif.).

The present invention provides isolated nucleic acid molecules comprising polynucleotides encoding a BM-HABP polypeptide (FIGS. 4A–C (SEQ ID NO:11)), the amino acid sequence of which was determined by sequencing a cloned cDNA (Clone HBMVC21). The BM-HABP protein shown in FIGS. 4A–C (SEQ ID NO:11) shares sequence homology with the *Mus musculus* TSG-6 protein (FIGS. 8A–D (SEQ ID NO:12)). The nucleotide sequence shown in FIGS. 4A–C (SEQ ID NO:10) was obtained by sequencing a cDNA clone (Clone HBMVC21). On Dec. 1, 1998, the plasmid corresponding to this clone was deposited with the American Type Culture Collection, 1080 University Blvd, Manassas, Va., 20110-2209, and was assigned accession number 203502. The deposited cDNA is contained in the pBluescript plasmid (Stratagene, La Jolla, Calif.).

As used herein, "full-length WF-HABP protein", "full-length WF-HABP receptor", "full-length receptor protein", "full-length WF-HABP", and "full-length WF-HABP polypeptide" refer to all polypeptides resulting from the alternate splicing of the genomic DNA sequences encoding proteins having regions of amino acid sequence identity and HA binding activity which correspond to the protein shown in FIGS. 1A–P (SEQ ID NO:2). The full-length WF-HABP protein shown in FIGS. 1A–P is an example of such a receptor protein.

As used herein, "WF-HABP protein", "WF-HABP fragments", "WF-HABP", partial WF-HABP", "WF-HABP", and "WF-HABP polypeptide" refer to all polypeptides resulting from the alternate splicing of the genomic DNA sequences encoding proteins having regions of amino acid sequence identity and HA binding activity which correspond to the protein shown in FIGS. 2A–D (SEQ ID NO:5). The WF-HABP protein shown in FIGS. 2A–D is an example of such a protein.

As used herein, "OE-HABP protein", "OE-HABP fragments", "partial OE-HABP", "OE-HABP", and "OE-HABP polypeptide" refer to all polypeptides resulting from the alternate splicing of the genomic DNA sequences encoding proteins having regions of amino acid sequence identity and HA binding activity which correspond to the protein shown in FIGS. 3A–C (SEQ ID NO:8). The OE-HABP protein shown in FIGS. 3A–C is an example of such a protein.

As used herein, "BM-HABP protein", "BM-HABP fragments", "partial BM-HABP", "BM-HABP", and "BM-HABP polypeptide" refer to all polypeptides resulting from the alternate splicing of the genomic DNA sequences encoding proteins having regions of amino acid sequence identity and HA binding activity which correspond to the protein shown in FIGS. 4A–C (SEQ ID NO:11). The BM-HABP protein shown in FIGS. 4A–C is an example of such a protein.

Nucleic Acid Molecules

Using the information provided herein, such as the nucleotide sequence in FIGS. 1A–P (SEQ ID NO:1), nucleic acid molecules of the present invention encoding the full-length WF-HABP polypeptides may be obtained using standard cloning and screening procedures, such as those used for cloning cDNAs using mRNA as starting material. Northern analysis has revealed expression of the full-length WF-HABP transcript in a variety of tissues. The highest level of expression was observed in the heart, placenta and lung, with next highest levels found in the liver, pancreas, and skeletal muscle, and lower expression found in the brain and kidney. Four major transcripts of 9.5, 4.5, 3.0 and 2.4 Kb were detected. The 9.5 Kb band appeared to be the predominant mRNA and was especially prominent in the placenta and the heart.

The expression pattern of the full-length WF-HABP was also examined in human smooth muscle cells (SMCs), human fetal lung fibroblasts (ETL), human umbilical vein endothelial cells (HUVECs), as well as in HL-60 and U937 cells. Full-length WF-HABP mRNA expression was not detected in either uninduced or TPA-stimulated HL-60 cells. A minor 2.4 Kb band was detected in all of the other cell types examined. Induction of U937 cells with TPA resulted in a slight decrease of the signal. However, it is noteworthy that full-length WF-HABP mRNAs of 9.5, 4.5 and 3.0 Kb were expressed exclusively by HUVECs.

Thus, any of these tissues or cell types provide a source of full-length WF-HABP mRNA. Additionally, any tissue or cell source may be utilized to routinely clone full-length WF-HABP genomic DNA using techniques known in the art. Illustrative of the invention, the nucleic acid molecule described in FIGS. 1A–P (SEQ ID NO:1) was discovered in a cDNA library derived from white fat tissue.

Using the information provided herein, such as the nucleotide sequence in FIGS. 2A–D (SEQ ID NO:4), nucleic acid molecules of the present invention encoding the WF-HABP polypeptides may be obtained using standard cloning and screening procedures, such as those used for cloning cDNAs using mRNA as starting material. Northern analysis has revealed expression of the WF-HABP transcript in a variety of tissues. The highest level of expression was observed in the heart, placenta and lung, with next highest levels found in the liver, pancreas, and skeletal muscle, and lower expression found in the brain and kidney. Four major transcripts of 9.5, 4.5, 3.0 and 2.4 Kb were detected. The 9.5 Kb band appeared to be the predominant mRNA and was especially prominent in the placenta and the heart.

The expression pattern of WF-HABP was also examined in human smooth muscle cells (SMCs), human fetal lung fibroblasts (ETL), human umbilical vein endothelial cells (HUVECs), as well as in HL-60 and U937 cells. WF-HABP mRNA expression was not detected in either uninduced or TPA-stimulated HL-60 cells. A minor 2.4 Kb band was detected in all of the other cell types examined. Induction of U937 cells with TPA resulted in a slight decrease of the signal. However, it is noteworthy that WF-HABP mRNAs of 9.5, 4.5 and 3.0 Kb were expressed exclusively by HUVECs.

Thus, any of these tissues or cell types provide a source of WF-HABP mRNA. Additionally, any tissue or cell source may be utilized to routinely clone WF-HABP genomic DNA using techniques known in the art. Illustrative of the invention, the nucleic acid molecule described in FIGS. 2A–D (SEQ ID NO:4) was discovered in a cDNA library derived from white fat tissue.

Using the information provided herein, such as the nucleotide sequence in FIGS. 3A–C (SEQ ID NO:7), nucleic acid molecules of the present invention encoding the OE-HABP polypeptides may be obtained using standard cloning and screening procedures, such as those used for cloning cDNAs using mRNA as starting material. Northern analysis has revealed expression of the OE-HABP transcript in a variety of tissues. The highest level of OE-HABP mRNA expression was detected in lung, placenta, and heart, with highest expression observed in the lung as a 2.2 Kb transcript. The expression pattern of OE-HABP was also examined in human smooth muscle cells (SMCs), human fetal lung fibroblasts (ETL), human umbilical vein endothelial cells (HUVECs), as well as in HL-60 and U937 cells. The 2.2 Kb OE-HABP transcript identified supra was expressed by both HUVECs and SMCs, but not by ETL, HL60 or U937 cells. Interestingly, U937 cells responded to stimulation with TPA by expressing a major new 4.3 Kb transcript and minor bands of 3.8, and 3 Kb.

Thus, any of these tissues or cell types provide a source of OE-HABP mRNA. Additionally, any tissue or cell source may be utilized to routinely clone OE-HABP genomic. DNA using techniques known in the art. Illustrative of the invention, the nucleic acid molecule described in FIGS. 3A–C (SEQ ID NO:7) was discovered in a cDNA library derived from osteoblast tissue.

Using the information provided herein, such as the nucleotide sequence in FIGS. 4A–C (SEQ ID NO:10), nucleic acid molecules of the present invention encoding the BM-HABP polypeptides may be obtained using standard cloning and screening procedures, such as those used for cloning cDNAs using mRNA as starting material. Northern analysis has revealed expression of the BM-HABP transcript in a variety of tissues. The highest level of BM-HABP mRNA expression was apparent only in the liver and appeared as a smear between 5 and 2 Kb. The expression of BM-HABP was also analyzed in human fetal brain, lung, liver and kidney and found that a distinct 9.5 Kb mRNA was expressed at an elevated level in fetal liver with a low level of signal also observed the lung.

The expression pattern of BM-HABP was also examined in human smooth muscle cells (SMC's), human fetal lung fibroblasts (ETL), human umbilical vein endothelial cells (HUVECs), as well as in HL-60 and U937 cells. There was no detectable mRNA expression of BM-HABP in any of the above cell lines.

Thus, any of these tissues or cell types provide a source of BM-HABP mRNA. Additionally, any tissue or cell source may be utilized to routinely clone BM-HABP genomic DNA using techniques known in the art. Illustrative of the invention, the nucleic acid molecule described in FIGS. 4A–C (SEQ ID NO:10) was discovered in a cDNA library derived from bone marrow tissue.

The determined nucleotide sequence of the full-length WF-HABP cDNA of FIGS. 1A–P (SEQ ID NO:1) contains an open reading frame encoding a polytopic polypeptide of about 2100 amino acid residues, with a HA-binding domain, EGF-like Type 1 domains, EGF-like Type 2 domains; laminin-type EGF domains; link protein domain; cytochrome P450 cysteine heme-iron ligand binding domains; a prokaryotic membrane lipoprotein lipid attachment site domains, and having a deduced molecular weight of about 231445.37 Da. The WF-HABP protein shown in FIGS. 1A–P (SEQ ID NO:2) is predicted to contain domains which are about 48% identical to the human hyaluronan binding protein TSG-6 protein depicted in SEQ ID NO:6 (see FIGS. 5A–T) using the computer program "MegAlign" (DNAstar suite of software programs). In addition to having homology, TSG-6 and the full-length WF-HABP are thought to share the same topological structure based upon their intrinsic hyaluronan binding activity. For example, like TSG-6, the full-length WF-HABP contains a hyaluronan binding domain. As discussed above, TSG-6 has been shown to be a hyaluronan binding protein and play a vital role in arthritis, antiinflammatory activity, and the vascular injury response.

The determined nucleotide sequence of the WF-HABP cDNA of FIGS. 2A–D (SEQ ID NO:4) contains an open reading frame encoding a polytopic polypeptide of about 457 amino acid residues, with a HA-binding domain, an EGF-like Type 2 domain, and a link protein domain, and having a deduced molecular weight of about 48448.90 Da. The WF-HABP protein shown in FIGS. 2A–D (SEQ ID NO:5) is predicted to be about 48% identical to the human hyaluronan binding protein TSG6 protein depicted in SEQ ID NO:6 (see FIGS. 6A–D) using the computer program "MegAlign" (DNAstar suite of software programs). In addition to having homology, TSG-6 and WF-HABP are thought to share the same topological structure based upon their intrinsic hyaluronan binding activity. For example, like TSG-6, WF-HABP contains a hyaluronan binding domain. As discussed above, TSG-6 has been shown to be a hyaluronan binding protein and play a vital role in arthritis, antiinflammatory activity, and the vascular injury response.

The determined nucleotide sequence of the OE-HABP cDNA of FIGS. 3A–C (SEQ ID NO:7) contains an open reading frame encoding a polytopic polypeptide of about 289 amino acid residues, with a HA-binding domain, 6 transmembrane domains, 4 extracellular domains, and a pore loop, and having a deduced molecular weight of about 33174.55 Da The OE-HABP protein shown in FIGS. 3A–C (SEQ ID NO:8) is predicted to be about 49% identical to the collagen link protein depicted in SEQ ID NO:9 (see FIGS. 7A–D) using the computer program "MegAlign" (DNAstar suite of software programs). In addition to having homology, collagen link protein and OE-HABP are thought to share the same topological structure based upon their intrinsic hyaluronan binding activity. For example, like collagen link protein, OE-HARP contains a hyaluronan binding domain. As discussed above, collagen link protein has been shown to be a hyaluronan binding protein and play a vital role in arthritis, antiinflammatory activity, and the vascular injury response.

The determined nucleotide sequence of the BM-HABP cDNA of FIGS. 4A–C (SEQ ID NO:10) contains an open reading frame encoding a polytopic polypeptide of about 353 amino acid residues, with a HA-binding domain, 6 transmembrane domains, 4 extracellular domains, and a pore loop, and having a deduced molecular weight of about 36063.32 Da. The BM-HABP protein shown in FIGS. 4A–C (SEQ ID NO:11) is predicted to be about 43% identical across amino acids 52 to 155 to the TSG-6 protein depicted in SEQ ID NO:12 (approximately 31% identical overall, see FIGS. 8A–D) using the computer program "MegAlign" (DNAstar suite of software programs). In addition to having homology, the TSG-6 protein and BM-HABP are thought to share the same topological structure based upon their intrinsic hyaluronan binding activity. For example, like the TSG-6 protein, BM-HABP contains a hyaluronan binding domain. As discussed above, TSG-6 protein has been shown to be a hyaluronan binding protein and play a vital role in arthritis, anti-inflammatory activity, and the vascular injury response.

Nucleic acid molecules of the present full-length WF-HABP invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand or complementary strand.

Nucleic acid molecules of the present WF-HABP invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand or complementary strand.

Nucleic acid molecules of the present OE-HABP invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand or complementary strand.

Nucleic acid molecules of the present BM-HABP invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand or complementary strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Isolated RNA molecules include in vivo or in vitro RNA transcripts of the DNA molecules of the present invention. Further examples of isolated DNA molecules include recombinant DNA molecules maintained in heterologous host cells or purified (partially or substantially) DNA molecules in solution. However, a nucleic acid contained in a clone that is a member of a library (e.g., a genomic or cDNA library) that has not been isolated from other members of the library (e.g., in the form of a homogeneous solution containing the clone and other members of the library) or which is contained on a chromosome preparation (e.g., a chromosome spread), is not "isolated" for the purposes of this invention. Isolated nucleic acid molecules according to the present invention may be produced naturally, recombinantly, or synthetically.

In one embodiment, nucleic acid molecules of the present invention include DNA molecules comprising an open reading frame (ORF) shown in FIGS. 1A–P (SEQ ID NO:1); and DNA molecules which comprise a sequence substantially different from those described above, but which, due to the degeneracy of the genetic code, still encode the full-length WF-HABP polypeptide shown in FIGS. 1A–P (SEQ ID NO:1). Of course, the genetic code is well known in the art. Thus, it would be routine for one skilled in the art to generate such degenerate variants.

In one embodiment, nucleic acid molecules of the present invention include DNA molecules comprising an open reading frame (ORF) shown in FIGS. 2A–D (SEQ ID NO:4); and DNA molecules which comprise a sequence substantially different from those described above, but which, due to the degeneracy of the genetic code, still encode WF-HABP polypeptide shown in FIGS. 2A–D (SEQ ID NO:4). Of course, the genetic code is well known in the art. Thus, it would be routine for one skilled in the art to generate such degenerate variants.

In one embodiment, nucleic acid molecules of the present invention include DNA molecules comprising an open reading frame (ORF) shown in FIGS. 3A–C (SEQ ID NO:8); and DNA molecules which comprise a sequence substantially different from those described above, but which, due to the degeneracy of the genetic code, still encode OE-HABP polypeptide shown in FIGS. 3A–C (SEQ ID NO:8). Of course, the genetic code is well known in the art. Thus, it would be routine for one skilled in the art to generate such degenerate variants.

In one embodiment, nucleic acid molecules of the present invention include DNA molecules comprising an open reading frame (ORF) shown in FIGS. 4A–C (SEQ ID NO:11); and DNA molecules which comprise a sequence substantially different from those described above, but which, due to the degeneracy of the genetic code, still encode BM-HABP polypeptide shown in FIGS. 4A–C (SEQ ID NO:11). Of course, the genetic code is well known in the art. Thus, it would be routine for one skilled in the art to generate such degenerate variants.

In another embodiment, the invention provides isolated nucleic acid molecules encoding the full-length WF-HABP polypeptide having the amino acid sequence. In a further embodiment, these nucleic acid molecules encode the full-length polypeptide lacking the N-terminal methionine (amino acid residues 2 to 2100 of SEQ ID NO:2). The invention further provides isolated nucleic acid molecules having the nucleotide sequences shown in FIGS. 1A–P (SEQ ID NO:1), the nucleotide sequence of the cDNA contained in the above-described deposited clone (clone HWFBG79); or nucleic acid molecules having a sequence complementary to one of the above sequences. Such isolated molecules, particularly DNA molecules, have uses that include, but are not limited to, probes for gene mapping by in situ hybridization with chromosomes, and for detecting expression of the full-length WF-HABP genes of the present invention in human tissue, for instance, by Northern blot analysis.

In another embodiment, the invention provides isolated nucleic acid molecules encoding the WF-HABP polypeptide having the amino acid sequence encoded by the cDNA clone contained in the plasmid deposited as ATCC Deposit No. 203503 on Dec. 1, 1998. In a further embodiment, these nucleic acid molecules encode the full-length polypeptide lacking the N-terminal methionine (amino acid residues 2 to 457 of SEQ ID NO:5). The invention further provides isolated nucleic acid molecules having the nucleotide sequences shown in FIGS. 2A–D (SEQ ID NO:4), the nucleotide sequence of the cDNA contained in the above-described deposited clone (clone HWFBG79); or nucleic acid molecules having a sequence complementary to one of the above sequences. Such isolated molecules, particularly DNA molecules, have uses that include, but are not limited to, probes for gene mapping by in situ hybridization with chromosomes, and for detecting expression of the WF-HABP genes of the present invention in human tissue, for instance, by Northern blot analysis.

In another embodiment, the invention provides isolated nucleic acid molecules encoding the OE-HABP polypeptide having the amino acid sequence encoded by the cDNA clone contained in the plasmid deposited as ATCC Deposit No. 203501 on Dec. 1, 1998. In a further embodiment, these nucleic acid molecules encode the full-length polypeptide lacking the N-terminal methionine (amino acid residues 2 to 289 of SEQ ID NO:8). The invention further provides isolated nucleic acid molecules having the nucleotide sequences shown in FIGS. 3A–C (SEQ ID NO:7), the nucleotide sequence of the cDNA contained in the above-described deposited clone (clone HOEDH76); or nucleic acid molecules having a sequence complementary to one of the above sequences. Such isolated molecules, particularly DNA molecules, have uses that include, but are not limited to, probes for gene mapping by in situ hybridization with chromosomes, and for detecting expression of the. OE-HABP genes of the present invention in human tissue, for instance, by Northern blot analysis.

In another embodiment, the invention provides isolated nucleic acid molecules encoding the BM-HABP polypeptide having the amino acid sequence encoded by the cDNA clone contained in the plasmid deposited as ATCC Deposit No. 203502 on Dec. 1, 1998. In a further embodiment, these nucleic acid molecules encode the full-length polypeptide lacking the N-terminal methionine (amino acid residues 2 to 353 of SEQ ID NO:11). The invention further provides isolated nucleic acid molecules having the nucleotide sequences shown in FIGS. 4A–C (SEQ ID NO:10), the nucleotide sequence of the cDNA contained in the above-described deposited clone (clone HBMVC21); or nucleic acid molecules having a sequence complementary to one of the above sequences. Such isolated molecules, particularly DNA molecules, have uses that include, but are not limited to, probes for gene mapping by in situ hybridization with chromosomes, and for detecting expression of the BM-HABP genies of the present invention in human tissue, for instance, by Northern blot analysis.

The present invention is further directed to fragments of the isolated nucleic acid molecules (i.e. polynucleotides) described herein. By a fragment of an isolated nucleic acid molecule having, for example, a nucleotide sequence encoding the polypeptide sequence depicted in FIGS. 1A–P (SEQ ID NO:2), the nucleotide sequence shown in FIGS. 1A–P (SEQ ID NO:1), or the complementary strand thereto, is intended fragments at least 15 nt, and more preferably at least 20 nt, still more preferably at least 30 nt, and even more preferably, at least 40, 50, 100, 150, 200, 250, 300, 325, 350, 375, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950, 5000, 5050, 5100, 5150, 5200, 5250, 5300, 5350, 5400, 5450, 5500, 5550, 5600, 5650, 5700, 5750, 5800, 5850, 5900, 5950, 6000, 6050, 6100, 6150, 6200, 6250, 6300, 6350, 6400, 6450, 6500, 6550, 6600, 6650, 6700, 6750 or 6777 nt in length. These fragments have numerous uses which include, but are not limited to, diagnostic probes and primers as discussed herein. Of course, larger fragments, are also useful according to the present invention as are fragments corresponding to most, if not all, of the nucleotide sequences as shown in FIGS. 1A–P (SEQ ID NO:11). By a fragment at least 20 nt in length, for example, is intended fragments which include 20 or more contiguous bases from, for example, the nucleotide sequence of the deposited cDNA, or the nucleotide sequence as shown in FIGS. 1A–P (SEQ ID NO:1).

The present invention is further directed to fragments of the isolated nucleic acid molecules (i.e. polynucleotides) described herein. By a fragment of an isolated nucleic acid molecule having, for example, the nucleotide sequence of the deposited cDNA (clone HWFBG79), a nucleotide sequence encoding the polypeptide sequence encoded by the deposited cDNA, a nucleotide sequence encoding the polypeptide sequence depicted in FIGS. 2A–D (SEQ ID NO:5), the nucleotide sequence shown in FIGS. 2A–D (SEQ ID NO:4), or the complementary strand thereto, is intended fragments at least 15 nt, and more preferably at least 20 nt, still more preferably at least 30 nt, and even more preferably, at least 40, 50, 100, 150, 200, 250, 300, 325, 350, 375, 400, 450, 500, 550, 600, 650, 700, 750, 800, 850, 900, 950, 1000, 1050, 1100, 1150, 1200, 1250, 1300, 1350, 1400, 1450, 1500, or 1522 nt in length. These fragments have numerous uses which include, but are not limited to, diagnostic probes and primers as discussed herein. Of course, larger fragments are also useful according to the present invention as are fragments corresponding to most, if not all, of the nucleotide sequences of the deposited cDNA (clone HWFBG79) or as shown in FIGS. 2A–D (SEQ ID NO:4). By a fragment at least 20 nt in length, for example, is intended fragments which include 20 or more contiguous bases from, for example, the nucleotide sequence of the deposited cDNA, or the nucleotide sequence as shown in FIGS. 2A–D (SEQ ID NO:4).

The present invention is further directed to fragments of the isolated nucleic acid molecules (i.e. polynucleotides) described herein. By a fragment of an isolated nucleic acid molecule having, for example, the nucleotide sequence of the deposited cDNA (clone HOEDH76), a nucleotide sequence encoding the polypeptide sequence encoded by the deposited cDNA, a nucleotide sequence encoding the polypeptide sequence depicted in FIGS. 3A–C (SEQ ID NO:7), the nucleotide sequence shown in FIGS. 3A–C (SEQ ID NO:7), or the complementary strand thereto, is intended fragments at least 15 nt, and more preferably at least 20 nt, still more preferably at least 30 nt, and even more preferably, at least 40, 50, 100, 150, 200, 250, 300, 325, 350, 375, 400, 450, 500, 550, 600, 650, 700, 750, 800, 850, 900, 950, or 985 nt in length. These fragments have numerous uses which include, but are not limited to, diagnostic probes and primers as discussed herein. Of course, larger fragments are also useful according to the present invention as are fragments corresponding to most, if not all, of the nucleotide sequences of the deposited cDNA (clone HOEDH76) or as shown in FIGS. 3A–C (SEQ ID NO:7). By a fragment at least 20 nt in length, for example, is intended fragments which include 20 or more contiguous bases from, for example, the nucleotide sequence of the deposited cDNA, or the nucleotide sequence as shown in FIGS. 3A–C (SEQ ID NO:7).

The present invention is further directed to fragments of the isolated nucleic acid molecules (i.e. polynucleotides) described herein. By a fragment of an isolated nucleic acid molecule having, for example, the nucleotide sequence of the deposited cDNA (clone HBMVC21), a nucleotide sequence encoding the polypeptide sequence encoded by the deposited cDNA, a nucleotide sequence encoding the polypeptide sequence depicted in FIGS. 4A–C (SEQ ID NO:10), the nucleotide sequence shown in FIGS. 4A–C (SEQ ID NO:10), or the complementary strand thereto, is intended fragments at least 15 nt, and more preferably at least 20 nt, still more preferably at least 30 nt, and even more preferably, at least 40, 50, 100, 150, 200, 250, 300, 325, 350, 375, 400, 450, 500, 550, 600, 650, 700, 750, 800, 850, 900, 950, 1000, 1050, 1100, 1150, 1200, 1250, or 1259 nt in length. These fragments have numerous uses which include, but are not limited to, diagnostic probes and primers as discussed herein. Of course, larger fragments are also useful according to the present invention as are fragments corresponding to most, if not all, of the nucleotide sequences of the deposited cDNA (clone HBMVC21) or as shown in FIGS. 4A–C (SEQ ID NO:10). By a fragment at least 20 nt in length, for example, is intended fragments which include 20 or more contiguous bases from, for example, the nucleotide sequence of the deposited cDNA, or the nucleotide sequence as shown in FIGS. 4A–C (SEQ ID NO:10).

Representative examples of the full-length WF-HABP polynucleotide fragments of the invention include, for example, fragments that comprise, or alternatively, consist of, a sequence from nucleotide 1 to 50, 51 to 100, 101 to 150 151 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, 951 to 1000, 1001 to 1050, 1051 to 1100, 1101 to 1150, 1151 to 1200, 1201 to 1250, 1251 to 1300, 1301 to 1350, 1351 to 1400, 1401 to 1450, 1451 to 1500, 1501 to 1550, 1551 to 1600, 1601 to 1650, 1651 to 1700, 1701 to 1750, 1751 to 1800, 1801 to 1850, 1851 to 1900, 1901 to 1950, 1951 to 2000, 2001 to 2050, 2051 to 2100, 2101 to 2150, 2151 to 2200, 2201 to 2250, 2251 to 2300, 2301 to 2350, 2351 to 2400, 2401 to 2450, 2451 to 2500, 2501 to 2550, 2551 to 2600, 2601 to 2650, 2651 to 2700, 2701 to 2750, 2751 to 2800, 2801 to 2850, 2900, 2901 to 2950, 2951 to 3000, 3001 to 3050, 3051 to 3100, 3101 to 3150, 3151 to 3200, 3201 to 3250, 3251 to 3300, 3301 to 3350, 3351 to 3400, 3401 to 3450, 3451 to 3500, 3501 to 3550, 3551 to 3600, 3601 to 3650, 3651 to 3700, 3701 to 3750, 3751 to 3800, 3801 to 3850, 3851 to 3900, 3901 to 3950, 4000, 4001 to 4050, 4051 to 4100, 4101 to 4150, 4151 to 4200, 4201 to 4250, 4251 to 4300, 4301 to 4350, 4351 to 4400, 4401 to 4450, 4451 to 4500, 4501 to 4550, 4551 to 4600, 4601 to 4650, 4651 to 4700, 4701 to 4750, 4751 to 4800, 4801 to 4850, 4851 to 4900, 4901 to 4950, 4951 to 5000, 5001 to 5050, 5051 to 5100, 5101 to 5150, 5151 to 5200, 5201 to 5250, 5251 to 5300, 5301 to 5350, 5351 to 5400, 5401 to 5450, 5451 to 5500, 5501 to 5550, 5551 to 5600, 5601, 5650, 5652 to 5700, 5701 to 5750, 5751 to 5800, 5801 to 5850, 5851 to 5900, 5901 to 5950, 5951 to 6000, 6050, 6051 to 6100, 6101 to 6150, 6151 to 6200, 6201 to 6250, 6251 to 6300, 6301 to 6350, 6351 to 6400, 6401 to 6450, 6451 to 6500, 6501 to 6550, 6551 to 6600, 6601 to 6650, 6651 to 6700, 6701 to 6750, 6751 to 6777 of SEQ ID NO:1, or the complementary strand thereto. In this context "about" includes the particularly recited ranges, larger or smaller by several (5, 4, 3, 2, or 1) nucleotides, at either terminus or at both termini.

Representative examples of WF-HABP polynucleotide fragments of the invention include, for example, fragments that comprise, or alternatively, consist of, a sequence from nucleotide 1 to 50, 51 to 100, 101 to 150, 151 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, 951 to 1000, 1001 to 1050, 1051 to 1100, 1101 to 1150, 1151 to 1200, 1201 to 1250, 1251 to 1300, 1301 to 1350, 1351 to 1400, 1401 to 1450, 1451 to 1500, and/or 1501 to 1522, of SEQ ID NO:4, or the complementary strand thereto, or the cDNA contained in the deposited clone. In this context "about" includes the particularly recited ranges, larger or smaller by several (5, 4, 3, 2, or 1) nucleotides, at either terminus or at both termini.

Representative examples of OE-HABP polynucleotide fragments of the invention include, for example, fragments that comprise, or alternatively, consist of, a sequence from nucleotide 1 to 50, 51 to 100, 101 to 150, 151 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, and/or 951 to 985, of SEQ ID NO:7, or the complementary strand thereto, or the cDNA contained in the deposited clone. In this context "about" includes the particularly recited ranges, larger or smaller by several (5, 4, 3, 2, or 1) nucleotides, at either terminus or at both termini.

Representative examples of BM-HABP polynucleotide fragments of the invention include, for example, fragments that comprise, or alternatively, consist of, a sequence from nucleotide 1 to 50, 51 to 100, 101 to 150, 151 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, 951 to 1000, 1001 to 1050, 1051 to 100, 1101 to 1150, 1151 to 1200, 1201 to 1250, and/or 1251 to 1259 of SEQ ID NO:10, or the complementary strand thereto, or the cDNA contained in the deposited clone. In this context "about" includes the particularly recited ranges, larger or smaller by several (5, 4, 3, 2, or 1) nucleotides, at either terminus or at both termini.

In specific embodiments, the polynucleotide fragments of the full-length WF-HABP invention comprise, or alternatively, consist of, a sequence from nucleotide 1262 to 4595, 4595 to 5552, 1220 to 1262, 1262 to 1300, 1301 to 1340, 1341 to 1380, 1381 to 1420, 1421 to 1460, 1461 to 1500, 1501 to 1540, 1541 to 1580, 1581 to 1620, 1621 to 1660, 1661 to 1700, 1701 to 1740, 1741 to 1780, 1781 to 1820, 1821 to 1860, 1861 to 1900, 1901 to 1940, 1941 to 1980, 1981 to 2020, 2021 to 2040, 2041 to 2080, 2081 to 2120, 2121 to 2160, 2161 to 2200, 2201 to 2240, 2241 to 2280, 2281 to 2320, 2321 to 2360, 2361 to 2400, 2401 to 2440, 2441 to 2480, 2481 to 2520, 2521 to 2560, 2561 to 2600, 2601 to 2640, 2641 to 2680, 2681 to 2720, 2721 to 2760, 2761 to 2800, 2801 to 2840, 2841 to 2880, 2881 to 2920, 2921 to 2960, 2961 to 3000, 3001 to 3040, 3041 to 3080, 3081 to 3120, 3121 to 3160, 3161 to 3200, 3201 to 3240, 3241 to 3280, 3281 to 3320, 3321 to 3360, 3361 to 3400, 3401 to 3440, 3441 to 3480, 3481 to 3520, 3521 to 3560, 3561 to 3600, 3601 to 3640, 3641 to 3680, 3681 to 3720, 3721 to 3760, 3761 to 3800, 3801 to 3840, 3841 to 3880, 3881 to 3920, 3921 to 3960, 3961 to 4000, 4001 to 4040, 4041 to 4080, 4081 to 4120, 4121 to 4160, 4161 to 4200, 4201 to 4240, 4241 to 4280, 4281 to 4320, 4321 to 4360, 4361 to 4400, 4401 to 4440, 4441 to 4480, 4481 to 4520, 4521 to 4560, 4561 to 4600, 4601 to 4640, 4641 to 4680, 4681 to 4720, 4721 to 4760, 4761 to 4800, 4801 to 4840, 4841 to 4880, 4881 to 4920, 4921 to 4960, 4961 to 5000, 5001 to 5040, 5041 to 5080, 5081 to 5120, 5121 to 5160, 5161, 5200, 5201 to 5240, 5241 to 5280, 5281 to 5320, 5321 to 5360, 5361 to 5400, 5401 to 5440, 5441 to 5480, 5481 to 5520, and/or 5521 to 5552, of SEQ ID NO:1 or the complementary strand thereto.

In specific embodiments, the polynucleotide fragments of the WF-HABP invention comprise, or alternatively, consist of, a sequence from nucleotide 1 to 688, 1 to 40, 41 to 80, 81 to 120, 121 to 160, 161 to 200, 201 to 240, 241 to 280, 281 to 320, 321 to 380, 381 to 420, 421 to 460, 461 to 500, 501 to 540, 541 to 580, 581 to 620, 621 to 660, 661 to 688, 301 to 612, 350 to 550 of SEQ ID NO:4, or the complementary strand thereto.

In specific embodiments, the polynucleotide fragments of the OE-HABP invention comprise, or alternatively, consist of, a sequence from nucleotide 250 to 975, 298 to 453, 746 to 985, 210 to 250, 251 to 290, 291 to 330, 331 to 370, 371 to 410, 411 to 450, 451 to 490, 491 to 530, 531 to 570, 571 to 610, 611 to 650, 651 to 690, 691 to 730, 731 to 770, 771 to 810, 811 to 850, 851 to 890, 891 to 930, 931 to 970, and/or 935 to 975 of SEQ ID NO:7, or the complementary strand thereto.

In specific embodiments, the polynucleotide fragments of the BM-HABP invention comprise, or alternatively, consist of, a sequence from nucleotide 1 to 458, 806 to 1259, 352 to 663, 1 to 40, 41 to 80, 81 to 120, 121 to 160, 161 to 200, 201 to 240, 241 to 280, 281 to 320, 321 to 380, 381 to 420, 421 to 460, 760 to 805, 806 to 850, 851 to 890, 891 to 930, 931 to 970, 971 to 1010, 1011 to 1050, 1051 to 1090, 1091 to 1130, 1131 to 1170, 1171 to 1210, 1211 to 1250, 1221 to 1259, 311 to 351, 352 to 390, 391 to 430, 431 to 470, 471 to 510, 511 to 550, 551 to 590, 591 to 630, and/or 631 to 663 of SEQ ID NO:10, or the complementary strand thereto.

Preferably, the polynucleotide fragments of the invention encode a polypeptide which demonstrates WF-HABP functional activity. By a polypeptide demonstrating "functional activity" is meant, a polypeptide capable of displaying one or more known functional activities associated with a full-length WF-HABP polypeptide. Such functional activities include, but are not limited to, biological activity (e.g., ion flux, cellular proliferation, cellular migration, cell adhesion), antigenicity [ability to bind (or compete with a full-length. WF-HABP polypeptide for binding) to an anti-full-length-WF-HABP antibody], immunogenicity (ability to generate antibody which binds to a full-length WF-HABP polypeptide), and ability to bind to a receptor or ligand for a full-length WF-HABP polypeptide (e.g., hyaluronan, or a choridroitin sulfate proteoglycan).

Preferably, the polynucleotide fragments of the invention encode a polypeptide which demonstrates WF-HABP functional activity. By a polypeptide demonstrating "functional activity" is meant, a polypeptide capable of displaying one or more known functional activities associated with a WF-HABP polypeptide. Such functional activities include, but are not limited to, biological activity (e.g., ion flux, cellular proliferation, cellular migration, cell adhesion), antigenicity [ability to bind (or compete with a WF-HABP polypeptide for binding) to an anti-WF-HABP antibody], immunogenicity (ability to generate antibody which binds to a WF-HABP polypeptide), and ability to bind to a receptor or ligand for a WF-HABP polypeptide (e.g., hyaluronan, or a chondroitin sulfate proteoglycan).

Preferably, the polynucleotide fragments of the invention encode a polypeptide which demonstrates OE-HABP functional activity. By a polypeptide demonstrating "functional activity" is meant, a polypeptide capable of displaying one or more known functional activities associated with a OE-HABP polypeptide. Such functional activities include, but are not limited to, biological activity (e.g., ion flux, cellular proliferation, cellular migration, cell adhesion), antigenicity [ability to bind (or compete with a OE-HABP polypeptide for binding) to an anti-OE-HABP antibody], immunogenicity (ability to generate antibody which binds to a OE-HABP polypeptide), and ability to bind to a receptor or ligand for a OE-HABP polypeptide (e.g., hyaluronan, or a chondroitin sulfate proteoglycan).

Preferably, the polynucleotide fragments of the invention encode a polypeptide which demonstrates BM-HABP functional activity. By a polypeptide demonstrating "functional activity" is meant, a polypeptide capable of displaying one or more known functional activities associated with a BM-HABP polypeptide. Such functional activities include, but are not limited to, biological activity (e.g., ion flux, cellular proliferation, cellular migration, cell adhesion), antigenicity [ability to bind (or compete with a BM-HABP polypeptide for binding) to an anti-BM-HABP antibody], immunogenicity (ability to generate antibody which binds to a BM-HABP polypeptide), and ability to bind to a receptor or ligand for a BM-HABP polypeptide (e.g., hyaluronan, or a chondroitin sulfate proteoglycan).

Preferred nucleic acid fragments of the invention include nucleic acid molecules encoding one or more full-length WF-HABP receptor domains. In particular embodiments, such nucleic acid fragments comprise, or alternatively consist of, nucleic acid molecules encoding: a polypeptide selected from the group consisting of: (a) an HA binding motif (amino acid residues E-1791 to C-1894 of SEQ ID NO:2); (b) EGF-like Type 1 domains (amino acid residues from C-375 to C-386, amino acid residues from C-943 to C-954, amino acid residues from C-987 to C-998, amino acid residues from C-1582 to C-1593, and amino acid residues from C-1626 to C-1637 of SEQ ID NO:2); (c) EGF-like Type 2 domains (amino acid residues from C-465 to C-478, amino acid residues from C-508 to C-521, amino acid residues from C-551 to C-564, amino acid residues from C-943 to C-957, amino acid residues from C-987 to C-998, amino acid residues from C-1027 to C-1040, amino acid residues from C-1069 to C-1082, amino acid residues from C-1111 to C-1125, amino acid residues from C-1582 to C-1596, amino acid residues from C-1582 to C-1596, amino acid residues from C-1626 to C-1637, amino acid residues from C-1663 to C-1676, amino acid residues from C-1747 to C-1760, and amino acid residues from C-1894 to C-1908 of SEQ ID NO:2); (d) laminin-type EGF domain (amino acid residues from C-943 to C-977, and amino acid residues from C-1582 to C-1616 of SEQ ID NO:2); (e) link protein domain (amino acid residues from C-1817 to C-1862 of SEQ ID NO:2); (f) cytochrome P450 cysteine heme-iron ligand binding domains (amino acid residues from F-344 to G-353, and amino acid residues from W-514 to A-523 of SEQ ID NO:2); (g) prokaryotic membrane lipoprotein lipid attachment site domains (amino acid residues from P-1103 to C-1113, and amino acid residues from T-1405 to C-1415 of SEQ ID NO:2; (h) any combination of polypeptides (a)–(g), and (i) the complementary strand of the sense strand encoding any of polypeptides (a)–(h).

Preferred nucleic acid fragments of the invention include nucleic acid molecules encoding one or more WF-HABP receptor domains. In particular embodiments, such nucleic acid fragments comprise, or alternatively consist of, nucleic acid molecules encoding: a polypeptide selected from the group consisting of: (a) an HA binding motif (amino acid residues E-91 to C-194 of SEQ ID NO:4); (b) EGF-like Type 2 domain (amino acid residues C-194 to C-208, of SEQ ID NO:4); (c) a link domain (amino acid residues CM-117 to C-162, of SEQ ID NO:4), (d) any combination of polypeptides (a)–(c); and (e) the complementary strand of the sense strand encoding any of polypeptides (a)–(d).

Preferred nucleic acid fragments of the invention include nucleic acid molecules encoding one or more OE-HABP receptor domains. In particular embodiments, such nucleic acid fragments comprise, or alternatively consist of, nucleic acid molecules encoding: a polypeptide selected from the group consisting of: (a) an-HA binding motif domain (amino acid residues P-97 to F-168, amino acid residues L-209 to C-286, of SEQ ID NO:7); (b) a link protein domain (amino acid residues C-188 to C-233 of SEQ ID NO:7); (c) any combination of polypeptides (a)–(b); and (d) the complementary strand of the sense strand encoding any of polypeptides (a)–(c).

Preferred nucleic acid fragments of the invention include nucleic acid molecules encoding one or more BM-HABP receptor domains. In particular embodiments, such nucleic acid fragments comprise, or alternatively consist of, nucleic acid molecules encoding: a polypeptide selected from the group consisting of: (a) an HA binding motif domain (amino acid residues Q-121 to L-215); and (b) the complementary strand of the sense strand encoding polypeptides (a). Type 1 domain, EGF-like Type 2 domain, laminin-type EGF domain, a link protein domain, cytochrome P450 cysteine heme-iron ligand binding domains, prokaryotic membrane lipoprotein lipid attachment site domains of the full-length WF-HABP have been predicted by computer analysis and homology determinations (See FIGS. 1A–P). Thus, as one of ordinary skill would appreciate, the amino acid residues constituting these domains may vary slightly (e.g., by 1 to 15 amino acid residues) depending on the criteria used to define each domain.

The amino acid residues constituting an HA binding motif domain, an EGF-like Type 2 domain, and a link domain of WF-HABP have been predicted by computer analysis and homology determinations (See FIGS. 2A–D). Thus, as one of ordinary skill would appreciate, the amino acid residues constituting these domains may vary slightly (e.g., by 1 to 15 amino acid residues) depending on the criteria used to define each domain.

The amino acid residues constituting an HA binding motif domain, and a link protein domain, of OE-HABP have been predicted by computer analysis and homology determinations (See FIGS. 3A–C). Thus, as one of ordinary skill would appreciate, the amino acid residues constituting these domains may vary slightly (e.g., by 1 to 15 amino acid residues) depending on the criteria used to define each domain.

The amino acid residues constituting an HA binding motif domain of BM-HABP have been predicted by computer analysis and homology determinations (See FIGS. 4A–C). Thus, as one of ordinary skill would appreciate, the amino acid residues constituting these domains may vary slightly (e.g., by 1 to 15 amino acid residues) depending on the criteria used to define each domain.

Preferred nucleic acid fragments of the invention also include nucleic acid molecules encoding epitope-bearing portions of the full-length WF-HABP. In particular, such nucleic acid fragments of the present invention include nucleic acid molecules encoding: a polypeptide comprising, or alternatively consisting of, amino acid residues: from M-1 to I9, from D-3 to T12, from F-26 to L-35, from I-50 to T-59, from T-54 to W-63, from S-81 to Q-90, from P-117 to P-124, from G-122 to Q-130, from S-152 to F-160, from P-165 to L-173, from D-171 to I-179, from K-207 to L-215, from N-225 to L-234, from P-270 to H-278, from H-272 to I-280, from T-295 to L-303, from D-304 to Y-312, from V-321 to Y-329, from E-336 to F-344, from P-346 to G-354, from C+-359 to D-367, from S-366 to A-374, from F-378 to C-386, from S-390 to Q-398, from Q-398 to V-406, from C-410 to G-418, from R-432 to D-440, from M-438 to L-446, from V-457 to C-465, from R-464 to E-472, from G-470 to C-478, from C-484 to C-492, from S-493 to G-551, from G-513 to C-521, from D-525 to G-533, from G-528 to H-536, from G-545 to L-554, from G-556 to C-564, from S-565 to G-573, from C-570 to H-578, from L-602 to A-610, from Q-620 to F-628, from Q-631 to V-639, from L-648 to L-656, from L-653 to V-661, from N-665 to R-673, from W-670 to R-678, from P-707 to G-715, from T-756 to G-764, from S767 to R-775, from T-788 to N-796, from N-809 to N-816, from L-826 to I-834, from E-853 to N-861, from C-862 to Q-870, from Q-875 to V-883, from S-889 to T-897, from A-899 to C-907, from C-916 to G-924, from G-929 to F-937, from F-937 to C-945, from L-959 to T-967, from Q-978 to S-986, from R-977 to P-1005, from Q-1006 to N-1014, from V-1018 to T-1026, from E-1042 to H-1050, from K-1061 to C-1069, from D-1073 to L-1081, from C-1111 to G-1119, from G-1119 to T-1124, from E-1126 to N-1134, from C-1131 to S-1139, from C-1144 to R-1152, from T-1147 to T-1155, from L-1176 to F-1184, from K-1193 to F-1201, from M-1211 to L-1219. G-1236 to D-1244, from L-1240 to Q-1248, from R-1260 to I-1268, from V-1277 to N-1285, from H-1302 to I-1310, from D-1307 to V-1315, from L-1340 to F-1348, from A-1360 to W-1368, from H-1371 to A-1379, from S-1414 to E-1422, from M-1424 to I-1432, from G-1426 to Q-1434, from P-1453 to D-1461, from F-1463 to N-1471, from P-1480 to E-1488, from Q-1487 to C-1495, from G-1524 to G-1532, from L-1529 to C-1537, from W-1542 to H-1550, from G-1549 to A-1557, from P-1559 to S-1567, from P-1565 to M-1573, from M-1573 to Q-1581, from G-1614 to G-1622, from D-1617 to S-1625, from F-1627 to P-1635, from E-1630 to E-1638, from A-1655 to C-1163, from L-1667to V-1675, from L-1681 to C-1689, from C-1689 to Q-1697, from L-1707 to W-1715, from C-1717 to D-1725, from D-1725 to E-1733, from S-1739 to C-1747, from G-1741 to C-1749, from L-1761 to D-1769, from G-1773 to D-1781, from H-1788 to V-1796, from A-1860 to G-1868, from G-1873 to R-1881. K-1876 to A-1884, from A-1893 to V-1901, from S-1906 to D-1914, from N-1734 to F-1942, from D-1944 to Y-1952, from S-1970 to A-1978, from D-1973 to A-1981, from N-1987 to D-1995, from S-2005 to S-2013, from L-2085 to G-2093, from Q-2100 to D-2108, from D-2103 to P-2111, from W-2112 to L-2120, from P-2136 to E-2144, from E-2143 to R-2151, from Cys-359 to Gly-363, from Pro-392 to His-395, from Pro-414 to Ser-416, from Pro-487 to Gly490, from Ser-515 to Asp-517, from Asn-574 to Gly-576, from Pro-708 to Gly-710, from Gin-1006 to Cys-1011, from Arg-1114 to Ser-1118, from Cys-1131 to Gly-1137, from Ser-1146 to Gly-1150, from Pro-1305 to Asp-1307, from Pro-1565 to Asp-1568, from Glu-1670 to Gly-1673, from Asp-1684 to Gly-1688, from Pro-1708 to Gly-1714, from Pro-1722 to about Gly-1726, from Asp-2010 to Ser-2013 of SEQ ID NO:2. The inventors have determined that the above polypeptides are antigenic regions of the full-length WF-HABP polypeptide. Methods for determining other such epitope-bearing portions of full-length WF-HABP polypeptides are described in detail below.

Preferred nucleic acid fragments of the invention also include nucleic acid molecules encoding epitope-bearing portions of WF-HABP. In particular, such nucleic acid fragments of the present invention include nucleic acid molecules encoding: a polypeptide comprising, or alternatively consisting of, amino acid residues: from L-7 to W-15, from C-17 to D-25, from G-26 to H-34, from S-39 to C-47, from L-42 to H-50, from L-61 to D-69, from P-75 to M-83, from H-88 to V-96, from V-159 to V-167, from G-173 to R-181, from N-177 to Y-185, from A-193 to V-201, from T-207 to V-215, from N-234 to F-242, from D-244 to Y-252, from V-259 to M-267, from N-287 to P-295, from S-305 to S-313, from L-386 to G-394, from D-404 to P-412, from W413 to L-421, from E-436 to E-444, from and/or from E-445 to I-453 of SEQ ID NO:5. The inventors have determined that the above polypeptides are antigenic regions of the WF-HABP polypeptide. Methods for determining other such epitope-bearing portions of WF-HABP polypeptides are described in detail below.

Preferred nucleic acid fragments of the invention also include nucleic acid molecules encoding epitope-bearing portions of BE-HABP. In particular, such nucleic acid fragments of the present invention include nucleic acid molecules encoding: a polypeptide comprising, or alternatively consisting of, amino acid residues: from Y-26 to N-34, from N-37 to N-45, from V-50 to L-58, from L-78 to V-86, from K-90 to E-98, from N-94 to L-102, from L-107 to Y-115, from R-110 to R-118, from V-119 to H-127, from K-125 to I-133, from L-136 to Y-144, from Y-141 to V-148, from D-150 to L-158, from Y-170 to Q-178. A204 to C-212, from R-230 to L-238, from S-244 to L-252, from H-249 to V-257, from and/or A-282 to K-289 of SEQ ID NO:8. The inventors have determined that the above polypeptides are antigenic regions of the OE-HABP polypeptide. Methods for determining other such epitope-bearing portions of OE-HABP polypeptides are described in detail below.

Preferred nucleic acid fragments of the invention also include nucleic acid molecules encoding epitope-bearing portions of BM-HABP. In particular, such nucleic acid fragments of the present invention include nucleic acid molecules encoding: a polypeptide comprising, or alternatively consisting of, amino acid residues: from T-2 to E-10, from H-7 to Y-15, from G-17 to E-25, from C-22 to D-30, from R-31 to C-39, from R-61 to L-69, from T-70 to C-78, from R-75 to H-83, from Y-93 to L-101, from L-107 to P-115, from S-120 to V-128, from Y-133 to E-141, from P-135 to W-143, from Y-148 to T-156, from S-193 to A-201, from S-195 to L-203, from N-220 to T-228, from L-229 to H-237, from L-264 to L-272, from P-271 to C-279, from C-279 to E-287, from A-292 to I-296, from S-301 to A-309, from and/or R-342 to F-350 of SEQ ID NO:11. The inventors have determined that the above polypeptides are antigenic regions of the BM-HABP polypeptide. Methods for determining other such epitope-bearing portions of BM-HABP polypeptides are described in detail below.

In another embodiment, the full-length WF-HABP invention provides isolated nucleic acid molecules comprising polynucleotides which hybridize, preferably under stringent hybridization conditions, to a portion of one or more of the nucleic acids (i.e., polynucleotides) described herein, such as, for instance, the cDNA clone contained in ATCC Deposit 203503, the polynucleotide sequence depicted in FIGS. 1A–P (SEQ ID NO:1) or the complementary strand thereto, and/or any of the polynucleotide fragments as described herein. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least 15 nucleotides (nt), and more preferably at least 20 nt, still more preferably at least 30 nt, and even more preferably 30–70, or 80–150 nt, or the entire length of the reference polynucleotide. By a portion of a polynucleotide of "at least 20 nt in length," for example, is intended 20 or more contiguous nucleotides from the nucleotide sequence of the reference polynucleotide (e.g., the complementary strand of the nucleotide sequence shown in FIGS. 1A–P (SEQ ID NO:1)). Of course, a polynucleotide which hybridizes only to a poly A sequence (such as the 3' terminal poly(A) tail of a cDNA sequence), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (i.e., practically any double-stranded cDNA clone generated using oligo dT as a primer). These polynucleotides have uses which include, but are not limited to, diagnostic probes and primers as discussed above and in more detail below.

In another embodiment, the WF-HABP invention provides isolated nucleic acid molecules comprising polynucleotides which hybridize, preferably under stringent hybridization conditions, to a portion of one or more of the nucleic acids (i.e., polynucleotides) described herein, such as, for instance, the cDNA clone contained in ATCC Deposit 203503, the polynucleotide sequence depicted in FIGS. 2A–D (SEQ ID NO:4) or the complementary strand thereto, and/or any of the polynucleotide fragments as described herein. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least 15 nucleotides (nt), and more preferably at least 20 nt, still more preferably at least 30 nt, and even more preferably 30–70, or 80–150 nt, or the entire length of the reference polynucleotide. By a portion of a polynucleotide of "at least 20 nt in length," for example, is intended 20 or more contiguous nucleotides from the nucleotide sequence of the reference polynucleotide (e.g., the deposited cDNA or the complementary strand of the nucleotide sequence shown in FIGS. 2A–D (SEQ ID NO:4)). Of course, a polynucleotide which hybridizes only to a poly A sequence (such as the 3' terminal poly(A) tail of a cDNA sequence), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (i.e., practically any double-stranded cDNA clone generated using oligo dT as a primer). These polynucleotides have uses which include, but are not limited to, diagnostic probes and primers as discussed above and in more detail below.

In another embodiment, the OE-HABP invention provides isolated nucleic acid molecules comprising polynuclcotides which hybridize, preferably under stringent hybridization conditions, to a portion of one or more of the nucleic acids (i.e., polynucleotides) described herein, such as, for instance, the cDNA clone contained in ATCC Deposit 203501, the polynucleotide sequence depicted in FIGS. 3A–C (SEQ ID NO:7) or the complementary strand thereto, and/or any of the polynucleotide fragments as described herein. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least 15 nucleotides (nt), and more preferably at least 20 nt, still more preferably at least 30 nt, and even more preferably 30–70, or 80–150 nt, or the entire length of the reference polynucleotide. By a portion of a polynucleotide of "at least 20 nt in length," for example, is intended 20 or more contiguous nucleotides from the nucleotide sequence of the reference polynucleotide (e.g., the deposited cDNA or the complementary strand of the nucleotide sequence shown in FIGS. 3A–C (SEQ ID NO:7)). Of course, a polynucleotide which hybridizes only to a poly A sequence (such as the 3' terminal poly(A) tail of a cDNA sequence), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (i.e., practically any double-stranded cDNA clone generated using oligo dT as a primer). These polynucleotides have uses which include, but are not limited to, diagnostic probes and primers as discussed above and in more detail below.

In another embodiment, the BM-HABP invention provides isolated nucleic acid molecules comprising polynucleotides which hybridize, preferably under stringent hybridization conditions, to a portion of one or more of the nucleic acids (i.e., polynucleotides) described herein, such as, for instance, the cDNA clone contained in ATCC Deposit 203502, the polynucleotide sequence depicted in FIGS. 4A–C (SEQ ID NO:10) or the complementary strand thereto, and/or any of the polynucleotide fragments as described herein. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least 15 nucleotides (nt), and more preferably at least 20 nt, still more preferably at least 30 nt, and even more preferably 30–70, or 80–150 nt, or the entire length of the reference polynucleotide. By a portion of a polynucleotide of "at least 20 nt in length," for example, is intended 20 or more contiguous nucleotides from the nucleotide sequence of the reference polynucleotide (e.g. the deposited cDNA or the complementary strand of the nucleotide sequence shown in FIGS. 4A–C (SEQ ID NO:10)). Of course, a polynucleotide which hybridizes only to a poly A sequence (such as the 3' terminal poly(A) tail of a cDNA sequence), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (i.e., practically any double-stranded cDNA clone generated using oligo dT as a primer). These polynucleotides have uses which include, but are not limited to, diagnostic probes and primers as discussed above and in more detail below.

In specific embodiments, the nucleic acid molecules hybridize to the complementary strand of nucleotides 1262 to 4595, 4595 to 5552, 1220 to 1262, 1262 to 1300, 1301 to 1340, 1341 to 1380, 1381 to 1420, 1421 to 1460, 1461 to 1500, 1501 to 1540, 1541 to 1580, 1581 to 1620, 1621 to 1660, 1661 to 1700, 1701 to 1740, 1741 to 1780, 1781 to 1820, 1821 to 1860, 1861 to 1900, 1901 to 1940, 1941 to 1980, 1981 to 2020, 2021 to 2040, 2041 to 2080, 2081 to 2120, 2121 to 2160, 2161 to 2200, 2201 to 2240, 2241 to 2280, 2281 to 2320, 2321 to 2360, 2361 to 2400, 2401 to 2440, 2441 to 2480, 2481 to 2520, 2521 to 2560, 2561 to 2600, 2601 to 2640, 2641 to 2680, 2681 to 2720, 2721 to 2760, 2761 to 2800, 2801 to 2840, 2841 to 2880, 2881 to 2920, 2921 to 2960, 2961 to 3000, 3001 to 3040, 3041 to 3080, 3081 to 3120, 3121 to 3160, 3161 to 3200, 3201 to 3240, 3241 to 3280, 3281 to 3320, 3321 to 3360, 3361 to 3400, 3401 to 3440, 3441 to 3480, 3481 to 3520, 3521 to 3560, 3561 to 3600, 3601 to 3640, 3641 to 3680, 3681 to 3720, 3721 to 3760, 3761 to 3800, 3801 to 3840, 3841 to 3880, 3881 to 3920, 3921 to 3960, 3961 to 4000, 400 to 4040, 4041 to 4080, 4081 to 4120, 4121 to 4160, 4161 to 4200, 4201 to 4240, 4241 to 4280, 4281 to 4320, 4321 to 4360, 4361 to 4400, 4401 to 4440, 4441 to 4480, 4481 to 4520, 4521 to 4560, 4561 to 4600, 4601 to 4640, 4641 to 4680, 4681 to 4720, 4721 to 4760, 4761 to 4800, 4801 to 4840, 4841 to 4880, 4881 to 4920, 4921 to 4960, 4961 to 5000, 5001 to 5040, 5041 to 5080, 5081 to 5120, 5121 to 5160, 5161, 5200, 5201 to 5240, 5241 to 5280, 5281 to 5320, 5321 to 5360, 5361 to 5400, 5401 to 5440, 5441 to 5480, 5481 to 5520, and/or 5521 to 5552, of SEQ ID NO:1.

In specific embodiments, the nucleic acid molecules hybridize to the complementary strand of nucleotides 1 to 688, 1 to 40, 41 to 80, 81 to 120, 121 to 160, 161 to 200, 201 to 240, 241 to 280, 281 to 320, 321 to 380, 381 to 420, 421 to 460, 461 to 500, 501 to 540, 541 to 580, 581 to 620, 621 to 660, 661 to 688, 301 to 612, 350 to 550 of SEQ ID NO:4.

In specific embodiments, the nucleic acid molecules hybridize to the complementary strand of nucleotides 1 to 50, 51 to 100, 101 to 150, 151 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, and/or 951 to 985, of SEQ ID NO:7.

In specific embodiments, the nucleic acid molecules hybridize to the complementary strand of nucleotides 1 to 458, 806 to 1259, 352 to 663, 1 to 40, 41 to 80, 81 to 120, 121 to 160, 161 to 200, 201 to 240, 241 to 280, 281 to 320, 321 to 380, 381 to 420, 421 to 460, 760 to 805, 806 to 850, 851 to 890, 891 to 930, 931 to 970, 971 to 1010, 1011 to 1050, 1051 to 1090, 1091 to 1130, 1131 to 1170, 1171 to 1210, 1211 to 1250, 1221 to 1259, 311 to 351, 352 to 390, 391 to 430, 431 to 470, 471 to 510, 511 to 550, 551 to 590, 591 to 630, and/or 631 to 663 of SEQ ID NO:10.

As indicated, nucleic acid molecules of the present invention which encode full-length WF-HABP polypeptides may include, but are not limited to, those encoding the amino acid sequences of the full-length polypeptide (SEQ ID NO:2), by itself; the coding sequence for full-length polypeptide together with additional, non-coding sequences, including for example, but not limited to, introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptides may be fused to a marker sequence, such as a sequence encoding a peptide which facilitates purification of the fused polypeptide. In certain preferred embodiments, the marker amino acid sequence is a hexa-histidine peptide, such as the tag provided in a pQE vector (Qiagen, Inc.), among others, many of which are commercially available. As described in Gentz et al., Proc. Natl. Acad. Sci. USA 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., Cell 37:767 (1984). As discussed below, other such fusion proteins include full-length WF-HABPs fused to IgG-Fc at the N- or C-terminus.

As indicated, nucleic acid molecules of the present invention which encode WF-HABP polypeptides may include, but are not limited to, those encoding the amino acid sequences of the full-length polypeptide (SEQ ID NO:5), by itself; the coding sequence for full-length polypeptide together with additional, non-coding sequences, including for example, but not limited to, introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptides may be fused to a marker sequence, such as a sequence encoding a peptide which facilitates purification of the fused polypeptide. In certain preferred embodiments, the marker amino acid sequence is a hexa-histidine peptide, such as the tag provided in a pQE vector (Qiagen, Inc.), among others, many of which are commercially available. As described in Gentz et al., Proc. Natl. Acad. Sci. USA 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., Cell 37:767 (1984). As discussed below, other such fusion proteins include WF-HABPs fused to IgG-Fc at the N- or C-terminus.

As indicated, nucleic acid molecules of the present invention which encode OE-HABP polypeptides may include, but are not limited to, those encoding the amino acid sequences of the full-length polypeptide (SEQ ID NO:8), by itself; the coding sequence for full-length polypeptide together with additional non-coding sequences, including for example, but not limited to, introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptides may be fused to a marker sequence, such as a sequence encoding a peptide which facilitates purification of the fused polypeptide. In certain preferred embodiments, the marker amino acid sequence is a hexa-histidine peptide, such as the tag provided in a pQE vector (Qiagen, Inc.), among others, many of which are commercially available. As described in Gentz et al., Proc. Natl. Acad. Sci. USA 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., Cell 37:767 (1984). As discussed below, other such fusion proteins include OE-HABPs fused to IgG-Fc at the N- or C-terminus.

As indicated, nucleic acid molecules of the present invention which encode BM-HABP polypeptides may include, but are not limited to, those encoding the amino acid sequences of the full-length polypeptide (SEQ ID NO:11), by itself; the coding sequence for full-length polypeptide together with additional, non-coding sequences, including for example, but not limited to, introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptides may be fused to a marker sequence, such as a sequence encoding a peptide which facilitates purification of the fused polypeptide. In certain preferred embodiments, the marker amino acid sequence is a hexa-histidine peptide, such as the tag provided in a pQE vector (Qiagen, Inc.), among others, many of which are commercially available. As described in Gentz et al., Proc. Natl. Acad. Sci. USA 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., Cell 37:767 (1984). As discussed below, other such fusion proteins include BM-HABPs fused to IgG-Fc at the N- or C-terminus.

The present invention further relates to variants of the nucleic acid molecules of the present, invention, which encode fragments (i.e., portions), analogs or derivatives of the full-length WF-HABP. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

The present invention further relates to variants of the nucleic acid molecules of the present invention, which encode fragments (i.e., portions), analogs or derivatives of WF-HABP. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

The present invention further relates to variants of the nucleic acid molecules of the present invention, which encode fragments (i.e., portions), analogs or derivatives of OE-HABP. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

The present invention further relates to variants of the nucleic acid molecules of the present invention, which encode fragments (i.e., portions), analogs or derivatives of BM-HABP. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

Such variants include those produced by nucleotide substitutions, deletions or additions, which may involve one or more nucleotides. The variants may be altered in coding regions, non-coding regions or both. Alterations n the coding regions may produce conservative or non-conservative amino acid substitutions, deletions or additions. Especially preferred among these are silent substitutions, additions and deletions, which do not alter the properties and activities of the full-length WF-HABP or fragments thereof. Also especially preferred in this regard are conservative substitutions.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of WF-HABP or fragments thereof. Also especially preferred in this regard are conservative substitutions.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of OE-HABP or fragments thereof. Also especially preferred in this regard are conservative substitutions.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of BM-HABP or fragments thereof. Also especially preferred in this regard are conservative substitutions.

Further embodiments of the invention include isolated nucleic acid molecules comprising a polynucleotide having a nucleotide sequence at least 90% identical, and more preferably at least 95%, 96%, 97%, 98% or 99% identical to: (a) a nucleotide sequence encoding the full-length WF-HABP polypeptide having the complete (i.e., full-length) amino acid sequence shown in FIGS. 1A–P (SEQ ID NO:2); (b) a nucleotide encoding the complete amino sequence shown in FIGS. 1A–P but lacking the N-terminal methionine (amino acid residues 2 to 2100 in (SEQ ID NO:2)); (c) a nucleotide sequence encoding the full-length WF-HABP polypeptide having the amino acid sequence corresponding to the cDNA clone contained in ATCC Deposit Number 203503; (d) a nucleotide sequence encoding the full-length WF-HABP polypeptide having the amino acid sequence corresponding to the cDNA clone contained in ATCC Deposit Number 203503 but lacking the N-terminal methionine; (e) a nucleotide sequence encoding an HA binding motif (amino acid residues E-1791 to C-1894 of SEQ ID NO:2); (f) a nucleotide sequence encoding EGF-like Type 1 domains (amino acid residues from C-375 to C-386, amino acid residues from C-943 to C-954, amino acid residues from C-987 to C-998, amino acid residues from C-1582 to C-1593, and amino acid residues from C-1626 to C-1637 of SEQ ID NO:2); (g) a nucleotide sequence encoding EGF-like Type 2 domains (amino acid residues from C-465 to C-478, amino acid residues from C-508 to C-521, amino acid residues from C-551 to C-564, amino acid residues from C-943 to C-957, amino acid residues from C-987 to C-998, amino acid residues from C-1027 to C-1040, amino acid residues from C-1069 to C-1082, amino acid residues from C-1111 to C-1125, amino acid residues from C-1582 to C-1596, amino acid residues from C-1582 to C-1596, amino acid residues from C-1626 to C-1637, amino acid residues from C-1663 to C-1676, amino acid residues from C-1747 to C-1760, and amino acid residues from C-1894 to C-1908 of SEQ ID NO:2); (h) a nucleotide sequence encoding a laminin-type EGF domain (amino acid residues from C-943 to C-977, and amino acid residues from C-1582 to C-1616 of SEQ ID NO:2); (I) a nucleotide sequence encoding a link protein domain (amino acid residues from C-1817 to C-1862 of SEQ ID NO:2); (j) a nucleotide sequence encoding a cytochrome P450 cysteine heme-iron ligand binding domains (amino acid residues from F-344 to G-353, and amino acid residues from W-514 to A-523 of SEQ ID NO:2); (k) a nucleotide sequence encoding a prokaryotic membrane lipoprotein lipid attachment site domains (amino acid residues from P-1103 to C-1113, and amino acid residues from T-1405 to C-1415 of SEQ ID NO:2); and (l) a nucleotide sequence complementary to any of the nucleotide sequences in (a), b), (c), (d), (e), (f), (g), (h), (I), (j) (k), or (l).

Further embodiments of the invention include isolated nucleic acid molecules comprising a polynucleotide having a nucleotide sequence at least 90% identical, and more preferably at least 95%, 96%, 97%, 98% or 99% identical to: (a) a nucleotide sequence encoding the WF-HABP polypeptide having the complete (i.e., full-length) amino acid sequence shown in FIGS. 2A–D (SEQ ID NO:5); (b) a nucleotide encoding the complete amino sequence shown in FIGS. 2A–D but lacking the N-terminal methionine (amino acid residues 2 to 457 in (SEQ ID NO:5)); (c) a nucleotide sequence encoding the WF-HABP polypeptide having the amino acid sequence encoded by the cDNA clone contained in ATCC Deposit Number 203503; (d) a nucleotide sequence encoding the WF-HABP polypeptide having the amino acid sequence encoded by the cDNA clone contained in ATCC Deposit Number 203503 but lacking the N-terminal methionine; (e) a nucleotide sequence encoding the HA binding motif (amino acid residues E-91 to C-194 of SEQ ID NO:5); (f) a nucleotide sequence encoding the EGF-like Type 2 domain (amino acid residues C-194 to C-208, of SEQ ID NO:5); (g) the nucleotide sequence encoding the link domain (amino acid residues C-117 to C-162, of SEQ ID NO:5); (h) any fragment described herein; (i) the polypeptide sequence of FIGS. 2A–D (SEQ ID NO:5) minus a portion, or all of, the HA binding domain, the EGF-like Type 2 domain, and the link domain of WF-HABP shown in FIGS. 2A–D (SEQ ID NO:5); and 0) a nucleotide sequence complementary to any of the nucleotide sequences in (a), (b), (c), (d), (e), (f), (g), (h), or (I).

Further embodiments of the invention include isolated nucleic acid molecules comprising a polynucleotide having a nucleotide sequence at least 90% identical, and more preferably at least 95%, 96%, 97%, 98% or 99% identical to: (a) a nucleotide sequence encoding the OE-HABP polypeptide having the complete (i.e., full-length) amino acid sequence shown in FIGS. 3A–C (SEQ ID NO:8); (b) a nucleotide encoding the complete amino sequence shown in FIGS. 3A–C but lacking the N-terminal *methionine (amino acid residues 2 to 289 in (SEQ ID NO:8)); (c) a nucleotide sequence encoding the OE-HABP polypeptide having the amino acid sequence encoded by the cDNA clone contained in ATCC Deposit Number 203501; (d) a nucleotide sequence encoding the OE-HABP polypeptide having the amino acid sequence encoded by the cDNA clone contained in ATCC Deposit Number 203501 but lacking the N-terminal methionine; (e) a nucleotide sequence encoding the HA binding motif domain (amino acid residues P-97 to F-168, amino acid residues L-209 to C-286, of SEQ ID NO:8); (f) a nucleotide sequence encoding the link protein domain (amino acid residues C-188 to C-233 of SEQ ID NO:8); (g) any fragment described herein; (h) the polypeptide sequence of FIGS. 3A–C (SEQ ID NO:8) minus a portion, or all of, the HA binding domain, and link protein domain of OE-HABP shown in FIGS. 3A–C (SEQ ID NO:8); and (i) a nucleotide sequence complementary to any of the nucleotide sequences in (a), (b), (c), (d), (e), (f), (g), or (h).

Further embodiments of the invention include isolated nucleic acid molecules comprising a polynucleotide having a nucleotide sequence at least 90% identical, and more preferably at least 95%, 96%, 97%, 98% or 99% identical to: (a) a nucleotide sequence encoding the BM-HABP polypeptide having the complete (i.e., full-length) amino acid sequence shown in FIGS. 4A–C (SEQ ID NO:11); (b) a nucleotide encoding the complete amino sequence shown in FIGS. 4A–C but lacking the N-terminal methionine (amino acid residues 2 to 353 in (SEQ ID NO:11)); (c) a nucleotide sequence encoding the BM-HABP polypeptide having the amino acid sequence encoded by the cDNA clone contained in ATCC Deposit Number 203502; (d) a nucleotide sequence encoding the BM-HABP polypeptide having the amino acid sequence encoded by the cDNA clone contained in ATCC Deposit Number 203502 but lacking the N-terminal methionine; (e) a nucleotide sequence encoding the HA binding motif domain (amino acid residues Q-121 to L-215 in (SEQ ID NO:11)); (f) any fragment described herein; (g) the polypeptide sequence of FIGS. 4A–C (SEQ ID NO:11) minus a portion, or all of, the HA binding domain of BM-HABP shown in FIGS. 4A–C (SEQ ID NO:11); and (h) a nucleotide sequence complementary to any of the nucleotide sequences in (a), (b), (c), (d), (e), (f), or (g).

By a polynucleotide having a nucleotide sequence at least, for example, 95% "identical" to a reference nucleotide sequence encoding a full-length WF-HABP polypeptide is intended that the nucleotide sequence of the polynucleotide is identical to the reference sequence except that the polynucleotide sequence may include up to five point mutations per each 100 nucleotides of the reference nucleotide sequence encoding a full-length WF-HABP. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be the entire full-length WF-HABP encoding nucleotide sequence shown in FIGS. 1A–P (SEQ ID NO:1) or any full-length WF-HABP polynucleotide fragment as described herein.

By a polynucleotide having a nucleotide sequence at least, for example, 95% "identical" to a reference nucleotide sequence encoding a WF-HABP polypeptide is intended that the nucleotide sequence of the polynucleotide is identical to the reference sequence except that the polynucleotide sequence may include up to five point mutations per each 100 nucleotides of the reference nucleotide sequence encoding WF-HABP. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be the entire WF-HABP encoding nucleotide sequence shown in FIGS. 2A–D (SEQ ID NO:4) or any WF-HABP polynucleotide fragment as described herein.

By a polynucleotide having a nucleotide sequence at least, for example, 95% "identical" to a reference nucleotide sequence encoding a OE-HABP polypeptide is intended that the nucleotide sequence of the polynucleotide is identical to the reference sequence except that the polynucleotide sequence may include up to five point mutations per each 100 nucleotides of the reference nucleotide sequence encoding OE-HABP. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be the entire OE-HABP encoding nucleotide sequence shown in FIGS. 3A–C (SEQ ID NO:7) or any OE-HABP polynucleotide fragment as described herein.

By a polynucleotide having a nucleotide sequence at least, for example, 95% "identical" to a reference nucleotide sequence encoding a BM-HABP polypeptide is intended that the nucleotide sequence of the polynucleotide is identical to the reference sequence except that the polynucleotide sequence may include up to five point mutations per each 100 nucleotides of the reference nucleotide sequence encoding BM-HABP. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be the entire BM-HABP encoding nucleotide sequence shown in FIGS. 4A–C (SEQ ID NO:10) or any BM-HABP polynucleotide fragment as described herein.

As a practical matter, whether any particular nucleic acid molecule is at least 90%, 95%, 96%, 97%, 98% or 99% identical to, for instance, the encoding nucleotide sequence shown in FIGS. 1A–P (SEQ ID NO:1), or to the nucleotide sequence of the deposited cDNA clone, can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, Advances in Applied Mathematics 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

As a practical matter, whether any particular nucleic acid molecule is at least 90%, 95%, 96%, 97%, 98% or 99% identical to, for instance, the encoding nucleotide sequence shown in FIGS. 2A–D (SEQ ID NO:4), or to the nucleotide sequence of the deposited cDNA clone, can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, Advances in Applied Mathematics 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

As a practical matter, whether any particular nucleic acid molecule is at least 90%, 95%, 96%, 97%, 98% or 99% identical to, for instance, the encoding nucleotide sequence shown in FIGS. 3A–C (SEQ ID NO:7), or to the nucleotide sequence of the deposited cDNA clone, can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, Advances in Applied Mathematics 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

As a practical matter, whether any particular nucleic acid molecule is at least 90%, 95%, 96%, 97%, 98% or 99% identical to, for instance, the encoding nucleotide sequence shown in FIGS. 4A–C (SEQ ID NO:10), or to the nucleotide sequence of the deposited cDNA clone, can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, Advances in Applied Mathematics 2:482–489 (1981), to find the best segment of homology between two sequences. When using Bestfit or any other sequence alignment program to determine whether a particular sequence is, for instance 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present full-length WF-HABP invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes-of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

In a specific embodiment, the identity between a reference (query) sequence (a sequence of the present WF-HABP invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB alignment of DNA sequences to calculate percent identity arc: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

In a specific embodiment, the identity between a reference (query) sequence (a sequence of the present OE-HABP invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

In a specific embodiment, the identity between a reference (query) sequence (a sequence of the present BM-HABP invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB alignment of DNA sequences to calculate percent identity are: Matrix=Unitary, k-tuple=4, Mismatch Penalty=1, Joining Penalty-30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

The present application is directed to nucleic acid molecules at least 90%, 95%, 96%, 97%, 98% or 99% identical to the nucleic acid sequences (i.e., polynucleotides) disclosed herein, irrespective of whether they encode a polypeptide having full-length WF-HABP functional activity. This is because even where a particular nucleic acid molecule does not encode a polypeptide having full-length WF-HABP functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having full-length WF-HABP functional activity include, but are not limited to, inter alia, (1) isolating a full-length WF-HABP receptor gene or allelic or splice variants thereof in a cDNA library; (2) in situ hybridization (e.g., "FISH") to metaphase chromosomal spreads to provide precise chromosomal location of a full-length WF-HABP receptor gene, as described in Verma et al., Human Chromosomes: A Manual of Basic Techniques, Pergamon Press, New York (1988); and (3) Northern Blot analysis for detecting full-length WF-HABP mRNA expression in specific tissues.

The present application is directed to nucleic acid molecules at least 90%, 95%, 96%, 97%, 98% or 99% identical to the nucleic acid sequences (i.e., polynucleotides) disclosed herein, irrespective of whether they encode a polypeptide having WF-HABP functional activity. This is because even where a particular nucleic acid molecule does not encode a polypeptide having WF-HABP functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having WF-HABP functional activity include, but are not limited to, inter alia, (1) isolating a WF-HABP receptor gene or allelic or splice variants thereof in a cDNA library; (2) in situ hybridization (e.g., "FISH") to metaphase chromosomal spreads to provide precise chromosomal location of a WF-HABP receptor gene, as described in Verma et al., Human Chromosomes: A Manual of Basic Techniques, Pergamon Press, New York (1988); and (3) Northern Blot analysis for detecting WF-HABP mRNA expression in specific tissues.

The present application is directed to nucleic acid molecules at least 90%, 95%, 96%, 97%, 98% or 99% identical to the nucleic acid sequences (i.e., polynucleotides) disclosed herein, irrespective of whether they encode a polypeptide having OE-HABP functional activity. This is because even where a particular nucleic acid molecule does not encode a polypeptide having OE-HABP functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having OE-HABP functional activity include, but are not limited to, inter alia, (1) isolating a OE-HABP receptor gene or allelic or splice variants thereof in a cDNA library; (2) in situ hybridization (e.g., "FISH") to metaphase chromosomal spreads to provide precise chromosomal location of a OE-HABP receptor gene, as described in Verma et al., Human Chromosomes: A Manual of Basic Techniques, Pergamon Press, New York (1988); and (3) Northern Blot analysis for detecting OE-HABP mRNA expression in specific tissues.

The present application is directed to nucleic acid molecules at least 90%, 95%, 96%, 97%, 98% or 99% identical to the nucleic acid sequences (i.e., polynucleotides) disclosed herein, irrespective of whether they encode a polypeptide having BM-HABP functional activity. This is because even where a particular nucleic acid molecule does not encode a polypeptide having BM-HABP functional activity, one of skill in the art would still know how to use the nucleic acid molecule for instance, as a hybridization probe or a polymerase chain reaction (PCR) primer. Uses of the nucleic acid molecules of the present invention that do not encode a polypeptide having BM-HABP functional activity include, but are not limited to, inter alia, (1) isolating a BM-HABP receptor gene or allelic or splice variants thereof in a cDNA library; (2) in situ hybridization (e.g., "FISH") to metaphase chromosomal spreads to provide precise chromosomal location of a BM-HABP receptor gene, as described in Verma et al., Human Chromosomes: A Manual of Basic Techniques, Pergamon Press, New York (1988); and (3) Northern Blot analysis for detecting BM-HABP mRNA expression in specific tissues.

Preferred, however, are nucleic acid molecules having sequences at least 90%, 95%, 96%, 97%, 98% or 99% identical to the nucleic acid sequences disclosed herein, which do, in fact, encode a polypeptide having full-length WF-HABP functional activity. By "a polypeptide having full-length WF-HABP receptor functional activity" is intended polypeptides exhibiting activity similar, but not necessarily identical, to an activity of full-length WF-HABPs of the present invention (either the full-length polypeptide, or the splice variants), as measured, for example, in a particular immunoassay or biological assay. For example, full-length WF-HABP activity can be measured by determining the ability of a full-length WF-HABP polypeptide to bind a full-length WF-HABP ligand (e.g., hyaluronan, or chondroitin sulfate proteoglycan). The full-length WF-HABP receptor activity may also be measured by determining the ability of a polypeptide, such as cognate ligand which is free or expressed on a cell surface, to induce cellular proliferation, cellular adhesion, or cellular migration.

Preferred, however, are nucleic acid molecules having sequences at least 90%, 95%, 96%, 97%, 98% or 99% identical to the nucleic acid sequences disclosed herein, which do, in fact, encode a polypeptide having WF-HABP functional activity. By "a polypeptide having WF-HABP receptor functional activity" is intended polypeptides exhibiting activity similar, but not necessarily identical, to an activity of WF-HABPs of the present invention (either the full-length polypeptide, or the splice variants), as measured, for example, in a particular immunoassay or biological assay. For example, WF-HABP activity can be measured by determining the ability of a WF-HABP polypeptide to bind a WF-HABP ligand (e.g., hyaluronan, or chondroitin sulfate proteoglycan). WF-HABP receptor activity may also be measured by determining the ability of a polypeptide, such as cognate ligand which is free or expressed on a cell surface, to induce cellular proliferation, cellular adhesion, or cellular migration.

Preferred, however, are nucleic acid molecules having sequences at least 90%, 95%, 96%, 97%, 98% or 99% identical to the nucleic acid sequences disclosed herein, which do, in fact, encode a polypeptide having OE-HABP functional activity. By "a polypeptide having OE-HABP receptor functional activity" is intended polypeptides exhibiting activity similar, but not necessarily identical, to an activity of OE-HABPs of the present invention (either the full-length polypeptide, or the splice variants), as measured, for example, in a particular immunoassay or biological assay. For example, OE-HABP activity can be measured by determining the ability of a OE-HABP polypeptide to bind a OE-HABP ligand (e.g., hyaluronan, or chondroitin sulfate proteoglycan). OE-HABP receptor activity may also be measured by determining the ability of a polypeptide, such as cognate ligand which is free or expressed on a cell surface, to induce cellular proliferation, cellular adhesion, or cellular migration.

Preferred, however, are nucleic acid molecules having sequences at least 90%, 95%, 96%, 97%, 98% or 99% identical to the nucleic acid sequences disclosed herein, which do, in fact, encode a polypeptide having BM-HABP functional activity. By "a polypeptide having BM-HABP receptor functional activity" is intended polypeptides exhibiting activity similar, but not necessarily identical, to an activity of BM-HABPs of the present invention (either the full-length polypeptide, or the splice variants), as measured, for example, in a particular immunoassay or biological assay. For example, BM-HABP activity can be measured by determining the ability of a BM-HABP polypeptide to bind a BM-HABP ligand (e.g., hyaluronan, or chondroitin sulfate proteoglycan). BM-HABP receptor activity may also be measured by determining the ability of a polypeptide, such as cognate ligand which is free or expressed on a cell surface, to induce cellular proliferation, cellular adhesion, or cellular migration.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence shown in FIGS. 1A–P (SEQ ID NO:1), or fragments thereof, will encode polypeptides "having full-length WF-HABP functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having full-length WF-HABP functional activity. This is because the skilled artisan is fully aware of amino acid substitutions that are either less likely or not likely to significantly effect protein function (e.g., replacing one aliphatic amino acid with a second aliphatic amino acid).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA, the nucleic acid sequence shown in FIGS. 2A–D (SEQ ID NO:4), or fragments thereof, will encode polypeptides "having WF-HABP functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having WF-HABP functional activity. This is because the skilled artisan is fully aware of amino acid substitutions that are either less likely or not likely to significantly effect protein function (e.g., replacing one aliphatic amino acid with a second aliphatic amino acid).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA, the nucleic acid sequence shown in FIGS. 3A–C (SEQ ID NO:7), or fragments thereof will encode polypeptides "having OE-HABP functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having OE-HABP functional activity. This is because the skilled artisan is fully aware of amino acid substitutions that are either less likely or not likely to significantly effect protein function (e.g., replacing one aliphatic amino acid with a second aliphatic amino acid).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA, the nucleic acid sequence shown in FIGS. 4A–C (SEQ ID NO:10), or fragments thereof, will encode polypeptides "having BM-HABP functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having BM-HABP functional activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions of the full-length WF-HABP invention is provided in Bowie et al., "Deciphering the Message in Protein Sequences: Tolerance to Amino Acid Substitutions," Science 247:1306–1310 (1990), wherein the authors indicate that proteins are surprisingly tolerant of amino acid substitutions.

For example, guidance concerning how to make phenotypically silent amino acid substitutions of the WF-HABP invention is provided in Bowie et al., "Deciphering the Message in Protein Sequences: Tolerance to Amino Acid Substitutions," Science 247:1306–1310 (1990), wherein the authors indicate that proteins are surprisingly tolerant of amino acid substitutions.

For example, guidance concerning how to make phenotypically silent amino acid substitutions of the OE-HABP invention is provided in Bowie et al., "Deciphering the Message in Protein Sequences: Tolerance to Amino Acid Substitutions," Science 247:1306–1310 (1990), wherein the authors indicate that proteins are surprisingly tolerant of amino acid substitutions.

For example, guidance concerning bow to make phenotypically silent amino acid substitutions of the BM-HABP invention is provided in Bowie et al., "Deciphering the Message in Protein Sequences: Tolerance to Amino Acid Substitutions," Science 247:1306–1310 (1990), wherein the authors indicate that proteins are surprisingly tolerant of amino acid substitutions.

Vectors and Host Cells

The present invention also relates to vectors which include the isolated DNA molecules (i.e., polynucleotides) of the present invention, host cells which are genetically engineered with the recombinant vectors, and the production of full-length WF-HABP polypeptides or fragments thereof using these host cells or host cells that have otherwise been genetically engineered, using techniques known in the art to express a polypeptide of the invention.

The present invention also relates to vectors which include the isolated DNA molecules (i.e., polynucleotides) of the present invention, host cells which are genetically engineered with the recombinant vectors, and the production of WF-HABP polypeptides or fragments thereof using these host cells or host cells that have otherwise been genetically engineered using techniques known in the art to express a polypeptide of the invention.

The present invention also relates to vectors which include the isolated DNA molecules (i.e., polynucleotides) of the present invention, host cells which are genetically engineered with the recombinant vectors, and the production of OE-HABP polypeptides or fragments thereof using these host cells or host cells that have otherwise been genetically engineered using techniques known in the art to express a polypeptide of the invention.

The present invention also relates to vectors which include the isolated DNA molecules (i.e., polynucleotides) of the present invention, host cells which are genetically engineered with the recombinant vectors, and the production of BM-HABP polypeptides or fragments thereof using these host cells or host cells that have otherwise been genetically engineered using techniques known in the art to express a polypeptide of the invention.

The full-length WF-HABP polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The WF-HABP polynucleotides may be joined to a vector containing a selectable marker for propagation in a host. Generally, a plasmid vector is introduced in a precipitate, such as a calcium phosphate precipitate, or in a complex with a charged lipid if the vector is a virus, it may be packaged in vitro using an appropriate packaging cell line and then transduced into host cells.

The OE-HABP polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The BM-HABP polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

In one embodiment, a polynucleotide of the full-length WF-HABP invention are operatively associated with an appropriate heterologous regulatory element (e.g., promoter or enhancer), such as the phage lambda PL promoter, the *E. coli* lac, trp and tac promoters, the SV40 early and late promoters and promoters of retroviral LTRs, to name a few. Other suitable promoters or enhancers will be known to the skilled artisan.

In one embodiment, a polynucleotide of the WF-HABP invention are operatively associated with an appropriate heterologous regulatory element (e.g., promoter or enhancer), such as the phage lambda PL promoter, the *E. coli* lac, trp and tac promoters, the SV40 early and late promoters and promoters of retroviral LTRs, to name a few. Other suitable promoters or enhancers will be known to the skilled artisan.

In one embodiment, a polynucleotide of the OE-HABP invention are operatively associated with an appropriate heterologous regulatory element (e.g., promoter or enhancer), such as the phage lambda PL promoter, the *E. coli* lac, trp and tac promoters, the SV40 early and late promoters and promoters of retroviral LTRs, to name a few. Other suitable promoters or enhancers will be known to the skilled artisan.

In one embodiment, a polynucleotide of the BM-HABP invention are operatively associated with an appropriate heterologous regulatory clement (e.g., promoter or enhancer), such as the phage lambda PL promoter, the *E. coli* lac, trp and tac promoters, the SV40 early and late promoters and promoters of retroviral LTRs, to name a few. Other suitable promoters or enhancers will be known to the skilled artisan.

In full-length WF-HABP embodiments in which vectors contain expression constructs, these constructs will further contain sites for transcription initiation, termination and, in the transcribed region, a ribosome binding site for translation. The coding portion of the mature transcripts expressed by the vector expression constructs will preferably include a translation initiating at the beginning and a termination codon (UAA, UGA or UAG) appropriately positioned at the end of the polypeptide to be translated.

In WF-HABP embodiments in which vectors contain expression constructs, these constructs will further contain sites for transcription initiation, termination and, in the transcribed region, a ribosome binding site for translation. The coding portion of the mature transcripts expressed by the vector expression constructs will preferably include a translation initiating at the beginning and a termination codon (UAA, UGA or UAG) appropriately positioned at the end of the polypeptide to be translated.

In OE-HABP embodiments in which vectors contain expression constructs, these constructs will further contain sites for transcription initiation, termination and, in the transcribed region, a ribosome binding site for translation. The coding portion of the mature transcripts expressed by the vector expression constructs will preferably include a translation initiating at the beginning and a termination codon (UAA, UGA or UAG) appropriately positioned at the end of the polypeptide to be translated.

In BM-HABP embodiments in which vectors contain expression constructs, these constructs will further contain sites for transcription initiation, termination and, in the transcribed region, a ribosome binding site for translation. The coding portion of the mature transcripts expressed by the vector expression constructs will preferably include a translation initiating at the beginning and a termination codon (UAA, UGA or UAG) appropriately positioned at the end of the polypeptide to be translated.

As indicated, the full-length WF-HABP expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate heterologous hosts include, but are riot limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pHE4, pA2; and PO4, pBS vectors, Phagescript vectors, Bluescript vectors, pNH8A, pNH16a, pNH18A, pNH46A, available from Stratagene; and ptrc99a, pKK223-3, pKK233-3, pWF-HABP40, pRIT5 available from Pharmacia Among preferred eukaryotic vectors are pWLNEO, pSV2CAT, pOG44, pXT1 and pSG available from Stratagene; pSVK3, pBPV, pMSG and pSVL available from Pharmacia. Other suitable vectors will be readily apparent to the'skilled artisan.

Selection of appropriate vectors and promoters for expression in a host cell is a well known procedure and the requisite techniques for expression vector construction, introduction of the vector into the host and expression in the host are routine skills in the art.

As indicated, the WF-HABP expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate heterologous hosts include, but arc not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pHE4, pA2; and PO4, pBS vectors, Phagescript vectors, Bluescript vectors, pNH8A, pNH16a, pNH18A, pNH46A, available from Stratagene; and ptrc99a, pKK223-3, pKK233-3, pWF-HABP40, pRIT5 available from Pharmacia. Among preferred eukaryotic vectors are pWLNEO, pSV2CAT, pOG44, pXT1 and pSG available from Stratagene; pSVK3, pBPV, pMSG and pSVL available from Pharmacia. Other suitable vectors will be readily apparent to the skilled artisan.

Selection of appropriate vectors and promoters for expression in a host cell is a well known procedure and the requisite techniques for expression vector construction, introduction of the vector into the host and expression in the host are routine skills in the art.

As indicated, the OE-HABP expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate heterologous hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pHE4, pA2; and PO4, pBS vectors, Phagescript vectors, Bluescript vectors, pNH8A, pNH16a, pNH18A, pNH46A, available from Stratagene; and ptrc99a, pKK223-3, pKK233-3, pWF-HABP40, pRIT5 available from Pharmacia. Among preferred eukaryotic vectors are pWLNEO, pSV2CAT, pOG44, pXT1 and pSG available from Stratagene; pSVK3, pBPV, pMSG and pSVL available from Pharmacia. Other suitable vectors will be readily apparent to the skilled artisan.

Selection of appropriate vectors and promoters for expression in a host cell is a well known procedure and the requisite techniques for expression vector construction, introduction of the vector into the host and expression in the host are routine skills in the art.

As indicated, the BM-HABP expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate heterologous hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pHE4, pA2; and PO4, pBS vectors, Phagescript vectors, Bluescript vectors, pNH8A, pNH16a, pNH18A, pNH46A, available from Stratagene; and ptrc99a, pKK223-3, pKK233-3, pWF-HABP40, pRIT5 available from Pharmacia. Among preferred eukaryotic vectors are pWLNEO, pSV2CAT, pOG44, pXT1 and pSG available from Stratagene; pSVK3, pBPV, pMSG and pSVL available from Pharmacia. Other suitable vectors will be readily apparent to the skilled artisan.

Selection of appropriate vectors and promoters for expression in a host cell is a well known procedure and the requisite techniques for expression vector construction, introduction of the vector into the host and expression in the host are routine skills in the art.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., full-length WF-HABP coding sequence), and/or to include genetic material (e.g., heterologous polynucleotide sequences) that is operably associated with full-length WF-HABP polynucleotides of the invention, and which activates, alters, and/or amplifies endogenous full-length WF-HABP polynucleotides. For example, techniques known in the art may be used to operably associate heterologous control regions (e.g., promoter and/or enhancer) and endogenous full-length WF-HABP polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., WF-HABP coding sequence), and/or to include genetic material (e.g., heterologous polynucleotide sequences) that is operably associated with WF-HABP polynucleotides of the invention, and which activates, alters, and/or amplifies endogenous WF-HABP polynucleotides. For example, techniques known in the art may be used to operably associate heterologous control regions (e.g., promoter and/or enhancer) and endogenous WF-HABP polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., OE-HABP coding sequence), and/or to include genetic material (e.g., heterologous polynucleotide sequences) that is operably associated with OE-HABP polynucleotides of the invention, and which activates, alters, and/or amplifies endogenous OE-HABP polynucleotides. For example, techniques known in the art may be used to operably associate heterologous control regions (e.g., promoter and/or enhancer) and endogenous OE-HABP polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., BM-HABP coding sequence), and/or to include genetic material (e.g., heterologous polynucleotide sequences) that is operably associated with BM-HABP polynucleotides of the invention, and which activates, alters, and/or amplifies endogenous BM-HABP polynucleotides. For example, techniques known in the art may be used to operably associate heterologous control regions (e.g., promoter and/or enhancer) and endogenous BM-HABP polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted full-length WF-HABP gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., glycosylation, phosphorylation, cleavage) of proteins. Appropriate cell lines can be chosen to ensure the desired modifications and processing of the foreign protein expressed.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986).

The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted WF-HABP gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., glycosylation, phosphorylation, cleavage) of proteins. Appropriate cell lines can be chosen to ensure the desired modifications and processing of the foreign protein expressed.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986).

The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted OE-HABP gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., glycosylation, phosphorylation, cleavage) of proteins. Appropriate cell lines can be chosen to ensure the desired modifications and processing of the foreign protein expressed.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986).

The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted BM-HABP gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., glycosylation, phosphorylation, cleavage) of proteins.

Appropriate cell lines can be chosen to ensure the desired modifications and processing of the foreign protein expressed.

Introduction of the construct into the host cell can be effected by calcium phosphate transfection, DEAE-dextran mediated transfection, cationic lipid-mediated transfection, electroporation, transduction infection or other methods. Such methods are described in many standard laboratory manuals, such as Davis et al., Basic Methods In Molecular Biology (1986).

The full-length WF-HABP polypeptide may be expressed in a modified form, such as a fusion protein (comprising the polypeptide joined via a peptide bond to a heterologous protein sequence (of a different protein)), and may include not only secretion signals, but also additional heterologous functional regions. Such a fusion protein can be made by ligating polynucleotides of the invention and the desired nucleic acid sequence encoding the desired amino acid sequence to each other, by methods known in the art, in the proper reading free, and expressing the fusion protein product by methods known in the art. Alternatively, such a fusion protein can be made by protein synthetic techniques, e.g., by use of a peptide synthesizer. Thus, for instance, a region of additional amino acids, particularly charged amino acids, may be added to the N-terminus of the polypeptide to improve stability and persistence in the host cell, during purification, or during subsequent handling and storage. Additionally, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, human hIL-5 receptor have been fused with Fc portions for the purpose of high-throughput screening assays to identify antagonists of hIL-5. See, Bennett et al., J. Mol. Recog. 8:52–58 (1995) and Johanson et al., J. Biol. Chem. 270(16):9459–9471 (1995).

The WF-HABP polypeptide may be expressed in a modified form, such as a fusion protein (comprising the polypeptide joined via a peptide bond to a heterologous protein sequence (of a different protein)), and may include not only secretion signals, but also additional heterologous functional regions. Such a fusion protein can be made by ligating polynucleotides of the invention and the desired nucleic acid sequence encoding the desired amino acid sequence to each other, by methods known in the art, in the proper reading frame, and expressing the fusion protein product by methods known in the art. Alternatively, such a fusion protein can be made by protein synthetic techniques, e.g., by use of a peptide synthesizer. Thus, for instance, a region of additional amino acids, particularly charged amino acids, may be added to the N-terminus of the polypeptide to improve stability and persistence in the host cell, during purification, or during subsequent handling and storage. Additionally, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, human hIL-5 receptor have been fused with Fc portions for the purpose of high-throughput screening assays to identify antagonists of hIL-5. See, Bennett et al., J. Mol. Recog. 8:52–58 (1995) and Johanson et al., J. Biol. Chem. 270(16):9459–9471 (1995).

The OE-HABP polypeptide may be expressed in a modified form, such as a fusion protein (comprising the polypeptide joined via a peptide bond to a heterologous protein sequence (of a different protein)), and may include not only secretion signals, but also additional heterologous functional regions. Such a fusion protein can be made by ligating polynucleotides of the invention and the desired nucleic acid sequence encoding the desired amino acid sequence to each other, by methods known in the art, in the proper reading frame, and expressing the fusion protein product by methods known in the art. Alternatively, such a fusion protein can be made by protein synthetic techniques, e.g., by use of a peptide synthesizer. Thus, for instance, a region of additional amino acids, particularly charged amino acids, may be added to the N-terminus of the polypeptide to improve stability and persistence in the host cell, during purification, or during subsequent handling and storage. Additionally, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fe part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, human hIL-5 receptor have been fused with Fc portions for the purpose of high-throughput screening assays to identify antagonists of hIL-5. See, Bennett et al., J. Mol. Recog. 8:52–58 (1995) and Johanson et al., J. Biol. Chem. 270(16):9459–9471 (1995).

The BM-HABP polypeptide may be expressed in a modified form, such as a fusion protein (comprising the polypeptide joined via a peptide bond to a heterologous protein sequence (of a different protein)), and may include not only secretion signals, but also additional heterologous functional regions. Such a fusion protein can be made by ligating polynucleotides of the invention and the desired nucleic acid sequence encoding the desired amino acid sequence to each other, by methods known in the art, in the proper reading frame, and expressing the fusion protein product by methods known in the art. Alternatively, such a fusion protein can be made by protein synthetic techniques, e.g., by use of a peptide synthesizer. Thus, for instance, a region of additional amino acids, particularly charged amino acids, may be added to the N-terminus of the polypeptide to improve stability and persistence in the host cell, during purification, or during subsequent handling and storage. Additionally, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, human hIL-5 receptor have been fused with Fc portions for the purpose of high-throughput screening assays to identify antagonists of hIL-5. See, Bennett et al., J. Mol. Recog. 8:52–58 (1995) and Johanson et al., J. Biol. Chem. 270(16):9459–9471 (1995).

Full-length WF-HABP polypeptides (including fragments, variants, derivatives, and analogs thereof) can be recovered and purified from recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, or alternatively, may be missing the N-terminal methionine, in some cases as a result of host-mediated processes.

WF-HABP polypeptides (including fragments, variants, derivatives, and analogs thereof) can be recovered and purified from recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides ,of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, or alternatively, may be missing the N-terminal methionine, in some cases as a result of host-mediated processes.

OE-HABP polypeptides (including fragments, variants, derivatives, and analogs thereof) can be recovered and purified from recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, or alternatively, may be missing the N-terminal methionine, in some cases as a result of host-mediated processes.

BM-HABP polypeptides (including fragments, variants, derivatives, and analogs thereof) can be recovered and purified from recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydrox lapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, or alternatively, may be missing the N-terminal methionine, in some cases as a result of host-mediated processes.

WF-HABP Polypeptides and Fragments

The invention further provides isolated full-length WF-HABP polypeptides corresponding to the amino acid sequence depicted in FIGS. 1A–P (SEQ ID NO:2), or a polypeptide comprising a fragment (i.e., portion) of the above polypeptides.

The polypeptides of the full-length WF-HABP invention may be membrane bound or may be in a soluble circulating form. Soluble peptides are defined by amino acid sequence wherein the sequence comprises the polypeptide sequence lacking transmembrane domains.

The invention further provides isolated WF-HABP polypeptides having the amino acid sequence encoded by the deposited cDNA (i.e., clone HWFBG79), the amino acid sequence depicted in FIGS. 2A–D (SEQ ID NO:5), or a polypeptide comprising a fragment (i.e., portion) of the above polypeptides.

The polypeptides of the WF-HABP invention may be membrane bound or may be in a soluble circulating form. Soluble peptides are defined by amino acid sequence wherein the sequence comprises the polypeptide sequence lacking transmembrane domains.

The invention further provides isolated OE-HABP polypeptides having the amino acid sequence encoded by the deposited cDNA (i.e., clone HOEDH76), the amino acid sequence depicted in FIGS. 3A–C (SEQ ID NO:8), or a polypeptide comprising a fragment (i.e., portion) of the above polypeptides.

The polypeptides of the OE-HABP invention may be membrane bound or may be in a soluble circulating form. Soluble peptides are defined by amino acid sequence wherein the sequence comprises the polypeptide sequence lacking transmembrane domains.

The invention further provides isolated BM-HABP the amino acid sequence encoded by the deposited cDNA (i.e., clone HBMVC21), the amino acid sequence depicted in FIGS. 4A–C (SEQ ID NO:11), or a polypeptide comprising a fragment (i.e., portion) of the above polypeptides.

The polypeptides of the BM-HABP invention may be membrane bound or may be in a soluble circulating form. Soluble peptides are defined by amino acid sequence wherein the sequence comprises the polypeptide sequence lacking transmembrane domains.

The polypeptides of the present invention are preferably provided in an isolated form. By "isolated polypeptide", is intended a polypeptide removed from its native environment. Thus, a polypeptide produced and contained within a recombinant host cell would be considered "isolated" for purposes of the present invention. Also intended as an "isolated polypeptide" are polypeptides that have been purified, partially or substantially, from a recombinant host. For example, recombinantly produced versions of the full-length WF-HABP polypeptides can be substantially purified by the one-step method described in Smith and Johnson, Gene 67:31–40 (1988).

The polypeptides of the present invention are preferably provided in an isolated form. By "isolated polypeptide", is intended a polypeptide removed from its native environment. Thus, a polypeptide produced and contained within a recombinant host cell would be considered "isolated" for purposes of the present invention. Also intended as an "isolated polypeptide" are polypeptides that have been purified, partially or substantially, from a recombinant host. For example, recombinantly produced versions of WF-HABP polypeptides can be substantially purified by the one-step method described in Smith and Johnson, Gene 67:3140 (1988).

The polypeptides of the present invention are preferably provided in an isolated form. By "isolated polypeptide", is intended a polypeptide removed from its native environment. Thus, a polypeptide produced and contained within a recombinant host cell would be considered "isolated" for purposes of the present invention. Also intended as an. "isolated polypeptide" are polypeptides that have been purified, partially or substantially, from a recombinant host. For example, recombinantly produced versions of OE-HABP polypeptides can be substantially purified by the one-step method described in Smith and Johnson, Gene 67:3140 (1988).

The polypeptides of the present invention are preferably provided in an isolated form. By "isolated polypeptide", is intended a polypeptide removed from its native environment. Thus, a polypeptide produced and contained within a recombinant host cell would be considered "isolated" for purposes of the present invention. Also intended as an "isolated polypeptide" are polypeptides that have been purified, partially or substantially, from a recombinant host. For example, recombinantly produced versions of BM-HABP polypeptides can be substantially purified by the one-step method described in Smith and Johnson, Gene 67:31–40 (1988).

Polypeptide fragments of the present invention include polypeptides comprising or alternatively, consisting of, an amino acid sequence contained in SEQ ID NO:2, or corresponding to nucleic acids which hybridize (e.g., under stringent hybridization conditions) to the nucleotide shown in FIGS. 1A–P (SEQ ID NO:1) or the complementary strand thereto. Protein fragments may be "free-standing," or comprised within a larger polypeptide of which the fragment forms a part or region, most preferably as a single continuous region. Representative examples of polypeptide fragments of the invention, include, for example, fragments that comprise or alternatively, consist of from amino acid residues: 1 to 50, 51 to 100, 101 to 150, 151 to 200, 201 to 250, 251 to 300, 301 to 350, 321 to 333, 351 to 400, 401 to 450,451 to 500, 501 to 550, 551 to 600, 576 to 606, 601 to 650, 651 to 700, 701 to 750, 751 to 800, 801 to 850, 851 to 900, 901 to 950, 1001 to 1050, 1051 to 1100, 1101 to 1150, 1151 to 1200, 1201 to 1250, 1251 to 1300, 1301 to 1350, 1351 to 1400, 1401 to 1450, 1451 to 1500, 1501 to 1550, 1551 to 1600, 1601 to 1650, 1651 to 1700, 1701 to 1750, 1751 to 1800, 1801 to 1850, 1851 to 1900, 1901 to 1950, 1951 to 2000, 2001 to 2050, 2051 to 2100 of SEQ ID NO:2. Moreover, polypeptide fragments can be at least 10, 20, 30, 40, 50, 60, 70, 80, 90, 100, 110, 120, 130, 140, 150, 175, 200, 250, 300, 350, 400, 450, 500, 600, 700, 800, 900, 1000, 1250, 1500, 1750, 2000, or 2100 amino acids in length.

Polypeptide fragments of the present invention include polypeptides comprising or alternatively, consisting of, an amino acid sequence contained in SEQ ID NO:5, corresponding to the cDNA contained in the deposited clone, or corresponding to nucleic acids which hybridize (e.g., under stringent hybridization conditions) to the nucleotide sequence contained in the deposited clone, or shown in FIGS. 2A–D (SEQ ID NO:5) or the complementary strand thereto. Protein fragments may be "free-standing," or comprised within a larger polypeptide of which the fragment forms a part or region, most preferably as a single continuous region. Representative examples of polypeptide fragments of the invention, include, for example, fragments that comprise or alternatively, consist of from amino acid residues: 1 to 50, 51 to 100, 101 to 150, 151 to 200, 201 to 250, 251 to 300, 301 to 350, 321 to 333, 351 to 400, 401 to 450, and/or 451 to 457 of SEQ ID NO:2. Moreover, polypeptide fragments can be at least 10, 20, 30, 40, 50, 60, 70, 80, 90, 100, 110, 120, 130, 140, 150, 175, 200, 250, 300, 350, 400, 450, or 457 amino acids in length.

Polypeptide fragments of the present invention include polypeptides comprising or alternatively, consisting of, an amino acid sequence contained in SEQ ID NO:8, corresponding to the cDNA contained in the deposited clone, or corresponding to nucleic acids which hybridize (e.g., under stringent hybridization conditions) to the nucleotide sequence contained in the deposited clone, or shown in FIGS. 3A–C (SEQ ID NO:8) or the complementary strand thereto. Protein fragments may be "free-standing," or comprised within a larger polypeptide of which the fragment forms a part or region, most preferably as a single continuous region. Representative examples of polypeptide fragments of the invention, include, for example, fragments that comprise or alternatively, consist of from amino acid residues: 1 to 50, 51 to 100, 101 to 150, 151 to 200, 201 to 250, and/or 251 to 289 of SEQ ID NO:5. Moreover, polypeptide fragments can be at least 10, 20, 30, 40, 50, 60, 70, 80, 90, 100, 110, 120, 130, 140, 150, 175, 200, 250, or 289 amino acids in length.

Polypeptide fragments of the present invention include polypeptides comprising or alternatively, consisting of, an amino acid sequence contained in SEQ ID NO:11, corresponding to the cDNA contained in the deposited clone, or corresponding to nucleic acids which hybridize (e.g., under stringent hybridization conditions) to the nucleotide sequence contained in the deposited clone, or shown in FIGS. 4A–C (SEQ ID NO:11) or the complementary strand thereto. Protein fragments may be "free-standing," or comprised within a larger polypeptide of which the fragment forms a part or region, most preferably as a single continuous region. Representative examples of polypeptide fragments of the invention, include, for example, fragments that comprise or alternatively, consist of from amino acid residues: 1 to 50, 51 to 100, 101 to 150, 151 to 200, 201 to 250, 251 to 300, 301 to 350, 351 to 353, of SEQ ID NO:11. Moreover, polypeptide fragments can be at least 10, 20, 30, 40, 50, 60, 70, 80, 90, 100, 110, 120, 130, 140, 150, 175, 200, 250, 300, 350, or 353 amino acids in length.

In additional embodiments, the polypeptide fragments of the invention comprise, or alternatively consist, of one or more full-length WF-HABP receptor domains. In particular embodiments, such polypeptide fragments comprise, or alternatively, consist of: (a) an HA binding motif (amino acid residues E-1791 to C-1894 of SEQ ID NO:2); (b) EGF-like Type 1 domains (amino acid residues from C-375 to C-386, amino acid residues from C-943 to C-954, amino acid residues from C-987 to C-998, amino acid residues from C-1582 to C-1593, and amino acid residues from C-1626 to C-1637 of SEQ ID NO:2); (c) EGF-like Type 2 domains (amino acid residues from C-465 to C-478, amino acid residues from C-508 to C-521, amino acid residues from C-551 to C-564, amino acid residues from C-943 to C-957, amino acid residues from C-987 to C-998, amino acid residues from C-1027 to C-1040, amino acid residues from C-1069 to C-1082, amino acid residues from C-1111 to C-1125, amino acid residues from C-1582 to C-1596, amino acid residues from C-1582 to C-1596, amino acid residues from C-1626 to C-1637, amino acid residues from C-1663 to C-1676, amino acid residues from C-1747 to C-1760, and amino acid residues from C-1894 to C-1908 of SEQ ID NO:2); (d) a laminin-type EGF domain (amino acid residues from C-943 to C-977, and amino acid residues from C-1582 to C-1616 of SEQ ID NO:2); (e) a link protein domain (amino acid residues from C-1817 to C-1862 of SEQ ID NO:2); (f) a cytochrome P450 cysteine heme-iron ligand binding domains (amino acid residues from F-344 to G-353, and amino acid residues from W-514 to A-523 of SEQ ID NO:2); (g) a prokaryotic membrane lipoprotein lipid attachment site domains (amino acid residues from P-1103 to C-1113, and amino acid residues from T-1405 to C-1415 of SEQ ID NO:2 or (h) any combination of polypeptides (a)–(g).

In additional embodiments, the polypeptide fragments of the invention comprise, or alternatively consist, of one or more WF-HABP receptor domains. In particular embodiments, such polypeptide fragments comprise, or alternatively, consist of: (a) an HA binding motif (amino acid residues E-91 to C-194 of SEQ ID NO:5); (b) an EGF-like Type 2 domain (amino acid residues C-194 to C-208, of SEQ ID NO:5); (c) a link domain (amino acid residues C-117 to C-162, of SEQ ID NO:5); (d) any fragment described herein; (e) the polypeptide sequence of FIGS. 2A–D (SEQ ID NO:5) minus a portion, or all of, the HA binding domain, the EGF-like Type 2 domain, and the link domain of WF-HABP shown in FIGS. 2A–D (SEQ ID NO:5); and (f) any combination of polypeptides (a)–(e).

In additional embodiments, the polypeptide fragments of the invention comprise, or alternatively consist, of one or more OE-HABP receptor domains. In particular embodiments, such polypeptide fragments comprise, or alternatively, consist of: (a) an HA binding motif domain (amino acid residues P-97 to F-168, amino acid residues L-209 to C-286, of SEQ ID NO:8); (b) a link protein domain (amino acid residues C-188 to C-233 of SEQ ID NO:8); (c) any fragment described herein, (d) the polypeptide sequence of FIGS. 3A–C (SEQ ID NO:8) minus a portion, or all of, the HA binding domain, and the link domain of OE-HABP shown in FIGS. 3A–C (SEQ ID NO:8); and (e) any combination of polypeptides (a)–(d).

In additional embodiments, the polypeptide fragments of the invention comprise, or alternatively consist, of one or more BM-HABP receptor domains. In particular embodiments, such polypeptide fragments comprise, or alternatively, consist of: (a) an HA binding motif domain (amino acid residues Q-121 to L-215 in (SEQ ID NO:11)); (b) any fragment described herein; (c) the polypeptide sequence of FIGS. 4A–C (SEQ ID NO:11) minus a portion, or all of, the HA binding domain of BM-HABP shown in FIGS. 4A–C (SEQ ID NO:11); and (d) any combination of polypeptides (a)–(c).

Among the especially preferred fragments of the invention are fragments characterized by structural or functional attributes of the full-length WF-HABP. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of full-length WF-HABP (SEQ ID NO:2). Certain preferred regions are those set out in FIGS.

3A–C and include, but are not limited to, regions of the aforementioned types identified by analysis of the amino acid sequence depicted in FIGS. 1A–P (SEQ ID NO:2), such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

Among the especially preferred fragments of the invention are fragments characterized by structural or functional attributes of WF-HABP. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of WF-HABP (SEQ ID NO:5). Certain preferred regions are those set out in FIGS. 3A–C and include, but are not limited to, regions of the aforementioned types identified by analysis of the amino acid sequence depicted in FIGS. 2A–D (SEQ ID NO:5), such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

Among the especially preferred fragments of the invention are fragments characterized by structural or functional attributes of the OE-HABP. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of OE-HABP (SEQ ID NO:8). Certain preferred regions are those set out in FIGS. 3A–C and include, but are not limited to, regions of the aforementioned types identified by analysis of the amino acid sequence depicted in FIGS. 3A–C (SEQ ID NO:8), such preferred regions include; Garnier-Robson predicted alpha-regions, beta-regions, turn-regions, and coil-regions;. Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

Among the especially preferred fragments of the invention are fragments characterized by structural or functional attributes of the BM-HABP. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of BM-HABP (SEQ ID NO:11). Certain preferred regions are those set out in FIGS. 3A–C and include, but are not limited to, regions of the aforementioned types identified by analysis of the amino acid sequence depicted in FIGS. 4A–C (SEQ ID NO:11), such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

In specific embodiments, polypeptide fragments of the full-length WF-HABP invention comprise, or alternatively consist of, amino acid residues: 365 to 375, 376 to 385, 386 to 395, 396 to 405, 406 to 415, 416 to 425, 426 to 435, 436 to 445, 446 to 455, 456 to 465, 466 to 475, 476 to 485, 486 to 495, 496 to 505, 506 to 515, 516 to 525, 526 to 535, 536 to 545, 546 to 555, 556 to 565, 566 to 575, 576 to 585, 586 to 595, 596 to 605, 606 to 615, 616 to 625, 626 to 635, 636 to 645, 646 to 655, 656 to 665, 666 to 675, 676 to 685, 686 to 695, 696 to 705, 706 to 715, 716 to 725, 726 to 735, 736 to 745, 746 to 755, 756 to 765, 766 to 775, 776 to 785, 786 to 795, 796 to 805, 806 to 815, 816 to 825, 826 to 835, 836 to 845, 846 to 855, 856 to 865, 866 to 875, 876 to 885, 886 to 895, 896 to 905, 906 to 915, 916 to 925, 926 to 935, 936 to 945, 946 to 955, 956 to 965, 966 to 975, 976 to 985, 986 to 995, 996 to 1005, 1006 to 1015, 1016 to 1025, 1026 to 1035, 1036 to 1045, 1046 to 1055, 1056 to 1065, 1066 to 1075, 1076 to 1085, 1086 to 1095, 1096 to 1105, 1106 to 1115, 1116 to 1125, 1126 to 1135, 1136 to 1145, 1146 to 1155, 1156 to 1165, 1166 to 1175, 1176 to 1185, 1186 to 1195, 1196 to 1205, 1206, 1215, 1216 to 1225, 1226 to 1235, 1236 to 1245, 1246 to 1255, 1256 to 1265, 1266 to 1275, 1276 to 1285, 1286 to 1295, 1296 to 1305, 1306 to 1315, 1316 to 1325, 1326 to 1335, 1336 to 1345, 1346 to 1355, 1356 to 1365, 1366 to 1375, 1376 to 1385, 1386 to 1395, 1396 to 1405, 1406 to 1415, 1416 to 1425, 1426 to 1435, 1436 to 1445, 1446 to 1455, 1456 to 1465, 1466 to 1475, 1476 to 1485, 1486 to 1495, 1496 to 1505, 1506 to 1515, 1516 to 1525 1526 to 1535, 1536 to 1545, 1546 to 1555, 1556 to 1565, 1566 to 1575, 1576 to 1585, 1586 to 1595, 1605, 1606 to 1615, 1616 to 1625, 1626 to 1635, 1636 to 1645, 1646 to 1655, 1656 to 1665, 1666 to 1675, 1676 to 1685, 1686 to 1695, 1696 to 1705, 1706 to 1715, 1716 to 1725, 1726 to 1735, 1736 to 1745, 1746 to 1755, 1756 to 1765, 1766 to 1775, 1776 to 1785, and/or 1786 to 1795 as depicted in FIGS. 1A–P (SEQ ID NO:2). Polynucleotides encoding these polypeptides are also encompassed by the invention.

In specific embodiments, polypeptide fragments of the WF-HABP invention comprise or alternatively consist of, amino acid residues: 1 to 10, 5 to 15, 16 to 25, 26 to 35, 36 to 45, 46 to 55, 56 to 65, 66 to 75, 76 to 85, 86 to 95, 96 to 105, 106 to 115, 116 to 125, 126 to 135, 136 to 145, 146 to 155, 156 to 165, 166 to 175, 176 to 185, 186 to 195, 196 to 205, 206 to 215, and/or 216 to 225 as depicted in FIGS. 2A–D (SEQ ID NO:5). Polynucleotides encoding these polypeptides are also encompassed by the invention.

In specific embodiments, polypeptide fragments of the OE-HABP invention comprise, or alternatively consist of, amino acid residues: 52 to 60, 61 to 70, 71 to 80, 81 to 90, 91 to 100, 101 to 110, 111 to 120, 200 to 209, 210 to 220, 221 to 230, 231 to 240, 241 to 250, 251 to 260, 261 to 270, 271 to 280, and/or 281 to 290 as depicted in FIGS. 3A–C (SEQ ID NO:8). Polynucleotides encoding these polypeptides are also encompassed by the invention.

In specific embodiments, polypeptide fragments of the BM-HABP invention comprise, or alternatively consist of, amino acid residues: 1 to 10, 11 to 20, 21 to 30, 31 to 40, 41 to 50, 51 to 60, 61 to 70, 71 to 80, 81 to 88, 200 to 209, 210 to 220, 221 to 230, 231 to 240, 241 to 250, 251 to 260, 261 to 270, 271 to 280, 281 to 290, 291 to 300, 301 to 310, 311 to 320, 321 to 330, 331 to 340, and/or 341 to 350, as depicted in FIGS. 4A–C (SEQ ID NO:11). Polynucleotides encoding these polypeptides are also encompassed by the invention.

Among the especially preferred fragments of the invention are fragments characterized by structural or functional attributes of WF-HABP, OE-HABP, and BM-HABP. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) WF-HABP (SEQ ID NO:2), WF-HABP (SEQ ID NO:5), complete (i.e., full-length) OE-HABP (SEQ ID NO:8), and complete (i.e., full-length) BM-HABP (SEQ ID NO:11). Certain preferred regions are those set out in FIGS. 9A–B, 10A–B, 11A–B, and 12A–B, respectively, and include, but are not limited to, regions of the aforementioned types identified by analysis of the amino acid sequence depicted in FIGS. 1A–P (SEQ ID NO:2), FIGS. 2A–D (SEQ ID NO:5), FIGS. 3A–C (SEQ ID NO:8), and FIGS. 4A–C (SEQ ID NO:11), and such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

In additional embodiments, the polynucleotides of the invention encode functional attributes of WF-HABP, OE-HABP, and BM-HABP. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of WF-HABP, OE-HABP, and BM-HABP.

The data representing the structural or functional attributes of WF-HABP, OE-HABP, and BM-HABP are set forth in FIGS. 1A–P, FIGS. 2A–D, FIGS. 3A–C, and FIGS. 4A–C, and/or Tables I–IV, as described above, was generated using the various modules and algorithms of the DNA*STAR set on default parameters. In a preferred embodiment, the data presented in columns VIII, IX, XIII, and XIV of Tables I–IV can be used to determine regions of WF-HABP, OE-HABP, and BM-HABP which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response.

Certain preferred regions of WF-HABP (SEQ ID NO:2) in these regards are set out in FIGS. 9A–B, but may, as shown in Table I, be represented or identified by using tabular representations of the data presented in FIGS. 9A–B. Certain preferred regions of WF-HABP (SEQ ID NO:5) in these regards are set out in FIGS. 10A–B, but may, as shown in Table II, be represented or identified by using tabular representations of the data presented in FIGS. 10A–B. Certain preferred regions of OE-HABP (SEQ ID NO:8) in these regards are set out in FIGS. 11A–B, but may, as shown in Table III, be represented or identified by using tabular representations of the data presented in FIGS. 1A–B. Certain preferred regions of BM-HABP (SEQ ID NO:11) in these regards are set out in FIGS. 12A–B, but may, as shown in Table IV, be represented or identified by using tabular representations of the data presented in FIGS. 12A–B. The DNA*STAR computer algorithm used to generate FIGS. 9A–B, FIGS. 10A–B, FIGS. 11A–B, and FIGS. 12A–B (set on the original default parameters) was used to present the data in FIGS. 9A–B, FIGS. 10A–B, FIGS. 11A–B, and FIGS. 12A–B in a tabular format (See Tables I–IV). The tabular format of the data in FIGS. 9A–B, FIGS. 10A–B, FIGS. 11A–B, and FIGS. 12A–B may be used to easily determine specific boundaries of a preferred region.

The above-mentioned preferred regions set out in FIGS. 9A–B, FIGS. 10A–B, FIGS. 11A–B, and FIGS. 12A–B and in Tables I–IV include, but are not limited to, regions of the aforementioned types identified by analysis of the amino acid sequence set out in FIGS. 1A–P, FIGS. 2A–D, FIGS. 3A–C, and FIGS. 4A–C, respectively. As set out in FIGS. 9A–B, FIGS. 10A–B, FIGS. 11A–B, and FIGS. 12A–B and in Tables I–IV, such preferred regions include Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index.

TABLE I

| Res Pos. | | I | II | III | IV | V | VI | VII | VIII | IX | X | XI | XII | XIII | XIV |
|---|---|---|---|---|---|---|---|---|---|---|---|---|---|---|---|
| Met | 1 | . | . | . | B | . | . | . | . | 0.40 | . | . | . | 0.99 | 1.06 |
| Met | 2 | . | . | . | B | . | . | . | . | 0.12 | * | . | . | 1.18 | 0.82 |
| Asp | 3 | . | . | . | . | . | T | T | . | 0.62 | * | . | . | 1.52 | 0.34 |
| Gln | 4 | . | . | . | . | . | T | T | . | 1.01 | * | . | . | 2.46 | 0.68 |
| Gly | 5 | . | . | . | . | . | T | T | . | 0.51 | * | . | F | 3.40 | 1.19 |
| Cys | 6 | . | . | . | B | . | . | T | . | 0.30 | * | . | F | 2.51 | 0.50 |
| Arg | 7 | . | . | . | B | B | . | . | . | 0.59 | * | . | F | 1.47 | 0.24 |
| Glu | 8 | . | . | . | B | B | . | . | . | 0.28 | * | . | . | 0.98 | 0.35 |
| Ile | 9 | . | . | . | B | B | . | . | . | −0.31 | * | . | . | 0.64 | 0.94 |
| Leu | 10 | . | . | . | B | B | . | . | . | −0.31 | * | . | . | 0.30 | 0.48 |
| Thr | 11 | . | . | . | B | B | . | . | . | 0.14 | * | . | F | −0.15 | 0.28 |
| Thr | 12 | . | . | . | . | B | T | . | . | −0.67 | * | . | F | −0.05 | 0.61 |
| Ala | 13 | . | . | . | . | B | . | . | C | −0.98 | . | . | F | −0.25 | 0.64 |
| Gly | 14 | . | . | . | . | . | . | T | C | −0.94 | * | . | F | 0.15 | 0.64 |
| Pro | 15 | . | . | . | . | . | . | T | C | −0.94 | * | . | F | 0.15 | 0.33 |
| Phe | 16 | . | . | . | B | . | . | T | . | −1.49 | . | . | . | −0.20 | 0.27 |
| Thr | 17 | . | . | . | B | . | . | T | . | −1.39 | . | . | . | −0.20 | 0.20 |
| Val | 18 | . | . | . | B | B | . | . | . | −1.10 | * | . | . | −0.60 | 0.20 |
| Leu | 19 | . | . | . | B | B | . | . | . | −1.61 | * | . | . | −0.60 | 0.31 |
| Val | 20 | . | . | . | B | B | . | . | . | −1.70 | * | . | . | −0.60 | 0.16 |
| Pro | 21 | . | . | . | B | B | . | . | . | −1.30 | * | . | F | −0.45 | 0.29 |
| Ser | 22 | . | . | . | B | . | . | T | . | −1.69 | * | . | F | −0.05 | 0.47 |
| Val | 23 | . | . | . | B | . | . | T | . | −1.13 | * | . | F | −0.05 | 0.55 |
| Ser | 24 | . | . | . | B | . | . | T | . | −0.62 | * | * | F | −0.05 | 0.48 |
| Ser | 25 | . | . | . | B | . | . | T | . | 0.34 | * | * | F | 0.25 | 0.48 |
| Phe | 26 | . | . | . | B | . | . | . | . | 0.24 | * | . | F | 1.04 | 1.25 |
| Ser | 27 | . | . | . | B | . | . | T | . | −0.06 | * | . | F | 1.48 | 1.35 |
| Ser | 28 | . | . | . | . | . | . | T | C | 0.80 | * | . | F | 1.17 | 1.00 |
| Arg | 29 | . | . | . | B | . | . | T | . | 0.51 | * | . | F | 1.36 | 1.85 |
| Thr | 30 | . | . | . | . | . | . | T | C | 0.51 | * | * | F | 2.40 | 1.40 |
| Met | 31 | . | . | . | . | . | . | . | C | 0.40 | . | . | . | 1.81 | 1.40 |
| Asn | 32 | . | . | . | . | . | . | T | C | 0.11 | * | . | . | 1.02 | 0.59 |
| Ala | 33 | . | . | . | . | . | . | T | C | 0.41 | . | . | . | 0.48 | 0.41 |
| Ser | 34 | . | . | . | . | . | . | T | C | 0.30 | * | * | . | 0.24 | 0.72 |
| Leu | 35 | . | . | . | B | . | . | T | . | −0.20 | . | * | . | 0.10 | 0.78 |
| Ala | 36 | . | . | A | B | . | . | . | . | −0.27 | * | * | . | −0.60 | 0.63 |
| Gln | 37 | . | . | A | B | . | . | . | . | −0.16 | * | . | . | −0.60 | 0.25 |
| Gln | 38 | . | . | A | B | . | . | . | . | 0.43 | * | . | . | −0.30 | 0.60 |
| Leu | 39 | . | . | A | B | . | . | . | . | 0.70 | * | * | . | 0.45 | 1.03 |
| Cys | 40 | . | . | A | B | . | . | . | . | 0.62 | * | . | . | 0.30 | 0.81 |
| Arg | 41 | . | . | A | B | . | . | . | . | 0.32 | * | . | . | −0.30 | 0.33 |
| Gln | 42 | . | . | A | B | . | . | . | . | −0.27 | * | . | . | −0.60 | 0.28 |
| His | 43 | . | . | A | B | . | . | . | . | −0.61 | * | . | . | −0.30 | 0.53 |
| Ile | 44 | . | . | A | B | . | . | . | . | 0.20 | * | . | . | −0.30 | 0.27 |
| Ile | 45 | . | . | A | B | . | . | . | . | 0.83 | * | . | . | −0.60 | 0.27 |
| Ala | 46 | . | . | A | B | . | . | . | . | −0.17 | * | . | . | −0.60 | 0.27 |
| Gly | 47 | . | . | A | B | . | . | . | . | −0.98 | . | . | . | −0.60 | 0.27 |
| Gln | 48 | . | . | A | B | . | . | . | . | −0.94 | . | . | . | −0.60 | 0.31 |
| His | 49 | . | . | A | B | . | . | . | . | −0.06 | . | . | . | −0.30 | 0.54 |
| Ile | 50 | . | . | A | B | . | . | . | . | 0.52 | * | * | . | 0.64 | 0.90 |
| Leu | 51 | . | . | A | B | . | . | . | . | 1.22 | * | . | . | 0.98 | 0.75 |
| Glu | 52 | . | . | A | B | . | . | . | . | 1.26 | * | * | F | 1.92 | 1.08 |
| Asp | 53 | . | . | . | . | . | T | T | . | 1.26 | * | . | F | 3.06 | 2.23 |
| Thr | 54 | . | . | . | . | . | T | T | . | 1.29 | . | * | F | 3.40 | 4.68 |
| Arg | 55 | . | . | . | . | . | T | T | . | 1.87 | * | . | F | 3.06 | 4.68 |
| Thr | 56 | . | . | . | . | . | T | T | . | 2.79 | . | . | F | 2.72 | 4.05 |
| Gln | 57 | . | . | . | . | B | T | . | . | 2.90 | . | * | F | 1.98 | 5.49 |
| Gln | 58 | . | . | . | . | B | T | . | . | 2.61 | * | * | F | 1.64 | 5.49 |
| Thr | 59 | . | . | . | . | B | . | . | C | 2.63 | * | . | F | 0.80 | 4.00 |
| Arg | 60 | . | . | . | . | B | T | . | . | 2.21 | . | * | F | 0.40 | 2.43 |
| Arg | 61 | . | . | . | . | B | T | . | . | 1.71 | * | . | F | 0.40 | 2.03 |
| Trp | 62 | . | . | . | . | B | T | . | . | 1.12 | * | . | . | −0.05 | 1.16 |
| Trp | 63 | . | . | . | . | B | . | . | C | 0.78 | * | . | . | −0.40 | 0.60 |
| Thr | 64 | . | . | . | . | B | . | . | C | 1.09 | * | . | . | −0.40 | 0.30 |
| Leu | 65 | . | . | . | . | B | . | . | C | 0.98 | * | . | . | −0.40 | 0.50 |
| Ala | 66 | . | . | . | . | B | . | . | C | −0.02 | * | . | . | −0.40 | 0.82 |
| Gly | 67 | . | . | . | . | B | . | . | C | −0.04 | . | . | F | 0.05 | 0.40 |
| Gln | 68 | . | . | . | . | B | . | . | C | −0.61 | . | . | F | 0.05 | 0.70 |
| Glu | 69 | . | . | . | B | B | . | . | . | −0.61 | . | * | F | −0.15 | 0.51 |
| Ile | 70 | . | . | . | B | B | . | . | . | −0.50 | . | * | F | −0.15 | 0.75 |
| Thr | 71 | . | . | . | B | B | . | . | . | 0.09 | * | * | . | −0.60 | 0.37 |
| Val | 72 | . | . | . | B | B | . | . | . | 0.43 | * | * | . | −0.60 | 0.35 |
| Thr | 73 | . | . | . | B | B | . | . | . | −0.27 | * | * | . | −0.60 | 0.85 |
| Phe | 74 | . | . | . | B | B | . | . | . | −0.58 | * | * | . | −0.60 | 0.51 |
| Asn | 75 | . | . | . | B | B | . | . | . | 0.36 | * | * | . | −0.60 | 1.00 |
| Gln | 76 | . | . | . | B | B | . | . | . | 0.42 | * | . | . | −0.15 | 1.38 |
| Phe | 77 | . | . | . | . | B | T | . | . | 0.98 | * | . | F | 0.10 | 2.50 |

TABLE I-continued

| Res Pos. |     | I   | II | III | IV | V | VI | VII | VIII | IX    | X | XI | XII | XIII  | XIV  |
|----------|-----|-----|----|-----|----|---|----|-----|------|-------|---|----|-----|-------|------|
| Thr      | 78  |     |    |     |    | B | T  |     |      | 1.04  | * | *  | F   | 0.40  | 2.08 |
| Lys      | 79  |     |    |     |    | B | T  |     |      | 1.79  | * | *  | F   | 0.10  | 1.88 |
| Tyr      | 80  |     |    |     |    |   | T  | T   |      | 1.54  | * | *  |     | 0.99  | 4.35 |
| Ser      | 81  |     |    |     |    |   | T  | T   |      | 1.59  | * | *  |     | 1.33  | 4.73 |
| Tyr      | 82  |     |    |     |    |   | T  | T   |      | 2.29  | * | *  |     | 2.27  | 4.73 |
| Lys      | 83  |     |    |     |    |   | T  | T   |      | 2.60  | * | *  |     | 2.61  | 5.04 |
| Tyr      | 84  |     |    |     |    |   | T  | T   |      | 2.34  | * | *  | F   | 3.40  | 6.51 |
| Lys      | 85  |     |    |     |    |   | T  | T   |      | 2.59  |   | *  | F   | 3.06  | 6.42 |
| Asp      | 86  |     |    |     | B  |   |    | T   |      | 2.89  |   | *  | F   | 2.32  | 5.56 |
| Gln      | 87  |     |    |     | B  |   |    | T   |      | 2.82  |   | *  | F   | 1.98  | 6.15 |
| Pro      | 88  |     |    |     | B  |   |    |     |      | 2.08  | * | *  | F   | 1.44  | 4.44 |
| Gln      | 89  |     |    |     | B  | B |    |     |      | 2.32  | * | *  | F   | 0.60  | 2.30 |
| Gln      | 90  |     |    |     | B  | B |    |     |      | 1.39  | * | *  | F   | 0.00  | 2.14 |
| Thr      | 91  |     |    |     | B  | B |    |     |      | 1.14  | * |    | F   | −0.45 | 0.97 |
| Phe      | 92  |     |    |     | B  | B |    |     |      | 1.19  |   | *  |     | −0.60 | 0.88 |
| Asn      | 93  |     |    |     | B  | B |    |     |      | 0.81  |   |    |     | −0.45 | 1.01 |
| Ile      | 94  |     |    |     | B  | B |    |     |      | 0.81  |   |    |     | −0.60 | 0.71 |
| Tyr      | 95  |     |    |     | B  |   |    |     |      | 0.81  |   |    |     | −0.25 | 1.32 |
| Lys      | 96  |     |    |     |    |   |    |     | C    | 0.23  |   |    |     | 0.25  | 1.32 |
| Ala      | 97  |     |    |     |    |   |    |     | C    | 0.34  |   |    | F   | 0.10  | 1.32 |
| Asn      | 98  |     |    |     |    |   |    |     | C    | −0.24 | * |    |     | 0.10  | 0.85 |
| Asn      | 99  |     |    |     | B  |   |    |     |      | 0.64  | * |    |     | 0.50  | 0.43 |
| Ile      | 100 |     |    |     | B  |   |    |     |      | 0.54  | * |    |     | −0.10 | 0.68 |
| Ala      | 101 |     |    |     | B  |   |    | T   |      | −0.36 | * |    |     | 0.10  | 0.42 |
| Ala      | 102 |     |    |     | B  |   |    | T   |      | −0.47 |   |    |     | −0.20 | 0.19 |
| Asn      | 103 |     |    |     | B  |   |    | T   |      | −0.50 |   | *  |     | −0.20 | 0.24 |
| Gly      | 104 |     |    |     | B  |   |    | T   |      | −1.36 | * | *  |     | −0.20 | 0.32 |
| Val      | 105 |     |    |     | B  | B |    |     |      | −1.32 | * | *  |     | −0.60 | 0.24 |
| Phe      | 106 |     |    |     | B  | B |    |     |      | −1.04 | * |    |     | −0.60 | 0.11 |
| His      | 107 |     |    |     | B  | B |    |     |      | −0.80 | * |    |     | −0.60 | 0.16 |
| Val      | 108 |     |    |     | B  | B |    |     |      | −1.61 | * | *  |     | −0.60 | 0.21 |
| Val      | 109 |     |    |     | B  | B |    |     |      | −1.16 | * | *  |     | −0.60 | 0.20 |
| Thr      | 110 |     |    |     | B  | B |    |     |      | −0.59 |   | *  |     | −0.30 | 0.29 |
| Gly      | 111 |     |    |     | B  | B |    |     |      | 0.11  |   | *  |     | −0.60 | 0.41 |
| Leu      | 112 |     |    |     | B  | B |    |     |      | −0.44 | * | *  |     | −0.60 | 0.96 |
| Arg      | 113 |     |    |     |    | B | T  |     |      | 0.20  |   | *  |     | −0.20 | 0.67 |
| Trp      | 114 |     |    |     |    | B | T  |     |      | 0.76  |   | *  |     | 0.25  | 1.05 |
| Gln      | 115 |     |    |     | B  | B |    |     |      | 0.72  |   | *  |     | −0.15 | 1.71 |
| Ala      | 116 |     |    |     | B  |   |    | T   | C    | 0.76  |   | *  | F   | 0.45  | 0.86 |
| Pro      | 117 |     |    |     |    |   | T  | T   |      | 1.36  |   | *  | F   | 0.50  | 1.19 |
| Ser      | 118 |     |    |     |    |   | T  | T   |      | 0.90  |   | *  | F   | 1.10  | 1.06 |
| Gly      | 119 |     |    |     |    |   |    | T   | C    | 1.19  |   |    | F   | 1.20  | 1.04 |
| Thr      | 120 |     |    |     |    |   |    | T   | C    | 0.98  |   |    | F   | 2.10  | 1.12 |
| Pro      | 121 |     |    |     |    |   |    | T   | C    | 1.61  |   |    | F   | 2.40  | 1.29 |
| Gly      | 122 |     |    |     |    |   |    | T   | C    | 1.93  |   |    | F   | 3.00  | 2.61 |
| Asp      | 123 |     |    |     |    |   |    | T   | C    | 1.92  | * |    | F   | 2.70  | 3.55 |
| Pro      | 124 |     |    |     |    |   |    | T   | C    | 1.38  | * |    | F   | 2.49  | 3.31 |
| Lys      | 125 |     |    |     | B  |   |    | T   |      | 1.34  | * |    | F   | 2.08  | 2.35 |
| Arg      | 126 |     |    |     | B  |   |    | T   |      | 1.56  | * |    | F   | 1.87  | 1.39 |
| Thr      | 127 |     |    |     | B  |   |    | T   |      | 1.01  | * |    | F   | 1.66  | 1.56 |
| Ile      | 128 |     |    |     | B  | B |    |     |      | 0.20  | * |    | F   | 0.90  | 0.55 |
| Gly      | 129 |     |    |     | B  | B |    |     |      | −0.18 | * |    | F   | 0.21  | 0.23 |
| Gln      | 130 |     |    |     | B  | B |    |     |      | −0.52 | * |    |     | −0.33 | 0.16 |
| Ile      | 131 |     |    |     | B  | B |    |     |      | −0.94 | * | *  |     | −0.42 | 0.31 |
| Leu      | 132 |     |    |     | B  | B |    |     |      | −0.63 |   |    |     | −0.51 | 0.45 |
| Ala      | 133 |     |    |     | B  | B |    |     |      | −0.33 | * |    |     | −0.30 | 0.45 |
| Ser      | 134 |     |    |     | B  | B |    |     |      | −0.69 |   | *  | F   | −0.15 | 0.65 |
| Thr      | 135 |     |    | A   |    |   |    |     | C    | −0.99 | * | *  | F   | 0.05  | 0.68 |
| Glu      | 136 |     |    | A   | B  |   |    |     |      | 0.01  | * | *  | F   | −0.15 | 0.90 |
| Ala      | 137 |     |    | A   |    |   |    |     | C    | 0.12  | * | *  |     | 0.65  | 1.32 |
| Phe      | 138 |     |    | A   |    |   |    |     | C    | 0.71  | * | *  |     | 0.50  | 0.79 |
| Ser      | 139 |     |    | A   |    |   |    |     | C    | 0.70  | * | *  |     | 0.80  | 0.79 |
| Arg      | 140 |     |    | A   | B  |   |    |     |      | 0.12  | * | *  |     | 0.45  | 1.13 |
| Phe      | 141 |     |    | A   | B  |   |    |     |      | −0.69 | * | *  |     | −0.30 | 0.91 |
| Glu      | 142 |     |    | A   | B  |   |    |     |      | −0.10 | * | *  |     | −0.30 | 0.56 |
| Thr      | 143 |     |    | A   | B  |   |    |     |      | 0.60  | * | *  |     | 0.30  | 0.50 |
| Ile      | 144 |     |    | A   | B  |   |    |     |      | 0.23  | * | *  |     | −0.30 | 0.92 |
| Leu      | 145 |     |    | A   | B  |   |    |     |      | −0.22 | * | *  |     | 0.30  | 0.29 |
| Glu      | 146 |     |    | A   |    |   | T  |     |      | −0.33 | * |    |     | 0.10  | 0.20 |
| Asn      | 147 |     |    |     |    |   | T  | T   |      | −0.54 |   |    |     | 0.20  | 0.23 |
| Cys      | 148 |     |    |     |    |   | T  | T   |      | −0.53 |   |    |     | 0.50  | 0.43 |
| Gly      | 149 |     |    |     |    |   | T  | T   |      | −0.53 |   |    |     | 1.10  | 0.33 |
| Leu      | 150 |     |    |     |    |   |    | T   | C    | −0.53 |   |    |     | 0.00  | 0.15 |
| Pro      | 151 |     |    |     | B  |   |    |     |      | −0.53 |   |    |     | −0.40 | 0.22 |
| Ser      | 152 |     |    |     | B  |   |    |     |      | −0.88 | * |    |     | −0.01 | 0.38 |
| Ile      | 153 |     |    |     | B  |   |    |     |      | −0.42 | * |    | F   | 0.23  | 0.45 |
| Leu      | 154 |     |    |     | B  |   |    |     |      | −0.42 | * |    | F   | 0.32  | 0.45 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Asp | 155 | . | . | . | B | . | . | . | . | 0.18 | * | * | F | 0.41 | 0.34 |
| Gly | 156 | . | . | . | . | . | . | T | C | −0.31 | * | . | F | 0.90 | 0.74 |
| Pro | 157 | . | . | . | . | . | . | T | C | −0.32 | . | * | F | 0.81 | 0.78 |
| Gly | 158 | . | . | . | . | . | . | T | C | −0.29 | . | . | F | 1.32 | 0.67 |
| Pro | 159 | . | . | . | B | . | . | T | . | −0.18 | . | * | F | 0.13 | 0.50 |
| Phe | 160 | . | . | . | B | B | . | . | . | −0.77 | . | * | . | −0.51 | 0.28 |
| Thr | 161 | . | . | . | B | B | . | . | . | −0.63 | . | . | . | −0.60 | 0.29 |
| Val | 162 | . | . | . | B | B | . | . | . | −0.72 | . | . | . | −0.60 | 0.29 |
| Phe | 163 | . | . | . | B | B | . | . | . | −0.38 | . | . | . | −0.60 | 0.45 |
| Ala | 164 | . | . | . | . | . | . | T | C | −0.17 | . | . | F | 0.15 | 0.50 |
| Pro | 165 | . | . | . | . | . | . | T | C | −0.06 | . | . | F | 0.60 | 1.16 |
| Ser | 166 | . | . | . | . | . | . | T | C | −0.60 | * | . | F | 0.60 | 1.35 |
| Asn | 167 | . | . | . | . | . | . | T | C | 0.26 | * | . | F | 1.05 | 0.99 |
| Glu | 168 | . | . | . | . | . | . | . | C | 0.66 | * | . | F | 1.30 | 1.07 |
| Ala | 169 | . | . | . | B | . | . | . | . | 0.43 | * | * | F | 1.10 | 1.07 |
| Val | 170 | . | . | . | B | . | . | . | . | 0.76 | * | . | F | 0.65 | 0.55 |
| Asp | 171 | . | . | . | B | . | . | . | . | 1.06 | * | . | F | 1.26 | 0.62 |
| Ser | 172 | . | . | . | B | . | . | . | . | 0.71 | * | . | F | 1.72 | 1.03 |
| Leu | 173 | . | . | . | B | . | . | T | . | 0.82 | * | * | F | 2.23 | 1.37 |
| Arg | 174 | . | . | . | B | . | . | T | . | 0.60 | * | . | F | 2.54 | 1.61 |
| Asp | 175 | . | . | . | . | . | T | T | . | 0.57 | * | . | F | 3.10 | 0.99 |
| Gly | 176 | . | . | . | . | . | T | T | . | 0.32 | * | . | F | 2.79 | 0.84 |
| Arg | 177 | . | . | . | B | B | . | . | . | −0.19 | * | . | F | 1.38 | 0.67 |
| Leu | 178 | . | . | . | B | B | . | . | . | −0.08 | * | . | . | 0.32 | 0.33 |
| Ile | 179 | . | . | . | B | B | . | . | . | −0.50 | * | . | . | −0.29 | 0.29 |
| Tyr | 180 | . | . | . | B | B | . | . | . | −1.09 | * | * | . | −0.60 | 0.21 |
| Leu | 181 | . | . | . | B | B | . | . | . | −1.09 | * | * | . | −0.60 | 0.26 |
| Phe | 182 | . | . | . | B | B | . | . | . | −2.01 | * | * | . | −0.60 | 0.37 |
| Thr | 183 | . | . | . | B | B | . | . | . | −1.50 | * | . | . | −0.60 | 0.19 |
| Ala | 184 | . | . | . | . | B | . | . | C | −0.57 | * | . | . | −0.40 | 0.32 |
| Gly | 185 | . | . | . | . | B | . | . | C | −1.13 | * | . | . | −0.10 | 0.73 |
| Leu | 186 | . | A | . | . | . | . | . | C | −0.32 | * | . | . | −0.10 | 0.42 |
| Ser | 187 | . | A | . | . | . | . | . | C | 0.38 | * | . | F | 0.05 | 0.72 |
| Lys | 188 | . | A | . | . | . | . | . | C | −0.12 | * | . | F | 0.80 | 1.25 |
| Leu | 189 | . | A | . | B | . | . | . | . | −0.39 | * | * | F | 0.60 | 1.25 |
| Gln | 190 | . | . | . | B | B | . | . | . | 0.07 | * | * | F | 0.45 | 0.69 |
| Glu | 191 | . | . | . | B | B | . | . | . | 0.63 | * | * | . | 0.60 | 0.68 |
| Leu | 192 | . | . | . | B | B | . | . | . | 0.90 | * | * | . | −0.15 | 1.29 |
| Val | 193 | . | . | . | B | B | . | . | . | −0.03 | * | * | . | 0.45 | 1.01 |
| Arg | 194 | . | . | . | B | B | . | . | . | 0.53 | * | * | . | −0.30 | 0.41 |
| Tyr | 195 | . | . | . | B | B | . | . | . | 0.53 | * | * | . | −0.60 | 0.78 |
| His | 196 | . | . | . | B | B | . | . | . | 0.50 | * | * | . | −0.45 | 1.69 |
| Ile | 197 | . | . | . | B | B | . | . | . | 0.97 | * | * | . | −0.45 | 1.17 |
| Tyr | 198 | . | . | . | . | . | T | . | . | 1.82 | * | * | . | 0.00 | 0.74 |
| Asn | 199 | . | . | . | . | . | T | T | . | 0.90 | . | * | . | 0.20 | 0.94 |
| His | 200 | . | . | . | . | . | T | T | . | 0.83 | . | * | . | 0.35 | 1.11 |
| Gly | 201 | . | . | . | . | . | . | T | C | 0.01 | * | * | . | 0.15 | 1.02 |
| Gln | 202 | . | . | . | . | . | . | T | C | 0.90 | * | * | . | 0.00 | 0.47 |
| Leu | 203 | . | . | . | B | B | . | . | . | 1.19 | * | . | . | −0.30 | 0.60 |
| Thr | 204 | . | . | . | B | B | . | . | . | 0.38 | * | * | . | 0.45 | 1.21 |
| Val | 205 | . | . | . | B | B | . | . | . | −0.48 | * | * | . | 0.30 | 0.58 |
| Glu | 206 | . | . | . | B | B | . | . | . | −0.43 | * | * | . | −0.30 | 0.49 |
| Lys | 207 | . | . | . | B | B | . | . | . | −0.39 | * | * | F | 0.62 | 0.46 |
| Leu | 208 | . | . | . | B | B | . | . | . | 0.08 | * | * | F | 1.24 | 1.23 |
| Ile | 209 | . | . | . | B | B | . | . | . | 0.50 | * | * | F | 1.26 | 0.70 |
| Ser | 210 | . | . | . | . | . | . | T | C | 0.47 | * | * | F | 2.03 | 0.69 |
| Lys | 211 | . | . | . | B | . | . | T | . | −0.34 | * | * | F | 1.70 | 0.59 |
| Gly | 212 | . | . | . | B | . | . | T | . | −0.70 | * | * | F | 1.53 | 0.69 |
| Arg | 213 | . | . | . | B | . | . | T | . | −0.49 | . | * | F | 1.36 | 0.74 |
| Ile | 214 | . | . | . | B | B | . | . | . | −0.19 | . | * | . | 0.64 | 0.37 |
| Leu | 215 | . | . | . | B | B | . | . | . | 0.11 | * | * | . | −0.43 | 0.37 |
| Thr | 216 | . | . | . | B | B | . | . | . | 0.07 | * | * | . | −0.30 | 0.31 |
| Met | 217 | . | . | . | B | B | . | . | . | −0.44 | * | * | . | −0.60 | 0.76 |
| Ala | 218 | . | . | . | B | B | . | . | . | −1.37 | * | * | . | −0.60 | 0.68 |
| Asn | 219 | . | . | . | B | B | . | . | . | −1.07 | * | . | . | −0.60 | 0.39 |
| Gln | 220 | . | . | . | B | B | . | . | . | −1.11 | . | . | . | −0.60 | 0.40 |
| Val | 221 | . | . | . | B | B | . | . | . | −0.80 | . | * | . | −0.60 | 0.29 |
| Leu | 222 | . | . | . | B | B | . | . | . | −1.09 | . | * | . | −0.60 | 0.29 |
| Ala | 223 | . | . | . | B | B | . | . | . | −0.80 | . | . | . | −0.60 | 0.12 |
| Val | 224 | . | . | . | B | B | . | . | . | −0.80 | . | * | . | −0.34 | 0.21 |
| Asn | 225 | . | . | . | B | B | . | . | . | −0.80 | . | * | . | 0.22 | 0.45 |
| Ile | 226 | . | . | . | B | B | . | . | . | −0.29 | * | * | . | 1.08 | 0.77 |
| Ser | 227 | . | . | . | B | . | . | T | . | 0.63 | * | * | F | 2.04 | 1.03 |
| Glu | 228 | . | . | . | B | . | . | T | . | 0.33 | * | * | F | 2.60 | 1.25 |
| Glu | 229 | . | . | . | B | . | . | T | . | 0.38 | * | * | F | 2.34 | 1.25 |
| Gly | 230 | . | . | . | B | . | . | T | . | −0.43 | * | * | F | 1.93 | 0.77 |
| Arg | 231 | . | . | . | B | B | . | . | . | 0.11 | * | * | F | 1.27 | 0.37 |

TABLE I-continued

| | Res Pos. | I | II | III | IV | V | VI | VII | VIII | IX | X | XI | XII | XIII | XIV |
|---|---|---|---|---|---|---|---|---|---|---|---|---|---|---|---|
| Ile | 232 | . | . | . | B | B | . | . | . | 0.20 | . | * | . | 0.56 | 0.21 |
| Leu | 233 | . | . | . | B | B | . | . | . | 0.20 | . | * | . | −0.30 | 0.33 |
| Leu | 234 | . | . | . | B | B | . | . | . | −0.14 | . | * | . | 0.30 | 0.29 |
| Gly | 235 | . | . | . | . | . | . | T | C | −0.66 | . | * | F | 0.45 | 0.41 |
| Pro | 236 | . | . | . | . | . | . | T | C | −0.98 | . | * | F | 0.45 | 0.37 |
| Glu | 237 | . | . | . | . | . | T | T | . | −0.90 | . | . | F | 0.65 | 0.69 |
| Gly | 238 | . | . | . | . | . | . | T | C | −0.09 | * | . | F | 0.45 | 0.57 |
| Val | 239 | . | . | . | B | . | . | . | . | 0.83 | * | . | F | 0.05 | 0.64 |
| Pro | 240 | . | . | . | B | . | . | . | . | 0.32 | . | . | . | 0.50 | 0.73 |
| Leu | 241 | . | . | . | B | B | . | . | . | 0.53 | . | * | . | −0.30 | 0.55 |
| Gln | 242 | . | . | . | B | B | . | . | . | −0.32 | . | * | . | 0.45 | 1.23 |
| Arg | 243 | . | . | . | B | B | . | . | . | −0.58 | . | * | . | 0.30 | 0.59 |
| Val | 244 | . | . | . | B | B | . | . | . | −0.31 | . | * | . | 0.30 | 0.71 |
| Asp | 245 | . | . | . | B | B | . | . | . | −0.69 | * | * | . | 0.30 | 0.41 |
| Val | 246 | . | . | . | B | B | . | . | . | 0.12 | * | * | . | 0.30 | 0.21 |
| Met | 247 | . | . | . | B | B | . | . | . | −0.22 | * | * | . | −0.30 | 0.46 |
| Ala | 248 | . | . | . | B | . | . | T | . | −1.19 | * | * | . | 0.10 | 0.27 |
| Ala | 249 | . | . | . | B | . | . | T | . | −1.22 | . | * | . | −0.20 | 0.27 |
| Asn | 250 | . | . | . | B | . | . | T | . | −1.26 | . | * | . | −0.20 | 0.19 |
| Gly | 251 | . | . | . | B | . | . | T | . | −1.00 | * | . | . | −0.20 | 0.26 |
| Val | 252 | . | . | . | B | B | . | . | . | −1.21 | * | . | . | −0.60 | 0.26 |
| Ile | 253 | . | . | . | B | B | . | . | . | −0.62 | * | . | . | −0.60 | 0.13 |
| His | 254 | . | . | . | B | B | . | . | . | −0.38 | * | . | . | −0.60 | 0.22 |
| Met | 255 | . | . | . | B | B | . | . | . | −1.27 | * | . | . | −0.60 | 0.29 |
| Leu | 256 | . | . | . | B | B | . | . | . | −1.73 | * | . | . | −0.60 | 0.29 |
| Asp | 257 | . | . | . | B | B | . | . | . | −1.69 | * | . | . | −0.60 | 0.18 |
| Gly | 258 | . | . | . | B | . | . | . | . | −1.01 | . | . | . | −0.40 | 0.15 |
| Ile | 259 | . | . | . | B | . | . | . | . | −1.19 | . | . | . | −0.40 | 0.28 |
| Leu | 260 | . | . | . | B | . | . | . | . | −0.90 | . | . | . | −0.10 | 0.26 |
| Leu | 261 | . | . | . | B | . | . | . | . | −0.98 | . | . | . | −0.40 | 0.38 |
| Pro | 262 | . | . | . | B | . | . | T | . | −1.79 | . | . | F | −0.05 | 0.38 |
| Pro | 263 | . | . | . | B | . | . | T | . | −1.66 | . | . | F | −0.05 | 0.38 |
| Thr | 264 | . | . | . | B | . | . | T | . | −1.66 | . | . | F | −0.05 | 0.71 |
| Ile | 265 | . | . | . | B | . | . | T | . | −1.66 | . | . | . | −0.20 | 0.32 |
| Leu | 266 | . | . | . | B | . | . | . | . | −1.06 | * | . | . | −0.40 | 0.17 |
| Pro | 267 | . | . | . | B | . | . | . | . | −0.80 | * | . | . | −0.40 | 0.18 |
| Ile | 268 | . | . | . | B | . | . | . | . | −0.62 | * | . | . | −0.40 | 0.52 |
| Leu | 269 | . | . | . | B | . | . | . | . | −0.98 | * | . | . | −0.10 | 0.86 |
| Pro | 270 | . | . | . | . | . | . | T | C | −0.39 | * | . | . | 0.90 | 0.30 |
| Lys | 271 | . | . | . | . | . | T | T | . | 0.42 | * | . | F | 1.55 | 0.57 |
| His | 272 | . | . | . | . | . | . | T | C | 0.63 | . | . | F | 2.40 | 1.20 |
| Cys | 273 | . | . | . | . | . | . | T | C | 1.52 | . | . | F | 3.00 | 1.34 |
| Ser | 274 | . | A | A | . | . | . | . | . | 2.30 | * | . | F | 2.10 | 1.16 |
| Glu | 275 | . | A | A | . | . | . | . | . | 2.56 | * | * | F | 1.80 | 1.16 |
| Glu | 276 | . | A | A | . | . | . | . | . | 1.62 | * | . | F | 1.50 | 4.34 |
| Gln | 277 | . | A | A | . | . | . | . | . | 0.80 | * | . | F | 1.20 | 2.27 |
| His | 278 | . | . | A | B | . | . | . | . | 0.88 | . | . | F | 0.75 | 0.97 |
| Lys | 279 | . | . | A | B | . | . | . | . | 0.83 | . | . | . | 0.30 | 0.57 |
| Ile | 280 | . | . | A | B | . | . | . | . | 0.53 | . | . | . | −0.30 | 0.32 |
| Val | 281 | . | . | A | B | . | . | . | . | −0.13 | . | . | . | −0.30 | 0.32 |
| Ala | 282 | . | . | A | . | . | T | . | . | −0.99 | . | * | . | 0.10 | 0.09 |
| Gly | 283 | . | . | . | . | . | T | T | . | −0.96 | . | . | . | 0.20 | 0.09 |
| Ser | 284 | . | . | . | B | . | . | T | . | −1.67 | . | * | . | 0.10 | 0.20 |
| Cys | 285 | . | . | . | B | . | . | T | . | −0.78 | . | * | . | 0.10 | 0.11 |
| Val | 286 | . | . | . | B | . | . | T | . | −0.51 | . | . | . | 0.10 | 0.19 |
| Asp | 287 | . | . | A | B | . | . | . | . | −0.73 | . | . | . | −0.30 | 0.14 |
| Cys | 288 | . | . | A | B | . | . | . | . | −0.39 | . | . | . | −0.30 | 0.22 |
| Gln | 289 | . | . | A | B | . | . | . | . | −0.40 | . | . | . | −0.30 | 0.48 |
| Ala | 290 | . | . | A | B | . | . | . | . | −0.03 | . | . | . | −0.30 | 0.41 |
| Leu | 291 | . | . | A | . | . | T | . | . | 0.51 | . | . | . | −0.05 | 1.03 |
| Asn | 292 | . | . | . | . | . | T | T | . | −0.16 | . | . | F | 0.65 | 0.86 |
| Thr | 293 | . | . | . | . | . | T | T | . | 0.30 | . | . | F | 0.35 | 0.45 |
| Ser | 294 | . | . | . | . | . | T | T | . | 0.09 | . | . | F | 0.35 | 0.85 |
| Thr | 295 | . | . | . | . | . | T | T | . | 0.68 | . | . | F | 0.65 | 0.82 |
| Cys | 296 | . | . | . | . | . | . | . | C | 1.19 | . | . | F | 0.25 | 0.91 |
| Pro | 297 | . | . | . | . | . | . | T | C | 0.33 | * | . | F | 0.45 | 0.91 |
| Pro | 298 | . | . | . | . | . | T | T | . | 0.69 | . | * | F | 0.65 | 0.47 |
| Asn | 299 | . | . | . | . | . | T | T | . | 0.18 | . | * | F | 1.40 | 1.75 |
| Ser | 300 | . | . | . | B | . | . | T | . | 0.49 | . | * | F | 0.85 | 0.94 |
| Val | 301 | . | . | . | B | B | . | . | . | 0.27 | . | * | F | 0.60 | 1.01 |
| Lys | 302 | . | . | . | B | B | . | . | . | −0.22 | . | * | F | 0.45 | 0.44 |
| Leu | 303 | . | . | . | B | B | . | . | . | −0.22 | . | * | . | −0.07 | 0.28 |
| Asp | 304 | . | . | . | B | B | . | . | . | −0.18 | . | * | . | 0.16 | 0.59 |
| Ile | 305 | . | . | . | B | B | . | . | . | 0.12 | . | * | . | 0.99 | 0.59 |
| Phe | 306 | . | . | . | B | B | . | . | . | 0.31 | . | * | . | 1.37 | 1.24 |
| Pro | 307 | . | . | . | B | . | . | T | . | −0.59 | . | * | F | 2.30 | 0.40 |
| Lys | 308 | . | . | . | . | . | T | T | . | −0.02 | * | * | F | 1.57 | 0.42 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Glu | 309 | . | . | . | B | . | . | T | . | -0.91 | * | * | . | 0.79 | 0.77 |
| Cys | 310 | . | . | . | B | . | . | T | . | -0.06 | * | . | . | 0.56 | 0.35 |
| Val | 311 | . | . | . | B | B | . | . | . | 0.64 | * | . | . | -0.07 | 0.24 |
| Tyr | 312 | . | . | . | B | B | . | . | . | 0.64 | . | . | . | -0.30 | 0.23 |
| Ile | 313 | . | . | . | B | B | . | . | . | 0.29 | . | . | . | -0.60 | 0.66 |
| His | 314 | . | . | . | B | B | . | . | . | -0.06 | . | . | . | -0.45 | 1.28 |
| Asp | 315 | . | . | . | B | . | . | T | . | -0.20 | . | . | F | 0.25 | 0.81 |
| Pro | 316 | . | . | . | . | . | T | T | . | 0.66 | . | * | F | 0.65 | 0.95 |
| Thr | 317 | . | . | . | . | . | T | T | . | 0.04 | . | . | F | 1.40 | 1.12 |
| Gly | 318 | . | . | . | B | . | . | T | . | 0.12 | . | . | F | 0.25 | 0.50 |
| Leu | 319 | . | . | A | B | . | . | . | . | 0.20 | * | . | . | -0.60 | 0.27 |
| Asn | 320 | . | . | A | B | . | . | . | . | 0.24 | * | . | . | -0.30 | 0.37 |
| Val | 321 | . | . | A | B | . | . | . | . | 0.11 | * | . | . | 0.51 | 0.74 |
| Leu | 322 | . | . | A | B | . | . | . | . | -0.24 | * | . | . | 0.72 | 0.89 |
| Lys | 323 | . | . | A | B | . | . | . | . | -0.49 | * | . | F | 1.08 | 0.30 |
| Lys | 324 | . | . | A | B | . | T | . | . | 0.02 | * | . | F | 1.69 | 0.41 |
| Gly | 325 | . | . | . | . | . | T | . | . | -0.22 | * | . | F | 2.10 | 0.66 |
| Cys | 326 | . | . | . | . | . | T | . | . | -0.03 | * | . | . | 1.94 | 0.52 |
| Ala | 327 | . | . | . | B | . | . | T | . | 0.78 | * | . | . | 0.73 | 0.14 |
| Ser | 328 | . | . | . | B | . | . | T | . | 0.73 | . | . | . | 0.22 | 0.22 |
| Tyr | 329 | . | . | . | B | . | . | T | . | 0.38 | * | * | . | 0.01 | 0.73 |
| Cys | 330 | . | . | . | . | B | T | . | . | -0.17 | . | . | . | -0.05 | 1.04 |
| Asn | 331 | . | . | . | . | B | T | . | . | -0.10 | * | . | . | -0.20 | 0.54 |
| Gln | 332 | . | . | . | B | B | . | . | . | 0.49 | . | . | F | -0.45 | 0.34 |
| Thr | 333 | . | . | . | B | B | . | . | . | 0.79 | . | . | F | 0.00 | 1.11 |
| Ile | 334 | . | . | . | B | B | . | . | . | 0.69 | . | . | . | 0.45 | 1.19 |
| Met | 335 | . | . | . | B | B | . | . | . | 0.69 | . | . | . | -0.02 | 0.68 |
| Glu | 336 | . | . | . | B | . | . | T | . | 0.02 | . | . | F | 0.81 | 0.25 |
| Gln | 337 | . | . | . | B | . | . | T | . | 0.07 | * | * | F | 1.09 | 0.19 |
| Gly | 338 | . | . | . | . | . | T | T | . | 0.03 | * | . | F | 2.37 | 0.39 |
| Cys | 339 | . | . | . | . | . | T | T | . | 0.22 | . | * | . | 2.80 | 0.22 |
| Cys | 340 | . | . | . | . | . | T | T | . | 0.12 | . | . | . | 1.62 | 0.11 |
| Lys | 341 | . | . | . | . | . | T | T | . | -0.22 | . | . | . | 1.04 | 0.10 |
| Gly | 342 | . | . | . | . | . | T | T | . | -0.43 | . | * | . | 0.76 | 0.18 |
| Phe | 343 | . | . | . | . | . | T | T | . | -0.09 | . | * | . | 0.48 | 0.52 |
| Phe | 344 | . | . | . | . | . | T | . | . | -0.09 | . | . | . | 0.90 | 0.43 |
| Gly | 345 | . | . | . | . | . | T | T | . | 0.27 | . | . | F | 0.56 | 0.24 |
| Pro | 346 | . | . | . | . | . | T | T | . | 0.22 | . | . | F | 0.77 | 0.39 |
| Asp | 347 | . | . | . | . | . | T | T | . | -0.10 | . | . | F | 1.28 | 0.78 |
| Cys | 348 | . | . | . | . | . | T | T | . | 0.39 | . | . | F | 2.09 | 0.43 |
| Thr | 349 | . | . | . | . | . | T | . | . | 0.74 | . | . | F | 2.10 | 0.43 |
| Gln | 350 | . | . | . | B | . | . | . | . | 0.74 | . | . | F | 1.49 | 0.25 |
| Cys | 351 | . | . | . | B | . | . | . | . | 0.26 | . | . | F | 0.88 | 0.47 |
| Pro | 352 | . | . | . | . | . | T | T | . | -0.04 | . | . | F | 0.77 | 0.28 |
| Gly | 353 | . | . | . | . | . | T | T | . | 0.62 | . | . | F | 0.56 | 0.22 |
| Gly | 354 | . | . | . | . | . | T | T | . | 0.72 | . | . | F | 0.35 | 0.65 |
| Phe | 355 | . | . | . | . | . | T | . | . | 0.06 | . | . | F | 0.45 | 0.65 |
| Ser | 356 | . | . | . | B | . | . | . | . | 0.48 | . | . | F | -0.25 | 0.35 |
| Asn | 357 | . | . | . | B | . | . | T | . | 0.34 | . | . | F | -0.05 | 0.56 |
| Pro | 358 | . | . | . | B | . | . | T | . | 0.73 | . | . | F | -0.05 | 0.63 |
| Cys | 359 | . | . | . | . | . | T | T | . | 0.73 | . | * | F | 1.25 | 0.95 |
| Tyr | 360 | . | . | . | . | . | T | T | . | 1.43 | . | * | F | 0.96 | 0.58 |
| Gly | 361 | . | . | . | . | . | T | T | . | 1.07 | . | * | F | 1.27 | 0.61 |
| Lys | 362 | . | . | . | . | . | T | T | . | 0.77 | . | . | F | 1.58 | 0.61 |
| Gly | 363 | . | . | . | . | . | T | T | . | 0.98 | . | * | F | 2.49 | 0.52 |
| Asn | 364 | . | . | . | . | . | T | T | . | 1.30 | . | . | F | 3.10 | 0.88 |
| Cys | 365 | . | . | . | B | . | . | T | . | 0.66 | . | * | F | 2.39 | 0.43 |
| Ser | 366 | . | . | . | B | . | . | T | . | 1.00 | . | * | F | 1.95 | 0.31 |
| Asp | 367 | . | . | . | B | . | . | T | . | 0.61 | . | * | F | 1.81 | 0.33 |
| Gly | 368 | . | . | . | B | . | . | T | . | 0.96 | . | * | F | 1.67 | 0.61 |
| Ile | 369 | . | . | . | . | . | T | . | . | 0.61 | . | * | F | 1.73 | 0.73 |
| Gln | 370 | . | . | . | B | . | . | T | . | 0.69 | . | * | F | 1.70 | 0.43 |
| Gly | 371 | . | . | . | . | . | T | T | . | 0.32 | . | . | F | 1.33 | 0.44 |
| Asn | 372 | . | . | . | . | . | T | T | . | -0.49 | . | . | F | 0.86 | 0.34 |
| Gly | 373 | . | . | . | . | . | T | T | . | -0.81 | . | * | F | 0.69 | 0.16 |
| Ala | 374 | . | . | . | B | . | . | . | . | -0.62 | . | * | . | -0.23 | 0.09 |
| Cys | 375 | . | . | . | B | . | . | . | . | -0.83 | . | . | . | -0.40 | 0.05 |
| Leu | 376 | . | . | . | B | . | . | . | . | -0.49 | . | . | . | -0.40 | 0.07 |
| Cys | 377 | . | . | . | B | . | . | . | . | -0.73 | . | . | . | -0.40 | 0.12 |
| Phe | 378 | . | . | . | B | . | . | T | . | -0.34 | . | . | . | 0.01 | 0.36 |
| Pro | 379 | . | . | . | . | . | T | T | . | -0.10 | . | . | F | 1.07 | 0.86 |
| Asp | 380 | . | . | . | . | . | T | T | . | -0.32 | . | . | F | 2.03 | 1.59 |
| Tyr | 381 | . | . | . | . | . | T | T | . | -0.10 | . | . | F | 1.64 | 1.29 |
| Lys | 382 | . | . | . | . | . | . | T | . | -0.10 | . | . | F | 2.10 | 0.84 |
| Gly | 383 | . | . | . | . | B | T | . | . | 0.57 | * | . | . | 1.54 | 0.27 |
| Ile | 384 | . | . | . | B | B | . | . | . | -0.11 | * | . | . | 0.03 | 0.23 |
| Ala | 385 | . | . | . | B | B | . | . | . | -0.78 | * | . | . | 0.12 | 0.08 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Cys | 386 | . | . | . | B | B | . | . | . | −0.83 | * | . | . | −0.39 | 0.04 |
| His | 387 | . | . | . | B | B | . | . | . | −0.88 | * | . | . | −0.60 | 0.09 |
| Ile | 388 | . | . | . | B | B | . | . | . | −0.74 | . | * | . | −0.60 | 0.14 |
| Cys | 389 | . | . | . | . | B | T | . | . | 0.14 | * | * | . | −0.20 | 0.39 |
| Ser | 390 | . | . | . | . | B | T | . | . | 0.78 | * | . | F | 0.59 | 0.46 |
| Asn | 391 | . | . | . | . | . | . | T | C | 1.41 | * | . | F | 1.88 | 1.32 |
| Pro | 392 | . | . | . | . | . | T | T | . | 1.10 | * | . | F | 2.42 | 3.34 |
| Asn | 393 | . | . | . | . | . | T | T | . | 1.99 | * | . | F | 2.76 | 2.47 |
| Lys | 394 | . | . | . | . | . | T | T | . | 2.66 | * | . | F | 3.40 | 2.66 |
| His | 395 | . | . | A | . | . | T | . | . | 2.29 | * | . | F | 2.66 | 2.98 |
| Gly | 396 | . | . | A | . | . | T | . | . | 2.29 | * | . | F | 2.17 | 0.99 |
| Glu | 397 | . | . | A | . | . | T | . | . | 2.50 | * | . | F | 1.83 | 0.86 |
| Gln | 398 | . | . | A | B | . | . | . | . | 2.50 | * | . | F | 1.49 | 1.09 |
| Cys | 399 | . | . | A | B | . | . | . | . | 1.79 | * | . | F | 1.40 | 1.85 |
| Gln | 400 | . | . | A | . | . | T | . | . | 1.48 | * | . | F | 1.90 | 0.57 |
| Glu | 401 | . | . | A | . | . | T | . | . | 1.16 | . | . | F | 2.15 | 0.33 |
| Asp | 402 | . | . | . | . | . | T | T | . | 0.30 | . | . | F | 2.50 | 0.33 |
| Cys | 403 | . | . | . | . | . | T | T | . | 0.27 | . | . | . | 2.10 | 0.14 |
| Gly | 404 | . | . | . | . | . | T | T | . | 0.59 | . | . | . | 1.85 | 0.11 |
| Cys | 405 | . | . | . | . | . | T | T | . | −0.22 | . | . | . | 1.00 | 0.07 |
| Val | 406 | . | . | . | B | B | . | . | . | −0.89 | . | . | . | −0.35 | 0.10 |
| His | 407 | . | . | . | B | B | . | . | . | −0.89 | . | . | . | −0.60 | 0.05 |
| Gly | 408 | . | . | . | B | B | . | . | . | −0.22 | . | * | . | −0.60 | 0.17 |
| Leu | 409 | . | . | . | B | . | . | . | . | 0.23 | . | * | . | −0.10 | 0.37 |
| Cys | 410 | . | . | . | B | . | . | . | . | 0.69 | . | * | . | 0.84 | 0.53 |
| Asp | 411 | . | . | . | . | . | T | . | . | 1.20 | . | * | F | 1.73 | 0.82 |
| Asn | 412 | . | . | . | . | . | T | . | . | 0.93 | . | . | F | 2.07 | 0.99 |
| Arg | 413 | . | . | . | . | . | . | T | C | 0.93 | . | . | F | 2.86 | 2.47 |
| Pro | 414 | . | . | . | . | . | T | T | . | 1.40 | . | . | F | 3.40 | 1.47 |
| Gly | 415 | . | . | . | . | . | T | T | . | 1.21 | . | . | F | 2.61 | 0.90 |
| Ser | 416 | . | . | . | . | . | T | T | . | 0.54 | . | . | F | 2.27 | 0.34 |
| Gly | 417 | . | . | . | . | . | T | . | . | 0.54 | . | . | F | 1.13 | 0.12 |
| Gly | 418 | . | . | . | B | . | . | . | . | 0.43 | * | . | F | 0.39 | 0.21 |
| Val | 419 | . | . | . | B | . | . | . | . | 0.30 | . | . | F | 0.05 | 0.27 |
| Cys | 420 | . | . | . | B | . | . | . | . | 0.33 | . | . | F | 0.05 | 0.27 |
| Gln | 421 | . | . | . | B | . | . | T | . | −0.03 | . | . | F | 0.25 | 0.39 |
| Gln | 422 | . | . | . | B | . | . | T | . | −0.28 | . | . | F | −0.05 | 0.28 |
| Gly | 423 | . | . | . | B | . | . | T | . | −0.14 | . | . | F | 0.25 | 0.53 |
| Thr | 424 | . | . | . | B | . | . | T | . | 0.37 | . | . | F | 0.25 | 0.47 |
| Cys | 425 | . | . | . | B | . | . | . | . | 0.33 | . | . | F | 0.05 | 0.27 |
| Ala | 426 | . | . | . | B | . | . | T | . | 0.03 | . | . | . | −0.20 | 0.24 |
| Pro | 427 | . | . | . | . | . | T | T | . | −0.31 | . | * | F | 0.35 | 0.22 |
| Gly | 428 | . | . | . | . | . | T | T | . | 0.14 | * | * | F | 0.35 | 0.41 |
| Phe | 429 | . | . | . | . | . | T | T | . | −0.24 | . | * | F | 1.25 | 0.79 |
| Ser | 430 | . | . | . | . | . | T | . | . | −0.24 | . | * | F | 0.45 | 0.44 |
| Gly | 431 | . | . | . | . | . | T | T | . | 0.34 | * | * | F | 0.65 | 0.24 |
| Arg | 432 | . | . | . | B | . | . | T | . | 0.56 | * | * | F | 0.25 | 0.44 |
| Phe | 433 | . | . | . | . | . | T | T | . | 0.60 | * | * | . | 1.44 | 0.57 |
| Cys | 434 | . | . | . | . | . | T | T | . | 0.70 | * | * | . | 1.78 | 0.78 |
| Asn | 435 | . | . | . | . | . | T | . | . | 0.66 | * | * | . | 1.92 | 0.39 |
| Glu | 436 | . | . | . | . | . | T | . | . | 1.00 | * | * | F | 1.81 | 0.45 |
| Ser | 437 | . | . | . | . | . | T | T | . | 0.22 | * | * | F | 3.40 | 1.40 |
| Met | 438 | . | . | . | . | . | T | T | . | 0.58 | . | . | F | 2.91 | 0.47 |
| Gly | 439 | . | . | . | . | . | T | T | . | 1.03 | . | . | F | 2.70 | 0.27 |
| Asp | 440 | . | . | . | . | . | T | T | . | 0.72 | . | . | F | 2.19 | 0.31 |
| Cys | 441 | . | . | . | . | . | T | . | . | 0.38 | . | . | F | 1.78 | 0.45 |
| Gly | 442 | . | . | . | . | . | . | T | C | −0.13 | . | . | F | 1.57 | 0.45 |
| Pro | 443 | . | . | . | . | . | T | T | . | −0.12 | * | . | F | 1.30 | 0.22 |
| Thr | 444 | . | . | . | . | . | T | T | . | 0.22 | . | . | F | 0.87 | 0.42 |
| Gly | 445 | . | . | . | . | . | T | T | . | 0.19 | . | . | F | 1.04 | 0.73 |
| Leu | 446 | . | . | A | B | . | . | . | . | 0.19 | . | . | . | −0.34 | 0.64 |
| Ala | 447 | . | . | A | B | . | . | . | . | 0.50 | . | . | . | −0.47 | 0.24 |
| Gln | 448 | . | . | A | B | . | . | . | . | −0.10 | . | . | . | −0.60 | 0.33 |
| His | 449 | . | . | A | B | . | . | . | . | 0.18 | . | . | . | −0.60 | 0.33 |
| Cys | 450 | . | . | A | B | . | . | . | . | −0.07 | * | * | . | −0.60 | 0.44 |
| His | 451 | . | . | A | B | . | . | . | . | 0.86 | * | * | . | −0.60 | 0.26 |
| Leu | 452 | . | . | A | B | . | . | . | . | 0.78 | * | * | . | −0.30 | 0.37 |
| His | 453 | . | . | A | . | . | T | . | . | −0.08 | * | * | . | 0.10 | 0.37 |
| Ala | 454 | . | . | A | . | . | T | . | . | −0.34 | * | * | . | −0.20 | 0.20 |
| Arg | 455 | . | . | A | . | . | T | . | . | 0.32 | * | * | . | 0.10 | 0.33 |
| Cys | 456 | . | . | A | B | . | . | . | . | 0.36 | * | * | . | −0.30 | 0.42 |
| Val | 457 | . | . | A | B | . | . | . | . | 0.82 | . | * | . | 0.61 | 0.72 |
| Ser | 458 | . | . | . | B | . | . | T | . | 0.00 | * | * | F | 1.77 | 0.36 |
| Gln | 459 | . | . | . | . | . | T | T | . | 0.00 | . | * | F | 1.58 | 0.50 |
| Glu | 460 | . | . | . | . | . | T | T | . | 0.00 | . | * | F | 1.89 | 0.68 |
| Gly | 461 | . | . | . | . | . | T | T | . | 0.00 | . | * | F | 3.10 | 1.00 |
| Val | 462 | . | . | . | . | . | T | . | . | 0.97 | . | * | . | 2.14 | 0.31 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Ala | 463 | . | . | . | B | . | . | . | . | 0.60 | . | * | . | 1.73 | 0.35 |
| Arg | 464 | . | . | . | B | . | . | . | . | -0.21 | . | * | . | 1.12 | 0.19 |
| Cys | 465 | . | . | . | B | . | . | . | . | -0.21 | . | * | . | 1.09 | 0.21 |
| Arg | 466 | . | . | . | B | . | . | . | . | -0.21 | . | * | . | 1.36 | 0.35 |
| Cys | 467 | . | . | . | B | . | . | T | . | -0.06 | . | * | . | 1.84 | 0.18 |
| Leu | 468 | . | . | . | B | . | . | . | . | 0.53 | . | * | . | 1.22 | 0.28 |
| Asp | 469 | . | . | . | . | . | T | T | . | 0.08 | . | * | . | 2.80 | 0.25 |
| Gly | 470 | . | . | . | . | . | T | T | . | 0.74 | * | * | F | 2.37 | 0.46 |
| Phe | 471 | . | . | . | . | . | T | . | . | 0.29 | * | . | F | 2.44 | 0.94 |
| Glu | 472 | . | . | . | . | . | T | . | . | 0.26 | . | . | F | 2.41 | 0.56 |
| Gly | 473 | . | . | . | . | . | T | T | . | 0.77 | . | . | F | 2.28 | 0.49 |
| Asp | 474 | . | . | . | . | . | T | T | . | 0.10 | . | . | F | 2.25 | 0.75 |
| Gly | 475 | . | . | . | . | . | T | T | . | 0.13 | . | . | F | 2.50 | 0.23 |
| Phe | 476 | . | . | . | . | . | T | T | . | 0.62 | . | . | . | 1.50 | 0.34 |
| Ser | 477 | . | . | . | . | . | T | . | . | 0.32 | . | . | . | 1.05 | 0.31 |
| Cys | 478 | . | . | . | . | . | T | . | . | 0.67 | . | . | . | 0.50 | 0.43 |
| Thr | 479 | . | . | . | . | . | . | . | C | 0.46 | . | . | F | 0.20 | 0.79 |
| Pro | 480 | . | . | . | . | . | T | . | . | 0.13 | . | . | F | 0.45 | 0.91 |
| Ser | 481 | . | . | . | . | . | T | . | . | 0.53 | . | . | F | 0.45 | 0.91 |
| Asn | 482 | . | . | . | . | . | . | T | C | 0.80 | . | . | F | 0.45 | 0.85 |
| Pro | 483 | . | . | . | . | . | T | T | . | 1.26 | . | . | F | 0.65 | 0.75 |
| Cys | 484 | . | . | . | . | . | T | T | . | 1.57 | * | . | F | 0.99 | 0.86 |
| Ser | 485 | . | . | . | B | . | T | T | . | 1.89 | * | . | F | 1.93 | 0.89 |
| His | 486 | . | . | . | B | . | . | T | . | 1.84 | * | . | F | 2.32 | 1.13 |
| Pro | 487 | . | . | . | B | . | . | T | . | 1.50 | * | . | F | 2.66 | 2.09 |
| Asp | 488 | . | . | . | . | . | T | T | . | 1.04 | * | . | F | 3.40 | 1.55 |
| Arg | 489 | . | . | . | . | . | T | T | . | 1.41 | * | . | F | 2.91 | 0.61 |
| Gly | 490 | . | . | . | . | . | T | . | . | 1.71 | . | . | F | 2.68 | 0.53 |
| Gly | 491 | . | . | . | . | . | T | . | . | 1.74 | . | . | F | 2.65 | 0.55 |
| Cys | 492 | . | . | . | . | . | T | T | . | 1.37 | . | * | F | 2.82 | 0.45 |
| Ser | 493 | . | . | . | . | . | . | T | C | 1.37 | . | * | F | 2.29 | 0.46 |
| Glu | 494 | . | . | . | . | . | T | T | . | 0.59 | . | * | F | 3.10 | 0.80 |
| Asn | 495 | . | . | . | B | . | . | T | . | 0.08 | . | . | F | 2.39 | 0.80 |
| Ala | 496 | . | . | . | B | . | . | . | . | 0.21 | . | . | . | 1.43 | 0.44 |
| Glu | 497 | . | . | . | B | . | . | . | . | 0.53 | . | . | . | 1.12 | 0.40 |
| Cys | 498 | . | . | . | B | . | . | . | . | 0.53 | * | . | . | 0.81 | 0.24 |
| Val | 499 | . | . | . | B | . | . | T | . | -0.28 | * | . | . | 0.70 | 0.32 |
| Pro | 500 | . | . | . | . | . | T | T | . | -0.62 | . | . | F | 0.65 | 0.15 |
| Gly | 501 | . | . | . | . | . | T | T | . | -0.34 | . | . | F | 0.35 | 0.28 |
| Ser | 502 | . | . | . | . | . | T | T | . | -0.38 | . | . | F | 0.35 | 0.55 |
| Leu | 503 | . | . | . | . | . | T | . | . | 0.26 | . | . | F | 0.45 | 0.49 |
| Gly | 504 | . | . | . | . | . | T | . | . | 0.44 | . | . | F | 0.15 | 0.67 |
| Thr | 505 | . | . | . | . | . | T | . | . | 0.34 | . | . | . | 0.00 | 0.27 |
| His | 506 | . | . | . | B | . | . | . | . | 0.02 | . | . | . | -0.40 | 0.47 |
| His | 507 | . | . | . | B | . | . | . | . | 0.29 | . | . | . | -0.40 | 0.25 |
| Cys | 508 | . | . | . | B | . | . | . | . | 1.14 | . | . | . | -0.40 | 0.24 |
| Thr | 509 | . | . | . | B | . | . | . | . | 1.14 | . | . | . | -0.10 | 0.35 |
| Cys | 510 | . | . | . | . | . | T | . | . | 1.17 | . | . | . | 0.30 | 0.26 |
| His | 511 | . | . | . | . | . | T | T | . | 0.90 | . | . | . | 0.20 | 0.50 |
| Lys | 512 | . | . | . | . | . | T | T | . | 0.59 | . | . | . | 0.50 | 0.47 |
| Gly | 513 | . | . | . | . | . | T | T | . | 1.26 | . | . | F | 0.65 | 0.86 |
| Trp | 514 | . | . | . | . | . | T | T | . | 1.22 | * | * | F | 1.71 | 1.06 |
| Ser | 515 | . | . | . | . | . | T | T | . | 2.00 | * | * | F | 1.87 | 0.52 |
| Gly | 516 | . | . | . | . | . | T | T | . | 1.18 | * | * | F | 2.33 | 1.03 |
| Asp | 517 | . | . | . | . | . | T | T | . | 0.47 | * | * | F | 2.49 | 0.73 |
| Gly | 518 | . | . | . | . | . | T | T | . | -0.04 | * | * | F | 3.10 | 0.29 |
| Arg | 519 | . | . | . | B | B | . | . | . | -0.34 | * | * | F | 1.69 | 0.22 |
| Val | 520 | . | . | . | B | B | . | . | . | -0.93 | . | * | . | 1.23 | 0.13 |
| Cys | 521 | . | . | . | B | B | . | . | . | -0.59 | * | * | . | 0.02 | 0.09 |
| Val | 522 | . | . | . | B | B | . | . | . | -0.59 | * | * | . | 0.01 | 0.08 |
| Ala | 523 | . | . | . | B | B | . | . | . | -0.91 | * | * | . | -0.30 | 0.19 |
| Ile | 524 | . | . | . | B | B | . | . | . | -1.02 | . | * | . | 0.30 | 0.19 |
| Asp | 525 | . | . | . | B | B | . | . | . | -0.98 | . | * | . | 0.60 | 0.44 |
| Glu | 526 | . | . | A | B | . | . | . | . | -0.31 | . | * | . | 0.60 | 0.36 |
| Cys | 527 | . | . | A | B | . | . | . | . | -0.31 | * | * | . | 0.91 | 0.85 |
| Glu | 528 | . | . | A | B | . | . | . | . | 0.39 | * | * | . | 1.22 | 0.38 |
| Leu | 529 | . | . | A | B | . | . | . | . | 0.93 | * | * | . | 1.53 | 0.43 |
| Asp | 530 | . | . | A | . | . | T | . | . | 0.59 | * | * | . | 2.24 | 0.79 |
| Val | 531 | . | . | . | . | . | T | T | . | -0.08 | . | * | F | 3.10 | 0.45 |
| Arg | 532 | . | . | . | . | . | T | T | . | 0.56 | . | * | F | 2.49 | 0.29 |
| Gly | 533 | . | . | . | . | . | T | T | . | 0.24 | . | * | F | 2.18 | 0.24 |
| Gly | 534 | . | . | . | . | . | T | T | . | 1.06 | . | * | F | 1.27 | 0.46 |
| Cys | 535 | . | . | . | . | . | T | . | . | 0.47 | . | * | . | 1.51 | 0.39 |
| His | 536 | . | . | A | B | . | . | . | . | 0.51 | . | * | . | 0.30 | 0.40 |
| Thr | 537 | . | . | A | B | . | . | . | . | -0.27 | . | * | . | -0.30 | 0.34 |
| Asp | 538 | . | . | A | B | . | . | . | . | -0.22 | . | . | . | -0.30 | 0.34 |
| Ala | 539 | . | . | A | B | . | . | . | . | -0.12 | . | . | . | -0.30 | 0.33 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Leu | 540 | . | . | . | B | B | . | . | . | −0.31 | . | . | . | −0.30 | 0.36 |
| Cys | 541 | . | . | . | B | B | . | . | . | −0.62 | . | . | . | −0.60 | 0.16 |
| Ser | 542 | . | . | . | B | B | . | . | . | −0.52 | * | . | . | −0.60 | 0.16 |
| Tyr | 543 | . | . | . | B | B | . | . | . | −0.87 | * | . | . | −0.60 | 0.29 |
| Val | 544 | . | . | . | B | B | . | . | . | −0.28 | . | . | . | −0.35 | 0.54 |
| Gly | 545 | . | . | . | . | . | . | T | C | 0.23 | * | . | * | F | 0.65 | 0.70 |
| Pro | 546 | . | . | . | . | . | T | T | . | 1.01 | . | . | * | F | 1.10 | 0.60 |
| Gly | 547 | . | . | . | . | . | T | T | . | 0.64 | . | . | * | F | 2.40 | 1.58 |
| Gln | 548 | . | . | . | . | . | T | T | . | 0.58 | . | . | * | F | 2.50 | 0.85 |
| Ser | 549 | . | . | . | B | . | . | . | . | 0.77 | . | . | * | F | 1.65 | 0.80 |
| Arg | 550 | . | . | . | B | . | . | . | . | 1.16 | * | . | * | F | 1.40 | 0.43 |
| Cys | 551 | . | . | . | B | . | . | T | . | 0.56 | * | . | * | F | 1.65 | 0.50 |
| Thr | 552 | . | . | . | B | . | . | T | . | 0.56 | . | . | * | . | 0.95 | 0.31 |
| Cys | 553 | . | . | . | B | . | . | T | . | −0.14 | . | . | * | . | 0.70 | 0.16 |
| Lys | 554 | . | . | . | B | . | . | T | . | −0.43 | * | . | * | . | −0.20 | 0.25 |
| Leu | 555 | . | . | . | B | . | . | . | . | −0.89 | * | . | * | . | −0.40 | 0.18 |
| Gly | 556 | . | . | . | B | . | . | . | . | −0.22 | . | . | * | . | −0.10 | 0.32 |
| Phe | 557 | . | . | . | B | . | . | . | . | −0.26 | . | . | * | . | 0.50 | 0.27 |
| Ala | 558 | . | . | . | . | . | T | . | . | 0.17 | . | . | * | . | 0.30 | 0.32 |
| Gly | 559 | . | . | . | . | . | T | T | . | 0.12 | . | . | * | . | 0.50 | 0.51 |
| Asp | 560 | . | . | . | . | . | T | T | . | 0.27 | . | . | . | . | 0.65 | 1.03 |
| Gly | 561 | . | . | . | . | . | T | T | . | 0.31 | . | . | . | . | 0.50 | 0.55 |
| Tyr | 562 | . | . | . | . | . | T | T | . | 0.80 | . | . | . | . | 1.10 | 0.74 |
| Gln | 563 | . | . | . | . | . | T | . | . | 0.50 | . | . | . | . | 0.90 | 0.68 |
| Cys | 564 | . | . | . | B | . | . | . | . | 0.84 | . | . | . | . | −0.17 | 0.48 |
| Ser | 565 | . | . | . | B | . | . | . | . | 0.63 | . | . | . | F | 0.51 | 0.52 |
| Pro | 566 | . | . | . | B | . | . | . | . | 0.31 | . | . | . | F | 1.34 | 0.46 |
| Ile | 567 | . | . | . | B | . | . | . | . | 0.67 | . | . | . | F | 0.97 | 0.46 |
| Asp | 568 | . | . | . | B | . | . | T | . | 0.08 | . | . | . | F | 2.30 | 0.67 |
| Pro | 569 | . | . | . | B | . | . | T | . | 0.40 | * | . | . | F | 1.77 | 0.44 |
| Cys | 570 | . | . | . | B | . | . | T | . | 0.70 | . | . | . | F | 1.79 | 0.62 |
| Arg | 571 | . | . | . | B | . | . | T | . | 0.57 | * | . | . | F | 2.11 | 0.60 |
| Ala | 572 | . | . | . | . | . | T | . | . | 1.11 | * | . | . | F | 2.03 | 0.38 |
| Gly | 573 | . | . | . | . | . | T | . | . | 0.44 | * | . | . | F | 2.05 | 0.71 |
| Asn | 574 | . | . | . | . | . | T | T | . | 0.62 | * | . | . | F | 2.50 | 0.19 |
| Gly | 575 | . | . | . | . | . | T | T | . | 0.94 | * | . | . | F | 1.65 | 0.26 |
| Gly | 576 | . | . | . | . | . | T | T | . | 0.02 | * | . | . | F | 1.40 | 0.26 |
| Cys | 577 | . | . | . | . | . | . | T | C | 0.61 | * | . | . | . | 0.50 | 0.13 |
| His | 578 | . | . | A | B | . | . | . | . | 0.14 | . | . | * | . | −0.05 | 0.23 |
| Gly | 579 | . | . | A | B | . | . | . | . | 0.14 | . | . | * | . | −0.30 | 0.19 |
| Leu | 580 | . | . | A | B | . | . | . | . | −0.10 | . | . | * | . | 0.30 | 0.63 |
| Glu | 581 | . | . | A | B | . | . | . | . | 0.24 | . | . | * | . | 0.30 | 0.47 |
| Leu | 582 | . | A | A | . | . | . | . | . | 0.32 | . | . | * | . | 0.30 | 0.76 |
| Glu | 583 | . | A | A | . | . | . | . | . | 0.32 | . | . | * | . | 0.30 | 0.93 |
| Ala | 584 | . | A | A | . | . | . | . | . | −0.03 | . | . | * | . | 0.30 | 0.73 |
| Asn | 585 | . | A | A | . | . | . | . | . | 0.48 | . | . | * | . | −0.30 | 0.77 |
| Ala | 586 | . | A | A | . | . | . | . | . | −0.41 | . | . | * | . | −0.30 | 0.59 |
| His | 587 | . | A | A | . | B | . | . | . | −0.30 | . | . | * | . | −0.60 | 0.41 |
| Phe | 588 | . | . | A | B | B | . | . | . | −0.54 | . | . | * | . | −0.60 | 0.22 |
| Ser | 589 | . | . | A | B | B | . | . | . | 0.04 | * | . | * | . | −0.60 | 0.34 |
| Ile | 590 | . | . | . | B | B | . | . | . | −0.24 | * | . | * | . | −0.60 | 0.44 |
| Phe | 591 | . | . | . | B | B | . | . | . | −0.47 | * | . | * | . | −0.60 | 0.53 |
| Tyr | 592 | . | . | . | B | B | . | . | . | −0.39 | * | . | * | . | −0.60 | 0.33 |
| Gln | 593 | . | . | . | . | B | T | . | . | 0.01 | * | . | . | . | −0.20 | 0.93 |
| Trp | 594 | . | . | . | . | B | T | . | . | −0.28 | * | . | . | . | −0.05 | 1.45 |
| Leu | 595 | . | . | . | . | B | . | . | C | 0.27 | * | . | . | . | −0.40 | 0.93 |
| Lys | 596 | . | . | . | . | B | T | . | . | 0.08 | * | . | . | F | 0.25 | 0.53 |
| Ser | 597 | . | . | . | . | . | T | . | . | 0.01 | * | . | . | F | 0.15 | 0.36 |
| Ala | 598 | . | . | . | . | . | T | . | . | −0.80 | * | . | . | F | 0.45 | 0.62 |
| Gly | 599 | . | . | . | . | . | T | . | . | −0.72 | . | . | . | . | 0.30 | 0.26 |
| Ile | 600 | . | . | . | B | . | . | . | . | −0.50 | . | . | * | . | −0.40 | 0.30 |
| Thr | 601 | . | . | . | B | . | . | . | . | −0.54 | . | . | . | . | −0.14 | 0.30 |
| Leu | 602 | . | . | . | B | . | . | . | . | −0.13 | . | . | * | . | 0.42 | 0.50 |
| Pro | 603 | . | . | . | B | . | . | T | . | 0.57 | * | . | * | . | 1.63 | 1.39 |
| Ala | 604 | . | . | . | B | . | . | T | . | 0.06 | * | . | * | F | 2.34 | 1.89 |
| Asp | 605 | . | . | . | B | . | . | T | . | 0.63 | * | . | * | F | 2.60 | 1.70 |
| Arg | 606 | . | . | . | B | . | . | T | . | 0.36 | * | . | * | F | 2.34 | 1.59 |
| Arg | 607 | . | . | . | B | B | . | . | . | 0.36 | * | . | * | F | 1.68 | 1.59 |
| Val | 608 | . | . | . | B | B | . | . | . | −0.29 | * | . | * | . | 1.12 | 0.78 |
| Thr | 609 | . | . | . | B | B | . | . | . | 0.09 | * | . | * | . | 0.56 | 0.30 |
| Ala | 610 | . | . | . | B | B | . | . | . | −0.21 | * | . | * | . | −0.30 | 0.23 |
| Leu | 611 | . | . | . | B | B | . | . | . | −0.32 | * | . | * | . | −0.60 | 0.42 |
| Val | 612 | . | . | . | B | . | . | T | . | −1.02 | * | . | * | . | 0.10 | 0.51 |
| Pro | 613 | . | . | . | . | . | . | T | C | −0.76 | . | . | . | F | 0.45 | 0.51 |
| Ser | 614 | . | . | . | . | . | . | T | C | −1.30 | * | . | * | F | 0.45 | 0.62 |
| Glu | 615 | . | . | . | B | . | . | T | . | −0.60 | * | . | * | F | 0.25 | 0.62 |
| Ala | 616 | . | . | A | B | . | . | . | . | 0.21 | * | . | . | . | 0.60 | 0.79 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Ala | 617 | . | . | A | B | . | . | . | . | 0.26 | * | * | . | 0.75 | 1.02 |
| Val | 618 | . | . | A | B | . | . | . | . | 0.17 | * | . | . | 0.30 | 0.49 |
| Arg | 619 | . | . | A | B | . | . | . | . | 0.26 | * | . | . | −0.30 | 0.64 |
| Gln | 620 | . | . | A | B | . | . | . | . | 0.26 | * | . | . | 0.04 | 0.99 |
| Leu | 621 | . | . | A | B | . | . | . | . | 0.84 | * | * | F | 1.28 | 2.30 |
| Ser | 622 | . | . | . | . | . | . | T | C | 1.54 | * | * | F | 2.52 | 1.96 |
| Pro | 623 | . | . | . | . | . | . | T | C | 1.81 | * | . | F | 2.86 | 2.22 |
| Glu | 624 | . | . | . | . | . | T | T | . | 1.00 | * | * | F | 3.40 | 2.72 |
| Asp | 625 | . | . | . | . | . | T | T | . | 0.71 | . | * | F | 3.06 | 1.76 |
| Arg | 626 | . | . | A | . | . | T | . | . | 0.71 | . | * | . | 1.87 | 1.19 |
| Ala | 627 | . | . | A | B | . | . | . | . | 1.01 | . | . | . | 0.98 | 0.57 |
| Phe | 628 | . | . | A | B | . | . | . | . | 1.01 | * | * | . | 0.04 | 0.59 |
| Trp | 629 | . | . | A | B | . | . | . | . | 1.12 | * | * | . | −0.60 | 0.47 |
| Leu | 630 | . | . | A | B | . | . | . | . | 0.81 | * | . | . | −0.60 | 0.90 |
| Gln | 631 | . | . | . | B | . | . | T | . | −0.11 | * | * | . | 0.07 | 1.50 |
| Pro | 632 | . | . | . | . | . | T | T | . | 0.27 | * | * | F | 0.74 | 1.18 |
| Arg | 633 | . | . | . | . | . | T | T | . | 0.97 | * | * | F | 1.16 | 2.21 |
| Thr | 634 | . | . | . | . | . | . | T | C | 0.44 | * | * | F | 1.68 | 2.05 |
| Leu | 635 | . | . | . | . | . | . | T | C | 0.40 | * | * | F | 1.20 | 1.10 |
| Pro | 636 | . | . | . | . | . | . | T | C | 0.51 | * | * | F | 0.93 | 0.42 |
| Asn | 637 | . | . | . | B | . | . | T | . | 0.13 | * | * | . | 0.46 | 0.56 |
| Leu | 638 | . | . | . | B | . | . | T | . | −0.01 | * | * | . | 0.34 | 0.69 |
| Val | 639 | . | . | A | B | . | . | . | . | −0.40 | * | * | . | −0.18 | 0.61 |
| Arg | 640 | . | . | A | B | . | . | . | . | −0.40 | * | * | . | −0.60 | 0.33 |
| Ala | 641 | . | . | A | B | . | . | . | . | −0.19 | . | . | . | −0.60 | 0.33 |
| His | 642 | . | . | A | B | . | . | . | . | −0.53 | . | . | . | −0.60 | 0.76 |
| Phe | 643 | . | . | A | B | . | . | . | . | −0.31 | . | * | . | −0.30 | 0.39 |
| Leu | 644 | . | . | A | B | . | . | . | . | −0.27 | . | * | . | −0.60 | 0.39 |
| Gln | 645 | . | . | A | . | . | . | . | C | −1.08 | . | * | . | −0.40 | 0.23 |
| Gly | 646 | . | . | A | . | . | . | . | C | −0.49 | . | . | . | −0.40 | 0.23 |
| Ala | 647 | . | . | A | . | . | . | . | C | −0.46 | . | . | . | −0.40 | 0.49 |
| Leu | 648 | . | . | A | . | . | . | . | C | 0.24 | . | . | . | 0.50 | 0.49 |
| Phe | 649 | A | A | . | . | . | . | . | . | 0.24 | . | . | . | 0.60 | 0.86 |
| Glu | 650 | A | A | . | . | . | . | . | . | −0.34 | * | . | . | 0.30 | 0.70 |
| Glu | 651 | A | A | . | . | . | . | . | . | 0.11 | * | . | F | 0.45 | 0.86 |
| Glu | 652 | A | A | . | . | . | . | . | . | −0.11 | * | . | F | 0.90 | 1.94 |
| Leu | 653 | A | A | . | . | . | . | . | . | 0.36 | * | . | . | 0.60 | 0.93 |
| Ala | 654 | A | A | . | . | . | . | . | . | 0.71 | * | * | . | 0.81 | 0.53 |
| Arg | 655 | A | A | . | . | . | . | . | . | 0.71 | * | * | . | 0.72 | 0.30 |
| Leu | 656 | . | . | . | . | . | . | T | C | 0.71 | * | * | . | 0.93 | 0.63 |
| Gly | 657 | . | . | . | . | . | . | T | C | −0.14 | * | . | F | 2.34 | 1.09 |
| Gly | 658 | . | . | . | . | . | . | T | C | 0.08 | * | * | F | 2.10 | 0.41 |
| Gln | 659 | . | . | . | B | . | . | T | . | 0.36 | * | * | F | 1.09 | 0.50 |
| Glu | 660 | . | . | A | B | . | . | . | . | −0.57 | * | * | F | 1.08 | 0.74 |
| Val | 661 | . | . | A | B | . | . | . | . | 0.24 | . | . | . | 0.12 | 0.61 |
| Ala | 662 | . | . | A | B | . | . | . | . | 0.38 | . | . | . | −0.09 | 0.57 |
| Thr | 663 | . | . | A | B | . | . | . | . | 0.41 | . | . | . | −0.30 | 0.51 |
| Leu | 664 | . | . | . | B | . | . | . | . | 0.10 | * | * | . | −0.40 | 0.99 |
| Asn | 665 | . | . | . | . | . | . | T | C | 0.21 | . | * | F | 0.30 | 1.41 |
| Pro | 666 | . | . | . | . | . | . | T | C | 0.78 | . | * | F | 1.20 | 1.92 |
| Thr | 667 | . | . | . | . | . | . | T | C | 1.37 | * | * | F | 0.60 | 2.45 |
| Thr | 668 | . | . | . | . | . | . | T | C | 0.79 | * | * | F | 1.20 | 2.63 |
| Arg | 669 | . | . | . | B | B | . | . | . | 1.71 | * | * | F | 0.60 | 1.19 |
| Trp | 670 | . | . | . | B | B | . | . | . | 1.71 | * | * | . | 0.70 | 1.62 |
| Glu | 671 | . | . | . | B | B | . | . | . | 1.03 | * | * | . | 1.25 | 1.81 |
| Ile | 672 | . | . | . | B | B | . | . | . | 1.04 | * | * | . | 1.05 | 0.65 |
| Arg | 673 | . | . | . | B | B | . | . | . | 1.01 | * | * | . | 0.70 | 0.82 |
| Asn | 674 | . | . | . | . | . | T | T | . | 1.01 | * | * | F | 2.50 | 0.47 |
| Ile | 675 | . | . | . | . | . | T | T | . | 0.44 | * | * | F | 2.40 | 1.31 |
| Ser | 676 | . | . | . | . | . | . | T | C | 0.16 | * | * | F | 1.80 | 0.50 |
| Gly | 677 | . | . | . | . | . | T | T | . | 0.19 | * | * | F | 0.85 | 0.33 |
| Arg | 678 | . | . | . | B | B | . | . | . | 0.08 | . | * | . | −0.35 | 0.34 |
| Val | 679 | . | . | . | B | B | . | . | . | 0.08 | * | * | . | −0.60 | 0.45 |
| Trp | 680 | . | . | . | B | B | . | . | . | 0.38 | * | * | . | −0.60 | 0.72 |
| Val | 681 | . | . | . | B | B | . | . | . | 0.38 | * | * | . | −0.60 | 0.37 |
| Gln | 682 | . | . | . | B | B | . | . | . | −0.13 | . | * | . | −0.60 | 0.67 |
| Asn | 683 | . | . | . | B | . | . | T | . | −0.24 | . | * | . | −0.20 | 0.48 |
| Ala | 684 | . | . | . | B | . | . | T | . | −0.24 | . | * | . | 0.85 | 1.07 |
| Ser | 685 | . | . | . | B | . | . | T | . | −0.54 | * | . | . | 0.70 | 0.46 |
| Val | 686 | . | . | . | B | . | . | T | . | 0.31 | * | . | . | 0.10 | 0.29 |
| Asp | 687 | . | . | A | B | . | . | . | . | −0.50 | * | . | . | 0.30 | 0.48 |
| Val | 688 | . | . | A | B | . | . | . | . | −1.31 | * | * | . | 0.30 | 0.29 |
| Ala | 689 | . | . | A | B | . | . | . | . | −1.31 | . | . | . | −0.30 | 0.33 |
| Asp | 690 | . | . | A | B | . | . | . | . | −1.32 | . | . | . | −0.30 | 0.20 |
| Leu | 691 | . | . | A | B | . | . | . | . | −0.47 | * | . | . | −0.60 | 0.38 |
| Leu | 692 | . | . | A | B | . | . | . | . | −0.81 | * | . | . | −0.30 | 0.61 |
| Ala | 693 | . | . | . | B | . | . | T | . | −0.81 | . | . | . | 0.10 | 0.36 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Thr | 694 | . | . | . | B | . | . | T | . | −1.03 | . | . | F | −0.05 | 0.33 |
| Asn | 695 | . | . | . | B | . | . | T | . | −1.07 | . | * | F | −0.05 | 0.33 |
| Gly | 696 | . | . | . | B | . | . | T | . | −1.14 | . | . | F | −0.05 | 0.44 |
| Val | 697 | . | . | . | B | B | . | . | . | −1.14 | * | . | . | −0.60 | 0.21 |
| Leu | 698 | . | . | . | B | B | . | . | . | −0.86 | * | . | . | −0.60 | 0.11 |
| His | 699 | . | . | . | B | B | . | . | . | −0.54 | * | * | . | −0.60 | 0.15 |
| Ile | 700 | . | . | . | B | B | . | . | . | −1.40 | * | . | . | −0.60 | 0.35 |
| Leu | 701 | . | . | . | B | B | . | . | . | −1.87 | * | . | . | −0.60 | 0.31 |
| Ser | 702 | . | . | . | B | B | . | . | . | −1.82 | * | . | . | −0.60 | 0.19 |
| Gln | 703 | . | . | . | B | B | . | . | . | −1.22 | * | * | . | −0.60 | 0.22 |
| Val | 704 | . | . | . | B | B | . | . | . | −1.40 | * | * | . | −0.60 | 0.42 |
| Leu | 705 | . | . | . | B | B | . | . | . | −0.40 | * | * | . | −0.60 | 0.48 |
| Leu | 706 | . | . | . | B | B | . | . | . | 0.07 | . | * | . | 0.04 | 0.54 |
| Pro | 707 | . | . | . | B | . | . | T | . | 0.37 | . | * | F | 0.93 | 0.72 |
| Pro | 708 | . | . | . | . | . | T | T | . | −0.49 | . | * | F | 2.42 | 1.46 |
| Arg | 709 | . | . | . | . | . | T | T | . | 0.16 | . | * | F | 2.76 | 1.32 |
| Gly | 710 | . | . | . | . | . | T | T | . | 0.62 | . | * | F | 3.40 | 1.32 |
| Asp | 711 | . | . | . | B | . | . | . | . | 1.09 | . | * | F | 2.31 | 0.84 |
| Val | 712 | . | . | . | B | . | . | T | . | 1.30 | . | * | F | 2.17 | 0.43 |
| Pro | 713 | . | . | . | B | . | . | T | . | 1.17 | * | * | F | 1.53 | 0.75 |
| Gly | 714 | . | . | . | . | . | T | T | . | 0.24 | * | * | F | 1.59 | 0.44 |
| Gly | 715 | . | . | . | . | . | T | T | . | −0.22 | . | . | F | 0.35 | 0.49 |
| Gln | 716 | . | . | A | B | . | . | . | . | −0.22 | . | . | F | −0.45 | 0.26 |
| Gly | 717 | . | . | A | B | . | . | . | . | 0.63 | * | . | F | −0.45 | 0.46 |
| Leu | 718 | . | . | A | B | . | . | . | . | 0.03 | * | . | F | −0.45 | 0.80 |
| Leu | 719 | . | . | A | B | . | . | . | . | 0.38 | * | . | F | −0.45 | 0.38 |
| Gln | 720 | . | . | A | B | . | . | . | . | −0.09 | * | . | . | −0.30 | 0.64 |
| Gln | 721 | . | . | A | B | . | . | . | . | −0.94 | * | . | . | −0.60 | 0.64 |
| Leu | 722 | . | . | A | B | . | . | . | . | −0.81 | . | . | . | −0.60 | 0.58 |
| Asp | 723 | . | . | A | B | . | . | . | . | −0.59 | * | . | . | −0.30 | 0.52 |
| Leu | 724 | . | . | A | B | . | . | . | . | −0.48 | . | . | . | −0.30 | 0.30 |
| Val | 725 | . | . | A | B | . | . | . | . | −0.78 | . | * | . | −0.60 | 0.32 |
| Pro | 726 | . | . | A | B | . | . | . | . | −1.59 | . | * | . | −0.60 | 0.25 |
| Ala | 727 | . | . | A | B | . | . | . | . | −1.48 | . | * | . | −0.60 | 0.25 |
| Phe | 728 | . | . | A | B | . | . | . | . | −1.37 | * | . | . | −0.60 | 0.30 |
| Ser | 729 | . | . | A | B | . | . | . | . | −0.56 | * | . | . | −0.60 | 0.38 |
| Leu | 730 | . | . | A | B | . | . | . | . | −0.51 | * | . | . | −0.30 | 0.64 |
| Phe | 731 | A | A | . | . | . | . | . | . | −1.11 | * | . | . | −0.30 | 0.61 |
| Arg | 732 | A | A | . | . | . | . | . | . | −0.52 | * | . | . | −0.30 | 0.38 |
| Glu | 733 | A | A | . | . | . | . | . | . | 0.14 | * | . | . | −0.30 | 0.79 |
| Leu | 734 | A | A | . | . | . | . | . | . | 0.41 | * | * | . | −0.15 | 1.25 |
| Leu | 735 | A | A | . | . | . | . | . | . | 0.88 | * | . | . | 0.30 | 0.87 |
| Gln | 736 | . | A | . | . | . | T | . | . | 0.77 | * | * | . | 0.10 | 0.49 |
| His | 737 | . | A | . | . | . | T | . | . | −0.20 | * | . | . | −0.20 | 0.49 |
| His | 738 | . | A | . | B | . | . | . | C | −0.41 | . | . | . | −0.40 | 0.45 |
| Gly | 739 | . | . | . | B | . | . | . | C | 0.40 | . | . | . | −0.40 | 0.40 |
| Leu | 740 | . | . | . | B | . | . | . | C | 0.32 | . | * | . | −0.40 | 0.51 |
| Val | 741 | . | . | . | B | . | . | . | C | 0.32 | . | * | . | −0.40 | 0.26 |
| Pro | 742 | . | A | B | . | . | . | . | . | −0.23 | . | . | . | −0.30 | 0.46 |
| Gln | 743 | . | A | B | . | . | . | . | . | −0.79 | . | . | F | −0.30 | 0.56 |
| Ile | 744 | . | A | B | . | . | . | . | . | −0.76 | . | . | . | −0.30 | 0.76 |
| Glu | 745 | . | A | B | . | . | . | . | . | −0.53 | . | * | . | 0.30 | 0.71 |
| Ala | 746 | . | A | B | . | . | . | . | . | 0.08 | . | . | . | −0.30 | 0.41 |
| Ala | 747 | . | A | B | B | . | . | . | . | −0.02 | . | * | . | −0.60 | 0.93 |
| Thr | 748 | . | A | B | B | . | . | . | . | −0.91 | . | * | . | −0.30 | 0.77 |
| Ala | 749 | . | A | B | B | . | . | . | . | −0.72 | . | . | . | −0.60 | 0.54 |
| Tyr | 750 | . | A | B | B | . | . | . | . | −1.58 | . | . | . | −0.60 | 0.46 |
| Thr | 751 | . | . | B | B | . | . | . | . | −1.20 | . | . | . | −0.60 | 0.24 |
| Ile | 752 | . | . | B | B | . | . | . | . | −0.92 | . | . | . | −0.60 | 0.36 |
| Phe | 753 | . | . | B | B | . | . | . | . | −0.61 | * | . | . | −0.60 | 0.33 |
| Val | 754 | . | . | B | B | . | . | . | . | 0.09 | * | . | . | −0.60 | 0.37 |
| Pro | 755 | . | . | B | . | . | T | . | . | 0.03 | * | . | F | 0.10 | 1.04 |
| Thr | 756 | . | . | . | . | . | T | C | . | −0.47 | * | . | F | 0.60 | 1.60 |
| Asn | 757 | . | . | . | . | . | T | C | . | 0.42 | * | . | F | 0.60 | 1.78 |
| Arg | 758 | . | . | . | . | . | T | C | . | 0.53 | . | . | F | 1.50 | 1.99 |
| Ser | 759 | . | A | . | . | . | . | C | . | 1.39 | . | . | F | 1.10 | 1.40 |
| Leu | 760 | . | A | B | . | . | . | . | . | 1.26 | * | * | F | 0.90 | 1.50 |
| Glu | 761 | . | A | B | . | . | . | . | . | 1.57 | * | * | F | 0.75 | 0.76 |
| Ala | 762 | . | A | . | . | T | . | . | . | 1.27 | * | * | F | 0.85 | 0.91 |
| Gln | 763 | . | A | . | . | T | . | . | . | 0.86 | * | * | F | 1.00 | 1.48 |
| Gly | 764 | . | A | . | . | T | . | . | . | 1.12 | . | * | F | 1.00 | 1.15 |
| Asn | 765 | . | . | . | . | . | T | C | . | 1.12 | . | * | F | 0.60 | 1.54 |
| Ser | 766 | . | . | . | . | . | T | C | . | 1.12 | . | . | F | 0.45 | 0.74 |
| Ser | 767 | . | . | . | . | . | T | C | . | 1.12 | . | * | F | 1.20 | 1.24 |
| His | 768 | . | . | . | . | . | T | C | . | 1.12 | . | * | F | 1.31 | 0.78 |
| Leu | 769 | . | . | . | . | . | . | C | . | 1.16 | . | . | . | 1.52 | 0.97 |
| Asp | 770 | . | . | . | . | . | T | T | . | 0.30 | * | . | . | 2.03 | 1.05 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Ala | 771 | . | . | . | B | . | . | T | . | 0.71 | * | * | F | 1.89 | 0.57 |
| Asp | 772 | . | . | . | B | . | . | T | . | 0.98 | . | * | F | 2.60 | 1.36 |
| Thr | 773 | . | . | . | B | . | . | T | . | 0.98 | . | * | F | 2.34 | 1.10 |
| Val | 774 | . | . | . | B | B | . | . | . | 0.93 | . | . | . | 1.23 | 1.49 |
| Arg | 775 | . | . | . | B | B | . | . | . | 0.08 | . | * | . | 0.82 | 0.66 |
| His | 776 | . | . | . | B | B | . | . | . | −0.14 | * | * | . | −0.34 | 0.34 |
| His | 777 | . | . | . | B | B | . | . | . | −0.49 | * | * | . | −0.60 | 0.38 |
| Val | 778 | . | . | . | B | B | . | . | . | −0.18 | . | * | . | −0.60 | 0.19 |
| Val | 779 | . | . | . | B | B | . | . | . | 0.09 | * | * | . | −0.60 | 0.24 |
| Leu | 780 | . | . | . | B | B | . | . | . | −0.83 | * | * | . | −0.60 | 0.18 |
| Gly | 781 | . | . | . | B | B | . | . | . | −1.10 | . | . | . | −0.60 | 0.20 |
| Glu | 782 | . | A | A | . | . | . | . | . | −1.67 | . | . | . | −0.30 | 0.36 |
| Ala | 783 | . | A | A | . | . | . | . | . | −0.81 | . | . | . | −0.30 | 0.43 |
| Leu | 784 | . | A | A | . | . | . | . | . | −0.27 | . | . | . | 0.30 | 0.76 |
| Ser | 785 | . | A | A | . | . | . | . | . | −0.27 | * | . | . | 0.30 | 0.63 |
| Met | 786 | . | A | A | . | . | . | . | . | 0.19 | * | . | . | −0.30 | 0.52 |
| Glu | 787 | . | A | A | . | . | . | . | . | 0.23 | * | . | . | 0.45 | 1.23 |
| Thr | 788 | . | A | A | . | . | . | . | . | 0.48 | * | . | F | 1.24 | 1.83 |
| Leu | 789 | . | A | A | . | . | . | . | . | 0.94 | * | . | F | 1.58 | 1.83 |
| Arg | 790 | . | . | . | . | . | T | T | . | 1.21 | * | . | F | 2.72 | 1.05 |
| Lys | 791 | . | . | . | . | . | T | T | . | 1.92 | * | . | F | 2.61 | 0.99 |
| Gly | 792 | . | . | . | . | . | T | T | . | 1.92 | * | . | F | 3.40 | 2.34 |
| Gly | 793 | . | . | . | . | . | . | T | C | 1.93 | * | * | F | 2.86 | 1.92 |
| His | 794 | . | . | . | . | . | . | T | C | 1.93 | * | . | F | 2.52 | 1.29 |
| Arg | 795 | . | . | . | B | . | . | T | . | 1.01 | * | . | F | 1.68 | 1.07 |
| Asn | 796 | . | . | . | B | . | . | T | . | 0.62 | . | * | F | 0.59 | 0.90 |
| Ser | 797 | . | . | . | B | . | . | T | . | 0.76 | . | . | F | 0.25 | 0.65 |
| Leu | 798 | . | . | . | B | . | . | . | . | 0.51 | . | . | F | 0.05 | 0.51 |
| Leu | 799 | . | . | . | . | . | . | . | C | 0.51 | . | * | F | −0.05 | 0.32 |
| Gly | 800 | . | . | . | . | . | . | . | C | 0.11 | * | * | F | −0.05 | 0.33 |
| Pro | 801 | . | . | . | . | . | . | . | C | −0.78 | * | . | . | −0.20 | 0.42 |
| Ala | 802 | . | . | . | B | B | . | . | . | −1.33 | . | . | . | −0.60 | 0.36 |
| His | 803 | . | . | . | B | B | . | . | . | −1.22 | . | . | . | −0.60 | 0.27 |
| Trp | 804 | . | . | . | B | B | . | . | . | −0.66 | . | . | . | −0.60 | 0.15 |
| Ile | 805 | . | . | . | B | B | . | . | . | −0.31 | . | . | . | −0.60 | 0.23 |
| Val | 806 | . | . | . | B | B | . | . | . | −0.13 | . | . | . | −0.60 | 0.27 |
| Phe | 807 | . | . | . | B | B | . | . | . | 0.16 | . | . | . | −0.60 | 0.35 |
| Tyr | 808 | . | . | . | B | . | . | . | . | −0.16 | . | . | . | −0.40 | 0.68 |
| Asn | 809 | . | . | . | . | . | T | . | . | 0.13 | . | . | . | 0.24 | 0.90 |
| His | 810 | . | . | . | . | . | T | T | . | 0.81 | . | . | F | 0.98 | 1.81 |
| Ser | 811 | . | . | . | . | . | . | T | C | 1.67 | . | * | F | 1.32 | 1.78 |
| Gly | 812 | . | . | . | . | . | . | T | C | 1.51 | . | * | F | 2.16 | 1.92 |
| Gln | 813 | . | . | . | . | . | . | T | C | 1.76 | . | * | F | 2.40 | 1.05 |
| Pro | 814 | . | . | . | . | . | . | . | C | 1.72 | * | * | F | 1.96 | 1.26 |
| Glu | 815 | . | . | . | B | . | . | . | . | 0.90 | * | * | F | 1.52 | 1.73 |
| Val | 816 | . | . | . | B | . | . | . | . | 0.99 | . | * | . | 0.38 | 0.74 |
| Asn | 817 | . | . | . | B | . | . | . | . | 0.52 | . | * | . | 0.14 | 0.74 |
| His | 818 | . | . | . | B | . | . | . | . | 0.52 | . | * | . | −0.10 | 0.35 |
| Val | 819 | . | . | . | B | . | . | . | . | 0.39 | . | . | . | −0.10 | 0.82 |
| Pro | 820 | . | . | . | . | . | . | . | C | 0.18 | . | * | . | 0.10 | 0.51 |
| Leu | 821 | . | . | . | . | . | . | . | C | 0.43 | . | . | . | 0.10 | 0.57 |
| Glu | 822 | . | . | . | . | . | . | . | C | −0.38 | . | . | F | 0.25 | 0.77 |
| Gly | 823 | . | . | . | B | . | . | . | . | −0.34 | . | * | F | 0.05 | 0.41 |
| Pro | 824 | . | . | A | B | . | . | . | . | −0.08 | . | * | F | 0.45 | 0.86 |
| Met | 825 | . | . | A | B | . | . | . | . | −0.08 | . | . | . | 0.30 | 0.50 |
| Leu | 826 | . | . | A | B | . | . | . | . | 0.39 | * | * | . | 0.01 | 0.78 |
| Glu | 827 | . | . | A | B | . | . | . | . | 0.50 | * | * | . | 0.32 | 0.50 |
| Ala | 828 | . | . | . | B | . | . | T | . | 0.54 | * | * | F | 1.78 | 0.99 |
| Pro | 829 | . | . | . | . | . | . | T | C | −0.06 | * | * | F | 2.74 | 1.61 |
| Gly | 830 | . | . | . | . | . | T | T | . | −0.34 | * | * | F | 3.10 | 0.77 |
| Arg | 831 | . | . | . | B | . | . | T | . | 0.12 | * | * | F | 1.49 | 0.53 |
| Ser | 832 | . | . | . | B | B | . | . | . | −0.69 | * | * | F | 0.78 | 0.34 |
| Leu | 833 | . | . | . | B | B | . | . | . | −0.40 | . | * | . | 0.32 | 0.28 |
| Ile | 834 | . | . | . | B | B | . | . | . | −0.53 | . | * | . | 0.01 | 0.19 |
| Gly | 835 | . | . | . | B | B | . | . | . | −1.04 | * | * | . | −0.60 | 0.14 |
| Leu | 836 | . | . | . | B | B | . | . | . | −1.97 | * | * | . | −0.60 | 0.13 |
| Ser | 837 | . | . | . | B | B | . | . | . | −1.98 | . | . | . | −0.60 | 0.15 |
| Gly | 838 | . | . | . | B | B | . | . | . | −2.02 | . | . | . | −0.60 | 0.22 |
| Val | 839 | . | . | . | B | B | . | . | . | −1.48 | . | * | . | −0.60 | 0.20 |
| Leu | 840 | . | . | . | B | B | . | . | . | −1.43 | * | . | . | −0.60 | 0.15 |
| Thr | 841 | . | . | . | B | B | . | . | . | −0.92 | . | * | . | −0.60 | 0.20 |
| Val | 842 | . | . | . | B | B | . | . | . | −0.51 | . | . | F | −0.45 | 0.36 |
| Gly | 843 | . | . | . | B | . | . | . | . | −0.83 | . | . | F | 0.05 | 0.85 |
| Ser | 844 | . | . | . | B | . | . | T | . | −0.79 | . | . | F | 0.85 | 0.32 |
| Ser | 845 | . | . | . | B | . | . | T | . | −0.01 | * | . | F | 0.25 | 0.35 |
| Arg | 846 | . | . | . | B | . | . | T | . | 0.00 | . | . | F | 0.85 | 0.49 |
| Cys | 847 | . | . | . | B | . | . | T | . | 0.82 | . | . | . | 0.70 | 0.49 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Leu | 848 | . | . | A | B | . | . | . | . | 0.58 | * | . | . | -0.30 | 0.49 |
| His | 849 | . | . | A | . | . | . | . | C | 0.88 | * | . | . | -0.10 | 0.25 |
| Ser | 850 | . | . | A | . | . | . | . | C | 0.59 | * | . | . | -0.10 | 0.82 |
| His | 851 | . | . | A | . | . | . | . | C | -0.33 | * | . | . | 0.05 | 1.01 |
| Ala | 852 | A | . | A | . | . | . | . | . | 0.44 | * | . | . | -0.30 | 0.61 |
| Glu | 853 | A | . | A | . | . | . | . | . | 1.26 | * | * | . | 0.30 | 0.89 |
| Ala | 854 | A | . | A | . | . | . | . | . | 1.33 | * | * | . | 0.75 | 1.13 |
| Leu | 855 | A | . | A | . | . | . | . | . | 0.97 | . | . | . | 1.03 | 2.24 |
| Arg | 856 | A | . | A | . | . | . | . | . | 0.14 | . | . | F | 1.31 | 0.69 |
| Glu | 857 | . | . | A | . | . | . | T | . | 0.73 | . | . | F | 1.99 | 0.51 |
| Lys | 858 | . | . | A | . | . | . | T | . | 0.07 | . | . | F | 2.27 | 0.99 |
| Cys | 859 | . | . | . | . | . | T | T | . | 0.34 | * | * | . | 2.80 | 0.27 |
| Val | 860 | . | . | . | . | . | T | T | . | 1.27 | * | * | . | 2.22 | 0.23 |
| Asn | 861 | . | . | . | . | . | T | T | . | 1.27 | * | * | . | 2.21 | 0.22 |
| Cys | 862 | . | . | . | B | . | . | T | . | 0.57 | * | * | . | 1.80 | 0.81 |
| Thr | 863 | . | . | . | . | . | T | . | . | 0.63 | * | * | . | 1.99 | 0.95 |
| Arg | 864 | . | . | . | . | . | T | . | . | 0.63 | * | * | . | 2.43 | 1.15 |
| Arg | 865 | . | . | . | . | . | T | . | . | 1.18 | * | * | . | 2.70 | 1.15 |
| Phe | 866 | . | . | . | . | . | T | . | . | 1.18 | * | * | . | 2.43 | 1.15 |
| Arg | 867 | . | . | . | . | . | T | . | . | 1.50 | * | * | . | 2.16 | 1.02 |
| Cys | 868 | . | . | . | . | . | T | T | . | 1.11 | . | * | . | 1.64 | 0.52 |
| Thr | 869 | . | . | . | . | . | T | T | . | 1.00 | . | * | F | 0.62 | 0.52 |
| Gln | 870 | . | . | . | . | . | T | T | . | 0.08 | . | * | F | 0.65 | 0.46 |
| Gly | 871 | . | . | . | . | . | T | T | . | 0.78 | . | * | F | 0.35 | 0.70 |
| Phe | 872 | . | . | . | B | . | . | . | . | 0.67 | . | * | . | -0.40 | 0.84 |
| Gln | 873 | . | . | . | B | . | . | . | . | 1.02 | . | . | . | -0.10 | 0.81 |
| Leu | 874 | . | . | . | B | . | . | . | . | 1.12 | . | * | . | 0.39 | 1.18 |
| Gln | 875 | . | . | . | B | . | . | . | . | 1.23 | * | * | F | 0.88 | 2.11 |
| Asp | 876 | . | . | . | . | . | T | . | . | 1.62 | * | * | F | 2.52 | 2.39 |
| Thr | 877 | . | . | . | . | . | . | T | C | 2.02 | * | * | F | 2.86 | 5.80 |
| Pro | 878 | . | . | . | . | . | T | T | . | 1.36 | * | * | F | 3.40 | 4.48 |
| Arg | 879 | . | . | . | . | . | T | T | . | 1.31 | * | . | F | 3.06 | 1.44 |
| Lys | 880 | . | . | . | . | . | T | T | . | 1.07 | . | . | F | 2.27 | 0.74 |
| Ser | 881 | . | . | . | B | B | . | . | . | 1.18 | . | . | . | 0.98 | 0.75 |
| Cys | 882 | . | . | . | B | B | . | . | . | 1.19 | . | . | . | 0.94 | 0.75 |
| Val | 883 | . | . | . | B | B | . | . | . | 1.06 | . | * | . | 0.30 | 0.50 |
| Tyr | 884 | . | . | . | B | . | . | T | . | 0.24 | . | * | . | 0.10 | 0.37 |
| Arg | 885 | . | . | . | B | . | . | T | . | -0.10 | * | * | F | -0.05 | 0.60 |
| Ser | 886 | . | . | . | B | . | . | . | . | -0.50 | * | * | F | 0.40 | 1.08 |
| Gly | 887 | . | . | . | . | . | T | T | . | -0.13 | * | . | F | 0.35 | 0.60 |
| Phe | 888 | . | . | . | . | . | T | . | . | 0.83 | * | . | . | 0.30 | 0.41 |
| Ser | 889 | . | . | . | B | . | . | . | . | 0.73 | * | * | . | 0.00 | 0.60 |
| Phe | 890 | . | . | . | . | . | T | . | . | -0.04 | * | * | . | 0.50 | 0.60 |
| Ser | 891 | . | . | . | . | . | T | T | . | -0.04 | * | . | . | 0.80 | 0.37 |
| Arg | 892 | . | . | . | . | . | T | T | . | 0.06 | * | . | F | 1.65 | 0.37 |
| Gly | 893 | . | . | . | . | . | T | T | . | 0.44 | * | . | . | 1.00 | 0.67 |
| Cys | 894 | . | . | . | . | . | T | T | . | 0.08 | * | . | . | 0.90 | 0.72 |
| Ser | 895 | . | . | . | . | B | T | . | . | 0.19 | * | . | . | 0.40 | 0.20 |
| Tyr | 896 | . | . | . | . | B | T | . | . | 0.53 | . | . | . | 0.00 | 0.20 |
| Thr | 897 | . | . | . | . | B | T | . | . | 0.47 | . | * | . | 0.20 | 0.75 |
| Cys | 898 | . | . | . | B | B | . | . | . | -0.08 | * | . | . | 0.45 | 1.12 |
| Ala | 899 | . | . | . | . | B | T | . | . | 0.59 | . | * | . | 0.10 | 0.50 |
| Lys | 900 | . | . | . | B | . | . | . | . | 0.03 | . | * | . | 0.50 | 0.60 |
| Lys | 901 | . | . | . | B | . | . | . | . | 0.07 | . | . | F | 0.65 | 0.83 |
| Ile | 902 | . | . | . | B | . | . | . | . | 0.38 | . | . | F | 0.80 | 1.28 |
| Gln | 903 | . | . | . | B | . | . | . | . | 0.38 | . | . | . | 0.95 | 1.07 |
| Val | 904 | . | . | . | B | . | . | T | . | 0.30 | . | . | . | 0.70 | 0.29 |
| Pro | 905 | . | . | . | B | . | . | T | . | 0.04 | . | . | . | 0.10 | 0.22 |
| Asp | 906 | . | . | . | . | . | T | T | . | -0.34 | . | * | . | 0.50 | 0.20 |
| Cys | 907 | . | . | . | B | . | . | T | . | -0.16 | * | . | . | 0.10 | 0.26 |
| Cys | 908 | . | . | . | B | . | . | T | . | -0.86 | * | . | . | 0.10 | 0.15 |
| Pro | 909 | . | . | . | . | . | T | T | . | -0.34 | * | . | . | 0.20 | 0.08 |
| Gly | 910 | . | . | . | . | . | T | T | . | -0.44 | * | . | . | 0.20 | 0.14 |
| Phe | 911 | . | . | . | . | . | T | T | . | -1.26 | * | . | . | 0.20 | 0.38 |
| Phe | 912 | . | . | . | . | . | T | . | . | -1.26 | . | . | . | 0.00 | 0.20 |
| Gly | 913 | . | . | . | . | . | T | . | . | -0.59 | * | . | . | 0.00 | 0.11 |
| Thr | 914 | . | . | . | B | . | . | . | . | -0.59 | * | . | . | -0.40 | 0.22 |
| Leu | 915 | . | . | . | . | . | T | . | . | -0.91 | . | . | . | 0.30 | 0.39 |
| Cys | 916 | . | . | . | B | . | . | . | . | -0.42 | * | . | . | 0.15 | 0.21 |
| Glu | 917 | . | . | . | B | . | . | . | . | -0.07 | . | . | F | 0.55 | 0.22 |
| Pro | 918 | . | . | . | . | . | T | . | . | -0.07 | . | . | F | 1.20 | 0.27 |
| Cys | 919 | . | . | . | . | . | T | T | . | -0.57 | . | . | F | 2.25 | 0.50 |
| Pro | 920 | . | . | . | . | . | T | . | . | -0.10 | . | . | F | 2.50 | 0.24 |
| Gly | 921 | . | . | . | . | . | T | T | . | 0.22 | . | . | F | 1.35 | 0.15 |
| Gly | 922 | . | . | . | . | . | T | T | . | -0.63 | . | . | F | 1.10 | 0.28 |
| Leu | 923 | . | . | . | . | B | T | . | . | -1.09 | . | . | F | 0.45 | 0.13 |
| Gly | 924 | . | . | . | . | B | B | . | . | -0.72 | . | . | F | -0.20 | 0.07 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Gly | 925 | . | . | B | B | . | . | . | . | −0.86 | . | . | . | −0.60 | 0.10 |
| Val | 926 | . | . | B | B | . | . | . | . | −0.54 | . | . | . | −0.60 | 0.12 |
| Cys | 927 | . | . | B | . | . | . | T | . | −0.54 | . | . | . | 0.10 | 0.16 |
| Ser | 928 | . | . | B | . | . | . | T | . | 0.27 | . | . | . | 0.10 | 0.16 |
| Gly | 929 | . | . | . | . | . | T | T | . | −0.06 | . | * | F | 0.91 | 0.38 |
| His | 930 | . | . | . | . | . | T | T | . | 0.29 | . | . | F | 1.17 | 0.38 |
| Gly | 931 | . | . | . | . | . | T | . | . | 1.14 | * | * | F | 1.23 | 0.49 |
| Gln | 932 | . | . | . | . | . | T | . | . | 1.92 | * | * | F | 2.09 | 0.83 |
| Cys | 933 | . | . | B | . | . | . | T | . | 1.52 | * | * | F | 2.60 | 1.19 |
| Gln | 934 | . | . | B | . | . | . | T | . | 1.06 | * | * | F | 2.04 | 1.04 |
| Asp | 935 | . | . | B | . | . | . | T | . | 0.74 | * | * | F | 1.88 | 0.50 |
| Arg | 936 | . | . | B | . | . | . | T | . | 0.79 | * | * | . | 1.72 | 0.92 |
| Phe | 937 | . | . | . | . | . | T | . | . | 0.44 | * | * | . | 1.91 | 0.71 |
| Leu | 938 | . | . | . | . | . | T | . | . | 1.11 | * | * | F | 2.05 | 0.42 |
| Gly | 939 | . | . | . | . | . | T | T | . | 0.44 | * | * | F | 2.50 | 0.37 |
| Ser | 940 | . | . | . | . | . | T | T | . | 0.41 | * | * | F | 1.65 | 0.23 |
| Gly | 941 | . | . | . | . | . | T | T | . | −0.37 | * | * | F | 1.40 | 0.38 |
| Glu | 942 | . | . | . | . | . | T | T | . | 0.30 | . | . | F | 1.75 | 0.21 |
| Cys | 943 | . | . | . | . | . | T | . | . | 1.11 | . | . | . | 1.15 | 0.21 |
| His | 944 | . | . | . | . | . | T | . | . | 1.11 | . | * | . | 0.90 | 0.37 |
| Cys | 945 | . | . | B | . | . | . | T | . | 0.71 | . | . | . | 0.70 | 0.21 |
| His | 946 | . | . | . | . | . | T | T | . | 1.02 | . | * | . | 0.50 | 0.34 |
| Glu | 947 | . | . | . | . | . | T | T | . | 0.68 | . | . | . | 0.50 | 0.34 |
| Gly | 948 | . | . | . | . | . | T | T | . | 1.03 | . | . | . | 0.50 | 0.62 |
| Phe | 949 | . | . | . | . | . | T | . | . | 0.48 | . | . | . | 0.30 | 0.66 |
| His | 950 | . | . | . | . | . | T | . | . | 0.48 | . | . | . | 0.30 | 0.39 |
| Gly | 951 | . | . | . | . | . | T | . | . | 0.51 | * | . | . | 0.00 | 0.21 |
| Thr | 952 | . | . | A | . | . | T | . | . | −0.34 | * | . | . | 0.10 | 0.42 |
| Ala | 953 | . | . | A | . | . | T | . | C | −0.67 | * | . | . | 0.10 | 0.23 |
| Cys | 954 | . | . | A | B | . | . | . | . | 0.03 | * | . | . | −0.30 | 0.12 |
| Glu | 955 | . | . | A | B | . | . | . | . | −0.74 | . | . | . | 0.30 | 0.15 |
| Val | 956 | . | . | A | B | . | . | . | . | −0.74 | * | . | . | 0.30 | 0.12 |
| Cys | 957 | . | . | A | B | . | . | . | . | −0.32 | * | . | . | 0.30 | 0.22 |
| Glu | 958 | . | . | A | B | . | . | . | . | 0.02 | * | . | . | 0.60 | 0.25 |
| Leu | 959 | . | . | A | B | . | . | . | . | 0.34 | * | . | . | −0.30 | 0.53 |
| Gly | 960 | . | . | A | . | . | T | . | . | 0.13 | * | . | . | 0.83 | 0.98 |
| Arg | 961 | . | . | . | . | . | T | . | . | 0.99 | * | . | F | 1.31 | 0.88 |
| Tyr | 962 | . | . | . | . | . | T | . | . | 0.99 | * | . | F | 0.99 | 1.71 |
| Gly | 963 | . | . | . | . | . | . | T | C | 0.68 | * | * | F | 0.97 | 0.93 |
| Pro | 964 | . | . | . | . | . | T | T | . | 1.14 | * | . | F | 1.30 | 0.68 |
| Asn | 965 | . | . | . | . | . | T | T | . | 0.63 | * | * | F | 0.87 | 0.43 |
| Cys | 966 | . | . | . | . | . | T | T | . | −0.14 | * | * | F | 1.04 | 0.32 |
| Thr | 967 | . | . | . | B | B | . | . | . | 0.10 | . | . | F | −0.19 | 0.11 |
| Gly | 968 | . | . | . | B | B | . | . | . | −0.22 | . | . | . | −0.17 | 0.12 |
| Val | 969 | . | . | . | B | B | . | . | . | −0.60 | . | . | . | −0.30 | 0.12 |
| Cys | 970 | . | . | . | B | B | . | . | . | −0.63 | . | . | . | −0.30 | 0.08 |
| Asp | 971 | . | . | . | B | B | . | . | . | −0.31 | * | . | . | −0.30 | 0.11 |
| Cys | 972 | . | . | . | B | . | . | T | . | −0.81 | * | . | . | 0.10 | 0.15 |
| Ala | 973 | . | . | . | . | . | T | T | . | −1.13 | * | . | . | 0.50 | 0.23 |
| His | 974 | . | . | . | . | . | T | T | . | −0.28 | * | . | . | 0.50 | 0.07 |
| Gly | 975 | . | . | . | . | . | T | T | . | 0.39 | * | . | . | 0.20 | 0.24 |
| Leu | 976 | . | . | . | B | . | . | . | . | 0.04 | * | . | . | −0.10 | 0.41 |
| Cys | 977 | . | . | . | B | . | . | T | . | −0.10 | * | . | . | 0.10 | 0.30 |
| Gln | 978 | . | . | . | B | . | . | T | . | 0.49 | * | . | . | 0.37 | 0.25 |
| Glu | 979 | . | . | . | B | . | . | T | . | 0.18 | . | * | F | 0.79 | 0.52 |
| Gly | 980 | . | . | . | B | . | . | T | . | 0.52 | . | * | F | 1.66 | 0.96 |
| Leu | 981 | . | . | . | . | . | T | . | . | 0.99 | . | * | F | 2.43 | 0.93 |
| Gln | 982 | . | . | . | . | . | T | . | . | 1.36 | . | * | F | 2.70 | 0.53 |
| Gly | 983 | . | . | . | . | . | T | T | . | 0.69 | * | * | F | 2.33 | 0.72 |
| Asp | 984 | . | . | . | . | . | T | T | . | −0.17 | . | . | F | 2.06 | 0.47 |
| Gly | 985 | . | . | . | . | . | T | T | . | −0.49 | . | * | F | 1.79 | 0.20 |
| Ser | 986 | . | . | . | . | . | T | T | . | 0.32 | * | * | F | 0.92 | 0.11 |
| Cys | 987 | . | . | . | B | B | . | . | . | −0.53 | . | * | . | −0.30 | 0.10 |
| Val | 988 | . | . | . | B | B | . | . | . | −0.53 | . | * | . | −0.60 | 0.08 |
| Cys | 989 | . | . | . | B | B | . | . | . | −0.82 | * | * | . | −0.60 | 0.06 |
| Asn | 990 | . | . | . | B | . | . | T | . | −0.48 | * | * | . | −0.20 | 0.11 |
| Val | 991 | . | . | . | B | . | . | T | . | −0.52 | * | . | . | −0.20 | 0.26 |
| Gly | 992 | . | . | . | . | . | T | T | . | −0.67 | * | . | . | 0.20 | 0.49 |
| Trp | 993 | . | . | . | . | . | T | T | . | 0.30 | * | * | . | 0.20 | 0.25 |
| Gln | 994 | . | . | . | B | . | . | . | . | 0.30 | * | * | . | −0.40 | 0.66 |
| Gly | 995 | . | . | . | B | . | . | . | . | 0.30 | * | * | . | −0.40 | 0.36 |
| Leu | 996 | . | . | A | B | . | . | . | . | 1.16 | * | * | . | −0.30 | 0.57 |
| Arg | 997 | . | . | A | B | . | . | . | . | 1.54 | * | * | . | 0.60 | 0.57 |
| Cys | 998 | . | . | A | . | . | . | T | . | 0.94 | * | * | F | 1.30 | 1.15 |
| Asp | 999 | . | . | A | . | . | . | T | . | 0.63 | * | * | F | 1.15 | 0.98 |
| Gln | 1000 | . | . | A | . | B | . | T | . | 0.68 | * | * | F | 1.15 | 0.72 |
| Lys | 1001 | . | . | A | . | B | . | T | . | 1.28 | * | * | F | 1.00 | 1.80 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Ile | 1002 | . | . | A | . | B | T | . | . | 1.17 | * | * | F | 1.30 | 1.66 |
| Thr | 1003 | . | . | . | B | B | . | . | . | 1.17 | . | . | F | 0.60 | 1.66 |
| Ser | 1004 | . | . | . | B | B | . | . | . | 0.96 | . | * | F | 0.45 | 0.45 |
| Pro | 1005 | . | . | . | . | . | T | . | . | 1.07 | . | . | F | 0.45 | 0.98 |
| Gln | 1006 | . | . | . | . | . | T | . | . | 1.07 | . | . | F | 1.54 | 1.34 |
| Cys | 1007 | . | . | . | B | . | . | T | . | 1.29 | . | . | F | 1.98 | 1.99 |
| Pro | 1008 | . | . | . | . | . | T | T | . | 1.60 | * | . | F | 2.57 | 0.69 |
| Arg | 1009 | . | . | . | . | . | T | T | . | 1.69 | * | . | F | 2.91 | 0.67 |
| Lys | 1010 | . | . | . | . | . | T | T | . | 1.90 | * | . | F | 3.40 | 1.92 |
| Cys | 1011 | . | . | . | . | . | T | . | . | 1.31 | * | * | F | 2.86 | 2.00 |
| Asp | 1012 | . | . | . | . | . | T | T | . | 1.98 | * | * | F | 2.72 | 1.03 |
| Pro | 1013 | . | . | . | . | . | T | T | . | 1.52 | * | . | F | 2.23 | 0.83 |
| Asn | 1014 | . | . | . | . | . | T | T | . | 0.56 | * | . | F | 1.59 | 0.83 |
| Ala | 1015 | . | . | . | B | . | . | T | . | 0.51 | * | * | . | 0.70 | 0.37 |
| Asn | 1016 | . | . | . | B | . | . | . | . | 1.18 | * | * | . | −0.10 | 0.41 |
| Cys | 1017 | . | . | . | B | . | . | . | . | 0.88 | * | . | . | 0.50 | 0.43 |
| Val | 1018 | . | . | . | B | . | . | T | . | 0.50 | . | . | . | 0.91 | 0.57 |
| Gln | 1019 | . | . | . | B | . | . | T | . | 0.16 | . | . | . | 1.12 | 0.36 |
| Asp | 1020 | . | . | . | B | . | . | T | . | 0.16 | . | . | F | 1.48 | 0.66 |
| Ser | 1021 | . | . | . | . | . | T | T | . | −0.14 | . | . | F | 2.09 | 0.90 |
| Ala | 1022 | . | . | . | . | . | T | . | . | 0.21 | . | . | F | 2.10 | 0.69 |
| Gly | 1023 | . | . | . | . | . | T | . | . | 0.40 | . | . | F | 1.89 | 0.60 |
| Ala | 1024 | . | . | . | . | . | T | . | . | −0.19 | . | . | F | 1.08 | 0.24 |
| Ser | 1025 | . | . | . | B | . | . | T | . | −0.86 | . | . | F | 0.67 | 0.24 |
| Thr | 1026 | . | . | . | B | . | . | T | . | −1.14 | . | . | . | 0.01 | 0.13 |
| Cys | 1027 | . | . | . | B | . | . | T | . | −1.14 | . | . | . | −0.20 | 0.13 |
| Ala | 1028 | . | . | . | B | . | . | T | . | −1.14 | . | . | . | −0.20 | 0.10 |
| Cys | 1029 | . | . | A | B | . | . | . | . | −0.80 | . | . | . | −0.60 | 0.07 |
| Ala | 1030 | . | . | A | B | . | . | . | . | −0.80 | . | . | . | −0.60 | 0.20 |
| Ala | 1031 | . | . | A | B | . | . | . | . | −0.83 | . | . | . | −0.60 | 0.26 |
| Gly | 1032 | . | . | A | . | . | T | . | . | −0.17 | . | . | . | −0.20 | 0.48 |
| Tyr | 1033 | . | . | . | . | . | T | . | . | 0.08 | . | . | . | 0.00 | 0.77 |
| Ser | 1034 | . | . | . | . | . | T | T | . | −0.14 | . | . | F | 0.65 | 0.75 |
| Gly | 1035 | . | . | . | . | . | T | T | . | −0.26 | . | . | F | 0.35 | 0.53 |
| Asn | 1036 | . | . | . | . | . | T | T | . | −0.33 | . | . | F | 0.35 | 0.29 |
| Gly | 1037 | . | . | . | . | . | T | T | . | −0.29 | . | . | F | 0.35 | 0.12 |
| Ile | 1038 | . | . | . | B | B | . | . | . | −0.04 | . | . | . | −0.60 | 0.16 |
| Phe | 1039 | . | . | . | B | B | . | . | . | −0.60 | . | * | . | −0.30 | 0.17 |
| Cys | 1040 | . | . | . | B | B | . | . | . | −0.26 | . | * | . | −0.60 | 0.13 |
| Ser | 1041 | . | . | . | B | . | . | . | . | −0.47 | . | * | . | 0.12 | 0.31 |
| Glu | 1042 | . | . | . | B | . | . | . | . | −0.79 | . | * | F | 1.09 | 0.55 |
| Val | 1043 | . | . | . | . | . | T | . | . | −0.49 | * | * | F | 1.71 | 0.55 |
| Asp | 1044 | . | . | . | . | . | . | T | C | 0.18 | * | * | F | 1.93 | 0.41 |
| Pro | 1045 | . | . | . | . | . | T | T | . | 0.50 | . | * | . | 2.20 | 0.32 |
| Cys | 1046 | . | . | . | . | . | T | T | . | 0.77 | . | * | . | 1.38 | 0.43 |
| Ala | 1047 | . | . | . | B | . | . | T | . | 0.42 | . | * | . | 1.36 | 0.35 |
| His | 1048 | . | . | . | . | . | T | . | . | 0.93 | . | * | . | 0.74 | 0.23 |
| Gly | 1049 | . | . | . | . | . | T | . | . | 0.27 | . | * | . | 0.52 | 0.42 |
| His | 1050 | . | . | . | . | . | T | . | . | 0.18 | . | . | . | 0.50 | 0.22 |
| Gly | 1051 | . | . | . | . | . | T | T | . | 0.63 | . | . | F | 0.65 | 0.22 |
| Gly | 1052 | . | . | . | . | . | T | T | . | 1.19 | . | * | F | 0.65 | 0.34 |
| Cys | 1053 | . | . | . | . | . | T | T | . | 0.63 | . | * | F | 0.65 | 0.34 |
| Ser | 1054 | . | . | . | . | . | . | . | C | 0.98 | . | * | F | 0.25 | 0.35 |
| Pro | 1055 | . | . | . | . | . | T | . | . | 0.34 | . | * | F | 0.45 | 0.56 |
| His | 1056 | . | . | . | . | . | T | T | . | 0.38 | . | . | . | 0.50 | 0.56 |
| Ala | 1057 | . | . | . | . | . | T | T | . | 0.77 | . | . | . | 0.50 | 0.61 |
| Asn | 1058 | . | . | . | . | . | T | T | . | 0.58 | . | . | . | 1.10 | 0.78 |
| Cys | 1059 | . | . | . | B | . | . | T | . | 0.29 | . | . | . | 0.10 | 0.43 |
| Thr | 1060 | . | . | . | B | . | . | . | . | 0.29 | . | . | . | 0.21 | 0.43 |
| Lys | 1061 | . | . | . | B | . | . | . | . | −0.02 | . | . | F | 0.67 | 0.41 |
| Val | 1062 | . | . | . | B | . | . | . | . | 0.57 | . | . | F | 0.98 | 0.76 |
| Ala | 1063 | . | . | . | B | . | . | T | . | 0.68 | . | . | F | 2.09 | 0.91 |
| Pro | 1064 | . | . | . | . | . | T | T | . | 1.03 | * | . | F | 3.10 | 0.89 |
| Gly | 1065 | . | . | . | . | . | T | T | . | 0.68 | * | . | F | 2.64 | 1.73 |
| Gln | 1066 | . | . | . | . | . | T | T | . | 0.32 | . | . | F | 2.18 | 0.92 |
| Arg | 1067 | . | . | . | . | . | T | . | . | 0.51 | . | . | F | 1.67 | 0.86 |
| Thr | 1068 | . | . | . | B | . | . | . | . | 1.10 | . | . | F | 0.96 | 0.47 |
| Cys | 1069 | . | . | . | B | . | . | . | . | 1.31 | . | . | . | 0.50 | 0.47 |
| Thr | 1070 | . | . | . | B | . | . | . | . | 1.31 | . | . | . | 0.50 | 0.40 |
| Cys | 1071 | . | . | . | B | . | . | T | . | 1.07 | . | . | . | 0.70 | 0.27 |
| Gln | 1072 | . | . | . | B | . | . | T | . | 0.36 | . | . | . | 0.10 | 0.80 |
| Asp | 1073 | . | . | . | . | . | T | T | . | 0.32 | . | . | . | 0.78 | 0.55 |
| Gly | 1074 | . | . | . | . | . | T | . | . | 0.99 | . | . | . | 1.21 | 1.01 |
| Tyr | 1075 | . | . | . | . | . | T | . | . | 0.96 | . | . | . | 1.74 | 0.97 |
| Met | 1076 | . | . | . | . | . | T | T | . | 1.62 | . | * | . | 2.22 | 0.58 |
| Gly | 1077 | . | . | . | . | . | T | T | . | 0.81 | . | . | F | 2.80 | 1.01 |
| Asp | 1078 | . | . | . | . | . | T | T | . | 0.14 | . | . | F | 2.37 | 0.53 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Gly | 1079 | . | . | . | . | . | . | T | C | 0.49 | . | . | F | 1.89 | 0.29 |
| Glu | 1080 | . | . | A | B | . | . | . | . | 0.73 | . | * | F | 1.01 | 0.50 |
| Leu | 1081 | . | . | A | B | . | . | . | . | 0.44 | . | * | . | 0.88 | 0.52 |
| Cys | 1082 | . | . | A | B | . | . | . | . | 0.79 | * | * | . | 0.30 | 0.37 |
| Gln | 1083 | . | . | A | B | . | . | . | . | 0.49 | * | * | . | 0.30 | 0.34 |
| Glu | 1084 | . | . | A | . | . | . | T | . | 0.17 | * | * | F | 0.25 | 0.56 |
| Ile | 1085 | . | . | A | . | . | . | T | . | −0.64 | * | * | F | 0.25 | 0.56 |
| Asn | 1086 | . | . | . | . | . | . | T | T | . | −0.72 | * | . | . | 0.50 | 0.27 |
| Ser | 1087 | . | . | . | . | . | . | T | T | . | −0.09 | * | . | . | 0.20 | 0.11 |
| Cys | 1088 | . | . | . | B | . | . | . | T | . | −0.12 | * | . | . | −0.20 | 0.21 |
| Leu | 1089 | . | . | . | B | . | . | . | T | . | −0.47 | * | . | . | −0.20 | 0.18 |
| Ile | 1090 | . | . | . | B | . | . | . | . | . | 0.08 | . | . | . | −0.40 | 0.13 |
| His | 1091 | . | . | . | . | . | T | . | . | −0.59 | . | . | . | 0.00 | 0.24 |
| His | 1092 | . | . | . | . | . | T | T | . | −0.32 | * | . | . | 0.20 | 0.16 |
| Gly | 1093 | . | . | . | . | . | T | T | . | −0.54 | * | . | . | 0.20 | 0.30 |
| Gly | 1094 | . | . | . | . | . | T | T | . | 0.23 | * | * | . | 0.20 | 0.16 |
| Cys | 1095 | . | . | . | . | . | T | T | . | 0.53 | * | * | . | 0.20 | 0.16 |
| His | 1096 | . | . | A | . | . | . | T | . | 0.57 | . | * | . | −0.20 | 0.16 |
| Ile | 1097 | . | . | A | B | . | . | . | . | −0.07 | . | * | . | −0.30 | 0.28 |
| His | 1098 | . | . | A | B | . | . | . | . | −0.61 | . | * | . | −0.30 | 0.28 |
| Ala | 1099 | . | . | A | B | . | . | . | . | −0.48 | . | . | . | −0.60 | 0.14 |
| Glu | 1100 | . | . | A | B | . | . | . | . | −0.12 | . | * | . | −0.30 | 0.32 |
| Cys | 1101 | . | . | A | B | . | . | . | . | −0.43 | . | * | . | −0.30 | 0.34 |
| Ile | 1102 | . | . | A | . | . | . | . | C | 0.24 | . | * | . | −0.10 | 0.33 |
| Pro | 1103 | . | . | . | . | . | T | T | . | 0.28 | * | . | F | 0.65 | 0.29 |
| Thr | 1104 | . | . | . | . | . | T | T | . | 0.87 | * | . | F | 0.35 | 0.95 |
| Gly | 1105 | . | . | . | . | . | . | T | C | 0.01 | * | . | F | 0.60 | 2.35 |
| Pro | 1106 | . | . | . | . | . | T | T | . | 0.38 | * | . | F | 0.80 | 1.13 |
| Gln | 1107 | . | . | . | . | . | T | . | . | 0.60 | * | . | F | 0.60 | 1.05 |
| Gln | 1108 | . | . | . | B | . | . | . | . | 0.51 | . | . | F | 0.05 | 0.57 |
| Val | 1109 | . | . | . | B | . | . | . | . | 0.16 | * | * | F | 0.05 | 0.49 |
| Ser | 1110 | . | . | . | B | . | . | . | . | 0.61 | * | * | . | −0.10 | 0.15 |
| Cys | 1111 | . | . | . | B | . | . | T | . | 0.82 | * | * | . | 0.70 | 0.17 |
| Ser | 1112 | . | . | . | B | . | . | T | . | 0.48 | * | * | . | 0.70 | 0.40 |
| Cys | 1113 | . | . | . | B | . | . | T | . | 0.23 | * | * | . | 1.00 | 0.30 |
| Arg | 1114 | . | . | . | . | . | T | T | . | 0.79 | * | * | F | 1.56 | 0.87 |
| Glu | 1115 | . | . | . | . | . | T | . | . | 0.74 | . | * | F | 1.67 | 0.87 |
| Gly | 1116 | . | . | . | . | . | T | . | . | 1.41 | . | * | F | 2.13 | 1.60 |
| Tyr | 1117 | . | . | . | . | . | T | . | . | 1.37 | . | * | F | 2.74 | 1.36 |
| Ser | 1118 | . | . | . | . | . | T | T | . | 1.14 | . | * | F | 3.10 | 0.78 |
| Gly | 1119 | . | . | . | . | . | T | T | . | 1.14 | . | * | F | 1.89 | 0.55 |
| Asp | 1120 | . | . | . | . | . | T | T | . | 0.83 | * | . | F | 2.18 | 0.69 |
| Gly | 1121 | . | . | . | . | . | T | T | . | 0.51 | * | . | F | 2.17 | 0.74 |
| Ile | 1122 | . | . | . | B | . | . | . | . | 0.76 | * | . | F | 0.96 | 0.40 |
| Arg | 1123 | . | . | . | B | . | . | . | . | 0.24 | * | . | F | 0.95 | 0.42 |
| Thr | 1124 | . | . | . | B | . | . | . | . | −0.22 | * | . | F | 0.65 | 0.35 |
| Cys | 1125 | . | . | . | B | . | . | . | . | −0.22 | * | . | . | −0.10 | 0.41 |
| Glu | 1126 | . | . | . | B | . | . | . | . | −0.09 | * | * | . | 0.80 | 0.35 |
| Leu | 1127 | . | . | . | B | . | . | . | . | 0.13 | * | * | . | 0.84 | 0.37 |
| Leu | 1128 | . | . | . | B | . | . | . | . | −0.28 | * | . | . | 1.18 | 0.37 |
| Asp | 1129 | . | . | . | B | . | . | T | . | 0.08 | * | . | F | 1.87 | 0.29 |
| Pro | 1130 | . | . | . | . | . | T | T | . | 0.74 | * | . | F | 2.61 | 0.70 |
| Cys | 1131 | . | . | . | . | . | T | T | . | 0.74 | * | . | F | 3.40 | 1.37 |
| Ser | 1132 | . | . | . | . | . | T | T | . | 1.21 | . | . | F | 3.06 | 1.32 |
| Lys | 1133 | . | . | . | . | . | T | . | . | 1.68 | . | * | F | 2.20 | 0.84 |
| Asn | 1134 | . | . | . | . | . | T | T | . | 1.01 | . | . | F | 2.34 | 1.56 |
| Asn | 1135 | . | . | . | . | . | T | T | . | 0.92 | . | . | F | 1.98 | 0.62 |
| Gly | 1136 | . | . | . | . | . | T | T | . | 1.38 | . | . | F | 1.77 | 0.42 |
| Gly | 1137 | . | . | . | . | . | T | T | . | 1.43 | . | . | F | 1.30 | 0.40 |
| Cys | 1138 | . | . | . | . | . | T | . | . | 0.80 | . | . | F | 0.67 | 0.39 |
| Ser | 1139 | . | . | . | B | . | . | T | . | 0.49 | . | . | F | 0.34 | 0.40 |
| Pro | 1140 | . | . | . | B | . | . | T | . | −0.18 | . | * | F | 0.21 | 0.58 |
| Tyr | 1141 | . | . | . | B | . | . | T | . | 0.21 | . | . | . | −0.07 | 0.58 |
| Ala | 1142 | . | . | . | B | . | . | T | . | 0.26 | . | . | . | 0.10 | 0.87 |
| Thr | 1143 | . | . | . | B | . | . | . | . | 0.61 | . | * | . | 0.24 | 0.75 |
| Cys | 1144 | . | . | . | B | . | . | T | . | 0.57 | . | * | F | 0.93 | 0.69 |
| Lys | 1145 | . | . | . | B | . | . | T | . | 0.78 | . | * | F | 1.87 | 0.68 |
| Ser | 1146 | . | . | . | . | . | T | T | . | 0.68 | . | * | F | 2.91 | 0.79 |
| Thr | 1147 | . | . | . | . | . | T | T | . | 1.27 | * | * | F | 3.40 | 1.45 |
| Gly | 1148 | . | . | . | . | . | T | T | . | 1.69 | * | * | F | 3.06 | 1.26 |
| Asp | 1149 | . | . | . | . | . | T | T | . | 2.04 | * | . | F | 2.72 | 1.84 |
| Gly | 1150 | . | . | . | . | . | T | T | . | 1.33 | * | . | F | 2.38 | 1.84 |
| Gln | 1151 | . | . | . | . | . | T | T | . | 1.32 | * | . | F | 1.89 | 0.99 |
| Arg | 1152 | . | . | . | B | . | . | . | . | 0.97 | . | . | F | 0.95 | 0.86 |
| Thr | 1153 | . | . | . | B | . | . | . | . | 1.31 | . | . | F | 0.65 | 0.47 |
| Cys | 1154 | . | . | . | B | . | . | T | . | 1.00 | . | . | F | 0.85 | 0.45 |
| Thr | 1155 | . | . | . | B | . | . | T | . | 0.76 | . | . | . | 0.70 | 0.33 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Cys | 1156 | . | . | . | B | . | . | T | . | 0.72 | . | . | . | 0.10 | 0.23 |
| Asp | 1157 | . | . | . | B | . | . | T | . | 0.30 | . | . | F | 0.25 | 0.59 |
| Thr | 1158 | . | . | . | B | . | . | . | . | −0.24 | . | . | F | 0.05 | 0.59 |
| Ala | 1159 | . | . | . | B | . | . | . | . | 0.08 | * | . | . | −0.10 | 0.81 |
| His | 1160 | . | . | . | B | . | . | . | . | 0.39 | * | . | . | −0.10 | 0.48 |
| Thr | 1161 | . | . | . | B | . | . | . | . | 0.71 | * | . | . | −0.10 | 0.56 |
| Val | 1162 | . | . | . | B | . | . | . | . | −0.10 | * | . | . | 0.50 | 0.55 |
| Gly | 1163 | . | . | . | . | . | T | T | . | −0.10 | * | . | F | 0.65 | 0.33 |
| Asp | 1164 | . | . | . | . | . | T | T | . | −0.18 | . | * | F | 0.65 | 0.33 |
| Gly | 1165 | . | . | . | . | . | T | T | . | −0.03 | . | * | F | 0.65 | 0.24 |
| Leu | 1166 | . | . | . | B | . | . | T | . | −0.31 | * | * | . | 0.70 | 0.47 |
| Thr | 1167 | . | . | A | B | . | . | . | . | 0.66 | * | * | . | 0.30 | 0.29 |
| Cys | 1168 | . | . | A | B | . | . | . | . | 0.14 | * | * | . | 0.30 | 0.57 |
| Arg | 1169 | . | . | A | B | . | . | . | . | −0.20 | * | * | . | 0.30 | 0.51 |
| Ala | 1170 | . | . | A | B | . | . | . | . | −0.67 | . | * | . | 0.30 | 0.35 |
| Arg | 1171 | . | . | A | B | . | . | . | . | 0.14 | . | * | . | 0.30 | 0.54 |
| Val | 1172 | . | . | A | B | . | . | . | . | −0.36 | . | * | . | 0.60 | 0.48 |
| Gly | 1173 | . | . | A | B | . | . | . | . | −0.50 | * | * | . | 0.30 | 0.39 |
| Leu | 1174 | . | . | A | B | . | . | . | . | −0.50 | * | * | . | −0.30 | 0.16 |
| Glu | 1175 | . | . | A | B | . | . | . | . | 0.09 | * | * | . | −0.30 | 0.43 |
| Leu | 1176 | . | . | A | B | . | . | . | . | 0.02 | * | * | . | 0.60 | 0.73 |
| Leu | 1177 | . | . | A | B | . | . | . | . | 0.84 | . | . | . | 0.75 | 1.77 |
| Arg | 1178 | . | A | A | . | . | . | . | . | 0.60 | . | . | F | 0.90 | 1.39 |
| Asp | 1179 | . | A | A | . | . | . | . | . | 1.11 | * | . | F | 0.90 | 1.70 |
| Lys | 1180 | . | A | A | . | . | . | . | . | 0.41 | * | . | F | 0.90 | 2.76 |
| His | 1181 | . | . | A | . | . | . | . | C | 0.52 | . | . | . | 0.95 | 1.22 |
| Ala | 1182 | . | . | A | . | . | . | . | C | 1.03 | . | * | . | 0.50 | 0.63 |
| Ser | 1183 | . | . | A | B | . | . | . | . | 0.11 | . | * | . | −0.30 | 0.42 |
| Phe | 1184 | . | . | A | B | . | . | . | . | 0.22 | . | * | . | −0.60 | 0.26 |
| Phe | 1185 | . | . | A | B | . | . | . | . | −0.63 | * | * | . | −0.60 | 0.50 |
| Ser | 1186 | . | . | A | B | . | . | . | . | −1.41 | * | * | . | −0.60 | 0.31 |
| Leu | 1187 | . | . | A | B | . | . | . | . | −0.82 | * | . | . | −0.60 | 0.29 |
| Arg | 1188 | . | . | A | B | . | . | . | . | −0.77 | . | * | . | −0.30 | 0.58 |
| Leu | 1189 | . | A | A | . | . | . | . | . | −0.02 | . | * | . | −0.30 | 0.68 |
| Leu | 1190 | . | A | A | . | . | . | . | . | 0.68 | . | * | . | 0.45 | 1.66 |
| Glu | 1191 | . | A | A | . | . | . | . | . | 0.17 | . | * | . | 0.75 | 1.47 |
| Tyr | 1192 | . | . | A | B | . | . | . | . | 1.02 | * | * | . | 0.79 | 1.47 |
| Lys | 1193 | . | . | A | B | . | . | . | . | 0.57 | . | * | F | 1.58 | 3.55 |
| Glu | 1194 | . | . | A | B | . | . | . | . | 1.38 | . | * | F | 1.92 | 2.03 |
| Leu | 1195 | . | . | . | . | . | T | T | . | 1.84 | . | * | F | 3.06 | 2.16 |
| Lys | 1196 | . | . | . | . | . | T | T | . | 1.63 | . | * | F | 3.40 | 1.07 |
| Gly | 1197 | . | . | . | . | . | T | T | . | 1.18 | . | * | F | 2.91 | 0.96 |
| Asp | 1198 | . | . | . | . | . | T | T | . | 0.82 | . | * | F | 2.42 | 1.00 |
| Gly | 1199 | . | . | . | . | . | . | T | C | −0.07 | . | * | F | 1.73 | 0.72 |
| Pro | 1200 | . | . | . | . | . | . | T | C | 0.04 | . | * | F | 0.79 | 0.51 |
| Phe | 1201 | . | . | . | B | . | . | T | . | −0.86 | . | * | . | −0.20 | 0.27 |
| Thr | 1202 | . | . | . | B | . | . | T | . | −0.72 | . | * | . | −0.20 | 0.20 |
| Ile | 1203 | . | . | . | B | B | . | . | . | −0.76 | . | * | . | −0.60 | 0.20 |
| Phe | 1204 | . | . | . | B | B | . | . | . | −1.00 | . | . | . | −0.60 | 0.31 |
| Val | 1205 | . | . | . | B | B | . | . | . | −0.79 | . | * | . | −0.60 | 0.22 |
| Pro | 1206 | . | . | . | B | B | . | . | . | −0.90 | . | . | . | −0.60 | 0.52 |
| His | 1207 | . | . | A | . | . | . | . | C | −1.19 | . | . | . | −0.40 | 0.50 |
| Ala | 1208 | . | . | A | . | . | . | . | C | −0.60 | * | . | . | −0.10 | 0.66 |
| Asp | 1209 | . | . | A | . | . | . | . | C | 0.10 | * | * | . | −0.10 | 0.58 |
| Leu | 1210 | . | . | A | . | . | . | . | C | 0.14 | . | * | . | −0.10 | 0.68 |
| Met | 1211 | . | . | . | B | . | . | T | . | 0.06 | * | * | . | 0.40 | 0.56 |
| Ser | 1212 | . | . | . | B | . | . | T | . | 0.09 | * | * | . | 0.70 | 0.45 |
| Asn | 1213 | . | . | . | . | . | . | T | C | 0.68 | * | * | F | 1.05 | 0.94 |
| Leu | 1214 | . | . | . | . | . | . | T | C | 0.68 | * | * | F | 2.40 | 1.58 |
| Ser | 1215 | . | . | . | . | . | . | T | C | 0.68 | . | . | F | 3.00 | 2.04 |
| Gln | 1216 | . | . | . | . | . | . | T | C | 0.69 | * | . | F | 2.40 | 1.05 |
| Asp | 1217 | . | A | . | . | . | . | T | . | 1.10 | * | * | F | 1.90 | 1.28 |
| Glu | 1218 | . | A | . | . | . | . | T | . | 0.21 | * | * | F | 1.90 | 1.87 |
| Leu | 1219 | . | . | A | B | . | . | . | . | 1.13 | . | * | . | 0.90 | 0.76 |
| Ala | 1220 | . | . | A | B | . | . | . | . | 0.84 | . | * | . | 0.60 | 0.89 |
| Arg | 1221 | . | . | A | B | . | . | . | . | 0.81 | . | * | . | 0.60 | 0.52 |
| Ile | 1222 | . | . | A | B | . | . | . | . | 0.92 | . | * | . | 0.30 | 0.86 |
| Arg | 1223 | . | . | A | B | . | . | . | . | 0.92 | . | * | . | 0.75 | 1.66 |
| Ala | 1224 | . | . | A | B | . | . | . | . | 0.92 | . | * | . | 0.75 | 1.47 |
| His | 1225 | . | . | A | B | . | . | . | . | 0.66 | . | . | . | 0.45 | 1.73 |
| Arg | 1226 | . | . | . | B | B | . | . | . | −0.16 | * | * | . | 0.30 | 0.65 |
| Gln | 1227 | . | . | . | B | B | . | . | . | 0.84 | * | * | . | −0.60 | 0.56 |
| Leu | 1228 | . | . | . | B | B | . | . | . | 0.49 | * | * | . | −0.30 | 0.81 |
| Val | 1229 | . | . | . | B | B | . | . | . | 1.04 | . | * | . | −0.30 | 0.65 |
| Phe | 1230 | . | . | . | B | B | . | . | . | 0.22 | . | * | . | −0.60 | 0.51 |
| Arg | 1231 | . | . | . | B | B | . | . | . | −0.74 | * | * | . | −0.60 | 0.46 |
| Tyr | 1232 | . | . | . | B | B | . | . | . | −1.09 | . | * | . | −0.60 | 0.46 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| His | 1233 | . | . | . | B | B | . | . | . | −0.94 | * | * | . | −0.60 | 0.52 |
| Val | 1234 | . | . | . | B | B | . | . | . | 0.02 | * | * | . | −0.60 | 0.14 |
| Val | 1235 | . | . | . | B | B | . | . | . | 0.83 | * | * | . | −0.60 | 0.18 |
| Gly | 1236 | . | . | . | B | B | . | . | . | −0.09 | * | * | . | 0.30 | 0.26 |
| Cys | 1237 | . | . | A | B | B | . | . | . | 0.27 | * | * | . | 0.30 | 0.29 |
| Arg | 1238 | . | . | A | B | B | . | . | . | 0.00 | * | * | . | 0.60 | 0.75 |
| Arg | 1239 | . | . | A | B | B | . | . | . | 0.86 | . | * | F | 0.90 | 1.02 |
| Leu | 1240 | . | . | A | B | B | . | . | . | 1.71 | . | . | F | 0.90 | 3.30 |
| Arg | 1241 | . | . | A | B | B | . | . | . | 1.24 | . | * | F | 0.90 | 2.81 |
| Ser | 1242 | . | . | A | . | . | . | . | C | 1.10 | . | * | F | 1.10 | 1.18 |
| Glu | 1243 | . | . | A | B | . | . | . | . | 0.99 | * | * | F | 0.90 | 1.18 |
| Asp | 1244 | . | . | A | B | . | . | . | . | 0.88 | . | * | F | 0.90 | 1.05 |
| Leu | 1245 | . | . | A | B | . | . | . | . | 1.34 | * | * | F | 0.90 | 1.35 |
| Leu | 1246 | . | . | A | B | . | . | . | . | 0.99 | * | . | F | 0.75 | 0.77 |
| Glu | 1247 | . | . | . | B | . | . | T | . | 0.70 | * | . | F | 0.85 | 0.73 |
| Gln | 1248 | . | . | . | B | . | . | T | . | 0.39 | * | . | F | −0.05 | 0.89 |
| Gly | 1249 | . | . | . | B | . | . | T | . | −0.20 | * | . | F | 0.40 | 1.55 |
| Tyr | 1250 | . | . | . | B | . | . | T | . | −0.20 | * | . | . | 0.10 | 0.91 |
| Ala | 1251 | . | . | A | B | . | . | . | . | 0.31 | * | . | . | −0.60 | 0.43 |
| Thr | 1252 | . | . | A | B | . | . | . | . | −0.03 | . | . | . | −0.60 | 0.58 |
| Ala | 1253 | . | . | A | B | . | . | . | . | −0.07 | * | . | . | −0.60 | 0.37 |
| Leu | 1254 | . | . | A | B | . | . | . | . | 0.07 | . | . | . | −0.60 | 0.50 |
| Ser | 1255 | . | . | A | B | . | . | . | . | −0.50 | * | . | . | −0.60 | 0.53 |
| Gly | 1256 | . | . | . | . | . | . | . | C | 0.20 | * | * | . | −0.20 | 0.44 |
| His | 1257 | . | . | . | . | . | . | T | C | −0.19 | . | * | . | 0.45 | 1.03 |
| Pro | 1258 | . | . | . | . | . | . | T | C | 0.10 | * | * | . | 0.30 | 0.67 |
| Leu | 1259 | . | . | . | . | . | . | T | C | 0.91 | * | * | . | 0.30 | 0.90 |
| Arg | 1260 | . | . | . | B | . | . | T | . | 1.32 | * | * | . | 1.19 | 1.15 |
| Phe | 1261 | . | . | . | B | . | . | . | . | 1.67 | * | * | . | 1.63 | 1.46 |
| Ser | 1262 | . | . | . | B | . | . | . | . | 1.36 | * | * | F | 2.12 | 3.06 |
| Glu | 1263 | . | . | . | . | . | . | . | C | 1.27 | * | * | F | 2.66 | 1.55 |
| Arg | 1264 | . | . | . | . | . | T | T | . | 1.19 | * | * | F | 3.40 | 2.39 |
| Glu | 1265 | . | . | . | . | . | T | T | . | 0.83 | * | * | F | 3.06 | 1.25 |
| Gly | 1266 | . | . | . | . | . | T | T | . | 0.72 | . | * | F | 2.72 | 1.13 |
| Ser | 1267 | . | . | . | . | . | T | T | . | 1.02 | * | . | F | 1.93 | 0.48 |
| Ile | 1268 | . | . | . | B | . | . | . | . | 1.02 | * | . | . | 0.24 | 0.44 |
| Tyr | 1269 | . | . | . | B | . | . | . | . | 0.21 | * | . | . | −0.10 | 0.75 |
| Leu | 1270 | . | . | A | B | . | . | . | . | −0.38 | * | * | . | −0.60 | 0.48 |
| Asn | 1271 | . | . | A | B | . | . | . | . | 0.08 | * | * | . | −0.60 | 0.70 |
| Asp | 1272 | . | . | A | B | . | . | . | . | −0.48 | * | * | . | −0.30 | 0.87 |
| Phe | 1273 | . | . | A | B | B | . | . | . | −0.44 | * | * | . | −0.30 | 0.78 |
| Ala | 1274 | . | . | A | B | B | . | . | . | −0.50 | * | . | . | 0.30 | 0.36 |
| Arg | 1275 | . | . | A | B | B | . | . | . | 0.01 | * | . | . | 0.30 | 0.29 |
| Val | 1276 | . | . | . | B | B | . | . | . | 0.01 | * | . | . | 0.00 | 0.45 |
| Val | 1277 | . | . | . | B | B | . | . | . | −0.02 | * | . | . | 0.90 | 0.74 |
| Ser | 1278 | . | . | . | . | . | . | T | C | 0.68 | * | . | F | 1.95 | 0.52 |
| Ser | 1279 | . | . | . | . | . | . | T | C | 0.68 | * | . | F | 2.40 | 1.20 |
| Asp | 1280 | . | . | . | . | . | . | T | C | −0.29 | * | . | F | 3.00 | 1.64 |
| His | 1281 | . | . | . | . | . | . | T | C | 0.57 | * | . | F | 2.55 | 0.91 |
| Glu | 1282 | . | . | . | . | . | . | . | C | 1.08 | * | . | . | 2.05 | 1.09 |
| Ala | 1283 | . | . | . | B | . | . | T | . | 0.49 | * | . | . | 1.60 | 0.64 |
| Val | 1284 | . | . | . | B | . | . | T | . | −0.02 | * | . | . | 0.40 | 0.33 |
| Asn | 1285 | . | . | . | B | . | . | T | . | −0.06 | * | . | . | 0.10 | 0.16 |
| Gly | 1286 | . | . | . | B | . | . | T | . | −0.72 | * | . | . | −0.20 | 0.21 |
| Ile | 1287 | . | . | . | B | B | . | . | . | −1.61 | * | . | . | −0.60 | 0.25 |
| Leu | 1288 | . | . | . | B | B | . | . | . | −1.02 | * | . | . | −0.60 | 0.11 |
| His | 1289 | . | . | . | B | B | . | . | . | −0.06 | * | * | . | −0.60 | 0.18 |
| Phe | 1290 | . | . | . | B | B | . | . | . | −0.91 | * | . | . | −0.30 | 0.51 |
| Ile | 1291 | . | . | . | B | B | . | . | . | −1.38 | * | * | . | −0.30 | 0.46 |
| Asp | 1292 | . | . | . | B | B | . | . | . | −1.30 | * | . | . | −0.30 | 0.28 |
| Arg | 1293 | . | . | . | B | B | . | . | . | −0.70 | * | * | . | −0.60 | 0.27 |
| Val | 1294 | . | . | . | B | B | . | . | . | −0.88 | * | * | . | −0.30 | 0.59 |
| Leu | 1295 | . | . | . | . | B | . | . | C | −0.18 | * | * | . | 0.50 | 0.54 |
| Leu | 1296 | . | . | . | . | B | . | . | C | 0.12 | . | * | . | 0.50 | 0.48 |
| Pro | 1297 | . | . | . | . | . | . | T | C | −0.69 | . | * | F | 0.45 | 0.65 |
| Pro | 1298 | . | . | . | . | . | . | T | C | −0.83 | . | * | F | 0.15 | 0.65 |
| Glu | 1299 | . | . | . | . | . | T | T | . | −0.27 | . | . | F | 0.80 | 1.08 |
| Ala | 1300 | . | . | . | B | . | . | T | . | 0.54 | . | . | . | −0.20 | 0.73 |
| Leu | 1301 | . | . | . | B | . | . | . | . | 1.14 | . | * | . | 0.24 | 0.82 |
| His | 1302 | . | . | . | B | . | . | . | . | 1.36 | . | . | . | 0.58 | 0.73 |
| Trp | 1303 | . | . | . | B | . | . | . | . | 1.57 | . | . | . | 1.07 | 1.21 |
| Glu | 1304 | . | . | . | . | . | . | T | C | 0.98 | . | . | . | 2.41 | 2.45 |
| Pro | 1305 | . | . | . | . | . | T | T | . | 1.36 | . | . | F | 3.40 | 1.82 |
| Asp | 1306 | . | . | . | . | . | T | T | . | 1.28 | . | * | F | 3.06 | 2.67 |
| Asp | 1307 | . | . | . | . | . | T | T | . | 1.10 | * | . | F | 2.98 | 1.08 |
| Ala | 1308 | . | . | . | . | . | . | . | C | 1.50 | * | . | F | 2.50 | 1.08 |
| Pro | 1309 | . | . | . | . | . | . | . | C | 1.61 | . | . | F | 2.42 | 1.27 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Ile | 1310 | . | . | . | . | . | . | . | C | 1.82 | * | . | F | 2.34 | 1.49 |
| Pro | 1311 | . | . | . | B | . | . | T | . | 0.97 | * | . | F | 2.60 | 2.37 |
| Arg | 1312 | . | . | . | B | . | . | T | . | 0.66 | . | . | F | 2.04 | 1.14 |
| Arg | 1313 | . | . | . | B | . | . | T | . | 0.66 | * | . | F | 1.78 | 2.34 |
| Asn | 1314 | . | . | . | B | . | . | T | . | 0.28 | * | . | F | 1.82 | 1.53 |
| Val | 1315 | . | . | A | B | B | . | . | . | 0.58 | * | . | . | 0.56 | 0.79 |
| Thr | 1316 | . | . | A | B | B | . | . | . | 0.79 | * | * | . | −0.30 | 0.41 |
| Ala | 1317 | . | . | A | B | B | . | . | . | 0.33 | * | . | . | −0.60 | 0.44 |
| Ala | 1318 | . | . | A | B | . | . | . | . | −0.48 | * | . | . | −0.60 | 0.58 |
| Ala | 1319 | . | . | A | B | . | . | . | . | −0.82 | * | * | . | −0.60 | 0.35 |
| Gln | 1320 | . | . | A | B | . | . | . | . | −0.21 | . | . | . | −0.60 | 0.34 |
| Gly | 1321 | . | . | . | B | . | . | T | . | 0.14 | . | * | . | −0.20 | 0.53 |
| Phe | 1322 | . | . | . | B | . | . | T | . | −0.16 | . | . | . | 0.25 | 1.05 |
| Gly | 1323 | . | . | . | B | . | . | T | . | −0.27 | * | . | . | −0.20 | 0.43 |
| Tyr | 1324 | . | . | . | B | . | . | T | . | 0.02 | * | . | . | −0.20 | 0.37 |
| Lys | 1325 | . | . | . | B | B | . | . | . | −0.32 | * | . | . | −0.60 | 0.58 |
| Ile | 1326 | . | . | . | B | B | . | . | . | −0.79 | * | . | . | −0.60 | 0.58 |
| Phe | 1327 | . | . | . | B | B | . | . | . | −0.90 | * | * | . | −0.60 | 0.30 |
| Ser | 1328 | . | . | . | B | B | . | . | . | −0.51 | * | * | . | −0.60 | 0.13 |
| Gly | 1329 | . | . | A | B | . | . | . | . | −1.12 | * | * | . | −0.60 | 0.36 |
| Leu | 1330 | . | . | A | B | . | . | . | . | −1.76 | * | * | . | −0.60 | 0.31 |
| Leu | 1331 | . | . | A | B | . | . | . | . | −1.21 | * | . | . | −0.30 | 0.23 |
| Lys | 1332 | . | . | A | B | . | . | . | . | −1.32 | * | * | . | −0.30 | 0.23 |
| Val | 1333 | . | . | A | B | . | . | . | . | −1.83 | * | * | . | −0.60 | 0.23 |
| Ala | 1334 | . | . | A | B | . | . | . | . | −1.70 | . | * | . | −0.60 | 0.23 |
| Gly | 1335 | . | . | A | B | . | . | . | . | −1.70 | . | . | . | −0.30 | 0.18 |
| Leu | 1336 | . | . | A | B | . | . | . | . | −1.70 | . | * | . | −0.60 | 0.20 |
| Leu | 1337 | . | . | A | B | . | . | . | . | −1.63 | * | * | . | −0.60 | 0.16 |
| Pro | 1338 | . | . | A | B | . | . | . | . | −0.78 | * | . | . | −0.60 | 0.32 |
| Leu | 1339 | . | . | A | B | . | . | . | . | −0.78 | * | . | . | −0.30 | 0.67 |
| Leu | 1340 | . | . | A | B | . | . | . | . | −0.73 | * | . | . | 0.56 | 0.83 |
| Arg | 1341 | . | . | A | B | . | . | . | . | 0.04 | * | . | . | 0.82 | 0.72 |
| Glu | 1342 | . | . | A | B | . | . | . | . | 0.97 | * | . | F | 1.38 | 1.18 |
| Ala | 1343 | . | . | A | . | . | T | . | . | 0.97 | * | . | F | 2.34 | 2.81 |
| Ser | 1344 | . | . | . | . | . | . | . | C | 1.08 | * | . | F | 2.60 | 2.21 |
| His | 1345 | . | . | . | . | . | . | . | C | 1.58 | * | . | . | 1.89 | 1.11 |
| Arg | 1346 | . | . | . | . | . | . | . | C | 0.87 | * | . | . | 1.03 | 1.58 |
| Pro | 1347 | . | . | . | . | . | T | . | . | 0.06 | * | . | . | 0.97 | 1.17 |
| Phe | 1348 | . | . | . | . | . | T | . | . | 0.36 | * | . | . | 0.26 | 0.71 |
| Thr | 1349 | . | . | . | B | . | . | . | . | 0.44 | * | . | . | −0.40 | 0.38 |
| Met | 1350 | . | . | . | B | . | . | . | . | 0.17 | * | . | . | −0.40 | 0.38 |
| Leu | 1351 | . | . | . | B | . | . | . | . | 0.06 | * | . | . | −0.40 | 0.63 |
| Trp | 1352 | . | . | . | B | . | . | T | . | −0.32 | . | . | . | −0.20 | 0.73 |
| Pro | 1353 | . | . | . | . | . | . | T | C | −0.21 | . | . | F | 0.15 | 0.75 |
| Thr | 1354 | . | . | . | . | . | . | T | C | −0.60 | * | * | F | 0.15 | 0.92 |
| Asp | 1355 | . | . | . | . | . | . | T | C | 0.11 | * | * | F | 0.15 | 0.75 |
| Ala | 1356 | . | . | A | B | . | . | . | . | 0.33 | * | * | . | 0.30 | 0.96 |
| Ala | 1357 | . | . | A | B | . | . | . | . | −0.19 | * | * | . | 0.30 | 0.67 |
| Phe | 1358 | . | . | A | B | . | . | . | . | −0.19 | * | * | . | 0.30 | 0.33 |
| Arg | 1359 | . | . | A | B | . | . | . | . | −0.09 | * | * | . | −0.26 | 0.51 |
| Ala | 1360 | . | . | A | B | . | . | . | . | −0.09 | * | * | . | 0.38 | 0.77 |
| Leu | 1361 | . | . | A | . | . | . | . | C | 0.61 | * | * | . | 1.67 | 1.49 |
| Pro | 1362 | . | . | . | . | . | . | T | C | 1.20 | * | * | F | 2.86 | 1.49 |
| Pro | 1363 | . | . | . | . | . | T | T | . | 1.31 | * | * | F | 3.40 | 2.56 |
| Asp | 1364 | . | . | . | . | . | T | T | . | 0.91 | * | . | F | 3.06 | 3.14 |
| Arg | 1365 | . | . | . | . | . | T | T | . | 0.69 | . | . | F | 2.42 | 2.13 |
| Gln | 1366 | . | . | A | B | . | . | . | . | 1.26 | . | . | . | 1.13 | 1.14 |
| Ala | 1367 | . | . | A | B | . | . | . | . | 1.43 | . | . | . | 0.19 | 1.07 |
| Trp | 1368 | . | . | A | B | . | . | . | . | 1.64 | . | . | . | −0.60 | 0.74 |
| Leu | 1369 | . | . | A | B | . | . | . | . | 1.64 | . | . | . | −0.60 | 0.74 |
| Tyr | 1370 | . | . | A | B | . | . | . | . | 1.50 | * | . | . | −0.15 | 1.23 |
| His | 1371 | . | . | A | B | . | . | . | . | 1.61 | . | . | . | −0.15 | 1.59 |
| Glu | 1372 | . | . | A | . | . | T | . | . | 2.20 | . | * | . | 1.15 | 3.77 |
| Asp | 1373 | . | . | A | . | . | T | . | . | 2.53 | . | * | F | 1.30 | 4.02 |
| His | 1374 | . | . | A | . | . | T | . | . | 2.53 | . | * | F | 1.30 | 5.90 |
| Arg | 1375 | . | . | A | . | . | T | . | . | 2.19 | . | * | F | 1.30 | 2.81 |
| Asp | 1376 | A | . | A | . | . | . | . | . | 1.63 | . | * | F | 0.90 | 1.70 |
| Lys | 1377 | A | . | A | . | . | . | . | . | 0.74 | . | * | F | 0.90 | 1.26 |
| Leu | 1378 | A | . | A | . | . | . | . | . | −0.07 | * | * | . | 0.60 | 0.45 |
| Ala | 1379 | A | . | A | . | . | . | . | . | 0.08 | * | * | . | −0.30 | 0.22 |
| Ala | 1380 | . | . | A | B | . | . | . | . | −0.38 | * | * | . | −0.30 | 0.22 |
| Ile | 1381 | . | . | A | B | . | . | . | . | −0.41 | * | * | . | −0.60 | 0.26 |
| Leu | 1382 | . | . | A | B | . | . | . | . | −1.06 | . | * | . | −0.30 | 0.35 |
| Arg | 1383 | . | . | A | B | . | . | . | . | −1.13 | . | * | . | −0.60 | 0.35 |
| Gly | 1384 | . | . | A | B | . | . | . | . | −0.43 | . | . | . | −0.60 | 0.35 |
| His | 1385 | . | . | A | B | . | . | . | . | 0.16 | . | . | . | 0.30 | 0.82 |
| Met | 1386 | . | . | A | B | . | . | . | . | 0.19 | . | . | . | 0.30 | 0.67 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Ile | 1387 | . | . | A | B | . | . | . | . | 1.00 | . | * | . | −0.30 | 0.51 |
| Arg | 1388 | . | . | A | B | . | . | . | . | 0.30 | * | . | . | 0.30 | 0.64 |
| Asn | 1389 | . | . | A | B | . | . | . | . | −0.17 | * | . | . | 0.30 | 0.66 |
| Val | 1390 | . | . | A | B | . | . | . | . | −0.72 | * | . | . | 0.30 | 0.77 |
| Glu | 1391 | . | . | A | B | . | . | . | . | −0.42 | * | . | . | 0.30 | 0.40 |
| Ala | 1392 | . | . | A | B | . | . | . | . | 0.47 | * | . | . | −0.30 | 0.33 |
| Leu | 1393 | . | . | A | B | . | . | . | . | −0.46 | * | . | . | 0.30 | 0.75 |
| Ala | 1394 | . | . | A | B | . | . | . | . | −0.67 | * | . | . | 0.30 | 0.36 |
| Ser | 1395 | . | . | . | B | . | . | . | . | 0.19 | * | . | F | 0.05 | 0.55 |
| Asp | 1396 | . | . | . | B | . | . | . | . | −0.62 | * | . | F | 0.20 | 1.06 |
| Leu | 1397 | . | . | . | B | . | . | T | . | −0.38 | * | . | F | 0.25 | 0.87 |
| Pro | 1398 | . | . | . | . | . | . | T | C | 0.22 | * | . | F | 0.45 | 0.64 |
| Asn | 1399 | . | . | . | . | . | T | T | . | 0.00 | . | * | F | 0.65 | 0.59 |
| Leu | 1400 | . | . | . | . | . | . | T | C | 0.41 | . | * | F | 0.15 | 0.59 |
| Gly | 1401 | . | . | . | . | . | . | T | C | 0.10 | . | . | F | 0.45 | 0.75 |
| Pro | 1402 | . | . | . | B | . | . | T | . | 0.31 | . | . | F | 0.25 | 0.67 |
| Leu | 1403 | . | . | . | B | . | . | T | . | 0.49 | . | . | F | 0.25 | 0.81 |
| Arg | 1404 | . | . | . | B | . | . | T | . | 0.14 | . | . | F | 0.40 | 1.11 |
| Thr | 1405 | . | . | . | B | . | . | T | . | 0.64 | . | . | . | 0.10 | 0.71 |
| Met | 1406 | . | . | . | B | . | . | T | . | 0.78 | . | * | . | 0.25 | 1.25 |
| His | 1407 | . | . | . | B | . | . | T | . | 0.10 | . | . | . | 0.70 | 0.98 |
| Gly | 1408 | . | . | . | B | . | . | T | . | 0.61 | * | * | F | −0.05 | 0.48 |
| Thr | 1409 | . | . | . | . | . | . | . | C | −0.20 | . | . | F | −0.05 | 0.65 |
| Pro | 1410 | . | . | . | B | . | . | . | . | −0.19 | . | . | F | −0.25 | 0.41 |
| Ile | 1411 | . | . | . | . | . | T | . | . | −0.26 | . | * | F | 0.15 | 0.56 |
| Ser | 1412 | . | . | . | B | . | . | . | . | −0.52 | * | . | . | −0.40 | 0.21 |
| Phe | 1413 | . | . | . | B | . | . | . | . | −0.07 | * | . | . | −0.06 | 0.18 |
| Ser | 1414 | . | . | . | B | . | . | . | . | −0.07 | . | * | . | 0.58 | 0.50 |
| Cys | 1415 | . | . | . | B | . | . | T | . | 0.26 | . | * | . | 1.12 | 0.54 |
| Ser | 1416 | . | . | . | . | . | T | T | . | 0.93 | . | * | F | 2.76 | 1.22 |
| Arg | 1417 | . | . | . | . | . | T | T | . | 0.89 | . | * | F | 3.40 | 1.41 |
| Thr | 1418 | . | . | . | . | . | . | T | C | 1.59 | . | . | F | 2.86 | 2.60 |
| Arg | 1419 | . | . | . | . | . | . | T | C | 1.08 | . | * | F | 2.52 | 3.36 |
| Pro | 1420 | . | . | . | . | . | . | T | C | 1.14 | . | * | F | 2.18 | 1.42 |
| Gly | 1421 | . | . | . | . | . | T | T | . | 0.59 | . | * | F | 1.59 | 0.97 |
| Glu | 1422 | . | . | . | B | . | . | T | . | 0.13 | . | * | F | 0.85 | 0.37 |
| Leu | 1423 | . | . | . | B | . | . | . | . | 0.44 | . | . | . | −0.10 | 0.24 |
| Met | 1424 | . | . | . | B | . | . | . | . | 0.33 | . | . | . | 0.50 | 0.41 |
| Val | 1425 | . | . | . | B | . | . | . | . | 0.54 | . | . | . | 0.80 | 0.40 |
| Gly | 1426 | . | . | . | B | . | . | T | . | 0.30 | . | * | . | 1.00 | 0.80 |
| Glu | 1427 | A | . | . | . | . | . | T | . | 0.41 | . | * | F | 1.15 | 0.82 |
| Asp | 1428 | A | . | . | . | . | . | T | . | 0.33 | * | * | F | 1.30 | 2.17 |
| Asp | 1429 | A | . | . | . | . | . | T | . | 0.08 | * | * | F | 1.30 | 1.54 |
| Ala | 1430 | A | . | . | . | B | . | . | . | 0.93 | * | * | F | 0.75 | 0.66 |
| Arg | 1431 | . | . | . | B | B | . | . | . | 1.39 | * | * | . | 0.60 | 0.68 |
| Ile | 1432 | . | . | . | B | B | . | . | . | 1.36 | * | * | . | 0.60 | 0.80 |
| Val | 1433 | . | . | . | B | B | . | . | . | 0.54 | * | * | . | 0.45 | 1.08 |
| Gln | 1434 | . | . | . | B | B | . | . | . | 0.33 | * | * | . | 0.30 | 0.45 |
| Arg | 1435 | . | . | . | B | B | . | . | . | 0.22 | * | * | . | −0.15 | 1.00 |
| His | 1436 | . | . | . | B | B | . | . | . | 0.11 | * | * | . | −0.45 | 1.17 |
| Leu | 1437 | . | . | . | B | B | . | . | . | 0.66 | . | . | . | 0.45 | 1.17 |
| Pro | 1438 | . | . | . | . | . | . | . | C | 1.17 | . | * | . | 0.70 | 0.59 |
| Phe | 1439 | . | . | . | . | . | T | T | . | 0.36 | . | . | . | 0.50 | 0.43 |
| Glu | 1440 | . | . | . | . | . | T | T | . | −0.34 | . | . | F | 0.35 | 0.43 |
| Gly | 1441 | . | . | . | . | . | T | T | . | −0.56 | . | * | F | 0.65 | 0.28 |
| Gly | 1442 | . | . | . | . | . | T | T | . | −0.09 | * | * | F | 0.35 | 0.51 |
| Leu | 1443 | . | . | . | . | . | . | . | C | −0.77 | * | * | . | 0.10 | 0.29 |
| Ala | 1444 | . | . | . | . | . | . | . | C | −0.07 | * | * | . | −0.20 | 0.21 |
| Tyr | 1445 | . | . | . | B | . | . | . | . | −0.07 | * | . | . | −0.40 | 0.35 |
| Gly | 1446 | . | . | . | B | . | . | . | . | −0.53 | * | . | . | −0.40 | 0.73 |
| Ile | 1447 | . | . | A | B | . | . | . | . | −1.00 | * | . | . | −0.60 | 0.59 |
| Asp | 1448 | . | . | A | B | . | . | . | . | −0.19 | * | . | F | −0.45 | 0.31 |
| Gln | 1449 | . | . | A | B | . | . | . | . | 0.19 | * | . | F | 0.45 | 0.55 |
| Leu | 1450 | . | . | A | B | . | . | . | . | 0.22 | * | . | F | 0.60 | 1.21 |
| Leu | 1451 | . | . | A | B | . | . | . | . | 0.22 | * | . | F | 0.60 | 1.12 |
| Glu | 1452 | . | . | A | B | . | . | . | . | 0.30 | * | . | F | 0.07 | 0.64 |
| Pro | 1453 | . | . | . | . | . | . | T | C | −0.04 | * | . | F | 0.89 | 0.64 |
| Pro | 1454 | . | . | . | . | . | T | T | . | −0.63 | * | * | F | 1.31 | 0.77 |
| Gly | 1455 | . | . | . | . | . | T | T | . | 0.29 | * | * | F | 2.13 | 0.45 |
| Leu | 1456 | . | . | . | . | . | T | T | . | 0.43 | . | * | . | 2.20 | 0.57 |
| Gly | 1457 | . | . | . | . | . | . | T | C | 0.43 | . | * | . | 1.18 | 0.20 |
| Ala | 1458 | . | . | . | B | . | . | T | . | 0.61 | . | * | . | 1.36 | 0.33 |
| Arg | 1459 | . | . | . | B | . | . | T | . | 0.12 | . | * | . | 1.14 | 0.55 |
| Cys | 1460 | . | . | . | B | . | . | T | . | 0.47 | . | * | . | 0.92 | 0.48 |
| Asp | 1461 | . | . | A | B | . | . | . | . | 0.97 | * | * | . | 0.60 | 0.82 |
| His | 1462 | . | . | A | B | . | . | . | . | 1.42 | * | * | . | 0.60 | 0.60 |
| Phe | 1463 | . | . | A | B | . | . | . | . | 1.80 | * | * | . | 1.05 | 2.21 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Glu | 1464 | . | . | A | B | . | . | . | . | 0.88 | * | . | F | 1.50 | 2.04 |
| Thr | 1465 | . | . | A | B | . | . | . | . | 1.66 | * | . | F | 1.50 | 1.24 |
| Arg | 1466 | . | . | . | B | . | . | . | . | 0.84 | * | * | F | 2.30 | 2.80 |
| Pro | 1467 | . | . | . | . | . | T | . | . | 0.88 | * | * | F | 3.00 | 1.33 |
| Leu | 1468 | . | . | . | . | . | T | . | . | 1.27 | * | * | . | 2.25 | 1.49 |
| Arg | 1469 | . | . | . | . | . | T | . | . | 0.60 | * | * | . | 1.95 | 1.10 |
| Leu | 1470 | . | . | . | . | . | T | . | . | 0.61 | * | . | . | 0.90 | 0.38 |
| Asn | 1471 | . | . | . | . | . | T | T | . | −0.39 | * | . | . | 0.80 | 0.62 |
| Thr | 1472 | . | . | . | B | . | . | T | . | −0.84 | . | * | . | 0.10 | 0.22 |
| Cys | 1473 | . | . | . | B | . | . | T | . | −0.38 | * | * | . | −0.20 | 0.14 |
| Ser | 1474 | . | . | . | B | . | . | T | . | −1.30 | * | * | . | −0.20 | 0.09 |
| Ile | 1475 | . | . | . | B | B | . | . | . | −0.49 | . | . | . | −0.60 | 0.05 |
| Cys | 1476 | . | . | . | B | B | . | . | . | −0.70 | . | . | . | −0.30 | 0.16 |
| Gly | 1477 | . | . | . | . | B | T | . | . | −0.60 | . | . | . | 0.10 | 0.19 |
| Leu | 1478 | . | . | . | . | . | T | . | . | −0.60 | . | . | . | 0.30 | 0.42 |
| Glu | 1479 | . | . | . | . | . | . | . | C | −0.51 | . | . | F | 0.25 | 0.42 |
| Pro | 1480 | . | . | . | . | . | . | . | C | 0.38 | . | . | F | 0.85 | 0.65 |
| Pro | 1481 | . | . | . | . | . | T | . | . | 0.70 | . | . | F | 1.54 | 1.36 |
| Cys | 1482 | . | . | . | . | . | . | T | C | 0.74 | * | . | F | 2.03 | 0.78 |
| Pro | 1483 | . | . | . | . | . | T | T | . | 1.56 | * | . | F | 2.27 | 0.67 |
| Glu | 1484 | . | . | . | . | . | T | T | . | 1.56 | . | . | F | 2.61 | 0.76 |
| Gly | 1485 | . | . | . | . | . | T | T | . | 1.77 | . | . | F | 3.40 | 2.44 |
| Ser | 1486 | . | . | . | . | . | . | . | C | 1.63 | . | . | F | 2.66 | 2.73 |
| Gln | 1487 | . | . | . | . | . | . | . | C | 2.00 | . | . | F | 2.62 | 1.56 |
| Glu | 1488 | . | . | . | . | . | T | . | . | 2.00 | . | . | F | 2.78 | 2.12 |
| Gln | 1489 | . | . | . | . | . | T | . | . | 2.00 | . | . | F | 2.74 | 2.44 |
| Gly | 1490 | . | . | . | . | . | . | . | C | 1.76 | . | . | F | 2.50 | 2.44 |
| Ser | 1491 | . | . | . | . | . | . | T | C | 1.39 | . | * | F | 3.00 | 1.42 |
| Pro | 1492 | . | . | . | . | . | . | T | C | 1.10 | . | * | F | 2.25 | 0.44 |
| Glu | 1493 | . | . | . | . | . | T | T | . | 1.21 | * | * | F | 1.55 | 0.47 |
| Ala | 1494 | . | . | . | . | . | T | T | . | 0.51 | * | * | . | 1.70 | 0.68 |
| Cys | 1495 | . | . | . | . | . | T | . | . | 0.61 | * | * | . | 0.60 | 0.38 |
| Trp | 1496 | . | . | . | B | . | . | . | . | 0.70 | * | * | . | −0.40 | 0.35 |
| Arg | 1497 | . | . | . | B | . | . | . | . | 0.96 | * | * | . | −0.40 | 0.53 |
| Phe | 1498 | . | . | . | B | . | . | . | . | 0.26 | * | * | . | −0.25 | 1.98 |
| Tyr | 1499 | . | . | . | B | . | . | . | . | 0.56 | * | * | . | −0.25 | 1.63 |
| Pro | 1500 | . | . | . | . | . | T | T | . | 0.91 | * | * | . | 0.20 | 0.88 |
| Lys | 1501 | . | . | . | . | . | T | T | . | 0.90 | * | * | . | 0.35 | 1.46 |
| Phe | 1502 | . | . | . | . | . | T | T | . | 0.58 | * | * | F | 0.50 | 1.25 |
| Trp | 1503 | . | . | . | . | . | T | T | . | 1.07 | * | * | F | 0.50 | 1.25 |
| Thr | 1504 | . | . | . | . | . | . | . | C | 0.50 | . | * | F | −0.05 | 0.97 |
| Ser | 1505 | . | . | . | . | . | . | T | C | 0.68 | . | * | F | 0.15 | 0.92 |
| Pro | 1506 | . | . | . | . | . | . | T | C | 0.33 | . | * | F | 0.30 | 1.19 |
| Pro | 1507 | . | . | . | . | . | . | T | C | 0.22 | . | . | F | 0.60 | 1.10 |
| Leu | 1508 | . | . | . | . | . | . | T | C | 0.17 | . | . | F | 0.15 | 0.68 |
| His | 1509 | . | . | . | . | . | . | T | C | −0.33 | * | * | . | 0.00 | 0.44 |
| Ser | 1510 | . | . | . | B | . | . | T | . | 0.08 | * | * | . | −0.20 | 0.23 |
| Leu | 1511 | . | . | . | B | . | . | T | . | −0.01 | * | . | . | 0.10 | 0.55 |
| Gly | 1512 | . | . | . | B | . | . | T | . | −0.66 | * | * | . | 0.10 | 0.54 |
| Leu | 1513 | . | . | . | B | B | . | . | . | −0.13 | * | . | . | −0.30 | 0.30 |
| Arg | 1514 | . | . | . | B | B | . | . | . | −0.96 | . | * | . | −0.60 | 0.38 |
| Ser | 1515 | . | . | . | B | B | . | . | . | −0.69 | . | * | . | −0.60 | 0.29 |
| Val | 1516 | . | . | . | B | B | . | . | . | −0.09 | * | * | . | −0.60 | 0.47 |
| Trp | 1517 | . | . | . | B | B | . | . | . | −0.04 | * | . | . | −0.60 | 0.37 |
| Val | 1518 | . | . | . | B | B | . | . | . | −0.04 | * | . | . | −0.60 | 0.37 |
| His | 1519 | . | . | . | B | . | . | T | . | −0.44 | . | . | . | −0.20 | 0.42 |
| Pro | 1520 | . | . | . | . | . | . | T | C | −0.49 | . | * | . | 0.00 | 0.42 |
| Ser | 1521 | . | . | . | . | . | T | T | . | 0.48 | . | * | F | 0.35 | 0.55 |
| Leu | 1522 | . | . | . | . | . | T | T | . | 0.56 | . | * | . | 0.50 | 0.80 |
| Trp | 1523 | . | . | . | . | . | T | . | . | 1.41 | . | . | . | 0.30 | 0.80 |
| Gly | 1524 | . | . | . | . | . | . | . | C | 1.10 | . | * | F | 0.71 | 1.03 |
| Arg | 1525 | . | . | . | . | . | . | . | C | 0.50 | . | * | F | 1.02 | 1.24 |
| Pro | 1526 | . | . | . | . | . | T | T | . | 0.46 | * | * | F | 1.58 | 0.97 |
| Gln | 1527 | . | . | . | . | . | T | T | . | 1.38 | * | * | F | 2.49 | 0.97 |
| Gly | 1528 | . | . | . | . | . | T | T | . | 1.32 | * | * | F | 3.10 | 0.97 |
| Leu | 1529 | . | . | . | . | . | T | T | . | 1.00 | * | * | F | 2.49 | 0.62 |
| Gly | 1530 | . | . | . | . | . | T | T | . | 0.86 | * | * | F | 2.46 | 0.19 |
| Arg | 1531 | . | . | . | . | . | T | T | . | 1.18 | * | * | F | 1.83 | 0.26 |
| Gly | 1532 | . | . | . | . | . | T | T | . | 1.18 | * | * | . | 2.25 | 0.63 |
| Cys | 1533 | . | . | . | . | . | T | T | . | 0.86 | * | * | . | 2.67 | 1.02 |
| His | 1534 | . | . | . | . | . | T | T | . | 0.81 | * | * | . | 2.80 | 0.28 |
| Arg | 1535 | . | . | . | B | . | . | T | . | 0.84 | * | * | . | 1.22 | 0.21 |
| Asn | 1536 | . | . | . | B | . | . | T | . | 0.42 | * | * | . | 0.94 | 0.56 |
| Cys | 1537 | . | . | . | B | . | . | T | . | 0.46 | . | * | . | 0.66 | 0.60 |
| Val | 1538 | . | . | . | B | B | . | . | . | 0.83 | * | * | . | −0.02 | 0.44 |
| Thr | 1539 | . | . | . | B | B | . | . | . | 0.91 | * | * | . | −0.60 | 0.29 |
| Thr | 1540 | . | . | . | . | B | T | . | . | 0.59 | * | * | F | 0.10 | 1.08 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Thr | 1541 | . | . | . | . | B | T | . | . | 0.29 | * | * | F | 0.10 | 2.24 |
| Trp | 1542 | . | . | . | . | B | T | . | . | 0.29 | . | * | F | 0.40 | 2.08 |
| Lys | 1543 | . | . | . | . | . | . | T | C | 0.48 | . | * | F | 0.45 | 0.77 |
| Pro | 1544 | . | . | . | . | . | T | T | . | 0.58 | . | . | F | 0.65 | 0.29 |
| Ser | 1545 | . | . | . | . | . | T | T | . | 0.54 | . | . | . | 0.50 | 0.42 |
| Cys | 1546 | . | . | . | . | . | T | T | . | 0.82 | . | . | . | 1.10 | 0.21 |
| Cys | 1547 | . | . | . | B | . | . | T | . | 0.87 | . | . | . | 0.34 | 0.18 |
| Pro | 1548 | . | . | . | . | . | T | T | . | 0.48 | . | . | . | 0.68 | 0.21 |
| Gly | 1549 | . | . | . | . | . | T | T | . | 0.39 | . | . | . | 0.92 | 0.40 |
| His | 1550 | . | . | . | . | . | T | T | . | 0.69 | . | . | F | 1.31 | 0.99 |
| Tyr | 1551 | . | . | . | . | . | T | . | . | 0.69 | . | . | F | 2.40 | 1.11 |
| Gly | 1552 | . | . | . | . | . | T | T | . | 1.36 | . | . | F | 1.61 | 0.60 |
| Ser | 1553 | . | . | . | . | . | T | T | . | 0.98 | . | . | F | 1.37 | 0.77 |
| Glu | 1554 | . | . | . | B | . | . | T | . | 0.66 | . | . | F | 0.73 | 0.49 |
| Cys | 1555 | . | . | . | B | . | . | T | . | 0.48 | . | . | . | 0.94 | 0.27 |
| Gln | 1556 | . | . | . | B | . | . | . | . | 0.38 | . | . | . | 0.50 | 0.31 |
| Ala | 1557 | . | . | . | B | . | . | . | . | 0.38 | . | . | . | 0.50 | 0.18 |
| Cys | 1558 | . | . | . | B | . | . | T | . | 0.47 | . | . | . | 0.10 | 0.33 |
| Pro | 1559 | . | . | . | . | . | T | T | . | 0.17 | . | . | F | 0.65 | 0.29 |
| Gly | 1560 | . | . | . | . | . | T | T | . | 0.53 | . | . | F | 0.65 | 0.39 |
| Gly | 1561 | . | . | . | . | . | . | T | C | 0.32 | . | . | F | 0.45 | 0.96 |
| Pro | 1562 | . | . | . | . | . | T | . | . | 0.24 | . | . | F | 1.39 | 0.96 |
| Ser | 1563 | . | . | . | . | . | . | . | C | 0.61 | . | . | F | 0.93 | 0.52 |
| Ser | 1564 | . | . | . | B | . | . | T | . | 0.82 | . | . | F | 1.27 | 0.71 |
| Pro | 1565 | . | . | . | B | . | . | T | . | 1.28 | . | . | F | 2.21 | 0.76 |
| Cys | 1566 | . | . | . | . | . | T | T | . | 1.28 | . | . | F | 3.40 | 1.12 |
| Ser | 1567 | . | . | . | . | . | T | T | . | 0.63 | . | . | F | 2.91 | 0.82 |
| Asp | 1568 | . | . | . | . | . | T | T | . | 0.27 | . | . | F | 2.57 | 0.40 |
| Arg | 1569 | . | . | . | B | . | . | T | . | −0.03 | . | . | F | 1.53 | 0.40 |
| Gly | 1570 | . | . | . | B | . | . | T | . | 0.18 | . | . | . | 1.04 | 0.29 |
| Val | 1571 | . | . | . | B | . | . | T | . | 0.50 | . | . | . | 1.00 | 0.29 |
| Cys | 1572 | . | . | . | B | . | . | T | . | 0.20 | . | . | . | 0.91 | 0.15 |
| Met | 1573 | . | . | . | B | . | . | T | . | −0.10 | . | . | . | 0.52 | 0.15 |
| Asp | 1574 | . | . | . | B | . | . | T | . | −0.56 | . | . | . | 0.73 | 0.27 |
| Gly | 1575 | . | . | . | . | . | T | T | . | −0.51 | . | . | F | 1.49 | 0.49 |
| Met | 1576 | . | . | . | . | . | T | . | . | 0.00 | . | . | F | 2.10 | 0.67 |
| Ser | 1577 | . | . | . | . | . | T | . | . | 0.67 | . | . | F | 1.89 | 0.39 |
| Gly | 1578 | . | . | . | . | . | T | T | . | 0.60 | * | . | F | 1.28 | 0.69 |
| Ser | 1579 | . | . | . | . | . | T | T | . | −0.21 | * | . | F | 1.07 | 0.37 |
| Gly | 1580 | . | . | . | . | . | T | T | . | −0.53 | * | * | F | 0.86 | 0.23 |
| Gln | 1581 | . | . | . | B | . | . | T | . | 0.18 | * | * | F | −0.05 | 0.12 |
| Cys | 1582 | . | . | . | B | . | . | . | . | 0.18 | * | * | . | −0.10 | 0.18 |
| Leu | 1583 | . | . | . | B | . | . | . | . | 0.18 | * | * | . | −0.10 | 0.25 |
| Cys | 1584 | . | . | . | B | . | . | T | . | −0.22 | * | * | . | 0.10 | 0.14 |
| Arg | 1585 | . | . | . | B | . | . | T | . | −0.47 | * | * | . | −0.20 | 0.23 |
| Ser | 1586 | . | . | . | . | . | T | T | . | −0.81 | * | * | F | 0.65 | 0.28 |
| Gly | 1587 | . | . | . | . | . | T | T | . | −0.46 | . | * | F | 0.65 | 0.52 |
| Phe | 1588 | . | . | . | . | . | T | . | . | −0.23 | . | . | F | 0.45 | 0.38 |
| Ala | 1589 | . | . | . | . | . | T | . | . | −0.23 | . | * | . | 0.00 | 0.29 |
| Gly | 1590 | . | . | . | . | . | T | . | . | −0.34 | . | * | . | 0.00 | 0.16 |
| Thr | 1591 | . | . | A | B | . | . | . | . | −0.86 | . | . | . | −0.30 | 0.31 |
| Ala | 1592 | . | . | A | B | . | . | . | . | −1.18 | . | . | . | −0.30 | 0.25 |
| Cys | 1593 | . | . | A | B | . | . | . | . | −1.07 | . | . | . | −0.30 | 0.14 |
| Glu | 1594 | . | . | A | B | . | . | . | . | −0.69 | . | . | . | −0.30 | 0.10 |
| Leu | 1595 | . | . | A | B | . | . | . | . | −0.69 | . | . | . | −0.30 | 0.15 |
| Cys | 1596 | . | . | A | B | . | . | . | . | −0.97 | . | . | . | −0.30 | 0.27 |
| Ala | 1597 | . | . | . | B | . | . | T | . | −1.08 | . | . | . | 0.10 | 0.16 |
| Pro | 1598 | . | . | . | . | . | T | T | . | −0.76 | . | * | . | 0.20 | 0.17 |
| Gly | 1599 | . | . | . | . | . | T | T | . | −0.97 | . | . | . | 0.20 | 0.31 |
| Ala | 1600 | . | . | . | . | . | T | T | . | −0.19 | . | . | . | 0.20 | 0.47 |
| Phe | 1601 | . | . | . | . | . | T | . | . | −0.19 | . | . | . | 0.00 | 0.41 |
| Gly | 1602 | . | . | . | . | . | . | T | C | 0.40 | . | * | . | 0.00 | 0.22 |
| Pro | 1603 | . | . | . | . | . | T | T | . | 0.02 | . | . | . | 0.20 | 0.38 |
| His | 1604 | . | . | . | . | . | T | T | . | −0.30 | * | . | . | 0.20 | 0.45 |
| Cys | 1605 | . | . | . | . | . | T | T | . | 0.40 | * | . | . | 0.20 | 0.24 |
| Gln | 1606 | . | . | A | . | . | . | T | . | 0.43 | . | . | . | 0.70 | 0.31 |
| Ala | 1607 | . | . | A | . | . | . | T | . | 0.47 | . | * | . | 0.10 | 0.12 |
| Cys | 1608 | . | . | A | B | B | . | . | . | −0.18 | * | * | . | −0.30 | 0.33 |
| Arg | 1609 | . | . | A | B | B | . | . | . | −0.18 | * | * | . | −0.30 | 0.14 |
| Cys | 1610 | . | . | . | B | B | . | . | . | 0.14 | . | * | . | −0.30 | 0.19 |
| Thr | 1611 | . | . | . | B | B | . | . | . | 0.26 | . | * | . | −0.30 | 0.35 |
| Val | 1612 | . | . | . | B | B | . | . | . | 0.18 | . | * | . | 0.30 | 0.35 |
| His | 1613 | . | . | . | B | B | . | . | . | 0.84 | . | * | . | −0.30 | 0.35 |
| Gly | 1614 | . | . | . | . | B | T | . | . | 0.73 | . | * | . | 0.70 | 0.40 |
| Arg | 1615 | . | . | . | B | . | . | . | . | 1.06 | * | * | F | 0.95 | 0.94 |
| Cys | 1616 | . | . | . | B | . | . | T | . | 0.56 | * | * | F | 1.42 | 0.68 |
| Asp | 1617 | . | . | . | B | . | . | T | . | 1.07 | . | * | F | 1.69 | 0.57 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Glu | 1618 | . | . | . | B | . | . | T | . | 0.76 | . | * | F | 1.96 | 0.29 |
| Gly | 1619 | . | . | . | . | . | T | T | . | 0.80 | * | * | F | 2.33 | 0.53 |
| Leu | 1620 | . | . | . | . | . | T | . | . | 0.34 | . | . | F | 2.70 | 0.43 |
| Gly | 1621 | . | . | . | . | . | T | . | . | 0.71 | . | . | F | 2.13 | 0.24 |
| Gly | 1622 | . | . | . | . | . | T | T | . | 0.04 | . | . | F | 1.46 | 0.33 |
| Ser | 1623 | . | . | . | . | . | T | T | . | −0.66 | . | . | F | 1.19 | 0.21 |
| Gly | 1624 | . | . | . | . | . | T | T | . | −0.98 | * | . | F | 0.62 | 0.19 |
| Ser | 1625 | . | . | . | B | . | . | T | . | −0.17 | * | . | F | −0.05 | 0.10 |
| Cys | 1626 | . | . | . | B | . | . | . | . | 0.18 | . | . | . | −0.10 | 0.13 |
| Phe | 1627 | . | . | . | B | . | . | . | . | 0.18 | . | . | . | 0.50 | 0.22 |
| Cys | 1628 | . | . | . | B | . | . | . | . | 0.19 | . | . | . | 0.75 | 0.16 |
| Asp | 1629 | . | . | . | . | . | T | T | . | 0.22 | * | . | . | 1.00 | 0.32 |
| Glu | 1630 | . | . | . | . | . | T | T | . | 0.18 | . | . | F | 1.40 | 0.53 |
| Gly | 1631 | . | . | . | . | . | T | T | . | 0.63 | . | . | F | 2.25 | 0.99 |
| Trp | 1632 | . | . | . | . | . | T | T | . | 1.44 | * | . | F | 2.50 | 0.91 |
| Thr | 1633 | . | . | . | . | . | . | . | C | 1.44 | * | * | F | 2.00 | 1.03 |
| Gly | 1634 | . | . | . | . | . | . | T | C | 1.44 | * | * | F | 1.20 | 0.56 |
| Pro | 1635 | . | . | . | . | . | . | T | C | 0.59 | * | * | F | 1.55 | 0.92 |
| Arg | 1636 | . | . | . | . | . | T | T | . | 0.93 | * | * | F | 1.50 | 0.47 |
| Cys | 1637 | . | . | . | B | . | . | T | . | 0.41 | . | * | . | 1.00 | 0.83 |
| Glu | 1638 | . | . | A | B | . | . | . | . | 0.72 | . | * | . | 0.30 | 0.44 |
| Val | 1639 | . | . | A | B | . | . | . | . | 0.26 | . | * | . | 0.60 | 0.39 |
| Gln | 1640 | . | . | A | B | . | . | . | . | 0.47 | . | * | . | 0.30 | 0.60 |
| Leu | 1641 | . | . | A | B | . | . | . | . | 0.14 | . | * | . | 0.30 | 0.60 |
| Glu | 1642 | . | . | A | B | . | . | . | . | −0.04 | . | * | . | −0.15 | 1.25 |
| Leu | 1643 | . | . | A | B | . | . | . | . | −0.71 | . | * | . | −0.30 | 0.54 |
| Gln | 1644 | . | . | A | B | . | . | . | . | −0.17 | . | * | . | −0.60 | 0.35 |
| Pro | 1645 | . | . | A | . | . | T | . | . | −0.38 | . | * | . | 0.10 | 0.29 |
| Val | 1646 | . | . | . | . | B | T | . | . | 0.22 | . | * | . | −0.20 | 0.55 |
| Cys | 1647 | . | . | . | . | B | T | . | . | −0.44 | . | . | . | 0.10 | 0.49 |
| Thr | 1648 | . | . | . | B | B | . | . | . | −0.22 | . | . | . | −0.60 | 0.17 |
| Pro | 1649 | . | . | . | . | . | . | T | C | −0.43 | . | . | F | 0.15 | 0.23 |
| Pro | 1650 | . | . | . | . | . | T | T | . | −0.22 | . | . | F | 0.35 | 0.66 |
| Cys | 1651 | . | . | . | . | . | T | T | . | 0.04 | . | . | . | 1.10 | 0.79 |
| Ala | 1652 | . | . | . | B | . | . | T | . | −0.14 | . | . | . | 0.70 | 0.52 |
| Pro | 1653 | . | . | A | B | . | . | . | . | −0.50 | * | * | . | −0.30 | 0.25 |
| Glu | 1654 | . | . | A | B | . | . | . | . | −0.18 | * | * | . | −0.30 | 0.25 |
| Ala | 1655 | . | . | A | B | . | . | . | . | −0.56 | * | * | . | 0.52 | 0.48 |
| Val | 1656 | . | . | A | B | . | . | . | . | −0.23 | * | * | . | 0.74 | 0.32 |
| Cys | 1657 | . | . | . | B | . | . | T | . | 0.36 | * | * | . | 1.36 | 0.18 |
| Arg | 1658 | . | . | . | . | . | T | T | . | 0.27 | * | * | . | 1.38 | 0.29 |
| Ala | 1659 | . | . | . | . | . | T | T | . | −0.40 | * | * | . | 2.20 | 0.52 |
| Gly | 1660 | . | . | . | . | . | T | T | . | 0.19 | * | * | F | 2.13 | 0.52 |
| Asn | 1661 | . | . | . | . | . | T | T | . | 0.38 | * | * | F | 2.21 | 0.46 |
| Ser | 1662 | . | . | . | . | . | T | T | . | 0.74 | * | * | F | 1.69 | 0.24 |
| Cys | 1663 | . | . | . | B | . | . | T | . | −0.18 | * | * | . | 0.92 | 0.33 |
| Glu | 1664 | . | . | . | B | . | . | T | . | 0.07 | . | . | . | 0.10 | 0.17 |
| Cys | 1665 | . | . | . | B | . | . | T | . | 0.17 | . | . | . | 0.10 | 0.12 |
| Ser | 1666 | . | . | . | B | . | . | T | . | 0.17 | . | * | . | −0.20 | 0.36 |
| Leu | 1667 | . | . | . | B | . | . | T | . | 0.12 | . | * | . | 1.04 | 0.36 |
| Gly | 1668 | . | . | . | . | . | T | T | . | 0.79 | . | * | . | 1.18 | 0.67 |
| Tyr | 1669 | . | . | . | . | . | T | . | . | 0.44 | . | * | . | 1.92 | 0.84 |
| Glu | 1670 | . | . | . | . | . | T | . | . | 1.22 | * | * | F | 2.56 | 1.01 |
| Gly | 1671 | . | . | . | . | . | T | T | . | 0.67 | . | * | F | 3.40 | 1.99 |
| Asp | 1672 | . | . | . | . | . | T | T | . | 0.81 | . | * | F | 2.91 | 0.94 |
| Gly | 1673 | . | . | . | . | . | T | T | . | 0.84 | * | * | F | 2.57 | 0.29 |
| Arg | 1674 | . | . | . | B | . | . | T | . | 0.23 | * | * | F | 1.53 | 0.43 |
| Val | 1675 | . | . | . | B | B | . | . | . | −0.36 | * | * | . | 0.64 | 0.19 |
| Cys | 1676 | . | . | . | B | B | . | . | . | −0.01 | . | * | . | −0.30 | 0.19 |
| Thr | 1677 | . | . | . | B | B | . | . | . | −0.82 | . | * | . | 0.30 | 0.16 |
| Val | 1678 | . | . | . | B | B | . | . | . | −1.14 | . | * | . | −0.60 | 0.18 |
| Ala | 1679 | . | . | . | B | B | . | . | . | −1.26 | * | * | . | −0.60 | 0.18 |
| Asp | 1680 | . | . | . | B | B | . | . | . | −0.40 | * | . | . | −0.30 | 0.22 |
| Leu | 1681 | . | . | . | B | . | . | . | . | −0.08 | * | . | . | 0.50 | 0.49 |
| Cys | 1682 | . | . | . | B | . | . | T | . | 0.20 | * | . | . | 0.95 | 0.48 |
| Gln | 1683 | . | . | . | B | . | . | T | . | 0.71 | . | . | . | 1.20 | 0.39 |
| Asp | 1684 | . | . | . | . | . | T | T | . | 0.96 | * | * | F | 1.40 | 0.47 |
| Gly | 1685 | . | . | . | . | . | T | T | . | 0.29 | * | . | F | 2.25 | 0.87 |
| His | 1686 | . | . | . | . | . | T | T | . | 0.80 | * | . | F | 2.50 | 0.27 |
| Gly | 1687 | . | . | . | . | . | T | T | . | 1.47 | . | . | F | 2.25 | 0.22 |
| Gly | 1688 | . | . | . | . | . | T | T | . | 1.43 | . | . | F | 2.00 | 0.38 |
| Cys | 1689 | . | . | . | . | . | T | T | . | 0.84 | * | . | F | 1.97 | 0.38 |
| Ser | 1690 | . | . | . | . | B | T | . | . | 1.19 | . | . | F | 1.74 | 0.39 |
| Glu | 1691 | . | . | . | . | B | . | . | . | 0.56 | . | . | . | 1.16 | 0.63 |
| His | 1692 | . | . | . | . | . | T | T | . | 0.60 | . | . | . | 1.98 | 0.63 |
| Ala | 1693 | . | . | . | . | . | T | T | . | 0.94 | . | . | . | 2.20 | 0.63 |
| Asn | 1694 | . | . | . | . | . | T | T | . | 0.76 | . | . | . | 1.98 | 0.63 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Cys | 1695 | . | . | . | . | . | T | T | . | 0.71 | . | . | . | 0.86 | 0.34 |
| Ser | 1696 | . | . | . | . | B | T | . | . | 0.40 | . | . | . | 0.54 | 0.34 |
| Gln | 1697 | . | . | . | . | B | T | . | . | −0.17 | . | . | F | 0.47 | 0.30 |
| Val | 1698 | . | . | . | . | B | T | . | . | −0.43 | . | . | F | −0.05 | 0.56 |
| Gly | 1699 | . | . | . | B | B | . | . | . | −0.74 | . | . | F | −0.45 | 0.31 |
| Thr | 1700 | . | . | . | B | B | . | . | . | −0.74 | * | . | . | −0.60 | 0.26 |
| Met | 1701 | . | . | . | B | B | . | . | . | −0.76 | * | . | . | −0.60 | 0.19 |
| Val | 1702 | . | . | . | B | B | . | . | . | −1.42 | . | . | . | −0.60 | 0.27 |
| Thr | 1703 | . | . | . | B | B | . | . | . | −1.38 | . | . | . | −0.60 | 0.10 |
| Cys | 1704 | . | . | . | B | B | . | . | . | −1.24 | . | . | . | −0.60 | 0.08 |
| Thr | 1705 | . | . | . | B | B | . | . | . | −0.93 | . | . | . | −0.60 | 0.17 |
| Cys | 1706 | . | . | . | B | B | . | . | . | −0.58 | . | . | . | 0.04 | 0.20 |
| Leu | 1707 | . | . | . | B | . | . | T | . | 0.28 | . | . | . | 0.48 | 0.59 |
| Pro | 1708 | . | . | . | B | . | . | T | . | 0.24 | . | . | F | 1.87 | 0.71 |
| Asp | 1709 | . | . | . | . | . | T | T | . | 0.91 | . | * | F | 2.76 | 1.31 |
| Tyr | 1710 | . | . | . | . | . | T | T | . | 0.88 | . | . | F | 3.40 | 2.65 |
| Glu | 1711 | . | . | . | . | . | T | . | . | 1.26 | . | . | F | 2.86 | 1.70 |
| Gly | 1712 | . | . | . | . | . | T | T | . | 1.77 | . | . | F | 2.42 | 1.07 |
| Asp | 1713 | . | . | . | . | . | T | T | . | 1.31 | . | * | F | 1.93 | 0.91 |
| Gly | 1714 | . | . | . | . | . | T | T | . | 1.42 | . | * | F | 1.59 | 0.28 |
| Trp | 1715 | . | . | . | . | . | T | T | . | 1.08 | . | * | . | 1.10 | 0.56 |
| Ser | 1716 | . | . | . | B | . | . | . | . | 1.19 | * | * | . | 0.50 | 0.34 |
| Cys | 1717 | . | . | . | . | . | T | . | . | 1.53 | * | * | . | 0.90 | 0.67 |
| Arg | 1718 | . | . | . | . | . | T | . | . | 1.32 | * | * | . | 1.39 | 1.03 |
| Ala | 1719 | . | . | . | . | . | T | . | . | 1.00 | . | * | F | 2.18 | 1.18 |
| Arg | 1720 | . | . | . | . | . | T | . | . | 0.98 | * | * | F | 2.52 | 1.18 |
| Asn | 1721 | . | . | . | . | . | . | T | C | 1.28 | * | * | F | 2.71 | 0.87 |
| Pro | 1722 | . | . | . | . | . | T | T | . | 1.60 | * | * | F | 3.40 | 1.44 |
| Cys | 1723 | . | . | . | . | . | T | T | . | 1.46 | * | * | F | 2.91 | 0.73 |
| Thr | 1724 | . | . | . | . | . | T | T | . | 2.16 | * | . | F | 2.58 | 0.62 |
| Asp | 1725 | . | . | . | . | . | T | . | . | 1.70 | * | . | F | 2.65 | 0.78 |
| Gly | 1726 | . | . | . | . | . | T | . | . | 1.36 | * | . | F | 2.77 | 1.44 |
| His | 1727 | . | . | . | . | . | T | T | . | 0.90 | * | . | F | 2.79 | 0.99 |
| Arg | 1728 | . | . | . | . | . | T | T | . | 1.27 | * | . | F | 3.10 | 0.32 |
| Gly | 1729 | . | . | . | . | . | T | T | . | 1.58 | * | . | F | 2.49 | 0.43 |
| Gly | 1730 | . | . | . | . | . | T | T | . | 1.54 | . | . | F | 2.48 | 0.55 |
| Cys | 1731 | . | . | . | . | . | T | . | . | 1.30 | . | . | F | 1.97 | 0.38 |
| Ser | 1732 | . | . | . | B | . | . | . | . | 1.33 | . | * | F | 0.96 | 0.39 |
| Glu | 1733 | . | . | . | B | . | . | . | . | 0.56 | * | * | . | 0.50 | 0.63 |
| His | 1734 | . | . | . | B | . | . | T | . | 0.09 | . | . | . | 0.70 | 0.63 |
| Ala | 1735 | . | . | . | B | . | . | T | . | 0.13 | * | . | . | 0.10 | 0.39 |
| Asn | 1736 | . | . | . | B | . | . | T | . | 0.49 | * | . | . | 0.10 | 0.30 |
| Cys | 1737 | . | . | . | B | . | . | T | . | 0.44 | * | . | . | −0.20 | 0.32 |
| Leu | 1738 | . | . | . | B | . | . | . | . | −0.37 | * | . | . | −0.40 | 0.31 |
| Ser | 1739 | . | . | . | . | . | T | T | . | −0.33 | . | . | F | 0.69 | 0.16 |
| Thr | 1740 | . | . | . | . | . | T | T | . | −0.06 | . | * | F | 1.03 | 0.48 |
| Gly | 1741 | . | . | . | . | . | T | T | . | 0.06 | . | . | F | 1.37 | 0.84 |
| Leu | 1742 | . | . | . | . | . | T | T | . | 0.83 | . | . | F | 2.76 | 1.23 |
| Asn | 1743 | . | . | . | . | . | T | T | . | 0.98 | . | * | F | 3.40 | 1.67 |
| Thr | 1744 | . | . | . | . | . | T | T | . | 1.28 | . | . | F | 2.61 | 0.90 |
| Arg | 1745 | . | . | . | . | . | T | T | . | 0.92 | . | . | F | 2.72 | 1.89 |
| Arg | 1746 | . | . | . | B | . | . | T | . | 1.23 | . | . | F | 1.83 | 0.63 |
| Cys | 1747 | . | . | . | B | . | . | . | . | 1.46 | . | . | . | 1.14 | 0.60 |
| Glu | 1748 | . | . | . | B | . | . | . | . | 1.11 | * | . | . | 0.80 | 0.31 |
| Cys | 1749 | . | . | . | B | . | . | . | . | 1.18 | * | . | . | 0.50 | 0.16 |
| His | 1750 | . | . | . | B | . | . | T | . | 0.21 | * | . | . | 0.10 | 0.45 |
| Ala | 1751 | . | . | . | B | . | . | T | . | −0.24 | * | * | . | −0.20 | 0.19 |
| Gly | 1752 | . | . | . | . | . | T | T | . | 0.42 | . | . | . | 0.20 | 0.36 |
| Tyr | 1753 | . | . | . | . | . | T | T | . | 0.08 | . | . | . | 0.50 | 0.44 |
| Val | 1754 | . | . | . | . | . | T | . | . | −0.07 | * | . | . | 0.30 | 0.43 |
| Gly | 1755 | . | . | . | . | . | T | T | . | −0.03 | * | . | . | 0.50 | 0.36 |
| Asp | 1756 | . | . | . | . | . | T | T | . | −0.11 | * | . | . | 0.50 | 0.40 |
| Gly | 1757 | . | . | . | B | . | . | T | . | −0.58 | * | . | . | 0.10 | 0.29 |
| Leu | 1758 | . | . | . | B | . | . | T | . | −0.33 | * | . | . | 0.10 | 0.24 |
| Gln | 1759 | . | A | B | . | . | . | . | . | 0.52 | * | . | . | 0.30 | 0.25 |
| Cys | 1760 | . | A | B | . | . | . | . | . | 0.57 | * | . | . | 0.60 | 0.43 |
| Leu | 1761 | . | A | B | . | . | . | . | . | 0.57 | * | . | . | 0.90 | 0.71 |
| Glu | 1762 | . | A | B | . | . | . | . | . | 0.70 | * | . | F | 1.65 | 0.71 |
| Glu | 1763 | . | A | . | . | . | T | . | . | 1.30 | * | . | F | 2.50 | 2.03 |
| Ser | 1764 | . | . | . | . | . | T | . | . | 0.44 | * | . | F | 3.00 | 3.82 |
| Glu | 1765 | . | . | . | . | . | . | . | C | 1.11 | * | . | F | 2.50 | 1.64 |
| Pro | 1766 | . | . | . | . | . | . | . | C | 2.03 | * | . | F | 2.20 | 1.58 |
| Pro | 1767 | . | . | . | . | . | T | . | . | 1.37 | * | . | F | 2.10 | 2.30 |
| Val | 1768 | . | . | . | . | . | T | . | . | 0.56 | * | . | F | 1.65 | 0.71 |
| Asp | 1769 | . | . | . | B | . | . | . | . | 0.51 | * | . | F | 0.65 | 0.38 |
| Arg | 1770 | . | . | . | B | . | . | . | . | 0.51 | * | . | F | 0.65 | 0.24 |
| Cys | 1771 | . | . | . | B | . | . | . | . | 0.51 | * | . | . | 0.50 | 0.57 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Leu | 1772 | . | . | . | . | . | T | . | . | 0.51 | * | . | F | 1.05 | 0.53 |
| Gly | 1773 | . | . | . | . | . | T | . | . | 1.16 | * | . | F | 1.05 | 0.42 |
| Gln | 1774 | . | . | . | . | . | . | . | C | 0.49 | * | . | F | 0.62 | 1.20 |
| Pro | 1775 | . | . | . | . | . | . | T | C | 0.34 | * | * | F | 0.89 | 0.78 |
| Pro | 1776 | . | . | . | . | . | . | T | C | 0.71 | . | . | F | 1.26 | 1.07 |
| Pro | 1777 | . | . | . | . | . | T | T | . | 1.52 | . | . | F | 1.53 | 0.83 |
| Cys | 1778 | . | . | . | . | . | T | T | . | 1.28 | . | . | . | 2.20 | 0.89 |
| His | 1779 | . | . | . | . | . | T | T | . | 0.68 | . | . | . | 1.98 | 0.58 |
| Ser | 1780 | . | . | . | B | . | . | T | . | 0.22 | . | . | . | 0.76 | 0.37 |
| Asp | 1781 | . | . | . | B | . | . | T | . | 0.12 | . | . | . | 0.54 | 0.37 |
| Ala | 1782 | . | . | . | B | . | . | T | . | 0.33 | . | . | . | 0.32 | 0.40 |
| Met | 1783 | . | . | . | B | . | . | . | . | 0.19 | . | . | . | 0.50 | 0.49 |
| Cys | 1784 | . | . | . | B | . | . | T | . | 0.19 | . | * | . | 0.70 | 0.24 |
| Thr | 1785 | . | . | . | B | . | . | T | . | −0.21 | . | * | . | 0.10 | 0.33 |
| Asp | 1786 | A | . | . | . | . | . | T | . | −0.21 | . | * | . | −0.20 | 0.29 |
| Leu | 1787 | A | . | . | . | . | . | T | . | 0.38 | . | * | . | −0.20 | 0.93 |
| His | 1788 | A | A | . | . | . | . | . | . | 1.02 | . | * | . | 0.45 | 1.12 |
| Phe | 1789 | A | A | . | . | . | . | . | . | 1.80 | * | * | . | 0.75 | 1.34 |
| Gln | 1790 | A | A | . | . | . | . | . | . | 1.52 | * | * | F | 0.90 | 3.17 |
| Glu | 1791 | A | A | . | . | . | . | . | . | 1.18 | . | * | F | 0.90 | 2.36 |
| Lys | 1792 | . | A | . | . | . | T | . | . | 1.13 | . | . | F | 1.30 | 2.69 |
| Arg | 1793 | . | A | . | . | . | T | . | . | 0.47 | . | . | F | 1.30 | 1.15 |
| Ala | 1794 | . | A | . | . | . | T | . | . | 1.13 | . | . | F | 1.15 | 0.58 |
| Gly | 1795 | . | A | . | . | . | T | . | . | 0.32 | . | . | . | 0.70 | 0.39 |
| Val | 1796 | . | A | B | . | . | . | . | . | 0.32 | . | * | . | −0.60 | 0.17 |
| Phe | 1797 | . | A | B | . | . | . | . | . | −0.31 | . | * | . | −0.60 | 0.28 |
| His | 1798 | . | A | B | . | . | . | . | . | −0.73 | . | * | . | −0.60 | 0.29 |
| Leu | 1799 | . | A | B | . | . | . | . | . | −0.44 | . | . | . | −0.60 | 0.56 |
| Gln | 1800 | . | A | B | . | . | . | . | . | −0.44 | . | * | . | −0.60 | 0.87 |
| Ala | 1801 | . | A | . | . | . | T | . | C | 0.20 | . | . | F | 0.25 | 0.63 |
| Thr | 1802 | . | A | . | . | . | T | . | . | 0.66 | . | * | F | 0.40 | 1.19 |
| Ser | 1803 | . | A | . | . | . | . | . | C | 0.34 | . | * | F | 0.20 | 1.07 |
| Gly | 1804 | . | . | . | . | . | . | T | C | 0.34 | . | * | F | 0.30 | 1.05 |
| Pro | 1805 | . | . | . | . | . | T | T | . | 0.34 | . | * | F | 0.35 | 0.60 |
| Tyr | 1806 | . | . | . | . | . | T | T | . | 0.23 | . | * | F | 0.35 | 0.72 |
| Gly | 1807 | . | . | . | . | . | . | T | C | 0.24 | . | * | . | 0.00 | 0.63 |
| Leu | 1808 | . | . | . | . | . | . | . | C | 0.54 | . | . | . | −0.20 | 0.55 |
| Asn | 1809 | . | A | B | . | . | . | . | . | 0.30 | . | . | . | −0.60 | 0.60 |
| Phe | 1810 | . | A | B | . | . | . | . | . | 0.51 | . | . | . | −0.30 | 0.62 |
| Ser | 1811 | . | A | B | . | . | . | . | . | 0.17 | . | . | . | 0.45 | 1.30 |
| Glu | 1812 | A | A | . | . | . | . | . | . | −0.08 | . | . | F | 0.45 | 0.81 |
| Ala | 1813 | A | A | . | . | . | . | . | . | 0.07 | . | * | . | 0.30 | 0.95 |
| Glu | 1814 | A | A | . | . | . | . | . | . | 0.07 | . | * | . | 0.60 | 0.38 |
| Ala | 1815 | A | A | . | . | . | . | . | . | 0.18 | . | * | . | 0.60 | 0.38 |
| Ala | 1816 | A | A | . | . | . | . | . | . | 0.48 | . | * | . | 0.30 | 0.38 |
| Cys | 1817 | A | A | . | . | . | . | . | . | 0.13 | . | * | . | 0.60 | 0.38 |
| Glu | 1818 | A | A | . | . | . | . | . | . | 0.13 | . | * | . | 0.30 | 0.37 |
| Ala | 1819 | A | A | . | . | . | . | . | . | −0.72 | . | * | . | 0.30 | 0.37 |
| Gln | 1820 | A | A | . | . | . | . | . | . | −0.94 | . | * | . | −0.30 | 0.52 |
| Gly | 1821 | A | A | . | . | . | . | . | . | −0.94 | . | . | . | −0.30 | 0.25 |
| Ala | 1822 | . | A | B | . | . | . | . | . | −0.58 | . | * | . | −0.60 | 0.25 |
| Val | 1823 | . | A | B | . | . | . | . | . | −1.28 | . | * | . | −0.60 | 0.19 |
| Leu | 1824 | . | A | B | . | . | . | . | . | −0.90 | . | . | . | −0.60 | 0.17 |
| Ala | 1825 | . | A | B | . | . | . | . | . | −0.90 | . | . | . | −0.60 | 0.25 |
| Ser | 1826 | . | A | B | . | . | . | . | . | −1.37 | . | . | . | −0.60 | 0.59 |
| Phe | 1827 | . | . | B | . | . | . | . | . | −1.08 | . | . | . | −0.40 | 0.59 |
| Pro | 1828 | . | . | . | . | . | . | . | C | −0.81 | . | . | . | −0.20 | 0.79 |
| Gln | 1829 | . | A | . | . | . | . | . | C | −0.59 | . | . | . | −0.40 | 0.59 |
| Leu | 1830 | . | A | B | . | . | . | . | . | 0.00 | . | . | . | −0.60 | 0.69 |
| Ser | 1831 | . | A | . | . | . | . | . | C | 0.30 | . | . | . | −0.10 | 0.78 |
| Ala | 1832 | . | A | B | . | . | . | . | . | 0.19 | . | . | . | −0.30 | 0.78 |
| Ala | 1833 | . | A | B | . | . | . | . | . | 0.06 | . | * | . | −0.60 | 0.78 |
| Gln | 1834 | . | A | B | . | . | . | . | . | −0.64 | . | * | . | −0.30 | 0.57 |
| Gln | 1835 | . | A | B | . | . | . | . | . | 0.13 | * | * | . | −0.60 | 0.49 |
| Leu | 1836 | . | A | B | . | . | . | . | . | −0.38 | * | * | . | −0.60 | 0.66 |
| Gly | 1837 | . | A | B | . | . | . | . | . | −0.46 | . | * | . | −0.60 | 0.31 |
| Phe | 1838 | . | A | B | . | . | . | . | . | −0.68 | . | * | . | −0.60 | 0.10 |
| His | 1839 | . | A | B | . | . | . | . | . | −1.28 | . | * | . | −0.60 | 0.10 |
| Leu | 1840 | . | A | B | . | . | . | . | . | −1.62 | . | * | . | −0.60 | 0.10 |
| Cys | 1841 | . | A | B | . | . | . | . | . | −1.10 | . | * | . | −0.60 | 0.11 |
| Leu | 1842 | . | A | B | . | . | . | . | . | −1.57 | . | . | . | −0.60 | 0.09 |
| Met | 1843 | . | A | B | . | . | . | . | . | −1.46 | . | * | . | −0.60 | 0.09 |
| Gly | 1844 | . | A | B | . | . | . | . | . | −1.42 | . | . | . | −0.60 | 0.16 |
| Trp | 1845 | . | A | B | . | . | . | . | . | −0.96 | . | . | . | −0.60 | 0.32 |
| Leu | 1846 | . | A | . | . | . | . | . | C | −0.59 | . | . | . | −0.40 | 0.32 |
| Ala | 1847 | . | A | . | . | . | . | . | C | −0.09 | . | . | . | −0.40 | 0.43 |
| Asn | 1848 | . | . | . | . | . | . | T | C | −0.08 | . | . | F | 0.15 | 0.59 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Gly | 1849 | . | . | . | . | . | T | T | . | 0.23 | . | . | F | 0.65 | 0.72 |
| Ser | 1850 | . | . | . | . | . | . | T | C | 0.31 | . | . | F | 0.45 | 0.97 |
| Thr | 1851 | . | . | . | . | . | . | T | C | 0.27 | . | . | F | 0.45 | 0.93 |
| Ala | 1852 | . | . | . | . | . | . | . | C | 0.00 | . | . | F | 0.25 | 0.70 |
| His | 1853 | . | . | . | B | B | . | . | . | −0.70 | . | . | . | −0.60 | 0.39 |
| Pro | 1854 | . | . | . | B | B | . | . | . | −0.57 | . | . | . | −0.60 | 0.23 |
| Val | 1855 | . | . | . | B | B | . | . | . | −1.12 | . | . | . | −0.60 | 0.36 |
| Val | 1856 | . | . | . | B | B | . | . | . | −1.40 | * | . | . | −0.60 | 0.19 |
| Phe | 1857 | . | . | . | B | B | . | . | . | −0.81 | * | . | . | −0.60 | 0.13 |
| Pro | 1858 | . | . | . | B | B | . | . | . | −1.44 | * | . | . | −0.60 | 0.29 |
| Val | 1859 | . | . | . | B | B | . | . | . | −1.58 | * | . | . | −0.29 | 0.21 |
| Ala | 1860 | . | . | . | B | B | . | . | . | −0.72 | * | . | . | 0.32 | 0.24 |
| Asp | 1861 | . | . | . | . | B | T | . | . | −0.21 | . | * | . | 1.63 | 0.24 |
| Cys | 1862 | . | . | . | . | . | T | T | . | 0.60 | . | * | . | 2.34 | 0.33 |
| Gly | 1863 | . | . | . | . | . | T | T | . | −0.04 | . | * | F | 3.10 | 0.63 |
| Asn | 1864 | . | . | . | . | . | T | T | . | 0.47 | . | * | F | 2.79 | 0.28 |
| Gly | 1865 | . | . | . | . | . | T | T | . | 0.17 | . | * | F | 2.18 | 0.52 |
| Arg | 1866 | . | . | . | B | B | . | . | . | −0.69 | . | * | F | 0.47 | 0.37 |
| Val | 1867 | . | . | . | B | B | . | . | . | −0.32 | . | * | . | 0.01 | 0.17 |
| Gly | 1868 | . | . | . | B | B | . | . | . | −0.79 | . | * | . | −0.30 | 0.23 |
| Ile | 1869 | . | . | . | B | B | . | . | . | −1.13 | . | * | . | −0.60 | 0.10 |
| Val | 1870 | . | . | . | B | B | . | . | . | −1.38 | . | * | . | −0.60 | 0.13 |
| Ser | 1871 | . | . | . | B | . | . | . | . | −1.38 | . | * | . | −0.40 | 0.13 |
| Leu | 1872 | . | . | . | B | . | . | . | . | −0.48 | . | * | . | −0.10 | 0.37 |
| Gly | 1873 | . | . | . | B | . | . | . | . | −0.13 | . | * | . | 0.50 | 0.99 |
| Ala | 1874 | . | . | . | . | . | . | . | C | −0.06 | * | * | F | 1.30 | 1.19 |
| Arg | 1875 | . | . | . | . | . | . | . | C | 0.50 | * | * | F | 1.00 | 1.19 |
| Lys | 1876 | . | . | . | . | . | . | . | C | 0.80 | . | * | F | 1.60 | 1.61 |
| Asn | 1877 | . | . | . | . | . | . | . | C | 1.72 | . | * | F | 1.90 | 2.76 |
| Leu | 1878 | . | . | . | . | . | . | . | C | 1.78 | . | * | F | 2.20 | 2.76 |
| Ser | 1879 | . | . | . | B | . | . | . | . | 2.37 | . | * | F | 2.30 | 1.45 |
| Glu | 1880 | . | . | . | . | B | . | T | . | 1.67 | . | * | F | 3.00 | 1.51 |
| Arg | 1881 | . | . | . | . | . | . | T | . | 1.38 | * | * | F | 2.70 | 1.85 |
| Trp | 1882 | . | . | . | . | . | T | . | . | 0.71 | . | * | . | 1.95 | 2.16 |
| Asp | 1883 | . | . | . | . | . | T | T | . | 0.82 | * | * | . | 1.70 | 0.67 |
| Ala | 1884 | . | . | . | . | . | T | T | . | 1.23 | * | * | . | 0.50 | 0.30 |
| Tyr | 1885 | . | . | . | B | . | . | T | . | 0.38 | * | * | . | −0.20 | 0.55 |
| Cys | 1886 | . | . | . | B | . | . | T | . | 0.27 | * | * | . | 0.10 | 0.24 |
| Phe | 1887 | . | . | . | B | B | . | . | . | 0.56 | * | . | . | −0.60 | 0.42 |
| Arg | 1888 | . | . | . | B | B | . | . | . | −0.30 | * | * | . | −0.30 | 0.45 |
| Val | 1889 | . | . | . | B | B | . | . | . | −0.30 | . | * | . | −0.30 | 0.62 |
| Gln | 1890 | . | . | . | B | B | . | . | . | −0.72 | * | * | . | 0.30 | 0.72 |
| Asp | 1891 | . | . | . | B | B | . | . | . | 0.06 | * | * | . | 0.30 | 0.20 |
| Val | 1892 | . | . | . | B | B | . | . | . | 0.09 | * | * | . | 0.30 | 0.52 |
| Ala | 1893 | . | . | . | B | B | . | . | . | 0.09 | * | * | . | 0.55 | 0.16 |
| Cys | 1894 | . | . | . | B | B | . | . | . | 0.94 | * | * | . | 1.10 | 0.19 |
| Arg | 1895 | . | . | . | B | B | . | . | . | 0.60 | * | * | . | 1.05 | 0.41 |
| Cys | 1896 | . | . | . | B | . | . | T | . | −0.10 | * | * | . | 2.00 | 0.40 |
| Arg | 1897 | . | . | . | . | . | T | T | . | −0.10 | * | * | F | 2.50 | 0.65 |
| Asn | 1898 | . | . | . | . | . | T | T | . | 0.14 | . | * | F | 2.25 | 0.25 |
| Gly | 1899 | . | . | . | . | . | T | T | . | 0.81 | . | * | F | 1.40 | 0.45 |
| Phe | 1900 | . | . | . | B | . | . | . | . | 0.36 | . | * | . | 1.00 | 0.39 |
| Val | 1901 | . | . | . | B | . | . | T | . | 0.13 | . | . | . | 0.35 | 0.24 |
| Gly | 1902 | . | . | . | . | . | T | T | . | −0.28 | . | . | F | 0.20 | 0.17 |
| Asp | 1903 | . | . | . | B | . | . | T | . | −0.59 | . | . | F | 0.25 | 0.26 |
| Gly | 1904 | . | . | . | B | . | . | T | . | −0.91 | * | . | F | 0.25 | 0.51 |
| Ile | 1905 | . | . | . | B | B | . | . | . | −0.21 | * | . | F | 0.45 | 0.28 |
| Ser | 1906 | . | . | . | B | B | . | . | . | 0.30 | * | * | F | 0.45 | 0.27 |
| Thr | 1907 | . | . | . | B | B | . | . | . | 0.69 | * | * | F | 0.02 | 0.27 |
| Cys | 1908 | . | . | . | B | . | . | . | . | −0.12 | * | . | F | 1.19 | 0.76 |
| Asn | 1909 | . | . | . | . | . | T | T | . | −0.59 | * | . | F | 1.76 | 0.47 |
| Gly | 1910 | . | . | . | . | . | T | T | . | 0.30 | * | . | F | 1.33 | 0.27 |
| Lys | 1911 | . | . | . | B | . | . | T | . | −0.26 | * | . | F | 1.70 | 0.83 |
| Leu | 1912 | . | . | A | B | . | . | . | . | −0.76 | * | . | . | 1.13 | 0.38 |
| Leu | 1913 | . | . | A | B | . | . | . | . | −0.68 | . | . | . | 0.21 | 0.32 |
| Asp | 1914 | . | . | A | B | . | . | . | . | −1.27 | . | . | . | 0.04 | 0.16 |
| Val | 1915 | . | . | A | B | . | . | . | . | −1.23 | * | . | . | −0.43 | 0.20 |
| Leu | 1916 | . | . | A | B | . | . | . | . | −1.87 | * | . | . | −0.60 | 0.35 |
| Ala | 1917 | . | . | A | B | . | . | . | . | −1.06 | * | . | . | −0.30 | 0.21 |
| Ala | 1918 | . | . | A | B | . | . | . | . | −0.94 | . | * | . | −0.60 | 0.45 |
| Thr | 1919 | . | . | A | B | . | . | . | . | −1.24 | . | * | . | −0.60 | 0.47 |
| Ala | 1920 | . | . | A | B | . | . | . | . | −0.70 | . | . | . | −0.60 | 0.63 |
| Asn | 1921 | . | . | A | B | . | . | . | . | −0.59 | . | * | . | −0.60 | 0.90 |
| Phe | 1922 | . | . | A | B | . | . | . | . | −0.24 | . | . | . | −0.60 | 0.54 |
| Ser | 1923 | . | . | A | B | . | . | . | . | 0.00 | . | . | . | −0.60 | 0.84 |
| Thr | 1924 | . | . | . | B | B | . | . | . | −0.29 | . | . | . | −0.60 | 0.52 |
| Phe | 1925 | . | . | . | B | B | . | . | . | −0.51 | . | . | . | −0.60 | 0.59 |

TABLE I-continued

| Res Pos. |  | I | II | III | IV | V | VI | VII | VIII | IX | X | XI | XII | XIII | XIV |
|---|---|---|---|---|---|---|---|---|---|---|---|---|---|---|---|
| Tyr | 1926 | . | . | . | B | B | . | . | . | −1.32 | . | . | . | −0.60 | 0.36 |
| Gly | 1927 | . | . | . | B | B | . | . | . | −0.97 | . | . | . | −0.60 | 0.21 |
| Met | 1928 | . | . | . | B | B | . | . | . | −0.91 | . | . | . | −0.60 | 0.24 |
| Leu | 1929 | . | . | . | B | B | . | . | . | −1.19 | . | . | . | −0.60 | 0.24 |
| Leu | 1930 | . | . | . | B | B | . | . | . | −0.49 | . | . | . | −0.60 | 0.24 |
| Gly | 1931 | . | . | . | . | . | . | . | C | −0.83 | . | . | . | −0.20 | 0.39 |
| Tyr | 1932 | . | . | A | B | . | . | . | . | −0.80 | . | . | . | −0.60 | 0.48 |
| Ala | 1933 | . | . | A | B | . | . | . | . | −0.20 | * | * | . | −0.60 | 0.84 |
| Asn | 1934 | . | . | A | B | . | . | . | . | 0.72 | * | * | . | −0.25 | 1.47 |
| Ala | 1935 | . | . | A | B | . | . | . | . | 1.19 | * | * | F | 0.40 | 1.84 |
| Thr | 1936 | . | . | . | B | . | . | T | . | 0.72 | * | * | F | 1.60 | 1.80 |
| Gln | 1937 | . | . | . | B | . | . | T | . | 0.97 | * | . | F | 1.65 | 0.93 |
| Arg | 1938 | . | . | . | B | . | . | T | . | 0.86 | * | . | F | 2.00 | 1.53 |
| Gly | 1939 | . | . | . | B | . | . | T | . | 0.04 | * | . | F | 1.65 | 0.92 |
| Leu | 1940 | . | . | A | B | . | . | . | . | 0.63 | * | . | . | 0.90 | 0.44 |
| Asp | 1941 | . | . | A | B | . | . | . | . | 0.24 | * | . | . | 0.70 | 0.37 |
| Phe | 1942 | . | . | A | B | . | . | . | . | −0.57 | * | . | . | −0.10 | 0.33 |
| Leu | 1943 | . | . | A | B | . | . | . | . | −0.68 | * | . | . | −0.60 | 0.33 |
| Asp | 1944 | . | . | A | B | . | . | . | . | −0.33 | * | . | . | 0.30 | 0.33 |
| Phe | 1945 | . | . | A | B | . | . | . | . | 0.48 | * | . | . | 0.30 | 0.63 |
| Leu | 1946 | . | . | A | B | . | . | . | . | −0.33 | * | . | . | 0.75 | 1.32 |
| Asp | 1947 | A | . | A | . | . | . | . | . | 0.06 | * | . | F | 0.75 | 0.65 |
| Asp | 1948 | A | . | A | . | . | . | . | . | 0.62 | . | * | F | 0.65 | 1.09 |
| Glu | 1949 | A | . | . | . | B | . | . | . | 0.67 | . | * | F | 0.70 | 2.06 |
| Leu | 1950 | A | . | . | . | B | . | . | . | 1.06 | . | * | . | 0.90 | 2.47 |
| Thr | 1951 | . | . | . | . | B | T | . | . | 1.06 | . | * | . | 1.35 | 2.14 |
| Tyr | 1952 | . | . | . | . | B | T | . | . | 0.36 | . | * | . | 0.50 | 1.02 |
| Lys | 1953 | . | . | . | B | B | . | . | . | −0.50 | . | . | F | −0.10 | 1.07 |
| Thr | 1954 | . | . | . | B | B | . | . | . | −0.71 | . | * | . | −0.45 | 0.55 |
| Leu | 1955 | . | . | . | B | B | . | . | . | −0.76 | . | * | . | −0.50 | 0.54 |
| Phe | 1956 | . | . | . | B | B | . | . | . | −0.44 | * | . | . | −0.55 | 0.20 |
| Val | 1957 | . | . | . | B | B | . | . | . | −0.20 | * | . | . | −0.60 | 0.22 |
| Pro | 1958 | . | . | . | B | . | . | . | . | −0.59 | * | . | . | −0.40 | 0.47 |
| Val | 1959 | . | . | . | B | . | . | . | . | −0.98 | * | . | . | 0.04 | 0.54 |
| Asn | 1960 | . | . | . | B | . | . | T | . | −1.02 | * | . | F | 0.53 | 0.63 |
| Glu | 1961 | . | . | . | B | . | . | T | . | −0.32 | * | . | F | 0.67 | 0.30 |
| Gly | 1962 | . | . | . | . | . | T | T | . | 0.53 | . | . | F | 1.81 | 0.68 |
| Phe | 1963 | . | . | . | B | . | . | T | . | 0.14 | * | . | . | 1.40 | 0.68 |
| Val | 1964 | . | . | . | B | . | . | . | . | 0.69 | . | . | . | 1.06 | 0.39 |
| Asp | 1965 | . | . | . | B | . | . | . | . | −0.12 | . | . | . | 0.32 | 0.57 |
| Asn | 1966 | . | . | . | B | . | . | . | . | −0.42 | . | . | . | −0.12 | 0.54 |
| Met | 1967 | . | . | . | B | . | . | . | . | −0.42 | . | . | . | 0.04 | 0.97 |
| Thr | 1968 | . | . | . | B | . | . | . | . | 0.07 | * | . | . | −0.10 | 0.58 |
| Leu | 1969 | . | . | . | . | . | . | . | C | 0.92 | * | . | F | −0.05 | 0.55 |
| Ser | 1970 | . | . | . | . | . | . | . | C | 0.11 | . | . | F | −0.05 | 0.90 |
| Gly | 1971 | . | . | . | . | . | . | T | C | 0.11 | . | * | F | 0.15 | 0.51 |
| Pro | 1972 | . | . | . | . | . | . | T | C | −0.10 | . | * | F | 0.60 | 1.08 |
| Asn | 1973 | . | . | . | . | . | . | T | C | 0.18 | . | * | F | 0.45 | 0.66 |
| Leu | 1974 | . | . | . | B | . | . | T | . | 0.40 | . | * | . | 0.10 | 0.91 |
| Glu | 1975 | . | . | . | B | . | . | . | . | 0.40 | . | * | . | −0.10 | 0.60 |
| Leu | 1976 | . | . | . | B | . | . | . | . | 0.74 | . | * | . | −0.10 | 0.50 |
| His | 1977 | . | . | . | B | . | . | T | . | 0.37 | . | * | . | 0.10 | 0.97 |
| Ala | 1978 | . | . | . | B | . | . | T | . | 0.06 | . | * | . | 0.70 | 0.57 |
| Ser | 1979 | . | . | . | B | . | . | T | . | 0.06 | . | * | . | −0.20 | 0.99 |
| Asn | 1980 | . | . | . | B | . | . | T | . | −0.76 | . | . | . | −0.20 | 0.60 |
| Ala | 1981 | . | . | A | B | . | . | . | . | −0.24 | . | . | . | −0.60 | 0.49 |
| Thr | 1982 | . | . | A | B | . | . | . | . | −0.80 | . | . | . | −0.60 | 0.49 |
| Leu | 1983 | . | . | A | B | . | . | . | . | −0.21 | . | . | . | −0.60 | 0.31 |
| Leu | 1984 | . | . | A | B | . | . | . | . | −0.50 | . | . | . | −0.60 | 0.49 |
| Ser | 1985 | . | . | A | B | . | . | . | . | −0.80 | . | . | . | −0.60 | 0.34 |
| Ala | 1986 | . | . | A | B | . | . | . | . | −0.21 | . | . | . | −0.35 | 0.56 |
| Asn | 1987 | . | . | A | B | . | . | . | . | −0.24 | . | . | F | 0.50 | 1.17 |
| Ala | 1988 | . | . | A | . | . | . | . | C | 0.61 | . | * | F | 0.80 | 0.86 |
| Ser | 1989 | . | . | . | . | . | T | T | . | 0.61 | . | . | F | 2.40 | 1.71 |
| Gln | 1990 | . | . | . | . | . | T | T | . | 0.10 | . | . | F | 2.50 | 0.88 |
| Gly | 1991 | . | . | . | . | . | T | T | . | 0.48 | . | . | F | 1.65 | 0.72 |
| Lys | 1992 | . | . | . | B | . | . | T | . | −0.11 | . | . | F | 1.00 | 0.83 |
| Leu | 1993 | . | . | . | B | . | . | . | . | 0.44 | . | . | F | 0.55 | 0.48 |
| Leu | 1994 | . | . | . | B | . | . | . | . | 0.44 | . | . | . | 0.15 | 0.66 |
| Pro | 1995 | . | . | . | B | . | . | . | . | 0.10 | . | * | . | −0.10 | 0.44 |
| Ala | 1996 | . | . | . | B | . | . | . | . | −0.37 | . | . | . | −0.40 | 0.53 |
| His | 1997 | . | . | . | B | . | . | T | . | −0.71 | . | * | . | −0.20 | 0.53 |
| Ser | 1998 | . | . | . | . | . | . | T | C | −0.71 | . | . | . | 0.30 | 0.46 |
| Gly | 1999 | . | . | . | B | . | . | T | . | −0.79 | . | * | . | −0.20 | 0.38 |
| Leu | 2000 | . | . | . | B | . | . | T | . | −1.47 | * | . | . | −0.20 | 0.19 |
| Ser | 2001 | . | . | . | B | B | . | . | . | −1.18 | * | . | . | −0.60 | 0.10 |
| Leu | 2002 | . | . | . | B | B | . | . | . | −1.14 | * | . | . | −0.60 | 0.14 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Ile | 2003 | . | . | . | B | B | . | . | . | −1.43 | * | . | . | −0.60 | 0.28 |
| Ile | 2004 | . | . | . | B | B | . | . | . | −1.43 | * | . | . | 0.00 | 0.21 |
| Ser | 2005 | . | . | . | B | B | . | . | . | −0.83 | * | . | . | 0.30 | 0.25 |
| Asp | 2006 | . | . | . | B | . | . | . | . | −0.53 | . | . | F | 0.95 | 0.56 |
| Ala | 2007 | . | . | . | B | . | . | . | . | 0.28 | . | . | F | 2.30 | 1.32 |
| Gly | 2008 | . | . | . | . | . | . | T | C | 0.87 | . | . | F | 3.00 | 1.59 |
| Pro | 2009 | . | . | . | . | . | . | T | C | 1.46 | * | . | F | 2.70 | 1.28 |
| Asp | 2010 | . | . | . | . | . | T | T | . | 1.47 | . | . | F | 2.30 | 1.69 |
| Asn | 2011 | . | . | . | . | . | T | T | . | 0.88 | . | . | F | 2.00 | 1.80 |
| Ser | 2012 | . | . | . | . | . | T | . | . | 1.26 | . | . | F | 0.90 | 1.17 |
| Ser | 2013 | . | . | . | . | . | T | . | . | 0.74 | . | . | F | 0.60 | 1.09 |
| Trp | 2014 | . | . | . | B | . | . | . | . | 0.37 | . | . | . | −0.40 | 0.50 |
| Ala | 2015 | . | . | . | B | . | . | . | . | 0.16 | . | . | . | −0.40 | 0.38 |
| Pro | 2016 | . | . | . | B | . | . | . | . | −0.19 | . | . | . | −0.40 | 0.44 |
| Val | 2017 | . | . | . | B | . | . | . | . | −0.20 | . | . | . | −0.40 | 0.41 |
| Ala | 2018 | . | . | . | B | . | . | T | . | −0.76 | . | . | . | −0.20 | 0.59 |
| Pro | 2019 | . | . | . | B | . | . | T | . | −1.32 | . | . | F | −0.05 | 0.28 |
| Gly | 2020 | . | . | . | B | . | . | T | . | −1.59 | . | . | F | −0.05 | 0.28 |
| Thr | 2021 | . | . | . | B | . | . | T | . | −1.68 | * | . | F | −0.05 | 0.21 |
| Val | 2022 | . | . | . | B | B | . | . | . | −0.71 | * | . | . | −0.60 | 0.18 |
| Val | 2023 | . | . | . | B | B | . | . | . | −1.01 | * | . | . | −0.30 | 0.36 |
| Val | 2024 | . | . | . | B | B | . | . | . | −1.69 | * | . | . | −0.60 | 0.17 |
| Ser | 2025 | . | . | . | B | B | . | . | . | −2.20 | * | . | . | −0.60 | 0.16 |
| Arg | 2026 | . | . | . | B | B | . | . | . | −2.18 | . | . | . | −0.60 | 0.16 |
| Ile | 2027 | . | . | . | B | B | . | . | . | −1.32 | . | . | . | −0.60 | 0.23 |
| Ile | 2028 | . | . | . | B | B | . | . | . | −1.36 | . | . | . | −0.30 | 0.29 |
| Val | 2029 | . | . | . | B | B | . | . | . | −1.10 | * | . | . | −0.60 | 0.10 |
| Trp | 2030 | . | . | . | B | B | . | . | . | −1.39 | * | . | . | −0.60 | 0.15 |
| Asp | 2031 | . | . | . | B | B | . | . | . | −2.20 | * | . | . | −0.60 | 0.21 |
| Ile | 2032 | . | . | . | B | B | . | . | . | −1.31 | . | . | . | −0.60 | 0.24 |
| Met | 2033 | . | . | . | B | B | . | . | . | −0.77 | . | . | . | −0.60 | 0.37 |
| Ala | 2034 | . | . | . | . | B | . | . | C | −0.80 | . | . | . | −0.40 | 0.22 |
| Phe | 2035 | . | . | . | . | B | T | . | . | −1.40 | . | . | . | −0.20 | 0.22 |
| Asn | 2036 | . | . | . | . | B | . | . | C | −1.43 | . | * | . | −0.40 | 0.16 |
| Gly | 2037 | . | . | . | B | B | . | . | . | −1.13 | * | . | . | −0.60 | 0.21 |
| Ile | 2038 | . | . | . | B | B | . | . | . | −1.34 | * | * | . | −0.60 | 0.25 |
| Ile | 2039 | . | . | . | B | B | . | . | . | −1.34 | * | . | . | −0.60 | 0.13 |
| His | 2040 | . | . | . | B | B | . | . | . | −0.94 | * | * | . | −0.60 | 0.13 |
| Ala | 2041 | . | . | . | B | B | . | . | . | −1.16 | * | . | . | −0.60 | 0.25 |
| Leu | 2042 | . | . | . | B | B | . | . | . | −1.62 | * | . | . | −0.60 | 0.54 |
| Ala | 2043 | . | . | . | B | B | . | . | . | −1.54 | * | . | . | −0.60 | 0.33 |
| Ser | 2044 | . | . | . | B | . | . | T | . | −1.24 | . | . | . | −0.20 | 0.27 |
| Pro | 2045 | . | . | . | . | . | . | T | C | −1.42 | . | . | . | 0.00 | 0.33 |
| Leu | 2046 | . | . | . | . | . | T | T | . | −1.04 | . | . | . | 0.20 | 0.50 |
| Leu | 2047 | . | . | . | B | . | . | T | . | −0.23 | . | . | . | −0.20 | 0.58 |
| Ala | 2048 | . | . | . | . | . | . | . | C | 0.14 | . | . | F | −0.05 | 0.65 |
| Pro | 2049 | . | . | . | . | . | . | T | C | 0.44 | . | . | F | 0.30 | 1.22 |
| Pro | 2050 | . | . | . | . | . | . | T | C | 0.07 | . | . | F | 0.60 | 2.57 |
| Gln | 2051 | . | . | . | . | . | . | T | C | 0.02 | . | . | F | 0.60 | 2.57 |
| Pro | 2052 | . | . | . | B | . | . | T | . | 0.02 | . | . | F | 0.40 | 1.23 |
| Gln | 2053 | . | . | A | B | . | . | . | . | 0.02 | . | . | F | −0.45 | 0.66 |
| Ala | 2054 | . | . | A | B | . | . | . | . | −0.16 | . | . | . | −0.60 | 0.38 |
| Val | 2055 | . | . | A | B | . | . | . | . | 0.06 | . | . | . | −0.60 | 0.32 |
| Leu | 2056 | . | . | A | B | . | . | . | . | −0.53 | . | . | . | −0.30 | 0.32 |
| Ala | 2057 | . | . | A | B | . | . | . | . | −0.53 | . | . | . | −0.30 | 0.32 |
| Xxx | 2058 | . | . | A | B | . | . | . | . | −0.74 | . | . | . | −0.30 | 0.66 |
| Glu | 2059 | . | . | A | B | . | . | . | . | −1.01 | . | . | F | 0.60 | 1.24 |
| Ala | 2060 | . | . | A | B | . | . | . | . | −0.74 | . | . | F | 0.45 | 0.91 |
| Pro | 2061 | . | . | A | B | . | . | . | . | −0.52 | . | . | F | 0.45 | 0.72 |
| Pro | 2062 | . | . | . | B | . | . | . | . | −0.28 | . | . | F | 0.05 | 0.42 |
| Val | 2063 | . | . | . | B | B | . | . | . | −0.74 | . | . | . | −0.60 | 0.41 |
| Ala | 2064 | . | . | . | B | B | . | . | . | −1.09 | . | . | . | −0.60 | 0.20 |
| Ala | 2065 | . | . | . | B | B | . | . | . | −1.09 | . | . | . | −0.60 | 0.13 |
| Gly | 2066 | . | . | . | B | B | . | . | . | −1.73 | . | . | . | −0.60 | 0.17 |
| Val | 2067 | . | . | . | B | B | . | . | . | −2.33 | . | . | . | −0.60 | 0.13 |
| Gly | 2068 | . | . | A | B | . | . | . | . | −2.07 | . | . | . | −0.60 | 0.10 |
| Ala | 2069 | . | . | A | B | . | . | . | . | −2.07 | . | . | . | −0.60 | 0.11 |
| Val | 2070 | . | . | A | B | . | . | . | . | −1.82 | . | . | . | −0.60 | 0.14 |
| Leu | 2071 | . | . | A | B | . | . | . | . | −2.07 | . | . | . | −0.60 | 0.14 |
| Ala | 2072 | . | . | A | B | . | . | . | . | −2.02 | . | . | . | −0.60 | 0.14 |
| Ala | 2073 | . | . | A | B | . | . | . | . | −2.49 | . | . | . | −0.60 | 0.16 |
| Gly | 2074 | . | . | A | B | . | . | . | . | −2.24 | . | . | . | −0.60 | 0.16 |
| Ala | 2075 | . | . | A | B | . | . | . | . | −2.20 | . | . | . | −0.60 | 0.16 |
| Leu | 2076 | . | . | A | B | . | . | . | . | −2.24 | . | . | . | −0.60 | 0.13 |
| Leu | 2077 | . | . | A | B | . | . | . | . | −2.24 | . | . | . | −0.60 | 0.10 |
| Gly | 2078 | . | . | A | B | . | . | . | . | −2.00 | . | . | . | −0.60 | 0.10 |
| Leu | 2079 | . | . | A | B | . | . | . | . | −2.24 | . | . | . | −0.60 | 0.11 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Val | 2080 | . | . | A | B | . | . | . | . | −2.47 | . | . | . | −0.60 | 0.14 |
| Ala | 2081 | . | . | A | B | . | . | . | . | −1.90 | . | . | . | −0.60 | 0.12 |
| Gly | 2082 | . | . | A | B | . | . | . | . | −1.90 | . | * | . | −0.60 | 0.22 |
| Ala | 2083 | . | . | A | B | . | . | . | . | −1.44 | . | * | . | −0.60 | 0.25 |
| Leu | 2084 | . | . | A | B | . | . | . | . | −1.22 | . | * | . | −0.60 | 0.48 |
| Tyr | 2085 | . | . | A | B | . | . | . | . | −0.26 | . | * | . | −0.26 | 0.49 |
| Leu | 2086 | . | . | A | B | . | . | . | . | −0.01 | . | * | . | 0.38 | 0.95 |
| Arg | 2087 | . | . | . | B | . | . | T | . | 0.38 | . | * | . | 1.27 | 1.14 |
| Ala | 2088 | . | . | . | B | . | . | T | . | 0.76 | . | * | F | 2.66 | 1.45 |
| Arg | 2089 | . | . | . | . | . | T | T | . | 0.97 | . | * | F | 3.40 | 2.72 |
| Gly | 2090 | . | . | . | . | . | T | T | . | 0.87 | . | * | F | 3.06 | 1.37 |
| Lys | 2091 | . | . | . | . | . | . | . | C | 0.98 | . | * | F | 2.32 | 1.35 |
| Pro | 2092 | . | . | . | B | . | . | T | . | 0.52 | . | * | F | 1.53 | 0.59 |
| Met | 2093 | . | . | . | . | . | T | T | . | 0.41 | . | * | . | 0.84 | 0.59 |
| Gly | 2094 | . | . | . | B | . | . | T | . | 0.00 | . | * | . | −0.20 | 0.26 |
| Phe | 2095 | . | . | . | B | . | . | T | . | −0.24 | * | . | . | −0.20 | 0.22 |
| Gly | 2096 | . | . | . | B | . | . | . | . | −0.99 | * | . | . | −0.40 | 0.23 |
| Phe | 2097 | . | . | A | B | . | . | . | . | −0.78 | . | . | . | −0.60 | 0.20 |
| Ser | 2098 | . | . | A | . | . | . | . | C | −0.77 | . | . | . | −0.40 | 0.40 |
| Ala | 2099 | . | . | A | . | . | . | . | C | −0.42 | . | . | . | −0.40 | 0.41 |
| Phe | 2100 | . | . | A | B | . | . | . | . | 0.28 | . | . | . | −0.30 | 0.81 |
| Gln | 2101 | . | . | A | B | . | . | . | C | 0.62 | . | * | . | 0.99 | 1.01 |
| Ala | 2102 | . | . | A | . | . | . | . | C | 0.73 | . | * | . | 1.63 | 1.68 |
| Glu | 2103 | . | . | A | . | . | . | . | C | 1.03 | * | * | F | 2.12 | 1.96 |
| Asp | 2104 | . | . | A | . | . | T | . | . | 1.62 | * | * | F | 2.66 | 1.89 |
| Asp | 2105 | . | . | . | . | . | T | T | . | 1.93 | * | * | F | 3.40 | 3.12 |
| Ala | 2106 | . | . | . | . | . | T | T | . | 1.23 | * | * | F | 3.06 | 2.30 |
| Asp | 2107 | . | . | . | . | . | T | T | . | 1.52 | * | * | F | 2.72 | 1.19 |
| Asp | 2108 | . | . | . | . | . | T | T | . | 1.31 | * | . | F | 2.23 | 0.96 |
| Xxx | 2109 | . | . | . | . | . | T | . | . | 1.02 | * | . | F | 1.54 | 1.47 |
| Phe | 2110 | . | . | . | . | . | . | . | C | 1.02 | * | . | F | 0.85 | 0.92 |
| Ser | 2111 | . | . | . | . | . | . | T | C | 1.61 | * | . | F | 0.45 | 0.96 |
| Pro | 2112 | . | . | . | . | . | . | T | C | 1.27 | * | . | F | 0.60 | 1.30 |
| Trp | 2113 | . | . | . | . | . | T | T | . | 0.96 | * | . | F | 0.80 | 1.48 |
| Gln | 2114 | . | . | . | . | . | . | T | C | 1.34 | * | . | F | 0.81 | 1.60 |
| Glu | 2115 | . | . | . | . | . | T | . | . | 1.83 | * | . | F | 1.02 | 1.66 |
| Gly | 2116 | . | . | . | . | . | T | . | . | 1.82 | . | . | F | 1.23 | 2.44 |
| Thr | 2117 | . | . | . | . | . | . | . | C | 1.22 | . | . | F | 1.84 | 2.03 |
| Asn | 2118 | . | . | . | . | . | T | . | C | 0.66 | . | . | F | 2.10 | 0.97 |
| Pro | 2119 | . | . | . | . | . | T | . | C | 0.27 | . | . | F | 0.99 | 0.73 |
| Thr | 2120 | . | . | B | . | . | T | . | . | −0.59 | . | . | F | 0.58 | 0.64 |
| Leu | 2121 | . | . | B | . | . | T | . | . | −0.46 | . | . | . | 0.22 | 0.30 |
| Val | 2122 | . | . | B | . | . | . | . | . | −0.14 | . | . | . | −0.19 | 0.30 |
| Xxx | 2123 | . | . | B | . | . | . | . | . | −0.36 | * | . | . | −0.40 | 0.33 |
| Val | 2124 | . | . | B | . | . | T | . | . | −1.00 | * | . | F | −0.05 | 0.62 |
| Pro | 2125 | . | . | B | . | . | T | . | . | −1.39 | * | . | F | −0.05 | 0.62 |
| Asn | 2126 | . | . | B | . | . | T | . | . | −0.92 | * | . | F | −0.05 | 0.42 |
| Pro | 2127 | . | . | B | . | . | T | . | . | −0.37 | . | . | F | −0.05 | 0.56 |
| Val | 2128 | . | . | B | . | . | . | . | . | 0.02 | . | . | F | −0.25 | 0.49 |
| Phe | 2129 | . | . | B | . | . | . | . | . | 0.57 | . | . | F | 0.05 | 0.50 |
| Gly | 2130 | . | . | . | . | . | T | T | . | 0.08 | . | . | F | 0.65 | 0.47 |
| Ser | 2131 | . | . | . | . | . | T | T | . | −0.59 | . | . | F | 0.35 | 0.55 |
| Asp | 2132 | . | . | B | . | . | . | T | . | −0.38 | . | . | F | −0.05 | 0.34 |
| Thr | 2133 | . | . | . | . | . | T | T | . | 0.27 | . | . | F | 1.25 | 0.60 |
| Phe | 2134 | . | . | B | . | . | . | . | . | 0.27 | * | . | . | 0.50 | 0.69 |
| Cys | 2135 | . | . | B | . | . | . | . | . | 0.61 | * | . | . | 0.21 | 0.36 |
| Glu | 2136 | . | . | B | . | . | . | . | . | 0.91 | * | . | . | 0.52 | 0.41 |
| Pro | 2137 | . | . | . | . | . | T | . | . | 0.61 | * | . | F | 1.98 | 0.79 |
| Phe | 2138 | . | . | . | . | . | T | . | . | 0.11 | * | . | F | 2.74 | 1.99 |
| Asp | 2139 | . | . | . | . | . | T | T | . | 0.00 | * | . | F | 3.10 | 0.95 |
| Asp | 2140 | . | . | . | . | . | . | T | C | 0.67 | * | . | F | 2.29 | 0.50 |
| Ser | 2141 | . | . | . | . | . | . | T | C | 0.67 | . | . | F | 2.13 | 1.01 |
| Leu | 2142 | . | . | . | . | . | . | T | C | 0.88 | . | . | F | 2.12 | 1.05 |
| Leu | 2143 | . | . | A | . | . | . | . | C | 0.88 | . | . | F | 1.41 | 1.05 |
| Glu | 2144 | . | . | A | . | . | . | . | C | 0.67 | . | . | F | 0.99 | 0.68 |
| Glu | 2145 | . | . | A | . | . | T | . | . | 0.67 | . | . | F | 1.68 | 1.27 |
| Asp | 2146 | . | . | A | . | . | T | . | . | 0.66 | . | . | F | 2.32 | 2.57 |
| Phe | 2147 | . | . | . | . | . | . | T | C | 1.47 | * | . | F | 2.86 | 2.14 |
| Pro | 2148 | . | . | . | . | . | T | T | . | 2.39 | * | * | F | 3.40 | 2.14 |
| Asp | 2149 | . | . | . | . | . | T | T | . | 1.50 | * | . | F | 3.06 | 2.51 |
| Thr | 2150 | A | . | . | . | . | . | T | . | 0.69 | * | . | F | 2.02 | 2.03 |
| Gln | 2151 | A | . | . | . | B | . | . | . | 0.38 | * | . | F | 1.28 | 1.08 |
| Arg | 2152 | . | . | B | . | B | . | . | . | 0.22 | * | . | F | 0.79 | 0.94 |
| Ile | 2153 | . | . | B | . | B | . | . | . | 0.48 | . | . | . | −0.30 | 0.48 |
| Leu | 2154 | . | . | B | . | B | . | . | . | 0.09 | . | . | . | 0.30 | 0.56 |

TABLE I-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Thr | 2155 | . | . | B | B | . | . | . | 0.01 | . | . | . | 0.30 | 0.36 |
| Val | 2156 | . | . | B | B | . | . | . | −0.38 | . | . | . | −0.30 | 0.66 |
| Lys | 2157 | . | . | B | B | . | . | . | −0.88 | . | . | . | −0.15 | 1.03 |

TABLE II

| Res Pos. | | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | B | . | . | . | −0.80 | . | . | . | −0.60 | 0.21 |
| Val | 2 | . | . | B | B | . | . | . | −1.08 | . | . | . | −0.60 | 0.24 |
| Thr | 3 | . | . | B | B | . | . | . | −1.50 | . | . | . | −0.60 | 0.10 |
| Cys | 4 | . | . | B | B | . | . | . | −1.32 | . | . | . | −0.60 | 0.08 |
| Thr | 5 | . | . | B | B | . | . | . | −0.93 | . | . | . | −0.60 | 0.17 |
| Cys | 6 | . | . | B | B | . | . | . | −0.58 | . | . | . | 0.04 | 0.20 |
| Leu | 7 | . | . | . | B | . | . | T | . | 0.28 | . | . | . | 0.48 | 0.59 |
| Pro | 8 | . | . | . | B | . | . | T | . | 0.24 | . | * | F | 1.87 | 0.71 |
| Asp | 9 | . | . | . | . | . | T | T | . | 0.91 | . | * | F | 2.76 | 1.31 |
| Tyr | 10 | . | . | . | . | . | T | T | . | 0.88 | * | * | F | 3.40 | 2.65 |
| Glu | 11 | . | . | . | . | . | T | . | . | 1.26 | * | . | F | 2.86 | 1.70 |
| Gly | 12 | . | . | . | . | . | T | T | . | 1.77 | * | . | F | 2.42 | 1.07 |
| Asp | 13 | . | . | . | . | . | T | T | . | 1.31 | . | * | F | 1.93 | 0.91 |
| Gly | 14 | . | . | . | . | . | T | T | . | 1.42 | . | * | F | 1.59 | 0.28 |
| Trp | 15 | . | . | . | . | . | T | T | . | 1.08 | . | * | . | 1.10 | 0.56 |
| Ser | 16 | . | . | . | B | . | . | . | . | 1.19 | * | * | . | 0.50 | 0.34 |
| Cys | 17 | . | . | . | . | . | T | . | . | 1.53 | * | * | . | 0.90 | 0.67 |
| Arg | 18 | . | . | . | . | . | T | . | . | 1.32 | * | * | . | 1.39 | 1.03 |
| Ala | 19 | . | . | . | . | . | T | . | . | 1.00 | * | * | F | 2.18 | 1.18 |
| Arg | 20 | . | . | . | . | . | T | . | . | 0.98 | * | * | F | 2.52 | 1.18 |
| Asn | 21 | . | . | . | . | . | . | T | C | 1.28 | * | * | F | 2.71 | 0.87 |
| Pro | 22 | . | . | . | . | . | T | T | . | 1.60 | * | * | F | 3.40 | 1.44 |
| Cys | 23 | . | . | . | . | . | T | T | . | 1.46 | * | * | F | 2.91 | 0.73 |
| Thr | 24 | . | . | . | . | . | T | T | . | 2.16 | * | * | F | 2.58 | 0.62 |
| Asp | 25 | . | . | . | . | . | T | . | . | 1.70 | * | . | F | 2.65 | 0.78 |
| Gly | 26 | . | . | . | . | . | T | . | . | 1.36 | * | . | F | 2.77 | 1.44 |
| His | 27 | . | . | . | . | . | T | T | . | 0.90 | * | . | F | 2.79 | 0.99 |
| Arg | 28 | . | . | . | . | . | T | T | . | 1.27 | * | . | F | 3.10 | 0.32 |
| Gly | 29 | . | . | . | . | . | T | T | . | 1.58 | * | . | F | 2.49 | 0.43 |
| Gly | 30 | . | . | . | . | . | T | T | . | 1.54 | * | . | F | 2.48 | 0.55 |
| Cys | 31 | . | . | . | . | . | T | . | . | 1.30 | . | * | F | 1.97 | 0.38 |
| Ser | 32 | . | . | . | B | . | . | . | . | 1.33 | . | * | F | 0.96 | 0.39 |
| Glu | 33 | . | . | . | B | . | . | . | . | 0.56 | * | * | . | 0.50 | 0.63 |
| His | 34 | . | . | . | B | . | . | T | . | 0.09 | . | . | . | 0.70 | 0.63 |
| Ala | 35 | . | . | . | B | . | . | T | . | 0.13 | * | . | . | 0.10 | 0.39 |
| Asn | 36 | . | . | . | B | . | . | T | . | 0.49 | * | . | . | 0.10 | 0.30 |
| Cys | 37 | . | . | . | B | . | . | T | . | 0.44 | * | . | . | −0.20 | 0.32 |
| Leu | 38 | . | . | . | B | . | . | . | . | −0.37 | * | . | . | −0.40 | 0.31 |
| Ser | 39 | . | . | . | . | . | T | T | . | −0.33 | * | . | F | 0.69 | 0.16 |
| Thr | 40 | . | . | . | . | . | T | T | . | −0.06 | . | * | F | 1.03 | 0.48 |
| Gly | 41 | . | . | . | . | . | T | T | . | 0.06 | * | . | F | 1.37 | 0.84 |
| Leu | 42 | . | . | . | . | . | T | T | . | 0.83 | . | * | F | 2.76 | 1.23 |
| Asn | 43 | . | . | . | . | . | T | T | . | 0.98 | . | * | F | 3.40 | 1.67 |
| Thr | 44 | . | . | . | . | . | T | T | . | 1.28 | . | . | F | 2.61 | 0.90 |
| Arg | 45 | . | . | . | . | . | T | T | . | 0.92 | . | . | F | 2.72 | 1.89 |
| Arg | 46 | . | . | . | B | . | . | T | . | 1.23 | . | * | F | 1.83 | 0.63 |
| Cys | 47 | . | . | . | B | . | . | . | . | 1.46 | . | . | . | 1.14 | 0.60 |
| Glu | 48 | . | . | . | B | . | . | . | . | 1.11 | * | . | . | 0.80 | 0.31 |
| Cys | 49 | . | . | . | B | . | . | . | . | 1.18 | * | . | . | 0.50 | 0.16 |
| His | 50 | . | . | . | B | . | . | T | . | 0.21 | * | . | . | 0.10 | 0.45 |
| Ala | 51 | . | . | . | B | . | . | T | . | −0.24 | * | * | . | 0.10 | 0.19 |
| Gly | 52 | . | . | . | . | . | T | T | . | 0.42 | . | . | . | 0.20 | 0.36 |
| Tyr | 53 | . | . | . | . | . | T | T | . | 0.08 | * | . | . | 0.50 | 0.44 |
| Val | 54 | . | . | . | . | . | T | . | . | −0.07 | * | . | . | 0.30 | 0.43 |
| Gly | 55 | . | . | . | . | . | T | T | . | −0.03 | * | . | . | 0.50 | 0.36 |
| Asp | 56 | . | . | . | . | . | T | T | . | −0.11 | * | . | . | 0.50 | 0.40 |
| Gly | 57 | . | . | . | B | . | . | T | . | −0.58 | * | . | . | 0.10 | 0.29 |
| Leu | 58 | . | . | . | B | . | . | T | . | −0.33 | * | . | . | 0.10 | 0.24 |
| Gln | 59 | . | A | B | . | . | . | . | . | 0.52 | * | . | . | 0.30 | 0.25 |
| Cys | 60 | . | A | B | . | . | . | . | . | 0.57 | * | . | . | 0.60 | 0.43 |
| Leu | 61 | . | A | B | . | . | . | . | . | 0.57 | * | . | . | 0.90 | 0.71 |
| Glu | 62 | . | A | B | . | . | . | . | . | 0.70 | * | . | F | 1.65 | 0.71 |
| Glu | 63 | . | A | . | . | T | . | . | . | 1.30 | * | . | F | 2.50 | 2.03 |
| Ser | 64 | . | . | . | . | T | . | . | . | 0.44 | * | . | F | 3.00 | 3.82 |
| Glu | 65 | . | . | . | . | . | . | . | C | 1.11 | * | . | F | 2.50 | 1.64 |
| Pro | 66 | . | . | . | . | . | . | . | C | 2.03 | * | . | F | 2.20 | 1.58 |

TABLE II-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Pro | 67 | . | . | . | . | . | T | . | . | 1.37 | * | . | F | 2.10 | 2.30 |
| Val | 68 | . | . | . | . | . | T | . | . | 0.56 | * | . | F | 1.65 | 0.71 |
| Asp | 69 | . | . | . | B | . | . | . | . | 0.51 | * | . | F | 0.65 | 0.38 |
| Arg | 70 | . | . | . | B | . | . | . | . | 0.51 | * | . | F | 0.65 | 0.24 |
| Cys | 71 | . | . | . | B | . | . | . | . | 0.51 | * | . | . | 0.50 | 0.57 |
| Leu | 72 | . | . | . | . | . | . | T | . | 0.51 | * | . | F | 1.05 | 0.53 |
| Gly | 73 | . | . | . | . | . | . | T | . | 1.16 | * | . | F | 1.05 | 0.42 |
| Gln | 74 | . | . | . | . | . | . | . | C | 0.49 | * | . | F | 0.62 | 1.20 |
| Pro | 75 | . | . | . | . | . | . | T | C | 0.34 | * | * | F | 0.89 | 0.78 |
| Pro | 76 | . | . | . | . | . | . | T | C | 0.71 | . | . | F | 1.26 | 1.07 |
| Pro | 77 | . | . | . | . | . | T | T | . | 1.52 | . | . | F | 1.53 | 0.83 |
| Cys | 78 | . | . | . | . | . | T | T | . | 1.28 | . | . | . | 2.20 | 0.89 |
| His | 79 | . | . | . | . | . | T | T | . | 0.68 | . | . | . | 1.98 | 0.58 |
| Ser | 80 | . | . | . | B | . | . | T | . | 0.22 | . | . | . | 1.36 | 0.37 |
| Asp | 81 | A | . | . | . | . | . | T | . | 0.12 | . | . | . | 0.54 | 0.37 |
| Ala | 82 | A | . | . | . | . | . | T | . | 0.33 | . | . | . | 0.32 | 0.40 |
| Met | 83 | A | . | . | . | . | . | . | . | 0.19 | . | . | . | 0.50 | 0.49 |
| Cys | 84 | A | . | . | . | . | . | T | . | 0.19 | . | * | . | 0.70 | 0.24 |
| Thr | 85 | A | . | . | . | . | . | T | . | -0.21 | . | * | . | 0.10 | 0.33 |
| Asp | 86 | A | . | . | . | . | . | T | . | -0.21 | . | * | . | -0.20 | 0.29 |
| Leu | 87 | A | . | . | . | . | . | T | . | 0.38 | . | * | . | -0.20 | 0.93 |
| His | 88 | A | A | . | . | . | . | . | . | 1.02 | * | * | . | 0.45 | 1.12 |
| Phe | 89 | A | A | . | . | . | . | . | . | 1.80 | * | * | . | 0.75 | 1.34 |
| Gln | 90 | A | A | . | . | . | . | . | . | 1.52 | * | * | F | 0.90 | 3.17 |
| Glu | 91 | A | A | . | . | . | . | . | . | 1.18 | . | * | F | 0.90 | 2.36 |
| Lys | 92 | A | A | . | . | . | . | . | . | 1.13 | . | . | F | 0.90 | 2.69 |
| Arg | 93 | A | A | . | . | . | . | . | . | 0.47 | . | . | F | 0.90 | 1.15 |
| Ala | 94 | A | A | . | . | . | . | . | . | 1.13 | . | . | F | 0.75 | 0.58 |
| Gly | 95 | A | A | . | . | . | . | . | . | 0.32 | . | . | . | 0.30 | 0.39 |
| Val | 96 | A | A | . | . | . | . | . | . | 0.32 | . | * | . | -0.60 | 0.17 |
| Phe | 97 | . | A | B | . | . | . | . | . | -0.31 | * | * | . | -0.60 | 0.28 |
| His | 98 | . | A | B | . | . | . | . | . | -0.73 | * | * | . | -0.60 | 0.29 |
| Leu | 99 | . | A | B | . | . | . | . | . | -0.44 | . | * | . | -0.60 | 0.56 |
| Gln | 100 | . | A | B | . | . | . | . | . | -0.44 | . | * | . | -0.60 | 0.87 |
| Ala | 101 | . | A | . | . | . | T | . | C | 0.20 | . | * | F | 0.25 | 0.63 |
| Thr | 102 | . | A | . | . | . | T | . | . | 0.66 | . | * | F | 0.40 | 1.19 |
| Ser | 103 | . | A | . | . | . | . | . | C | 0.34 | . | * | F | 0.20 | 1.07 |
| Gly | 104 | . | . | . | . | . | . | T | C | 0.34 | . | * | F | 0.30 | 1.05 |
| Pro | 105 | . | . | . | . | . | T | T | . | 0.34 | . | * | F | 0.35 | 0.60 |
| Tyr | 106 | . | . | . | . | . | T | T | . | 0.23 | . | * | F | 0.35 | 0.72 |
| Gly | 107 | . | . | . | . | . | . | T | C | 0.24 | . | * | . | 0.00 | 0.63 |
| Leu | 108 | . | . | . | . | . | . | . | C | 0.54 | . | * | . | -0.20 | 0.55 |
| Asn | 109 | . | . | A | B | . | . | . | . | 0.30 | . | . | . | -0.60 | 0.60 |
| Phe | 110 | . | . | A | B | . | . | . | . | 0.51 | . | . | . | -0.30 | 0.62 |
| Ser | 111 | A | A | . | . | . | . | . | . | 0.17 | . | . | . | 0.45 | 1.30 |
| Glu | 112 | A | A | . | . | . | . | . | . | -0.08 | . | . | F | 0.45 | 0.81 |
| Ala | 113 | A | A | . | . | . | . | . | . | 0.07 | . | * | . | 0.30 | 0.95 |
| Glu | 114 | A | A | . | . | . | . | . | . | 0.07 | . | * | . | 0.60 | 0.38 |
| Ala | 115 | A | A | . | . | . | . | . | . | 0.18 | . | * | . | 0.60 | 0.38 |
| Ala | 116 | A | A | . | . | . | . | . | . | 0.48 | . | * | . | 0.30 | 0.38 |
| Cys | 117 | A | A | . | . | . | . | . | . | 0.13 | . | * | . | 0.60 | 0.38 |
| Glu | 118 | A | A | . | . | . | . | . | . | 0.13 | * | * | . | 0.30 | 0.37 |
| Ala | 119 | A | A | . | . | . | . | . | . | -0.72 | . | * | . | 0.30 | 0.37 |
| Gln | 120 | A | A | . | . | . | . | . | . | -0.94 | . | * | . | -0.30 | 0.52 |
| Gly | 121 | A | A | . | . | . | . | . | . | -0.94 | . | * | . | -0.30 | 0.25 |
| Ala | 122 | A | A | . | . | . | . | . | . | -0.58 | . | * | . | -0.60 | 0.25 |
| Val | 123 | A | A | . | . | . | . | . | . | -1.28 | . | * | . | -0.60 | 0.19 |
| Leu | 124 | . | A | B | . | . | . | . | . | -0.90 | . | * | . | -0.60 | 0.17 |
| Ala | 125 | . | A | B | . | . | . | . | . | -0.90 | . | . | . | -0.60 | 0.25 |
| Ser | 126 | . | A | B | . | . | . | . | . | -1.37 | * | . | . | -0.60 | 0.59 |
| Phe | 127 | . | . | B | . | . | . | . | . | -1.08 | . | . | . | -0.40 | 0.59 |
| Pro | 128 | A | . | . | . | . | . | . | . | -0.81 | * | . | . | -0.40 | 0.79 |
| Gln | 129 | A | A | . | . | . | . | . | . | -0.59 | . | . | . | -0.60 | 0.59 |
| Leu | 130 | A | A | . | . | . | . | . | . | 0.00 | . | . | . | -0.60 | 0.69 |
| Ser | 131 | A | A | . | . | . | . | . | . | 0.30 | . | . | . | -0.30 | 0.78 |
| Ala | 132 | A | A | . | . | . | . | . | . | 0.19 | . | . | . | -0.30 | 0.78 |
| Ala | 133 | A | A | . | . | . | . | . | . | 0.06 | . | * | . | -0.60 | 0.78 |
| Gln | 134 | A | A | . | . | . | . | . | . | -0.64 | . | * | . | -0.30 | 0.57 |
| Gln | 135 | A | A | . | . | . | . | . | . | 0.13 | * | * | . | -0.60 | 0.49 |
| Leu | 136 | A | A | . | . | . | . | . | . | -0.38 | * | * | . | -0.60 | 0.66 |
| Gly | 137 | . | A | B | . | . | . | . | . | -0.46 | . | * | . | -0.60 | 0.31 |
| Phe | 138 | . | A | B | . | . | . | . | . | -0.68 | . | * | . | -0.60 | 0.10 |
| His | 139 | . | A | B | . | . | . | . | . | -1.28 | . | * | . | -0.60 | 0.10 |
| Leu | 140 | . | A | B | . | . | . | . | . | -1.62 | . | * | . | -0.60 | 0.10 |
| Cys | 141 | . | A | B | . | . | . | . | . | -1.10 | . | * | . | -0.60 | 0.11 |
| Leu | 142 | . | A | B | . | . | . | . | . | -1.57 | . | * | . | -0.60 | 0.09 |
| Met | 143 | . | A | B | . | . | . | . | . | -1.46 | . | * | . | -0.60 | 0.09 |

TABLE II-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Gly | 144 | A | A | . | . | . | . | . | . | −1.42 | . | . | . | −0.60 | 0.16 |
| Trp | 145 | A | A | . | . | . | . | . | . | −0.96 | . | . | . | −0.60 | 0.32 |
| Leu | 146 | A | A | . | . | . | . | . | . | −0.59 | . | . | . | −0.60 | 0.32 |
| Ala | 147 | . | A | . | . | . | . | . | C | −0.09 | . | . | . | −0.40 | 0.43 |
| Asn | 148 | . | . | . | . | . | . | T | C | −0.08 | . | . | F | 0.15 | 0.59 |
| Gly | 149 | . | . | . | . | . | T | T | . | 0.23 | . | . | F | 0.65 | 0.72 |
| Ser | 150 | . | . | . | . | . | . | T | C | 0.31 | . | . | F | 0.45 | 0.97 |
| Thr | 151 | . | . | . | . | . | . | T | C | 0.27 | . | . | F | 0.45 | 0.93 |
| Ala | 152 | . | . | . | . | . | . | . | C | 0.00 | . | . | F | 0.25 | 0.70 |
| His | 153 | . | . | . | B | B | . | . | . | −0.70 | . | . | . | −0.60 | 0.39 |
| Pro | 154 | . | . | . | B | B | . | . | . | −0.57 | * | . | . | −0.60 | 0.23 |
| Val | 155 | . | . | . | B | B | . | . | . | −1.12 | . | . | . | −0.60 | 0.36 |
| Val | 156 | . | . | . | B | B | . | . | . | −1.40 | * | . | . | −0.60 | 0.19 |
| Phe | 157 | . | . | . | B | B | . | . | . | −0.81 | * | . | . | −0.60 | 0.13 |
| Pro | 158 | . | . | . | B | B | . | . | . | −1.44 | * | . | . | −0.60 | 0.29 |
| Val | 159 | . | . | . | B | B | . | . | . | −1.58 | * | . | . | −0.29 | 0.21 |
| Ala | 160 | . | . | . | B | B | . | . | . | −0.72 | * | . | . | 0.32 | 0.24 |
| Asp | 161 | . | . | . | . | B | T | . | . | −0.21 | . | * | . | 1.63 | 0.24 |
| Cys | 162 | . | . | . | . | . | T | T | . | 0.60 | * | * | . | 2.34 | 0.33 |
| Gly | 163 | . | . | . | . | . | T | T | . | −0.04 | . | * | F | 3.10 | 0.63 |
| Asn | 164 | . | . | . | . | . | T | T | . | 0.47 | . | * | F | 2.79 | 0.28 |
| Gly | 165 | . | . | . | . | . | T | T | . | 0.17 | . | * | F | 2.18 | 0.52 |
| Arg | 166 | . | . | . | B | B | . | . | . | −0.69 | . | * | F | 0.47 | 0.37 |
| Val | 167 | . | . | . | B | B | . | . | . | −0.32 | . | * | . | 0.01 | 0.17 |
| Gly | 168 | . | . | . | B | B | . | . | . | −0.79 | . | * | . | −0.30 | 0.23 |
| Ile | 169 | . | . | . | B | B | . | . | . | −1.13 | . | * | . | −0.60 | 0.10 |
| Val | 170 | . | . | . | B | B | . | . | . | −1.38 | . | * | . | −0.60 | 0.13 |
| Ser | 171 | . | . | . | B | . | . | . | . | −1.38 | . | * | . | −0.40 | 0.13 |
| Leu | 172 | . | . | . | B | . | . | . | . | −0.48 | * | * | . | −0.10 | 0.37 |
| Gly | 173 | . | . | . | B | . | . | . | . | −0.13 | . | * | . | 0.50 | 0.99 |
| Ala | 174 | . | A | . | . | . | . | . | . | −0.06 | * | * | F | 1.10 | 1.19 |
| Arg | 175 | . | . | . | . | . | . | . | C | 0.50 | * | * | F | 1.00 | 1.19 |
| Lys | 176 | . | . | . | . | . | . | . | C | 0.80 | . | * | F | 1.30 | 1.61 |
| Asn | 177 | . | . | . | . | . | . | . | C | 1.72 | . | * | F | 1.60 | 2.76 |
| Leu | 178 | . | . | . | . | . | . | . | C | 1.78 | . | * | F | 1.90 | 2.76 |
| Ser | 179 | . | . | . | B | . | . | . | . | 2.37 | * | * | F | 2.00 | 1.45 |
| Glu | 180 | A | . | . | . | . | . | . | . | 1.67 | . | * | F | 2.30 | 1.51 |
| Arg | 181 | . | . | . | . | . | T | . | . | 1.38 | * | * | F | 3.00 | 1.85 |
| Trp | 182 | A | . | . | . | . | . | . | . | 0.71 | * | * | . | 1.85 | 2.16 |
| Asp | 183 | A | . | . | . | . | . | T | . | 0.82 | * | * | . | 1.60 | 0.67 |
| Ala | 184 | A | . | . | . | . | . | T | . | 1.23 | * | * | . | 0.40 | 0.30 |
| Tyr | 185 | A | . | . | . | . | . | T | . | 0.38 | * | * | . | 0.10 | 0.55 |
| Cys | 186 | . | . | . | B | . | . | T | . | 0.27 | * | * | . | 0.10 | 0.24 |
| Phe | 187 | . | . | . | B | B | . | . | . | 0.56 | * | * | . | −0.60 | 0.42 |
| Arg | 188 | . | . | . | B | B | . | . | . | −0.30 | * | * | . | −0.30 | 0.45 |
| Val | 189 | . | . | . | B | B | . | . | . | −0.30 | * | * | . | −0.30 | 0.62 |
| Gln | 190 | . | . | . | B | B | . | . | . | −0.72 | * | * | . | 0.30 | 0.72 |
| Asp | 191 | . | . | . | B | B | . | . | . | 0.06 | * | * | . | 0.30 | 0.20 |
| Val | 192 | . | . | . | B | B | . | . | . | 0.09 | * | * | . | 0.30 | 0.52 |
| Ala | 193 | . | . | . | B | B | . | . | . | 0.09 | * | * | . | 0.55 | 0.16 |
| Cys | 194 | . | . | . | B | B | . | . | . | 0.94 | * | * | . | 1.10 | 0.19 |
| Arg | 195 | . | . | . | B | B | . | . | . | 0.60 | * | * | . | 1.05 | 0.41 |
| Cys | 196 | . | . | . | B | . | . | T | . | −0.10 | * | * | . | 2.00 | 0.40 |
| Arg | 197 | . | . | . | . | . | T | T | . | −0.10 | * | * | F | 2.50 | 0.65 |
| Asn | 198 | . | . | . | . | . | T | T | . | 0.14 | . | * | F | 2.25 | 0.25 |
| Gly | 199 | . | . | . | . | . | T | T | . | 0.81 | . | * | F | 1.40 | 0.45 |
| Phe | 200 | . | . | . | B | . | . | . | . | 0.36 | . | * | . | 1.00 | 0.39 |
| Val | 201 | . | . | . | B | . | . | T | . | 0.13 | . | * | . | 0.35 | 0.24 |
| Gly | 202 | . | . | . | . | . | T | T | . | −0.28 | . | . | F | 0.50 | 0.17 |
| Asp | 203 | . | . | . | B | . | . | T | . | −0.59 | * | . | F | 0.25 | 0.26 |
| Gly | 204 | . | . | . | B | . | . | T | . | −0.91 | * | . | F | 0.25 | 0.51 |
| Ile | 205 | . | . | . | B | B | . | . | . | −0.21 | * | . | F | 0.45 | 0.28 |
| Ser | 206 | . | . | . | B | B | . | . | . | 0.30 | * | * | F | 0.45 | 0.27 |
| Thr | 207 | . | . | . | B | B | . | . | . | 0.69 | * | * | F | 0.02 | 0.27 |
| Cys | 208 | . | . | . | B | . | . | T | . | −0.12 | * | * | F | 1.19 | 0.76 |
| Asn | 209 | . | . | . | . | . | T | T | . | −0.59 | * | . | F | 1.76 | 0.47 |
| Gly | 210 | . | . | . | . | . | T | T | . | 0.30 | * | . | F | 1.33 | 0.27 |
| Lys | 211 | . | . | . | B | . | . | T | . | −0.26 | * | . | F | 1.70 | 0.83 |
| Leu | 212 | . | A | . | B | . | . | . | . | −0.76 | * | * | F | 1.13 | 0.38 |
| Leu | 213 | . | A | . | B | . | . | . | . | −0.68 | * | . | . | 0.21 | 0.32 |
| Asp | 214 | . | A | . | B | . | . | . | . | −1.27 | * | . | . | 0.04 | 0.16 |
| Val | 215 | . | A | . | B | . | . | . | . | −1.23 | * | . | . | −0.43 | 0.20 |
| Leu | 216 | A | A | . | . | . | . | . | . | −1.87 | * | . | . | −0.60 | 0.35 |
| Ala | 217 | A | A | . | . | . | . | . | . | −1.06 | * | . | . | −0.30 | 0.21 |
| Ala | 218 | A | A | . | . | . | . | . | . | −0.94 | . | * | . | −0.60 | 0.45 |
| Thr | 219 | A | A | . | . | . | . | . | . | −1.24 | * | * | . | −0.60 | 0.47 |
| Ala | 220 | A | A | . | . | . | . | . | . | −0.70 | . | . | . | −0.60 | 0.63 |

TABLE II-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Asn | 221 | A | A | . | . | . | . | . | . | −0.59 | . | * | . | −0.60 | 0.90 |
| Phe | 222 | . | A | B | . | . | . | . | . | −0.24 | . | . | . | −0.60 | 0.54 |
| Ser | 223 | . | A | B | . | . | . | . | . | 0.00 | . | * | . | −0.60 | 0.84 |
| Thr | 224 | . | . | B | B | . | . | . | . | −0.29 | . | . | . | −0.60 | 0.52 |
| Phe | 225 | . | . | B | B | . | . | . | . | −0.51 | . | . | . | −0.60 | 0.59 |
| Tyr | 226 | . | . | B | B | . | . | . | . | −1.32 | . | . | . | −0.60 | 0.36 |
| Gly | 227 | . | . | B | B | . | . | . | . | −0.97 | . | . | . | −0.60 | 0.21 |
| Met | 228 | . | . | B | B | . | . | . | . | −0.91 | . | . | . | −0.60 | 0.24 |
| Leu | 229 | . | . | B | B | . | . | . | . | −1.19 | . | . | . | −0.60 | 0.24 |
| Leu | 230 | . | . | B | B | . | . | . | . | −0.49 | . | . | . | −0.60 | 0.24 |
| Gly | 231 | . | . | . | . | . | . | . | C | −0.83 | . | . | . | −0.20 | 0.39 |
| Tyr | 232 | . | A | B | . | . | . | . | . | −0.80 | . | . | . | −0.60 | 0.48 |
| Ala | 233 | A | A | . | . | . | . | . | . | −0.20 | * | * | . | −0.60 | 0.84 |
| Asn | 234 | . | A | B | . | . | . | . | . | 0.72 | . | * | . | −0.19 | 1.47 |
| Ala | 235 | . | A | B | . | . | . | . | . | 1.19 | * | * | F | 0.52 | 1.84 |
| Thr | 236 | . | . | B | . | . | T | . | . | 0.72 | * | * | F | 1.78 | 1.80 |
| Gln | 237 | . | . | B | . | . | T | . | . | 0.97 | * | * | F | 1.89 | 0.93 |
| Arg | 238 | . | . | B | . | . | T | . | . | 0.86 | * | * | F | 2.60 | 1.53 |
| Gly | 239 | . | . | B | . | . | T | . | . | 0.04 | * | . | F | 1.89 | 0.92 |
| Leu | 240 | . | A | B | . | . | . | . | . | 0.63 | * | . | . | 1.08 | 0.44 |
| Asp | 241 | . | A | B | . | . | . | . | . | 0.24 | * | . | . | 0.82 | 0.37 |
| Phe | 242 | . | A | B | . | . | . | . | . | −0.57 | * | . | . | −0.04 | 0.33 |
| Leu | 243 | . | A | B | . | . | . | . | . | −0.68 | * | . | . | −0.60 | 0.33 |
| Asp | 244 | . | A | B | . | . | . | . | . | −0.33 | * | . | . | 0.30 | 0.33 |
| Phe | 245 | A | A | . | . | . | . | . | . | 0.48 | * | . | . | 0.30 | 0.63 |
| Leu | 246 | A | A | . | . | . | . | . | . | −0.33 | * | . | . | 0.75 | 1.32 |
| Asp | 247 | A | A | . | . | . | . | . | . | 0.06 | * | . | F | 0.75 | 0.65 |
| Asp | 248 | A | A | . | . | . | . | . | . | 0.62 | . | * | F | 0.60 | 1.09 |
| Glu | 249 | A | . | . | B | . | . | . | . | 0.67 | . | * | F | 0.60 | 2.06 |
| Leu | 250 | A | . | . | B | . | . | . | . | 1.06 | . | * | . | 0.75 | 2.47 |
| Thr | 251 | A | . | . | B | . | . | . | . | 1.06 | . | * | . | 0.75 | 2.14 |
| Tyr | 252 | A | . | . | B | . | . | . | . | 0.36 | . | * | . | −0.15 | 1.02 |
| Lys | 253 | A | . | . | B | . | . | . | . | −0.50 | . | . | F | −0.30 | 1.07 |
| Thr | 254 | . | . | B | B | . | . | . | . | −0.71 | . | * | . | −0.60 | 0.55 |
| Leu | 255 | . | . | B | B | . | . | . | . | −0.76 | . | * | . | −0.60 | 0.54 |
| Phe | 256 | . | . | B | B | . | . | . | . | −0.44 | * | . | . | −0.60 | 0.20 |
| Val | 257 | . | . | B | B | . | . | . | . | −0.20 | * | . | . | −0.60 | 0.22 |
| Pro | 258 | . | . | B | . | . | . | . | . | −0.59 | * | . | . | −0.40 | 0.47 |
| Val | 259 | . | . | B | . | . | . | . | . | −0.98 | * | . | . | −0.10 | 0.54 |
| Asn | 260 | . | . | B | . | . | . | T | . | −1.02 | * | . | F | 0.25 | 0.63 |
| Glu | 261 | A | . | . | . | . | . | T | . | −0.32 | * | . | F | 0.25 | 0.30 |
| Gly | 262 | A | . | . | . | . | . | T | . | 0.53 | * | . | F | 0.85 | 0.68 |
| Phe | 263 | A | . | . | . | . | . | T | . | 0.14 | * | . | . | 0.70 | 0.68 |
| Val | 264 | A | . | . | . | . | . | . | . | 0.69 | * | . | . | 0.50 | 0.39 |
| Asp | 265 | . | . | B | . | . | . | . | . | −0.12 | . | . | . | −0.10 | 0.57 |
| Asn | 266 | . | . | B | . | . | . | . | . | −0.42 | . | . | . | −0.40 | 0.54 |
| Met | 267 | . | . | B | . | . | . | . | . | −0.42 | . | . | . | −0.10 | 0.97 |
| Thr | 268 | . | . | B | . | . | . | . | . | 0.07 | * | . | . | 0.50 | 0.58 |
| Leu | 269 | . | . | . | . | . | . | . | C | 0.92 | * | . | F | −0.05 | 0.55 |
| Ser | 270 | . | . | . | . | . | . | . | C | 0.11 | . | . | F | −0.05 | 0.90 |
| Gly | 271 | . | . | . | . | . | . | T | C | 0.11 | . | * | F | 0.15 | 0.51 |
| Pro | 272 | . | . | . | . | . | . | T | C | −0.10 | . | * | F | 0.60 | 1.08 |
| Asn | 273 | A | . | . | . | . | . | T | . | 0.18 | . | * | F | 0.25 | 0.66 |
| Leu | 274 | A | . | . | . | . | . | T | . | 0.40 | . | * | . | 0.10 | 0.91 |
| Glu | 275 | A | . | . | . | . | . | . | . | 0.40 | . | * | . | −0.10 | 0.60 |
| Leu | 276 | A | . | . | . | . | . | . | . | 0.74 | . | * | . | −0.10 | 0.50 |
| His | 277 | A | . | . | . | . | . | T | . | 0.37 | . | * | . | 0.10 | 0.97 |
| Ala | 278 | A | . | . | . | . | . | T | . | 0.06 | . | * | . | 0.70 | 0.57 |
| Ser | 279 | A | . | . | . | . | . | T | . | 0.06 | . | * | . | −0.20 | 0.99 |
| Asn | 280 | A | . | . | . | . | . | T | . | −0.76 | . | . | . | −0.20 | 0.60 |
| Ala | 281 | A | A | . | . | . | . | . | . | −0.24 | . | . | . | −0.60 | 0.49 |
| Thr | 282 | A | A | . | . | . | . | . | . | −0.80 | . | . | . | −0.60 | 0.49 |
| Leu | 283 | A | A | . | . | . | . | . | . | −0.21 | . | . | . | −0.60 | 0.31 |
| Leu | 284 | A | A | . | . | . | . | . | . | −0.50 | . | . | . | −0.60 | 0.49 |
| Ser | 285 | A | A | . | . | . | . | . | . | −0.80 | . | . | . | −0.60 | 0.34 |
| Ala | 286 | A | A | . | . | . | . | . | . | −0.21 | . | . | . | −0.60 | 0.56 |
| Asn | 287 | A | A | . | . | . | . | . | . | −0.24 | . | . | F | 0.00 | 1.17 |
| Ala | 288 | A | A | . | . | . | . | . | . | 0.61 | . | * | F | 0.45 | 0.86 |
| Ser | 289 | A | . | . | . | . | . | T | . | 0.61 | . | * | F | 1.00 | 1.71 |
| Gln | 290 | A | . | . | . | . | . | T | . | 0.10 | . | . | F | 0.85 | 0.88 |
| Gly | 291 | . | . | . | . | . | T | T | . | 0.48 | . | . | F | 0.65 | 0.72 |
| Lys | 292 | . | . | B | . | . | . | T | . | −0.11 | . | . | F | 0.25 | 0.83 |
| Leu | 293 | . | . | B | . | . | . | . | . | 0.44 | . | . | F | 0.05 | 0.48 |
| Leu | 294 | . | . | B | . | . | . | . | . | 0.44 | . | * | . | −0.10 | 0.66 |
| Pro | 295 | . | . | B | . | . | . | . | . | 0.10 | . | * | . | −0.10 | 0.44 |
| Ala | 296 | . | . | B | . | . | . | . | . | −0.37 | . | . | . | −0.40 | 0.53 |
| His | 297 | A | . | . | . | . | . | T | . | −0.71 | . | * | . | −0.20 | 0.53 |

TABLE II-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Ser | 298 | A | . | . | . | . | . | T | . | −0.71 | * | . | . | 0.10 | 0.46 |
| Gly | 299 | A | . | . | . | . | . | T | . | −0.79 | . | * | . | −0.20 | 0.38 |
| Leu | 300 | . | . | . | B | . | . | T | . | −1.47 | * | * | . | −0.20 | 0.19 |
| Ser | 301 | . | . | . | B | B | . | . | . | −1.18 | * | . | . | −0.60 | 0.10 |
| Leu | 302 | . | . | . | B | B | . | . | . | −1.14 | * | . | . | −0.60 | 0.14 |
| Ile | 303 | . | . | . | B | B | . | . | . | −1.43 | * | . | . | −0.60 | 0.28 |
| Ile | 304 | . | . | . | B | B | . | . | . | −1.43 | * | . | . | 0.00 | 0.21 |
| Ser | 305 | . | . | . | B | B | . | . | . | −0.83 | * | . | . | 0.30 | 0.25 |
| Asp | 306 | . | . | . | B | . | . | . | . | −0.53 | . | . | F | 0.95 | 0.56 |
| Ala | 307 | . | . | . | B | . | . | . | . | 0.28 | . | . | F | 2.30 | 1.32 |
| Gly | 308 | . | . | . | . | . | . | T | C | 0.87 | * | . | F | 3.00 | 1.59 |
| Pro | 309 | . | . | . | . | . | . | T | C | 1.46 | * | . | F | 2.70 | 1.28 |
| Asp | 310 | . | . | . | . | . | T | T | . | 1.47 | . | . | F | 2.30 | 1.69 |
| Asn | 311 | . | . | . | . | . | T | T | . | 0.88 | . | . | F | 2.00 | 1.80 |
| Ser | 312 | . | . | . | . | . | T | . | . | 1.26 | . | . | F | 0.90 | 1.17 |
| Ser | 313 | . | . | . | . | . | T | . | . | 0.74 | . | . | F | 0.60 | 1.09 |
| Trp | 314 | . | . | . | B | . | . | . | . | 0.37 | . | . | . | −0.40 | 0.50 |
| Ala | 315 | . | . | . | B | . | . | . | . | 0.16 | . | . | . | −0.40 | 0.38 |
| Pro | 316 | . | . | . | B | . | . | . | . | −0.19 | . | . | . | −0.40 | 0.44 |
| Val | 317 | . | . | . | B | . | . | . | . | −0.20 | . | . | . | −0.40 | 0.41 |
| Ala | 318 | . | . | . | B | . | . | T | . | −0.76 | . | . | . | −0.20 | 0.59 |
| Pro | 319 | . | . | . | B | . | . | T | . | −1.32 | . | . | F | −0.05 | 0.28 |
| Gly | 320 | . | . | . | B | . | . | T | . | −1.59 | . | . | F | −0.05 | 0.28 |
| Thr | 321 | . | . | . | B | . | . | T | . | −1.68 | * | . | F | −0.05 | 0.21 |
| Val | 322 | . | . | . | B | B | . | . | . | −0.71 | * | * | . | −0.60 | 0.18 |
| Val | 323 | . | . | . | B | B | . | . | . | −1.01 | * | . | . | −0.30 | 0.36 |
| Val | 324 | . | . | . | B | B | . | . | . | −1.69 | * | * | . | −0.60 | 0.17 |
| Ser | 325 | . | . | . | B | B | . | . | . | −2.20 | * | . | . | −0.60 | 0.16 |
| Arg | 326 | . | . | . | B | B | . | . | . | −2.18 | . | . | . | −0.60 | 0.16 |
| Ile | 327 | . | . | . | B | B | . | . | . | −1.32 | * | . | . | −0.60 | 0.23 |
| Ile | 328 | . | . | . | B | B | . | . | . | −1.36 | * | . | . | −0.30 | 0.29 |
| Val | 329 | . | . | . | B | B | . | . | . | −1.10 | * | . | . | −0.60 | 0.10 |
| Trp | 330 | . | . | . | B | B | . | . | . | −1.39 | * | . | . | −0.60 | 0.15 |
| Asp | 331 | . | . | . | B | B | . | . | . | −2.20 | * | . | . | −0.60 | 0.21 |
| Ile | 332 | . | . | . | B | B | . | . | . | −1.31 | . | . | . | −0.60 | 0.24 |
| Met | 333 | A | . | . | . | B | . | . | . | −0.77 | . | . | . | −0.60 | 0.37 |
| Ala | 334 | A | . | . | . | B | . | . | . | −0.80 | . | . | . | −0.60 | 0.22 |
| Phe | 335 | A | . | . | . | B | . | . | . | −1.40 | . | * | . | −0.60 | 0.22 |
| Asn | 336 | A | . | . | . | B | . | . | . | −1.43 | . | * | . | −0.60 | 0.16 |
| Gly | 337 | A | . | . | . | B | . | . | . | −1.13 | * | . | . | −0.60 | 0.21 |
| Ile | 338 | A | . | . | . | B | . | . | . | −1.34 | * | * | . | −0.60 | 0.25 |
| Ile | 339 | A | . | . | . | B | . | . | . | −1.34 | * | . | . | −0.60 | 0.13 |
| His | 340 | . | . | . | B | B | . | . | . | −0.94 | * | . | . | −0.60 | 0.13 |
| Ala | 341 | . | . | . | B | B | . | . | . | −1.16 | * | . | . | −0.60 | 0.25 |
| Leu | 342 | . | . | . | B | B | . | . | . | −1.62 | * | . | . | −0.60 | 0.54 |
| Ala | 343 | . | . | . | B | B | . | . | . | −1.54 | * | . | . | −0.60 | 0.33 |
| Ser | 344 | . | . | . | B | . | . | T | . | −1.24 | * | . | . | −0.20 | 0.27 |
| Pro | 345 | . | . | . | . | . | . | T | C | −1.42 | . | . | . | 0.00 | 0.33 |
| Leu | 346 | . | . | . | . | . | T | T | . | −1.04 | . | . | . | 0.20 | 0.50 |
| Leu | 347 | . | . | . | B | . | . | T | . | −0.23 | * | . | . | −0.20 | 0.58 |
| Ala | 348 | . | . | . | . | . | . | . | C | 0.14 | . | . | F | −0.05 | 0.65 |
| Pro | 349 | . | . | . | . | . | . | T | C | 0.44 | . | * | F | 0.30 | 1.22 |
| Pro | 350 | . | . | . | . | . | . | T | C | 0.07 | . | . | F | 0.60 | 2.57 |
| Gln | 351 | . | . | . | . | . | . | T | C | 0.02 | . | * | F | 0.60 | 2.57 |
| Pro | 352 | A | . | . | . | . | . | T | . | 0.02 | . | . | F | 0.40 | 1.23 |
| Gln | 353 | . | . | A | B | . | . | . | . | 0.02 | . | * | F | −0.45 | 0.66 |
| Ala | 354 | . | . | A | B | . | . | . | . | −0.16 | . | . | . | −0.60 | 0.38 |
| Val | 355 | . | . | A | B | . | . | . | . | 0.06 | . | * | . | −0.60 | 0.32 |
| Leu | 356 | . | . | A | B | . | . | . | . | −0.53 | . | * | . | −0.30 | 0.32 |
| Ala | 357 | . | . | A | B | . | . | . | . | −0.53 | . | . | . | −0.30 | 0.32 |
| Xxx | 358 | . | . | A | B | . | . | . | . | −0.74 | . | . | . | −0.30 | 0.66 |
| Glu | 359 | A | . | A | B | . | . | . | . | −1.01 | . | . | F | 0.60 | 1.24 |
| Ala | 360 | . | . | A | B | . | . | . | . | −0.74 | . | . | F | 0.45 | 0.91 |
| Pro | 361 | A | . | A | . | . | . | . | . | −0.52 | . | . | F | 0.45 | 0.72 |
| Pro | 362 | A | . | A | . | . | . | . | . | −0.28 | . | . | F | 0.65 | 0.42 |
| Val | 363 | A | . | . | . | B | . | . | . | −0.74 | . | . | . | −0.60 | 0.41 |
| Ala | 364 | A | . | . | . | B | . | . | . | −1.09 | . | . | . | −0.60 | 0.20 |
| Ala | 365 | A | . | . | . | B | . | . | . | −1.09 | . | . | . | −0.60 | 0.13 |
| Gly | 366 | A | . | . | . | B | . | . | . | −1.73 | . | . | . | −0.60 | 0.17 |
| Val | 367 | A | . | . | . | B | . | . | . | −2.33 | . | . | . | −0.60 | 0.13 |
| Gly | 368 | . | A | . | B | . | . | . | . | −2.07 | . | . | . | −0.60 | 0.10 |
| Ala | 369 | . | A | . | B | . | . | . | . | −2.07 | . | . | . | −0.60 | 0.11 |
| Val | 370 | . | A | . | B | . | . | . | . | −1.82 | . | . | . | −0.60 | 0.14 |
| Leu | 371 | A | A | . | . | . | . | . | . | −2.07 | . | . | . | −0.60 | 0.14 |
| Ala | 372 | A | A | . | . | . | . | . | . | −2.02 | . | . | . | −0.60 | 0.14 |
| Ala | 373 | A | A | . | . | . | . | . | . | −2.49 | . | . | . | −0.60 | 0.16 |
| Gly | 374 | A | A | . | . | . | . | . | . | −2.24 | . | . | . | −0.60 | 0.16 |

TABLE II-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Ala | 375 | A | A | . | . | . | . | . | . | −2.20 | . | . | . | −0.60 | 0.16 |
| Leu | 376 | A | A | . | . | . | . | . | . | −2.24 | . | . | . | −0.60 | 0.13 |
| Leu | 377 | A | A | . | . | . | . | . | . | −2.24 | . | . | . | −0.60 | 0.10 |
| Gly | 378 | . | A | B | . | . | . | . | . | −2.00 | . | . | . | −0.60 | 0.10 |
| Leu | 379 | . | A | B | . | . | . | . | . | −2.24 | . | . | . | −0.60 | 0.11 |
| Val | 380 | A | A | . | . | . | . | . | . | −2.47 | . | . | . | −0.60 | 0.14 |
| Ala | 381 | A | A | . | . | . | . | . | . | −1.90 | . | . | . | −0.60 | 0.12 |
| Gly | 382 | A | A | . | . | . | . | . | . | −1.90 | . | * | . | −0.60 | 0.22 |
| Ala | 383 | A | A | . | . | . | . | . | . | −1.44 | . | * | . | −0.60 | 0.25 |
| Leu | 384 | A | A | . | . | . | . | . | . | −1.22 | . | * | . | −0.60 | 0.48 |
| Tyr | 385 | . | A | B | . | . | . | . | . | −0.26 | . | * | . | −0.26 | 0.49 |
| Leu | 386 | . | A | B | . | . | . | . | . | −0.01 | . | * | . | 0.38 | 0.95 |
| Arg | 387 | . | . | B | . | . | T | . | . | 0.38 | . | * | . | 1.27 | 1.14 |
| Ala | 388 | . | . | B | . | . | T | . | . | 0.76 | . | * | F | 2.66 | 1.45 |
| Arg | 389 | . | . | . | . | T | T | . | . | 0.97 | . | * | F | 3.40 | 2.72 |
| Gly | 390 | . | . | . | . | T | T | . | . | 0.87 | . | * | F | 3.06 | 1.37 |
| Lys | 391 | . | . | . | . | . | . | . | C | 0.98 | . | * | F | 2.32 | 1.35 |
| Pro | 392 | . | . | B | . | . | T | . | . | 0.52 | . | * | F | 1.53 | 0.59 |
| Met | 393 | . | . | . | . | T | T | . | . | 0.41 | . | * | . | 0.84 | 0.59 |
| Gly | 394 | . | . | B | . | . | T | . | . | 0.00 | . | * | . | −0.20 | 0.26 |
| Phe | 395 | . | . | B | . | . | T | . | . | −0.24 | * | . | . | −0.20 | 0.22 |
| Gly | 396 | . | . | B | . | . | . | . | . | −0.99 | * | . | . | −0.40 | 0.23 |
| Phe | 397 | . | A | B | . | . | . | . | . | −0.78 | . | . | . | −0.60 | 0.20 |
| Ser | 398 | A | A | . | . | . | . | . | . | −0.77 | . | * | . | −0.60 | 0.40 |
| Ala | 399 | A | A | . | . | . | . | . | . | −0.42 | . | . | . | −0.60 | 0.41 |
| Phe | 400 | A | A | . | . | . | . | . | . | 0.28 | . | * | . | −0.30 | 0.81 |
| Gln | 401 | A | A | . | . | . | . | . | . | 0.62 | . | * | . | 0.45 | 1.01 |
| Ala | 402 | A | A | . | . | . | . | . | . | 0.73 | . | * | . | 0.75 | 1.68 |
| Glu | 403 | A | A | . | . | . | . | . | . | 1.03 | * | * | F | 0.90 | 1.96 |
| Asp | 404 | A | A | . | . | . | . | . | . | 1.62 | . | * | F | 1.21 | 1.89 |
| Asp | 405 | A | . | . | . | . | . | T | . | 1.93 | * | * | F | 1.92 | 3.12 |
| Ala | 406 | A | . | . | . | . | . | T | . | 1.23 | * | * | F | 2.23 | 2.30 |
| Asp | 407 | A | . | . | . | . | . | T | . | 1.52 | * | * | F | 2.54 | 1.19 |
| Asp | 408 | . | . | . | . | . | T | T | . | 1.31 | * | . | F | 3.10 | 0.96 |
| Xxx | 409 | . | . | . | . | . | T | . | . | 1.02 | * | . | F | 2.44 | 1.47 |
| Phe | 410 | . | . | . | . | . | . | . | C | 1.02 | * | . | F | 1.78 | 0.92 |
| Ser | 411 | . | . | . | . | . | . | T | C | 1.61 | * | . | F | 1.07 | 0.96 |
| Pro | 412 | . | . | . | . | . | . | T | C | 1.27 | * | . | F | 0.91 | 1.30 |
| Trp | 413 | . | . | . | . | . | T | T | . | 0.96 | * | . | F | 0.80 | 1.48 |
| Gln | 414 | . | . | . | . | . | . | T | C | 1.34 | * | . | F | 0.81 | 1.60 |
| Glu | 415 | . | . | . | . | . | T | . | . | 1.83 | * | . | F | 1.02 | 1.66 |
| Gly | 416 | . | . | . | . | . | T | . | . | 1.82 | * | . | F | 1.23 | 2.44 |
| Thr | 417 | . | . | . | . | . | . | . | C | 1.22 | . | . | F | 1.84 | 2.03 |
| Asn | 418 | . | . | . | . | . | . | T | C | 0.66 | . | . | F | 2.10 | 0.97 |
| Pro | 419 | . | . | . | . | . | . | T | C | 0.27 | . | . | F | 0.99 | 0.73 |
| Thr | 420 | . | . | B | . | . | . | T | . | −0.59 | . | . | F | 0.58 | 0.64 |
| Leu | 421 | . | . | B | . | . | . | T | . | −0.46 | . | . | . | 0.22 | 0.30 |
| Val | 422 | . | . | B | . | . | . | . | . | −0.14 | . | . | . | −0.19 | 0.30 |
| Xxx | 423 | . | . | B | . | . | . | . | . | −0.36 | * | . | . | −0.40 | 0.33 |
| Val | 424 | . | . | B | . | . | . | T | . | −1.00 | * | . | F | −0.05 | 0.62 |
| Pro | 425 | . | . | B | . | . | . | T | . | −1.39 | * | . | F | −0.05 | 0.62 |
| Asn | 426 | . | . | B | . | . | . | T | . | −0.92 | * | . | F | −0.05 | 0.42 |
| Pro | 427 | . | . | B | . | . | . | T | . | −0.37 | . | . | F | −0.05 | 0.56 |
| Val | 428 | . | . | B | . | . | . | . | . | 0.02 | . | . | F | −0.25 | 0.49 |
| Phe | 429 | . | . | B | . | . | . | . | . | 0.57 | . | . | F | 0.05 | 0.50 |
| Gly | 430 | . | . | . | . | . | T | T | . | 0.08 | . | . | F | 0.65 | 0.47 |
| Ser | 431 | . | . | . | . | . | T | T | . | −0.59 | . | . | F | 0.35 | 0.55 |
| Asp | 432 | . | . | B | . | . | . | T | . | −0.38 | . | . | F | −0.05 | 0.34 |
| Thr | 433 | . | . | . | . | . | T | T | . | 0.27 | * | . | F | 1.25 | 0.60 |
| Phe | 434 | . | . | B | . | . | . | . | . | 0.27 | * | . | . | 0.80 | 0.69 |
| Cys | 435 | . | . | B | . | . | . | . | . | 0.61 | * | . | . | 0.50 | 0.36 |
| Glu | 436 | . | . | B | . | . | . | . | . | 0.91 | * | . | . | 0.80 | 0.41 |
| Pro | 437 | . | . | . | . | . | T | . | . | 0.61 | * | . | F | 2.25 | 0.79 |
| Phe | 438 | . | . | . | . | . | T | . | . | 0.11 | * | . | F | 3.00 | 1.99 |
| Asp | 439 | A | . | . | . | . | . | T | . | 0.00 | * | . | F | 2.35 | 0.95 |
| Asp | 440 | A | . | . | . | . | . | T | . | 0.67 | * | . | F | 1.75 | 0.50 |
| Ser | 441 | A | . | . | . | . | . | T | . | 0.67 | * | . | F | 1.60 | 1.01 |
| Leu | 442 | A | . | . | . | . | . | T | . | 0.88 | . | * | F | 1.60 | 1.05 |
| Leu | 443 | A | A | . | . | . | . | . | . | 0.88 | . | * | F | 0.90 | 1.05 |
| Glu | 444 | A | A | . | . | . | . | . | . | 0.67 | . | . | F | 0.45 | 0.68 |
| Glu | 445 | A | A | . | . | . | . | . | . | 0.67 | . | . | F | 0.60 | 1.27 |
| Asp | 446 | A | A | . | . | . | . | . | . | 0.66 | * | . | F | 0.90 | 2.57 |
| Phe | 447 | A | . | . | . | . | . | T | . | 1.47 | * | * | F | 1.30 | 2.14 |
| Pro | 448 | A | . | . | . | . | . | T | . | 2.39 | * | * | F | 1.30 | 2.14 |
| Asp | 449 | A | . | . | . | . | . | T | . | 1.50 | * | * | F | 1.30 | 2.51 |
| Thr | 450 | A | . | . | . | . | . | T | . | 0.69 | * | . | F | 1.00 | 2.03 |
| Gln | 451 | A | . | . | B | . | . | . | . | 0.38 | * | * | F | 0.60 | 1.08 |

TABLE II-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Arg | 452 | A | . | . | . | B | . | . | . | 0.22 | * | . | F | 0.45 | 0.94 |
| Ile | 453 | . | . | . | B | B | . | . | . | 0.48 | . | . | . | −0.30 | 0.48 |
| Leu | 454 | . | . | . | B | B | . | . | . | 0.09 | . | . | . | 0.30 | 0.56 |
| Thr | 455 | . | . | . | B | B | . | . | . | 0.01 | . | . | . | 0.30 | 0.36 |
| Val | 456 | . | . | . | B | B | . | . | . | −0.38 | . | . | . | −0.30 | 0.66 |
| Lys | 457 | . | . | . | B | B | . | . | . | −0.88 | . | . | . | −0.15 | 1.03 |

TABLE III

| Res Pos. | | I | II | III | IV | V | VI | VII | VIII | IX | X | XI | XII | XIII | XIV |
|---|---|---|---|---|---|---|---|---|---|---|---|---|---|---|---|
| Met | 1 | . | A | A | . | . | . | . | . | −1.43 | . | . | . | −0.60 | 0.25 |
| Gly | 2 | . | A | A | . | . | . | . | . | −1.86 | . | . | . | −0.60 | 0.16 |
| Leu | 3 | . | . | A | B | . | . | . | . | −2.32 | . | . | . | −0.60 | 0.10 |
| Leu | 4 | . | . | A | B | . | . | . | . | −2.14 | . | . | . | −0.60 | 0.08 |
| Leu | 5 | . | . | A | B | . | . | . | . | −2.57 | . | . | . | −0.60 | 0.12 |
| Leu | 6 | . | . | A | B | . | . | . | . | −2.78 | . | . | . | −0.60 | 0.12 |
| Val | 7 | . | . | A | B | . | . | . | . | −3.24 | . | . | . | −0.60 | 0.12 |
| Pro | 8 | . | . | A | B | . | . | . | . | −3.24 | . | . | . | −0.60 | 0.12 |
| Leu | 9 | . | . | A | B | . | . | . | . | −2.64 | . | . | . | −0.60 | 0.12 |
| Leu | 10 | . | . | A | B | . | . | . | . | −2.18 | . | . | . | −0.60 | 0.25 |
| Leu | 11 | . | . | A | B | . | . | . | . | −1.67 | . | . | . | −0.60 | 0.16 |
| Leu | 12 | . | . | . | B | . | . | T | . | −1.06 | . | . | . | −0.20 | 0.26 |
| Pro | 13 | . | . | . | B | . | . | T | . | −1.19 | . | . | F | −0.05 | 0.50 |
| Gly | 14 | . | . | . | . | . | T | T | . | −1.19 | . | . | F | 0.35 | 0.60 |
| Ser | 15 | . | . | . | . | . | T | T | . | −0.59 | . | . | F | 0.35 | 0.60 |
| Tyr | 16 | . | . | . | B | . | . | . | . | −0.48 | . | . | . | −0.40 | 0.60 |
| Gly | 17 | . | . | . | B | . | . | . | . | 0.09 | . | . | . | −0.40 | 0.53 |
| Leu | 18 | . | . | . | B | B | . | . | . | 0.06 | . | . | . | −0.60 | 0.62 |
| Pro | 19 | . | . | . | B | B | . | . | . | 0.06 | . | . | . | −0.60 | 0.62 |
| Phe | 20 | . | . | . | B | B | . | . | . | −0.34 | . | . | . | −0.60 | 0.62 |
| Tyr | 21 | . | . | . | B | B | . | . | . | −0.34 | . | . | . | −0.60 | 0.65 |
| Tyr | 22 | . | . | . | B | B | . | . | . | −0.24 | . | . | . | −0.60 | 0.65 |
| Gly | 23 | . | . | . | B | B | . | . | . | 0.27 | . | . | . | −0.45 | 1.18 |
| Phe | 24 | . | . | . | B | B | . | . | . | 0.48 | . | . | . | −0.45 | 1.01 |
| Tyr | 25 | . | . | . | B | B | . | . | . | 0.88 | . | . | . | −0.45 | 1.04 |
| Tyr | 26 | . | . | . | . | . | T | T | . | 0.53 | . | . | . | 0.65 | 1.41 |
| Ser | 27 | . | . | . | . | . | . | T | C | 0.78 | . | . | F | 0.90 | 1.64 |
| Asn | 28 | . | . | . | . | . | T | T | . | 1.12 | . | . | F | 1.40 | 1.69 |
| Ser | 29 | . | . | . | . | . | . | T | C | 1.82 | . | . | F | 2.40 | 1.80 |
| Ala | 30 | . | . | . | . | . | T | . | C | 2.07 | . | . | F | 3.00 | 2.32 |
| Asn | 31 | . | . | . | . | . | . | . | C | 1.50 | . | . | F | 2.50 | 2.32 |
| Asp | 32 | . | . | . | . | . | T | T | . | 1.46 | . | . | F | 2.30 | 1.43 |
| Gln | 33 | . | . | . | B | . | . | T | . | 1.46 | . | . | F | 1.60 | 1.40 |
| Asn | 34 | . | . | . | B | . | . | T | . | 1.41 | . | . | F | 1.30 | 1.40 |
| Leu | 35 | . | . | . | B | . | . | T | . | 1.97 | . | . | F | 1.15 | 0.83 |
| Gly | 36 | . | . | . | . | . | T | . | . | 1.62 | * | . | F | 1.05 | 0.65 |
| Asn | 37 | . | . | . | . | . | T | T | . | 1.67 | . | . | F | 1.55 | 0.40 |
| Gly | 38 | . | . | . | . | . | . | T | C | 1.67 | . | . | F | 2.25 | 0.97 |
| His | 39 | . | . | . | . | . | . | T | C | 0.86 | . | . | F | 3.00 | 1.64 |
| Gly | 40 | . | . | . | . | . | . | T | C | 1.28 | . | . | F | 2.55 | 0.84 |
| Lys | 41 | . | . | . | B | . | . | . | . | 1.62 | * | . | F | 2.00 | 1.09 |
| Asp | 42 | . | . | . | B | . | . | . | . | 1.28 | * | . | F | 1.70 | 1.28 |
| Leu | 43 | . | . | . | B | . | . | T | . | 0.77 | * | . | F | 1.60 | 1.28 |
| Xxx | 44 | . | . | . | B | . | . | T | . | 0.84 | * | * | F | 0.85 | 0.48 |
| Asn | 45 | . | A | . | B | . | . | T | . | 0.38 | * | . | F | 0.85 | 0.57 |
| Gly | 46 | . | A | . | . | . | . | T | . | −0.52 | * | . | F | 0.25 | 0.57 |
| Val | 47 | . | . | . | B | B | . | . | . | −1.38 | * | * | F | −0.15 | 0.33 |
| Lys | 48 | . | . | . | B | B | . | . | . | −0.57 | * | * | F | −0.45 | 0.15 |
| Leu | 49 | . | . | . | B | B | . | . | . | −0.49 | * | . | . | −0.30 | 0.27 |
| Val | 50 | . | . | . | B | B | . | . | . | −0.70 | * | . | . | −0.30 | 0.52 |
| Val | 51 | . | . | . | B | B | . | . | . | −0.36 | * | * | . | 0.30 | 0.40 |
| Glu | 52 | . | . | . | B | B | . | . | . | 0.50 | * | * | F | 0.45 | 0.85 |
| Thr | 53 | . | A | . | . | . | . | . | . | 0.14 | * | . | F | 1.10 | 1.97 |
| Pro | 54 | . | A | . | . | . | . | . | . | 0.14 | . | . | F | 1.10 | 3.83 |
| Glu | 55 | . | A | . | . | . | . | . | . | 0.30 | * | . | F | 1.10 | 1.83 |
| Glu | 56 | . | A | . | . | B | . | . | . | 0.84 | * | . | F | 0.60 | 1.10 |
| Thr | 57 | . | A | . | . | B | . | . | . | 0.60 | . | . | F | 0.60 | 1.02 |
| Leu | 58 | . | A | . | . | B | . | . | . | 0.91 | . | . | . | −0.30 | 0.93 |
| Phe | 59 | . | A | . | . | B | . | . | . | 0.78 | . | . | . | −0.60 | 0.93 |
| Thr | 60 | . | A | . | . | B | . | . | . | 0.19 | . | . | . | −0.60 | 0.63 |
| Tyr | 61 | . | A | . | . | . | . | T | . | −0.11 | . | . | . | −0.20 | 0.78 |
| Gln | 62 | . | . | . | . | . | T | T | . | −0.66 | . | . | . | 0.35 | 1.20 |
| Gly | 63 | . | . | . | . | . | T | T | . | −0.73 | . | . | F | 0.35 | 0.62 |

TABLE III-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Ala | 64 | . | . | . | . | . | T | T | . | −0.84 | . | . | . | 0.20 | 0.28 |
| Ser | 65 | . | . | . | B | B | . | . | . | −0.74 | . | . | . | −0.60 | 0.13 |
| Val | 66 | . | . | . | B | B | . | . | . | −1.17 | . | * | . | −0.60 | 0.21 |
| Ile | 67 | . | . | . | B | B | . | . | . | −1.06 | . | * | . | −0.60 | 0.11 |
| Leu | 68 | . | . | . | B | . | . | T | . | −0.96 | . | * | . | 0.10 | 0.16 |
| Pro | 69 | . | . | . | B | . | . | T | . | −0.26 | . | * | . | −0.20 | 0.34 |
| Cys | 70 | . | . | . | B | . | . | T | . | −0.20 | . | * | . | 0.10 | 0.94 |
| Arg | 71 | . | . | . | B | . | . | T | . | 0.66 | . | * | . | 0.25 | 1.79 |
| Tyr | 72 | . | . | . | B | . | . | . | . | 1.33 | . | * | . | 0.65 | 2.00 |
| Arg | 73 | . | . | . | . | . | T | . | . | 1.56 | . | * | . | 1.05 | 5.78 |
| Tyr | 74 | . | . | A | B | . | . | . | . | 0.96 | . | * | . | 0.75 | 2.98 |
| Glu | 75 | . | . | A | B | . | . | . | . | 0.77 | . | * | . | −0.15 | 1.57 |
| Pro | 76 | . | . | A | B | . | . | . | . | 0.36 | . | * | . | −0.10 | 0.59 |
| Ala | 77 | . | . | A | B | . | . | . | . | 0.39 | . | * | . | 0.10 | 0.51 |
| Leu | 78 | . | . | A | B | . | . | . | . | 0.39 | * | . | . | 0.30 | 0.45 |
| Val | 79 | . | . | A | B | . | . | . | . | 0.74 | * | . | . | 0.50 | 0.58 |
| Ser | 80 | . | . | . | B | . | . | T | . | −0.11 | * | . | F | 2.00 | 1.12 |
| Pro | 81 | . | . | . | B | . | . | T | . | 0.21 | . | * | F | 1.80 | 1.00 |
| Arg | 82 | . | . | . | B | . | . | T | . | −0.06 | . | * | F | 1.90 | 2.65 |
| Arg | 83 | . | . | . | B | . | . | T | . | 0.80 | . | * | F | 1.70 | 1.47 |
| Val | 84 | . | . | . | B | B | . | . | . | 1.37 | . | * | . | 0.95 | 1.90 |
| Arg | 85 | . | . | . | B | B | . | . | . | 1.38 | * | * | . | 0.75 | 1.02 |
| Val | 86 | . | . | . | B | B | . | . | . | 1.63 | * | * | . | −0.30 | 0.55 |
| Lys | 87 | . | . | . | B | B | . | . | . | 0.71 | * | * | . | −0.15 | 1.47 |
| Trp | 88 | . | . | . | B | B | . | . | . | 0.30 | * | * | . | −0.30 | 0.62 |
| Trp | 89 | . | . | . | B | B | . | . | . | 1.16 | . | * | . | −0.45 | 1.12 |
| Lys | 90 | . | . | . | B | B | . | . | . | 1.04 | . | * | . | 0.30 | 0.97 |
| Leu | 91 | . | . | . | . | . | . | . | C | 1.56 | * | . | F | 0.70 | 1.48 |
| Ser | 92 | . | . | . | . | . | . | T | C | 0.92 | * | . | F | 1.80 | 1.40 |
| Glu | 93 | . | . | . | . | . | . | T | C | 1.00 | * | . | F | 2.25 | 0.71 |
| Asn | 94 | . | . | . | . | . | . | T | C | 1.29 | . | * | F | 2.40 | 1.32 |
| Gly | 95 | . | . | . | . | . | . | T | C | 1.29 | . | . | F | 3.00 | 1.71 |
| Ala | 96 | . | . | . | . | . | . | . | C | 2.10 | . | . | F | 2.50 | 1.97 |
| Pro | 97 | A | . | . | . | . | . | . | . | 1.54 | . | . | F | 2.00 | 2.05 |
| Glu | 98 | A | . | . | . | . | . | . | . | 0.73 | . | . | F | 1.70 | 1.54 |
| Lys | 99 | A | . | . | . | B | . | . | . | −0.12 | . | . | F | 1.20 | 1.25 |
| Asp | 100 | A | . | . | . | B | . | . | . | −0.37 | . | . | F | 0.75 | 0.60 |
| Val | 101 | A | . | . | . | B | . | . | . | −0.67 | . | . | . | 0.60 | 0.35 |
| Leu | 102 | A | . | . | . | B | . | . | . | −0.80 | . | * | . | −0.30 | 0.12 |
| Val | 103 | A | . | . | . | B | . | . | . | −1.61 | . | * | . | −0.60 | 0.07 |
| Ala | 104 | A | . | . | . | B | . | . | . | −1.54 | . | * | . | −0.60 | 0.08 |
| Ile | 105 | A | . | . | . | B | . | . | . | −1.58 | . | * | . | −0.60 | 0.19 |
| Gly | 106 | A | . | . | . | . | . | . | . | −0.61 | . | * | . | −0.40 | 0.35 |
| Leu | 107 | . | . | . | B | . | . | . | . | −0.10 | . | * | . | 0.50 | 0.68 |
| Arg | 108 | . | . | . | B | . | . | . | . | 0.06 | . | * | . | 0.93 | 1.31 |
| His | 109 | . | . | . | B | . | . | . | . | 0.30 | * | * | . | 1.21 | 1.15 |
| Arg | 110 | . | . | . | B | . | . | T | . | 1.19 | * | * | . | 1.69 | 1.37 |
| Ser | 111 | . | . | . | . | . | T | T | . | 1.29 | . | * | F | 2.82 | 1.17 |
| Phe | 112 | . | . | . | . | . | T | T | . | 2.10 | . | * | F | 2.80 | 1.35 |
| Gly | 113 | . | . | . | . | . | T | T | . | 1.64 | * | * | F | 2.52 | 1.19 |
| Asp | 114 | . | . | . | . | . | T | . | . | 1.79 | * | * | F | 1.29 | 0.88 |
| Tyr | 115 | . | . | . | . | . | T | T | . | 0.82 | * | * | F | 1.96 | 1.99 |
| Gln | 116 | . | . | . | . | . | T | T | . | 1.09 | * | * | F | 1.68 | 1.49 |
| Gly | 117 | . | . | . | B | . | . | T | . | 0.98 | * | * | F | 1.00 | 1.22 |
| Arg | 118 | . | . | . | B | . | . | T | . | 1.43 | * | * | F | −0.05 | 0.64 |
| Val | 119 | . | . | . | B | B | . | . | . | 1.43 | * | * | . | 0.30 | 0.72 |
| His | 120 | . | . | . | B | B | . | . | . | 1.68 | * | * | . | 0.45 | 1.27 |
| Leu | 121 | A | . | . | . | B | . | . | . | 1.72 | * | * | . | 0.75 | 1.08 |
| Arg | 122 | A | . | . | . | . | . | T | . | 2.07 | * | * | F | 1.30 | 2.91 |
| Gln | 123 | A | . | . | . | . | . | T | . | 1.92 | * | * | F | 1.30 | 3.71 |
| Asp | 124 | A | . | . | . | . | . | T | . | 2.78 | . | * | F | 1.30 | 6.12 |
| Lys | 125 | A | . | . | . | . | . | T | . | 1.96 | . | * | F | 1.30 | 5.22 |
| Glu | 126 | A | . | . | . | . | . | . | . | 2.47 | . | * | . | 1.10 | 2.24 |
| His | 127 | A | . | . | . | . | . | . | . | 1.97 | . | . | F | 1.10 | 1.79 |
| Asp | 128 | A | . | . | . | . | . | T | . | 1.97 | * | * | . | 1.15 | 1.15 |
| Val | 129 | A | . | . | . | . | . | T | . | 1.08 | * | * | . | 1.15 | 1.15 |
| Ser | 130 | A | . | . | . | . | . | T | . | 1.03 | . | * | F | 0.85 | 0.59 |
| Xxx | 131 | A | . | . | . | . | . | T | . | 0.64 | * | * | F | 0.85 | 0.61 |
| Glu | 132 | A | A | . | . | . | . | . | . | −0.13 | * | * | F | 0.60 | 1.06 |
| Ile | 133 | A | A | . | . | . | . | . | . | −0.02 | . | * | F | −0.15 | 0.65 |
| Gln | 134 | A | A | . | . | . | . | . | . | 0.02 | . | * | F | 0.45 | 1.00 |
| Xxx | 135 | A | A | . | . | . | . | . | . | 0.32 | . | . | . | 0.30 | 0.47 |
| Leu | 136 | . | A | . | B | . | . | . | . | 0.71 | . | . | . | 0.79 | 1.17 |
| Arg | 137 | . | A | . | B | . | . | . | . | 0.47 | . | . | . | 1.43 | 1.13 |
| Leu | 138 | . | A | . | B | . | . | . | . | 1.01 | . | * | . | 1.47 | 1.38 |
| Glu | 139 | . | A | . | . | . | T | . | . | 1.12 | * | * | F | 2.36 | 1.66 |
| Asp | 140 | . | . | . | . | . | T | T | . | 1.27 | . | * | F | 3.40 | 1.66 |

TABLE III-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Tyr | 141 | . | . | . | . | . | T | T | . | 2.19 | . | * | F | 2.76 | 3.16 |
| Gly | 142 | . | . | . | . | . | T | T | . | 1.41 | * | * | F | 2.72 | 3.57 |
| Arg | 143 | . | . | . | . | . | T | T | . | 2.22 | * | * | . | 1.93 | 1.15 |
| Tyr | 144 | . | . | . | B | . | . | . | . | 1.37 | * | * | . | 0.99 | 1.27 |
| Arg | 145 | . | . | . | B | . | . | . | . | 0.98 | * | * | . | 0.80 | 0.95 |
| Cys | 146 | . | . | . | B | . | . | . | . | 1.22 | * | * | . | 0.80 | 0.62 |
| Glu | 147 | . | . | . | B | . | . | . | . | 1.22 | * | * | . | 0.80 | 0.66 |
| Val | 148 | . | . | . | B | . | . | T | . | 0.30 | * | * | . | 1.00 | 0.33 |
| Xxx | 149 | . | . | . | B | . | . | T | . | 0.54 | * | * | . | 0.70 | 0.51 |
| Asp | 150 | . | . | . | B | . | . | T | . | 0.43 | . | * | F | 1.15 | 0.51 |
| Gly | 151 | A | . | . | . | . | . | T | . | 1.10 | * | . | F | 1.30 | 1.16 |
| Leu | 152 | A | . | . | . | . | . | . | . | 0.80 | * | . | F | 1.10 | 1.56 |
| Glu | 153 | A | . | . | . | . | . | . | . | 1.31 | * | . | F | 1.10 | 1.26 |
| Asp | 154 | A | . | . | . | . | . | T | . | 0.89 | * | . | F | 1.30 | 1.26 |
| Glu | 155 | A | . | . | . | . | . | T | . | 0.03 | * | . | F | 1.30 | 1.26 |
| Ser | 156 | A | . | . | . | . | . | T | . | 0.38 | . | . | F | 1.15 | 0.54 |
| Gly | 157 | A | . | . | . | . | . | T | . | 0.38 | . | . | F | 1.15 | 0.56 |
| Leu | 158 | A | A | . | . | . | . | . | . | 0.38 | . | * | F | 0.45 | 0.27 |
| Val | 159 | A | A | . | . | . | . | . | . | −0.43 | . | * | . | 0.30 | 0.34 |
| Glu | 160 | A | A | . | . | . | . | . | . | −0.32 | * | * | . | −0.30 | 0.29 |
| Leu | 161 | A | A | . | . | . | . | . | . | −0.37 | * | * | . | 0.30 | 0.68 |
| Glu | 162 | A | A | . | . | . | . | . | . | −0.88 | * | * | . | 0.60 | 0.91 |
| Leu | 163 | A | . | . | B | . | . | . | . | −0.92 | * | * | . | 0.60 | 0.39 |
| Arg | 164 | A | . | . | B | . | . | . | . | −0.77 | * | * | . | −0.30 | 0.35 |
| Gly | 165 | . | . | . | B | T | . | . | . | −0.98 | . | * | . | 0.10 | 0.17 |
| Val | 166 | . | . | B | B | . | . | . | . | −0.41 | . | * | . | −0.60 | 0.33 |
| Val | 167 | . | . | B | B | . | . | . | . | −0.41 | * | * | . | −0.60 | 0.26 |
| Phe | 168 | . | . | B | . | . | . | T | . | 0.10 | * | . | . | −0.20 | 0.46 |
| Pro | 169 | . | . | B | . | . | . | T | . | −0.22 | * | . | . | −0.20 | 0.83 |
| Tyr | 170 | . | . | . | . | . | T | T | . | 0.12 | . | . | . | 0.63 | 1.73 |
| Gln | 171 | . | . | . | . | . | . | T | C | 0.63 | . | * | F | 0.86 | 3.21 |
| Ser | 172 | . | . | . | . | . | . | T | C | 1.60 | . | * | F | 1.44 | 2.05 |
| Pro | 173 | . | . | . | . | . | T | T | . | 2.06 | . | * | F | 2.52 | 2.56 |
| Asn | 174 | . | . | . | . | . | T | T | . | 2.27 | . | * | F | 2.80 | 2.32 |
| Gly | 175 | . | . | . | . | . | T | T | . | 1.81 | . | * | F | 2.52 | 3.00 |
| Arg | 176 | . | . | . | . | . | T | . | . | 1.81 | . | * | F | 1.44 | 1.68 |
| Tyr | 177 | . | . | . | B | . | . | . | . | 1.41 | . | * | . | 0.61 | 1.68 |
| Gln | 178 | . | . | A | B | . | . | . | . | 1.59 | . | * | . | −0.17 | 1.47 |
| Phe | 179 | . | . | A | B | . | . | . | . | 1.59 | . | * | . | −0.45 | 1.02 |
| Asn | 180 | . | . | A | B | . | . | . | . | 1.59 | . | * | . | −0.45 | 1.13 |
| Phe | 181 | . | . | A | . | . | T | . | . | 1.48 | * | * | . | 0.10 | 0.64 |
| His | 182 | . | . | A | . | . | T | . | . | 1.72 | . | * | . | 0.25 | 1.29 |
| Glu | 183 | . | . | A | . | . | T | . | . | 0.87 | . | * | F | 1.00 | 1.39 |
| Gly | 184 | . | . | A | . | . | T | . | . | 0.90 | . | . | F | 0.40 | 1.19 |
| Gln | 185 | . | . | A | . | . | T | . | . | 0.31 | * | . | F | 0.85 | 0.47 |
| Gln | 186 | A | A | . | . | . | . | . | . | 1.01 | * | . | F | 0.45 | 0.27 |
| Val | 187 | A | A | . | . | . | . | . | . | 1.04 | . | . | . | 0.30 | 0.48 |
| Cys | 188 | A | A | . | . | . | . | . | . | 0.46 | . | . | . | 0.30 | 0.48 |
| Ala | 189 | A | A | . | . | . | . | . | . | 0.21 | . | . | . | −0.30 | 0.28 |
| Glu | 190 | A | A | . | . | . | . | . | . | −0.64 | . | . | . | −0.30 | 0.38 |
| Gln | 191 | A | A | . | . | . | . | . | . | −1.50 | . | . | . | −0.30 | 0.53 |
| Ala | 192 | A | A | . | . | . | . | . | . | −1.23 | . | . | . | −0.30 | 0.39 |
| Ala | 193 | A | A | . | . | . | . | . | . | −0.87 | . | . | . | −0.30 | 0.23 |
| Val | 194 | A | A | . | . | . | . | . | . | −0.98 | . | . | . | −0.60 | 0.17 |
| Val | 195 | A | A | . | . | . | . | . | . | −0.98 | . | . | . | −0.60 | 0.15 |
| Ala | 196 | A | A | . | . | . | . | . | . | −0.98 | . | . | . | −0.60 | 0.26 |
| Ser | 197 | A | A | . | . | . | . | . | . | −1.20 | * | . | . | −0.30 | 0.60 |
| Phe | 198 | A | A | . | . | . | . | . | . | −1.31 | * | * | . | −0.60 | 0.66 |
| Glu | 199 | A | A | . | . | . | . | . | . | −0.34 | * | * | . | −0.60 | 0.57 |
| Gln | 200 | A | A | . | . | . | . | . | . | −0.08 | * | . | . | −0.30 | 0.83 |
| Leu | 201 | A | A | . | . | . | . | . | . | 0.22 | * | * | . | −0.30 | 0.97 |
| Phe | 202 | A | A | . | . | . | . | . | . | 0.52 | * | . | . | −0.30 | 0.59 |
| Arg | 203 | A | A | . | . | . | . | . | . | 1.22 | * | * | . | −0.30 | 0.59 |
| Ala | 204 | A | A | . | . | . | . | . | . | 0.88 | * | . | . | 0.45 | 1.24 |
| Trp | 205 | A | A | . | . | . | . | . | . | 0.07 | * | . | . | 0.67 | 1.42 |
| Glu | 206 | A | A | . | . | . | . | . | . | 0.88 | * | . | F | 0.89 | 0.60 |
| Glu | 207 | A | A | . | . | . | . | . | . | 1.29 | * | * | F | 1.11 | 0.99 |
| Gly | 208 | . | . | . | . | . | T | T | . | 0.51 | * | . | F | 2.13 | 0.99 |
| Leu | 209 | . | . | . | . | . | T | T | . | 1.10 | * | . | . | 2.20 | 0.30 |
| Asp | 210 | . | . | . | . | . | T | T | . | 0.80 | * | . | . | 1.38 | 0.28 |
| Trp | 211 | . | . | . | . | . | T | T | . | 0.46 | * | . | . | 0.86 | 0.29 |
| Cys | 212 | A | . | . | . | . | . | . | . | 0.17 | . | . | . | 0.04 | 0.35 |
| Asn | 213 | . | . | . | . | . | T | T | . | −0.30 | . | . | . | 0.42 | 0.22 |
| Ala | 214 | . | . | . | . | . | T | T | . | 0.51 | . | . | . | 0.20 | 0.17 |
| Gly | 215 | . | . | . | . | . | T | T | . | 0.51 | . | . | . | 0.20 | 0.55 |
| Trp | 216 | . | . | . | . | . | . | T | C | 0.21 | . | . | . | 0.30 | 0.57 |
| Leu | 217 | . | . | . | . | . | . | . | C | 0.57 | . | . | . | −0.20 | 0.57 |

TABLE III-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Gln | 218 | . | . | . | B | . | . | . | . | −0.29 | . | . | F | −0.25 | 0.84 |
| Asp | 219 | . | . | . | B | . | . | . | . | 0.30 | . | . | F | −0.25 | 0.59 |
| Ala | 220 | . | . | . | B | B | . | . | . | 0.40 | . | . | F | 0.00 | 1.24 |
| Thr | 221 | . | . | . | B | B | . | . | . | 0.48 | . | * | . | −0.15 | 1.12 |
| Val | 222 | . | . | . | B | B | . | . | . | 0.40 | . | . | . | −0.15 | 1.04 |
| Gln | 223 | . | . | . | B | B | . | . | . | −0.20 | . | * | . | −0.60 | 0.72 |
| Tyr | 224 | . | . | . | B | B | . | . | . | −1.01 | . | * | . | −0.60 | 0.50 |
| Pro | 225 | . | . | . | B | B | . | . | . | −0.63 | * | * | . | −0.60 | 0.55 |
| Ile | 226 | . | . | . | B | B | . | . | . | −0.21 | * | . | . | −0.60 | 0.49 |
| Met | 227 | . | . | . | B | B | . | . | . | 0.64 | * | . | . | −0.60 | 0.61 |
| Leu | 228 | . | . | . | B | B | . | . | . | 0.43 | * | . | . | −0.30 | 0.69 |
| Pro | 229 | . | . | . | B | B | . | . | . | 0.01 | . | . | F | 0.25 | 1.52 |
| Arg | 230 | . | . | . | B | . | . | . | . | −0.12 | . | . | F | 0.55 | 0.82 |
| Gln | 231 | . | . | . | B | . | . | T | . | 0.42 | . | . | F | 1.60 | 0.99 |
| Pro | 232 | . | . | . | . | . | T | T | . | 0.81 | * | . | F | 2.25 | 0.63 |
| Cys | 233 | . | . | . | . | . | T | T | . | 1.62 | * | . | F | 2.50 | 0.50 |
| Gly | 234 | . | . | . | . | . | T | T | . | 1.02 | * | . | F | 2.25 | 0.48 |
| Gly | 235 | . | . | . | . | . | . | T | C | 0.32 | * | . | F | 1.80 | 0.26 |
| Pro | 236 | . | . | . | . | . | . | T | C | 0.11 | . | . | F | 0.95 | 0.48 |
| Asp | 237 | . | . | . | B | . | . | T | . | −0.02 | * | . | F | 1.10 | 0.75 |
| Leu | 238 | . | . | . | B | . | . | T | . | −0.21 | * | * | F | 0.85 | 0.75 |
| Ala | 239 | . | . | . | B | . | . | T | . | 0.24 | * | * | F | 0.25 | 0.36 |
| Pro | 240 | . | . | . | B | . | . | T | . | 0.29 | * | * | F | 0.85 | 0.42 |
| Gly | 241 | . | . | . | B | . | . | T | . | 0.26 | * | * | F | 0.25 | 0.69 |
| Val | 242 | . | . | . | B | . | . | T | . | −0.09 | * | * | F | 0.40 | 1.07 |
| Arg | 243 | . | . | . | B | . | . | T | . | 0.51 | * | . | F | 0.25 | 0.69 |
| Ser | 244 | . | . | . | B | . | . | T | . | 1.21 | * | . | F | 0.74 | 1.07 |
| Tyr | 245 | . | . | . | B | . | . | T | . | 1.39 | * | * | F | 1.68 | 2.83 |
| Gly | 246 | . | . | . | . | . | . | T | C | 1.84 | * | . | F | 2.22 | 1.96 |
| Pro | 247 | . | . | . | . | . | T | T | . | 2.81 | * | . | F | 2.76 | 2.87 |
| Arg | 248 | . | . | . | . | . | T | T | . | 1.89 | * | . | F | 3.40 | 3.59 |
| His | 249 | . | . | . | B | . | . | T | . | 2.16 | * | . | F | 2.66 | 2.99 |
| Arg | 250 | . | . | . | B | . | . | T | . | 2.51 | * | . | F | 2.54 | 2.63 |
| Arg | 251 | . | . | . | B | . | . | . | . | 2.61 | * | . | . | 2.07 | 2.63 |
| Leu | 252 | . | . | . | B | . | . | . | . | 2.82 | * | * | . | 1.95 | 3.03 |
| His | 253 | . | . | . | . | . | T | T | . | 1.86 | * | * | . | 2.43 | 2.58 |
| Arg | 254 | . | . | . | . | . | T | T | . | 1.19 | * | . | . | 2.20 | 0.98 |
| Tyr | 255 | . | . | . | . | . | T | T | . | 0.41 | * | . | . | 1.53 | 1.03 |
| Asp | 256 | . | . | . | B | . | . | T | . | −0.40 | * | . | . | 0.76 | 0.40 |
| Val | 257 | . | . | . | B | B | . | . | . | −0.18 | . | . | . | −0.16 | 0.18 |
| Phe | 258 | . | . | . | B | B | . | . | . | −0.46 | . | . | . | −0.38 | 0.12 |
| Cys | 259 | . | . | . | B | B | . | . | . | −1.16 | . | * | . | −0.60 | 0.10 |
| Phe | 260 | . | . | . | B | B | . | . | . | −1.72 | . | . | . | −0.60 | 0.14 |
| Ala | 261 | A | . | . | . | B | . | . | . | −2.11 | . | . | . | −0.60 | 0.13 |
| Thr | 262 | A | . | . | . | B | . | . | . | −1.60 | . | * | . | −0.60 | 0.31 |
| Ala | 263 | A | . | . | . | B | . | . | . | −0.79 | * | * | . | −0.60 | 0.35 |
| Leu | 264 | A | . | . | . | . | . | T | . | −0.98 | . | * | . | 0.10 | 0.68 |
| Xxx | 265 | A | . | . | . | . | . | T | . | −0.52 | . | * | F | 0.25 | 0.35 |
| Gly | 266 | . | . | . | . | . | T | T | . | −0.18 | . | * | F | 0.35 | 0.54 |
| Arg | 267 | . | . | . | B | . | . | T | . | −0.68 | . | * | . | −0.05 | 1.03 |
| Val | 268 | . | . | . | B | B | . | . | . | −0.48 | . | * | . | −0.60 | 0.67 |
| Tyr | 269 | . | . | . | B | B | . | . | . | 0.30 | . | * | . | −0.60 | 0.86 |
| Tyr | 270 | . | . | . | B | B | . | . | . | 0.48 | . | * | . | −0.60 | 0.60 |
| Leu | 271 | . | . | . | B | B | . | . | . | 0.82 | . | * | . | −0.45 | 1.25 |
| Xxx | 272 | . | . | . | B | B | . | . | . | 0.32 | . | * | . | −0.45 | 1.38 |
| His | 273 | . | . | . | B | . | . | T | . | 0.37 | . | . | F | 0.40 | 1.13 |
| Pro | 274 | . | . | . | . | . | . | T | C | 0.30 | . | . | F | 0.60 | 1.13 |
| Glu | 275 | A | . | . | . | . | . | T | . | −0.27 | . | . | F | 1.00 | 1.27 |
| Xxx | 276 | A | . | . | . | . | . | T | . | 0.23 | . | . | F | 0.25 | 0.77 |
| Leu | 277 | A | A | . | . | . | . | . | . | 0.23 | . | . | . | −0.30 | 0.72 |
| Thr | 278 | A | A | . | . | . | . | . | . | −0.32 | * | . | . | −0.30 | 0.53 |
| Leu | 279 | A | A | . | . | . | . | . | . | 0.00 | . | . | . | −0.60 | 0.42 |
| Thr | 280 | A | A | . | . | . | . | . | . | 0.00 | * | . | F | −0.15 | 1.00 |
| Xxx | 281 | A | A | . | . | . | . | . | . | −0.20 | * | . | F | 0.60 | 1.20 |
| Ala | 282 | A | A | . | . | . | . | . | . | −0.06 | * | . | F | 0.60 | 1.46 |
| Arg | 283 | A | A | . | . | . | . | . | . | 0.26 | * | . | F | 0.75 | 0.54 |
| Glu | 284 | A | A | . | . | . | . | . | . | 1.07 | * | . | . | 0.60 | 0.74 |
| Ala | 285 | A | A | . | . | . | . | . | . | 1.42 | * | . | . | 0.75 | 1.26 |
| Cys | 286 | A | A | . | . | . | . | . | . | 1.42 | * | . | . | 0.75 | 1.29 |
| Gln | 287 | A | A | . | . | . | . | . | . | 1.62 | * | . | . | 0.60 | 0.95 |
| Glu | 288 | A | A | . | . | . | . | . | . | 1.12 | . | . | . | 0.75 | 1.20 |
| Lys | 289 | A | A | . | . | . | . | . | . | 0.73 | . | . | . | 0.75 | 2.87 |

TABLE IV

| Res Pos. | | I | II | III | IV | V | VI | VII | VIII | IX | X | XI | XII | XIII | XIV |
|---|---|---|---|---|---|---|---|---|---|---|---|---|---|---|---|
| Met | 1 | . | . | . | B | . | . | . | . | 0.13 | . | * | . | 0.24 | 0.82 |
| Thr | 2 | . | . | . | . | . | . | . | C | 0.57 | . | * | . | 0.78 | 0.63 |
| Gly | 3 | . | . | . | . | . | . | T | C | 0.92 | . | * | . | 1.92 | 0.99 |
| Pro | 4 | . | . | . | . | . | T | T | . | 1.36 | . | * | . | 2.61 | 1.36 |
| Gly | 5 | . | . | . | . | . | T | T | . | 1.08 | . | * | F | 3.40 | 1.89 |
| Lys | 6 | . | A | . | . | . | . | T | . | 1.68 | . | * | F | 2.66 | 1.02 |
| His | 7 | . | A | A | . | . | . | . | . | 1.32 | . | * | F | 1.92 | 1.15 |
| Lys | 8 | . | A | A | . | . | . | . | . | 1.71 | . | * | F | 1.60 | 0.62 |
| Cys | 9 | . | A | A | . | . | . | . | . | 1.62 | . | * | . | 1.28 | 0.62 |
| Glu | 10 | . | A | A | . | . | . | . | . | 1.93 | . | * | . | 1.11 | 0.61 |
| Cys | 11 | . | . | . | B | . | . | T | . | 1.64 | . | * | . | 1.68 | 0.42 |
| Lys | 12 | . | . | . | B | . | . | T | . | 0.82 | . | * | . | 1.70 | 1.22 |
| Ser | 13 | . | . | . | B | . | . | T | . | 0.43 | . | * | . | 1.38 | 0.52 |
| His | 14 | . | . | . | B | . | . | T | . | 1.10 | . | * | . | 0.61 | 0.96 |
| Tyr | 15 | . | . | . | B | . | . | . | . | 0.76 | . | * | . | 0.84 | 0.80 |
| Val | 16 | . | . | . | B | . | . | . | . | 0.61 | . | . | . | 0.07 | 0.59 |
| Gly | 17 | . | . | . | . | . | T | T | . | 0.57 | . | . | . | 0.20 | 0.36 |
| Asp | 18 | . | . | . | . | . | T | T | . | 0.20 | * | . | . | 0.50 | 0.37 |
| Gly | 19 | . | . | . | . | . | . | T | C | 0.23 | * | . | . | 0.30 | 0.27 |
| Leu | 20 | . | . | . | . | . | . | T | C | 0.27 | * | . | . | 0.90 | 0.47 |
| Asn | 21 | . | . | . | . | . | . | . | C | 1.12 | * | . | . | 0.70 | 0.43 |
| Cys | 22 | . | . | A | B | . | . | . | . | 1.47 | * | . | . | 0.30 | 0.76 |
| Glu | 23 | . | . | A | B | . | . | . | . | 0.66 | * | . | F | 0.90 | 1.59 |
| Pro | 24 | . | A | A | . | . | . | . | . | 0.79 | . | . | F | 0.75 | 0.81 |
| Glu | 25 | . | . | A | . | . | T | . | . | 0.71 | . | * | F | 1.00 | 2.35 |
| Gln | 26 | . | A | A | . | . | . | . | . | 0.71 | . | . | F | 0.45 | 0.95 |
| Leu | 27 | . | A | A | . | . | . | . | . | 1.49 | * | . | F | 0.60 | 1.03 |
| Pro | 28 | . | A | A | . | . | . | . | . | 0.82 | . | . | . | 0.91 | 1.16 |
| Ile | 29 | . | . | . | B | . | . | . | . | 0.22 | * | . | . | 0.82 | 0.36 |
| Asp | 30 | . | . | . | B | . | . | . | . | 0.22 | * | . | . | 0.38 | 0.36 |
| Arg | 31 | . | . | . | B | . | . | . | . | 0.22 | * | . | . | 1.14 | 0.40 |
| Cys | 32 | . | . | . | B | . | . | . | . | 1.03 | * | . | . | 1.60 | 0.96 |
| Leu | 33 | . | . | . | B | . | . | . | . | 0.90 | * | . | . | 1.44 | 0.92 |
| Gln | 34 | . | . | . | . | . | T | T | . | 1.79 | * | . | F | 2.03 | 0.47 |
| Asp | 35 | . | . | . | . | . | T | T | . | 1.12 | * | . | F | 1.72 | 1.51 |
| Asn | 36 | . | . | . | . | . | T | T | . | 0.98 | * | * | F | 1.41 | 0.98 |
| Gly | 37 | . | . | . | . | . | T | T | . | 1.06 | * | * | F | 1.25 | 0.77 |
| Gln | 38 | . | . | A | . | . | T | . | . | 1.87 | * | * | F | 0.85 | 0.47 |
| Cys | 39 | . | A | A | . | . | . | . | . | 1.28 | . | * | . | 0.30 | 0.48 |
| His | 40 | . | A | A | . | . | . | . | . | 1.32 | . | * | . | 0.30 | 0.49 |
| Ala | 41 | . | A | A | . | . | . | . | . | 0.66 | . | * | . | 0.60 | 0.57 |
| Asp | 42 | . | A | A | . | . | . | . | . | 0.14 | . | * | . | 0.30 | 0.57 |
| Ala | 43 | . | A | . | . | B | . | . | . | 0.14 | . | * | . | 0.30 | 0.31 |
| Lys | 44 | . | A | . | . | B | . | . | . | 0.00 | . | * | . | 0.60 | 0.51 |
| Cys | 45 | . | A | . | . | B | . | . | . | 0.00 | . | * | . | 0.60 | 0.25 |
| Val | 46 | . | A | . | . | B | . | . | . | −0.11 | . | * | . | 0.30 | 0.34 |
| Asp | 47 | . | A | . | . | B | . | . | . | −0.11 | * | * | . | −0.30 | 0.15 |
| Leu | 48 | . | . | . | B | B | . | . | . | 0.48 | * | * | . | −0.60 | 0.48 |
| His | 49 | . | A | . | . | B | . | . | . | 0.12 | * | * | . | −0.15 | 1.08 |
| Phe | 50 | . | . | . | B | B | . | . | . | 0.48 | . | * | . | 0.30 | 0.93 |
| Gln | 51 | . | A | . | . | B | . | . | . | 0.48 | . | * | . | −0.15 | 1.63 |
| Asp | 52 | . | . | . | . | B | T | . | . | 0.13 | . | * | F | 0.25 | 0.89 |
| Thr | 53 | . | . | . | . | B | T | . | . | 0.09 | . | . | F | 0.40 | 1.01 |
| Thr | 54 | . | . | . | B | B | . | . | . | −0.58 | * | . | F | −0.15 | 0.43 |
| Val | 55 | . | . | . | B | B | . | . | . | 0.09 | * | . | . | −0.60 | 0.23 |
| Gly | 56 | . | . | . | B | B | . | . | . | −0.72 | . | * | . | −0.60 | 0.21 |
| Val | 57 | . | . | . | B | B | . | . | . | −0.61 | . | * | . | −0.60 | 0.12 |
| Phe | 58 | . | . | . | B | B | . | . | . | −0.60 | . | * | . | −0.60 | 0.32 |
| His | 59 | . | . | . | B | B | . | . | . | −0.50 | . | * | . | −0.60 | 0.43 |
| Leu | 60 | . | . | . | B | B | . | . | . | −0.46 | . | * | . | −0.60 | 0.90 |
| Arg | 61 | . | . | . | B | B | . | . | . | −0.46 | . | * | F | −0.45 | 0.86 |
| Ser | 62 | . | . | . | . | . | . | T | C | 0.40 | . | * | F | 0.45 | 0.63 |
| Pro | 63 | . | . | . | . | . | T | T | . | 0.86 | . | * | F | 0.80 | 1.32 |
| Leu | 64 | . | . | . | . | . | T | T | . | 0.93 | . | * | F | 0.80 | 1.05 |
| Gly | 65 | . | . | . | . | . | T | T | . | 0.93 | * | * | F | 0.80 | 1.57 |
| Gln | 66 | . | . | A | B | . | . | . | . | 0.51 | . | * | F | −0.15 | 0.84 |
| Tyr | 67 | . | . | A | B | . | . | . | . | 0.11 | . | * | F | −0.30 | 1.47 |
| Lys | 68 | . | . | A | B | . | . | . | . | 0.32 | . | * | . | −0.45 | 1.28 |
| Leu | 69 | . | . | A | B | . | . | . | . | 1.18 | * | * | . | −0.15 | 1.24 |
| Thr | 70 | . | . | A | B | . | . | . | . | 0.93 | . | * | . | 0.45 | 1.58 |
| Phe | 71 | . | A | A | . | . | . | . | . | 1.04 | * | * | . | 0.60 | 0.80 |
| Asp | 72 | . | A | A | . | . | . | . | . | 1.29 | * | * | F | 0.90 | 1.89 |
| Lys | 73 | . | A | A | . | . | . | . | . | 0.66 | * | . | F | 0.90 | 2.27 |
| Ala | 74 | . | A | A | . | . | . | . | . | 0.80 | * | . | F | 0.90 | 2.65 |
| Arg | 75 | . | A | A | . | . | . | . | . | 0.52 | * | . | F | 0.75 | 0.85 |
| Glu | 76 | . | A | A | . | . | . | . | . | 1.22 | * | . | F | 0.75 | 0.43 |
| Ala | 77 | . | A | A | . | . | . | . | . | 1.22 | * | . | . | 0.60 | 0.68 |

TABLE IV-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Cys | 78 | A | A | . | . | . | . | . | . | 0.59 | . | * | . | 0.60 | 0.60 |
| Ala | 79 | A | A | . | . | . | . | . | . | 0.59 | . | . | . | 0.60 | 0.35 |
| Asn | 80 | A | A | . | . | . | . | . | . | 0.17 | . | . | . | 0.30 | 0.35 |
| Glu | 81 | A | A | . | . | . | . | . | . | −0.43 | . | . | . | 0.30 | 0.95 |
| Ala | 82 | A | A | . | . | . | . | . | . | −0.43 | . | . | . | 0.30 | 0.93 |
| Ala | 83 | A | A | . | . | . | . | . | . | −0.08 | * | . | . | 0.30 | 0.58 |
| Thr | 84 | A | A | . | . | . | . | . | . | 0.27 | . | . | . | −0.30 | 0.49 |
| Met | 85 | A | A | . | . | . | . | . | . | 0.27 | . | . | . | −0.60 | 0.76 |
| Ala | 86 | A | A | . | . | . | . | . | . | 0.27 | . | . | . | −0.45 | 1.20 |
| Thr | 87 | A | . | . | . | . | . | T | . | 0.04 | . | . | . | −0.05 | 1.44 |
| Tyr | 88 | A | . | . | . | . | . | T | . | 0.33 | . | . | . | −0.05 | 1.20 |
| Asn | 89 | A | . | . | . | . | . | T | . | 0.40 | . | . | . | −0.05 | 1.60 |
| Gln | 90 | A | . | . | . | . | . | T | . | 0.61 | . | . | . | −0.05 | 1.73 |
| Leu | 91 | . | . | B | . | . | . | . | . | 1.20 | . | . | . | −0.25 | 1.41 |
| Ser | 92 | A | . | . | . | . | . | . | . | 1.56 | . | . | . | −0.25 | 1.52 |
| Tyr | 93 | A | A | . | . | . | . | . | . | 1.21 | . | * | . | −0.15 | 1.76 |
| Xxx | 94 | A | A | . | . | . | . | . | . | 1.26 | . | * | F | 0.00 | 2.15 |
| Gln | 95 | A | A | . | . | . | . | . | . | 1.01 | . | * | F | 0.90 | 3.21 |
| Lys | 96 | A | A | . | . | . | . | . | . | 1.79 | . | * | F | 0.60 | 3.21 |
| Ala | 97 | . | A | B | . | . | . | . | . | 1.28 | . | * | F | 0.60 | 3.42 |
| Lys | 98 | . | A | B | . | . | . | . | . | 0.86 | . | * | F | 0.60 | 1.63 |
| Tyr | 99 | . | A | B | . | . | . | . | . | 0.94 | * | * | . | −0.30 | 0.44 |
| His | 100 | . | A | B | . | . | . | . | . | 0.36 | * | * | . | −0.30 | 0.58 |
| Leu | 101 | . | A | B | . | . | . | . | . | −0.03 | . | * | . | −0.30 | 0.29 |
| Cys | 102 | . | A | B | . | . | . | . | . | 0.27 | . | * | . | −0.60 | 0.18 |
| Ser | 103 | . | . | B | . | . | . | T | . | −0.59 | . | . | . | −0.20 | 0.14 |
| Ala | 104 | . | . | . | . | . | . | T | C | −0.34 | . | . | . | 0.00 | 0.14 |
| Gly | 105 | . | . | . | . | T | T | . | . | −0.62 | . | . | . | 0.20 | 0.46 |
| Trp | 106 | A | . | . | . | . | . | T | . | −0.16 | . | . | . | 0.10 | 0.50 |
| Leu | 107 | A | . | . | . | . | . | . | . | 0.62 | * | * | . | −0.15 | 0.49 |
| Glu | 108 | . | . | B | . | . | . | T | . | 0.07 | * | . | F | 1.35 | 0.96 |
| Thr | 109 | . | . | B | . | . | . | T | . | 0.07 | * | . | F | 1.00 | 0.68 |
| Gly | 110 | . | . | . | . | T | T | . | . | 0.17 | * | . | F | 2.25 | 0.83 |
| Arg | 111 | . | . | . | . | T | T | . | . | 0.24 | * | . | F | 2.50 | 0.75 |
| Val | 112 | . | . | B | . | . | . | . | . | 0.74 | * | . | . | 0.90 | 0.81 |
| Ala | 113 | . | . | B | . | . | . | . | . | 0.16 | * | * | . | 0.80 | 1.18 |
| Tyr | 114 | . | . | B | . | . | . | T | . | −0.23 | . | * | . | 0.60 | 0.61 |
| Pro | 115 | . | . | B | . | . | . | T | . | −0.48 | . | * | . | 0.05 | 0.71 |
| Thr | 116 | . | . | B | . | . | . | T | . | −0.89 | . | * | . | −0.20 | 0.71 |
| Ala | 117 | . | . | B | . | . | . | T | . | −0.03 | . | . | . | −0.20 | 0.61 |
| Phe | 118 | . | . | B | . | . | . | . | . | 0.56 | . | . | . | −0.40 | 0.68 |
| Ala | 119 | . | . | B | . | . | . | . | . | 0.13 | . | . | . | −0.40 | 0.76 |
| Ser | 120 | . | . | B | . | . | . | T | . | 0.00 | . | . | F | 0.08 | 0.40 |
| Gln | 121 | . | . | . | . | . | T | T | . | 0.01 | . | . | F | 0.61 | 0.46 |
| Asn | 122 | . | . | . | . | . | T | T | . | 0.26 | . | . | F | 1.04 | 0.61 |
| Cys | 123 | . | . | . | . | . | T | T | . | 0.10 | . | . | F | 1.77 | 0.45 |
| Gly | 124 | . | . | . | . | . | T | T | . | −0.17 | . | . | F | 1.30 | 0.19 |
| Ser | 125 | . | . | . | . | . | T | T | . | −0.21 | * | . | F | 0.87 | 0.09 |
| Gly | 126 | . | . | B | . | . | . | T | . | −1.10 | * | . | F | 0.34 | 0.16 |
| Val | 127 | . | . | B | . | . | . | T | . | −1.96 | * | . | . | 0.06 | 0.12 |
| Val | 128 | . | . | B | B | . | . | . | . | −1.29 | * | . | . | −0.47 | 0.06 |
| Gly | 129 | . | . | B | B | . | . | . | . | −1.19 | * | . | . | −0.60 | 0.11 |
| Ile | 130 | . | . | B | B | . | . | . | . | −1.23 | * | . | . | −0.60 | 0.23 |
| Val | 131 | . | . | B | B | . | . | . | . | −1.10 | * | * | . | −0.60 | 0.31 |
| Asp | 132 | . | . | B | . | . | . | T | . | −0.13 | * | * | . | 0.10 | 0.48 |
| Tyr | 133 | . | . | B | . | . | . | T | . | 0.51 | * | * | . | 0.85 | 1.33 |
| Gly | 134 | . | . | B | . | . | . | T | . | 0.86 | * | * | F | 1.34 | 2.78 |
| Pro | 135 | . | . | . | . | . | . | T | C | 1.79 | * | * | F | 2.18 | 2.68 |
| Arg | 136 | . | . | . | . | . | . | T | C | 2.34 | * | * | F | 2.52 | 3.42 |
| Pro | 137 | . | . | . | . | . | . | T | C | 2.34 | * | * | F | 2.86 | 4.63 |
| Asn | 138 | . | . | . | . | . | T | T | . | 1.99 | . | . | F | 3.40 | 5.18 |
| Lys | 139 | . | . | . | . | . | . | T | C | 2.04 | . | . | F | 2.86 | 2.62 |
| Ser | 140 | . | . | . | . | . | . | . | C | 2.26 | * | . | F | 2.02 | 1.78 |
| Glu | 141 | . | . | B | . | . | . | . | . | 1.29 | * | . | F | 1.78 | 1.85 |
| Met | 142 | A | . | B | B | . | . | . | . | 0.80 | . | . | . | 0.64 | 0.69 |
| Trp | 143 | A | . | . | B | . | . | . | . | 0.13 | . | . | . | −0.30 | 0.44 |
| Asp | 144 | A | . | . | B | . | . | . | . | −0.16 | . | . | . | −0.60 | 0.14 |
| Val | 145 | A | . | . | B | . | . | . | . | 0.26 | * | . | . | −0.60 | 0.22 |
| Phe | 146 | A | . | . | B | . | . | . | . | −0.34 | * | * | . | −0.60 | 0.40 |
| Cys | 147 | A | . | . | B | . | . | . | . | 0.30 | * | * | . | −0.30 | 0.24 |
| Tyr | 148 | A | . | . | . | . | . | . | . | 0.59 | * | . | . | 0.21 | 0.65 |
| Arg | 149 | . | . | . | . | . | T | . | . | −0.27 | * | . | . | 1.67 | 1.25 |
| Met | 150 | . | . | . | . | . | T | . | . | 0.59 | . | . | . | 1.98 | 1.73 |
| Lys | 151 | . | . | . | . | . | T | . | . | 0.62 | * | * | F | 2.74 | 1.77 |
| Asp | 152 | . | . | . | . | . | T | T | . | 0.98 | . | . | F | 3.10 | 0.48 |
| Val | 153 | A | . | . | . | . | . | T | . | 0.83 | . | * | F | 2.09 | 0.71 |
| Asn | 154 | . | . | B | . | . | . | T | . | 0.77 | . | * | . | 1.63 | 0.45 |

TABLE IV-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Cys | 155 | . | . | . | B | . | . | T | . | 0.51 | * | * | . | 1.32 | 0.54 |
| Thr | 156 | . | . | . | B | B | . | . | . | 0.12 | * | * | F | 0.16 | 0.54 |
| Xxx | 157 | . | . | . | B | B | . | . | . | −0.12 | . | * | F | 0.45 | 0.33 |
| Lys | 158 | . | . | . | B | B | . | . | . | −0.12 | * | * | F | −0.15 | 0.97 |
| Val | 159 | . | . | . | B | B | . | . | . | −0.47 | * | * | . | −0.30 | 0.50 |
| Gly | 160 | . | . | . | B | B | . | . | . | 0.20 | . | * | . | −0.30 | 0.39 |
| Tyr | 161 | . | . | . | B | B | . | . | . | 0.17 | * | . | . | 0.30 | 0.32 |
| Val | 162 | . | . | . | B | . | . | T | . | −0.14 | * | . | . | 0.10 | 0.43 |
| Gly | 163 | . | . | . | B | . | . | T | . | −0.49 | * | . | . | −0.20 | 0.38 |
| Asp | 164 | . | . | . | B | . | . | T | . | 0.12 | * | . | . | −0.20 | 0.32 |
| Gly | 165 | . | . | . | B | . | . | T | . | 0.17 | * | . | . | −0.20 | 0.68 |
| Phe | 166 | . | . | . | B | . | . | . | . | 0.07 | * | . | . | −0.10 | 0.92 |
| Ser | 167 | . | . | . | B | . | . | . | . | 0.92 | * | * | . | −0.10 | 0.55 |
| Tyr | 168 | . | . | . | . | . | T | . | . | 0.46 | * | . | . | 0.20 | 0.89 |
| Ser | 169 | . | . | . | . | . | . | T | C | −0.36 | * | . | F | 0.15 | 0.85 |
| Gly | 170 | . | . | . | . | . | T | T | . | −0.01 | * | . | F | 0.35 | 0.52 |
| Asn | 171 | . | . | . | . | . | . | T | C | −0.17 | * | . | F | 0.15 | 0.58 |
| Leu | 172 | . | . | . | B | B | . | . | . | −0.68 | * | . | . | −0.60 | 0.32 |
| Leu | 173 | . | . | . | B | B | . | . | . | −1.03 | * | . | . | −0.60 | 0.27 |
| Gln | 174 | . | . | . | B | B | . | . | . | −1.03 | * | . | . | −0.60 | 0.16 |
| Val | 175 | . | . | . | B | B | . | . | . | −1.39 | * | . | . | −0.60 | 0.27 |
| Leu | 176 | . | . | . | B | B | . | . | . | −1.60 | * | . | . | −0.60 | 0.28 |
| Met | 177 | . | . | . | B | B | . | . | . | −1.09 | * | . | . | −0.60 | 0.25 |
| Ser | 178 | . | . | . | B | B | . | . | . | −1.09 | * | * | . | −0.60 | 0.45 |
| Phe | 179 | . | . | . | B | . | . | T | . | −1.40 | * | . | . | −0.20 | 0.45 |
| Pro | 180 | . | . | . | . | . | . | T | C | −0.54 | * | . | . | 0.00 | 0.66 |
| Ser | 181 | . | . | . | . | . | . | T | C | −0.43 | * | . | F | 0.15 | 0.79 |
| Leu | 182 | . | . | . | . | . | . | T | C | −0.64 | * | . | F | 0.15 | 0.79 |
| Thr | 183 | . | . | . | . | . | . | . | C | −0.66 | * | . | F | −0.05 | 0.42 |
| Asn | 184 | . | . | . | . | . | . | . | C | 0.04 | * | . | . | −0.20 | 0.45 |
| Phe | 185 | . | A | A | . | . | . | . | . | −0.60 | * | . | . | −0.60 | 0.95 |
| Leu | 186 | . | . | A | B | . | . | . | . | −1.11 | * | . | . | −0.60 | 0.49 |
| Thr | 187 | . | . | A | B | . | . | . | . | −0.89 | * | . | . | −0.60 | 0.25 |
| Glu | 188 | . | . | A | B | . | . | . | . | −0.82 | * | . | . | −0.60 | 0.29 |
| Val | 189 | A | . | A | . | . | . | . | . | −1.12 | * | . | . | −0.60 | 0.56 |
| Leu | 190 | . | . | A | B | . | . | . | . | −0.42 | * | . | . | −0.60 | 0.52 |
| Ala | 191 | A | . | A | . | . | . | . | . | 0.09 | . | . | . | −0.30 | 0.48 |
| Tyr | 192 | A | . | . | . | . | . | T | . | 0.10 | . | . | . | 0.10 | 0.86 |
| Ser | 193 | . | . | . | . | . | . | T | C | −0.49 | * | * | F | 0.90 | 1.40 |
| Asn | 194 | . | . | . | . | . | . | T | C | 0.48 | * | * | F | 1.50 | 1.40 |
| Ser | 195 | . | . | . | . | . | . | T | C | 0.94 | . | * | F | 2.40 | 1.76 |
| Ser | 196 | . | . | . | . | . | . | T | C | 1.64 | . | * | F | 3.00 | 1.30 |
| Ala | 197 | . | . | . | . | . | . | T | C | 1.30 | . | * | F | 2.70 | 1.58 |
| Arg | 198 | A | . | . | . | . | . | T | . | 0.90 | . | * | F | 2.20 | 1.19 |
| Gly | 199 | A | . | . | . | . | . | T | . | 0.09 | . | * | F | 1.45 | 0.77 |
| Arg | 200 | A | A | . | . | . | . | . | . | 0.39 | . | * | F | 0.75 | 0.63 |
| Ala | 201 | A | A | . | . | . | . | . | . | 0.66 | * | * | . | 0.60 | 0.56 |
| Phe | 202 | A | A | . | . | . | . | . | . | 0.43 | * | * | . | 0.30 | 0.76 |
| Leu | 203 | A | A | . | . | . | . | . | . | 0.01 | * | * | . | −0.30 | 0.32 |
| Glu | 204 | A | A | . | . | . | . | . | . | 0.36 | * | * | . | −0.60 | 0.46 |
| His | 205 | A | A | . | . | . | . | . | . | −0.57 | * | * | . | −0.30 | 0.89 |
| Leu | 206 | A | A | . | . | . | . | . | . | −0.28 | * | * | . | −0.30 | 0.89 |
| Thr | 207 | A | A | . | . | . | . | . | . | −0.47 | * | * | F | 0.45 | 0.69 |
| Asp | 208 | A | A | . | . | . | . | . | . | 0.46 | * | * | F | −0.45 | 0.35 |
| Leu | 209 | A | A | . | . | . | . | . | . | 0.11 | * | * | . | 0.30 | 0.84 |
| Ser | 210 | . | . | . | B | B | . | . | . | −0.17 | * | * | F | 0.45 | 0.57 |
| Ile | 211 | . | . | . | B | B | . | . | . | −0.17 | . | * | F | 0.45 | 0.50 |
| Arg | 212 | . | . | . | B | B | . | . | . | −0.56 | . | * | F | −0.15 | 0.50 |
| Gly | 213 | . | . | . | B | B | . | . | . | −1.41 | . | * | F | −0.45 | 0.32 |
| Thr | 214 | . | . | . | B | B | . | . | . | −0.81 | . | * | F | −0.45 | 0.34 |
| Leu | 215 | . | . | . | B | B | . | . | . | −0.51 | * | * | . | −0.60 | 0.27 |
| Phe | 216 | . | . | . | B | B | . | . | . | 0.38 | * | * | . | −0.60 | 0.47 |
| Val | 217 | . | . | . | B | B | . | . | . | −0.03 | . | * | F | −0.45 | 0.52 |
| Pro | 218 | . | . | . | B | B | . | . | . | −0.03 | . | . | F | −0.45 | 0.85 |
| Gln | 219 | . | . | . | . | . | T | . | . | −0.53 | . | . | F | 0.15 | 0.97 |
| Asn | 220 | . | . | . | . | . | . | T | C | −0.07 | . | . | F | 0.60 | 1.08 |
| Ser | 221 | . | . | . | . | . | . | T | C | 0.63 | . | . | F | 0.45 | 0.69 |
| Gly | 222 | . | . | . | . | . | . | T | C | 1.49 | . | . | F | 1.05 | 0.69 |
| Leu | 223 | . | . | . | . | . | . | T | C | 1.70 | . | . | F | 1.05 | 0.69 |
| Gly | 224 | . | . | . | . | . | . | . | C | 1.39 | . | . | F | 1.15 | 0.89 |
| Glu | 225 | . | . | . | B | . | . | . | . | 0.58 | . | . | F | 1.10 | 1.30 |
| Asn | 226 | . | . | . | B | . | . | . | . | 0.58 | . | . | F | 0.80 | 1.30 |
| Glu | 227 | . | . | . | B | . | . | . | . | 0.58 | . | * | F | 1.10 | 1.76 |
| Thr | 228 | A | . | . | . | . | . | . | . | 1.50 | * | * | F | 1.10 | 1.01 |
| Leu | 229 | A | . | . | . | . | . | T | . | 1.84 | * | . | F | 1.30 | 1.23 |
| Ser | 230 | A | . | . | . | . | . | T | . | 0.96 | * | . | F | 1.30 | 1.18 |
| Gly | 231 | A | . | . | . | . | . | T | . | 0.96 | * | . | F | 0.85 | 0.57 |

TABLE IV-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Arg | 232 | A | . | . | . | . | . | T | . | 0.92 | * | . | F | 1.30 | 1.21 |
| Asp | 233 | A | A | . | . | . | . | . | . | 1.20 | * | * | F | 0.90 | 1.23 |
| Ile | 234 | A | A | . | . | . | . | . | . | 1.20 | * | . | F | 0.90 | 1.69 |
| Glu | 235 | A | A | . | . | . | . | . | . | 0.91 | * | . | . | 0.60 | 0.71 |
| His | 236 | A | A | . | . | . | . | . | . | 1.26 | * | . | . | 0.30 | 0.43 |
| His | 237 | A | A | . | . | . | . | . | . | 0.29 | * | . | . | −0.30 | 0.98 |
| Leu | 238 | A | . | . | B | . | . | . | . | −0.01 | * | * | . | −0.30 | 0.42 |
| Ala | 239 | A | . | . | B | . | . | . | . | 0.28 | * | . | . | −0.60 | 0.42 |
| Asn | 240 | A | . | . | B | . | . | . | . | −0.42 | * | . | . | −0.60 | 0.30 |
| Val | 241 | A | . | . | B | . | . | . | . | −1.09 | * | . | . | −0.60 | 0.32 |
| Ser | 242 | A | . | B | B | . | . | . | . | −1.30 | * | . | . | −0.60 | 0.27 |
| Met | 243 | . | . | B | B | . | . | . | . | −0.49 | * | . | . | −0.60 | 0.27 |
| Phe | 244 | . | . | B | B | . | . | . | . | 0.10 | * | * | . | −0.60 | 0.57 |
| Phe | 245 | . | . | B | B | . | . | . | . | −0.71 | . | . | . | −0.60 | 0.72 |
| Tyr | 246 | . | . | B | . | . | . | T | . | −0.71 | . | . | . | −0.20 | 0.60 |
| Asn | 247 | . | . | B | . | . | . | T | . | −0.41 | . | . | . | −0.20 | 0.51 |
| Asp | 248 | . | . | . | . | . | T | T | . | −0.16 | . | . | . | 0.20 | 0.95 |
| Leu | 249 | . | . | . | . | . | . | T | C | 0.23 | * | . | . | 0.30 | 0.60 |
| Val | 250 | . | . | . | . | . | T | T | C | 0.62 | * | . | F | 0.65 | 0.54 |
| Asn | 251 | . | . | . | . | . | T | T | . | 0.06 | . | . | F | 0.65 | 0.47 |
| Gly | 252 | . | . | . | . | . | . | T | C | 0.06 | . | . | F | 0.15 | 0.47 |
| Thr | 253 | . | . | . | B | . | . | T | . | −0.26 | * | * | F | 0.10 | 1.09 |
| Thr | 254 | . | . | . | B | B | . | . | . | 0.67 | * | * | F | −0.15 | 0.97 |
| Leu | 255 | . | . | . | B | B | . | . | . | 0.71 | . | * | F | 0.60 | 1.93 |
| Gln | 256 | . | . | . | B | B | . | . | . | 0.37 | * | * | F | 0.00 | 1.10 |
| Thr | 257 | . | . | . | B | B | . | . | . | 0.41 | * | * | F | −0.15 | 0.76 |
| Arg | 258 | . | . | . | B | B | . | . | . | 0.77 | * | * | F | 0.00 | 1.23 |
| Leu | 259 | . | . | . | B | B | . | . | . | 0.27 | * | * | F | 0.90 | 1.42 |
| Gly | 260 | . | . | . | . | B | T | . | . | 0.27 | * | * | F | 0.85 | 0.81 |
| Ser | 261 | . | . | . | . | B | . | . | C | −0.62 | * | * | F | 0.65 | 0.34 |
| Lys | 262 | . | . | . | B | B | . | . | . | −0.62 | * | * | F | −0.45 | 0.29 |
| Leu | 263 | . | . | . | B | B | . | . | . | −0.73 | * | * | F | −0.15 | 0.42 |
| Leu | 264 | . | . | . | B | B | . | . | . | 0.19 | * | * | . | 0.64 | 0.53 |
| Ile | 265 | . | . | . | B | B | . | . | . | 0.53 | . | * | . | 0.98 | 0.52 |
| Thr | 266 | . | . | . | B | . | . | T | . | 0.83 | . | * | F | 2.02 | 1.08 |
| Asp | 267 | . | . | . | B | . | . | T | . | 0.58 | . | * | F | 2.66 | 2.19 |
| Arg | 268 | . | . | . | . | . | T | T | . | 0.58 | . | . | F | 3.40 | 4.84 |
| Gln | 269 | . | . | . | B | . | . | T | . | 1.36 | . | . | F | 2.66 | 2.77 |
| Asp | 270 | . | . | . | . | . | . | . | C | 2.03 | . | . | F | 2.32 | 2.25 |
| Pro | 271 | . | . | . | . | . | . | . | C | 2.03 | . | . | F | 1.98 | 1.78 |
| Leu | 272 | . | . | . | . | . | . | . | C | 2.03 | . | . | F | 1.34 | 1.48 |
| His | 273 | . | . | . | . | . | . | T | C | 1.61 | . | . | F | 1.20 | 1.54 |
| Pro | 274 | . | . | . | . | . | . | T | C | 1.72 | . | * | F | 0.60 | 1.43 |
| Thr | 275 | . | . | . | . | . | T | T | . | 1.06 | * | . | F | 1.40 | 3.41 |
| Glu | 276 | . | . | . | B | . | . | T | . | 0.41 | * | . | F | 1.30 | 1.34 |
| Thr | 277 | . | . | . | B | . | . | . | . | 1.22 | * | . | F | 0.96 | 0.64 |
| Arg | 278 | . | . | . | B | . | . | . | . | 0.91 | . | * | F | 1.57 | 0.75 |
| Cys | 279 | . | . | . | B | . | . | T | . | 1.23 | . | . | . | 1.93 | 0.43 |
| Val | 280 | . | . | . | B | . | . | T | . | 1.54 | . | . | F | 2.39 | 0.58 |
| Asp | 281 | . | . | . | . | . | T | T | . | 1.23 | . | * | F | 3.10 | 0.49 |
| Gly | 282 | . | . | . | . | . | T | T | . | 0.73 | . | * | F | 2.94 | 1.33 |
| Arg | 283 | . | . | A | . | . | T | . | . | 0.62 | . | * | F | 2.23 | 1.47 |
| Asp | 284 | . | . | A | . | . | T | . | . | 1.00 | . | * | F | 1.92 | 1.53 |
| Thr | 285 | A | A | . | . | . | . | . | . | 1.86 | . | * | F | 0.91 | 1.63 |
| Leu | 286 | A | A | . | . | . | . | . | . | 0.97 | . | * | . | 0.75 | 1.39 |
| Glu | 287 | A | A | . | . | . | . | . | . | 0.64 | . | * | . | 0.30 | 0.58 |
| Trp | 288 | . | A | B | B | . | . | . | . | −0.06 | . | * | . | −0.30 | 0.22 |
| Asp | 289 | A | A | . | B | . | . | . | . | −0.36 | . | * | . | −0.30 | 0.26 |
| Ile | 290 | A | A | . | B | . | . | . | . | −0.04 | . | * | . | −0.30 | 0.20 |
| Cys | 291 | A | A | . | B | . | . | . | . | 0.42 | . | * | . | −0.47 | 0.31 |
| Ala | 292 | . | . | . | . | . | T | T | . | −0.47 | . | * | . | 1.36 | 0.19 |
| Ser | 293 | . | . | . | . | . | T | T | . | −0.49 | . | * | F | 0.74 | 0.19 |
| Asn | 294 | . | . | . | . | . | T | T | . | −0.52 | . | . | F | 0.87 | 0.50 |
| Gly | 295 | . | . | . | . | . | T | T | . | −0.49 | * | . | F | 1.30 | 0.67 |
| Ile | 296 | . | . | . | B | B | . | . | . | −0.71 | * | . | F | 0.07 | 0.37 |
| Thr | 297 | . | . | . | B | B | . | . | . | −0.42 | * | . | . | −0.21 | 0.16 |
| His | 298 | . | . | . | B | B | . | . | . | −0.01 | * | . | . | −0.34 | 0.22 |
| Val | 299 | . | . | . | B | B | . | . | . | −0.40 | * | . | . | −0.17 | 0.61 |
| Ile | 300 | . | . | . | B | B | . | . | . | −0.87 | * | . | . | −0.04 | 0.54 |
| Ser | 301 | . | . | . | B | B | . | . | . | 0.07 | * | . | . | 0.22 | 0.33 |
| Arg | 302 | . | . | . | B | B | . | . | . | −0.21 | * | . | . | 1.08 | 0.89 |
| Xxx | 303 | . | . | . | . | B | T | . | . | −0.39 | * | . | F | 2.04 | 1.28 |
| Leu | 304 | . | . | . | . | B | T | . | . | 0.26 | * | . | F | 2.60 | 1.48 |
| Lys | 305 | . | . | . | . | B | . | . | C | 0.56 | * | . | F | 2.14 | 1.17 |
| Ala | 306 | . | . | . | . | . | . | . | C | 0.64 | * | . | F | 1.63 | 0.92 |
| Pro | 307 | . | . | . | . | . | . | . | C | −0.32 | * | . | F | 1.52 | 1.73 |
| Pro | 308 | . | . | . | . | . | . | . | C | −0.24 | . | * | F | 1.11 | 0.64 |

TABLE IV-continued

| Res Pos. | | I | II | III | IV | V | VI | VII | VIII | IX | X | XI | XII | XIII | XIV |
|---|---|---|---|---|---|---|---|---|---|---|---|---|---|---|---|
| Ala | 309 | . | . | . | B | B | . | . | . | −0.24 | . | * | F | −0.45 | 0.92 |
| Pro | 310 | . | . | . | B | B | . | . | . | −0.68 | . | . | . | −0.60 | 0.49 |
| Val | 311 | . | . | . | B | B | . | . | . | −0.12 | . | . | . | −0.60 | 0.40 |
| Thr | 312 | . | . | . | B | B | . | . | . | −0.22 | . | . | . | −0.60 | 0.54 |
| Leu | 313 | . | . | . | B | B | . | . | . | −0.36 | . | . | . | −0.60 | 0.51 |
| Xxx | 314 | . | . | . | B | B | . | . | . | −0.58 | . | . | . | −0.60 | 0.68 |
| His | 315 | . | . | . | B | B | . | . | . | −0.71 | . | . | F | −0.60 | 0.39 |
| Thr | 316 | . | . | . | B | B | . | . | . | −0.24 | . | . | F | −0.45 | 0.46 |
| Gly | 317 | . | . | . | . | . | . | . | C | −0.28 | . | . | F | 0.25 | 0.46 |
| Leu | 318 | . | . | . | . | . | . | . | C | −0.36 | . | . | F | 0.25 | 0.34 |
| Gly | 319 | . | . | . | . | . | T | T | . | −0.67 | . | . | F | 0.35 | 0.16 |
| Xxx | 320 | . | . | . | . | . | . | T | C | −1.02 | . | . | . | 0.00 | 0.14 |
| Gly | 321 | . | . | . | B | . | . | T | . | −1.10 | * | . | . | −0.20 | 0.22 |
| Ile | 322 | . | . | . | B | . | . | T | . | −1.64 | . | . | . | −0.20 | 0.29 |
| Phe | 323 | . | . | . | B | B | . | . | . | −1.72 | . | . | . | −0.60 | 0.16 |
| Xxx | 324 | . | . | . | B | B | . | . | . | −2.19 | . | . | . | −0.60 | 0.11 |
| Xxx | 325 | . | . | . | B | B | . | . | . | −2.66 | . | . | . | −0.60 | 0.13 |
| Ile | 326 | . | . | . | B | B | . | . | . | −2.62 | . | . | . | −0.60 | 0.11 |
| Ile | 327 | . | . | . | B | B | . | . | . | −2.08 | . | . | . | −0.60 | 0.13 |
| Leu | 328 | . | . | . | B | B | . | . | . | −1.97 | . | . | . | −0.60 | 0.10 |
| Val | 329 | . | . | . | B | B | . | . | . | −2.43 | . | . | . | −0.60 | 0.14 |
| Thr | 330 | . | . | . | B | B | . | . | . | −2.63 | . | . | . | −0.60 | 0.15 |
| Gly | 331 | A | . | . | . | B | . | . | . | −2.56 | . | . | . | −0.60 | 0.18 |
| Ala | 332 | A | . | . | . | B | . | . | . | −2.26 | . | . | . | −0.60 | 0.20 |
| Val | 333 | A | . | . | . | B | . | . | . | −2.03 | . | . | . | −0.60 | 0.14 |
| Ala | 334 | A | . | . | . | B | . | . | . | −1.42 | . | . | . | −0.60 | 0.15 |
| Leu | 335 | A | . | . | . | B | . | . | . | −1.41 | . | . | . | −0.60 | 0.23 |
| Ala | 336 | A | . | . | . | B | . | . | . | −1.31 | . | . | . | −0.60 | 0.41 |
| Ala | 337 | A | . | . | . | B | . | . | . | −1.42 | * | * | . | −0.60 | 0.63 |
| Tyr | 338 | A | . | . | . | B | . | . | . | −0.46 | * | * | . | −0.60 | 0.67 |
| Ser | 339 | A | . | . | . | . | . | . | . | −0.76 | . | * | . | −0.45 | 1.29 |
| Tyr | 340 | . | . | . | B | B | . | . | . | 0.06 | . | * | . | −0.60 | 0.90 |
| Phe | 341 | . | . | . | B | B | . | . | . | 0.76 | * | * | . | −0.26 | 0.92 |
| Arg | 342 | . | . | . | B | B | . | . | . | 1.39 | * | * | . | 0.53 | 1.35 |
| Ile | 343 | . | . | . | B | B | . | . | . | 1.32 | * | * | . | 1.47 | 1.72 |
| Asn | 344 | . | . | . | B | . | . | T | . | 0.73 | * | * | F | 2.66 | 2.86 |
| Arg | 345 | . | . | . | . | . | T | T | . | 0.63 | * | * | F | 3.40 | 1.02 |
| Lys | 346 | . | . | . | . | . | T | T | . | 0.63 | * | * | F | 2.76 | 1.45 |
| Thr | 347 | . | . | . | . | . | T | T | . | 0.13 | * | * | F | 2.27 | 0.78 |
| Ile | 348 | . | . | . | B | . | . | . | . | 0.99 | * | . | F | 1.33 | 0.51 |
| Gly | 349 | . | . | . | B | . | . | . | . | 0.29 | . | . | . | 0.24 | 0.35 |
| Phe | 350 | . | . | A | B | . | . | . | . | −0.21 | . | . | . | −0.60 | 0.21 |
| Xxx | 351 | . | . | A | B | . | . | . | . | −0.64 | . | . | . | −0.60 | 0.38 |
| His | 352 | . | . | A | B | . | . | . | . | −0.72 | . | . | . | −0.60 | 0.49 |
| Phe | 353 | . | . | A | B | . | . | . | . | −0.22 | . | . | . | −0.60 | 0.72 |

Among highly preferred fragments in this regard are those that comprise regions of WF-HABP, OE-HABP, and BM-HABP that combine several structural features, such as several of the features set out above.

Other preferred fragments are biologically active WF-HABP, OE-HABP, and BM-HABP fragments. Biologically active fragments are those exhibiting activity similar, but not necessarily identical, to an activity of the WF-HABP, OE-HABP, and BM-HABP polypeptides. The biological activity of the fragments may include an improved desired activity, or a decreased undesirable activity.

The WF-HABP, OE-HABP, and BM-HABP inventions also provide polypeptides comprising epitope-bearing portions of the polypeptides of the invention. The present invention encompasses polypeptides comprising, or alternatively consisting of, an epitope of the polypeptide having an amino acid sequence of SEQ ID NOs: 2, 5, 8, or 11, or an epitope of the polypeptide sequence encoded by a polynucleotide sequence contained in ATCC deposit Nos. 203501, 203502, and 203503, or encoded by a polynucleotide that hybridizes to the complement of the sequence of SEQ ID NOs: 2, 5, 8, or 11, or contained in ATCC deposit Nos. 203501, 203502, and 203503 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NOs: 2, 5, 8, 11), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767–778 (1984); Sutcliffe et al., Science 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2): 76–82 (1998); Hansson, et al., J. Mol. Biol. 287:265–76 (1999); and Lorenzo and Blasco, Biotechniques 24(2): 308–13 (1998) (each of these patents and publications ate hereby incorporated by reference in its entirety). In one embodiment, alteration of polynucleotides corresponding to SEQ ID NOs: 1, 4, 7, or 10, and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Non-limiting examples of antigenic polypeptides that can be used to generate full-length WF-HABP receptor-specific antibodies include: a polypeptide comprising amino acid residues: from M-1 to 19, from D-3 to T12, from F-26 to L-35, from I-50 to T-59, from T-54 to W-63, from S-81 to Q-90, from P-117 to P-124, from G-122 to Q-130, from S-152 to F-160, from P-165 to L-173, from D-171 to I-179, from K-207 to L-215, from N-225 to L-234, from P-270 to H-278, from H-272 to I-280, from T-295 to L-303, from D-304 to Y-312, from V-321 to Y-329, from E-336 to F-344, from P-346 to G-354, from C-359 to D-367, from S-366 to A-374, from F-378 to C-386, from S-390 to Q-398, from Q-398 to V-406, from C-410 to G-418, from R-432 to D-440, from M-438 to L-446, from V-457 to C-465, from R-464 to E-472, from G-470 to C-478, from C-484 to C-492, from S-493 to G-501, from G-513 to C-521, from D-525 to G-533, from G-528 to H-536, from G-545 to L-554, from G-556 to C-564, from S-565 to G-573, from C-570 to H-578, from L-602 to A-610, from Q-620 to F-628, from Q-631 to V-639, from L-648 to L-656, from L-653 to V-661, from N-665 to R-673, from W-670 to R-678, from P-707 to G-715, from T-756 to G-764, from S-767 to R-775, from T-788 to N-796, from N-809 to N-816, from L-826 to I-834, from E-853 to N-861, from C-862 to Q-870, from Q-875 to V-883, from S-889 to T-897, from A-899 to C-907, from C-916 to G-924, from G-929 to F-937, from F-937 to C-945, from L-959 to T-967, from Q-978 to S-986, from R-977 to P-1005, from Q-1006 to N-1014, from V-1018 to T-1026, from E-1042 to H-1050, from K-1061 to C-1069, from D-1073 to L-1081, from C-1111 to G-1119, from G-1119 to T-1124, from E-1126 to N-1134, from C-1131 to S-1139, from C-1144 to R-1152, from T-1147 to T-1155, from L-1176 to F-1184, from K-1193 to F-1201, from M-1211 to L-1219. G-1236 to D-1244, from L-1240 to Q-1248, from R-1260 to 1-1268, from V-1277 to N-1285, from H-1302 to I-1310, from D-1307 to V-1315, from L-1340 to F-1348, from A-1360 to W-1368, from H-1371 to A-1379, from S-1414 to E-1422, from M-1424 to I-1432, from G-1426 to Q-1434, from P-1453 to D-1461, from F-1-463 to N-1471, from P-1480 to E-1488, from Q-1487 to C-1495, from G-1524 to G-1532, from L-1529 to C-1537, from W-1542 to H-1550, from G-1549 to A-1557, from P-1559 to S-1567, from P-1565 to M-1573, from M-1573 to Q-1581, from G-1614 to G-1622, from D-1617 to S-1625, from F-1627 to P-1635, from E-1630 to E-1638, from A-1655 to CM-1163, from L-1667 to V-1675, from L-1681 to C-1689, from C-1689 to Q-1697, from L-1707 to W-1715, from C-1717 to D-1725, from D-1725 to E-1733, from S-1739 to C-1747, from G-1741 to C-1749, from L-1761 to D-1769, from G-1773 to D-1781, from H-1788 to V-1796, from A-1860 to G-1868, from G-1873 to R-1881. K-1876 to A-1884, from A-1893 to V-1901, from S-1906 to D-1914, from N-1734 to F-1942, from D-19,44 to Y-1952, from S-1970 to A-1978, from D-1973 to A-1981, from N-1987 to D-1995, from S-2005 to S-2013, from L-2085 to G-2093, from Q-2100 to D-2108, from D-2103 to P-2111, from W-2112 to L-2120, from P-2136 to E-2144, from E-2143 to R-2151, from Cys-359 to Gly-363, from Pro-392 to His-395, from Pro-414 to Ser-416, from Pro-487 to Gly-490, from Ser-515 to Asp-517, from Asn-574 to Gly-576, from Pro-708 to Gly-710, from Gin-1006 to Cys-1011, from Arg-1114 to Ser-1118, from Cys-1131 to Gly-1137, from Ser-1146 to Gly-1150, from Pro-1305 to Asp-1307, from Pro-1565 to Asp-1568, from Glu-1670 to Gly-1673, from Asp-1684 to Gly-1688, from Pro-1708 to Gly-1714, from Pro-1722 to about Gly-1726, from Asp-2010 to Ser-2013 of SEQ ID NO:2. In further preferred embodiments, polypeptide fragments of the invention compose 2, 3, 4, 5, 6, 7, 8, 9, 10, 15, or 20 of the above recited full-length WF-HABP antigenic regions. As indicated above, the inventors have determined that the above polypeptide fragments are antigenic regions of the full-length WF-HABP polypeptide.

Non-limiting examples of antigenic polypeptides that can be used to generate WF-HABP receptor-specific antibodies include: a polypeptide comprising amino acid residues: from L-7 to W-15, from C-17 to D-25, from G-26 to H-34, from S-39 to C-47, from L-42 to H-50, from L-61 to D-69, from P-75 to M-83, from H-88 to V-96, from V-159 to V-167, from G-173 to R-181, from N-177 to Y-185, from A-193 to V-201, from T-207 to V-215, from N-234 to F-242, from D-244 to Y-252, from V-259 to M-267, from N-287 to P-295, from S-305 to S-313, from L-386 to G-394, from D-404 to P-412, from W-413 to L-421, from E-436 to E-444, from and/or from E-445 to 1453 of SEQ ID NO:5. In further preferred embodiments, polypeptide fragments of the invention compose 2, 3, 4, 5, 6, 7, 8, 9, 10, 15, or 20 of the above recited WF-HABP antigenic regions. As indicated above, the inventors have determined that the above polypeptide fragments are antigenic regions of the WF-HABP polypeptide.

Non-limiting examples of antigenic polypeptides that can be used to generate OE-HABP receptor-specific antibodies include: a polypeptide comprising amino acid residues: from Y-26 to N-34, from N-37 to N-45, from V-50 to L-58, from L-78 to V-86, from K-90 to E-98, from N-94 to L-102, from L-107 to Y-115, from R-110 to R-118, from V-119 to H-127, from K-125 to I-133, from L-136 to Y-144, from Y-141 to V-148, from D-150 to L-158, from Y-170 to Q-178. A204 to C-212, from R-230 to L-238, from S-244 to L-252, from H-249 to V-257, from and/or A-282 to K-289 of SEQ ID NO:8. In further preferred embodiments, polypeptide fragments of the invention compose 2, 3, 4, 5, 6, 7, 8, 9, 10, 15, or 20 of the above recited OE-HABP antigenic regions. As indicated above, the inventors have determined that the above polypeptide fragments are antigenic regions of the OE-HABP polypeptide.

Non-limiting examples of antigenic polypeptides that can be used to generate BM-HABP receptor-specific antibodies include: a polypeptide comprising amino acid residues: from T-2 to E-10, from H-7 to Y-15, from G-17 to E-25, from C-22 to D-30, from R-31 to C-39, from R-61 to L-69, from T-70 to C-78, from R-75 to H-83, from Y-93 to L-101, from L-107 to P-115, from S-120 to V-128, from Y-133 to E-141, from P-135 to W-143, from Y-148 to T-156, from S-193 to A-201, from S-195 to L-203, from N-220 to T-228, from L-229 to H-237, from L-264 to L-272, from P-271 to C-279, from C-279 to E-287, from A-292 to I-296, from S-301 to A-309, from and/or R-342 to F-350 of SEQ ID NO:11. In further preferred embodiments, polypeptide fragments of the invention compose 2, 3, 4, 5, 6, 7, 8, 9, 10, 15, or 20 of the above recited BM-HABP antigenic regions. As indicated above, the inventors have determined that the above polypeptide fragments are antigenic regions of the BM-HABP polypeptide.

For many proteins, it is known in the art that one or more amino acids may be deleted from the N-terminus or C-terminus without substantial loss of biological function. However, even if deletion of one or more amino acids from the N-terminus or C-terminus of a protein results in modification or loss of one or more biological functions of the protein, other full-length WF-HABP functional activities may still be retained. For example, in many instances, the ability of the shortened protein to induce and/or bind to antibodies which recognize the full-length WF-HABP (preferably antibodies that bind specifically to the full-length WF-HABP) will be retained irrespective of the size or location of the deletion. Whether a particular polypeptide lacking N-terminal and/or C-terminal residues of a complete protein retains such immunologic activities can readily be determined by routine methods described herein and otherwise known in the art.

For many proteins, it is known in the art that one or more amino acids may be deleted from the N-terminus or C-terminus without substantial loss of biological function. However, even if deletion of one or more amino acids from the N-terminus or C-terminus of a protein results in modification or loss of one or more biological functions of the protein, other WF-HABP functional activities may still be retained. For example, in many instances, the ability of the shortened protein to induce and/or bind to antibodies which recognize WF-HABP (preferably antibodies that bind specifically to WF-HABP) will be retained irrespective of the size or location of the deletion. Whether a particular polypeptide lacking N-terminal and/or C-terminal residues of a complete protein retains such immunologic activities can readily be determined by routine methods described herein and otherwise known in the art.

For many proteins, it is known in the art that one or more amino acids may be deleted from the N-terminus or C-terminus without substantial loss of biological function. However, even if deletion of one or more amino acids from the N-terminus or C-terminus of a protein results in modification or loss of one or more biological functions of the protein, other OE-HABP functional activities may still be retained. For example, in many instances, the ability of the shortened protein to induce and/or bind to antibodies which recognize OE-HABP (preferably antibodies that bind specifically to OE-HABP) will be retained irrespective of the size or location of the deletion. Whether a particular polypeptide lacking N-terminal and/or C-terminal residues of a complete protein retains such immunologic activities can readily be determined by routine methods described herein and otherwise known in the art.

For many proteins, it is known in the art that one or more amino acids may be deleted from the N-terminus or C-terminus without substantial loss of biological function. However, even if deletion of one or more amino acids from the N-terminus or C-terminus of a protein results in modification or loss of one or more biological functions of the protein, other BM-HABP functional activities may still be retained. For example, in many instances, the ability of the shortened protein to induce and/or bind to antibodies which recognize BM-HABP (preferably antibodies that bind specifically to BM-HABP) will be retained irrespective of the size or location of the deletion. Whether a particular polypeptide lacking N-terminal and/or C-terminal residues of a complete protein retains such immunologic activities can readily be determined by routine methods described herein and otherwise known in the art.

In one embodiment, the present invention further provides polypeptides having one or more residues deleted from the amino terminus of the amino acid sequence of the full-length WF-HABP polypeptide depicted in FIGS. 1A–P (SEQ ID NO:2). Particularly, in one embodiment, N-terminal deletions of the full-length WF-HABP polypeptide can be described by the general formula m to 2156, where m is an integer from 1 to 2155 corresponding to the position of amino acids identified in SEQ ID NO:2 and preferably, corresponds to one of the N-terminal amino acid residues identified in the N-terminal deletions specified herein. In specific embodiments, N-terminal deletions of the full-length WF-HABP polypeptide of the invention comprise, or alternatively, consist of, amino acid residues: M-2 to K-2157; D-3 to K-2157; Q-4 to K-2157; G-5 to K-2157; C-6 to K-2157; R-7 to K-2157; E-8 to K-2157; I-9 to K-2157; L-10 to K-2157; T-11 to K-2157; T-12 to K-2157; A-13 to K-2157; G-14 to K-2157; P-15 to K-2157; F-16 to K-2157; T-17 to K-2157; V-18 to K-2157; L-19 to K-2157; V-20 to K-2157; P-21 to K-2157; S-22 to K-2157; V-23 to K-2157; S-24 to K-2157; S-25 to K-2157; F-26 to K-2157; S-27 to K-2157; S-28 to K-2157; R-29 to K-2157; T-30 to K-2157; M-31 to K-2157; N-32 to K-2157; A-33 to K-2157; S-34 to K-2157; L-35 to K-2157; A-36 to K-2157; Q-37 to K-2157; Q-38 to K-2157; L-39 to K-2157; C-40 to K-2157; R-41 to K-2157; Q-42 to K-2157; H-43 to K-2157; I-44 to K-2157; 145 to K-2157; A-46 to K-2157; G-47 to K-2157; Q-48 to K-2157; H-49 to K-2157; I-50 to K-2157; L-51 to K-2157; E-52 to K-2157; D-53 to K-2157; T-54 to K-2157; R-55 to K-2157; T-56 to K-2157; Q-57 to K-2157; Q-58 to K-2157; T-59 to K-2157; R-60 to K-2157; R-61 to K-2157; W-62 to K-2157; W-63 to K-2157; T-64 to K-2157; L-65 to K-2157; A-66 to K-2157; G-67 to K-2157; Q-68 to K-2157; E-69 to K-2157; I-70 to K-2157; T-71 to K-2157; V-72 to K-2157; T-73 to K-2157; F-74 to K-2157; N-75 to K-2157; Q-76 to K-2157; F-77 to K-2157; T-78 to K-2157; K-79 to K-2157; Y-80 to K-2157; S-81 to K-2157; Y-82 to K-2157; K-83 to K-2157; Y-84 to K-2157; K-85 to K-2157; D-86 to K-2157; Q-87 to K-2157; P-88 to K-2157; Q-89 to K-2157; Q-90 to K-2157; T-91 to K-2157; F-92 to K-2157; N-93 to K-2157; I-94 to K-2157; Y-95 to K-2157; K-96 to K-2157; A-97 to K-2157; N-98 to K-2157; N-99 to K-2157; I-100 to K-2157; A-101 to K-2157; A-102 to K-2157; N-103 to K-2157; G-104 to K-2157; V-105 to K-2157; F-106 to K-2157; H-107 to K-2157; V-108 to K-2157; V-109 to K-2157; T-110 to K-2157; G-111 to K-2157; L-112 to K-2157; R-113 to K-2157; W-114 to K-2157; Q-115 to K-2157; A-116 to K-2157; P-117 to K-2157; S-118 to K-2157; G-119 to K-2157; T-120 to K-2157; P-121 to K-2157; G-122 to K-2157; D-123 to K-2157; P-124 to K-2157; K-125 to K-2157; R-126 to K-2157; T-127 to K-2157; I-128 to K-2157; G-129 to K-2157; Q-130 to K-2157; I-131 to K-2157; L-132 to K-2157; A-133 to K-2157; S-134 to K-2157; T-135 to K-2157; E-136 to K-2157; A-137 to K-2157; F-138 to K-2157; S-139 to K-2157; R-140 to K-2157; F-141 to K-2157; E-142 to K-2157; T-143 to K-2157; I-144 to K-2157; L-145 to K-2157; E-146 to K-2157; N-147 to K-2157; C-148 to K-2157; G-149 to K-2157; L-150 to K-2157; P-151 to K-2157; S-152 to K-2157; I-153 to K-2157; L-154 to K-2157; D-155 to K-2157; G-156 to K-2157; P-157 to K-2157; G-158 to K-2157; P-159 to K-2157; F-160 to K-2157; T-161 to K-2157; V-162 to K-2157; F-163 to K-2157; A-164 to K-2157; P-165 to K-2157; S-166 to K-2157; N-167 to K-2157; E-168 to K-2157; A-169 to K-2157; V-170 to K-2157; D-171 to K-2157; S-172 to K-2157; L-173 to K-2157; R-174 to K-2157; D-175 to K-2157; G-176 to K-2157; R-177 to K-2157; L-178 to K-2157; I-179 to K-2157; Y-180 to K-2157; L-181 to K-2157; F-182 to K-2157; T-183 to K-2157; A-184 to K-2157; G-185 to K-2157; L-186 to K-2157; S-187 to K-2157; K-188 to K-2157; L-189 to K-2157; Q-190 to K-2157; E-191 to K-2157; L-192 to K-2157; V-193 to K-2157; R-194 to K-2157; Y-195 to K-2157; H-196 to K-2157; I-197 to K-2157; Y-198 to K-2157; N-199 to K-2157; H-200 to K-2157; G-201 to K-2157; Q-202 to K-2157; L-203 to K-2157; T-204 to K-2157; V-205 to K-2157; E-206 to K-2157; K-207 to K-2157; L-208 to K-2157; I-209 to K-2157; S-210 to K-2157; K-211 to K-2157; G-212 to K-2157; R-213 to K-2157; I-214 to K-2157; L-215 to K-2157; T-216 to K-2157; M-217 to K-2157; A-218 to K-2157; N-219 to K-2157; Q-220 to K-2157; V-221 to K-2157; L-222 to K-2157; A-223 to K-2157; V-224 to K-2157; N-225 to K-2157; I-226 to K-2157; S-227 to K-2157; E-228 to K-2157; E-229 to K-2157; G-230 to K-2157; R-231 to K-2157; I-232 to K-2157; L-233 to K-2157; L-234 to K-2157; G-235 to K-2157; P-236 to K-2157; E-237 to K-2157; G-238 to K-2157; V-239 to K-2157; P-240 to K-2157; L-241 to K-2157; Q-242 to K-2157; R-243 to K-2157; V-244 to K-2157; D-245 to K-2157; V-246 to K-2157; M-247 to K-2157; A-248 to K-2157; A-249 to K-2157; N-250 to K-2157; G-251 to K-2157; V-252 to K-2157; I-253 to K-2157; H-254 to K-2157; M-255 to K-2157; L-256 to K-2157; D-257 to K-2157; G-258 to K-2157; I-259 to K-2157; L-260 to K-2157; L-261 to K-2157; P-262 to K-2157; P-263 to K-2157; T-264 to K-2157; I-265 to K-2157; L-266 to K-2157; P-267 to K-2157; I-268 to K-2157; L-269 to K-2157; P-270 to K-2157; K-271 to K-2157; H-272 to K-2157; C-273 to K-2157; S-274 to K-2157; E-275 to K-2157; E-276 to K-2157; Q-277 to K-2157; H-278 to K-2157; K-279 to K-2157; I-280 to K-2157; V-281 to K-2157; A-282 to K-2157; G-283 to K-2157; S-284 to K-2157; C-285 to K-2157; V-286 to K-2157; D-287 to K-2157; C-288 to K-2157; Q-289 to K-2157; A-290 to K-2157; L-291 to K-2157; N-292 to K-2157; T-293 to K-2157; S-294 to K-2157; T-295 to K-2157; C-296 to K-2157; P-297 to K-2157; P-298 to K-2157; N-299 to K-2157; S-300 to K-2157; V-301 to K-2157; K-302 to K-2157; L-303 to K-2157; D-304 to K-2157; I-305 to K-2157; F-306 to K-2157; P-307 to K-2157; K-308 to K-2157; E-309 to K-2157; C-310 to K-2157; V-311 to K-2157; Y-312 to K-2157; I-313 to K-2157; H-314 to K-2157; D-315 to K-2157; P-316 to K-2157; T-317 to K-2157; G-318 to K-2157; L-319 to K-2157; N-320 to K-2157; V-321 to K-2157; L-322 to K-2157; K-323 to K-2157; K-324 to K-2157; G-325 to K-2157; C-326 to K-2157; A-327 to K-2157; S-328 to K-2157; Y-329 to K-2157; C-330 to K-2157; N-331 to K-2157; Q-332 to K-2157; T-333 to K-2157; I-334 to K-2157; M-335 to K-2157; E-336 to K-2157; Q-337 to K-2157; G-338 to K-2157; C-339 to K-2157; C-340 to K-2157; K-341 to K-2157; G-342 to K-2157; F-343 to K-2157; F-344 to K-2157; G-345 to K-2157; P-346 to K-2157; D-347 to K-2157; C-348 to K-2157; T-349 to K-2157; Q-350 to K-2157; C-351 to K-2157; P-352 to K-2157; G-353 to K-2157; G-354 to K-2157; F-355 to K-2157; S-356 to K-2157; N-357 to K-2157; P-358 to K-2157; C-359 to K-2157; Y-360 to K-2157; G-361 to K-2157; K-362 to K-2157; G-363 to K-2157; N-364 to K-2157; C-365 to K-2157; G-366 to K-2157; D-367 to K-2157; G-368 to K-2157; I-369 to K-2157; Q-370 to K-2157; G-371 to K-2157; N-372 to K-2157; G-373 to K-2157; A-374 to K-2157; C-375 to K-2157; L-376 to K-2157; C-377 to K-2157; F-378 to K-2157; P-379 to K-2157; D-380 to K-2157; Y-381 to K-2157; K-382 to K-2157; G-383 to K-2157; I-384 to K-2157; A-385 to K-2157; C-386 to K-2157; H-387 to K-2157; I-388 to K-2157; C-389 to K-2157; S-390 to K-2157; N-391 to K-2157; P-392 to K-2157; N-393 to K-2157; K-394 to K-2157; H-395 to K-2157; G-396 to K-2157; E-397 to K-2157; Q-398 to K-2157; C-399 to K-2157; Q-400 to K-2157; E-401 to K-2157; D-402 to K-2157; C-403 to K-2157; G-404 to K-2157; C-405 to K-2157; V-406 to K-2157; H-407 to K-2157; G-408 to K-2157; L-409 to K-2157; C-410 to K-2157; D-411 to K-2157; N-412 to K-2157; R-413 to K-2157; P-414 to K-2157; G-415 to K-2157; S-416 to K-2157; G-417 to K-2157; G-418 to K-2157; V-419 to K-2157; C-420 to K-2157; Q-421 to K-2157; Q-422 to K-2157; G-423 to K-2157; T-424 to K-2157; C-425 to K-2157; A-426 to K-2157; P-427 to K-2157; G-428 to K-2157; F-429 to K-2157; S-430 to K-2157; G-431 to K-2157; R-432 to K-2157; F-433 to K-2157; C-434 to K-2157; N-435 to K-2157; E-436 to K-2157; S-437 to K-2157; M-438 to K-2157; G-439 to K-2157; D-440 to K-2157; C-441 to K-2157; G-442 to K-2157; P-443 to K-2157; T-444 to K-2157; G-445 to K-2157; L-446 to K-2157; A-447 to K-2157; Q-448 to K-2157; H-449 to K-2157; C-450 to K-2157; H-451 to K-2157; L-452 to K-2157; H-453 to K-2157; A-454 to K-2157; R-455 to K-2157; C-456 to K-2157; V-457 to K-2157; S-458 to K-2157; Q-459 to K-2157; E-460 to K-2157; G-461 to K-2157; V-462 to K-2157; A-463 to K-2157; R-464 to K-2157; C-465 to K-2157; R-466 to K-2157; C-467 to K-2157; L-468 to K-2157; D-469 to K-2157; G-470 to K-2157; F-471 to K-2157; E-472 to K-2157; G-473 to K-2157; D-474 to K-2157; G-475 to K-2157; F-476 to K-2157; S-477 to K-2157; C-478 to K-2157; T-479 to K-2157; P-480 to K-2157; S-481 to K-2157; N-482 to K-2157; P-483 to K-2157; C-484 to K-2157; S-485 to K-2157; H-486 to K-2157; P-487 to K-2157; D-488 to K-2157; R-489 to K-2157; G-490 to K-2157; G-491 to K-2157; C-492 to K-2157; S-493 to K-2157; E-494 to K-2157; N-495 to K-2157; A-496 to K-2157; E-497 to K-2157; C-498 to K-2157; V-499 to K-2157; P-500 to K-2157; G-501 to K-2157; S-502 to K-2157; L-503 to K-2157; G-504 to K-2157; T-505 to K-2157; H-506 to K-2157; H-507 to K-2157; C-508 to K-2157; T-509 to K-2157; C-510 to K-2157; H-511 to K-2157; K-512 to K-2157; G-513 to K-2157; W-514 to K-2157; S-515 to K-2157; G-516 to K-2157; D-517 to K-2157; G-518 to K-2157; R-519 to K-2157; V-520 to K-2157; C-521 to K-2157; V-522 to K-2157; A-523 to K-2157; I-524 to K-2157; D-525 to K-2157; E-526 to K-2157; C-527 to K-2157; E-528 to K-2157; L-529 to K-2157; D-530 to K-2157; V-531 to K-2157; R-532 to K-2157; G-533 to K-2157; G-534 to K-2157; C-535 to K-2157; H-536 to K-2157; T-537 to K-2157; D-538 to K-2157; A-539 to K-2157; L-540 to K-2157; C-541 to K-2157; S-542 to K-2157; Y-543 to K-2157; V-544 to K-2157; G-545 to K-2157; P-546 to K-2157; G-547 to K-2157; Q-548 to K-2157; S-549 to K-2157; R-550 to K-2157; C-551 to K-2157; T-552 to K-2157; C-553 to K-2157; K-554 to K-2157; L-555 to K-2157; G-556 to K-2157; F-557 to K-2157; A-558 to K-2157; G-559 to K-2157; D-560 to K-2157; G-561 to K-2157; Y-562 to K-2157; Q-563 to K-2157; C-564 to K-2157; S-565 to K-2157; P-566 to K-2157; I-567 to K-2157; D-568 to K-2157; P-569 to K-2157; C-570 to K-2157; R-571 to K-2157; A-572 to K-2157; G-573 to K-2157; N-574 to K-2157; G-575 to K-2157; G-576 to K-2157; C-577 to K-2157; H-578 to K-2157; G-579 to K-2157; L-580 to K-2157; E-581 to K-2157; L-582 to K-2157; E-583 to K-2157; A-584 to

K-2157; N-585 to K-2157; A-586 to K-2157; H-587 to K-2157; F-588 to K-2157; S-589 to K-2157; I-590 to K-2157; F-591 to K-2157; Y-592 to K-2157; Q-593 to K-2157; W-594 to K-2157; L-595 to K-2157; K-596 to K-2157; S-597 to K-2157; A-598 to K-2157; G-599 to K-2157; I-600 to K-2157; T-601 to K-2157; L-602 to K-2157; P-603 to K-2157; A-604 to K-2157; D-605 to K-2157; R-606 to K-2157; R-607 to K-2157; V-608 to K-2157; T-609 to K-2157; A-610 to K-2157; L-611 to K-2157; V-612 to K-2157; P-613 to K-2157; S-614 to K-2157; E-615 to K-2157; A-616 to K-2157; A-617 to K-2157; V-618 to K-2157; R-619 to K-2157; Q-620 to K-2157; L-621 to K-2157; S-622 to K-2157; P-623 to K-2157; E-624 to K-2157; D-625 to K-2157; R-626 to K-2157; A-627 to K-2157; F-628 to K-2157; W-629 to K-2157; L-630 to K-2157; Q-631 to K-2157; P-632 to K-2157; R-633 to K-2157; T-634 to K-2157; L-635 to K-2157; P-636 to K-2157; N-637 to K-2157; L-638 to K-2157; V-639 to K-2157; R-640 to K-2157; A-641 to K-2157; H-642 to K-2157; F-643 to K-2157; L-644 to K-2157; Q-645 to K-2157; G-646 to K-2157; A-647 to K-2157; L-648 to K-2157; F-649 to K-2157; E-650 to K-2157; E-651 to K-2157; E-652 to K-2157; L-653 to K-2157; A-654 to K-2157; R-655 to K-2157; L-656 to K-2157; G-657 to K-2157; G-658 to K-2157; Q-659 to K-2157; E-660 to K-2157; V-661 to K-2157; A-662 to K-2157; T-663 to K-2157; L-664 to K-2157; N-665 to K-2157; P-666 to K-2157; T-667 to K-2157; T-668 to K-2157; R-669 to K-2157; W-670 to K-2157; E-671 to K-2157; I-672 to K-2157; R-673 to K-2157; N-674 to K-2157; I-675 to K-2157; S-676 to K-2157; G-677 to K-2157; R-678 to K-2157; V-679 to K-2157; W-680 to K-2157; V-681 to K-2157; Q-682 to K-2157; N-683 to K-2157; A-684 to K-2157; S-685 to K-2157; V-686 to K-2157; D-687 to K-2157; V-688 to K-2157; A-689 to K-2157; D-690 to K-2157; L-691 to K-2157; L7692 to K-2157; A-693 to K-2157; T-694 to K-2157; N-695 to K-2157; G-696 to K-2157; V-697 to K-2157; L-698 to K-2157; H-699 to K-2157; I-700 to K-2157; L-701 to K-2157; S-702 to K-2157; Q-703 to K-2157; V-704 to K-2157; L-705 to K-2157; L-706 to K-2157; P-707 to K-2157; P-708 to K-2157; R-709 to K-2157; G-710 to K-2157; D-711 to K-2157; V-712 to K-2157; P-713 to K-2157; G-714 to K-2157; G-715 to K-2157; Q-716 to K-2157; G-717 to K-2157; L-718 to K-2157; L-719 to K-2157; Q-720 to K-2157; Q-721 to K-2157; L-722 to K-2157; D-723 to K-2157; L-724 to K-2157; V-725 to K-2157; P-726 to K-2157; A-727 to K-2157; F-728 to K-2157; S-729 to K-2157; L-730 to K-2157; F-731 to K-2157; R-732 to K-2157; E-733 to K-2157; L-734 to K-2157; L-735 to K-2157; Q-736 to K-2157; H-737 to K-2157; H-738 to K-2157; G-739 to K-2157; L-740 to K-2157; V-741 to K-2157; P-742 to K-2157; Q-743 to K-2157; I-744 to K-2157; E-745 to K-2157; A-746 to K-2157; A-747 to K-2157; T-748 to K-2157; A-749 to K-2157; Y-750 to K-2157; T-751 to K-2157; I-752 to K-2157; F-753 to K-2157; V-754 to K-2157; P-755 to K-2157; T-756 to K-2157; N-757 to K-2157; R-758 to K-2157; S-759 to K-2157; L-760 to K-2157; E-761 to K-2157; A-762 to K-2157; Q-763 to K-2157; G-764 to K-2157; N-765 to K-2157; S-766 to K-2157; S-767 to K-2157; H-768 to K-2157; L-769 to K-2157; D-770 to K-2157; A-771 to K-2157; D-772 to K-2157; T-773 to K-2157; V-774 to K-2157; R-775 to K-2157; H-776 to K-2157; H-777 to K-2157; V-778 to K-2157; V-779 to K-2157; L-780 to K-2157; G-781 to K-2157; E-782 to K-2157; A-783 to K-2157; L-784 to K-2157; S-785 to K-2157; M-786 to K-2157; E-787 to K-2157; T-788 to K-2157; L-789 to K-2157; R-790 to K-2157; K-791 to K-2157; G-792 to K-2157; G-793 to K-2157; H-794 to K-2157; R-795 to K-2157; N-796 to K-2157; S-797 to K-2157; L-798 to K-2157; L-799 to K-2157; G-800 to K-2157; P-801 to K-2157; A-802 to K-2157; H-803 to K-2157; W-804 to K-2157; I-805 to K-2157; V-806 to K-2157; F-807 to K-2157; Y-808 to K-2157; N-809 to K-2157; H-810 to K-2157; S-811 to K-2157; G-812 to K-2157; Q-813 to K-2157; P-814 to K-2157; E-815 to K-2157; V-816 to K-2157; N-817 to K-2157; H-818 to K-2157; V-819 to K-2157; P-820 to K-2157; L-821 to K-2157; E-822 to K-2157; G-823 to K-2157; P-824 to K-2157; M-825 to K-2157; L-826 to K-2157; E-827 to K-2157; A-828 to K-2157; P-829 to K-2157; G-830 to K-2157; R-831 to K-2157; S-832 to K-2157; L-833 to K-2157; I-834 to K-2157; G-835 to K-2157; L-836 to K-2157; S-837 to K-2157; G-838 to K-2157; V-839 to K-2157; L-840 to K-2157; T-841 to K-2157; V-842 to K-2157; G-843 to K-2157; S-844 to K-2157; S-845 to K-2157; R-846 to K-2157; C-847 to K-2157; L-848 to K-2157; H-849 to K-2157; S-850 to K-2157; H-851 to K-2157; A-852 to K-2157; E-853 to K-2157; A-854 to K-2157; L-855 to K-2157; R-856 to K-2157; E-857 to K-2157; K-858 to K-2157; C-859 to K-2157; V-860 to K-2157; N-861 to K-2157; C-862 to K-2157; T-863 to K-2157; R-864 to K-2157; R-865 to K-2157; F-866 to K-2157; R-867 to K-2157; C-868 to K-2157; T-869 to K-2157; Q-870 to K-2157; G-871 to K-2157; F-872 to K-2157; Q-873 to K-2157; L-874 to K-2157; Q-875 to K-2157; D-876 to K-2157; T-877 to K-2157; P-878 to K-2157; R-879 to K-2157; K-880 to K-2157; S-881 to K-2157; C-882 to K-2157; V-883 to K-2157; Y-884 to K-2157; R-885 to K-2157; S-886 to K-2157; G-887 to K-2157; F-888 to K-2157; S-889 to K-2157; F-890 to K-2157; S-891 to K-2157; R-892 to K-2157; G-893 to K-2157; C-894 to K-2157; S-895 to K-2157; Y-896 to K-2157; T-897 to K-2157; C-898 to K-2157; A-899 to K-2157; K-900 to K-2157; K-901 to K-2157; I-902 to K-2157; Q-903 to K-2157; V-904 to K-2157; P-905 to K-2157; D-906 to K-2157; C-907 to K-2157; C-908 to K-2157; P-909 to K-2157; G-910 to K-2157; F-911 to K-2157; F-912 to K-2157; G-913 to K-2157; T-914 to K-2157; L-915 to K-2157; C-916 to K-2157; E-917 to K-2157; P-918 to K-2157; C-919 to K-2157; P-920 to K-2157; G-921 to K-2157; G7922 to K-2157; L-923 to K-2157; G-924 to K-2157; G-925 to K-2157; V-926 to K-2157; C-927 to K-2157; S-928 to K-2157; G-929 to K-2157; H-930 to K-2157; G-931 to K-2157; Q-932 to K-2157; C-933 to K-2157; Q-934 to K-2157; D-935 to K-2157; R-936 to K-2157; F-937 to K-2157; L-938 to K-2157; G-939 to K-2157; S-940 to K-2157; G-941 to K-2157; E-942 to K-2157; C-943 to K-2157; H-944 to K-2157; C-945 to K-2157; H-946 to K-2157; E-947 to K-2157; G-948 to K-2157; F-949 to K-2157; H-950 to K-2157; G-951 to K-2157; T-952 to K-2157; A-953 to K-2157; C-954 to K-2157; E-955 to K-2157; V-956 to K-2157; C-957 to K-2157; E-958 to K-2157; L-959 to K-2157; G-960 to K-2157; R-961 to K-2157; Y-962 to K-2157; G-963 to K-2157; P-964 to K-2157; N-965 to K-2157; C-966 to K-2157; T-967 to K-2157; G-968 to K-2157; V-969 to K-2157; C-970 to K-2157; D-971 to K-2157; C-972 to K-2157; A-973 to K-2157; H-974 to K-2157; G-975 to K-2157; L-976 to K-2157; C-977 to K-2157; Q-978 to K-2157; E-979 to K-2157; G-980 to K-2157; L-981 to K-2157; Q-982 to K-2157; G-983 to K-2157; D-984 to K-2157; G-985 to K-2157; S-986 to

K-2157; C-987 to K-2157; V-988 to K-2157; C-989 to
K-2157; N-990 to K-2157; V-991 to K-2157; G-992 to
K-2157; W-993 to K-2157; Q-994 to K-2157; G-995 to
K-2157; L-996 to K-2157; R-997 to K-2157; C-998 to
K-2157; D-999 to K-2157; Q-1000 to K-2157; K-1001 to
K-2157; I-1002 to K-2157; T-1003 to K-2157; S-1004 to
K-2157; P-1005 to K-2157; Q-1006 to K-2157; C-1007 to
K-2157; P-1008 to K-2157; R-1009 to K-2157; K-1010 to
K-2157; C-1011 to K-2157; D-1012 to K-2157; P-1013 to
K-2157; N-1014 to K-2157; A-1015 to K-2157; N-1016 to
K-2157; C-1017 to K-2157; V-1018 to K-2157; Q-1019 to
K-2157; D-1020 to K-2157; S-1021 to K-2157; A-1022 to
K-2157; 0-1023 to K-2157; A-1024 to K-2157; S-1025 to
K-2157; T-1026 to K-2157; C-1027 to K-2157; A-1028 to
K-2157; C-1029 to K-2157; A-1030 to K-2157; A-1031 to
K-2157; G-1032 to K-2157; Y-1033 to K-2157; S-1034 to
K-2157; G-1035 to K-2157; N-1036 to K-2157; G-1037 to
K-2157; I-1038 to K-2157; F-1039 to K-2157; C-1040 to
K-2157; S-1041 to K-2157; E-1042 to K-2157; V-1043 to
K-2157; D-1044 to K-2157; P-1045 to K-2157; C-1046 to
K-2157; A-1047 to K-2157; H-1048 to K-2157; G-1049 to K-2157; H-1050 to K-2157; G-1051 to K-2157; G-1052 to K-2157; C-1053 to K-2157; S-1054 to K-2157; P-1055 to K-2157; H-1056 to K-2157; A-1057 to K-2157; N-1058 to K-2157; C-1059 to K-2157; T-1060 to K-2157; K-1061 to K-2157; V-1062 to K-2157; A-1063 to K-2157; P-1064 to K-2157; G-1065 to K-2157; Q-1066 to K-2157; R-1067 to K-2157; T-1068 to K-2157; C-1069 to K-2157; T-1070 to K-2157; C-1071 to K-2157; Q-1072 to K-2157; D-1073 to K-2157; G-1074 to K-2157; Y-1075 to K-2157; M-1076 to K-2157; G-1077 to K-2157; D-1078 to K-2157; G-1079 to K-2157; E-1080 to K-2157; L-1081 to K-2157; C-1082 to K-2157; Q-1083 to K-2157; E-1084 to K-2157; I-1085 to K-2157; N-1086 to K-2157; S-1087 to K-2157; C-1088 to K-2157; L-1089 to K-2157; I-1090 to K-2157; H-1091 to K-2157; H-1092 to K-2157; G-1093 to K-2157; G-1094 to K-2157; C-1095 to K-2157; H-1096 to K-2157; I-1097 to K-2157; H-1098 to K-2157; A-1099 to K-2157; E-1100 to K-2157; C-1101 to K-2157; I-1102 to K-2157; P-1103 to K-2157; T-1104 to K-2157; G-1105 to K-2157; P-1106 to K-2157; Q-1107 to K-2157; Q-1108 to K-2157; V-1109 to K-2157; S-1110 to K-2157; C-1111 to K-2157; S-1112 to K-2157; C-1113 to K-2157; R-1114 to K-2157; E-1115 to K-2157; G-1116 to K-2157; Y-1117 to K-2157; S-1118 to K-2157; G-1119 to K-2157; D-1120 to K-2157;G-1121 to K-2157; I-1122 to K-2157; R-1123 to K-2157; T-1124 to K-2157; C-1125 to K-2157; E-1126 to K-2157; L-1127 to K-2157; L-1128 to K-2157; D-1129 to K-2157; P-1130 to K-2157; C-1131 to K-2157; S-1132 to K-2157; K-1133 to K-2157; N-1134 to K-2157;N-1135 to K-2157; G-1136 to K-2157; G-1137 to K-2157; C-1138 to K-2157; S-1139 to K-2157; P-1140 to K-2157; Y-1141 to K-2157; A-1142 to K-2157; T-1143 to K-2157; C-1144 to K-2157; K-1145 to K-2157; S-1146 to K-2157; T-1147 to K-2157; G-1148 to K-2157; D-1149 to K-2157; G-1150 to K-2157; Q-1151 to K-2157; R-1152 to K-2157; T-1153 to K-2157; C-1154 to K-2157; T-1155 to K-2157; C-1156 to K-2157; D-1157 to K-2157; T-1158 to K-2157; A-1159 to K-2157; H-1160 to K-2157; T-1161 to K-2157; V-1162 to K-2157; G-1163 to K-2157; D-1164 to K-2157; G-1165 to K-2157; L-1166 to K-2157; T-1167 to K-2157; C-1168 to K-2157; R-1169 to K-2157; A-1170 to K-2157; R-1171 to K-2157; V-1172 to K-2157; G-1173 to K-2157; L-1174 to K-2157; E-1175 to K-2157; L-1176 to K-2157; L-1177 to K-2157; R-1178 to K-2157; D-1179 to K-2157; K-1180 to K-2157; H-1181 to K-2157; A-1182 to K-2157; S-1183 to K-2157; F-1184 to K-2157; F-1185 to K-2157; S-1186 to K-2157; L-1187 to K-2157; R-1188 to K-2157; L-1189 to K-2157; L-1190 to K-2157; E-1191 to K-2157; Y-1192 to K-2157; K-1193 to K-2157; E-1194 to K-2157; L-1195 to K-2157; K-1196 to K-2157; G-1197 to K-2157; D-1198 to K-2157; G-1199 to K-2157; P-1200 to K-2157; F-1201 to K-2157; T-1202 to K-2157; I-1203 to K-2157; F-1204 to K-2157; V-1205 to K-2157; P-1206 to K-2157; H-1207 to K-2157; A-1208 to K-2157; D-1209 to K-2157; L-1210 to K-2157; M-1211 to K-2157; S-1212 to K-2157; N-1213 to K-2157; L-1214 to K-2157; S-1215 to K-2157; Q-1216 to K-2157; D-1217 to K-2157; E-1218 to K-2157; L-1219 to K-2157; A-1220 to K-2157; R-1221 to K-2157; I-1222 to K-2157; R-1223 to K-2157; A-1224 to K-2157; H-1225 to K-2157; R-1226 to K-2157; Q-1227 to K-2157; L-1228 to K-2157; V-1229 to K-2157; F-1230 to K-2157; R-1231 to K-2157; Y-1232 to K-2157; H-1233 to K-2157; V-1234 to K-2157; V-1235 to K-2157; G-1236 to K-2157; C-1237 to K-2157; R-1238 to K-2157; R-1239 to K-2157; L-1240 to K-2157; R-1241 to K-2157; S-1242 to K-2157; E-1243 to K-2157; D-1244 to K-2157; L-1245 to K-2157; L-1246 to K-2157; E-1247 to K-2157; Q-1248 to K-2157; G-1249 to K-2157; Y-1250 to K-2157; A-1251 to K-2157; T-1252 to K-2157; A-1253 to K-2157; L-1254 to K-2157; S-1255 to K-2157; G-1256 to K-2157; H-1257 to K-2157; P-1258 to K-2157; L-1259 to K-2157; R-1260 to K-2157; F-1261 to K-2157; S-1262 to K-2157; E-1263 to K-2157; R-1264 to K-2157; E-1265 to K-2157; G-1266 to K-2157; S-1267 to K-2157; I-1268 to K-2157; Y-1269 to K-2157; L-1270 to K-2157; N-1271 to K-2157; D-1272 to K-2157; F-1273 to K-2157; A-1274 to K-2157; R-1275 to K-2157; V-1276 to K-2157; V-1277 to K-2157; S-1278 to K-2157; S-1279 to K-2157; D-1280 to K-2157; H-1281 to K-2157; E-1282 to K-2157; A-1283 to K-2157; V-1284 to K-2157; N-1285 to K-2157; G-1286 to K-2157; I-1287 to K-2157; L-1288 to K-2157; H-1289 to K-2157; F-1290 to K-2157; I-1291 to K-2157; D-1292 to K-2157; R-1293 to K-2157; V-1294 to K-2157; L-1295 to K-2157; L-1296 to K-2157; P-1297 to K-2157; P-1298 to K-2157; E-1299 to K-2157; A-1300 to K-2157; L-1301 to K-2157; H-1302 to K-2157; W-1303 to K-2157; E-1304 to K-2157; P-1305 to K-2157; D-1306 to K-2157; D-1307 to K-2157; A-1308 to K-2157; P-1309 to K-2157; I-1310 to K-2157; P-1311 to K-2157; R-1312 to K-2157; R-1313 to K-2157; N-1314 to K-2157; V-1315 to K-2157; T-1.316 to K-2157; A-1317 to K-2157; A-1318 to K-2157; A-1319 to K-2157; Q-1320 to K-2157; G-1321 to K-2157; F-1322 to K-2157; G-1323 to K-2157; Y-1324 to K-2157; K-1325 to K-2157; I-1326 to K-2157; F-1327 to K-2157; S-1328 to K-2157; G-1329 to K-2157; L-1330 to K-2157; L-1331 to K-2157; K-1332 to K-2157; V-1333 to K-2157; A-1334 to K-2157; G-1335 to K-2157; L-1336 to K-2157; L-1337 to K-2157; P-1338 to K-2157; L-1339 to K-2157; L-1340 to K-2157; R-1341 to K-2157; E-1342 to K-2157; A-1343 to K-2157; S-1344 to K-2157; H-1345 to K-2157; R-1346 to K-2157; P-1347 to K-2157; F-1348 to K-2157; T-1349 to K-2157; M-1350 to K-2157; L-1351 to K-2157; W-1352 to K-2157; P-1353 to K-2157; T-1354 to K-2157; D-1355 to K-2157; A-1356 to K-2157; A-1357 to K-2157; F-1358 to K-2157; R-1359 to K-2157; A-1360 to K-2157; L-1361 to K-2157; P-1362 to K-2157; P-1363 to K-2157; D-1364 to K-2157; R-1365 to K-2157; Q-1366 to K-2157; A-1367 to K-2157; W-1368 to K-2157; L-1369 to K-2157; Y-1370 to K-2157; H-1371 to K-2157; E-1372 to K-2157; D-1373 to K-2157; H-1374 to K-2157; R-1375 to K-2157; D-1376 to K-2157; K-1377 to K-2157; L-1378 to K-2157; A-1379 to K-2157; A-1380 to K-2157; I-1381 to K-2157; L-1382 to K-2157; R-1383 to K-2157; G-1384 to K-2157; H-1385 to K-2157; M-1386 to K-2157; I-1387 to K-2157; R-1388 to

K-2157; N-1389 to K-2157; V-1390 to K-2157; E-1391 to
K-2157; A-1392 to K-2157; L-1393 to K-2157; A-1394 to
K-2157; S-1395 to K-2157; D-1396 to K-2157; L-1397 to
K-2157; P-1398 to K-2157; N-1399 to K-2157; L-1400 to
K-2157; G-1401 to K-2157; P-1402 to K-2157; L-1403 to
K-2157; R-1404 to K-2157; T-1405 to K-2157; M-1406 to
K-2157; H-1407 to K-2157; G-1408 to K-2157; T-1409 to
K-2157; P-1410 to K-2157; I-1411 to K-2157; S-1412 to
K-2157; F-1413 to K-2157; S-1414 to K-2157; C-1415 to
K-2157; S-1416 to K-2157; R-1417 to K-2157; T-1418 to
K-2157; R-1419 to K-2157; P-1420 to K-2157; G-1421 to
K-2157; E-1422 to K-2157; L-1423 to K-2157; M-1424 to
K-2157; V-1425 to K-2157; G-1426 to K-2157; E-1427 to
K-2157; D-1428 to K-2157; D-1429 to K-2157; A-1430 to
K-2157; R-1431 to K-2157; I-1432 to K-2157; V-1433 to
K-2157; Q-1434 to K-2157; R-1435 to K-2157; H-1436 to
K-2157; L-1437 to K-2157; P-1438 to K-2157; F-1439 to
K-2157; E-1440 to K-2157; G-1441 to K-2157; G-1442 to
K-2157; L-1443 to K-2157; A-1444 to K-2157; Y-1445 to
K-2157; G-1446 to K-2157; I-1447 to K-2157; D-1448 to
K-2157; Q-1449 to K-2157; L-1450 to K-2157; L-1451 to K-2157; E-1452 to K-2157; P-1453 to K-2157; P-1454 to K-2157; G-1455 to K-2157; L-1456 to K-2157; G-1457 to K-2157; A-1458 to K-2157; R-1459 to K-2157; C-1460 to K-2157; D-1461 to K-2157; H-1462 to K-2157; F-1463 to K-2157; E-1464 to K-2157; T-1465 to K-2157; R-1466 to K-2157; P-1467 to K-2157; L-1468 to K-2157; R-1469 to K-2157; L-1470 to K-2157; N-1471 to K-2157; T-1472 to K-2157; C-1473 to K-2157; S-1474 to K-2157; I-1475 to K-2157; C-1476 to K-2157; G-1477 to K-2157; L-1478 to K-2157; E-1479 to K-2157; P-1480 to K-2157; P-1481 to K-2157; C-1482 to K-2157; P-1483 to K-2157; E-1484 to K-2157; G-1485 to K-2157; S-1486 to K-2157; Q-1487 to K-2157; E-1488 to K-2157; Q-1489 to K-2157; G-1490 to K-2157; S-1491 to K-2157; P-1492 to K-2157; E-1493 to K-2157; A-1494 to K-2157; C-1495 to K-2157; W-1496 to K-2157; R-1497 to K-2157; F-1498 to K-2157; Y-1499 to K-2157; P-1500 to K-2157; K-1501 to K-2157; F-1502 to K-2157; W-1503 to K-2157; T-1504 to K-2157; S-1505 to K-2157; P-1506 to K-2157; P-1507 to K-2157; L-1508 to K-2157; H-1509 to K-2157; S-1510 to K-2157; L-1511 to K-2157; G-1512 to K-2157; L-1513 to K-2157; R-1514 to K-2157; S-1515 to K-2157; V-1516 to K-2157; W-1517 to K-2157; V-1518 to K-2157; H-1519 to K-2157; P-1520 to K-2157; S-1521 to K-2157; L-1522 to K-2157; W-1523 to K-2157; G-1524 to K-2157; R-1525 to K-2157; P-1526 to K-2157; Q-1527 to K-2157; G-1528 to K-2157; L-1529 to K-2157; G-1530 to K-2157; R-1531 to K-2157; G-1532 to K-2157; C-1533 to K-2157; H-1534 to K-2157; R-1535 to K-2157; N-1536 to K-2157; C-1537 to K-2157; V-1538 to K-2157; T-1539 to K-2157; T-1540 to K-2157; T-1541 to K-2157; W-1542 to K-2157; K-1543 to K-2157; P-1544 to K-2157; S-1545 to K-2157; C-1546 to K-2157; C-1547 to K-2157; P-1548 to K-2157; G-1549 to K-2157; H-1550 to K-2157; Y-1551 to K-2157; G-1552 to K-2157; S-1553 to K-2157; E-1554 to K-2157; C-1555 to K-2157; Q-1556 to K-2157; A-1557 to K-2157; C-1558 to K-2157; P-1559 to K-2157; G-1560 to K-2157; G-1561 to K-2157; P-1562 to K-2157; S-1563 to K-2157; S-1564 to K-2157; P-1565 to K-2157; C-1566 to K-2157; S-1567 to K-2157; D-1568 to K-2157; R-1569 to K-2157; G-1570 to K-2157; V-1571 to K-2157; C-1572 to K-2157; M-1573 to K-2157; D-1574 to K-2157; G-1575 to K-2157; M-1576 to K-2157; S-1577 to K-2157; G-1578 to K-2157; S-1579 to K-2157; G-1580 to K-2157; Q-1581 to K-2157; C-1582 to K-2157; L-1583 to K-2157; C-1584 to K-2157; R-1585 to K-2157; S-1586 to K-2157; G-1587 to K-2157; F-1588 to K-2157; A-1589 to K-2157; G-1590 to K-2157; T-1591 to K-2157; A-1592 to K-2157; C-1593 to K-2157; E-1594 to K-2157; L-1595 to K-2157; C-1596 to K-2157; A-1597 to K-2157; P-1598 to K-2157; G-1599 to K-2157; A-1600 to K-2157; F-1601 to K-2157; G-1602 to K-2157; P-1603 to K-2157; H-1604 to K-2157; C-1605 to K-2157; Q-1606 to K-2157; A-1607 to K-2157; C-1608 to K-2157; R-1609 to K-2157; C-1610 to K-2157; T-1611 to K-2157; V-1612 to K-2157; H-1613 to K-2157; G-1614 to K-2157; R-1615 to K-2157; C-1616 to K-2157; D-1617 to K-2157; E-1618 to K-2157; G-1619 to K-2157; L-1620 to K-2157; G-1621 to K-2157; G-1622 to K-2157; S-1623 to K-2157; G-1624 to K-2157; S-1625 to K-2157; C-1626 to K-2157; F-1627 to K-2157; C-1628 to K-2157; D-1629 to K-2157; E-1630 to K-2157; G-1631 to K-2157; W-1632 to K-2157; T-1633 to K-2157; G-1634 to K-2157; P-1635 to K-2157; R-1636 to K-2157; C-1637 to K-2157; E-1638 to K-2157; V-1639 to K-2157; Q-1640 to K-2157; L-1641 to K-2157; E-1642 to K-2157; L-1643 to K-2157; Q-1644 to K-2157; P-1645 to K-2157; V-1646 to K-2157; C-1647 to K-2157; T-1648 to K-2157; P-1649 to K-2157, P-1650 to K-2157; C-1651 to K-2157; A-1652 to K-2157; P-1653 to K-2157; E-1654 to K-2157; A-1655 to K-2157; V-1656 to K-2157; C-1657 to K-2157; R-1658 to K-2157; A-1659 to K-2157; G-1660 to K-2157; N-1661 to K-2157; S-1662 to K-2157; C-1663 to K-2157; E-1664 to K-2157; C-1665 to K-2157; S-1666 to K-2157; L-1667 to K-2157; G-1668 to K-2157; Y-1669 to K-2157; E-1670 to K-2157; G-1671 to K-2157; D-1672 to K-2157; G-1673 to K-2157; R-1,674 to K-2157; V-1675 to K-2157; C-1676 to K-2157; T-1677 to K-2157; V-1678 to K-2157; A-1679 to K-2157; D-1680 to K-2157; L-1681 to K-2157; C-1682 to K-2157; Q-1683 to K-2157; D-1684 to K-2157; G-1685 to K-2157; H-1686 to K-2157; G-1687 to K-2157; G-1688 to K-2157; C-1689 to K-2157; S-1690 to K-2157; E-1691 to K-2157; H-1692 to K-2157; A-1693 to K-2157; N-1694 to K-2157; C-1695 to K-2157; S-1696 to K-2157; Q-1697 to K-2157; V-1698 to K-2157; G-1699 to K-2157; T-1700 to K-2157; M-1701 to K-2157; V-1702 to K-2157; T-1703 to K-2157; C-1704 to K-2157; T-1705 to K-2157; C-1706 to K-2157; L-1707 to K-2157; P-1708 to K-2157; D-1709 to K-2157; Y-1710 to K-2157; E-1711 to K-2157; G-1712 to K-2157; D-1713 to K-2157; G-1714 to K-2157; W-1715 to K-2157; S-1716 to K-2157; C-1717 to K-2157; R-1718 to K-2157; A-1719 to K-2157; R-1720 to K-2157; N-1721 to K-2157; P-1722 to K-2157; C-1723 to K-2157; T-1724 to K-2157; D-1725 to K-2157; G-1726 to K-2157; H-1727 to K-2157; R-1728 to K-2157; G-1729 to K-2157; G-1730 to K-2157; C-1731 to K-2157; S-1732 to K-2157; E-1733 to K-2157; H-1734 to K-2157; A-1735 to K-2157; N-1736 to K-2157; C-1737 to K-2157; L-1738 to K-2157; S-1739 to K-2157; T-1740 to K-2157; G-1741 to K-2157; L-1742 to K-2157; N-1743 to K-2157; T-1744 to K-2157; R-1745 to K-2157; R-1746 to K-2157; C-1747 to K-2157; E-1748 to K-2157; C-1749 to K-2157; H-1750 to K-2157; A-1751 to K-2157; G-1752 to K-2157; Y-1753 to K-2157; V-1754 to K-2157; G-1755 to K-2157; D-1756 to K-2157; G-1757 to K-2157; L-1758 to K-2157; Q-1759 to K-2157; C-1760 to K-2157; L-1761 to K-2157; E-1762 to K-2157; E-1763 to K-2157; S-1764 to K-2157; E-1765 to K-2157; P-1766 to K-2157; P-1767 to K-2157; V-1768 to K-2157; D-1769 to K-2157; R-1770 to K-2157; C-1771 to K-2157; L-1772 to K-2157; G-1773 to K-2157; Q-1774 to K-2157; P-1775 to K-2157; P-1776 to K-2157; P-1777 to K-2157; C-1778 to K-2157; H-1779 to K-2157; S-1780 to K-2157; D-1781 to K-2157; A-1782 to K-2157; M-1783 to K-2157; C-1784 to K-2157; T-1785 to K-2157; D-1786 to K-2157; L-1787 to K-2157; H-1788 to K-2157; F-1789 to K-2157; Q-1790 to

K-2157; E-1791 to K-2157; K-1792 to K-2157; R-1793 to K-2157; A-1794 to K-2157; G-1795 to K-2157; V-1796 to K-2157; F-1797 to K-2157; H-1798 to K-2157; L-1799 to K-2157; Q-1800 to K-2157; A-1801 to K-2157; T-1802 to K-2157; S-1803 to K-2157; G-1804 to K-2157; P-1805 to K-2157; Y-1806 to K-2157; G-1807 to K-2157; L-1808 to K-2157; N-1809 to K-2157; F-1810 to K-2157; S-1811 to K-2157; E-1812 to K-2157; A-1813 to K-2157; E-1814 to K-2157; A-1815 to K-2157; A-1816 to K-2157; C-1817 to K-2157; E-1818 to K-2157; A-1819 to K-2157; Q-1820 to K-2157; G-1821 to K-2157; A-1822 to K-2157; V-1823 to K-2157; L-1824 to K-2157; A-1825 to K-2157; S-1826 to K-2157; F-1827 to K-2157; P-1828 to K-2157; Q-1829 to K-2157; L-1830 to K-2157; S-1831 to K-2157; A-1832 to K-2157; A-1833 to K-2157; Q-1834 to K-2157; Q-1835 to K-2157; L-1836 to K-2157; G-1837 to K-2157; F-1838 to K-2157; H-1839 to K-2157; L-1840 to K-2157; C-1841 to K-2157; L-1842 to K-2157; M-1843 to K-2157; G-1844 to K-2157; W-1845 to K-2157; L-1846 to K-2157; A-1847 to K-2157; N-1848 to K-2157; G-1849 to K-2157; S-1850 to K-2157; T-1851 to K-2157; A-1852 to K-2157; H-1853 to K-2157; P-1854 to K-2157; V-1855 to K-2157; V-1856 to K-2157; F-1857 to K-2157; P-1858 to K-2157; V-1859 to K-2157; A-1860 to K-2157; D-1861 to K-2157; C-1862 to K-2157; G-1863 to K-2157; N-1864 to K-2157; G-1865 to K-2157; R-1866 to K-2157; V-1867 to K-2157; G-1868 to K-2157; I-1869 to K-2157; V-1870 to K-2157; S-1871 to K-2157; L-1872 to K-2157; G-1873 to K-2157; A-1874 to K-2157; R-1875 to K-2157; K-1876 to K-2157; N-1877 to K-2157; L-1878 to K-2157; S-1879 to K-2157; E-1880 to K-2157; R-1881 to K-2157; W-1882 to K-2157; D-1883 to K-2157; A-1884 to K-2157; Y-1885 to K-2157; C-1886 to K-2157; F-1887 to K-2157; R-1888 to K-2157; V-1889 to K-2157; Q-1890 to K-2157; D-1891 to K-2157; V-1892 to K-2157; A-1893 to K-2157; C-1894 to K-2157; R-1895 to K-2157; C-1896 to K-2157; R-1897 to K-2157; N-1898 to K-2157; G-1899 to K-2157; F-1900 to K-2157; V-1901 to K-2157; G-1902 to K-2157; D-1903 to K-2157; G-1904 to K-2157; I-1905 to K-2157; S-1906 to K-2157; T-1907 to K-2157; C-1908 to K-2157; N-1909 to K-2157; G-1910 to K-2157; K-1911 to K-2157; L-1912 to K-2157; L-1913 to K-2157; D-1914 to K-2157; V-1915 to K-2157; L-1916 to K-2157; A-1917 to K-2157; A-1918 to K-2157; T-1919 to K-2157; A-1920 to K-2157; N-1921 to K-2157; F-1922 to K-2157; S-1923 to K-2157; T-1924 to K-2157; F-1925 to K-2157; Y-1926 to K-2157; G-1927 to K-2157; M-1928 to K-2157; L-1929 to K-2157; L-1930 to K-2157; G-1931 to K-2157; Y-1932 to K-2157; A-1933 to K-2157; N-1934 to K-2157; A-1935 to K-2157; T-1936 to K-2157; Q-1937 to K-2157; R-1938 to K-2157; G-1939 to K-2157; L-1940 to K-2157; D-1941 to K-2157; F-1942 to K-2157; L-1943 to K-2157; D-1944 to K-2157; F-1945 to K-2157; L-1946 to K-2157; D-1947 to K-2157; D-1948 to K-2157; E-1949 to K-2157; L-1950 to K-2157; T-1951 to K-2157; Y-1952 to K-2157; K-1953 to K-2157; T-1954 to K-2157; L-1955 to K-2157; F-1956 to K-2157; V-1957 to K-2157; P-1958 to K-2157; V-1959 to K-2157; N-1960 to K-2157; E-1961 to K-2157; G-1962 to K-2157; F-1963 to K-2157; V-1964 to K-2157; D-1965 to K-2157; N-1966 to K-2157; M-1967 to K-2157; T-1968 to K-2157; L-1969 to K-2157; S-1970 to K-2157; G-1971 to K-2157; P-1972 to K-2157; N-1973 to K-2157; L-1974 to K-2157; E-1975 to K-2157; L-1976 to K-2157; H-1977 to K-2157; A-1978 to K-2157; S-1979 to K-2157; N-1980 to K-2157; A-1981 to K-2157; T-1982 to K-2157; L-1983 to K-2157; L-1984 to K-2157; S-1985 to K-2157; A-1986 to K-2157; N-1987 to K-2157; A-1988 to K-2157; S-1989 to K-2157; Q-1990 to K-2157; G-1991 to K-2157; K-1992 to K-2157; L-1993 to K-2157; L-1994 to K-2157; P-1995 to K-2157; A-1996 to K-2157; H-1997 to K-2157; S-1998 to K-2157; G-1999 to K-2157; L-2000 to K-2157; S-2001 to K-2157; L-2002 to K-2157; I-2003 to K-2157; I-2004 to K-2157; S-2005 to K-2157; D-2006 to K-2157; A-2007 to K-2157; G-2008 to K-2157; P-2009 to K-2157; D-2010 to K-2157; N-2011 to K-2157; S-2012 to K-2157; S-2013 to K-2157; W-2014 to K-2157; A-2015 to K-2157; P-2016 to K-2157; V-2017 to K-2157; A-2018 to K-2157; P-2019 to K-2157; G-2020 to K-2157; T-2021 to K-2157; V-2022 to K-2157; V-2023 to K-2157; V-2024 to K-2157; S-2025 to K-2157; R-2026 to K-2157; I-2027 to K-2157; I-2028 to K-2157; V-2029 to K-2157; W-2030 to K-2157; D-2031 to K-2157; I-2032 to K-2157; M-2033 to K-2157; A-2034 to K-2157; F-2035 to K-2157; N-2036 to K-2157; G-2037 to K-2157; I-2038 to K-2157; I-2039 to K-2157; H-2040 to K-2157; A-2041 to K-2157; L-2042 to K-2157; A-2043 to K-2157; S-2044 to K-2157; P-2045 to K-2157; L-2046 to K-2157; L-2047 to K-2157; A-2048 to K-2157; P-2049 to K-2157; P-2050 to K-2157; Q-2051 to K-2157; P-2052 to K-2157; Q-2053 to K-2157; A-2054 to K-2157; V-2055 to K-2157; L-2056 to K-2157; A-2057 to K-2157; X-2058 to K-2157; E-2059 to K-2157; A-2060 to K-2157; P-2061 to K-2157; P-2062 to K-2157; V-2063 to K-2157; A-2064 to K-2157; A-2065 to K-2157; G-2066 to K-2157; V-2067 to K-2157; G-2068 to K-2157; A-2069 to K-2157; V-2070 to K-2157; L-2071 to K-2157; A-2072 to K-2157; A-2073 to K-2157; G-2074 to K-2157; A-2075 to K-2157; L-2076 to K-2157; L-2077 to K-2157; G-2078 to K-2157; L-2079 to K-2157; V-2080 to K-2157; A-2081 to K-2157; G-2082 to K-2157; A-2083 to K-2157; L-2084 to K-2157; Y-2085 to K-2157; L-2086 to K-2157; R-2087 to K-2157; A-2088 to K-2157; R-2089 to K-2157; G-2090 to K-2157; K-2091 to K-2157; P-2092 to K-2157; M-2093 to K-2157; G-2094 to K-2157; F-2095 to K-2157; G-2096 to K-2157; F-2097 to K-2157; S-2098 to K-2157; A-2099 to K-2157; F-2100 to K-2157; Q-2101 to K-2157; A-2102 to K-2157; E-2103 to K-2157; D-2104 to K-2157; D-2105 to K-2157; A-2106 to K-2157; D-2107 to K-2157; D-2108 to K-2157; X-2109 to K-2157; F-2110 to K-2157; S-2111 to K-2157; P-2112 to K-2157; W-2113 to K-2157; Q-2114 to K-2157; E-2115 to K-2157; G-2116 to K-2157; T-2117 to K-2157; N-2118 to K-2157; P-2119 to K-2157; T-2120 to K-2157; L-2121 to K-2157; V-2122 to K-2157; X-2123 to K-2157; V-2124 to K-2157; P-2125 to K-2157; N-2126 to K-2157; P-2127 to K-2157; V-2128 to K-2157; F-2129 to K-2157; G-2130 to K-2157; S-2131 to K-2157; D-2132 to K-2157; T-2133 to K-2157; F-2134 to K-2157; C-2135 to K-2157; E-2136 to K-2157; P-2137 to K-2157; F-2138 to K-2157; D-2139 to K-2157; D-2140 to K-2157; S-2141 to K-2157; L-2142 to K-2157; L-2143 to K-2157; E-2144 to K-2157; E-2145 to K-2157; D-2146 to K-2157; F-2147 to K-2157; P-2148 to K-2157; D-2149 to K-2157; T-2150 to K-2157; Q-2151 to K-2157; R-2152 to K-2157; of SEQ ID NO:2. Polynucleotides encoding these polypeptides are also encompassed by the invention.

Further embodiments of the invention are directed to C-terminal deletions of the full-length WF-HABP polypeptide described by the general formula 1 to n, where n is an integer from 2–2157 corresponding to the position of amino acid residue identified in SEQ ID NO:2 and preferably, corresponds to one of the C-terminal amino acid residues identified in the C-terminal deletions specified herein. In specific embodiments, C terminal deletions of the full-length WF-HABP polypeptide of the invention comprise, or alternatively, consist of, amino acid residues: M-1 to V-2156; M-1 to T-2155; M-1 to L-2154; M-1 to I-2153; M-1 to R-2152; M-1 to Q-2151; M-1 to T-2150; M-1 to D-2149; M-1 to P-2148; M-1 to F-2147; M-1 to D-2146; M-1 to E-2145; M-1 to E-2144; M-1 to L-2143; M-1 to L-2142; M-1 to S-2141; M-1 to D-2140; M-1 to D-2139; M-1 to F-2138; M-1 to P-2137; M-1 to E-2136; M-1 to C-2135; M-1 to F-2134; M-1 to T-2133; M-1 to D-2132; M-1 to S-2131; M-1 to G-2130; M-1 to F-2129; M-1 to V-2128; M-1 to P-2127; M-1 to N-2126; M-1 to P-2125; M-1 to V-2124; M-1 to X-2123; M-1 to V-2122; M-1 to L-2121; M-1 to T-2120; M-1 to P-2119; M-1 to N-2118; M-1 to T-2117; M-1 to G-2116; M-1 to E-2115; M-1 to Q-2114; M-1 to W-2113; M-1 to P-2112; M-1 to S-2111; M-1 to F-2110; M-1 to X-2109; M-1 to D-2108; M-1 to D-2107; M-1 to A-2106; M-1 to D-2105; M-1 to D-2104; M-1 to E-2103; M-1 to A-2102; M-1 to Q-2101; M-1 to F-2100; M-1 to A-2099; M-1 to S-2098; M-1 to F-2097; M-1 to G-2096; M-1 to F-2095; M-1 to G-2094; M-1 to M-2093; M-1 to P-2092; M-1 to K-2091; M-1 to G-2090; M-1 to R-2089; M-1 to A-2088; M-1 to R-2087; M-1 to L-2086; M-1 to Y-2085; M-1 to L-2084; M-1 to A-2083; M-1 to G-2082; M-1 to A-2081; M-1 to V-2080; M-1 to L-2079; M-1 to G-2078; M-1 to L-2077; M-1 to L-2076; M-1 to A-2075; M-1 to G-2074; M-1 -to A-2073; M-1 to A-2072; M-1 to L-2071; M-1 to V-2070; M-1 to A-2069; M-1 to G-2068; M-1 to V-2067; M-1 to G-2066; M-1 to A-2065; M-1 to A-2064; M-1 to V-2063; M-1 to P-2062; M-1 to P-2061; M-1 to A-2060; M-1 to E-2059; M-1 to X-2058; M-1 to A-2057; M-1 to L-2056; M-1 to V-2055; M-1 to A-2054; M-1 to Q-2053; M-1 to P-2052; M-1 to Q-2051; M-1 to P-2050; M-1 to P-2049; M-1 to A-2048; M-1 to L-2047; M-1 to L-2046; M-1 to P-2045; M-1 to S-2044; M-1 to A-2043; M-1 to L-2042; M-1 to A-2041; M-1 to H-2040; M-1 to I-2039; M-1 to I-2038; M-1 to G-2037; M-1 to N-2036; M-1 to F-2035; M-1 to A-2034; M-1 to M-2033; M-1 to I-2032; M-1 to D-2031; M-1 to W-2030; M-1 to V-2029; M-1 to I-2028; M-1 to I-2027; M-1 to R-2026; M-1 to S-2025; M-1 to V-2024; M-1 to V-2023; M-1 to V-2022; M-1 to T-2021; M-1 to G-2020; M-1 to P-2019; M-1 to A-2018; M-1 to V-2017; M-1 to P-2016; M-1 to A-2015; M-1 to W-2014; M-1 to S-2013; M-1 to S-2012; M-1 to N-2011; M-1 to D-2010; M-1 to P 2009; M-1 to G-2008; M-1 to A-2007; M-1 to D-2006; M-1 to S-2005; M-1 to I-2004; M-1 to I-2003; M-1 to L-2002; M-1 to S-2001; M-1 to L-2000; M-1 to G-1999; M-1 to S-1998; M-1 to H-1997; M-1 to A-1996; M-1 to P-1995; M-1 to L-1994; M-1 to L-1993; M-1 to K-1992; M-1 to G-1991; M-1 to Q-1990; M-1 to S-1989; M-1 to A-1988; M-1 to N-1987; M-1 to A-1986; M-1 to S-1985; M-1 to L-1:984; M-1 to L-1983; M-1 to T-1982; M-1 to A-1981; M-1 to N-1980; M-1 to S-1979; M-1 to A-1978; M-1 to H-1977; M-1 to L-1976; M-1 to E-1975; M-1 to L-1974; M-1 to N-1973; M-1 to P-1972; M-1 to G-1971; M-1 to S-1970; M-1 to L-1969; M-1 to T-1968; M-1 to M-1967; M-1 to N-1966; M-1 to D-1965; M-1 to V-1964; M-1 to F-1963; M-1 to G-1962; M-1 to E-1961; M-1 to N-1960; M-1 to V-1959; M-1 to P-1958; M-1 to V-1957; M-1 to F-1956; M-1 to L-1955; M-1 to T-1954; M-1 to K-1953; M-1 to Y-1952; M-1 to T-1951; M-1 to L-1950; M-1 to E-1949; M-1 to D-1948; M-1 to D-1947; M-1 to L-1946; M-1 to F-1945; M-1 to D-1944; M-1 to L-1943; M-1 to F-1942; M-1 to D-1941; M-1 to L-1940; M-1 to G-1939; M-1 to R-1938; M-1 to Q-1937; M-1 to T-1936; M-1 to A-1935; M-1 to N-1934; M-1 to A-1933; M-1 to Y-1932; M-1 to G-1931; M-1 to L-1930; M-1 to L-1929; M-1 to M-1928; M-1 to G-1927; M-1 to Y-1926; M-1 to F-1925; M-1 to T-1924; M-1 to S-1923; M-1 to F-1922; M-1 to N-1921; M-1 to A-1920; M-1 to T-1919; M-1 to A-1918; M-1 to A-1917; M-1 to L-1916; M-1 to V-1915; M-1 to D-1914; M-1 to L-1913; M-1 to L-1912; M-1 to K-1911; M-1 to G-1910; M-1 to N-1909; M-1 to C-1908; M-1 to T-1907; M-1 to S-1906; M-1 to I-1905; M-1 to G-1904; M-1 to D-1903; M-1 to G-1902; M-1 to V-1901; M-1 to F-1900; M-1 to G-1899; M-1 to N-1898; M-1 to R-1897; M-1 to C-1896; M-1 to R-1895; M-1 to C-1894; M-1 to A-1893; M-1 to V-1892; M-1 to D-1891; M-1 to Q-1890; M-1 to V-1889; M-1 to R-1888; M-1 to F-1887; M-1 to C-1886; M-1 to Y-1885; M-1 to A-1884; M-1 to D-1883; M-1 to W-1882; M-1 to R-1881; M-1 to E-1880; M-1 to S-1879; M-1 to L-1878; M-1 to N-1877; M-1 to K-1876; M-1 to R-1875; M-1 to A-1874; M-1 to G-1873; M-1 to L-1872; M-1 to S-1871; M-1 to V-1870; M-1 to I-1869; M-1 to G-1868; M-1 to V-1867; M-1 to R-1866 to G-1865 ; M-1 to N-1864; M-1 to G-1863; M-1 to C-1862; M-1 to D-1861; M-1 to A-1860; M-1 to V-1859; M-1 to P-1858; M-1 to F-1857; M-1 to V-1856; M-1 to V-1855; M-1 to P-1854; M-1 to H-1853; M-1 to A-1852; M-1 to T-1851; M-1 to S-1850; M-1 to G-1849; M-1 to N-1848; M-1 to A-1847; M-1 to L-1846; M-1 to W-1845; M-1 to G-1844; M-1 to M-1843; M-1 to L-1842; M-1 to C-1841; M-1 to L-1840; M-1 to H-1839; M-1 to F-1838; M-1 to G-1837; M-1 to L-1836; M-1 to Q-1835; M-1 to Q-1834; M-1 to A-1833; M-1 to A-1832; M-1 to S-1831; M-1 to L-1830; M-1 to Q-1829; M-1 to P-1828; M-1 to F-1827; M-1 to S-1826; M-1 to A-1825; M-1 to L-1824; M-1 to V-1823; M-1 to A-1822; M-1 to G-1821; M-1 to Q-1820; M-1 to A-1819; M-1 to E-1818; M-1 to C-1817; M-1 to A-1816; M-1 to A-1815; M-1 to E-1814; M-1 to A-1813; M-1 to E-1812; M-1 to S-1811; M-1 to F-1810; M-1 to N-1809; M-1 to L-1808; M-1 to G-1807; M-1 to Y-1806; M-1 to P-1805; M-1 to G-1804; M-1 to S-1803; M-1 to T-1802; M-1 to A-1801; M-1 to Q-1800; M-1 to L-1799; M-1 to H-1798; M-1 to I-1797; M-1 to V-1796; M-1 to G-1795; M-1 to A-1794; M-1 to R-1793; M-1 to K-1792; M-1 to E-1791; M-1 to Q-1790; M-1 to F-1789; M-1 to H-1788; M-1 to L-1787; M-1 to D-1786; M-1 to T-1785; M-1 to C-1784; M-1 to M-1783; M-1 to A-1782; M-1 to D-1781; M-1 to S-1780; M-1 to H-1779; M-1 to C-1778; M-1 to P-1777; M-1 to P-1776; M-1 to P-1775; M-1 to Q-1774; M-1 to G-1773; M-1 to L-1772; M-1 to C-1771; M-1 to R-1770; M-1 to D-1769; M-1 to V-1768; M-1 to P-1767; M-1 to P-1766; M-1 to E-1765; M-1 to S-1764; M-1 to E-1763; M-1 to E-1762; M-1 to L-1761; M-1 to C-1760; M-1 to Q-1759; M-1 to L-1758; M-1 to G-1757; M-1 to D-1756; M-1 to G-1755; M-1 to V-1754; M-1 to Y-1753; M-1 to G-1752; M-1 to A-1751:; M-1 to H-1750; M-1 to C-1749; M-1 to E-1748; M-1 to C-1747; M-1 to R-1746; M-1 to R-1745; M-1 to T-1744; M-1 to N-1743; M-1 to L-1742; M-1 to G-1741; M-1 to T-1740; M-1 to S-1739; M-1 to L-1738; M-1 to C-1737; M-1 to N-1736; M-1 to A-1735; M-1 to H-1734; M-1 to E-1733; M-1 to S-1732; M-1 to C-1731; M-1 to G-1730; M-1 to G-1729; M-1 to R-1728; M-1 to H-1727; M-1 to G-1726; M-1 to D-1725; M-1 to T-1724; M-1 to C-1723; M-1 to P-1722; M-1 to N-1721; M-1 to R-1720; M-1 to A-1719; M-1 to R-1718; M-1 to C-1717; M-1 to S-1716; M-1 to W-1715; M-1 to G-1714; M-1 to D-1713; M-1 to G-1712; M-1 to E-1711; M-1 to Y-1710; M-1 to D-1709; M-1 to P-1708; M-1 to L-1707; M-1 to C-1706; M-1 to T-1705; M-1 to C-1704; M-1 to T-1703; M-1 to V-1702; M-1 to M-1701; M-1 to T-1700; M-1 to G-1699; M-1 to V-1698; M-1 to Q-1697; M-1 to S-1696; M-1 to C-1695; M-1 to N-1694; M-1 to A-1693; M-1 to H-1692; M-1 to E-1691; M-1 to S-1690; M-1 to C-1689; M71 to G-1688; M-1 to E-1687; M-1 to H-1686; M-1 to G-1685; M-1 to D-1684; M-1 to Q-1683; M-1 to C-1682; M-1 to L-1681; M-1 to D-1680; M-1 to A-1679; M-1 to V-1678;

M-1 to T-1677; M-1 to C-1676; M-1 to V-1675; M-1 to R-1674; M-1 to G-1673; M-1 to D-1672; M-1 to G-1671; M-1 to E-1670; M-1 to Y-1669; M-1 to G-1668; M-1 to L-1667; M-1 to S-1666; M-1 to C-1665; M-1 to E-1664; M-1 to C-1663; M-1 to S-1662; M-1 to N-1661; M-1 to G-1660; M-1 to A-1659; M-1 to R-1658; M-1 to C-1657; M-1 to V-1656; M-1 to A-1655; M-1 to E-1654; M-1 to P-1653; M-1 to A-1652; M-1 to C-1651; M-1 to P-1650; M-1 to P-1649; M-1 to T-1648; M-1 to C-1647; M-1 to V-1646; M-1 to P-1645; M-1 to Q-1644; M-1 to L-1643; M-1 to E-1642; M-1 to L-1641; M-1 to Q-1640; M-1 to V-1639; M-1 to E-1638; M-1 to C-1637; M-1 to R-1636; M-1 to P-1635; M-1 to G-1634; M-1 to T-1633; M-1 to W-1632; M-1 to G-1631; M-1 to E-1630; M-1 to D-1629; M-1 to C-1628; M-1 to F-1627; M-1 to C-1626; M-1 to S-1625; M-1 to G-1624; M-1 to S-1623; M-1 to G-1622; M-1 to G-1621; M-1 to L-1620; M-1 to G-1619; M-1 to E-1618; M-1 to D-1617; M-1 to C-1616; M-1 to R-1615; M-1 to G-1614; M-1 to H-1613; M-1 to V-1612; M-1 to T-1611; M-1 to C-1610; M-1 to R-1609; M-1 to C-1608; M-1 to A-1607; M-1 to Q-1606; M-1 to C-1605; M-1 to H-1604; M-1 to P-1603; M-1 to G-1602; M-1 to F-1601; M-1 to A-1600; M-1 to G-1599; M-1 to P-1598; M-1 to A-1597; M-1 to C-1596; M-1 to L-1595; M-1 to E-1594; M-1 to C-1593; M-1 -to A-1592; M-1 to T-1591; M-1 to G-1590; M-1 to A-1589; M-1 to F-1588; M-1 to G-1587; M-1 to S-1586; M-1 to R-1585; M-1 to C-1584; M-1 to L-1583; M-1 to C-1582; M-1 to Q-1581; M-1 to G-1580; M-1 to S-1579; M-1 to G-1578; M-1 to S-1577; M-1 to M-1576; M-1 to G-1575; M-1 to D-1574; M-1 to M-1573; M-1 to C-1572; M-1 to V-1571; M-1 to G-1570; M-1 to R-1569; M-1 to D-1568; M-1 to S-1567; M-1 to C-1566; M-1 to P-1565; M-1 to S-1564; M-1 to S-1563; M-1 to P-1562; M-1 to G-1561; M-1 to G-1560; M-1 to P-1559; M-1 to C-1558; M-1 to A-1557; M-1 to Q-1556; M-1 to C-1555; M-1 to E-1554; M-1 to S-1553; M-1 to G-1552; M-1 to Y-1551; M-1 to H-1550; M-1 to G-1549; M-1 to P-1548; M-1 to C-1547; M-1 to C-1546; M-1 to S-1545; M-1 to P-1544; M-1 to K-1543; M-1 to W-1542; M-1 to T-1541; M-1 to T-1540; M-1 to T-1539; M-1 to V-1538; M-1 to C-1537; M-1 to N-1536; M-1 to R-1535; M-1 to H-1534; M-1 to C-1533; M-1 to G-1532; M-1 to R-1531; M-1 to G-1530; M-1 to L-1529; M-1 to G-1528; M-1 to Q-1527; M-1 to P-1526; M-1 to R-1525; M-1 to G-1524; M-1 to W-1523; M-1 to L-1522; M-1 to S-1521; M-1 to P-1520; M-1 to H-1519; M-1 to V-1518; M-1 to W-1517; M-1 to V-1516; M-1 to S-1515; M-1 to R-1514; M-1 to L-1513; M-1 to G-1512; M-1 to L-1511; M-1 to S-1510; M-1 to H-1509; M-1 to L-1508; M-1 to P-1507; M-1 to P-1506; M-1 to S-1505; M-1 to T-1504; M-1 to W-1503; M-1 to F-1502; M-1 to K-1501; M-1 to P-1500; M-1 to Y-1499; M-1 to F-1498; M-1 to R-1497; M-1 to W-1496; M-1 to C-1495; M-1 to A-1494; M-1 to E-1493; M-1 to P-1492; M-1 to S-1491; M-1 to G-1490; M-1 to Q-1489; M-1 to E-1488; M-1 to Q-1487; M-1 to S-1486; M-1 to G-1485; M-1 to E-1484; M-1 to P-1483; M-1 to C-1482; M-1 to P-1481; M-1 to P-1480; M-1 to E-1479; M-1 to L-1478; M-1 to G-1477; M-1 to C-1476; M-1 to I-1475; M-1 to S-1474; M-1 to C-1473; M-1 to T-1472; M-1 to N-1471; M-1 to L-1470; M-1 to R-1469; M-1 to L-1468; M-1 to P-1467; M-1 to R-1466; M-1 to T-1465; M-1 to E-1464; M-1 to F-1463; M-1 to H-1462; M-1 to D-1461; M-1 to C-1460; M-1 to R-1459; M-1 to A-1458; M-1 to G-1457; M-1 to L-1456; M-1 to G-1455; M-1 to P-1454; M-1 to P-1453; M-1 to E-1452; M-1 to L-1451; M-1 to L-1450; M-1 to Q-1449; M-1 to D-1448; M-1 to I-1447; M-1 to G-1446; M-1 to Y-1445; M-1 to A-1444; M-1 to L-1443; M-1 to G-1442; M-1 to G-1441; M-1 to E-1440; M-1 to F-1439; M-1 to P-1438; M-1 to L-1437; M-1 to H-1436; M-1 to R-1435; M-1 to Q-1434; M-1 to V-1433; M-1 to I-1432; M-1 to R-1431; M-1 to A-1430; M-1 to D-1429; M-1 to D-1428; M-1 to E-1427; M-1 to G-1426; M-1 to V-1425; M-1 to M-1424; M-1 to L-1423; M-1 to E-1422; M-1 to G-1421; M-1 to P-1420; M-1 to R-1419; M-1 to T-1418; M-1 to R-1417; M-1 to S-1416; M-1 to C-1415; M-1 to S-1414; M-1 to F-1413; M-1 to S-1412; M-1 to I-1411; M-1 to P-1410; M-1 to T-1409; M-1 to G-1408; M-1 to H-1407; M-1 to M-1406; M-1 to T-1405; M-1 to R-1404; M-1 to L-1403; M-1 to P-1402; M-1 to G-1401; M-1 to L-1400; M-1 to N-1399; M-1 to P-1398; M-1 to L-1397; M-1 to D-1396; M-1 to S-1395; M-1 to A-1394; M-1 to L-1393; M-1 to A-1392; M-1 to E-1391; M-1 to V-1390; M-1 to N-1389; M-1 to R-1388; M-1 to I-1387; M-1 to M-1386; M-1 to H-1385; M-1 to G-1384; M-1 to R-1383; M-1 to L-1382; M-1 to I-1381; M-1 to A-1380; M-1 to A-1379; M-1 to L-1378; M-1 to K-1377; M-1 to D-1376; M-1 to R-1375; M-1 to H-1374; M-1 to D-1373; M-1 to E-1372; M-1 to H-1371; M-1 to Y-1370; M-1 to L-1369; M-1 to W-1368; M-1 to A-1367; M-1 to Q-1366; M-1 to R-1365; M-1 to D-1364; M-1 to P-1363; M-1 to P-1362; M-1 to L-1361; M-1 to A-1360; M-1 to R-1359; M-1 to F-1358; M-1 to A-1357; M-1 to A-1356; M-1 to D-1355; M-1 to T-1354; M-1 to P-1353; M-1 to W-1352; M-1 to L-1351; M-1 to M-1350; M-1 to T-1349; M-1 to F-1348; M-1 to P-1347; M-1 to R-1346; M-1 to H-1345; M-1 to S-1344; M-1 to A-1343; M-1 to E-1342; M-1 to R-1341; M-1 to L-1340; M-1 to L-1339; M-1 to P-1338; M-1 to L-1337; M-1 to L-1336; M-1 to G-1335; M-1 to A-1334; M-1 to V-1333; M-1 to K-1332; M-1 to L-1331; M-1 to L-1330; M-1 to G-1329; M-1 to S-1328; M-1 to F-1327; M-1 to I-1326; M-1 to K-1325; M-1 to Y-1324; M-1 to G-1323; M-1 to F-1322; M-1 to G-1321; M-1 to Q-1320; M-1 to A-1319; M-1 to A-1318; M-1 to A-1317; M-1 to T-1316; M-1 to V-1315; M-1 to N-1314; M-1 to R-1313; M-1 to R-1312; M-1 to P-1311; M-1 to I-1310; M-1 to P-1309; M-1 to A-1308; M-1 to D-1307; M-1 to D-1306; M-1 to P-1305; M-1 to E-1304; M-1 to W-1303; M-1 to H-1302; M-1 to L-1301; M-1 to A-1300; M-1 to E-1299; M-1 to P-1298; M-1 to P-1297; M-1 to L-1296; M-1 to L-1295; M-1 to V-1294; M-1 to R-1293; M-1 to D-1292; M-1 to I-1291; M-1 to F-1290; M-1 to H-1289; M-1 to L-1288; M-1 to I-1287; M-1 to G-1286; M-1 to N-1285; M-1 to V-1284; M-1 to A-1283; M-1 to E-1282; M-1 to H-1281; M-1 to D-1280; M-1 to S-1279; M-1 to S-1278; M-1 to V-1277; M-1 to V-1276; M-1 to R-1275; M-1 to A-1274; M-1 to F-1273; M-1 to D-1272; M-1 to N-1271; M-1 to L-1270; M-1 to Y-1269; M-1 to I-1268; M-1 to S-1267; M-1 to G-1266; M-1 to E-1265; M-1 to R-1264; M-1 to E-1263; M-1 to S-1262; M-1 to F-1261; M-1 to R-1260; M-1 to L-1259; M-1 to P-1258; M-1 to H-1257; M-1 to G-1256; M-1 to S-1255; M-1 to L-1254; M-1 to A-1253; M-1 to T-1252; M-1 to A-1251; M-1 to Y-1250; M-1 to G-1249; M-1 to Q-1248; M-1 to E-1247; M-1 to L-1246; M-1 to L-1245; M-1 to D-1244; M-1 to E-1243; M-1 to S-1242; M-1 to R-1241; M-1 to L-1240; M-1 to R-1239; M-1 to R-1238; M-1 to C-1237; M-1 to G-1236; M-1 to V-1235; M-1 to V-1234; M-1 to H-1233; M-1 to Y-1232; M-1 to R-1231; M-1 to F-1230; M-1 to V-1229; M-1 to L-1228; M-1 to Q-1227; M-1 to R-1226; M-1 to H-1225; M-1 to A-1224; M-1 to R-1223; M-1 to I-1222; M-1 to R-1221; M-1 to A-1220; M-1 to L-1219; M-1 to E-1218; M-1 to D-1217; M-1 to Q-1216; M-1 to S-1215; M-1 to L-1214; M-1 to N-1213; M-1 to S-1212; M-1 to M-1211; M-1 to L-1210; M-1 to D-1209; M-1 to A-1208; M-1 to H-1207; M-1 to P-1206; M-1 to V-1205; M-1 to

F-1204; M-1 to I-1203; M-1 to T-1202; M-1 to F-1201; M-1 to P-1200; M-1 to G-1199; M-1 to D-1198; M-1 to G-1197; M-1 to K-1196; M-1 to L-1195; M-1 to E-1194; M-1 to K-1193; M-1 to Y-1192; M-1 to E-1191; M-1 to L-1190; M-1 to L-1189; M-1 to R-1188; M-1 to L-1187; M-1 to S-1186; M-1 to F-1185; M-1 to F-1184; M-1 to S-1183; M-1 to A-1182; M-1 to H-1181; M-1 to K-1180; M-1 to D-1179; M-1 to R-1178; M-1 to L-1177; M-1 to L-1176; M-1 to E-1175; M-1 to L-1174; M-1 to G-1173; M-1 to V-1172; M-1 to R-1171; M-1 to A-1170; M-1 to R-1169; M-1 to C-1168; M-1 to T-1167; M-1 to L-1166; M-1 to G-1165; M-1 to D-1164; M-1 to G-1163; M-1 to V-1162; M-1 to T-1161; M-1 to H-1160; M-1 to A-1159; M-1 to T-1158; M-1 to D-1157; M-1 to C-1156; M-1 to T-1155; M-1 to C-1154; M-1 to T-1153; M-1 to R-1152; M-1 to Q-1151; M-1 to G-1150; M-1 to D-1149; M-1 to G-1148; M-1 to T-1147; M-1 to S-1146; M-1 to K-1145; M-1 to C-1144; M-1 to T-1143; M-1 to A-1142; M-1 to Y-1141; M-1 to P-1140; M-1 to S-1139; M-1 to C-1138; M-1 to G-1137; M-1 to G-1136; M-1 to N-1135; M-1 to N-1134; M-1 to K-1133; M-1 to S-1132; M-1 to C-1131; M-1 to P-1130; M-1 to D-1129; M-1 to L-1128; M-1 to L-1127; M-1 to E-1126; M-1 to C-1125; M-1 to T-1124; M-1 to R-1123; M-1 to I-1122; M-1 to G-1121; M-1 to D-1120; M-1 to G-1119; M-1 to S-1118; M-1 to Y-1117; M-1 to G-1116; M-1 to E-1115; M-1 to R-1114; M-1 to C-1113; M-1 to S-1112; M-1 to C-1111; M-1 to S-1110; M-1 to V-1109; M-1 to Q-1108; M-1 to Q-1107; M-1 to P-1106; M-1 to G-1105; M-1 to T-1104; M-1 to P-1103; M-1 to I-1102; M-1 to C-1101; M-1 to E-1100; M-1 to A-1099; M-1 to H-1098; M-1 to I-1097; M-1 to H-1096; M-1 to C-1095; M-1 to G-1094; M-1 to G-1093; M-1 to H-1092; M-1 to H-1091; M-1 to I-1090; M-1 to L-1089; M-1 to C-1088; M-1 to S-1087; M-1 to N-1086; M-1 to I-108s; M-1 to E-1084; M-1 to Q-1083; M-1 to C-1082; M-1 to L-1081; M-1 to E-1080; M-1 to G-1079; M-1 to D-1078; M-1 to G-1077; M-1 to M-1076; M-1 to Y-1075; M-1 to G-1074; M-1 to D-1073; M-1 to Q-1072; M-1 to C-1071; M-1 to T-1070; M-1 to C-1069; M-1 to T-1068; M-1 to R-1067; M-1 to Q-1066; M-1 to G-1065; M-1 to P-1064; M-1 to A-1063; M-1 to V-1062; M-1 to K-1061; M-1 to T-1060; M-1 to C-1059; M-1 to N-1058; M-1 to A-1057; M-1 to H-1056; M-1 to P-1055; M-1 to S-1054; M-1 to C-1053; M-1 to G-1052; M-1 to G-1051; M-1 to H-1050; M-1 to G-1049; M-1 to H-1048; M-1 to A-1047; M-1 to C-1046; M-1 to P-1045; M-1 to D-1044; M-1 to V-1043; M-1 to E-1042; M-1 to S-1041; M-1 to C-1040; M-1 to F-1039; M-1 to I-1038; M-1 to G-1037; M-1 to N-1036; M-1 to G-1035; M-1 to S-1034; M-1 to Y-1033; M-1 to G-1032; M-1 to A-1031; M-1 to A-1030; M-1 to C-1029; M-1 to A-1028; M-1 to C-1027; M-1 to T-1026; M-1 to S-1025; M-1 to A-1024; M-1 to G-1023; M-1 to A-1022; M-1 to S-1021; M-1 to D-1020; M-1 to Q-1019; M-1 to V-1018; M-1 to C-1017; M-1 to N-1016; M-1 to A-1015; M-1 to N-1014; M-1 to P-1013; M-1 to D-1012; M-1 to C-1011; M-1 to K-1010; M-1 to R-1009; M-1 to P-1008; M-1 to C-1007; M-1 to Q-1006; M-1 to P-1005; M-1 to S-1004; M-1 to T-1003; M-1 to I-1002; M-1 to K-1001; M-1 to Q-1000; M-1 to D-999; M-1 to C-998; M-1 to R-997; M-1 to L-996; M-1 to G-995; M-1 to Q-994; M-1 to W-993; M-1 to G-992; M-1 to V-991; M-1 to N-990; M-1 to C-989; M-1 to V-988; M-1 to C-987; M-1 to S-986; M-1 to G-985; M-1 to D-984; M-1 to G-983; M-1 to Q-982; M-1 to L-981; M-1 to G-980; M-1 to E-979; M-1 to Q-978; M-1 to C-977; M-1 to L-976; M-1 to G-975; M-1 to H-974; M-1 to A-973; M-1 to C-972; M-1 to D-971; M-1 to C-970; M-1 to V-969; M-1 to G-968; M-1 to T-967; M-1 to C-966; M-1 to N-965; M-1 to P-964; M-1 to G-963; M-1 to Y-962; M-1 to R-961; M-1 to G-960; M-1 to L-959; M-1 to E-958; M-1 to C-957; M-1 to V-956; M-1 to E-955; M-1 to C-954; M-1 to A-953; M-1 to T-952; M-1 to G-951; M-1 to H-950; M-1 to F-949; M-1 to G-948; M-1 to E-947; M-1 to H-946; M-1 to C-945; M-1 to H-944; M-1 to C-943; M-1 to E-942; M-1 to G-941; M-1 to S-940; M-1 to G-939; M-1 to L-938; M-1 to F-937; M-1 to R-936; M-1 to D-935; M-1 to Q-934; M-1 to C-933; M-1 to Q-932; M-1 to G-931; M-1 to H-930; M-1 to G-929; M-1 to S-928; M-1 to C-927; M-1 to V-926; M-1 to G-925; M-1 to G-924; M-1 to L-923; M-1 to G-922; M-1 to G-921; M-1 to P-920; M-1 to C-919; M-1 to P-918; M-1 to E-917; M-1 to C-916; M-1 to L-915; M-1 to T-914; M-1 to G-913; M-1 to F-912; M-1 to F-911; M-1 to G-910; M-1 to P-909; M-1 to C-908; M-1 to C-907; M-1 to D-906; M-1 to P-905; M-1 to V-904; M-1 to Q-903; M-1 to I-902; M-1 to K-901; M-1 to K-900; M-1 to A-899; M-1 to C-898; M-1 to T-897; M-1 to Y-896; M-1 to S-895; M-1 to C-894; M-1 to G-893; M-1 to R-892; M-1 to S-891; M-1 to F-890; M-1 to S-889; M-1 to F-888; M-1 to G-887; M-1 to S-886; M-1 to R-885; M-1 to Y-884; M-1 to V-883; M-1 to C-882; M-1 to S-881; M-1 to K-880; M-1 to R-879; M-1 to P-878; M-1 to T-877; M-1 to D-876; M-1 to Q-875; M-1 to L-874; M-1 to Q-873; M-1 to F-872; M-1 to G-871; M-1 to Q-870; M-1 to T-869; M-1 to C-868; M-1 to R-867; M-1 to F-866; M-1 to R-865; M-1 to R-864; M-1 to T-863; M-1 to C-862; M-1 to N-861; M-1 to V-860; M-1 to C-859; M-1 to K-858; M-1 to E-857; M-1 to R-856; M-1 to L-855; M-1 to A-854; M-1 to E-853; M-1 to A-852; M-1 to H-851; M-1 to S-850; M-1 to H-849; M-1 to L-848; M-1 to C-847; M-1 to R-846; M-1 to S-845; M-1 to S-844; M-1 to G-843; M-1 to V-842; M-1 to T-841; M-1 to L-840; M-1 to V-839; M-1 to G-838; M-1 to S-837; M-1 to L-836; M-1 to G-835; M-1 to I-834; M-1 to L-833; M-1 to S-832; M-1 to R-831; M-1 to 0G-830; M-1 to P-829; M-1 to A-828; M-1 to E-827; M-1 to L-826; M-1 to M-825; M-1 to P-824; M-1 to G-823; M-1 to E-822; M-1 to L-821; M-1 to P-820; M-1 to V-819; M-1 to H-818; M-1 to N-817; M-1 to V-816; M-1 to E-815; M-1 to P-814; M-1 to Q-813; M-1 to G-812; M-1 to S-811; M-1 to H-810; M-1 to N-809; M-1 to Y-808; M-1 to F-807; M-1 to V-806; M-1 to I-805; M-1 to W-804; M-1 to H-803; M-1 to A-802; M-1 to P-801; M-1 to G-800; M-1 to L-799; M-1 to L-798; M-1 to S-797; M-1 to N-796; M-1 to R-795; M-1 to H-794; M-1 to G-793; M-1 to G-792; M-1 to K-791; M-1 to R-790; M-1 to L-789; M-1 to T-788; M-1 to E-787; M-1 to M-786; M-1 to S-785; M-1 to L-784; M-1 to A-783; M-1 to E-782; M-1 to G-781; M-1 to L-780; M-1 to V-779; M-1 to V-778; M-1 to H-777; M-1 to H-776; M-1 to 1 R-775; M-1 to V-774; M-1 to T-773; M-1 to D-772; M-1 to A-771; M-1 to D-770; M-1 to L-769; M-1 to H-768; M-1 to S-767; M-1 to S-766; M-1 to N-765; M-1 to G-764; M-1 to Q-763; M-1 to A-762; M-1 to E-761; M-1 to L-760; M-1 to S-759; M-1 to R-758; M-1 to N-757; M-1 to T-756; M-1 to P-755; M-1 to V-754; M-1 to F-753; M-1 to I-752; M-1 to T-751; M-1 to Y-750; M-1 to A-749; M-1 to T-748; M-1 to A-747; M-1 to A-746; M-1 to E-745; M-1 to I-744; M-1 to Q-743; M-1 to P-742; M-1 to V-741; M-1 to L-740; M-1 to G-739; M-1 to H-738; M-1 to H-737; M-1 to Q-736; M-1 to L-735; M-1 to L-734; M-1 to E-733; M-1 to R-732; M-1 to F-731; M-1 to L-730; M-1 to S-729; M-1 to F-728; M-1 to A-727; M-1 to P-726; M-1 to V-725; M-1 to L-724; M-1 to D-723; M-1 to L-722; M-1 to Q-721; M-1 to Q-720; M-1 to L-719; M-1 to L-718; M-1 to G-717; M-1 to Q-716; M-1 to G-715; M-1 to G-714; M-1 to P-713; M-1 to V-712; M-1 to D-711; M-1 to G-710; M-1 to R-709; M-1 to P-708; M-1 to P-707; M-1 to L-706; M-1 to L-705; M-1 to V-704; M-1 to Q-703; M-1 to S-702; M-1 to L-701; M-1 to I-700; M-1 to H-699; M-1 to L-698; M-1 to V-697; M-1 to G-696; M-1 to N-695; M-1 to T-694; M-1 to A-693; M-1 to L-692; M-1 to L-691; M-1 to D-690; M-1 to A-689; M-1 to V-688; M-1 to D-687; M-1 to V-686; M-1 to S-685; M-1 to A-684; M-1 to N-683; M-1 to Q-682; M-1 to V-681; M-1 to W-680; M-1 to V-679; M-1 to R-678; M-1 to G-677; M-1 to S-676; M-1 to I-675; M-1 to N-674; M-1 to R-673; M-1 to I-672; M-1 to E-671; M-1 to W-670; M-1 to R-669; M-1 to T-668; M-1 to T-667; M-1 to P-666; M-1 to N-665; M-1 to L-664; M-1 to T-663; M-1 to A-662; M-1 to V-661; M-1 to E-660; M-1 to Q-659; M-1 to G-658; M-1 to G-657; M-1 to L-656; M-1 to R-655; M-1 to A-654; M-1 to L-653; M-1 to E-652; M-1 to E-651; M-1 to E-650; M-1 to F-649; M-1 to L-648; M-1 to A-647; M-1 to G-646; M-1 to Q-645; M-1 to L-644; M-1 to F-643; M-1 to H-642; M-1 to A-641; M-1 to R-640; M-1 to V-639; M-1 to L-638; M-1 to N-637; M-1 to P-636; M-1 to L-635; M-1 to T-634; M-1 to R-633; M-1 to P-632; M-1 to Q-631; M-1 to L-630; M-1 to W-629; M-1 to F-628; M-1 to A-627; M-1 to R-626; M-1 to D-625; M-1 to E-624; M-1 to P-623; M-1 to S-622; M-1 to L-621; M-1 to Q-620; M-1 to R-619; M-1 to V-618; M-1 to A-617; M-1 to A-616; M-1 to E-615; M-1 to S-614; M-1 to P-613; M-1 to V-612; M-1 to L-61 ; M-1 to A-610; M-1 to T-609; M-1 to V-608; M-1 to R-607; M-1 to R-606; M-1 to D-605; M-1 to A-604; M-1 to P-603; M-1 to L-602; M-1 to T-601; M-1 to I-600; M-1 to G-599; M-1 to A-598; M-1 to S-597; M-1 to K-596; M-1 to L-595; M-1 to W-594; M-1 to Q-593; M-1 to Y-592; M-1 to F-591; M-1 to I-590; M-1 to S-589; M-1 to F-588; M-1 to H-587; M-1 to A-586; M-1 to N-585; M-1 to A-584; M-1 to E-583; M-1 to L-582; M-1 to E-581; M-1 to L-580; M-1 to G-579; M-1 to H-578; M-1 to C-577; M-1 to G-576; M-1 to G-575; M-1 to N-574; M-1 to G-573; M-1 to A-572; M-1 to R-571; M-1 to C-570; M-1 to P-569; M-1 to D-568; M-1 to I-567; M-1 to P-566; M-1 to S-565; M-1 to C-564; M-1 to Q-563; M-1 to Y-562; M-1 to G-561; M-1 to D-560; M-1 to G-559; M-1 to A-558; M-1 to F-557; M-1 to G-556; M-1 to L-555; M-1 to K-554; M-1 to C-553; M-1 to T-552; M-1 to C-551; M-1 to R-550; M-1 to S-549; M-1 to Q-548; M-1 to G-547; M-1 to P-546; M-1 to G-545; M-1 to V-544; M-1 to Y-543; M-1 to S-542; M-1 to C-541; M-1 to L-540; M-1 to A-539; M-1 to D-538; M-1 to T-537; M-1 to H-536; M-1 to C-535; M-1 to G-534; M-1 to G-533; M-1 to R-532; M-1 to V-531; M-1 to D-530; M-1 to L-529; M-1 to E-528; M-1 to C-527; M-1 to E-526; M-1 to D-525; M-1 to I-524; M-1 to A-523; M-1 to V-522; M-1 to C-521; M-1 to V-520; M-1 to R-519; M-1 to G-518; M-1 to D-517; M-1 to G-516; M-1 to S-515; M-1 to W-514; M-1 to G-513; M-1 to K-512; M-1 to H-511; M-1 to C-510; M-1 to T-509; M-1 to C-508; M-1 to H-507; M-1 to H-506; M-1 to T-505; M-1 to G-504; M-1 to L-503; M-1 to S-502; M-1 to G-501; M-1 to P-500; M-1 to V-499; M-1 to C-498; M-1 to E-497; M-1 to A-496; M-1 to N-495; M-1 to E-494; M-1 to S-493; M-1 to C-492; M-1 to G-491; M-1 to G-490; M-1 to R-489; M-1 to D-488; M-1 to P-487; M-1 to H-486; M-1 to S-485; M-1 to C-484; M-1 to P-483; M-1 to N-482; M-1 to S-481; M-1 to P-480; M-1 to T-479; M-1 to C-478; M-1 to S-477; M-1 to F-476; M-1 to G-475; M-1 to D-474; M-1 to G-473; M-1 to E-472; M-1 to F-471; M-1 to G-470; M-1 to D-469; M-1 to L-468; M-1 to C-467; M-1 to R-466; M-1 to C-465; M-1 to R-464; M-1 to A-463; M-1 to V-462; M-1 to G-461; M-1 to E-460; M-1 to Q-459; M-1 to S-458; M-1 to V-457; M-1 to C-456; M-1 to R-455; M-1 to A-454; M-1 to H-453; M-1 to L-452; M-1 to H-451; M-1 to C-450; M-1 to H-449; M-1 to Q-448; M-1 to A-447; M-1 to L-446; M-1 to G-445; M-1 to T-444; M-1 to P-443; M-1 to G-442; M-1 to C-441; M-1 to D-440; M-1 to G-439; M-1 to M-438; M-1 to S-437; M-1 to E-436; M-1 to N-435; M-1 to C-434; M-1 to F-433; M-1 to R-432; M-1 to G-431; M-1 to S-430; M-1 to F-429; M-1 to G-428; M-1 to P-427; M-1 to A-426; M-1 to C-425; M-1 to T-424; M-1 to G-423; M-1 to Q-422; M-1 to Q-421; M-1 to C-420; M-1 to V-419; M-1 to G-418; M-1 to G-417; M-1 to S-416; M-1 to G-415; M-1 to P-414; M-1 to R-413; M-1 to N-412; M-1 to D-411; M-1 to C-410; M-1 to L-409; M-1 to G-408; M-1 to H-407; M-1 to V-406; M-1 to C-405; M-1 to G-404; M-1 to C-403; M-1 to D-402; M-1 to E-401; M-1 to Q-400; M-1 to C-399; M-1 to Q-398; M-1 to E-397; M-1 to G-396; M-1 to H-395; M-1 to K-394; M-1 to N-393; M-1 to P-392; M-1 to N-391; M-1 to S-390; M-1 to C-389; M-1 to I-388; M-1 to H-387; M-1 to C-386; M-1 to A-385; M-1 to I-384; M-1 to G-383; M-1 to K-382; M-1 to Y-381; M-1 to D-380; M-1 to P-379; M-1 to F-378; M-1 to C-377; M-1 to L-376; M-1 to C-375; M-1 to A-374; M-1 to G-373; M-1 to N-372; M-1 to G-371; M-1 to Q-370; M-1 to I-369; M-1 to G-368; M-1 to D-367; M-1 to S-366; M-1 to C-365; M-1 to N-364; M-1 to G-363; M-1 to K-362; M-1 to G-361; M-1 to Y-360; M-1 to C-359; M-1 to P-358; M-1 to N-357; M-1 to S-356; M-1 to F-355; M-1 to G-354; M-1 to G-353; M-1 to P-352; M-1 to C-351; M-1 to Q-350; M-1 to T-349; M-1 to C-348; M-1 to D-347; M-1 to P-346; M-1 to G-345; M-1 to F-344; M-1 to F-343; M-1 to G-342; M-1 to K-341; M-1 to C-340; M-1 to C-339; M-1 to G-338; M-1 to Q-337; M-1 to E-336; M-1 to M-335; M-1 to I-334; M-1 to T-333; M-1 to Q-332; M-1 to N-331; M-1 to C-330; M-1 to Y-329; M-1 to S-328; M-1 to A-327; M-1 to C-326; M-1 to G-325; M-1 to K-324; M-1 to K-323; M-1 to L-322; M-1 to V-321; M-1 to N-320; M-1 to L-319; M-1 to G-318; M-1 to T-317; M-1 to P-316; M-1 to D-315; M-1 to H-314; M-1 to I-313; M-1 to Y-312; M-1 to V-311; M-1 to C-310; M-1 to E-309; M-1 to K-308; M-1 to P-307; M-1 to F-306; M-1 to I-305; M-1 to D-304; M-1 to L-303; M-1 to K-302; M-1 to V-301; M-1 to S-300; M-1 to N-299; M-1 to P-298; M-1 to P-297; M-1 to C-296; M-1 to T-295; M-1 to S-294; M-1 to T-293; M-1 to N-292; M-1 to L-291; M-1 to A-290; M-1 to Q-289; M-1 to C-288; M-1 to D-287; M-1 to V-286; M-1 to C-285; M-1 to S-284; M-1 to G-283; M-1 to A-282; M-1 to V-281; M-1 to I-280; M-1 to K-279; M-1 to H-278; M-1 to Q-277; M-1 to E-276; M-1 to E-275; M-1 to S-274; M-1 to C-273; M-1 to H-272; M-1 to K-271; M-1 to P-270; M-1 to L-269; M-1 to I-268; M-1 to P-267; M-1 to L-266; M-1 to I-265; M-1 to T-264; M-1 to P-263; M-1 to P-262; M-1 to L-261; M-1 to L-260; M-1 to I-259; M-1 to G-258; M-1 to D-257; M-1 to L-256; M-1 to M-255; M-1 to H-254; M-1 to I-253; M-1 to V-252; M-1 to G-251; M-1 to N-250; M-1 to A-249; M-1 to A-248; M-1 to M-247; M-1 to V-246; M-1 to D-245; M-1 to V-244; M-1 to R-243; M-1 to Q-242; M-1 to L-241; M-1 to P-240; M-1 to V-239; M-1 to G-238; M-1 to E-237; M-1 to P-236; M-1 to G-235; M-1 to L-234; M-1 to L-233; M-1 to I-232; M-1 to R-231; M-1 to G-230; M-1 to E-229; M-1 to E-228; M-1 to S-227; M-1 to I-226; M-1 to N-225; M-1 to V-224; M-1 to A-223; M-1 to L-222; M-1 to V-221; M-1 to Q-220; M-1 to N-219; M-1 to A-218; M-1 to M-217; M-1 to T-216; M-1 to L-215; M-1 to I-214; M-1 to R-213; M-1 to G-212; M-1 to K-211; M-1 to S-210; M-1 to I-209; M-1 to L-208; M-1 to K-207; M-1 to E-206; M-1 to V-205; M-1 to T-204; M-1 to L-203; M-1 to Q-202; M-1 to G-201; M-1 to H-200; M-1 to N-199; M-1 to Y-198; M-1 to I-197; M-1 to H-196; M-1 to Y-195; M-1 to R-194; M-1 to V-193; M-1 to L-192; M-1 to E-191; M-1 to Q-190; M-1 to L-189; M-1 to K-188; M-1 to S-187; M-1 to L-186; M-1 to G-185; M-1 to A-184; M-1 to T-183; M-1 to F-182; M-1 to L-181; M-1 to Y-180; M-1 to I-179; M-1 to I-178; M-1 to R-177; M-1 to G-176; M-1 to D-175; M-1 to R-174; M-1 to L-173; M-1 to S-172; M-1 to D-171; M-1 to V-170; M-1 to A-169; M-1 to E-168; M-1 to N-167; M-1 to S-166; M-1 to P-165; M-1 to A-164; M-1 to F-163; M-1 to V-162; M-1 to T-161; M-1 to F-160; M-1 to P-159; M-1 to G-158; M-1 to P-157; M-1 to

G-156; M-1 to D-155; M-1 to L-154; M-1 to I-153; M-1 to S-152; M-1 to P-151; M-1 to L-150; M-1 to G-149; M-1 to C-148; M-1 to N-147; M-1 to E-146; M-1 to L-145; M-1 to I-144; M-1 to T-143; M-1 to E-142; M-1 to F-141; M-1 to R-140; M-1 to S-139; M-1 to F-138; M-1 to A-137; M-1 to E-136; M-1 to T-135; M-1 to S-134; M-1 to A-133; M-1 to L-132; M-1 to I-131; M-1 to Q-130; M-1 to G-129; M-1 to I-128; M-1 to T-127; M-1 to R-126; M-1 to K-125; M-1 to P-124; M-1 to D-123; M-1 to G-122; M-1 to P-121; M-1 to T-120; M-1 to G-119; M-1 to S-118; M-1 to P-117; M-1 to A-116; M-1 to Q-115; M-1 to W-114; M-1 to R-113; M-1 to L-112; M-1 to G-111; M-1 to T-110; M-1 to V-109; M-1 to V-108; M-1 to H-107; M-1 to F-106; M-1 to V-105; M-1 to G-104; M-1 to N-103; M-1 to A-102; M-1 to A-101; M-1 to I-100; M-1 to N-99; M-1 to N-98; M-1 to A-97; M-1 to K-96; M-1 to Y-95; M-1 to I-94; M-1 to N-93; M-1 to F-92; M-1 to T-91; M-1 to Q-90; M-1 to Q-89; M-1 to P-88; M-1 to Q-87; M-1 to D-86; M-1 to K-85; M-1 to Y-84; M-1 to K-83; M-1 to Y-82; M-1 to S-81; M-1 to Y-80; M-1 to K-79; M-1 to T-78; M-1 to F-77; M-1 to Q-76; M-1 to N-75; M-1 to F-74; M-1 to T-73; M-1 to V-72; M-1 to T-71; M-1 to I-70; M-1 to E-69; M-1 to Q-68; M-1 to G-67; M-1 to A-66; M-1 to L-65; M-1 to T-64; M-1 to W-63; M-1 to W-62; M-1 to R-61; M-1 to R-60; M-1 to T-59; M-1 to Q-58; M-1 to Q-57; M-1 to T-56; M-1 to R-55; M-1 to T-54; M-1 to D-53; M-1 to E-52; M-1 to L-51; M-1 to I-50; M-1 to H-49; M-1 to Q-48; M-1 to G-47; M-1 to A-46; M-1 to I-45; M-1 to I-44; M-1 to H-43; M-1 to Q-42; M-1 to R-41; M-1 to C-40; M-1 to L-39; M-1 to Q-38; M-1 to Q-37; M-1 to A-36; M-1 to L-35; M-1 to S-34; M-1 to A-33; M-1 to N-32; M-1 to M-31; M-1 to T-30; M-1 to R-29; M-1 to S-28; M-1 to S-27; M-1 to F-26; M-1 to S-25; M-1 to S-24; M-1 to V-23; M-1 to S-22; M-1 to P-21; M-1 to V-20; M-1 to L-19; M-1 to V-18; M-1 to T-17; M-1 to F-16; M-1 to P-15; M-1 to G-14; M-1 to A-13; M-1 to T-12; M-1 to T-11; M-1 to L-10; M-1 to I-9; M-1 to E-8; M-1 to R-7; M-1 to C-6; of SEQ ID NO:2. Polynucleotides encoding these polypeptides are also encompassed by the invention.

In one embodiment, the present invention further provides polypeptides having one or more residues deleted from the amino terminus of the amino acid sequence of the WF-HABP polypeptide depicted in FIGS. 2A–D (SEQ ID NO:5) or encoded by the cDNA of the deposited clone. Particularly, in one embodiment, N-terminal deletions of the WF-HABP polypeptide can be described by the general formula m to 457, where m is an integer from 1 to 456 corresponding to the position of amino acids identified in SEQ ID NO:5 and preferably, corresponds to one of the N-terminal amino acid residues identified in the N-terminal deletions specified herein. In specific embodiments, N-terminal deletions of the WF-HABP polypeptide of the invention comprise, or alternatively, consist of, amino acid residues: N-terminal deletions of the WF-HABP polypeptide of the invention shown as SEQ ID NO:5 include polypeptides comprising the amino acid sequence of residues: V-2 to K-457; T-3 to K-457, C-4 to K-457; T-5 to K-457; C-6 to K-457; L-7 to K-457; P-8 to K-457; D-9 to K-457; Y-10 to K-457; E-1l to K-457; G-12 to K-457; D-13 to K-457; G-14 to K-457; W-15 to K-457; S-16 to K-457; C-17 to K-457; R-18 to K-457; A-19 to K-457; R-20 to K-457; N-21 to K-457; P-22 to K-457; C-23 to K-457; T-24 to K-457; D-25 to K-457; G-26 to K-457; H-27 to K-457; R-28 to K-457; G-29to K-457; G-30 to K-457; C-31 to K-457; S-32 to K-457; E-33 to K-457; H-34 to K-457; A-35 to K-457; N-36 to K-457; C-37 to K-457; L-38 to K-457; S-39 to K-457; T-40 to K-457; G-41 to K-457; L-42 to K-457; N-43 to K-457; T-44 to K-457; R-45 to K-457; R-46 to K-457; C-47 to K-457; E-48 to K-457; C-49 to K-457; H-SO to K-457; A-51 to K-457; G-52 to K-457; Y-53 to K-457; V-54 to K-457; G-55 to K-457; D-56 to K-457; G-57 to K-457; L-58 to K-457; Q-59 to K-457; C-60 to K-457; L-61 to K-457; E-62 to K-457; E-63 to K-457; S-64 to K-457; E-65 to K-457; P-66 to K-457; P-67 to K-457; V-68 to K-457; D-69 to K-457; R-70 to K-457; C-71 to K-457; L-72 to K-457; G-73 to K-457; Q-74 to K-457; P-75 to K-457; P-76 to K-457; P-77 to K-457; C-78 to K-457; H-79 to K-457; S-80 to K-457; D-81 to K-457; A-82 to K-457; M-83 to K-457; C-84 to K-457; T-85 to K-457; D-86 to K-457; L-87 to K-457; H-88 to K-457; F-89 to K-457; Q-90 to K-457; E-91 to K-457; K-92 to K-457; R-93 to K-457; A-94 to K-457; G-95 to K-457; V-96 to K-457; F-97 to K-457; H-98 to K-457; L-99 to K-457; Q-100 to K-457; A-101 to K-457; T-102 to K-457; S-103 to K-457; G-104 to K-457; P-105 to K-457; Y-106 to K-457; G-107 to K-457; L-108 to K-457; N-109 to K-457; F-110 to K-457; S-111 to K-457; E-112 to K-457; A-113 to K-457; E-114 to K-457; A-115 to K-457; A-116 to K-457; C-117 to K-457; E-118 to K1457; A-119 to K-457; Q-120 to K-457; G-121 to K-457; A-122 to K-457; V-123 to K-457; L-124 to K-457; A-125 to K-457; S-126 to K-457; F-127 to K-457; P-128 to K-457; Q-129 to K-457; L-130 to K-457; S-131 to K-457; A-132 to K-457; A-133 to K-457; Q-134 to K-457; Q-135 to K-457; L-136 to K-457; G-137 to K-457; F-138 to K-457; H-139 to K-457; L-140 to K-457; C-141 to K-457; L-142 to K-457; M-143 to K-457; G-144 to K-457; W-145 to K-457; L-146 to K-457; A-147 to K-457; N-148 to K-457; G-149 to K-457; S-150 to K-457; T-151 to K-457; A-152 to K-457; H-153 to K-457; P-154 to K-457; V-155 to K-457; V-156 to K-457; F-157 to K-457; P-158 to K-457; V-159 to K-457; A-160 to K-457; D-161 to K-457; C-162 to K-457; G-163 to K-457; N-164 to K-457; G-165 to K-457; R-166 to K-457; V-167 to K-457; G-168 to K-457; I-169 to K-457; V-170 to K-457; S-171 to K-457; L-172 to K-457; G-173 to K-457; A-174 to K-457; R-175 to K-457; K-176 to K-457; N-177 to K-457; L-178 to K-457; S-179 to K-457; E-180 to K-457; R-181 to K-457; W-182 to K-457; D-183 to K-457; A-184 to K-457; Y-185 to K-457; C-186 to K-457; F-187 to K-457; R-188 to K-457; V-189 to K-457; Q-190 to K-457; D-191 to K-457; V-192 to K-457; A-193 to K-457; C-194 to K-457; R-195 to K-457; C-196 to K-457; R-197 to K-457; N-198 to K-457; G-199 to K-457; F-200 to K-457; V-201 to K-457; G-202 to K-457; D-203 to K-457; G-204 to K-457; I-205 to K-457; S-206 to K-457; T-207 to K-457; C-208 to K1457; N-209 to K-457; G-210 to K-457; K-211 to K-457; L-212 to K-457; L-213 to K-457; D-214 to K-457; V-215 to K-457; L-216 to K-457; A-217 to K-457; A-218 to K-457; T-219 to K-457; A-220 to K-457; N-221 to K-457; F-222 to K-457; S-223 to K-457; T-224 to K-457; F-225 to K-457; Y-226 to K-457; G-227 to K-457; M-228 to K-457; L-229 to K-457; L-230 to K-457; G-231 to K-457; Y-232 to K-457; A-233 to K-457; N-234 to K-457; A-235 to K-457; T-236 to K-457; Q-237 to K-457; R-238 to K-457; G-239 to K-457; L-240 to K-457; D-241 to K-457; F-242 to K-457; L-243 to K-457; D-244 to K-457; F-245 to K-457; L-246 to K-457; D-247 to K-457; D-248 to K-457; E-249 to K-457; L-250 to K-457; T-251 to K-457; Y-252 to K-457; K-253 to K-457; T-254 to K-457; L-255 to K-457; F-256 to K-457; V-257 to K-457; P-258 to K-457; V-259 to K-457; N-260 to K-457; E-261 to K-457; G-262 to K-457; F-263 to K-457; V-264 to K-457; D-265 to K-457; N-266 to K-457; M-267 to K-457; T-268 to K-457; L-269 to K-457; S-270 to K-457; G-271 to K-457; P-272 to K-457; N-273 to K-457; L-274 to K-457; E-275 to K-457; L-276 to K-457; H-277 to K-457; A-278 to K-457; S-279 to K-457; N-280 to K-457; A-281 to K-457; T-282 to K-457; L-283 to K-457;

L-284 to K-457; S-285 to K-457; A-286 to K-457; N-287 to K-457; A-288 to K-457; S-289 to K-457; Q-290 to K-457; G-291 to K-457; K-292 to K-457; L-293 to K-457; L-294 to K-457; P-295 to K-457; A-296 to K-457; H-297 to K-457; S-298 to K-457; G-299 to K-457; L-300 to K-457; S-301 to K-457; L-302 to K-457; I-303 to K-457; I-304 to K-457; S-305 to K-457; D-306 to K-457; A-307 to K-457; G-308 to K-457; P-309 to K-457; D-310 to K-457; N-31.1 to K-457; S-312 to K-457; S-313 to K-457; W-314 to K-457; A-315 to K-457; P-316 to K-457; V-317 to K-457; A-318 to K-457; P-319 to K-457; G-320 to K-457; T-321 to K-457; V-322 to K-457; V-323 to K-457; V-324 to K-457; S-325 to K-457; R-326 to K-457; I-327 to K-457; I-328 to K-457; V-329 to K-457; W-330 to K-457; D-331 to K-457; I-332 to K-457; M-333 to K-457; A-334 to K-457; F-335 to K-457; N-336 to K-457; G-337 to K-457; I-338 to K-457; I-339 to K-457; H-340 to K-457; A-341 to K-457; L-342 to K-457; A-343 to K-457; S-344 to K-457; P-345 to K-457; L-346 to K-457; L-347 to K-457; A-348 to K-457; P-349 to K-457; P-350 to K-457; Q-351 to K-457; P-352 to K-457; Q-353 to K-457; A-354 to K-457; V-355 to K-457; L-356 to K-457; A-357 to K-457; X-358 to K-457; E-359 to K-457; A-360 to K-457; P-361 to K-457; P-362 to K-457; V-363 to K-457; A-364 to K-457; A-365 to K-457; G-366 to K-457; V-367 to K-457; G-368 to K-457; A-369 to K-457; V-370 to K-457; L-371 to K-457; A-372 to K-457; A-373 to K-457; G-374 to K-457; A-375 to K-457; L-376 to K-457; L-377 to K-457; G-378 to K-457; L-379 to K-457; V-380 to K-457; A-381 to K-457; G-382 to K-457; A-383 to K-457; L-384 to K-457; Y-385 to K-457; L-386 to K-457; R-387 to K-457; A-388 to K-457; R-389 to K-457; G-390 to K-457; K-391 to K-457; P-392 to K-457; M-393 to K-457; G-394 to K-457; F-395 to K-457; G-396 to K-457; F-397 to K-457; S-398 to K-457; A-399 to K-457; F-400 to K-457; Q-401 to K-457; A-402 to K-457; EA03 to K-457; D-404 to K-457; D-405 to K-457; A-406 to K-457; D-407 to K-457; D-408 to K-457; X-409 to K-457; F-410 to K-457; S-411 to K-457; P-412 to K-457; W-413 to K-457; Q-414 to K-457; E-415 to K-457; G-416 to K-457; T-417 to K-457; N-418 to K-457; P-419 to K-457; T-420 to K-457; L-421 to K-457, V-422 to K-457; X-423 to K-457; V-424 to K-457; P-425 to K-457; N-426 to K-457; P-427 to K-457; V-428 to K-457; F-429 to K-457; G-430 to K-457; S-431 to K-457; D-432 to K-457; T-433 to K-457; F-434 to K-457; C-435 to K-457; E-436 to K-457; P-437 to K-457; F-438 to K-457; D-439 to K-457; D-440 to K-457; S-441 to K-457; L-442 to K-457; L-443 to K-457; E-444 to K-457; E-445 to K-457; D-446 to K-457; F-447 to K-457; P-448 to K-457; D-449 to K-457; T-450 to K-457; Q-451 to K-457; R-452 to K-457; of SEQ ID NO:5. Polynucleotides encoding these polypeptides are also encompassed by the invention.

Further embodiments of the invention are directed to C-terminal deletions of the WF-HABP polypeptide described by the general formula 1 to n, where n is an integer from 2–457 corresponding to the position of amino acid residue identified in SEQ ID NO:5 and preferably, corresponds to one of the C-terminal amino acid residues identified in the C-terminal deletions specified herein. In specific embodiments, C terminal deletions of the WF-HABP polypeptide of the invention comprise, or alternatively, consist of, amino acid residues: M-1 to V-456; M-1 to T-455; M-1 to L-454; M-1 to I-453; M-1 to R-452; M-1 to Q-451; M-1 to T-450; M-1 to D-449; M-1 to P-448; M-1 to F-447; M-1 to D-446; M-1 to E-445; M-1 to E-444; M-1 to L-443; M-1 to L-442; M-1 to S-441; M-1 to D-440; M-1 to D-439; M-1 to F-438; M-1 to P-437; M-1 to E-436; M-1 to C-435; M-1 to F-434; M-1 to T-433; M-1 to D-432; M-1 to S-431; M-1 to G-430; M-1 to F-429; M-1 to V-428; M-1 to P-427; M-1 to N-426; M-1 to P-425; M-1 to V-424; M-1 to X-423; M-1 to V-422; M-1 to L-421; M-1 to T-420; M-1 to P-419; M-1 to N-418; M-1 to T-417; M-1 to G-416; M-1 to E-415; M-1 to Q-414; M-1 to W-413; M-1 to P-412; M-1 to S-411; M-1 to F-410; M-1 to X-409; M-1 to D-408; M-1 to D-407; M-1 to A-406; M-1 to D-405; M-1 to D-404; M-1 to E-403; M-1 to A-402; M-1 to Q-401; M-1 to F-400; M-1 to A-399; M-1 to S-398; M-1 to F-397; M-1 to G-396; M-1 to F-395; M-1 to G-394; M-1 to M-393; M-1 to P-392; M-1 to K-391; M-1 to G-390; M-1 to R-389; M-1 to A-388; M-1 to R-387; M-1 to L-386; M-1 to Y-385; M-1 to L-384; M-1 to A-383; M-1 to G-382; M-1 to A-381; M-1 to V-380; M-1 to L-379; M-1 to G-378; M-1 to L-377; M-1 to L-376; M-1 to A-375; M-1 to G-374; M-1 to A-373; M-1 to A-372; M-1 to L-371; M-1 to V-370; M-1 to A-369; M-1 to G-368; M-1 to V-367; M-1 to G-366; M-1 to A-365; M-1 to A-364; M-1 to V-363; M-1 to P-362; M-1 to P-361; M-1 to A-360; M-1 to E-359; M-1 to X-358; M-1 to A-357; M-1 to L-356; M-1 to V-355; M-1 to A-354; M-1 to Q-353; M-1 to P-352; M-1 to Q-351; M-1 to P-350; M-1 to P-349; M-1 to A-348; M-1 to L-347; M-1 to L-346; M-1 to P-345; M-1 to S-344; M-1 to,A-343; M-1 to L-342; M-1 to A-341; M-1 to H-340; M-1 to I-339; M-1 to I-338; M-1 to G-337; M-1 to N-336; M-1 to F-335; M-1 to A-334; M-1 to M-333; M-1 to I-332; M-1 to D-331; M-1 to W-330; M-1 to V-329; M-1 to I-328; M-1 to I-327; M-1 to R-326; M-1 to S-325; M-1 to V-324; M-1 to V-323; M-1 to V-322; M-1 to T-321; M-1 to G-320; M-1 to P7319; M-1 to A-318; M-1 to V-317; M-1 to P-316; M-1 to A-315; M-1 to W-314; M-1 to S-313; M-1 to S-312; M-1 to N-311; M-1 to D-310; M-1 to P-309; M-1 to G-308; M-1 to A-307; M-1 to D-306; M-1 to S-305; M-1 to I-304; M-1 to I-303; M-1 to L-302; M-1 to S-301; M-1 to L-300; M-1 to G-299; M-1 to S-298; M-1 to H-297; M-1 to A-296; M-1 to P-295; M-1 to L-294; M-1 to L-293; M-1 to K-292; M-1 to G-291; M-1 to Q-290; M-1 to S-289; M-1 to A-288; M-1 to N-287; M-1 to A-286; M-1 to S-285; M-1 to L-284; M-1 to L-283; M-1 to T-282; M-1 to A-281; M-1 to N-280; M-1 to S-279; M-1 to A-278; M-1 to H-277; M-1 to L-276; M-1 to E-275; M-1 to L-274; M-1 to N-273; M-1 to P-272; M-1 to G-271; M-1 to S-270; M-1 to L-269; M-1 to T-268; M-1 to M-267; M-1 to N-266; M-1 to D-265; M-1 to V-264; M-1 to F-263; M-1 to G-262; M-1 to E-261; M-1 to N-260; M-1 to V-259; M-1 to P-258; M-1 to V-257; M-1 to F-256; M-1 to L-255; M-1 to T-254; M-1 to K-253; M-1 to Y-252; M-1 to T-251; M-1 to L-250; M-1 to E-249; M-1 to D-248; M-1 to D-247; M-1 to L-246; M-1 to F-245; M-1 to D-244; M-1 to L-243; M-1 to F-242; M-1 to D-241; M-1 to L-240; M-1 to G-239; M-1 to R-238; M-1 to Q-237; M-1 to T-236; M-1 to A-235; M-1 to N-234; M-1 to A-233; M-1 to Y-232; M-1 to G-231; M-1 to L-230; M-1 to L-229; M-1 to M-228; M-1 to G-227; M-1 to Y-226; M-1 to F-225; M-1 to T-224; M-1 to S-223; M-1 to F-222; M-1 to N-221; M-1 to A-220; M-1 to T-219; M-1 to A-218; M-1 to A-217; M-1 to L-216; M-1 to V-215; M-1 to D-214; M-1 to L-213; M-1 to L-212; M-1 to K-211; M-1 to G-210; M-1 to N-209; M-1 to C-208; M-1 to T-207; M-1 to S-206; M-1 to I-205; M-1 to G-204; M-1 to D-203; M-1 to G-202; M-1 to V-201; M-1 to F-200; M-1 to G-199; M-1 to N-198; M-1 to R-197; M-1 to C-196; M-1 to R-195; M-1 to C-194; M-1 to A-193; M-1 to V-192; M-1 to D-191; M-1 to Q-190; M-1 to V-189; M-1 to R-188; M-1 to F-187; M-1 to C-186; M-1 to Y-185; M-1 to A-184; M-1 to D-183; M-1 to W-182; M-1 to R-181; M-1 to E-180; M-1 to S-179; M-1 to L-178; M-1 to N-177; M-1 to K-176; M-1 to R-175; M-1 to A-174; M-1 to G-173; M-1 to L-172; M-1 to S-171; M-1 to V-170; M-1 to I-169; M-1 to G-168; M-1 to V-167; M-1 to R-166; M-1 to G-165; M-1 to N-164; M-1 to G-163;

M-1 to C-162; M-1 to D-161; M-1 to A-160; M-1 to V-159; M-1 to P-158; M-1 to F-157; M-1 to V-156; M-1 to V-155; M-1 to P-154; M-1 to H-153; M-1 to A-152; M-1 to T-151; M-1 to S-150; M-1 to G-149; M-1 to N-148; M-1 to A-147; M-1 to L-146; M-1 to W-145; M-1 to G-144; M-1 to M-143; M-1 to L-142; M-1 to C-141; M-1 to L-140; M-1 to H-139; M-1 to F-138; M-1 to G-137; M-1 to L-136; M-1 to Q-135; M-1 to Q-134; M-1 to A-133; M-1 to A-132; M-1 to S-131; M-1 to L-130; M-1 to Q-129; M-1 to P-128; M-1 to F-127; M-1 to S-126; M-1 to A-125; M-1 to L-124; M-1 to V-123; M-1 to A-122; M-1 to G-121; M-1 to Q-120; M-1 to A-119; M-1 to E-118; M-1 to C-117; M-1 to A-116; M-1 to A-115; M-1 to E-114; M-1 to A-113; M-1 to E-112; M-1 to S-111; M-1 to F-110; M-1 to N-109; M-1 to L-108; M-1 to G-107; M-1 to Y-106; M-1 to P-105; M-1 to G-104; M-1 to S-103; M-1 to T-102; M-1 to A-101; M-1 to Q-100; M-1 to L-99; M-1 to H-98; M-1 to F-97; M-1 to V-96; M-1 to G-95; M-1 to A-94; M-1 to R-93; M-1 to K-92; M-1 to E-91; M-1 to Q-90; M-1 to F-89; M-1 to H-88; M-1 to L-87; M-1 to D-86; M-1 to T-85; M-1 to C-84; M-1 to M-83; M-1 to A-82; M-1 to D-81; M-1 to S-80; M-1 to H-79; M-1 to C-78; M-1 to P-77; M-1 to P-76; M-1 to P-75; M-1 to Q-74; M-1 to G-73; M-1 to L-72; M-1 to C-71; M-1 to R-70; M-1 to D-69; M-1 to V-68; M-1 to P-67; M-1 to P-66; M-1 to E-65; M-1 to S-64; M-1 to E-63; M-1 to E-62; M-1 to L-61; M-1 to C-60; M-1 to Q-59; M-1 to L-58; M-1 to G-57; M-1 to D-56; M-1 to G-55; M-1 to V-54; M-1 to Y-53; M-1 to G-52; M-1 to A-51; M-1 to H-50; M-1 to C-49; M-1 to E-48; M-1 to C-47; M-1 to R-46; M-1 to R-45; M-1 to T-44; M-1 to N-43; M-1 to L-42; M-1 to G-41; M-1 to T-40; M-1 to S-39; M-1 to L-38; M-1 to C-37; M-1 to N-36; M-1 to A-35; M-1 to H-34; M-1 to E-33; M-1 to S-32; M-1 to C-31; M-1 to G-30; M-1 to G-29; M-1 to R-28; M-1 to H-27; M-1 to G-26; M-1 to D-25; M-1 to T-24; M-1 to C-23; M-1 to P-22; M-1 to N-21; M-1 to R-20; M-1 to A-19; M-1 to R-18; M-1 to C-17; M-1 to S-16; M-1 to W-15; M-1 to G-14; M-1 to D-13; M-1 to G-12; M-1 to E-11; M-1 to Y-10; M-1 to D-9; M-1 to P-8; M-1 to L-7; of SEQ ID NO:5. Polynucleotides encoding these polypeptides are also encompassed by the invention.

In one embodiment, the present invention further provides polypeptides having one or more residues deleted from the amino terminus of the amino acid sequence of the OE-HABP polypeptide depicted in FIGS. 3A–C (SEQ ID NO:8) or encoded by the cDNA of the deposited clone. Particularly, in one embodiment, N-terminal deletions of the OE-HABP polypeptide can be described by the general formula m to 289, where m is an integer from 1 to 288 corresponding to the position of amino acids identified in SEQ ID NO:8 and preferably, corresponds to one of the N-terminal amino acid residues identified in the N-terminal deletions specified herein. In specific embodiments, N-terminal deletions of the OE-HABP polypeptide of the invention comprise, or alternatively, consist of, amino acid residues: G-2 to K-289; L-3 to K-289; L-4 to K-289; L-5 to K-289; L-6 to K-289; V-7 to K-289; P-8 to K-289; L-9 to K-289; L-10 to K-289; L-11 to K-289; L-12 to K-289; P-13 to K-289; G-14 to K-289; S-15 to K-289; Y-16 to K-289; G-17 to K-289; L-18 to K-289; P-19 to K-289; F-20 to K-289; Y-21 to K-289; Y-22 to K-289; G-23 to K-289; F-24 to K-289; Y-25 to K-289; Y-26 to K-289; S-27 to K-289; N-28 to K-289; S-29 to K-289; A-30 to K-289; N-31 to K-289; D-32 to K-289; Q-33 to K-289; N-34 to K-289; L-35 to K-289; G-36 to K-289; N-37 to K-289; G-38 to K-289; H-39 to K-289; G-40 to K-289; K-41 to K-289; D-42 to K-289; L-43 to K-289; X-44 to K-289; N-45 to K-289; G-46 to K-289; V-47 to K-289; K-48 to K-289; L-49 to K-289; V-50 to K-289; V-51 to K-289; E-52 to K-289; T-53 to K-289; P-54 to K-289; E-55 to K-289; E-56 to K-289; T-57 to K-289; L-58 to K-289; F-59 to K-289; T-60 to K-289; Y-61 to K-289; Q-62 to K-289; G-63 to K-289; A-64 to K-289; S-65 to K-289; V-66 to K-289; I-67 to K-289; L-68 to K-289; P-69 to K-289; C-70 to K-289; R-71 to K-289; Y-72 to K-289; R-73 to K-289; Y-74 to K-289; E-75 to K-289; P-76 to K-289; A-77 to K-289; L-78 to K-289; V-79 to K-289; S-80 to K-289; P-81 to K-289; R-82 to K-289; R-83 to K-289; V-84 to K-289; R-85 to K-289; V-86 to K-289; K-87 to K-289; W-88 to K-289; W-89 to K-289; K-90 to K-289; L-91 to K-289; S-92 to K-289; E-93 to K-289; N-94 to K-289; G-95 to K-289; A-96 to K-289; P-97 to K-289; E-98 to K-289; K-99 to K-289; D-100 to K-289; V-101 to K-289; L-102 to K-289; V-103 to K-289; A-104 to K-289; I-105 to K-289; G-106 to K-289; L-107 to K-289; R-108 to K-289; H-109 to K-289; R-110 to K-289; S-111 to K-289; F-112 to K-289; G-113 to K-289; D-114 to K-289; Y-115 to K-289; Q-116 to K-289; G-117 to K-289; R-118 to K-289; V-119 to K-289; H-120 to K-289; L-121 to K-289; R-122 to K-289; Q-123 to K-289; D-124 to K-289; K-125 to K-289; E-126 to K-289; H-127 to K-289; D-128 to K-289; V-129 to K-289; S-130 to K-289; X-131 to K-289; E-132 to K-289; I-133 to K-289; Q-134 to K-289; X-135 to K-289; L-136 to K-289; R-137 to K-289; L-138 to K-289; E-139 to K-289; D-140 to K-289; Y-141 to K-289; G-142 to K-289; R-143 to K-289; Y-144 to K-289; R-145 to K-289; C-146 to K-289; E-147 to K-289; V-148 to K-289; X-149 to K-289; D-150 to K-289; G-151 to K-289; L-152 to K-289; E-153 to K-289; D-154 to K-289; E-155 to K-289; S-156 to K-289; G-157 to K-289; L-158 to K-289; V-159 to K-289; E-160 to K-289; L-161 to K-289; E-162 to K-289; L-163 to K-289; R-164 to K-289; G-165 to K-289; V-166 to K-289; V-167 to K-289; F-168 to K-289; P-169 to K-289; Y-170 to K-289; Q-171 to K-289; S-172 to K-289; P-173 to K-289; N-174 to K-289; 0-175 to K-289; R-176 to K-289; Y-177 to K-289; Q-178 to K-289; F-179 to K-289; N-180 to K-289; F-181 to K-289; H-182 to K-289; E-183 to K-289; G-184 to K-289; Q-185 to K-289; Q-186 to K-289; V-187 to K-289; C-188 to K-289; A-189 to K-289; E-190 to K-289; Q-191 to K-289; A-192 to K-289; A-193 to K-289; V-194 to K-289; V-195 to K-289; A-196 to K-289; S-197 to K-289; F-198 to K-289; E-199 to K-289; Q-200 to K-289; L-201 to K-289; F-202 to K-289; R-203 to K-289; A-204 to K-289; W-205 to K-289; E-206 to K-289; E-207 to K-289; G-208 to K-289; L-209 to K-289; D-210 to K-289; W-211 to K-289; C-212 to K-289; N-213 to K-289; A-214 to K-289; G-215 to K-289; W-216 to K-289; L-217 to K-289; Q-218 to K-289; D-219 to K-289; A-220 to K-289; T-221 to K-289; V-222 to K-289; Q-223 to K-289; Y-224 to K-289; P-225 to K-289; I-226 to K-289; M-227 to K-289; L-228 to K-289; P-229 to K-289; R-230 to K-289; Q-231 to K-289; P-232 to K-289; C-233 to K-289; G-234 to K-289; G-235 to K-289; P-236 to K-289; D-237 to K-289; L-238 to K-289; A-239 to K-289; P-240 to K-289; G-241 to K-289; V-242 to K-289; R-243 to K-289; S-244 to K-289; Y-245 to K-289; G-246 to K-289; P-247 to K-289; R-248 to K-289; H-249 to K-289; R-250 to K-289; R-251 to K-289; L-252 to K-289; H-253 to K-289; R-254 to K-289; Y-255 to K-289; D-256 to K-289; V-257 to K-289; F-258 to K-289; C-259 to K-289; F-260 to K-289; A-261 to K-289; T-262 to K-289; A-263 to K-289; L-264 to K-289; X-265 to K-289; G-266 to K-289; R-267 to K-289; V-268 to K-289; Y-269 to K-289; Y-270 to K-289; L-271 to K-289; X-272 to K-289; H-273 to K-289; P-274 to K-289; E-275 to K-289; X-276 to K-289; L-277 to K-289; T-278 to K-289; L-279 to K-289; T-280 to K-289; X-281 to K-289; A-282 to K-289; R-283 to K-289; E-284 to K-289; of SEQ ID NO:8. Polynucleotides encoding these polypeptides are also encompassed by the invention.

Further embodiments of the invention are directed to C-terminal deletions of the OE-HABP polypeptide described by the general formula 1 to n, where n is an integer from 2–289 corresponding to the position of amino acid residue identified in SEQ ID NO:8 and preferably, corresponds to one of the C-terminal amino acid residues identified in the C-terminal deletions specified herein. In specific embodiments, C terminal deletions of the OE-HABP polypeptide of the invention comprise, or alternatively, consist of, amino acid residues: M-1 to E-288; M-1 to Q-287; M-1 to C-286; M-1 to A-285; M-1 to E-284; M-1 to R-283; M-1 to A-282; M-1 to X-281; M-1 to T-280; M-1 to L-279; M-1 to T-278; M-1 to L-277; M-1 to X-276; M-1 to E-275; M-1 to P-274; M-1 to H-273; M-1 to X-272; M-1 to L-271; M-1 to Y-270; M-1 to Y-269; M-1 to V-268; M-1 to R-267; M-1 to G-266; M-1 to X-265; M-1 to L-264; M-1 to A-263; M-1 to T-262; M-1 to A-261; M-1 to F-260; M-1 to C-259; M-1 to F-258; M-1 to V-257; M-1 to D-256; M-1 to Y-255; M-1 to R-254; M-1 to H-253; M-1 to L-252; M-1 to R-251; M-1 to R-250; M-1 to H-249; M-1 to R-248; M-1 to P-247; M-1 to G-246; M-1 to Y-245; M-1 to S-244; M-1 to R-243; M-1 to V-242; M-1 to G-241; M-1 to P-240; M-1 to A-239; M-1 to L-238; M-1 to D-237; M-1 to P-236; M-1 to G-235; M-1 to G-234; M-1 to C-233; M-1 to P-232; M-1 to Q-231; M-1 to R-230; M-1 to P-229; M-1 to L-228; M-1 to M-227; M-1 to I-226; M-1 to P-225; M-1 to Y-224; M-1 to Q-223; M-1 to V-222; M-1 to T-221; M-1 to A-220; M-1 to D-219; M-1 to Q-218; M-1 to L-217; M-1 to W-216; M-1 to G-215; M-1 to A-214; M-1 to N-213; M-1 to C-212; M-1 to W-211; M-1 to D-210; M-1 to L-209; M-1 to G-208; M-1 to E-207; M-1 to E-206; M-1 to W-205; M-1 to A-204; M-1 to R-203; M-1 to F-202; M-1 to L-201; M-1 to Q-200; M-1 to E-199; M-1 to F-198; M-1 to S-197; M-1 to A-196; M-1 to V-195; M-1 to V-194; M-1 to A-193; M-1 to A-192; M-1 to Q-191; M-1 to E-190; M-1 to A-189; M-1 to C-188; M-1 to V-187; M-1 to Q-186; M-1 to Q-185; M-1 to G-184; M-1 to E-183; M-1 to H-182; M-1 to F-181; M-1 to N-180; M-1 to F-179; M-1 to Q-178; M-1 to Y-177; M-1 to R-176; M-1 to G-175; M-1 to N-174; M-1 to P-173; M-1 to S-172; M-1 to Q-171; M-1 to Y-170; M-1 to P-169; M-1 to F-168; M-1 to V-167; M-1 to V-166; M-1 to G-165; M-1 to R-164; M-1 to L-163; M-1 to E-162; M-1 to L-161; M-1 to E-160; M-1 to V-159; M-1 to L-158; M-1 to G-157; M-1 to S-156; M-1 to E-155; M-1 to D-154; M-1 to E-153; M-1 to L-152; M-1 to G-151; M-1 to D-150; M-1 to X-149; M-1 to V-148; M-1 to E-147; M-1 to C-146; M-1 to R-145; M-1 to Y-144; M-1 to R-143; M-1 to G-142; M-1 to Y-141; M-1 to D-140; M-1 to E-139; M-1 to L-138; M-1 to R-137; M-1 to L-136; M-1 to X-135; M-1 to Q-134; M-1 to I-133; M-1 to E-132; M-1 to X-131; M-1 to S-130; M-1 to V-129; M-1 to D-128; M-1 to H-127; M-1 to E-126; M-1 to K-125; M-1 to D-124; M-1 to Q-123; M-1 to R-122; M-1 to L-121; M-1 to H-120; M-1 to V-119; M-1 to R-118; M-1 to G-117; M-1 to Q-116; M-1 to Y-115; M-1 to D-114; M-1 to G-113; M-1 to F-112; M-1 to S-111; M-1 to R-110; M-1 to H-109; M-1 to R-108; M-1 to L-107; M-1 to G-106; M-1 to I-105; M-1 to A-104; M-1 to V-103; M-1 to L-102; M-1 to V-101; M-1 to D-100; M-1 to K-99; M-1 to E-98; M-1 to P-97; M-1 to A-96; M-1 to G-95; M-1 to N-94; M-1 to E-93; M-1 to S-92; M-1 to L-91; M-1 to K-90; M-1 to W-89; M-1 to W-88; M-1 to K-87; M-1 to V-86; M-1 to R-85; M-1 to V-84; M-1 to R-83; M-1 to R-82; M-1 to P-81; M-1 to S-80; M-1 to V-79; M-1 to L-78; M-1 to A-77; M-1 to P-76; M-1 to E-75; M-1 to Y-74; M-1 to R-73; M-1 to Y-72; M-1 to R-71; M-1 to C-70; M-1 to P-69; M-1 to L-68; M-1 to I-67; M-1 to V-66; M-1 to S-65; M-1 to A-64; M-1 to G-63; M-1 to Q-62; M-1 to Y-61; M-1 to T-60; M-1 to F-59; M-1 to L-58; M-1 to T-57; M-1 to E-56; M-1 to E-55; M-1 to P-54; M-1 to T-53; M-1 to E-52; M-1 to V-51; M-1 to V-50; M-1 to L-49; M-1 to K-48; M-1 to V-47; M-1 to G-46; M-1 to N-45; M-1 to X-44; M-1 to L-43; M-1 to D-42; M-1 to K-41; M-1 to G-40; M-1 to H-39; M-1 to G-38; M-1 to N-37; M-1 to G-36; M-1 to L-35; M-1 to N-34; M-1 to Q-33; M-1 to D-32; M-1 to N-31; M-1 to A-30; M-1 to S-29; M-1 to N-28; M-1 to S-27; M-1 to Y-26; M-1 to Y-25; M-1 to F-24; M-1 to G-23; M-1 to Y-22; M-1 to Y-21; M-1 to F-20; M-1 to P-19; M-1 to L-18; M-1 to G-17; M-1 to Y-16; M-1 to S-15; M-1 to G-14; M-1 to P-13; M-1 to L-12; M-1 to L-11; M-1 to L-10; M-1 to L-9; M-1 to P-8; M-1 to V-7; of SEQ ID NO:8. Polynucleotides encoding these polypeptides are also encompassed by the invention.

In one embodiment, the present invention further provides polypeptides having one or more residues deleted from the amino terminus of the amino acid sequence of the BM-HABP polypeptide depicted in FIGS. 4A–C (SEQ ID NO:11) or encoded by the cDNA of the deposited clone. Particularly; in one embodiment, N-terminal deletions of the BM-HABP polypeptide can be described by the general formula m to 353, where m is an integer from 1 to 354 corresponding to the position of amino acids identified in SEQ ID NO:11 and preferably, corresponds to one of the N-terminal amino acid residues identified in the N-terminal deletions specified herein. In specific embodiments, N-terminal deletions of the BM-HABP polypeptide of the invention comprise, or alternatively, consist of, amino acid residues: N-terminal deletions of the BM-HABP polypeptide of the invention shown as SEQ ID NO:11 include polypeptides comprising the amino acid sequence of residues: N-terminal deletions of the BM-HABP polypeptide of the invention shown as SEQ ID NO:11 include polypeptides comprising the amino acid sequence of residues: N-terminal deletions of the BM-HABP polypeptide of the invention shown as SEQ ID NO:11 include polypeptides comprising the amino acid sequence of residues: T-2 to F-353; G-3 to F-353; P-4 to F-353; G-5 to F-353; K-6 to F-353; H-7 to F-353; K-8 to F-353; C-9 to F-353; E-10 to F-353; C-11 to F-353; K-12 to F-353; S-13 to F-353; H-14 to F-353; Y-15 to F-353; V-16 to F-353; G-17 to F-353; D-18 to F-353; G-19 to F-353; L-20 to F-353; N-21 to F-353; C-22 to F-353; E-23 to F-353; P-24 to F-353; E-25 to F-353; Q-26 to F-353; L-27 to F-353; P-28 to F-353; I-29 to F-353; D-30 to F-353; R-31 to F-353; C-32 to F-353; L-33 to F-353; Q-34 to F-353; D-35 to F-353; N-36 to F-353; G-37 to F-353; Q-38 to F-353; C-39 to F-353; H-40 to F-353; A-41 to F-353; D-42 to F-353; A-43 to F-353; K-44 to F-353; C-45 to F-353; V-46 to F-353; D-47 to F-353; L-48 to F-353; H-49 to F-353; F-50 to F-353; Q-51 to F-353; D-52 to F-353; T-53 to F-353; T-54 to F-353; V-55 to F-353; G-56 to F-353; V-57 to F-353; F-58 to F-353; H-59 to F-353; L-60 to F-353; R-61 to F-353; S-62 to F-353; P-63 to F-353; L-64 to F-353; G-65 to F-353; Q-66 to F-353; Y-67 to F-353; K-68 to F-353; L-69 to F-353; T-70 to F-353; F-71 to F-353; D-72 to F-353; K-73 to F-353; A-74 to F-353; R-75 to F-353; E-76 to F-353; A-77 to F-353; C-78 to F-353; A-79 to F-353; N-80 to F-353; E-81 to F-353; A-82 to F-353; A-83 to F-353; T-84 to F-353; M-85 to F-353; A-86 to F-353; T-87 to F-353; Y-88 to F-353; N-89 to F-353; Q-90 to F-353; L-91 to F-353; S 92 to F-353; Y-93 to F-353; X-94 to F-353; Q-95 to F-353; K-96 to F-353; A-97 to F-353; K-98 to F-353; Y-99 to F-353; H-100 to F-353; L-101 to F-353; C-102 to F-353; S-103 to F-353; A-104 to F-353; G-105 to F-353; W-106 to F-353; L-107 to F-353; E-108 to F-353; T-109 to F-353; G-110 to F-353; R-111 to F-353; V-112 to F-353; A-113 to F-353; Y-114 to F-353; P-115 to F-353; T-116 to F-353; A-117 to F-353; F-118 to F-353; A-9 to F-353; S-120 to F-353; Q-121 to F-353; N-122 to F-353; C-123 to F-353; G-124 to F-353; S-125 to F-353; G-126 to F-353; V-127 to F-353; V-128 to F-353; G-129 to F-353; I-130 to F-353; V-131 to F-353; D-132 to F-353; Y-133 to F-353; G-134 to F-353; P-135 to F-353; R-136 to F-353; P-137 to F-353; N-138 to F-353; K-139 to F-353; S-140 to F-353; E-141 to F-353; M-142 to F-353; W-143 to F-353; D-144 to F-353; V-145 to F-353; F-146 to F-353; C-147 to F-353; Y-148 to F-353; R-149 to F-353; M-150 to F-353; K-151 to F-353; D-152 to F-353; V-153 to F-353; N-154 to F-353; C-155 to F-353; T-156 to F-353; X-157 to F-353; K-158 to F-353; V-159 to F-353; G-1.60 to F-353; Y-161 to F-353; V-162 to F-353; G-163 to F-353; D-164 to F-353; G-165 to F-353; F-166 to F-353; S-167 to F-353; Y-168 to F-353; S-169 to F-353; G-170 to F-353; N-171 to F-353; L-172 to F-353; L-173 to F-353; Q-174 to F-353; V-175 to F-353; L-176 to F-353; M-177 to F-353; S-178 to F-353; F-179 to F-353; P-180 to F-353; S-181 to F-353; L-182 to F-353; T-183 to F-353; N-184 to F-353; F-185 to F-353; L-186 to F-353; T-187 to F-353; E-188 to F-353; V-189 to F-353; L-190 to F-353; A-191 to F-353; Y-192 to F-353; S-193 to F-353; N-194 to F-353; S-195 to F-353; S-196 to F-353; A-197 to F-353; R-198 to F-353; G-199 to F-353; R-200 to F-353; A-201 to F-353; F-202 to F-353; L203 to F-353; E-204 to F-353; H-205 to F-353; L-206 to F-353; T-207 to F-353; D-208 to F-353; L-209 to F-353; S-210 to F-353; I-211 to F-353; R-212 to F-353; G-213 to F-353; T-214 to F-353; L-215 to F-353; F-216 to F-353; V-217 to F-353; P-218 to F-353; Q-219 to F-353; N-220 to F-353; S-221 to F-353; G-222 to F-353; L-223 to F-353; G-224 to F-353; E-225 to F-353; N-226 to F-353; E-227 to F-353; T-228 to F-353; L-229 to F-353; S-230 to F-353; G-231 to F-353; R-232 to F-353; D-233 to F-353; I-234 to F-353; F-235 to F-353; H-236 to F-353; H-237 to F-353; L-238 to F-353; A-239 to F-353; N-240 to F-353, V-241 to F-353; S-242 to F-353; M-243 to F-353; F-244 to F-353; F-245 to F-353; Y-246 to F-353; N-247 to F-353; D-248 to F-353; L-249 to F-353; V-250 to F-353; N-251 to F-353; G-252 to F-353; T-253 to F-353; T-254 to F-353; L-255 to F-353; Q-256 to F-353; T-257 to F-353; R-258 to F-353; L-259 to F-353; G-260 to F-353; S-261 to F-353; K-262 to F-353; L-263 to F-353; L-264 to F-353; I-265 to F-351; T-266 to F-353; D-267 to F-353; R-268 to F-353; Q-269 to F-353; D-270 to F-353; P-271 to F-353; L-272 to F-353; H-273 to F-353; P-274 to F-353; T-275 to F-353; E-276 to F-353; T-277 to F-353; R-278 to F-353; C-279 to F-353; V-280 to F-353; D-281 to F-353; G-282 to F-353; R-283 to F-353; D-284 to F-353; T-285 to F-353; L-286 to F-353; E-287 to F-353; W-288 to F-353; D-289 to F-353; I-290 to F-353; C-291 to F-353; A-292 to F-353; S-293 to F-353; N-294 to F-353; G-295 to F-353; I-296 to F-353; T-297 to F-353; H-298 to F-353; V-299 to F-353; I-300 to F-353; S-301 to F-353; R-302 to F-353; X-303 to F-353; L-304 to F-353; K-305 to F-353; A-306 to F-353; P-307 to F-353; P-308 to F-353; A-309 to F-353; P-310 to F-353; V-311 to F-353; T-312 to F-353; L-313 to F-353; X-314 to F-353; H-315 to F-353; T-316 to F-353; G-317 to,F-353; L-318 to F-353; G-319 to F-353; X-320 to F-353; G-321 to F-353; I-322 to F-353; F-323 to F-353; X-324 to F-353; X-325 to F-353; I-326 to F-353; I-327 to F-353; L-328 to F-353; V-329 to F-353; T-330 to F-353; G-331 to F-353; A-332 to F-353; V-333 to F-353; A-334 to F-353; L-335 to F-353; A-336 to F-353; A-337 to F-353; Y-338 to F-353; S-339 to F-353; Y-340 to F-353; F-341 to F-353; R-342 to F-353; I-343 to F-353; N-344 to F-353; R-345 to F-353; K-346 to F-353; T-347 to F-353; I-348 to F-353; of SEQ ID NO:11. Polynucleotides encoding these polypeptides are also encompassed by the invention.

Further embodiments of the invention are directed to C-terminal deletions of the BM-HABP polypeptide described by the general formula 1 to n, where n is an integer from 2–353 corresponding to the position of amino acid residue identified in SEQ ID NO:11 and preferably, corresponds to one of the C-terminal amino acid residues identified in the C-terminal deletions specified herein. In specific embodiments, C terminal deletions of the BM-HABP polypeptide of the invention comprise, or alternatively, consist of, amino acid residues: M-1 to H-352; M-1 to X-351; M-1 to F-350; M-1 to G-349; M-1 to I-348; M-1 to T-347; M-1 to K-346; M-1 to R-345; M-1 to N-344; M-1 to I-343; M-1 to R-342; M-1 to F-341; M-1 to Y-340; M-1 to S-339; M-1 to Y-338; M-1 to A-337; M-1 to A-336; M-1 to L-335; M-1 to A-334; M-1 to V-333; M-1 to A-332; M-1 to G-331; M-1 to T-330; M-1 to V-329; M-1 to L-328; M-1 to I-327; M-1 to I-326; M-1 to X-325; M-1 to X-324; M-1 to F-323; M-1 to I-322; M-1 to G-321; M-1 to X-320; M-1 to G-319; M-1 to L-318; M-1 to G-317; M-1 to T-316; M-1 to H-315; M-1 to X-314; M-1 to L-313; M-1 to T-312; M-1 to V-311; M-1 to P-310; M-1 to A-309; M-1 to P-308; M-1 to P-307; M-1 to A-306; M-1 to K-305; M-1 to L-304; M-1 to X-303; M-1 to R-302; M-1 to S-301; M-1 to I-300; M-1 to V-299, M-1 to H-298; M-1 to T-297; M-1 to I-296; M-1 to G-295; M-1 to N-294; M-1 to S-293; M-1 to A-292; M-1 to C-291; M-1 to I-290; M-1 to D-289; M-1 to W-288; M-1 to E-287; M-1 to L-286; M-1 to T-285; M-1 to D-284; M-1 to R-283; M-1 to G-282; M-1 to D-281; M-1 to V-280; M-1 to C-279; M-1 to R-278; M-1 to T-277; M-1 to E-276; M-1 to T-275; M-1 to P-274; M-1 to H-273; M-1 to L-272; M-1 to P-271; M-1 to D-270; M-1 to Q-269; M-1 to R-268; M-1 to D-267; M-1 to T-266; M-1 to I-265; M-1 to L-264; M-1 to L-263; M-1 to K-262; M-1 to S-261; M-1 to G-260; M-1 to L-259; M-1 to R-258; M-1 to T-257; M-1 to Q-256; M-1 to L-255; M-1 to T-254; M-1 to T-253; M-1 to G-252; M-1 to N-251; M-1 to V-250; M-1 to L-249; M-1 to D-248; M-1 to N-247; M-1 to Y-246; M-1 to F-245; M-1 to F-244; M-1 to M-243; M-1 to S-242; M-1 to V-241; M-1 to N-240; M-1 to A-239; M-1 to L-238; M-1 to H-237; M-1 to H-236; M-1 to E-235; M-1 to I-234; M-1 to D-233; M-1 to R-232; M-1 to G-231; M-1 to S-230; M-1 to L-229; M-1 to T-228; M-1 to E-227; M-1 to N-226; M-1 to E-225; M-1 to G-224; M-1 to L-223; M-1 to G-222; M-1 to S-221; M-1 to N-220; M-1 to Q-219; M-1 to P-218; M-1 to V-217; M-1 to F-216; M-1 to L-215; M-1 to T-214; M-1 to G-213; M-1 to R-212; M-1 to I-211; M-1 to S-210; M-1 to L-209; M-1 to D-208; M-1 to T-207; M-1 to L-206; M-1 to H-205; M-1 to E-204; M-1 to L-203; M-1 to F-202; M-1 to A-201; M-1 to R-200; M-1 to G-199; M-1 to,R-198; M-1 to A-197; M-1 to S-196; M-1 to S-195; M-1 to N-194; M-1 to S-193; M-1 to Y-192; M-1 to A-191; M-1 to L-190; M-1 to V-189; M-1 to E-188; M-1 to T-187; M-1 to L-186; M-1 to F-185; M-1 to N-184; M-1 to T-183; M-1 to L-182; M-1 to S-181; M-1 to P-180; M-1 to F-179; M-1 to S-178; M-1 to M-177; M-1 to L-176; M-1 to V-175; M-1 to Q-174; M-1 to L-173; M-1 to L-172; M-1 to N-171; M-1 to G-170; M-1 to S-169; M-1 to Y-168; M-1 to S-167; M-1 to F-166; M-1 to,G-165; M-1 to D-164; M-1 to G-163; M-1 to V-162; M-1 to Y-161; M-1 to G-160; M-1 to V-159; M-1 to K-158; M-1 to X-157; M-1 to T-156; M-1 to C-155; M-1 to N-154; M-1 to V-153; M-1 to D-152; M-1 to K-151; M-1 to M-150; M-1 to R-149; M-1 to Y-148; M-1 to C-147; M-1 to F-146; M-1 to V-145; M-1 to D-144; M-1 to W-143; M-1 to M-142; M-1 to E-141; M-1 to S-140; M-1 to K-139; M-1 to N-138; M-1 to P-137; M-1 to R-136; M-1 to P-135; M-1 to G-134; M-1 to Y-133; M-1 to D-132; M-1 to V-131; M-1 to I-130; M-1 to G-129; M-1 to V-128; M-1 to V-127; M-1 to G-126; M-1 to S-125; M-1 to G-124; M-1 to C-123; M-1 to N-122; M-1 to Q-121; M-1 to S-120; M-1 to A-119; M-1 to F-118; M-1 to A-117; M-1 to T-116; M-1 to P-115; M-1 to Y-114; M-1 to A-113; M-1 to V-112; M-1 to R-111; M-1 to G-110; M-1 to T-109; M-1 to E-108; M-1 to L-107; M-1 to W-106; M-1 to G-105; M-1 to A-104; M-1 to S-103; M-1 to C-102; M-1 to L-101; M-1 to H-100; M-1 to Y-99; M-1 to K-98; M-1 to A-97; M-1 to K-96; M-1 to Q-95; M-1 to X-94; M-1 to Y-93; M-1 to S-92; M-1 to L-91; M-1 to Q-90; M-1 to N-89; M-1 to Y-88; M-1 to T-87; M-1 to A-86; M-1 to M-85; M-1 to T-84; M-1 to A-83; M-1 to A-82; M-1 to E-81; M-1 to N-80; M-1 to A-179; M-1 to C-78; M-1 to A-77; M-1 to E-76; M-1 to R-75; M-1 to A-74; M-1 to K-73; M-1 to D-72; M-1 to F-71; M-1 to T-70; M-1 to L-69; M-1 to K-68; M-1 to Y-67; M-1 to Q-66; M-1 to G-65; M-1 to L-64; M-1 to P-63; M-1 to S-62; M-1 to R-61; M-1 to L-60; M-1 to H-59; M-1 to F-58; M-1 to V-57; M-1 to G-56; M-1 to V-55; M-1 to T-54; M-1 to T-53; M-1 to D-52; M-1 to Q-51; M-1 to F-50; M-1 to H-49; M-1 to L-48; M-1 to D-47; M-1 to V-46; M-1 to C-45; M-1 to K-44; M-1 to A-43; M-1 to D-42; M-1 to A-41; M-1 to H-40; M-1 to C-39; M-1 to Q-38; M-1 to G-37; M-1 to N-36; M-1 to D-35; M-1 to Q-34; M-1 to L-33; M-1 to C-32; M-1 to R-31; M-1 to D-30; M-1 to I-29; M-1 to P-28; M-1 to L-27; M-1 to Q-26; M-1 to E-25; M-1 to P-24; M-1 to E-23; M-1 to C-22; M-1 to N-21; M-1 to L-20; M-1 to G-19; M-1 to D-18; M-1 to G-17; M-1 to V-16; M-1 to Y-15; M-1 to H-14; M-1 to S-13; M-1 to K-12; M-1 to C-11; M-1 to E-10; M-1 to C-9; M-1 to K-8; M-1 to H-7; of SEQ ID NO:11. Polynucleotides encoding these polypeptides are also encompassed by the invention.

Further embodiments of the full-length WF-HABP invention are directed to polypeptide fragments comprising, or alternatively, consisting of, amino acids described by the general formula m to n, where m and n are integers corresponding to any one of the amino acid residues specified above for these symbols, respectively.

Further embodiments of the WF-HABP invention are directed to polypeptide fragments comprising, or alternatively, consisting of, amino acids described by the general formula m to n, where m and n are integers corresponding to any one of the amino acid residues specified above for these symbols, respectively.

Further embodiments of the OE-HABP invention are directed to polypeptide fragments comprising, or alternatively, consisting of, amino acids described by the general formula m to n, where m and n are integers corresponding to any one of the amino acid residues specified above for these symbols, respectively.

Further embodiments of the BM-HABP invention are directed to polypeptide fragments comprising, or alternatively, consisting of, amino acids described by the general formula m to n, where m and n are integers corresponding to any one of the amino acid residues specified above for these symbols, respectively.

It will be recognized in the art that some amino acid sequences of the full-length WF-HABPs can be varied without significant effect to the structure or function of the protein. If such differences in sequence are contemplated, it should be remembered that there will be critical areas on the protein which determine activity. Thus, the invention further includes variations of full-length WF-HABPs which show substantial full-length WF-HABP receptor activity or which include regions of full-length WF-HABP proteins such as the polypeptide portions discussed below. Such mutants include deletions, insertions, inversions, repeats, and type substitutions. As indicated above, guidance concerning which amino acid changes are likely to be phenotypically silent can be found in Bowie et al., "Deciphering the Message in Protein Sequences: Tolerance to Amino Acid Substitutions," Science 247:1306–1310 (1990).

It will be recognized in the art that some amino acid sequences of the WF-HABPs can be varied without significant effect to the structure or function of the protein. If such differences in sequence are contemplated, it should be remembered that there will be critical areas on the protein which determine activity. Thus, the invention further includes variations of WF-HABPs which show substantial WF-HABP receptor activity or which include regions of WF-HABP proteins such as the polypeptide portions discussed below. Such mutants include deletions, insertions, inversions, repeats, and type substitutions. As indicated above, guidance concerning which amino acid changes are likely to be phenotypically silent can be found in Bowie et al., "Deciphering the Message in Protein Sequences: Tolerance to Amino Acid Substitutions," Science 247:1306–1310 (1990).

It will be recognized in the art that some amino acid sequences of the OE-HABPs can be varied without significant effect to the structure or function of the protein. If such differences in sequence are contemplated, it should be remembered that there will be critical areas on the protein which determine activity. Thus, the invention further includes variations of OE-HABPs which show substantial OE-HABP receptor activity or which include regions of OE-HABP proteins such as the polypeptide portions discussed below. Such mutants include deletions, insertions, inversions, repeats, and type substitutions. As indicated above, guidance concerning which amino acid changes are likely to be phenotypically silent can be found in Bowie et al., "Deciphering the Message in Protein Sequences: Tolerance to Amino Acid Substitutions," Science 247:1306–1310 (1990).

It will be recognized in the art that some amino acid sequences of the BM-HABPs can be varied without significant effect to the structure or function of the protein. If such differences in sequence are contemplated, it should be remembered that there will be critical areas on the protein which determine activity. Thus, the invention further includes variations of BM-HABPs which show substantial BM-HABP receptor activity or which include regions of BM-HABP proteins such as the polypeptide portions discussed below. Such mutants include deletions, insertions, inversions, repeats, and type substitutions. As indicated above, guidance concerning which amino acid changes are likely to be phenotypically silent can be found in Bowie et al., "Deciphering the Message in Protein Sequences: Tolerance to Amino Acid Substitutions," Science 247: 1306–1310 (1990).

Thus, the fragment, derivative or analog of the polypeptide of FIGS. 1A–P (SEQ ID NO:2), may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the full-length WF-HABP polypeptide is fused with another compound, such as a compound to increase the half-life of the polypeptide (for example, polyethylene glycol), or (iv) one in which the additional amino acids are fused to the full length polypeptide, such as an IgG Fe fusion region peptide or leader or secretory sequence or a sequence which is employed for purification of the full-length WF-HABP polypeptide or a proprotein sequence. Such fragments, derivatives and analogs are deemed to be within the scope of those skilled in the art from the teachings herein.

Thus, the fragment derivative or analog of the polypeptide of FIGS. 2A–D (SEQ ID NO:5), or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the WF-HABP polypeptide is fused with another compound, such as a compound to increase the half-life of the polypeptide (for example, polyethylene glycol), or (iv) one in which the additional amino acids are fused to the full length polypeptide, such as an IgG Fe fusion region peptide or leader or secretory sequence or a sequence which is employed for purification of the WF-HABP polypeptide or a proprotein sequence. Such fragments, derivatives and analogs are deemed to be within the scope of those skilled in the art from the teachings herein.

Thus, the fragment, derivative or analog of the polypeptide of FIGS. 3A–C (SEQ ID NO:8), or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the OE-HABP polypeptide is fused with another compound, such as a compound to increase the half-life of the polypeptide (for example, polyethylene glycol), or (iv) one in which the additional amino acids are fused to the full length polypeptide, such as an IgG Fe fusion region peptide or leader or secretory sequence or a sequence which is employed for purification of the OE-HABP polypeptide or a proprotein sequence. Such fragments, derivatives and analogs are deemed to be within the scope of those skilled in the art from the teachings herein.

Thus, the fragment, derivative or analog of the polypeptide of FIGS. 4A–C (SEQ ID NO:11), or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the BM-HABP polypeptide is fused with another compound, such as a compound to increase the half-life of the polypeptide (for example, polyethylene glycol), or (iv) one in which the additional amino acids are fused to the full length polypeptide, such as an IgG Fc fusion region peptide or leader or secretory sequence or a sequence which is employed for purification of the BM-HABP polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in polypeptides with reduced positive charge to improve the characteristics of the full-length WF-HABP polypeptides. The prevention of aggregation is highly desirable. Aggregation of polypeptides not only results in a loss of activity but can also be problematic when preparing pharmaceutical formulations, because they can be immunogenic. (Pinckard et al., Clin. Exp. Immunol. 2:331–340 (1967); Robbins et al., Diabetes 36:838–845 (1987); Cleland et al., Crit. Rev. Therapeutic Drug Carrier Systems 10:307–377 (1993)).

Of particular interest are substitutions of charged amino acids with another charged amino acid and with neutral or negatively charged amino acids. The latter results in polypeptides with reduced positive charge to improve the characteristics of the WF-HABP polypeptides. The prevention of aggregation is highly desirable. Aggregation of polypeptides not only results in a loss of activity but can also be problematic when preparing pharmaceutical formulations, because they can be immunogenic. (Pinckard et al., Clin. Exp. Immunol. 2:331–340 (1967); Robbins et al., Diabetes 36:838–845 (1987); Cleland et al., Crit. Rev. Therapeutic Drug Carrier Systems 10:307–377 (1993)).

Of particular interest are substitutions of charged amino acids with another charged amino acid and with neutral or negatively charged amino acids. The latter results in polypeptides with reduced positive charge to improve the characteristics of the OE-HABP polypeptides. The prevention of aggregation is highly desirable. Aggregation of polypeptides not only results in a loss of activity but can also be problematic when preparing pharmaceutical formulations, because they can be immunogenic. (Pinckard et al., Clin. Exp. Immunol. 2:331–340 (1967); Robbins et al., Diabetes 36:838–845 (1987); Cleland et al., Crit. Rev. Therapeutic Drug Carrier Systems 10:307–377 (1993)).

Of particular interest are 'substitutions of charged amino acids with another charged amino acid and with neutral or negatively charged amino acids. The latter results in polypeptides with reduced positive charge to improve the characteristics of the BM-HABP polypeptides. The prevention of aggregation is highly desirable. Aggregation of polypeptides not only results in a loss of activity but can also be problematic when preparing pharmaceutical formulations, because they can be immunogenic. (Pinckard et al., Clin. Exp. Immunol. 2:331–340 (1967); Robbins et al., Diabetes 36:838–845 (1987); Cleland et al., Crit. Rev. Therapeutic Drug Carrier Systems 10:307–377 (1993)).

The replacement of amino acids can also change the selectivity of binding to cell surface receptors. For example, Ostade et al. (Nature 361:266–268 (1993)) describes certain mutations resulting in selective binding of TNF-a to only one of the two known types of TNF receptors. Thus, full-length WF-HABPs of the present invention may include one or more amino acid substitutions, deletions or additions, either from natural mutations or human manipulation.

The replacement of amino acids can also change the selectivity of binding to cell surface receptors. For example, Ostade et al. (Nature 361:266–268 (1993)) describes certain mutations resulting in selective binding of TNF-a to only one of the two known types of TNF receptors. Thus, WF-HABPs of the present invention may include one or more amino acid substitutions, deletions or additions, either from natural mutations or human manipulation.

The replacement of amino acids can also change the selectivity of binding to cell surface receptors. For example, Ostade et al. (Nature 361:266–268 (1993)) describes certain mutations resulting in selective binding of TNF-a to only one of the two known types of TNF receptors. Thus, OE-HABPs of the present invention may include one or more amino acid substitutions, deletions or additions, either from natural mutations or human manipulation.

The replacement of amino acids can also change the selectivity of binding to cell surface receptors. For example, Ostade et al. (Nature 361:266–268 (1993)) describes certain mutations resulting in selective binding of TNF-a to only one of the two known types of TNF receptors. Thus, BM-HABPs of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In specific embodiments, the number of substitutions, additions or deletions in the amino acid sequence of FIGS. 1A–P (SEQ ID NO:2) and/or any of the polypeptide fragments described herein (e.g., the HA-binding, EGF-like, or link domains) is 100, 90, 80, 75, 70, 60, 50, 40, 35, 30, 25, 20, 15, 10, 9, 8, 7, 6, 5, 4, 3, 2, 1 or 150–100, 100–50, 50–20, 20–10, 5–10, 1–5 1–3 or 1–2.

In specific embodiments, the number of substitutions, additions or deletions in the amino acid sequence of FIGS. 2A–D (SEQ ID NO:5) and/or any of the polypeptide fragments described herein (e.g., the HA-binding, EGF-like, or link domains) is 100, 90, 80, 75, 70, 60, 50, 40, 35, 30, 25, 20, 15, 10, 9, 8, 7, 6, 5, 4, 3, 2, 1 or 150–100, 100–50, 50–20, 20–10, 5–10, 1–5, 1–3 or, 1–2.

In specific embodiments, the number of substitutions, additions or deletions in the amino acid sequence of FIGS. 3A–C (SEQ ID NO:8) and/or any of the polypeptide fragments described herein (e.g., the HA-binding, EGF-like, or link domains) is 100, 90, 80, 75, 70, 60, 50, 40, 35, 30, 25, 20, 15, 10, 9, 8, 7, 6, 5, 4, 3 2, 1 or 150–100, 100–50, 50–20, 20–10, 5–10, 1–5, 1–3 or 1–2.

In specific embodiments, the number of substitutions, additions or deletions in the amino acid sequence of FIGS. 4A–C (SEQ ID NO:11) and/or any of the polypeptide fragments described herein (e.g., the HA-binding, EGF-like, or link domains) is 100, 90, 80, 75, 70, 60, 50, 40, 35, 30, 25, 20, 15, 10, 9, 8, 7, 6, 5, 4, 3, 2, 1 or 150–100, 100–50, 50–20, 20–10, 5–10, 1–5, 1–3 or 1–2.

Amino acids in the full-length WF-HABP polypeptides of the present invention that are essential for function can be identified by methods known in the art, such as site-directed mutagenesis or alanine-scanning mutagenesis (Cunningham and Wells, Science 244:1081–1085 (1989)). The latter procedure introduces single alanine mutations at every residue in the molecule. The resulting mutant molecules are then tested for biological activity such as receptor binding to its ligand in vitro, or in vitro (e.g., hyaluronan or chondroitin proteoglycan sulfates). Sites that are critical for ligand-receptor binding can also be determined by structural analysis such as crystallization, nuclear magnetic resonance or photoaffinity labeling (Smith et al., J. Mol. Biol. 224:899–904 (1992) and de Vos et al., Science 255:306–312 (1992)).

Amino acids in the WF-HABP polypeptides of the present invention that are essential for function can be identified by methods known in the art, such as site-directed mutagenesis or alanine-scanning mutagenesis (Cunningham and Wells, Science 244:1081–1085 (1989)). The latter procedure introduces single alanine mutations at every residue in the molecule. The resulting mutant molecules are then tested for biological activity such as receptor binding to its ligand in vitro, or in vitro (e.g., hyaluronan or chondroitin proteoglycan sulfates). Sites that are critical for ligand-receptor binding can also be determined by structural analysis such as crystallization, nuclear magnetic resonance or photoaffinity labeling (Smith et al., J. Mol. Biol. 224:899–904 (1992) and de Vos et al., Science 255:306–312 (1992)).

Amino acids in the OE-HABP polypeptides of the present invention that are essential for function can be identified by methods known in the art, such as site-directed mutagenesis or alanine-scanning mutagenesis (Cunningham and Wells, Science 244:1081–1085 (1989)). The latter procedure introduces single alanine mutations at every residue in the molecule. The resulting mutant molecules are then tested for biological activity such as receptor binding to its ligand in vitro, or in vitro (e.g., hyaluronan or chondroitin proteoglycan sulfates). Sites that are critical for ligand-receptor binding can also be determined by structural analysis such as crystallization, nuclear magnetic resonance or photoaffinity labeling (Smith et al., J. Mol. Biol. 224:899–904 (1992) and de Vos et al., Science 255:306–312 (1992)).

Amino acids in the BM-HABP polypeptides of the present invention that are essential for function can be identified by methods known in the art, such as site-directed mutagenesis or alanine-scanning mutagenesis (Cunningham and Wells, Science 244:1081–1085 (1989)). The latter procedure introduces single alanine mutations at every residue in the molecule. The resulting mutant molecules are then tested for biological activity such as receptor binding to its ligand in vitro, or in vitro (e.g., hyaluronan or chondroitin proteoglycan sulfates). Sites that are critical for ligand-receptor binding can also be determined by structural analysis such as crystallization, nuclear magnetic resonance or photoaffinity labeling (Smith et al., J. Mol. Biol. 224:899–904 (1992) and de Vos et al., Science 255:306–312 (1992)).

The polypeptides of the present invention also include the polypeptide of FIGS. 1A–P (SEQ ID NO:2); the polypeptides of FIGS. 1A–P (SEQ ID NO:2) minus the N-terminal methionine; the polypeptide sequence of any of the full-length WF-HABP domains described herein; the polypeptide sequence of FIGS. 1A–P (SEQ ID NO:2) minus a portion, or all of, one or more of the HA-binding domain, the EGF-like Type 1 domains, the EOF-like type I domains, laminin-type EGF domains, the link protein domain, the cytochrome P-450 cysteine heme-iron ligand binding domain, prokaryotic membrane lipoprotein lipid attachment site domains of the full-length WF-HABP shown in FIGS. 1A–P (SEQ ID NO:2); and polypeptides which are at least 80% identical, more preferably at least 85%, 90% or 95% identical, still more preferably at least 96%, 97%, 98% or 99% identical to the polypeptides described above, and also include portions of such polypeptides with at least 30 amino acids and more preferably at least 50 amino acids.

The polypeptides of the present invention also include the polypeptide encoded by the deposited cDNA; the polypeptide of FIGS. 2A–D (SEQ ID NO:5); the polypeptides of FIGS. 2A–D (SEQ ID NO:5) minus the N-terminal methionine; the polypeptide sequence of any of the WF-HABP domains described herein; the polypeptide sequence of FIGS. 2A–D (SEQ ID NO:5) minus a portion, or all of, the HA binding motif, the EGF-like Type 2 domain, and a link domain domain WF-HABP shown in FIGS. 2A–D (SEQ ID NO:5); and polypeptides which are at least 80% identical, more preferably at least 85%, 90% or 95% identical, still more preferably at least 96%, 97%, 98% or 99% identical to the polypeptides described above, and also include portions of such polypeptides with at least 30 amino acids and more preferably at least 50 amino acids.

The polypeptides of the present invention also include the polypeptide encoded by the deposited cDNA; the polypeptide of FIGS. 3A–C (SEQ ID NO:8); the polypeptides of FIGS. 3A–C (SEQ ID NO:8) minus the N-terminal methionine; the polypeptide sequence of any of the OE-HABP domains described herein; the polypeptide sequence of FIGS. 3A–C (SEQ ID NO:8) minus a portion, or all of, the HA binding motif domain, and a link protein domain shown in FIGS. 3A–C (SEQ ID NO:8); and polypeptides which are at least 80% identical, more preferably at least 85%, 90% or 95% identical, still more preferably at least 96%, 97%, 98% or 99% identical to the polypeptides described above, and also include portions of such polypeptides with at least 30 amino acids and more preferably at least 50 amino acids.

The polypeptides of the present invention also include the polypeptide encoded by the deposited cDNA; the polypeptide of FIGS. 4A–C (SEQ ID NO:11); the polypeptides of FIGS. 4A–C (SEQ ID NO:11) minus the N-terminal methionine; the polypeptide sequence of any of the BM-HABP domains described herein; the polypeptide sequence of FIGS. 4A–C (SEQ ID NO:11) minus a portion, or all of, the HA binding motif domain, shown in FIGS. 4A–C (SEQ ID NO:11); and polypeptides which are at least 80% identical, more preferably at least 85%, 90% or 95% identical, still more preferably at least 96%, 97%, 98% or 99% identical to the polypeptides described above, and also include portions of such polypeptides with at least 30 amino acids and more preferably at least 50 amino acids.

By a polypeptide having an amino acid sequence at least, for example, 95% "identical" to a reference amino acid sequence of a full-length WF-HABP polypeptide is intended that the amino acid sequence of the polypeptide is identical to the reference sequence except that the polypeptide sequence may include up to five amino acid alterations per each 100 amino acids of the reference amino acid of a full-length WF-HABP receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

By a polypeptide having an amino acid sequence at least, for example, 95% "identical" to a reference amino acid sequence of a WF-HABP polypeptide is intended that the amino acid sequence of the polypeptide is identical to the reference sequence except that the polypeptide sequence may include up to five amino acid alterations per each 100 amino acids of the reference amino acid of a WF-HABP receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

By a polypeptide having an amino acid sequence at least, for example, 95% "identical" to a reference amino acid sequence of a OE-HABP polypeptide is intended that the amino acid sequence of the polypeptide is identical to the reference sequence except that the polypeptide sequence may include up to five amino acid alterations per each 100 amino acids of the reference amino acid of a OE-HABP receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

By a polypeptide having an amino acid sequence at least, for example, 95% "identical" to a reference amino acid sequence of a BM-HABP polypeptide is intended that the amino acid sequence of the polypeptide is identical to the reference sequence except that the polypeptide sequence may include up to five amino acid alterations per each 100 amino acids of the reference amino acid of a BM-HABP receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIGS. 1A–P (SEQ ID NO:2), or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

As a practical matter, whether any particular polypeptide is at least 90%, 95%, 96%, 97%, 98% or 99% identical to, for instance, the amino acid sequence shown in FIGS. 2A–D (SEQ ID NO:5), the amino acid sequence encoded by the deposited cDNA clone, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

As a practical matter, whether any particular polypeptide is at least 90%, 95%, 96%, 97%, 98% or 99% identical to, for instance, the amino acid sequence shown in FIGS. 3A–C (SEQ ID NO:8), the amino acid sequence encoded by the deposited cDNA clone, or fragments thereof, can,be determined conventionally using known computer programs such the Bestfit program (Wisconsin Sequence Analysis Package, Version 8 for Unix, Genetics Computer Group, University Research Park, 575 Science Drive, Madison, Wis. 53711). When using. Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

As a practical matter, whether any particular polypeptide is at least 90%, 95%, 96%, 97%, 98% or 99% identical to, for instance, the amino acid sequence shown in FIGS. 4A–C (SEQ ID NO:11), the amino acid sequence encoded by the deposited cDNA clone, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment of the full-length WF-HABP invention, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

In a specific embodiment of the WF-HABP invention, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

In a specific embodiment of the OE-HABP invention, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the—final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

In a specific embodiment of the BM-HA1P invention, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The polypeptides of the present full-length WF-HABP invention have uses which include, but are not limited to, molecular weight marker on SDS-PAGE gels or on molecular sieve gel filtration columns using methods well known to those of skill in the art.

The polypeptides of the present WF-HABP invention have uses which include, but are not limited to, molecular weight marker on SDS-PAGE gels or on molecular sieve gel filtration columns using methods well known to those of skill in the art.

The polypeptides of the present OE-HABP invention have uses which include, but are not limited to, molecular weight marker on SDS-PAGE gels or on molecular sieve gel filtration columns using methods well known to those of skill in the art.

The polypeptides of the present BM-HABP invention have uses which include, but are not limited to, molecular weight marker on SDS-PAGE gels or on molecular sieve gel filtration columns using methods well known to those of skill in the art.

Detection of Disease States

Cells which express full-length WF-HABP polypeptides and which are believed to be subject to increased levels of the full-length WF-HABP ligand hyaluronan during inflammatory and immunological conditions include, for example, connective cells and tissues, white fat, endothelial cells, vascular cells, atherosclerotic plaques, human umbilical vein endothelial cells (HUVECs), and other cells or tissues of highly vascularized organs or connective tissues. In addition, Northern blots revealed high levels of expression of 9.5, 4.5, 3.0 and 2.4 Kb transcripts in the heart, placenta and lung, with lower levels found in the liver, pancreas, and skeletal muscle. The 9.5 Kb band appeared to be the predominant mRNA and was especially prominent in the placenta and the heart. By "a cellular response to a hylauronan receptor family ligand" is intended any genotypic, phenotypic, and/or morphologic change to a cell, cell line, tissue, tissue culture or patient that is induced by a hyaluronan receptor family ligand or stimuli (e.g. cytokines, injury, or IL-1b or TNF-a induction). As indicated, such cellular responses include not only normal physiological responses to hyaluronan receptor family ligands or stimuli (e.g. cytokines, injury, or IL-1b or TNF-a induction), but also diseases associated with aberrant rheological function, water homeostasis, and aberrant cell secretion, activation, survival, proliferation, migration and differentiation.

Cells which express WF-HABP polypeptides and which are believed to be subject to increased levels of the WF-HABP ligand hyaluronan during inflammatory and immunological conditions include, for example, connective cells and tissues, white fat, endothelial cells, vascular cells, atherosclerotic plaques, human umbilical vein endothelial cells (HUVECs), and other cells or tissues of highly vascularized organs or connective tissues. In addition, Northern blots revealed high levels of expression of 9.5, 4.5, 3.0 and 2.4 Kb transcripts in the heart, placenta and lung, with lower levels found in the liver, pancreas, and skeletal muscle. The 9.5 Kb band appeared to be the predominant mRNA and was especially prominent in the placenta and the heart. By "a cellular response to a hylauronan receptor family ligand" is intended any genotypic, phenotypic, and/or morphologic change to a cell, cell line, tissue, tissue culture or patient that is induced by a hyaluronan receptor family ligand or stimuli (e.g. cytokines, injury, or IL-1b or TNF-a induction). As indicated, such cellular responses include not only normal physiological responses to hyaluronan receptor family ligands or stimuli (e.g. cytokines, injury, or IL-1b or TNF-a induction), but also diseases associated with aberrant rheological function, water homeostasis, and aberrant cell secretion, activation, survival, proliferation, migration and differentiation.

Cells which express OE-HABP polypeptides and which are believed to be subject to increased levels of the OE-HABP ligand hyaluronan during inflammatory and immunological conditions include, for example connective cells and tissues, osteoblasts, skeletal cells, endothelial cells, vascular cells, atherosclerotic plaques, human umbilical vein endothelial cells (HUVECs), SMC (human saphenous vein smooth muscle cells) and other cells or tissues of highly vascularized organs, or connective and/or joint tissues, such as the synovium. In addition, Northern blots revealed high levels of expression of OE-HABP mRNA in lung, placenta, and heart, with highest expression observed in the lung as a 2.2 Kb transcript. By "a cellular response to a hylauronan receptor family ligand" is intended any genotypic, phenotypic, and/or morphologic change to a cell, cell line, tissue, tissue culture or patient that is induced by a hyaluronan receptor family ligand or stimuli (e.g. cytokines, injury, or IL-1b or TNF-a induction). As indicated, such cellular responses include not only normal physiological responses to hyaluronan receptor family ligands or stimuli (e.g. cytokines, injury, or IL-1b or TNF-a induction), but also diseases associated with aberrant rheological function, water homeostasis, and aberrant cell secretion, activation, survival, proliferation, migration and differentiation.

Cells which express BM-HABP polypeptides and which are believed to be subject to increased levels of the BM-HABP ligand hyaluronan during inflammatory and immunological conditions include, for example connective cells and tissues, bone marrow, immune and/or hematopoietic cells, hepatocytes, endothelial cells, pulmonary and cardiovascular tissues, and other cells of developing tissues. In addition, Northern blots revealed high levels of expression of BM-HABP mRNA in human fetal brain, lung, liver and kidney with a distinct 9.5 Kb mRNA transcript expressed at an elevated level in fetal liver and a low level in the lung. By "a cellular response to a hylauronan receptor family ligand" is intended any genotypic, phenotypic, and/or morphologic change to a cell, cell line, tissue, tissue culture or patient that is induced by a hyaluronan receptor family ligand or stimuli (e.g. cytokines, injury, or IL-1b or TNF-a induction). As indicated, such cellular responses include not only normal physiological responses to hyaluronan receptor family ligands or stimuli (e.g. cytokines, injury, or IL-1b or TNF-a induction), but also diseases associated with aberrant rheological function, water homeostasis, and aberrant cell secretion, activation, survival, proliferation, migration and differentiation.

Thus, it is believed that certain tissues in mammals with certain diseases (e.g., vascular conditions, diseases associated with increased or decreased cell survival, secretion, activation, migration, differentiation, and proliferation; inflammatory diseases; ischemia; aberrant host defense; aberrant immune surveillance; arthritis; autoimmunity; (e.g., lupus erythematosus (SLE), rheumatoid arthritis (RA), insulin-dependent diabetes, multiple sclerosis (MS), giant cell arteritis, polyarteritis nodosa, myasthenia gravis, scleroderma, and graft versus host disease): immune dysfunction; and allergy), express significantly altered (e.g., enhanced or decreased) levels of the full-length WF-HABP polypeptide and mRNA encoding the full-length WF-HABP polypeptide when compared to a corresponding "standard" mammal, i.e., a mammal of the same species not having the disease. Diseases associated with increased cell survival, include cancers (such as follicular lymphomas, carcinomas with p53 mutations, and hormone-dependent tumors); autoimmune disorders (such as systeic lupus erythematosus and immune-related glomerulonephritis rheumatoid arthritis) and viral infections (such as herpes viruses, pox viruses and adenoviruses), information graft v. host disease, acute graft rejection, and chronic graft rejection. Diseases associated with decreased cell survival, include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia.

Thus, it is believed that certain tissues in mammals with certain diseases (e.g., vascular conditions, diseases associated with increased or decreased cell survival, secretion, activation, migration, differentiation, and proliferation; inflammatory diseases; ischemia; aberrant host defense; aberrant immune surveillance; arthritis; autoimmunity; (e.g., lupus erythematosus (SLE), rheumatoid arthritis (RA), insulin-dependent diabetes, multiple sclerosis (MS), giant cell arteritis polyarteritis nodosa, myasthenia gravis, scleroderma, and graft versus host disease): immune dysfunction; and allergy), express significantly altered (e.g., enhanced or decreased) levels of the WF-HABP polypeptide and mRNA encoding the WF-HABP polypeptide when compared to a corresponding "standard" mammal, i.e., a mammal of the same species not having the disease. Diseases associated with increased cell survival, include cancers (such as follicular lymphomas, carcinomas with p53 mutations, and hormone-dependent tumors); autoimmune disorders (such as systemic lupus erythematosus and immune-related glomerulonephritis rheumatoid arthritis) and viral infections (such as herpes viruses, pox viruses and adenoviruses), information graft v. host disease, acute graft rejection, and chronic graft rejection. Diseases associated with decreased cell survival, include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia.

Thus, it is believed that certain tissues in mammals with certain diseases (e.g., vascular conditions, diseases associated with increased or decreased cell survival, secretion, activation, migration, differentiation, and proliferation; inflammatory diseases; ischemia; aberrant host defense;, aberrant immune surveillance; arthritis; autoimmunity; (e.g., lupus erythematosus (SLE), rheumatoid arthritis (RA), insulin-dependent diabetes, multiple sclerosis (MS), giant cell arteritis, polyarteritis nodosa, myasthenia gravis, scleroderma, and graft versus host disease); immune dysfunction; and allergy), express significantly altered (e.g., enhanced or decreased) levels of the OE-HABP polypeptide and mRNA encoding the OE-HABP polypeptide when compared to a corresponding "standard" mammal, i.e., a mammal of the same species not having the disease. Diseases associated with increased cell survival, include cancers (such as follicular lymphomas, carcinomas with p53 mutations, and hormone-dependent tumors); autoimmune disorders (such as systemic lupus erythematosus and immune-related glomerulonephritis rheumatoid arthritis) and viral infections (such as herpes viruses, pox viruses and adenoviruses), information graft v. host disease, acute graft rejection, and chronic graft rejection. Diseases associated with decreased cell survival, include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia.

Thus, it is believed that certain tissues in mammals with certain diseases (e.g., vascular conditions, diseases associated with increased or decreased cell survival, secretion, activation, migration, differentiation, and proliferation; inflammatory diseases; ischemia; aberrant host defense; aberrant immune surveillance; arthritis; autoimmunity; (e.g., lupus erythematosus (SLE), rheumatoid arthritis (RA), insulin-dependent diabetes, multiple sclerosis (MS), giant cell arteritis, polyarteritis nodosa, myasthenia gravis, scleroderma, and graft versus host disease): immune dysfunction; and allergy), express significantly altered (e.g., enhanced or decreased) levels of the BM-HABP polypeptide and mRNA encoding the BM-HABP polypeptide when compared to a corresponding "standard" mammal, i.e., a mammal of the same species not having the disease. Diseases associated with increased cell survival, include cancers (such as follicular lymphomas, carcinomas with p53 mutations, and hormone-dependent tumors); autoimmune disorders (such as systemic lupus erythematosus and immune-related glomerulonephritis rheumatoid arthritis) and viral infections (such as herpes viruses, pox viruses and adenoviruses), information graft v. host disease, acute graft rejection, and chronic graft rejection. Diseases associated with decreased cell survival, include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia.

Further, it is believed that altered levels of the full-length WF-HABP polypeptide can be detected in certain body fluids (e.g., sera, plasma, urine, synovial fluid, bronchoalveolar lavage, and spinal fluid) from mammals with the disorder when compared to sera from mammals of the same species not having the disorder. Thus, the invention provides a diagnostic method useful during diagnosis, which involves assaying the expression level of the gene encoding the full-length WF-HABP polypeptide in mammalian cells or body fluid and comparing the gene expression level with a standard full-length WF-HABP gene expression level, whereby an increase or decrease in the gene expression level over the standard is indicative of the disease.

Further, it is believed that altered levels of the WF-HABP polypeptide can be detected in certain body fluids (e.g., sera, plasma, urine, synovial fluid, bronchoalveolar lavage, and spinal fluid) from mammals with the disorder when compared to sera from mammals of the same species not having the disorder. Thus, the invention provides a diagnostic method useful during diagnosis, which involves assaying the expression level of the gene encoding the WF-HABP polypeptide in mammalian cells or body fluid and comparing the gene expression level with a standard WF-HABP gene expression level, whereby an increase or decrease in the gene expression level over the standard is indicative of the disease.

Further, it is believed that altered levels of the OE-HABP polypeptide can be detected in certain body fluids (e.g., sera, plasma, urine, synovial fluid, bronchoalveolar lavage, and spinal fluid) from mammals with the disorder when compared to sera from mammals of the same species not having the disorder. Thus, the invention provides a diagnostic method useful during diagnosis, which involves assaying the expression level of the gene encoding the OE-HABP polypeptide in mammalian cells or body fluid and comparing the gene expression level with a standard OE-HABP gene expression level, whereby an increase or decrease, in the gene expression level over the standard is indicative of the disease.

Further, it is believed that altered levels of the BM-HABP polypeptide can be detected in certain body fluids (e.g., sera, plasma, urine, synovial, and spinal fluid) from mammals with the disorder when compared to sera from mammals of the same species not having the disorder. Thus, the invention provides a diagnostic method useful during diagnosis, which involves assaying the expression level of the gene encoding the BM-HABP polypeptide in mammalian cells or body fluid and comparing the gene expression level with a standard BM-HABP gene expression level, whereby an increase or decrease in the gene expression level over the standard is indicative of the disease.

By "assaying" the expression level of the gene encoding the full-length WF-HABP polypeptide" is intended qualitatively or quantitatively measuring or estimating the level of the full-length. WF-HABP polypeptide or the level of the mRNA encoding the full-length WF-HABP polypeptide in a first biological sample either directly (e.g., by determining or estimating absolute polypeptide or mRNA level) or relatively (e.g., by comparing to the full-length WF-HABP polypeptide level or mRNA level in a second biological sample).

Preferably, the full-length WF-HABP protein level or mRNA level in the first biological sample is measured or estimated and compared to a standard full-length WF-HABP receptor protein level or mRNA level, the standard being taken from a second biological sample obtained from an individual not having the disease state. As will be appreciated in the art, once a standard full-length WF-HABP receptor protein level or mRNA level is known, it can be used repeatedly as a standard for comparison.

By "assaying" the expression level of the gene encoding the WF-HABP polypeptide" is intended qualitatively or quantitatively measuring or estimating the level of the WF-HABP polypeptide or the level of the mRNA encoding the WF-HABP polypeptide in a first biological sample either directly (e.g., by determining or estimating absolute polypeptide or mRNA level) or relatively (e.g., by comparing to the WF-HABP polypeptide level or mRNA level in a second biological sample). Preferably, the WF-HABP protein level or mRNA level in the first biological sample is measured or estimated and compared to a standard WF-HABP receptor protein level or mRNA level, the standard being taken from a second biological sample obtained from an individual not having the disease state. As will be appreciated in the art, once a standard WF-HABP receptor protein level or mRNA level is known, it can be used repeatedly as a standard for comparison.

By "assaying" the expression level of the gene encoding the OE-HABP polypeptide" is intended qualitatively or quantitatively measuring or estimating the level of the OE-HABP polypeptide or the level of the mRNA encoding the OE-HABP polypeptide in a first biological sample either directly (e.g., by determining or estimating absolute polypeptide or mRNA level) or relatively (e.g., by comparing to the OE-HABP polypeptide level or mRNA level in a second biological sample). Preferably, the OE-HABP protein level or mRNA level in the first biological sample is measured or estimated and compared to a standard OE-HABP receptor protein level or mRNA level, the standard being taken from a second biological sample obtained from an individual not having the disease state. As will be appreciated in the art, once a standard OE-HABP receptor protein level or mRNA level is known, it can be used repeatedly as a standard for comparison.

By "assaying" the expression level of the gene encoding the BM-HABP polypeptide" is intended qualitatively or quantitatively measuring or estimating the level of the BM-HABP polypeptide or the level of the mRNA encoding the BM-HABP polypeptide in a first biological sample either directly (e.g., by determining or estimating absolute polypeptide or mRNA level) or relatively (e.g., by comparing to the BM-HABP polypeptide level or mRNA level in a second biological sample). Preferably, the BM-HABP protein level or mRNA level in the first biological, sample is measured or estimated and compared to a standard BM-HABP receptor protein level or mRNA level, the standard being taken from a second biological sample obtained from an individual not having the disease state. As will be appreciated in the art, once a standard BM-HABP receptor protein level or mRNA level is known, it can be used repeatedly as a standard for comparison.

By "biological sample" is intended any biological sample obtained from an individual, cell line, tissue culture, or other source which contains full-length WF-HABP receptor protein or mRNA. Biological samples include mammalian body fluids (such as sera, plasma, urine, lymph, pulmonary sputum or surfactant, synovial fluid and spinal fluid), and heart, placenta, lung, liver, pancreas, skeletal muscle, connective cells and tissues, white fat, endothelial cells, vascular cells, atherosclerotic plaques, human umbilical vein endothelial cells (HUVECs), and other cells or tissues of highly vascularized organs or connective tissues. Methods for obtaining tissue biopsies and body fluids from mammals are well known in the art. Where the biological sample is to include mRNA, a tissue biopsy is the preferred source.

By "biological sample" is intended any biological sample obtained from an individual, cell line, tissue culture, or other source which contains WF-HABP receptor protein or mRNA. Biological samples include mammalian body fluids. (such as sera, plasma, urine, lymph, pulmonary sputum or surfactant, synovial fluid and spinal fluid), and heart, placenta, lung, liver, pancreas, skeletal muscle, connective cells and tissues, white fat, endothelial cells, vascular cells, atherosclerotic plaques, human umbilical vein endothelial cells (HUVECs), and other cells or tissues of highly vascularized organs or connective tissues. Methods for obtaining tissue biopsies and body fluids from mammals are well known in the art. Where the biological sample is to include mRNA, a tissue biopsy is the preferred source.

By "biological sample" is intended any biological sample obtained from an individual, cell line, tissue culture, or other source which contains OE-HABP receptor protein or mRNA. Biological samples include mammalian body fluids (such as sera, plasma, lymph, urine, pulmonary sputum or surfactant, synovial fluid and spinal fluid), and heart, placenta, lung, liver, pancreas, skeletal muscle, connective cells and tissues, osteoblasts, endothelial cells, vascular cells, atherosclerotic plaques, human umbilical vein endothelial cells (HUVECs), SMC (human saphenous vein smooth muscle cells), and other cells or tissues of highly vascularized organs, connective or skeletal tissues, such as the synovium. Methods for obtaining tissue biopsies and body fluids from mammals are well known in the art. Where the biological sample is to include mRNA, a tissue biopsy is the preferred source.

By "biological sample" is intended any biological sample obtained from an individual, cell line, tissue culture, or other source which contains BM-HABP receptor protein or mRNA. Biological samples include mammalian body fluids (such as sera, plasma, lymph, urine, pulmonary sputum or surfactant, synovial fluid and spinal fluid), human fetal brain, lung, liver, kidney, connective cells and tissues, bone marrow, endothelial cells, and other cells or tissues of developmental tissues. Methods for obtaining tissue biopsies and body fluids from mammals are well known in the art. Where the biological sample is to include mRNA, a tissue biopsy is the preferred source.

Where a diagnosis has already been made according to conventional methods, the present invention is useful as a prognostic indicator, whereby patients exhibiting altered full-length WF-HABP gene expression will experience a worse clinical outcome relative to patients expressing the, gene at a normal level.

Where a diagnosis has already been made according to conventional methods, the present invention is useful as a prognostic indicator, whereby patients exhibiting altered WF-HABP gene expression will experience a worse clinical outcome relative to patients expressing the gene at a normal level.

Where a diagnosis has already been made according to conventional methods, the present invention is useful as a prognostic indicator, whereby patients exhibiting altered OE-HABP gene expression will experience a worse clinical outcome relative to patients expressing the gene at a normal level.

Where a diagnosis has already been made according to conventional methods, the present invention is useful as a prognostic indicator, whereby patients exhibiting altered BM-HABP gene expression will experience a worse clinical outcome relative to patients expressing the gene at a normal level.

Nucleic acids for diagnosis may be obtained from a biological sample of a subject, such as from blood, urine, saliva, lymph, tissue biopsy or autopsy material, using techniques known in the art. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled full-length WF-HABP nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (see, e.g., Myers et al., Science 230:1242 (1985)). Sequence changes at specific locations may also be revealed by nuclease protection assays, such as RNase and S1 protection or the chemical cleavage method (see Cotton et al., Proc. Natl. Acad. Sci. USA 85:4397–4401 (1985)). In another embodiment, an array of oligonucleotides probes comprising full-length WF-HABP polynucleotide sequences or fragments thereof, can be constructed to conduct efficient screening of e.g., genetic mutations. Array technology methods are well known and have general applicability and can be used to address a variety of questions in molecular genetics including gene expression, genetic linkage, and genetic variability (see for example, Chee et al., Science 274:610–613 (1996)).

Nucleic acids for diagnosis may be obtained from a biological sample of a subject, such as from blood, urine, saliva, lymph, tissue biopsy or autopsy material, using techniques known in the art. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled WF-HABP nucleotide sequences. Perfectly matched-sequences can be distinguished from mismatched-duplexes by RNase digestion or by differences in melting temperatures. DNA sequence differences may also be detected by alterations in electrophoretic mobility of DNA fragments in gels, with or without denaturing agents, or by direct DNA sequencing (see, e.g., Myers et al., Science 230:1242 (1985)). Sequence changes at specific locations may also be revealed by nuclease protection assays, such as RNase and S1 protection or the chemical cleavage method (see Cotton et al., Proc. Natl. Acad. Sci. USA 85:4397–4401 (1985)). In another embodiment, an array of oligonucleotides probes consisting of WF-HABP polynucleotide sequences or fragments thereof, can be constructed to conduct efficient screening of e.g., genetic mutations. Array technology methods are well known and have general applicability and can be used to address a variety of questions in molecular genetics including gene expression, genetic linkage, and genetic variability (see for example, Chee et al., Science 274:610–613 (1996)).

Nucleic acids for diagnosis may be obtained from a biological sample of a subject, such as from blood, urine, saliva, lymph, tissue biopsy or autopsy material, using techniques known in the art. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled OE-HABP nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (see, e.g., Myers et al., Science 230:1242 (1985)). Sequence changes at specific locations may also be revealed by nuclease protection assays, such as RNase and S1 protection or the chemical cleavage method (see Cotton et al., Proc. Natl. Acad. Sci. USA 85:4397–4401 (1985)). In another embodiment, an array of oligonucleotides probes comprising OE-HABP polynucleotide sequences or fragments thereof, can be constructed to conduct efficient screening of e.g., genetic mutations. Array technology methods are well known and have general applicability and can be used to address a variety of questions in molecular genetics including gene expression, genetic linkage, and genetic variability (see for example, Chee et al., Science 274:610–613 (1996)).

Nucleic acids for diagnosis may be obtained from a biological sample of a subject, such as from blood, urine, saliva, lymph, tissue biopsy or autopsy material, using techniques known in the art. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled BM-HABP nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (see, e.g., Myers et al., Science 230:1242 (1985)). Sequence changes at specific locations may also be revealed by nuclease protection assays, such as RNase and S1 protection or the chemical cleavage method (see Cotton et al., Proc. Natl. Acad. Sci. USA 85:4397–4401 (1985)). In another embodiment, an array of oligonucleotides probes comprising BM-HABP polynucleotide sequences or fragments thereof, can be constructed to conduct efficient screening of e.g., genetic mutations. Array technology methods are well known and have general applicability and can be used to address a variety of questions in molecular genetics including gene expression, genetic linkage, and genetic variability (see for example, Chee et al., Science 274:610–613 (1996)).

The diagnostic assays offer a process for diagnosing or determining a susceptibility to specific diseases through detection of mutation in the full-length WF-HABP gene by the methods described herein or otherwise known in the art.

The diagnostic assays offer a process for diagnosing or determining a susceptibility to specific diseases through detection of mutation in the WF-HABP gene by the methods described herein or otherwise known in the art.

The diagnostic assays offer a process for diagnosing or determining a susceptibility to specific diseases through detection of mutation in the OE-HABP gene by the methods described herein or otherwise known in the art.

The diagnostic assays offer a process for diagnosing or determining a susceptibility to specific diseases through detection of mutation in the BM-HABP gene by the methods described herein or otherwise known in the art.

In addition, specific diseases can be diagnosed by methods comprising those which derive a sample from a subject with an abnormally decreased or increased level of full-length WF-HABP polypeptide or mRNA. Decreased or increased expression can be measured at the RNA level using any of the methods well known in the art, which include, but are not limited to, Northern blot analysis, (Harada et al., Cell 63:303–312 (1990)), S1 nuclease mapping (Fijita et al., Cell 49:357–367 (1987)), RNAse protection, the polymerase chain reaction (PCR), reverse transcription in combination with the polymerase chain reaction (RT-PCR) (Makino et al., Technique 2:295–301 (1990), reverse transcription in combination with the ligase chain reaction (RT-LCR) and other hybridization methods.

In addition, specific diseases can be diagnosed by methods comprising those which derive a sample from a subject with an abnormally decreased or increased level of WF-HABP polypeptide or mRNA. Decreased or increased expression can be measured at the RNA level using any of the methods well known in the art, which include, but are not limited to, Northern blot analysis, (Harada et al., Cell 63:303–312 (1990)), S1 nuclease mapping (Fijita et al., Cell 49:357–367 (1987)), RNAse protection, the polymerase chain reaction (PCR), reverse transcription in combination with the polymerase chain reaction (RT-PCR) (Makino et al., Technique 2:295–301 (1990), reverse transcription in combination with the ligase chain reaction (RT-LCR) and other hybridization methods.

In addition, specific diseases can be diagnosed by methods comprising those which derive a sample from a subject with an abnormally decreased or increased level of OE-HABP polypeptide or mRNA. Decreased or increased expression can be measured at the RNA level using any of the methods well known in the art, which include, but are not limited to, Northern blot analysis, (Harada et al., Cell 63:303–312 (1990)), S1 nuclease mapping (Fijita et al., Cell 49:357–367 (1987)), RNAse protection, the polymerase chain reaction (PCR), reverse transcription in combination with the polymerase chain reaction (RT-PCR) (Makino et al., Technique 2:295–301 (1990), reverse transcription in combination with the ligase chain reaction (RT-LCR) and other hybridization methods.

In addition, specific diseases can be diagnosed by methods comprising those which derive a sample from a subject with an abnormally decreased or increased level of BM-HABP polypeptide or mRNA. Decreased or increased expression can be measured at the RNA level using any of the methods well known in the art, which include, but are not limited to, Northern blot analysis, (Harada et al., Cell 63:303–312 (1990)), S1 nuclease mapping (Fijita et al., Cell 49:357–367 (1987)), RNAse protection, the polymerase chain reaction (PCR), reverse transcription in combination with the polymerase chain reaction (RT-PCR) (Makino et al., Technique 2:295–301 (1990), reverse transcription in combination with the ligase chain reaction (RT-LCR) and other hybridization methods.

Assaying full-length WF-HABP polypeptide levels in a biological sample can be by any techniques known in the art, which include, but are not limited to, radioimmunoassays, competitive-binding assays, Western Blot analysis and enzyme linked immunosorbent assays (ELISAs) and other antibody-based techniques. For example, full-length WF-HABP polypeptide expression in tissues can be studied with classical immunohistological methods (Jalkanen et al., J. Cell. Biol. 101:976–985 (1985); Jalkanen et al., J. Cell. Biol. 105:3087–3096(1987)).

Assaying WF-HABP polypeptide levels in a biological sample can be by any techniques known in the art, which include, but are not limited to, radioimmunoassays, competitive-binding assays, Western Blot analysis and enzyme linked immunosorbent assays (ELISAs) and other antibody-based techniques. For example, WF-HABP polypeptide expression in tissues can be studied with classical immunohistological methods (Jalkanen et al., J. Cell. Biol. 101:976–985 (1985); Jalkanen et al., J. Cell. Biol. 105:3087–3096 (1987)).

Assaying OE-HABP polypeptide levels in a biological sample can be by any techniques known in the art, which include, but are not limited to, radioimmunoassays, competitive-binding assays, Western Blot analysis and enzyme linked immunosorbent assays (ELISAs) and other antibody-based techniques. For example, OE-HABP polypeptide expression in tissues can be studied with classical immunohistological methods (Jalkanen et al., J. Cell. Biol. 101:976–985 (1985); Jalkanen et al., J. Cell. Biol. 105:3087–3096 (1987)).

Assaying BM-HABP polypeptide levels in a biological sample can be by any techniques known in the art, which include, but are not limited to, radioimmunoassays, competitive-binding assays, Western Blot analysis and enzyme linked immunosorbent assays (ELISAs) and other antibody-based techniques. For example, BM-HABP polypeptide expression in tissues can be studied with classical immunohistological methods (Jalkanen et al., J. Cell. Biol. 101:976–985 (1985); Jalkanen et al., J. Cell. Biol. 105:3087–3096 (1987)).

Suitable labels for the full-length WF-HABP invention are known in the art and include enzyme labels, such as, Glucose oxidase, and radioisotopes, such as iodine ($^{125}$I, $^{121}$I), carbon ($^{14}$C), sulfur ($^{35}$S), tritium ($^{3}$H), indium (121In), and technetium ($^{99m}$Tc), and fluorescent labels, such as fluorescein and rhodamine, and biotin.

Suitable labels for the WF-HABP invention are known in the art and include enzyme labels, such as, Glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

Suitable labels for the OE-HABP invention are known in the art and include enzyme labels, such as, Glucose oxidase, and radioisotopes, such as iodine ($^{125}$I, $^{121}$I), carbon ($^{14}$C), sulfur ($^{35}$S), tritium ($^{3}$H), indium ($^{121}$In), and technetium ($^{99m}$Tc), and fluorescent labels, such as fluorescein and rhodamine, and biotin.

Suitable labels for the BM-HABP invention are known in the art and include enzyme labels, such as, Glucose oxidase, and radioisotopes, such as iodine ($^{125}$I, $^{121}$I), carbon ($^{14}$C), sulfur ($^{35}$S), tritium ($^{3}$H) indium ($^{121}$In), and technetium ($^{99m}$Tc), and fluorescent labels, such as fluorescein and rhodamine, and biotin.

Antibodies

Further polypeptides of the invention relate to antibodies and T-cell antigen receptors (TCR) which immunospecifically bind a polypeptide, polypeptide fragment, or variant of SEQ ID NOs: 2, 5, 8, or 11, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention) and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60% less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described, herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies maybe specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen et al., Cancer Res. 58(16):3668–3678 (1998); Harrop et al., J. Immunol. 161 (4):1786–1794 (1998); Zhu et al., Cancer Res. 58(15): 3209–3214 (1998); Yoon et al., J. Immunol. 160(7): 3170–3179 (1998); Prat et al., J. Cell. Sci. 111 (Pt2): 237–247 (1998); Pitard et al., J. Immunol. Methods 205(2): 177–190 (1997); Liautard et al., Cytokine 9(4):233–241 (1997); Carlson et al., J. Biol. Chem. 272(17): 11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen of interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared Using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples (e.g., Example 16). In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Arnes et al., J. Immunol. Methods 184:177–186 (1995); Kettleborough et al., Eur. J. Immunol. 24:952–958 (1994); Persic et al., Gene 187 9–18 (1997); Burton et al. Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489–498 (1991); Studnicka et al., Protein Engineering 7(6):805–814 (1994); Roguska et al., PNAS 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homologous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NOs: 2, 5, 8, or 11.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., Bio-Techniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851–855 (1984); Neuberger et al., Nature 312:604–608 (1984); Takeda et al., Nature 314:452454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction-of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5) :155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can for dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al. Proc. Natl. Acad. Sci. USA 89:11337–11341(1992) (said references incorporated by reference in their entireties).

As discussed, supra, the polypeptides corresponding to a polypeptide; polypeptide fragment, or a variant of SEQ ID NO: 2, 5, 8, or 11 may be fused or conjugated to the above antibody portions to increase the in vivo half life of the polypeptides or for use in immunoassays using methods known in the art. Further, the polypeptides corresponding to SEQ ID NO: 2, 5, 8, or 11 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fe part after the fusion protein has been expressed, detected, and purified, would be desired. For example, the Fe portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QLAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mereaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum(II) (DDP) cisplatin), anthracyclines (e.g., daunorubicin (formerly daunomycin) and doxorubicin), antibiotics (e.g., dactinomycin (formerly actinomycin), bleomycin, mithramycin, and anthraycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., *Int. Immunol.*, 6:1567–1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell*, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.0 1 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen. (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/ or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5): 155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342:435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435438 (1989)).

In a specific embodiment, viral vectors that contains nucleic acid sequences encoding an antibody of the invention are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431434 (1991); Rosenfeld et al., Cell 68:143–155 (1992); Mastrangeli et al., J. Clin. Invest. 91:225–234 (1993); PCT Publication WO94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al, Meth. Enzymol. 217:618–644 (1993); Cline, Pharmac. Ther. 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. Diagnosis and Imaging Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976–985 (1985); Jalkanen, et al., J. Cell . Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes; eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads; dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Agonists and Antagonists of WF-HABP

In one embodiment, the present invention is directed to a method for identifying compounds that interact with (e.g., bind to) full-length WF-HABP polypeptides (including, but not limited to full-length WF-HABP, and one or more hyaluronan binding domains of full-length WF-HABP). Compounds identified may be useful, for example, in modulating the activity full-length WF-HABP gene products; in elaborating the biological function of full-length WF-HABP; in screens for identifying compounds that disrupt normal full-length WF-HABP interactions; or may in themselves disrupt such interactions and therefore may have uses which include, for example, regulators of hematopoiesis and/or of the immune response.

In one embodiment, the present invention is directed to a method for identifying compounds that interact with (e.g., bind to) WF-HABP polypeptides (including, but not limited to WF-HABP, and one or more hyaluronan binding domains of WF-HABP). Compounds identified may be useful, for example, in modulating the activity WF-HABP gene products; in elaborating the biological function of WF-HABP; in screens for identifying compounds that disrupt normal WF-HABP interactions; or may in themselves disrupt such interactions and therefore may have uses which include, for example, regulators of hematopoiesis and/or of the immune response.

In one embodiment, the present invention is directed to a method for identifying compounds that interact with (e.g., bind to) OE-HABP polypeptides (including, but not limited to OE-HABP, and one or more hyaluronan binding domains of OE-HABP). Compounds identified may be useful, for example, in modulating the activity OE-HABP gene products; in elaborating the biological function of OE-HABP; in screens for identifying compounds that disrupt normal OE-HABP interactions; or may in themselves disrupt such interactions and therefore may have uses which include, for example, regulators of hematopoiesis and/or of the immune response.

In one embodiment, the present invention is directed to a method for identifying compounds that interact with (e.g., bind to) BM-HABP polypeptides (including, but not limited to BM-HABP, and one or more hyaluronan binding domains of BM-HABP). Compounds identified may be useful, for example, in modulating the activity BM-HABP gene products; in elaborating the biological function of BM-HABP; in screens for identifying compounds that disrupt normal BM-HABP interactions; or may in themselves disrupt such interactions and therefore may have uses which include, for example, regulators of hematopoiesis, and/or of the immune response.

The principle of the assays used to identify compounds that bind to full-length WF-HABP involves preparing a reaction mixture of full-length WF-HABP and the test compound under conditions and for a time sufficient to allow the two components to interact and bind, thus forming a complex which can be removed and/or detected in the reaction mixture. The full-length WF-HABP polypeptide species used can vary depending upon the goal of the screening assay. For example, where agonists of the natural ligand are sought, the full length WF-HABP, or a soluble truncated full-length WF-HABP (e.g., containing one or more binding domains (i.e. EGF-like type II domain, EGF-like type 2 domain, laminin-type EGF, cytochrome P450 cysteine heme-iron ligand binding domains, prokaryotic membrane lipoprotein lipid attachment site domains), a peptide corresponding to a full-length WF-HABP hyaluronan binding domain or a fusion protein containing a full-length WF-HABP hyaluronan binding domain fused to a polypeptide that affords advantages in the assay system (e.g., labeling, isolation of the resulting complex, etc.) can be utilized. Where compounds that interact with a full-length WF-HABP binding domain are sought to be identified, peptides corresponding to the full-length WF-HABP binding domain and fusion proteins containing a full-length WF-HABP binding domain can be used.

The principle of the assays used to identify compounds that bind to WF-HABP involves preparing a reaction mixture of WF-HABP and the test compound under conditions and for a time sufficient to allow the two components to interact and bind, thus forming a complex which can be removed and/or detected in the reaction mixture. The WF-HABP polypeptide species used can vary depending upon the goal of the screening assay. For example, where agonists of the natural ligand are sought, the WF-HABP, or a soluble truncated WF-HABP (e.g., containing one or more binding domains (i.e. EGF-like type 2 domain, link-protein binding domain), a peptide corresponding to a WF-HABP hyaluronan binding domain or a fusion protein containing a WF-HABP hyaluronan binding domain fused to a polypeptide that affords advantages in the assay system (e.g., labeling, isolation of the resulting complex, etc.) can be utilized. Where compounds that interact with a WF-HABP binding domain are sought to be identified, peptides corresponding to the WF-HABP binding domain and fusion proteins containing a WF-HABP binding domain can be used.

The principle of the assays used to identify compounds that bind to OE-HABP involves preparing a reaction mixture of OE-HABP and the test compound under conditions and for a time sufficient to allow the two components to interact and bind, thus forming a complex which can be removed and/or detected in the reaction mixture. The OE-HABP polypeptide species used can vary depending upon the goal of the screening assay. For example, where agonists of the natural ligand are sought, the OE-HABP, or a soluble truncated OE-HABP (e.g., containing one or more binding domains (i.e. link-protein binding domain), a peptide corresponding to a OE-HABP hyaluronan binding domain or a fusion protein containing a OE-HABP hyaluronan binding domain fused to a polypeptide that affords advantages in the assay system (e.g., labeling, isolation of the resulting complex, etc.) can be utilized. Where compounds that interact with a OE-HABP binding domain are sought to be identified, peptides corresponding to the OE-HABP binding domain and fusion proteins containing a OE-HABP binding domain can be used.

The principle of the assays used to identify compounds that bind to BM-HABP involves preparing a reaction mixture of BM-HABP and the test compound under conditions and for a time sufficient to allow the two components to interact and bind, thus forming a complex which can be removed and/or detected in the reaction mixture. The BM-HABP polypeptide species used can vary depending upon the goal of the screening assay. For example, where agonists of the natural ligand are sought, the BM-HABP, or a soluble. truncated BM-HABP (e.g., containing one or more binding domains (i.e. link-protein binding domain), a peptide corresponding to a BM-HABP hyaluronan binding domain or a fusion protein containing a BM-HABP hyaluronan binding domain fused to a polypeptide that affords advantages in the assay system (e.g., labeling, isolation of the resulting complex, etc.) can be utilized. Where compounds that interact with a BM-HABP binding domain are sought to be identified, peptides corresponding to the BM-HABP binding domain and fusion proteins containing a BM-HABP binding domain can be used.

The compounds that may be screened in accordance with the invention include, but are not limited to, soluble peptides, including but not limited to those found in random peptide libraries; (see, e.g., Lan et al., Nature 354:82–84 (1991); Houghten, R. et al., Nature 354:84–86 (1991)), cell or tissue lysates, and biological samples (e.g, cells, tissue, sera and lymph). Such compounds may also be found in random peptide expression libraries, and genomic or cDNA expression libraries, or combinatorial chemistry-derived molecular libraries made of D- and/or L-configuration amino acids; phosphopeptides (including, but not limited to members of random or partially degenerate, directed phosphopeptide libraries; see, e.g., Songyang et al., Cell 72:767–778 (1993)); antibodies (including, but not limited to, polyclonal, monoclonal, humanized, anti-idiotypic, chimeric or single chain antibodies, and FAb, F(ab')2 and FAb expression library fragments, and epitope-binding fragments thereof); and small organic or inorganic molecules.

Numerous experimental methods may be used to select and detect polypeptides that bind with full-length WF-HABP, including, but not limited to, protein affinity chromatography, hyaluronan or proteoglycan affinity chromatography, affinity blotting, immunoprecipitation, cross-linking, and library based methods such as protein probing, phage display and the two-hybrid system. See generally, Phizicky et al., Microbiol. Rev. 59:94–123 (1995). Once isolated, such a full-length WF-HABP-binding polypeptide can be identified and can, in turn, be used, in conjunction with standard techniques, to identify polypeptides with which it interacts. For example, at least a portion of the amino acid sequence of a polypeptide that interacts with full-length WF-HABP can be ascertained using techniques well known to those of skill in the art, such as via the Edman degradation technique. (See, e.g., Creighton, 1983, "Proteins: Structures and Molecular Principles", W.H. Freeman & Co., N.Y., pp. 34–49). The amino acid sequence obtained may be used as a guide for the generation of oligonucleotide mixtures that can be used to screen for gene sequences encoding such polypeptides. Screening may be accomplished, for example, by standard hybridization or PCR techniques. Techniques for the generation of oligonucleotide mixtures and the screening are well-known. (See, e.g., Sambrook et al., Molecular Cloning: A Laboratory Manual, 2nd Edit., (1989), Cold Spring Harbor Laboratory Press; and PCR Protocols: A Guide to Methods and Applications, 1990, Innis, M. et al., eds. Academic Press, Inc., New York).

Numerous experimental methods may be used to select and detect polypeptides that bind with WF-HABP, including, but not limited to, protein affinity chromatography, hyaluronan or proteoglycan affinity chromatography, affinity blotting, immunoprecipitation, cross-linking, and library based methods such as protein probing, phage display and the two-hybrid system. See generally, Phizicky et al., Microbiol. Rev. 59:94–123 (1995). Once isolated, such a WF-HABP-binding polypeptide can be identified and can, in turn, be used, in conjunction with standard techniques, to identify polypeptides with which it interacts. For example, at least a portion of the amino acid sequence of a polypeptide that interacts with WF-HABP can be ascertained using techniques well known to those of skill in the art, such as via the Edman degradation technique. (See, e.g., Creighton, 1983, "Proteins: Structures and Molecular Principles", W.H. Freeman & Co., N.Y., pp. 34–49). The amino acid sequence obtained may be used as a guide for the generation of oligonucleotide mixtures that can be used to screen for gene sequences encoding such polypeptides. Screening may be accomplished, for example, by standard hybridization or PCR techniques. Techniques for the generation of oligonucleotide mixtures and the screening are well-known. (See, e.g., Sambrook et al., Molecular Cloning: A Laboratory Manual, 2nd Edit., (1989), Cold Spring Harbor Laboratory Press; and PCR Protocols: A Guide to Methods and Applications, 1990, Innis, M. et al., eds. Academic Press, Inc., New York).

Numerous experimental methods may be used to select and detect polypeptides that bind with OE-HABP, including, but not limited to, protein affinity chromatography, hyaluronan or proteoglycan affinity chromatography, affinity blotting, immunoprecipitation, cross-linking, and library based methods such as protein probing, phage display and the two-hybrid system. See generally, Phizicky et al., Microbiol. Rev. 59:94–123 (1995). Once isolated, such a OE-HABP-binding polypeptide can be identified and can, in turn, be used, in conjunction with standard techniques, to identify polypeptides with which it interacts. For example, at least a portion of the amino acid sequence of a polypeptide that interacts with OE-HABP can be ascertained using techniques well known to those of skill in the art, such as via the Edman degradation technique. (See, e.g., Creighton, 1983, "Proteins: Structures and Molecular Principles", W.H. Freeman & Co., N.Y., pp. 34–49). The amino acid sequence obtained may be used as a guide for the generation of oligonucleotide mixtures that can be used to screen for gene sequences encoding such polypeptides. Screening may be accomplished, for example, by standard hybridization or PCR techniques. Techniques for the generation of oligonucleotide mixtures and the screening are well-known. (See, e.g., Sambrook et al., Molecular Cloning: A Laboratory Manual, 2nd Edit., (1989), Cold Spring Harbor Laboratory Press; and PCR Protocols: A Guide to Methods and Applications, 1990, Innis, M. et al., eds. Academic Press, Inc., New York).

Numerous experimental methods may be used to select and detect polypeptides that bind with BM-HABP, including, but not limited to, protein affinity chromatography, hyaluronan or proteoglycan affinity chromatography, affinity blotting, immunoprecipitation, cross-linking, and library based methods such as protein probing, phage display and the two-hybrid system. See generally, Phizicky et al., Microbiol. Rev. 59:94–123 (1995). Once isolated, such a BM-HABP-binding polypeptide can be identified and can in turn, be used, in conjunction with standard techniques, to identify polypeptides with which it interacts. For example, at least a portion of the amino acid sequence of a polypeptide that interacts with BM-HABP can be ascertained using techniques well known to those of skill in the art, such as via the Edman degradation technique. (See, e.g., Creighton, 1983, "Proteins: Structures and Molecular Principles", W.H. Freeman & Co., N.Y., pp. 34–49). The amino acid sequence obtained may be used as a guide for the generation of oligonucleotide mixtures that can be used to screen for gene sequences encoding such polypeptides. Screening may be accomplished, for example, by standard hybridization or PCR techniques. Techniques for the generation of oligonucleotide mixtures and the screening are well-known. (See, e.g., Sambrook et al., Molecular Cloning: A Laboratory Manual, 2nd Edit., (1989), Cold Spring Harbor Laboratory Press; and PCR Protocols: A Guide to Methods and Applications, 1990, Innis, M. et al., eds. Academic Press, Inc., New York).

Additionally, methods may be employed which result in the simultaneous identification of genes which encode polypeptides interacting with full-length WF-HABP. These methods include, for example, probing expression libraries, in a manner similar to the well known technique of antibody probing of gt11 libraries, using labeled full-length WF-HABP polypeptide, such as a full-length WF-HABP fusion protein wherein a full-length WF-HABP domain is fused to a marker (e.g., an enzyme, fluor, luminescent protein, or dye), or an Ig-Fc domain. For example, the two-hybrid system may be used to detect interaction between full-length WF-HABP and candidate proteins for which genes encoding the candidate polypeptides are available by constructing the appropriate hybrids and testing for reporter gene activity. If an interaction is detected using the two-hybrid method, deletions can be made in the DNA encoding the candidate interacting polypeptide or the full-length WF-HABP polypeptide to identify a minimal domain for interaction. Alternatively, the two-hybrid system can be used to screen available organismal and/or mammalian tissue specific libraries of activation domain hybrids to identify polypeptides that bind to a full-length WF-HABP polypeptide. These screens result in the immediate availability of the cloned gene for any new polypeptide identified. In addition, since multiple clones that encode overlapping regions of protein are often identified, the minimal domain for interaction may be readily apparent from the initial screen.

Additionally, methods may be employed which result in the simultaneous identification of genes which encode polypeptides interacting with WF-HABP. These methods include, for example, probing expression libraries, in a manner similar to the well known technique of antibody probing of gt11 libraries, using labeled WF-HABP polypeptide, such as a WF-HABP fusion protein wherein a WF-HABP domain is fused to a marker (e.g., an enzyme, fluor, luminescent protein, or dye), or an Ig-Fc domain. For example, the two-hybrid system may be used to detect interaction between WF-HABP and candidate proteins for which genes encoding the candidate polypeptides are available by constructing the appropriate hybrids and testing for reporter gene activity. If an interaction is detected using the two-hybrid method, deletions can be made in the DNA encoding the candidate interacting polypeptide or the WF-HABP polypeptide to identify a minimal domain for interaction. Alternatively, the two-hybrid system can be used to screen available organismal and/or mammalian tissue specific libraries of activation domain hybrids to identify polypeptides that bind to a WF-HABP polypeptide. These screens result in the immediate availability of the cloned gene for any new polypeptide identified. In addition, since multiple clones that encode overlapping regions of protein are often identified, the minimal domain for interaction may be readily apparent from the initial screen.

Additionally, methods may be employed which result in the simultaneous identification of genes which encode polypeptides interacting with OE-HABP. These methods include, for example, probing expression libraries, in a manner similar to the well known technique of antibody probing of gt11 libraries, using labeled OE-HABP polypeptide, such as a OE-HABP fusion protein wherein a OE-HABP domain is fused to a marker (e.g., an enzyme, fluor, luminescent protein, or dye), or an Ig-Fc domain. For example, the two-hybrid system may be used to detect interaction between OE-HABP and candidate proteins for which genes encoding the candidate polypeptides are available by constructing the appropriate hybrids and testing for reporter gene activity. If an interaction is detected using the two-hybrid method, deletions can be made in the DNA encoding the candidate interacting polypeptide or the OE-HABP polypeptide to identify a minimal domain for interaction. Alternatively, the two-hybrid system can be used to screen available organismal and/or mammalian tissue specific libraries of activation domain hybrids to identify polypeptides that bind to a OE-HABP polypeptide. These screens result in the immediate availability of the cloned gene for any new polypeptide identified. In addition, since multiple clones that encode overlapping regions of protein are often identified, the minimal domain for interaction may be readily apparent from the initial screen.

Additionally, methods may be employed which result in the simultaneous identification of genes which encode polypeptides interacting with BM-HABP. These methods include, for example, probing expression libraries, in a manner similar to the well known technique of antibody probing of gt11 libraries, using labeled BM-HABP polypeptide, such as a BM-HABP fusion protein wherein a BM-HABP domain is fused to a marker (e.g., an enzyme, fluor, luminescent protein, or dye), or an Ig-Fc domain. For example, the two-hybrid system may be used to detect interaction between BM-HABP and candidate proteins for which genes encoding the candidate polypeptides are available by constructing the appropriate hybrids and testing for reporter gene activity. If an interaction is detected using the two-hybrid method, deletions can be made in the DNA encoding the candidate interacting polypeptide or the BM-HABP polypeptide to identify a minimal domain for interaction. Alternatively, the two-hybrid system can be used to screen available organismal and/or mammalian tissue specific libraries of activation domain hybrids to identify polypeptides that bind to a BM-HABP polypeptide. These screens result in the immediate availability of the cloned gene for any new polypeptide identified. In addition, since multiple clones that encode overlapping regions of protein are often identified, the minimal domain for interaction may be readily apparent from the initial screen.

Assays may also be used that identify compounds which bind to full-length WF-HABP gene regulatory sequences (e.g., promoter or enhancer sequences) and which may modulate full-length WF-HABP gene expression. See e.g., Platt, J. Biol. Chem. 269:28558–28562 (1994), which is incorporated herein by reference in its entirety.

Assays may also be used that identify compounds which bind to WF-HABP gene regulatory sequences (e.g., promoter or enhancer sequences) and which may modulate WF-HABP gene expression. See e.g., Platt, J. Biol. Chem. 269:28558–28562: (1994), which is incorporated herein by reference in its entirety.

Assays may also be used that identify compounds which bind to OE-HABP gene regulatory sequences (e.g., promoter or enhancer sequences) and which may modulate OE-HABP gene expression. See e.g., Platt, J. Biol. Chem. 269:28558–28562 (1994), which is incorporated herein by reference in its entirety.

Assays may also be used that identify compounds which bind to BM-HABP gene regulatory sequences (e.g., promoter or enhancer sequences) and which may modulate BM-HABP gene expression. See e.g., Platt, J. Biol. Chem. 269:28558–28562 (1994), which is incorporated herein by reference in its entirety.

The screening assays can be conducted in a variety of ways. For example, one method to conduct such an assay would involve anchoring the full-length WF-HABP polypeptide (e.g., fusion protein) or the test substance onto a solid phase and detecting full-length WF-HABP/test compound complexes anchored on the solid phase at the end of the reaction. In one embodiment of such a method, the full-length WF-HABP reactant may be anchored onto a solid surface, and the test compound, which is not anchored, may be labeled, either directly or indirectly.

The screening assays can be conducted in a variety of ways. For example, one method to conduct such an assay would involve anchoring the WF-HABP polypeptide (e.g., fusion protein) or the test substance onto a solid phase and detecting WF-HABP/test compound complexes anchored on the solid phase at the end of the reaction. In one embodiment of such a method, the WF-HABP reactant may be anchored onto a solid surface, and the test compound, which is not anchored, may be labeled, either directly or indirectly.

The screening assays can be conducted in a variety of ways. For example, one method to conduct such an assay would involve anchoring the OE-HABP polypeptide (e.g., fusion protein) or the test substance onto a solid phase and detecting OE-HABP/test compound complexes anchored on the solid phase at the end of the reaction. In one embodiment of such a method, the OE-HABP reactant may be anchored onto a solid surface, and the test compound, which is not anchored, may be labeled, either directly or indirectly.

The screening assays can be conducted in a variety of ways. For example, one method to conduct such an assay would involve anchoring the BM-HABP polypeptide (e.g., fusion protein) or the test substance onto a solid phase and detecting BM-HABP/test compound complexes anchored on the solid phase at the end of the reaction. In one embodiment of such a method, the BM-HABP reactant may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the polypeptide and drying. Alternatively, an immobilized antibody, preferably a monoclonal antibody, specific for the polypeptide to be immobilized may be used to anchor the polypeptide to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for full-length WF-HABP polypeptide or fusion protein or the test compound to anchor any complexes formed in solution, and a labeled antibody specific for the other component of the possible complex to detect anchored complexes.

Alternatively, a reaction can be conducted in a liquid phase, the reaction products separated from unreacted components, and complexes detected; e.g., using an immobilized antibody specific for WF-HABP polypeptide or fusion protein or the test compound to anchor any complexes formed in solution, and a labeled antibody specific for the other component of the possible complex to detect anchored complexes.

Alternatively, a reaction can be conducted in a liquid phase, the reaction products separated from unreacted components, and complexes detected; e.g., using an immobilized antibody specific for OE-HABP polypeptide or fusion protein or the test compound to anchor any complexes formed in solution, and a labeled antibody specific for the other component of the possible complex to detect anchored complexes.

Alternatively, a reaction can be conducted in a liquid phase, the reaction products separated from unreacted components, and complexes detected; e.g., using an immobilized antibody specific for BM-HABP polypeptide or fusion protein or the test compound to anchor any complexes formed in solution, and a labeled antibody specific for the other component of the possible complex to detect anchored complexes.

Alternatively, cell-based assays can be used to identify compounds that interact with WF-HABP. Such cell-based systems can include, for example, recombinant or non-recombinant cells, such as cell lines, which express the WF-HABP. For example spleen, lymph node, peripheral blood leukocytes, lung, thymus, heart, placenta, brain, bone marrow, nd liver cells, or cell lines derived from spleen, lymph node, peripheral blood leukocytes, lung, thymus, heart, placenta, brain, bone marrow, and liver cells can be used. In addition, expression host cells (e.g., COS cells, CHO cells, HEK 293 cells, fibroblasts) genetically engineered (e.g., by transfection or transduction of WF-HABP DNA) to express a functional WF-HABP and to respond to activation by the natural WF-HABP ligand (e.g., a vanilloid compound, such as, for example, capsaicin), e.g., as measured by a chemical or phenotypic change, induction of another host cell gene, change in ion flux (e.g., $Ca^{+2}$), etc., can be used as an end point in the assay. Interaction of the test compound with, for example, one or more WF-HABP extracellular domains expressed by the host cell can be determined by comparison or competition with WF-HABP ligands (e.g., vanilloid compounds such as, capsaicin), by the ability to induce a WF-HABP mediated cellular response (e.g., ion (e.g., $Ca^{+2}$) flux), and other techniques known in the art. (See generally Caterina et al., Nature 389:816–824 (1997) which is herein incorporated by reference in its entirety). Thus, the present invention also provides a screening method for identifying compounds capable eliciting a cellular response induced by WF-HABP receptors, which involves contacting cells which express WF-HABP with the candidate compound, and comparing the cellular response to that observed in absence of the candidate compound (i.e., the standard); whereby, an increased cellular response over the standard indicates that the compound is an agonist.

Cellular responses that may be assayed according to this embodiment, include, but are not limited to alterations in the expression of the WF-HABP gene, e.g., by assaying cell lysates for WF-HABP mRNA transcripts (e.g., by Northern analysis) or for WF-HABP expressed in the cell; compounds which regulate or modulate expression of the WF-HABP gene are good candidates as therapeutics. Additionally, activity of the WF-HABP signal transduction pathway itself (e.g., cation flux, such as calcium flux) can be routinely assayed using techniques known in the art (see, e.g, Caterina et al., Nature 389:816–824 (1997), the contents of which are herein incorporated by reference in its entirety).

In another embodiment, the present invention is directed to a method for inhibiting an activity (e.g., ion flux (e.g., $Ca^{+2}$) flux), of WF-HABP induced by a WF-HABP ligand or WF-HABP stimulus (e.g., temperature), which involves administering to a cell which expresses a WF-HABP polypeptide, an effective amount of a WF-HABP receptor ligand, analog or an antagonist capable of decreasing WF-HABP mediated signaling. Preferably, WF-HABP receptor mediated signaling is decreased to treat a disease wherein increased ion flux is exhibited. An antagonist can include soluble forms of the WF-HABP and antibodies directed against the WF-HABP polypeptides which block WF-HABP receptor mediated signaling. Preferably, WF-HABP receptor mediated signaling is decreased to treat a disease, or to decrease survival, secretion, proliferation, migration and/or differentiation of cells.

In an additional embodiment, the present invention is directed to a method for increasing an activity (e.g., ion (e.g., $Ca^{+2}$) flux), induced by a WF-HABP ligand (e.g., a vanilloid, such as, capsaicin) or WF-HABP stimulus (e.g., heat), which involves administering to a cell which expresses a WF-HABP polypeptide an effective amount of an agonist capable of increasing WF-HABP receptor mediated signaling. Preferably, WF-HABP receptor mediated signaling is increased to treat a disease wherein decreased ion flux is exhibited. Agonists of the present invention include monoclonal antibodies directed against the WF-HABP polypeptides which stimulate WF-HABP receptor mediated signaling. Preferably, WF-HABP receptor mediated signaling is increased to treat a disease, and to increase survival, secretion, proliferation, migration, and/or differentiation of cells.

By "agonist" is intended naturally occurring and synthetic compounds capable of eliciting or enhancing ion (e.g., $Ca^{+2}$) flux mediated by WF-HABP polypeptides. Such agonists include agents which increase expression of WF-HABP receptors or increase the sensitivity of the expressed receptor. By "antagonist" is intended naturally occurring and synthetic compounds capable of inhibiting WF-HABP mediated ion (e.g., $Ca^{+2}$) flux. Such antagonists include agents which decrease expression of WF-HABP receptors or decrease the sensitivity of the expressed receptor. Whether any candidate "agonist" or "antagonist" of the present invention can enhance or inhibit a WF-HABP mediated cellular response, such as, for example, ion flux, and cell proliferation, survival, and differentiation can be determined using art-known ligand/receptor cellular response assays, and ion flux assays, including those described herein.

Thus, the present invention also provides a screening method for identifying compounds capable of enhancing or inhibiting a cellular response induced by WF-HABP receptors. The method involves contacting cells which express WF-HABP polypeptides with the candidate compound in the presence of a WF-HABP ligand (e.g., a vanilloid compound, such as, capsaicin) or other stimulus (e.g., heat), assaying a cellular response (e.g., ion (e.g., $Ca^{+2}$) flux), and comparing the cellular response to a standard cellular response, the standard being assayed when contact is made between the WF-HABP ligand and WF-HABP, or when WF-HABP is exposed to the stimulus, in absence of the candidate compound; whereby, an increased cellular response over the standard indicates that the compound is an agonist of the WF-HABP-mediated signaling pathway and a decreased cellular response over the standard indicates that the compound is an antagonist of the WF-HABP-mediated signaling pathway. By "assaying a cellular response" is intended qualitatively or quantitatively measuring a cellular response to a candidate compound and/or a WF-HABP ligand or WF-HABP stimulus (e.g., determining or estimating an increase or decrease in ion (e.g., $Ca^{+2}$) flux). By the invention, a cell expressing a WF-HABP polypeptide can be contacted with either an endogenous or exogenously administered WF-HABP ligand.

One such screening technique involves the use of cells which express the receptor (for example, transfected kidney-derived HEK293 cells) in a system which measures intracellular $Ca^{+2}$ changes caused by receptor activation, for example, as described Caterina et al., Nature, 389:816–824 (1997). For example, compounds may be contacted with a cell which expresses the WF-HABP polypeptide of the present invention and ion (e.g., $Ca^{+2}$) flux, may be measured to determine whether the potential compound activates (i.e., leads to elevated ion flux) or inhibits the receptor.

Another method involves screening for compounds which inhibit activation of the receptor polypeptide of the present invention (i.e., antagonists) by determining inhibition of binding of labeled ligand to cells which have the receptor on the surface thereof. Such a method involves transfecting a eukaryotic cell with DNA encoding the WF-HABP polypeptide such that the cell expresses the receptor on its surface and contacting the cell with a compound in the presence of a labeled form of a WF-HABP ligand (e.g., a vanilloid compound, such as capsaicin). The ligand can be labeled, e.g., by radioactivity. The amount of labeled ligand bound to the receptors is measured, e.g., by measuring radioactivity of the WF-HABP polypeptide. If the compound binds to the receptor as determined by a reduction of labeled ligand which binds to the receptors, the binding of labeled ligand to the WF-HABP polypeptide is inhibited.

Soluble forms of the polypeptides of the present invention may be utilized in the ligand binding assay described above. These forms of WF-HABP are contacted with ligands in the extracellular medium after they are secreted. A determination is then made as to whether the secreted protein will bind to WF-HABP receptor ligands.

Agonists according to the present invention include compounds such as, for example, vanilloid receptor ligand peptide fragments, and neurotransmitters. Preferred agonists include WF-HABP polypeptide fragments of the invention and/or polyclonal and monoclonal antibodies raised against a WF-HABP polypeptide, or a fragment thereof.

WF-HABP polypeptides and polynucleotides and compounds identified as WF-HABP agonists or antagonists using assays described herein or otherwise known in the art, have uses which include, but are not limited to, treating diseases, regulating hematopoiesis, regulating immune responses, regulating cell survival, activation, secretion, migration and differentiation, regulating pain, and in developing analgesic agents and in furthering our understanding of pain insensitivity and pain syndromes.

Prophylactic and Therapeutic Methods

It is to be understood that although the following discussion is specifically directed to human patients, the teachings are also applicable to any animal that expresses the full-length WF-HABP.

As noted above, the full-length WF-HABP is structurally related to members of the hyaluronan receptor family and shares significant homology with the human TSG-6 and link proteins which have been demonstrated to be involved in the formation and stability of the extracellular matrix, cellular migration, cellular proliferation, cellular adhesion, and is believed to be involved in diverse human diseases which include, but are not limited to arthritis, delayed-type hypersensitivity reactions, integumentary disorders, hematopoiesis, lymphocyte activation, inflammatory conditions, vascular disorders, and metastasis. Thus, it is likely that the full-length WF-HABP is active in modulating growth regulatory activities (e.g., cell survival, secretion, differentiation and/or cell proliferation). Further, the full-length WF-HABP, like TSG-6, might be involved in the adhesion and migration of cells which leads to conditions such as inflammation and ischemia. Correspondingly, the novel expression profile of full-length WF-HABP suggests that it may play a role in a broader variety of cell types than observed for TSG-6. Particularly, the full-length WF-HABP is expressed on vascular and non-vascular tissues and cells, though most notably in vascular tissues such as heart, placenta, lung, liver, kidney, human umbilical vein endothelial cells (HUVEC), and smooth muscle cells (SMC). Thus, the full-length WF-HABP plays a potential role in regulating a varitey of cellular functions, particularly cellular adhesion for cells, such as, vascular cells (e.g., HUVEC, SMC, etc.), and this interaction is likely to result in activation, survival, proliferation, migration, and differentiation, as well as the regulation of cytokine profiles by such cells. The full-length WF-HABP potentially mediates the interaction of other cells to cells in which the full-length WF-HABP is expressed. Thus the full-length WF-HABP is likely to play a role in influencing various diseases or medical conditions, including, but not limited to, inflammation, host defense, immune surveillance, arthritis, MS, autoimmunity, immune dysfunction, and allergy. Additionally, the full-length WF-HABP appears to be expressed in other cell populations (e.g., endothelial cells, mesenchymal cells, epithelial cells, musclular) and thus the full-length WF-HABP likely regulates adhesion onto these cells, thereby regulating their survival, differentiation, morphology, and proliferation. Accordingly, it is likely that the full-length WF-HABP plays a role in other physiological or disease conditions, including, cancer, angiogenesis, wound healing, fibrosis, metastasis and tissue regeneration.

As noted above, the WF-HABP is structurally related to members of the hyaluronan receptor family and shares significant homology with the human TSG-6 and link proteins which have been demonstrated to be involved in the formation and stability of the extracellular matrix, cellular migration, cellular proliferation, cellular adhesion, and is believed to be involved in diverse human diseases which include, but are not limited to arthritis, delayed-type hypersensitivity reactions, integumentary disorders, hematopoiesis, lymphocyte activation, inflammatory conditions, vascular disorders, and metastasis. Thus, it is likely that the WF-HABP is active in modulating growth regulatory activities (e.g., cell survival, secretion, differentiation and/or cell proliferation). Further, the WF-HABP, like TSG-6, might be involved in the adhesion and migration of cells which leads to conditions such as inflammation and ischemia. Correspondingly, the novel expression profile of WF-HABP suggests that it may play a role in a broader variety of cell types than observed for TSG-6. Particularly, the WF-HABP is expressed on vascular and non-vascular tissues and cells, though most notably in vascular tissues such as heart, placenta, lung, liver, kidney, human umbilical vein endothelial cells (HUVEC), and smooth muscle cells (SMC). Thus, the WF-HABP plays a potential role in regulating a varitey of cellular functions, particularly cellular adhesion for cells, such as, vascular cells (e.g., HUVEC, SMC, etc.), and this interaction is likely to result in activation, survival, proliferation, migration, and differentiation, as well as the regulation of cytokine profiles by such cells. WF-HABP potentially mediates the interaction of other cells to cells in which WF-HABP is expressed. Thus the WF-HABP is likely to play a role in influencing various diseases or medical conditions, including, but not limited to, inflammation, host defense, immune surveillance, arthritis, MS, autoimmunity, immune dysfunction, and allergy. Additionally, the WF-HABP appears to be expressed in other cell populations (e.g., endothelial cells, mesenchymal cells, epithelial cells, musclular) and thus the WF-HABP likely regulates adhesion onto these cells, thereby regulating their survival, differentiation, morphology, and proliferation. Accordingly, it is likely that the WF-HABP plays a role in other physiological or disease conditions, including, cancer, angiogenesis, wound healing, fibrosis, metastasis and tissue regeneration.

As noted above, the OE-HABP is structurally related to members of the hyaluronan receptor family and shares significant homology with the cartilage link proteins which have been demonstrated to be involved in the formation and stability of the extracellular matrix, cellular migration, cellular proliferation, cellular adhesion, and is believed to be involved in diverse human diseases which include, but are not limited to arthritis, delayed-type hypersensitivity reactions, integumentary disorders, hematopoiesis, lymphocyte activation, inflammatory conditions, vascular disorders, and metastasis. Thus, it is likely that the OE-HABP is active in modulating growth regulatory activities (e.g., cell survival, secretion, differentiation and/or cell proliferation). Further, the OE-HABP, like Link, might be involved in the adhesion and migration of cells which leads to conditions such as inflammation and ischemia. Correspondingly, the novel expression profile of OE-HABP suggests that it may play a role in a broader variety of cell types than observed for the link protein. Particularly, the OE-HABP is expressed on vascular and non-vascular tissues and cells, though most notably in vascular tissues such as heart, placenta, lung, human umbilical vein endothelial cells (HUVEC), and smooth muscle cells (SMC). Thus, the OE-HABP plays a potential role in regulating a varitey of cellular functions, particularly cellular adhesion for cells, such as, vascular cells. (e.g., HUVEC, SMC, etc.), and this interaction is likely to result in activation, survival, proliferation, migration, and differentiation, as well as the regulation of cytokine profiles by such cells. OE-HABP potentially mediates the interaction of other cells to cells in which OE-HABP is expressed. Thus the OE-HABP is likely to play a role in influencing various diseases or medical conditions, including, but not limited to, inflammation, host defense, immune surveillance, arthritis, MS, autoimmunity, immune dysfunction, and allergy. In fact, link protein is thought to be a potential autoantigen in the development of arthritis and ankylosing spondylitis, and therefore, OE-HABP may play a role in the pathogenesis of these diseases. Additionally, the OE-HABP appears to be expressed in other cell populations (e.g., endothelial cells, mesenchymal cells, epithelial cells, musclular) and thus the OE-HABP likely regulates adhesion onto these cells, thereby regulating their survival, differentiation, morphology, and proliferation. Accordingly, it is likely that the OE-HABP plays a role in other physiological or disease conditions, including, cancer, angiogenesis, wound healing, fibrosis, metastasis and tissue regeneration.

As noted above, the BM-HABP is structurally related to members of the hyaluronan receptor family and shares significant homology with the TSG-6 proteins which have been demonstrated to be involved in the formation and stability of the extracellular matrix, cellular migration, cellular proliferation, cellular adhesion, and is believed to be involved in diverse human diseases which include, but are not limited to arthritis, delayed-type hypersensitivity reactions, integumentary disorders, hematopoiesis, lymphocyte activation, inflammatory conditions, vascular disorders, and metastasis. Thus, it is likely that the BM-HABP is active in modulating growth regulatory activities (e.g., cell survival, secretion, differentiation and/or cell proliferation). Further, the BM-HABP, like TSG-6, might be involved in the adhesion and migration of cells which leads to conditions such as inflammation and ischemia. Correspondingly, the novel expression profile of BM-HABP suggests that it may play a role in a broader variety of cell types than observed for TSG-6. Particularly, the BM-HABP is expressed in liver tissue. Unlike TSG-6, significant expression within vascular tissues was not detected suggesting BM-HABP may play a more divergent role in other tissues. However, based upon the strucutural similarity to TSG-6, BM-HABP may play a potential role in regulating a variety of cellular functions, particularly cellular adhesion for cells, such as, endothelial cells (e.g., liver, etc.), and this interaction is likely to result in activation, survival, proliferation, migration, and differentiation, as well as the regulation of cytokine profiles by such cells. Thus the BM-HABP is likely to play a role in influencing various diseases or medical conditions, including, but not limited to, inflammation, host defense, immune surveillance, arthritis, MS, autoimmunity, immune dysfunction, and allergy. Additionally, the BM-HABP appears to be expressed in other cell populations (e.g., endothelial cells, mesenchymal cells, epithelial cells, metabolic) and thus the BM-HABP likely regulates adhesion onto these cells, thereby regulating their survival, differentiation, morphology, and proliferation. Accordingly, it is likely that the BM-HABP plays a role in other physiological or disease conditions, including, cancer, angiogenesis, wound healing, fibrosis, metastasis and tissue regeneration.

Any method which neutralizes or enhances full-length WF-HABP mediated signaling can be used to modulate growth regulatory activities (e.g., cell proliferation, metastasis), and other activities mediated by full-length WF-HABP activity, such as, for example, extravasation, inflammation, host defense, immune surveillance, arthritis, MS, autoimmunity, immune dysfunction, allergy, cancer, angiogenesis, wound healing, water homeostasis, macromolecular filtration, lubrication, fibrosis, and tissue regeneration.

Any method which neutralizes or enhances WF-HABP mediated signaling can be used to modulate growth regulatory activities (e.g., cell proliferation, metastasis), and other activities mediated by WF-HABP activity, such as, for example, extravasation, inflammation, host defense, immune surveillance, arthritis, MS, autoimmunity, immune dysfunction, allergy, cancer, angiogenesis, wound healing, water homeostasis, macromolecular filtration, lubrication, fibrosis, and tissue regeneration.

Any method which neutralizes or enhances OE-HABP mediated signaling can be used to modulate growth regulatory activities (e.g., cell proliferation, metastasis), and other activities mediated by OE-HABP activity, such as, for example, extravasation, inflammation, host defense, immune surveillance, arthritis, MS, autoimmunity, immune dysfunction, allergy, cancer, angiogenesis, wound healing, water homeostasis, macromolecular filtration, lubrication, fibrosis, and tissue regeneration.

Any method which neutralizes or enhances BM-HABP mediated signaling can be used to modulate growth regulatory activities (e.g., cell proliferation, metastasis), and other activities mediated by BM-HABP activity, such as, for example, extravasation, inflammation, host defense, immune surveillance, arthritis, MS, autoimmunity, immune dysfunction, allergy, cancer, angiogenesis, wound healing, water homeostasis, macromolecular filtration, lubrication, fibrosis, and tissue regeneration.

Full-length WF-HABP polynucleotides or polypeptides (including full-length WF-HABP fragments, variants, derivatives, and analogs, and full-length WF-HABP agonists and antagonists as described herein) may be useful in treating disorders associated with rheological aberrations, autoimmunity, inflammation, proliferation and metastasis. Additionally, these compounds may be useful in treating, preventing, or activating cell death (e.g., of hematopoietic cells during processes of inflammation or tissue injury).

WF-HABP polynucleotides or polypeptides (including WF-HABP fragments, variants, derivatives, and analogs, and WF-HABP agonists and antagonists as described herein) may be useful in treating disorders associated with rheological aberrations, autoimmunity, inflammation, proliferation and metastasis. Additionally, these compounds may be useful in treating, preventing, or activating cell death (e.g., of hematopoietic cells during processes of inflammation or tissue injury).

OE-HABP polynucleotides or polypeptides (including OE-HABP fragments, variants, derivatives, and analogs, and OE-HABP agonists and antagonists as described herein) may be useful in treating disorders associated with rheological aberrations, autoimmunity, inflammation, proliferation and metastasis. Additionally, these compounds may be useful in treating, preventing, or activating cell death (e.g., of hematopoietic cells during processes of inflammation or tissue injury).

BM-HABP polynucleotides or polypeptides (including BM-HABP fragments, variants, derivatives, and analogs, and BM-HABP agonists and antagonists as described herein) may be useful in treating disorders associated with rheological aberrations, autoimmunity, inflammation, proliferation and metastasis. Additionally, these compounds may be useful in treating, preventing, or activating cell death (e.g., of hematopoietic cells during processes of inflammation or tissue injury).

Full-length WF-HABP polynucleotides or polypeptides (including full-length WF-HABP fragments, variants, derivatives, and analogs, and full-length WF-HABP agonists and antagonists as described herein) may be useful in treating disorders associated with extracellular matrix genesis, integumentary disorders, edema, hemophilia, and hydrovasation. Additionally, these compounds may be useful in treating, preventing, or activating cell migration (e.g., of hematopoietic cells during processes of inflammation or tissue injury). Such traits would particularly be useful when cells, near sites of surgery or injury, are induced to express full-length WF-HABP polynucleotides or polypeptides. Due to the exclusionary, and water homeostasis properties of members of the HA receptor family, such expression could inhibit vascular leakage of interstitual, plasma, blood, or other bodily fluid, while simulatanously recruiting immune and/or hematopoietic cells.

WF-HABP polynucleotides or polypeptides (including WF-HABP fragments, variants, derivatives, and analogs, and WF-HABP agonists and antagonists as described herein) may be useful in treating disorders associated with extracellular matrix genesis, integumentary disorders, edema, hemophilia, and hydrovasation. Additionally, these compounds may be useful in treating, preventing, or activating cell migration (e.g., of hematopoietic cells during processes of inflammation or tissue injury). Such traits would particularly be useful when cells, near sites of surgery or injury, are induced to express WF-HABP polynucleotides or polypeptides. Due to the exclusionary, and water homeostasis properties of members of the HA receptor family, such expression could inhibit vascular leakage of interstitual, plasma, blood, or other bodily fluid, while simulatanously recruiting immune and/or hematopoietic cells.

OE-HABP polynucleotides or polypeptides (including OE-HABP fragments, variants, derivatives, and analogs, and OE-HABP agonists and antagonists as described herein) may be useful in treating disorders associated with extracellular matrix genesis, integumentary disorders, edema, hemophilia, and hydrovasation. Additionally, these compounds may be useful in treating, preventing, or activating cell migration (e.g., of hematopoietic cells during processes of inflammation or tissue injury). Such traits would particularly be useful when cells, near sites of surgery or injury, are induced to express OE-HABP polynucleotides or polypeptides. Due to the exclusionary, and water homeostasis properties of members of the HA receptor family, such expression could inhibit vascular leakage of interstitial, plasma, blood, or other bodily fluid, while simulatanously recruiting immune and/or hematopoietic cells.

BM-HABP polynucleotides or polypeptides (including BM-HABP fragments, variants, derivatives, and analogs, and BM-HABP agonists and antagonists as described herein) may be useful in treating disorders associated with extracellular matrix genesis, integumentary disorders, edema, hemophilia, and hydrovasation. Additionally, these compounds may be useful in treating, preventing, or activating cell migration (e.g., of hematopoietic cells during processes of inflammation or tissue injury). Such traits would particularly be useful when cells, near sites of surgery or injury, are induced to express BM-HABP polynucleotides or polypeptides. Due to the exclusionary, and water homeostasis properties of members of the HA receptor family, such expression could inhibit vascular leakage of interstitual, plasma, blood, or other bodily fluid, while simulatanously recruiting immune and/or hematopoietic cells.

Similarly, full-length WF-HABP polynucleotides or polypeptides (including full-length WF-HABP fragments, variants, derivatives, and analogs, and full-length WF-HABP agonists and antagonists as described herein) may be useful in treating disorders associated with hemophilial conditions, since HA receptor members have been shown to maintain separation of integumentary surfaces during shear, blunt, and viscous forces which may inhibit the likelihood of injury by establishing a lubricative benefit to the immediate tissues.

Similarly, WF-HABP polynucleotides or polypeptides (including WF-HABP fragments, variants, derivatives, and analogs, and WF-HABP agonists and antagonists as described herein) may be useful in treating disorders associated with hemophilial conditions, since HA receptor members have been shown to maintain separation of integumentary surfaces during shear, blunt, and viscous forces which may inhibit the likelihood of injury by establishing a lubricative benefit to the immediate tissues.

Similarly, OE-HABP polynucleotides or polypeptides (including OE-HABP fragments, variants, derivatives, and analogs, and OE-HABP agonists and antagonists as described herein) may be useful in treating disorders associated with hemophilial conditions, since HA receptor members have been shown to maintain separation of integumentary surfaces during shear, blunt, and viscous forces which may inhibit the likelihood of injury by establishing a lubricative benefit to the immediate tissues.

Similarly, BM-HABP polynucleotides or polypeptides (including BM-HABP fragments, variants, derivatives, and analogs, and BM-HABP agonists and antagonists as described herein) may be useful in treating disorders associated with hemophilial conditions, since HA receptor members have been shown to maintain separation of integumentary surfaces during shear, blunt, and viscous forces which may inhibit the likelihood of injury by establishing a lubricative benefit to the immediate tissues.

Full-length WF-HABP polypeptides or polynucleotides (including full-length WF-HABP fragments, variants, derivatives, and analogs, and full-length WF-HABP agonists and antagonists as described herein) may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, full-length WF-HABP polynucleotides or polypeptides can be used as a marker or detector of a particular immune system disease or disorder.

WF-HABP polypeptides or polynucleotides (including WF-HABP fragments, variants, derivatives, and analogs, and WF-HABP agonists and antagonists as described herein) may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, WF-HABP polynucleotides or polypeptides can be used as a marker or detector of a particular immune system disease or disorder.

OE-HABP polypeptides or polynucleotides (including OE-HABP fragments, variants, derivatives, and analogs, and OE-HABP agonists and antagonists as described herein) may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, OE-HABP polynucleotides or polypeptides can be used as a marker or detector of a particular immune system disease or disorder.

BM-HABP polypeptides or polynucleotides (including BM-HABP fragments, variants, derivatives, and analogs, and BM-HABP agonists and antagonists as described herein) may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, BM-HABP polynucleotides or polypeptides can be used as a marker or detector of a particular immune system disease or disorder.

Full-length WF-HABP polypeptides or polynucleotides (including full-length WF-HABP fragments, variants, derivatives, and analogs, and full-length WF-HABP agonists and antagonists as described herein) may be useful in treating deficiencies or disorders of the integumentary system, by activating or inhibiting the proliferation, differentiation, or growth of integumentary cells and tissues, in addition to stimulating the development of the extracellular matrix. Hyaluronan, and thus HA receptors, are known to play an integral role in the development of the extracellular matrix which provides, for example, exclusionary benefits to the surrounding cells and tissues. Thus, such a barrier serves to protect cells behind its protective cloak from immune cell damage or detection, impedes viral infection through exclusion of the infectious particles, and may provide enabling benefit to cells during growth cycles, such as during mitosis. The etiology of these integumentary deficiencies or disorders may be genetic, somatic, such as cancer or some autoimmune disorders, acquired (e.g., by chemotherapy or toxins or radiation), or infectious. Moreover, full-length WF-HABP polynucleotides or polypeptides can be used as a marker or detector of a particular integumentary system disease or disorder.

WF-HABP polypeptides or polynucleotides (including WF-HABP fragments, variants, derivatives, and analogs, and WF-HABP agonists and antagonists as described herein) may be useful in treating deficiencies or disorders of the integumentary system, by activating or inhibiting the proliferation, differentiation, or growth of integumentary cells and tissues, in addition to stimulating the development of the extracellular matrix. Hyaluronan, and thus HA receptors, are known to play an integral role in the development of the extracellular matrix which provides, for example, exclusionary benefits to the surrounding cells and tissues. Thus, such a barrier serves to protect cells behind its protective cloak from immune cell damage or detection, impedes viral infection through exclusion of the infectious particles, and may provide enabling benefit to cells during growth cycles, such as during mitosis. The etiology of these integumentary deficiencies or disorders may be genetic, somatic, such as cancer or some autoimmune disorders, acquired (e.g., by chemotherapy or toxins or radiation), or infectious. Moreover, WF-HABP polynucleotides or polypeptides can be used as a marker or detector of a particular integumentary system disease or disorder.

OE-HABP polypeptides or polynucleotides (including OE-HABP fragments, variants, derivatives, and analogs, and OE-HABP agonists and antagonists as described herein) may be useful in treating deficiencies or disorders of the integumentary system, by activating or inhibiting the proliferation, differentiation, or growth of integumentary cells and tissues, in addition to stimulating the development of the extracellular matrix. Hyaluronan, and thus HA receptors, are known to play an integral role in the development of the extracellular matrix which provides, for example, exclusionary benefits to the surrounding cells and tissues. Thus, such a barrier serves to protect cells behind its protective cloak from immune cell damage or detection, impedes viral infection through exclusion of the infectious particles, and may provide enabling benefit to cells during growth cycles, such as during mitosis. The etiology of these integumentary deficiencies or disorders may be genetic, somatic, such as cancer or some autoimmune disorders, acquired (e.g., by chemotherapy or toxins or radiation), or infectious. Moreover, OE-HABP polynucleotides or polypeptides can be used as a marker or detector of a particular integumentary system disease or disorder.

BM-HABP polypeptides or polynucleotides (including BM-HABP fragments, variants, derivatives, and analogs, and BM-HABP agonists and antagonists as described herein) may be useful in treating deficiencies or disorders of the integumentary system, by activating or inhibiting the proliferation, differentiation, or growth of integumentary cells and tissues, in addition to stimulating the development of the extracellular matrix. Hyaluronan, and thus HA receptors, are known to play an integral role in the development of the extracellular matrix which provides, for example, exclusionary benefits to the surrounding cells and tissues. Thus, such a barrier serves to protect cells behind its protective cloak from immune cell damage or detection, impedes viral infection through exclusion of the infectious particles, and may provide enabling benefit to cells during growth cycles, such as during mitosis. The etiology of these integumentary deficiencies or disorders may be genetic, somatic, such as cancer or some autoimmune disorders, acquired (e.g., by chemotherapy or toxins or radiation), or infectious. Moreover, BM-HABP polynucleotides or polypeptides can be used as a marker or detector of a particular integumentary system disease or disorder.

Full-length WF-HABP polynucleotides or polypeptides (including full-length WF-HABP fragments, variants, derivatives, and analogs, and full-length WF-HABP agonists and antagonists as described herein) may be useful in treating or detecting deficiencies or disorders of hematopoietic cells. As further discussed below, full-length WF-HABP polypeptides, polynucleotides, and/or full-length WF-HABP agonists or antagonists could be used to increase differentiation and proliferation of hematopoietic cells, including the pluripotent stem cells, in an effort to treat those disorders associated with a decrease in certain (or many) types of hematopoietic cells. Examples of immunologic deficiency syndromes include, but are not limited to: blood protein disorders (e.g. agrammaglobulinemia, dysgamaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskort-Aldrich Disorder, anemia, thrombocytopenia, or hemoglobinuria. Moreover, full-length WF-HABP polypeptides, polynucleotides and/or full-length WF-HABP antagonists can be used to infections of viral, bacterial, or fungal origins through exclusion. Additionally, full-length WF-HABP polypeptides, polynucleotides and/or full-length WF-HABP antagonists can be used to treat or prevent the killing of hematopoietic cells and other cells during processes of inflammation or tissue injury.

WF-HABP polynucleotides or polypeptides (including WF-HABP fragments, variants, derivatives, and analogs, and WF-HABP agonists and antagonists as described herein) may be useful in treating or detecting deficiencies or disorders of hematopoietic cells. As further discussed below, WF-HABP polypeptides, polynucleotides, and/or WF-HABP agonists or antagonists could be used to increase differentiation and proliferation of hematopoietic cells, including the pluripotent stem cells, in an effort to treat those disorders associated with a decrease in certain (or many) types of hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidaldysfunction, severe combined immunodeficiency (SCIDs), Wiskott-Aldrich Disorder, anemia, thrombocytopenia, or hemoglobinuria. Moreover, WF-HABP polypeptides, polynucleotides and/or WF-HABP antagonists can be used to infections of viral, bacterial, or fungal origins through exclusion. Additionally, WF-HABP polypeptides, polynucleotides and/or WF-HABP antagonists can be used to treat or prevent the killing of hematopoietic cells and other cells during processes of inflammation or tissue injury.

OE-HABP polynucleotides or polypeptides (including OE-HABP fragments, variants, derivatives, and analogs, and OE-HABP agonists and antagonists as described herein) may be useful in treating or detecting deficiencies or disorders of hematopoietic cells. As further discussed below, OE-HABP polypeptides, polynucleotides, and/or OE-HABP agonists or antagonists could be used to increase differentiation and proliferation of hematopoietic cells, including the pluripotent stem cells, in an effort to treat those disorders associated with a decrease in certain (or many) types of hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria. Moreover, OE-HABP HABP polypeptides, polynucleotides and/or OE-HABP antagonists can be used to infections of viral, bacterial, or fungal origins through exclusion. Additionally, OE-HABP polypeptides, polynucleotides and/or OE-HABP antagonists can be used to treat or prevent the killing of hematopoietic cells and other cells during processes of inflammation or tissue injury.

BM-HABP polynucleotides or polypeptides (including BM-HABP fragments, variants, derivatives, and analogs, and BM-HABP agonists and antagonists as described herein) may be useful in treating or detecting deficiencies or disorders of hematopoietic cells. As further discussed below, BM-HABP polypeptides, polynucleotides, and/or BM-HABP agonists or antagonists could be used to increase differentiation and proliferation of hematopoietic cells, including the pluripotent stem cells, in an effort to treat those disorders associated with a decrease in certain (or many) types of hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria. Moreover, BM-HABP HABP polypeptides, polynucleotides and/or BM-HABP antagonists can be used to infections of viral, bacterial, or fungal origins through exclusion. Additionally, BM-HABP polypeptides, polynucleotides and/or BM-HABP antagonists can be used to treat or prevent the killing of hematopoietic cells and other cells during processes of inflammation or tissue injury.

Moreover, full-length WF-HABP polypeptides or polynucleotides (including full-length WF-HABP fragments, variants, derivatives, and analogs, and full-length WF-HABP agonists and antagonists as described herein) can also be used to modulate hemostatic (the stopping of bleeding) or thrombolytic activity (clot formation). For example, by increasing hemostatic or thrombolytic activity, full-length WF-HABP polynucleotides or polypeptides could be used to treat blood coagulation disorders (e.g., afibrinogenemia, factor deficiencies), blood platelet disorders (e.g. thrombocytopenia), or wounds resulting from trauma, surgery, or other causes. Alternatively, full-length WF-HABP polynucleotides, polypeptides and/or full-length WF-HABP agonists or antagonists that can decrease hemostatic or thrombolytic activity could be used to inhibit or dissolve clotting, important in the treatment of heart attacks (infarction), strokes, or scarring.

Moreover, WF-HABP polypeptides or polynucleotides (including WF-HABP fragments, variants, derivatives, and analogs, and WF-HABP agonists and antagonists as described herein) can also be used to modulate hemostatic (the stopping of bleeding) or thrombolytic activity (clot formation). For example, by increasing hemostatic or thrombolytic activity, WF-HABP polynucleotides or polypeptides could be used to treat blood coagulation disorders (e.g., afibrinogenemia, factor deficiencies), blood platelet disorders (e.g. thrombocytopenia), or wounds resulting from trauma, surgery, or other causes. Alternatively, WF-HABP polynucleotides, polypeptides and/or WF-HABP agonists or antagonists that can decrease hemostatic or thrombolytic activity could be used to inhibit or dissolve clotting, important in the treatment of heart attacks (infarction), strokes, or scarring.

Moreover, OE-HABP polypeptides or polynucleotides (including OE-HABP fragments, variants, derivatives, and analogs, and OE-HABP agonists and antagonists as described herein) can also be used to modulate hemostatic (the stopping of bleeding) or thrombolytic activity (clot formation). For example, by increasing hemostatic or thrombolytic activity, OE-HABP polynucleotides or polypeptides could be used to treat blood coagulation disorders (e.g., afibrinogenemia, factor deficiencies), blood platelet disorders (e.g. thrombocytopenia), or wounds resulting from trauma, surgery, or other causes. Alternatively, OE-HABP polynucleotides, polypeptides and/or OE-HABP agonists or antagonists that can decrease hemostatic or thrombolytic activity could be used to inhibit or dissolve clotting, important in the treatment of heart attacks (infarction), strokes, or scarring.

Moreover, BM-HABP polypeptides or polynucleotides (including BM-HABP fragments, variants, derivatives, and analogs, and BM-HABP agonists and antagonists as described herein) can also be used to modulate hemostatic (the stopping of bleeding) or thrombolytic activity (clot formation). For example, by increasing hemostatic or thrombolytic activity, BM-HABP polynucleotides or polypeptides could be used to treat blood coagulation disorders (e.g., afibrinogenemia, factor deficiencies), blood platelet disorders (e.g. thrombocytopenia), or wounds resulting from trauma, surgery, or other causes. Alternatively, BM-HABP polynucleotides, polypeptides and/or BM-HABP agonists or antagonists that can decrease hemostatic or thrombolytic activity could be used to inhibit or dissolve clotting, important in the treatment of heart attacks (infarction), strokes, or scarring.

Full-length WF-HABP polynucleotides or polypeptides (including full-length WF-HABP fragments, variants; derivatives, and analogs, and full-length WF-HABP agonists or full-length WF-HABP antagonists as described herein) may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of full-length WF-HABP polypeptides or polynucleotides and/or full-length WF-HABP agonists or full-length WF-HABP antagonists that can inhibit an immune response, particularly the proliferation, differentiation, or chemotaxis of T-cells, may be an effective therapy in preventing autoimmune disorders. Examples of autoimmune disorders that can be treated or detected by full-length WF-HABP include, but are not limited to: Addison's Disease, hemolytic anemia, antiphospholipid syndrome, rheumatoid arthritis, dermatitis, allergic encephalomyelitis, glomereulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

WF-HABP polynucleotides or polypeptides (including WF-HABP fragments, variants, derivatives, and analogs, and WF-HABP agonists or WF-HABP antagonists as described herein) may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of WF-HABP polypeptides or polynucleotides and/or WF-HABP antagonist or WF-HABP antagonists that can inhibit an immune response, particularly the proliferation, differentiation, or chemotaxis of T-cells, may be an effective therapy in preventing autoimmune disorders. Examples of autoimmune disorders that can be treated or detected by WF-HABP include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary inflammation, Guillain-Barre Syndrome, insulin dependent diabetes mellitus, and autoimmune inflammatory eye disease.

OE-HABP polynucleotides or polypeptides (including OE-HABP fragments, variants, derivatives, and analogs, and OE-HABP agonists or OE-HABP antagonists as described herein) may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of OE-HABP polypeptides or polynucleotides and/or OE-HABP agonists or OE-HABP antagonists that can inhibit an immune response, particularly the proliferation, differentiation, or chemotaxis of T-cells, may be an effective therapy in preventing autoimmune disorders. Examples of autoimmune disorders that can be treated or detected by OE-HABP include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitus, and autoimmune inflammatory eye disease.

BM-HABP polynucleotides or polypeptides (including BM-HABP fragments, variants, derivatives, and analogs, and BM-HABP agonists or BM-HABP antagonists as described herein) may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of BM-HABP polypeptides or polynucleotides and/or BM-HABP agonists or BM-HABP antagonists that can inhibit an immune response, particularly the proliferation, differentiation, or chemotaxis of T-cells, may be an effective therapy in preventing autoimmune disorders. Examples of autoimmune disorders that can be treated or detected by BM-HABP include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitus, and autoimmune inflammatory eye disease.

Similarly, allergic reactions and conditions, such as asthma (particularly allergic asthma) or other respiratory problems may also be treated by full-length WF-HABP polypeptides, full-length WF-HABP polynucleotides or full-length WF-HABP agonists or full-length WF-HABP antagonists. Moreover, full-length WF-HABP can be used to treat anaphylaxis, hypersensitivity to an antigenic molecule, or blood group incompatibility.

Similarly, allergic reactions and conditions, such as asthma particularly allergic asthma) or other respiratory problems may also be treated by WF-HABP polypeptides, WF-HABP polynucleotides or WF-HABP agonists or WF-HABP antagonists. Moreover, WF-HABP can be used to treat anaphylaxis, hypersensitivity to an antigenic molecule, or blood group incompatibility.

Similarly, allergic reactions and conditions, such as asthma (particularly allergic asthma) or other respiratory problems may also be treated by OE-HABP polypeptides, OE-HABP polynucleotides or OE-HABP agonists or OE-HABP antagonists. Moreover, OE-HABP can be used to treat anaphylaxis, hypersensitivity to an antigenic molecule, or blood group incompatibility.

Similarly, allergic reactions and conditions such as asthma (particularly allergic asthma) or other respiratory problems may also be treated by BM-HABP polypeptides, BM-HABP polynucleotides or BM-HABP agonists or BM-HABP antagonists. Moreover, BM-HABP can be used to treat anaphylaxis, hypersensitivity to an antigenic molecule, or blood group incompatibility.

Full-length WF-HABP polynucleotides or polypeptides (including full-length WF-HABP fragments, variants, derivatives, and analogs, and full-length WF-HABP agonists and full-length WF-HABP antagonists as described herein) may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of full-length WF-HABP polypeptides or polynucleotides and/or full-length WF-HABP agonists or antagonists that inhibits an immune response, particularly the proliferation, differentiation, or chemotaxis of T-cells, including the ability of immune cells to bind to other cells, or the extracellular matrix, may be an effective therapy in preventing organ rejection or GVHD.

WF-HABP polynucleotides or polypeptides (including WF-HABP fragments, variants, derivatives, and analogs, and WF-HABP agonists and WF-HABP antagonists as described herein) may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of WF-HABP polypeptides or polynucleotides and/or WF-HABP agonists or antagonists that inhibits an immune response, particularly the proliferation, differentiation, or chemotaxis of T-cells, including the ability of immune cells to bind to other cells, or the extracellular matrix, may be an effective therapy in preventing organ rejection or GVHD.

OE-HABP polynucleotides or polypeptides (including QE-HABP fragments, variants, derivatives, and analogs, and OE-HABP agonists and OE-HABP antagonists as described herein) may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of OE-HABP polypeptides or polynucleotides and/or OE-HABP agonists or antagonists that inhibits an immune response, particularly the proliferation, differentiation, or chemotaxis of T-cells, including the ability of immune cells to bind to other cells, or the extracellular matrix, may be an effective therapy in preventing organ rejection or GVHD.

BM-HABP polynucleotides or polypeptides (including BM-HABP fragments, variants, derivatives, and analogs, and BM-HABP agonists and BM-HABP antagonists as described herein) may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of BM-HABP polypeptides or polynucleotides and/or BM-HABP agonists or antagonists that inhibits an immune response, particularly the proliferation, differentiation, or chemotaxis of T-cells, including the ability of immune cells to bind to other cells, or the extracellular matrix, may be an effective therapy in preventing organ rejection or GVHD.

Similarly, full-length WF-HABP polypeptides or polynucleotides (including full-length WF-HABP fragments, variants, derivatives, and, analogs, and full-length WF-HABP agonists and full-length WF-HABP antagonists as described herein) may also be used to modulate inflammation. For example, full-length WF-HABP polypeptides or polynucleotides and/or full-length WF-HABP agonists and antagonists of the invention may inhibit the proliferation and differentiation of cells involved in an inflammatory response or alternatively may be involved in killing of hematopoietic cells during processes of inflammation or tissue injury. Moreover, full-length WF-HABP polypeptides or polynucleotides and/or full-length WF-HABP agonists and antagonists of the invention may inhibit inflammation via steric exclusion of immune cells to sites of injury, inhibiting interaction of immune cells with the extracellular matrix, or by inhibiting immune cell locomotion and migration. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from overproduction of cytokines (e.g., TNF or IL-1). Additionally, these molecules may be used to treat or prevent killing of hematopoietic cells and/or other cells during processes of inflammation or tissue injury.

Similarly, WF-HABP polypeptides or polynucleotides (including WF-HABP fragments, variants, derivatives, and analogs, and WF-HABP agonists and WF-HABP antagonists as described herein) may also be used to modulate inflammation. For example, WF-HABP polypeptides or polynucleotides and/or WF-HABP agonists and antagonists of the invention may inhibit the proliferation and differentiation of cells involved in an inflammatory response or alternatively may be involved in killing of hematopoietic cells during processes of inflammation or tissue injury. Moreover, WF-HABP polypeptides or polynucleotides and/or WF-HABP agonists and antagonists of the invention may inhibit inflammation via steric exclusion of immune cells to sites of injury, inhibiting interaction of immune cells with the extracellular matrix, or by inhibiting immune cell locomotion and migration. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1). Additionally, these molecules may be used to treat or prevent killing of hematopoictic cells and/or other cells during processes of inflammation or tissue injury.

Similarly, OE-HABP polypeptides or polynucleotides (including OE-HABP fragments, variants, derivatives, and analogs, and OE-HABP agonists and OE-HABP antagonists as described herein) may also be used to modulate inflammation. For example, OE-HABP polypeptides or polynucleotides and/or OE-HABP agonists and antagonists of the invention may inhibit the proliferation and differentiation of cells involved in an inflammatory response or alternatively may be involved in killing of hematopoietic cells during processes of inflammation or tissue injury. Moreover, OE-HABP polypeptides or polynucleotides and/or OE-HABP agonists and antagonists of the invention may inhibit inflammation via steric exclusion of immune cells to sites of injury, inhibiting interaction of immune cells with the extracellular matrix, or by inhibiting immune cell locomotion and migration. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1). Additionally, these molecules may be used to treat or prevent killing of hematopoietic cells and/or other cells during processes of inflammation or tissue injury.

Similarly, BM-HABP polypeptides or polynucleotides (including BM-HABP fragments, variants, derivatives, and analogs, and BM-HABP agonists and BM-HABP antagonists as described herein) may also be used to modulate inflammation. For example, BM-HABP polypeptides or polynucleotides and/or BM-HABP agonists and antagonists of the invention may inhibit the proliferation and differentiation of cells involved in an inflammatory response or alternatively may be involved in killing of hematopoietic cells during processes of inflammation or tissue injury. Moreover, BM-HABP polypeptides or polynucleotides and/or BM-HABP agonists and antagonists of the invention may inhibit inflammation via steric exclusion of immune cells to sites of injury, inhibiting interaction of immune cells with the extracellular matrix, or by inhibiting immune cell locomotion and migration. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1). Additionally, these molecules may be used to treat or prevent killing of hematopoietic cells and/or other cells during processes of inflammation or tissue injury.

Full-length WF-HABP polypeptides or polynucleotides (including full-length WF-HABP fragments, variants, derivatives, and analogs, and full-length WF-HABP agonists and antagonists as described herein) can be used to treat or detect hyperproliferative disorders, including neoplasms. Full-length WF-HABP polypeptides or polynucleotides and/or full-length WF-HABP agonists or antagonists, may inhibit the proliferation of the disorder through direct or indirect interactions (e.g. inhibiting ability of proliferative cells to adhere to the tissue matrix or other cells). Alternatively, full-length WF-HABP polypeptides or polynucleotides and/or full-length WF-HABP agonists or antagonists may proliferate other cells which can inhibit the hyperproliferative disorder. For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

WF-HABP polypeptides or polynucleotides (including WF-HABP fragments, variants, derivatives, and analogs, and WF-HABP agonists and antagonists as described herein) can be used to treat or detect hyperproliferative disorders, including neoplasms. WF-HABP polypeptides or polynucleotides and/or WF-HABP agonists or antagonists, may inhibit the proliferation of the disorder through direct or indirect interactions (e.g. inhibiting ability of proliferative cells to adhere to the tissue matrix or other cells). Alternatively, WF-HABP polypeptides or polynucleotides and/or WF-HABP agonists or antagonists may proliferate other cells which can inhibit the hyperproliferative disorder. For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

OE-HABP polypeptides or polynucleotides (including OE-HABP fragments, variants, derivatives, and analogs, and OE-HABP agonists and antagonists as described herein) can be used to treat or detect hyperproliferative disorders, including neoplasms. OE-HABP polypeptides or polynucleotides and/or OE-HABP agonists or antagonists, may inhibit the proliferation of the disorder through direct or indirect interactions (e.g. inhibiting ability of proliferative cells to adhere to the tissue matrix or other cells). Alternatively, OE-HABP polypeptides or polynucleotides and/or OE-HABP agonists or antagonists may proliferate other cells which can inhibit the hyperproliferative disorder. For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

BM-HABP polypeptides or polynucleotides (including BM-HABP fragments, variants, derivatives, and analogs, and BM-HABP agonists and antagonists as described herein) can be used to treat or detect hyperproliferative disorders, including neoplasms. BM-HABP polypeptides or polynucleotides and/or BM-HABP agonists or antagonists, may inhibit the proliferation of the disorder through direct or indirect interactions (e.g. inhibiting ability of proliferative cells to adhere to the tissue matrix or other cells). Alternatively, BM-HABP polypeptides or polynucleotides and/or BM-HABP agonists or antagonists may proliferate other cells which can inhibit the hyperproliferative disorder. For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by full-length WF-HABP polynucleotides or polypeptides and/or full-length WF-HABP agonists or antagonists include, but are not limited to, neoplasms located in the: blood, abdomen, bone, lung, breast, digestive system, liver, pancreas, prostate, peritoneum, endocrine glands (adrenal, parathyroid, pituitary, testicles, ovary, thymus, thyroid) eye, head and neck, nervous (central and peripheral), lymphatic system, hematopoietic tissue, pelvic, skin, soft tissue, spleen, thoracic, and urogenital.

Examples of hyperproliferative disorders that can be treated or detected by WF-HABP polynucleotides or polypeptides and/or WF-HABP agonists or antagonists include, but are not limited to, neoplasms located in the: blood, abdomen, bone, lung, breast, digestive system, liver, pancreas, prostate, peritoneum, endocrine glands (adrenal, parathyroid, pituitary, testicles, ovary, thymus, thyroid), eye, head and neck, nervous (central and peripheral), lymphatic system, hematopoietic tissue, pelvic, skin, soft tissue, spleen, thoracic, and urogenital.

Examples of hyperproliferative disorders that can be treated or detected by OE-HABP polynucleotides or polypeptides and/or OE-HABP agonists or antagonists include, but are not limited to, neoplasms located in the: blood, abdomen, bone, lung, breast, digestive system, liver, pancreas, prostate, peritoneum, endocrine glands (adrenal, parathyroid, pituitary, testicles, ovary, thymus, thyroid), eye, head and neck; nervous (central and peripheral), lymphatic system, hematopoietic tissue, pelvic, skin, soft tissue, spleen, thoracic, and urogenital.

Examples of hyperproliferative disorders that can be treated or detected by BM-HABP polynucleotides or polypeptides and/or BM-HABP agonists or antagonists include, but are not limited to, neoplasms located in the: blood, abdomen, bone, lung, breast, digestive system, liver, pancreas, prostate, peritoneum, endocrine glands (adrenal, parathyroid, pituitary, testicles, ovary, thymus, thyroid), eye, head and neck, nervous (central and peripheral), lymphatic system, hematopoietic tissue, pelvic, skin, soft tissue, spleen, thoracic, and urogenital.

Similarly, other hyperproliferative disorders can also be treated or detected by full-length WF-HABP polynucleotides or polypeptides and/or full-length WF-HABP agonists or antagonists. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Similarly, other hyperproliferative disorders can also be treated or detected by WF-HABP polynucleotides or polypeptides and/or WF-HABP agonists or antagonists. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Similarly, other hyperproliferative disorders can also be treated or detected by OE-HABP polynucleotides or polypeptides and/or OE-HABP agonists or antagonists. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Similarly, other hyperproliferative disorders can also be treated or detected by BM-HABP polynucleotides or polypeptides and/or BM-HABP agonists or antagonists. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Full-length WF-HABP polypeptides or polynucleotides (including full-length WF-HABP fragments, variants, derivatives, and analogs, and full-length WF-HABP agonists and antagonists as described herein) can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, full-length WF-HABP polypeptides or polynucleotides and/or full-length WF-HABP agonists or antagonists may also directly inhibit the infectious agent, without necessarily eliciting an immune response (e.g. enhancing the integrity of the extracellular matrix to efficiently occlude infectious agents).

WF-HABP polypeptides or polynucleotides (including WF-HABP fragments, variants, derivatives, and analogs, and WF-HABP agonists and antagonists as described herein) can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, WF-HABP polypeptides or polynucleotides and/or WF-HABP agonists or antagonists may also directly inhibit the infectious agent, without necessarily eliciting an immune response (e.g. enhancing the integrity of the extracellular matrix to efficiently occlude infectious agents).

OE-HABP polypeptides or polynucleotides (including OE-HABP fragments, variants, derivatives, and analogs, and OE-HABP agonists and antagonists as described herein) can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, OE-HABP polypeptides or polynucleotides and/or OE-HABP agonists or antagonists may also directly inhibit the infectious agent, without necessarily eliciting an immune response (e.g. enhancing the integrity of the extracellular matrix to efficiently occlude infectious agents).

BM-HABP polypeptides or polynucleotides (including BM-HABP fragments, variants, derivatives, and analogs, and BM-HABP agonists and antagonists as described herein) can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, BM-HABP polypeptides or polynucleotides and/or BM-HABP agonists or antagonists may also directly inhibit the infectious agent, without necessarily eliciting an immune response (e.g. enhancing the integrity of the extracellular matrix to efficiently occlude infectious agents).

Viruses are one example of an infectious agent that can cause disease or symptoms that can be treated by full-length WF-HABP polynucleotides or polypeptides and/or full-length WF-HABP agonists or antagonists. Examples of viruses, include, but are not limited to, the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome; hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. Full-length WF-HABP polypeptides or polynucleotides and/or full-length WF-HABP agonists or antagonists can be used to treat any of these symptoms or diseases.

Viruses are one example of an infectious agent that can cause disease or symptoms that can be treated by WF-HABP polynucleotides or polypeptides and/or WF-HABP agonists or antagonists. Examples of viruses, include, but are not limited to, the following DNA and RNA viral families: Arbovirus, Adenoviridae, Arenaviridae, Arterivirus, Bimaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia Rubella, sexually transmitted diseases, skin diseases (e.g., Kaposi's, warts), and viremia. WF-HABP polypeptides or polynucleotides and/or WF-HABP agonists or antagonists can be used to treat any of these symptoms or diseases.

Viruses are one example of an infectious agent that can cause disease or symptoms that can be treated by OE-HABP polynucleotides or polypeptides and/or OE-HABP agonists or antagonists. Examples of viruses, include, but are not limited to, the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. OE-HABP polypeptides or polynucleotides and/or OE-HABP agonists or antagonists can be used to treat any of these symptoms or diseases.

Viruses are one example of an infectious agent that can cause disease or symptoms that can be treated by BM-HABP polynucleotides or polypeptides and/or BM-HABP agonists or antagonists. Examples of viruses, include, but are not limited to, the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. BM-HABP polypeptides or polynucleotides and/or BM-HABP agonists or antagonists can be used to treat any of these symptoms or diseases.

Similarly, bacterial or fungal agents that can cause disease or symptoms and that can be treated by full-length WF-HABP polynucleotides or polypeptides and/or full-length WF-HABP agonists or antagonists include, but are not limited to, the following Gram-Negative and Gram-positive bacterial families and fungi: Actinomycetales (e.g., *Corynebacterium, Mycobacterium, Norcardia*), Aspergillosis, Bacillaceae (e.g., Anthrax, *Clostridium*), Bacteroidaceae, Blastomycosis, *Bordetella, Borrelia*, Brucellosis, Candidiasis, *Campylobacter*, Coccidioidomycosis, Cryptococcosis, Deratocycoses, Enterobacteriaceae (*Klebsiella, Salmonella, Serratia, Yersinia*), Erysipelothrix, *Helicobacter*, Legionellosis, Leptospirosis, *Listeria*, Mycoplasmatales, Neisseriaceae (e.g., *Acinetobacter*, Gonorrhea, Menigococcal), Pasteurellacea Infections (e.g., *Actinobacillus, Heamophilus, Pasteurella*), *Pseudomonas*, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, *tuberculosis*, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, *Tuberculosis*, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract, infections, wound infections. Full-length WF-HABP polypeptides or polynucleotides and/or full-length WF-HABP agonists or antagonists can be used to treat or detect any of these symptoms or diseases.

Similarly, bacterial or fungal agents that can cause disease or symptoms and that can be treated by WF-HABP polynucleotides or polypeptides and/or WF-HABP agonists or antagonists include, but are not limited to, the following Gram-Negative and Gram-positive bacterial families and fungi: Actinomycetales (e.g., *Corynebacterium, Mycobacterium, Norcardia*), Aspergillosis, Bacillaceae (e.g., Anthrax, *Clostridium*), Bacteroidaceae, Blastomycosis, *Bordetella, Borrelia*, Brucellosis, Candidiasis, *Campylobacter*, Coccidioidomycosis, Cryptococcosis, Dermatocycoses, Enterobacteriaceae (*Klebsiella, Salmonella, Serratia, Yersinia*), Erysipelothrix, *Helicobacter*, Legionellosis, Leptospirosis, *Listeria*, Mycoplasmatales, Neisseriaceae (e.g., *Acinetobacter*, Gonorrhea, Menigococcal), Pasteurellacea Infections (e.g., *Actinobacillus, Heamophilus, Pasteurella*), *Pseudomonas*, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, *tuberculosis*, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, *Tuberculosis*, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. WF-HABP polypeptides or polynucleotides and/or WF-HABP agonists or antagonists can be used to treat or detect any of these symptoms or diseases.

Similarly, bacterial or fugal agents that can cause disease or symptoms and that can be treated by OE-HABP polynucleotides or polypeptides and/or OE-HABP agonists or antagonists include, but are not limited to, the following Gram-Negative and Gram-positive bacterial families and fungi: Actinomycetales (e.g., *Corynebacterium, Mycobacterium, Norcardia*), Aspergillosis, Bacillaceae (e.g., Anthrax, *Clostridium*), Bacteroidaceae, Blastomycosis, *Bordetella, Borrelia*, Brucellosis, Candidiasis, *Campylobacter*, Coccidioidomycosis, Cryptococcosis, Dermatocycoses, Enterobacteriaceae (*Klebsiella, Salmonella, Serratia, Yersinia*), Erysipelothrix, *Helicobacter*, Legionellosis, Leptospirosis, *Listeria*, Mycoplasmatales, Neisseriaceae (e.g., *Acinetobacter*, Gonorrhea, Menigococcal), Pasteurellacea Infections (e.g., *Actinobacillus, Heamophilus, Pasteurella*), Pseudomonas, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, *tuberculosis*, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, *Tuberculosis*, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. OE-HABP polypeptides or polynucleotides and/or OE-HABP agonists or antagonists can be used to treat or detect any of these symptoms or diseases.

Similarly, bacterial or fungal agents that can cause disease or symptoms and that can be treated by BM-HABP polynucleotides or polypeptides and/or BM-HABP agonists or antagonists include, but are not limited to, the following Gram-Negative and Gram-positive bacterial families and fungi: Actinomycetales (e.g., *Corynebacterium, Mycobacterium, Norcardia*), Aspergillosis, Bacillaceae (e.g., Anthrax, *Clostridium*), Bacteroidaceae, Blastomycosis, *Bordetella, Borrelia*, Brucellosis, Candidiasis, *Campylobacter*, Coccidioidomycosis, Cryptococcosis, Dermatocycoses, Enterobacteriaceae (*Klebsiella, Salmonella, Serratia, Yersinia*), Erysipelothrix, *Helicobacter*, Legionellosis, Leptospirosis, *Listeria*, Mycoplasmatales, Neisseriaceae (e.g., *Acinetobacter*, Gonorrhea, Menigococcal), Pasteurellacea Infections (e.g., *Actinobacillus, Heamophilus, Pasteurella*), Pseudomonas, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, *tuberculosis*, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, *Tuberculosis*, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. BM-HABP polypeptides or polynucleotides and/or BM-HABP agonists or antagonists can be used to treat or detect any of these symptoms or diseases.

Moreover, parasitic agents causing disease or symptoms that can be treated by full-length WF-HABP polynucleotides or polypeptides and/or WF-HABP agonists or antagonists include, but are not limited to, the following families: Amebiasis, Babesiosis, Coccidiosis, Cryptosporidiosis, Dientamoebiasis, Dourine, Ectoparasitic, Giardiasis, Hemimthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis full-length WF-HABP polypeptides or polynucleotides and/or full-length WF-HABP agonists or antagonists can be used to treat or detect any of these symptoms or diseases.

Moreover, parasitic agents causing disease or symptoms that can be treated by WF-HABP polynucleotides or polypeptides and/or WF-HABP agonists or antagonists include, but are not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. WF-HABP polypeptides or polynucleotides and/or WF-HABP agonists or antagonists can be used to treat or detect any of these symptoms or diseases.

Moreover, parasitic agents causing disease or symptoms that can be treated by OE-HABP polynucleotides or polypeptides and/or OE-HABP agonists or antagonists include, but are not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. OE-HABP polypeptides or polynucleotides and/or OE-HABP agonists or antagonists can be used to treat or detect any of these symptoms or diseases.

Moreover, parasitic agents causing disease or symptoms that can be treated by BM-HABP polynucleotides or polypeptides and/or BM-HABP agonists or antagonists include, but are not limited to, the following families: Amebiasis, Babesiosis, Coccidiosis, Cryptosporidiosis, Dientamoebiasis, Dourine, Ectoparasitic, Giardiasis, Helminthasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. BM-HABP polypeptides or polynucleotides and/or BM-HABP agonists or antagonists can be used to treat or detect any of these symptoms or diseases.

Full-length WF-HABP polynucleotides or polypeptides (including full-length WF-HABP fragments, variants, derivatives, and analogs, and full-length WF-HABP agonists and antagonists as described herein) can be used to differentiate, proliferate, and attract cells, leading to the regeneration of tissues. (See, Science 276:59–87 (1997). The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage. Tissues that may be regenerated using the present invention include organs (e.g., pancreas, liver, intestine, kidney, skin, endothelium), muscle (smooth, skeletal or cardiac), vascular (including vascular endothelium), nervous, hematopoietic, and skeletal (bone, cartilage, tendon, and ligament) tissue. Preferably, regeneration occurs without or decreased scarring. Regeneration also may include angiogenesis. Additionally, these compounds can be used to treat or prevent cell death (e.g., hematopoietic cell death) during processes of inflammation or tissue injury.

WF-HABP polynucleotides or polypeptides (including WF-HABP fragments, variants, derivatives, and analogs, and WF-HABP agonists and antagonists as described herein) can be used to differentiate, proliferate, and attract cells, leading to the regeneration of tissues. (See, Science 276:59–87 (1997). The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage. Tissues that may be regenerated using the present invention include organs (e.g., pancreas, liver, intestine, kidney, skin, endothelium), muscle (smooth, skeletal or cardiac), vascular (including vascular endothelium), nervous, hematopoietic, and skeletal (bone, cartilage, tendon, and ligament) tissue. Preferably, regeneration occurs without or decreased scarring. Regeneration also may include angiogenesis. Additionally, these compounds can be used to treat or prevent cell death (e.g., hematopoietic cell death) during processes of inflammation or tissue injury.

OE-HABP polynucleotides or polypeptides (including OE-HABP fragments, variants, derivatives, and analogs, and OE-HABP agonists and antagonists as described herein) can be used to differentiate, proliferate, and attract cells, leading to the regeneration of tissues. (See, Science 276:59–87 (1997). The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage. Tissues that may be regenerated using the present invention include organs (e.g., pancreas, liver, intestine, kidney, skin, endothelium), muscle (smooth, skeletal or cardiac), vascular (including vascular endothelium), nervous, hematopoietic, and skeletal (bone, cartilage, tendon, and ligament) tissue. Preferably, regeneration occurs without or decreased scarring. Regeneration also may include angiogenesis. Additionally, these compounds can be used to treat or prevent cell death (e.g., hematopoietic cell death) during processes of inflammation or tissue injury.

BM-HABP polynucleotides or polypeptides (including BM-HABP fragments, variants, derivatives, and analogs, and BM-HABP agonists and antagonists as described herein) can be used to differentiate, proliferate, and attract cells, leading to the regeneration of tissues. (See, Science 276:59–87 (1997). The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage. Tissues that may be regenerated using the present invention include organs (e.g., pancreas, liver, intestine, kidney, skin, endothelium), muscle (smooth, skeletal or cardiac), vascular (including vascular endothelium), nervous, hematopoietic, and skeletal (bone, cartilage, tendon, and ligament) tissue. Preferably, regeneration occurs without or decreased scarring. Regeneration also may include angiogenesis. Additionally, these compounds can be used to treat or prevent cell death (e.g., hematopoietic cell death) during processes of inflammation or tissue injury.

Moreover, full-length WF-HABP polynucleotides or polypeptides (including full-length WF-HABP fragments, variants, derivatives, and analogs, and full-length WF-HABP agonists and antagonists as described herein) may increase regeneration of tissues difficult to heal, such as diabetic ulcers, gangrene lesions, or open-wounds occurring secondary to immune compromised conditions. For example, increased tendon/ligament regeneration would quicken recovery time after damage. Full-length WF-HABP polynucleotides or polypeptides and/or full-length WF-HABP agonists or antagonists of the present invention could also be used prophylactically in an effort to avoid damage. Specific diseases that could be treated include tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Moreover, WF-HABP polynucleotides or polypeptides (including WF-HABP fragments, variants, derivatives, and analogs, and WF-HABP agonists and antagonists as described herein) may increase regeneration of tissues difficult to heal, such as diabetic ulcers, gangrene lesions, or open-wounds occurring secondary to immune-compromised conditions. For example, increased tendon/ligament regeneration would quicken recovery time after damage. WF-HABP polynucleotides or polypeptides and/or WF-HABP agonists or antagonists of the present invention could also be used prophylactically in an effort to avoid damage. Specific diseases that could be treated include tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Moreover, OE-HABP polynucleotides or polypeptides (including OE-HABP fragments, variants, derivatives, and analogs, and OE-HABP agonists and antagonists as described herein) may increase regeneration of tissues difficult to heal, such as diabetic ulcers, gangrene lesions, or open-wounds occurring secondary to immune-compromised conditions. For example, increased tendon/ligament regeneration would quicken recovery time after damage. OE-HABP polynucleotides or polypeptides and/or OE-HABP agonists or antagonists of the present invention could also be used prophylactically in an effort to avoid damage. Specific diseases that could be treated include tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Moreover, BM-HABP polynucleotides or polypeptides (including BM-HABP fragments, variants, derivatives, and analogs, and BM-HABP agonists and antagonists as described herein) may increase regeneration of tissues difficult to heal, such as diabetic ulcers, gangrene lesions, or open-wounds occurring secondary to immune-compromised conditions. For example, increased tendon/ligament regeneration would quicken recovery time after damage. BM-HABP polynucleotides or polypeptides and/or BM-HABP agonists or antagonists of the present invention could also be used prophylactically in an effort to avoid damage. Specific diseases that could be treated include tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using full-length WF-HABP polynucleotides or polypeptides and/or full-length WF-HABP agonists or antagonists to proliferate and differentiate nerve cells. Diseases that could be treated using this method include central and peripheral nervous system diseases, neuropathies, or mechanical and traumatic disorders (e.g., spinal cord disorders, bead trauma, cerebrovascular disease, and stroke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the full-length WF-HABP polynucleotides or polypeptides and/or full-length WF-HABP agonists or antagonists. Moreover, the present invention could be used to recruit beneficial cells or cell types to areas of neural tissue damage or injury, particularly cells which either have the endogenous function of protecting such tissue from additional damage, or which are capable of healing the damaged or diseased tissue through the localized secretion of therapeutic peptides.

Similarly, nerve and brain tissue could also be regenerated by using WF-HABP polynucleotides or polypeptides and/or WF-HABP agonists or antagonists to proliferate and differentiate nerve cells. Diseases that could be treated using this method include central and peripheral nervous system diseases, neuropathies or mechanical and traumatic disorders (e.g., spinal cord disorders, head trauma, cerebrovascular disease, and stroke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the WF-HABP polynucleotides or polypeptides and/or WF-HABP agonists or antagonists. Moreover, the present invention could be used to recruit beneficial cells or cell types to areas of neural tissue damage or injury, particularly cells which either have the endogenous function of protecting such tissue from additional damage, or which are capable of healing the damaged or diseased tissue through the localized secretion of therapeutic peptides.

Similarly, nerve and brain tissue could also be regenerated by using OE-HABP polynucleotides or polypeptides and/or OE-HABP agonists or antagonists to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stroke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the OE-HABP polynucleotides or polypeptides and/or OE-HABP agonists or antagonists. Moreover, the present invention could,be used to recruit beneficial cells or cell types to areas of neural tissue damage or injury, particularly cells which either have the endogenous function of protecting such tissue from additional damage, or which are capable of healing the damaged or diseased tissue through the localized secretion of therapeutic peptides.

Similarly, nerve and brain tissue could also be regenerated by using BM-HABP polynucleotides or polypeptides and/or BM-HABP agonists or antagonists to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stroke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the BM-HABP polynucleotides or polypeptides and/or BM-HABP agonists or antagonists. Moreover, the present invention could be used to recruit beneficial cells or cell types to areas of neural tissue damage or injury, particularly cells which either have the endogenous function of protecting such tissue from additional damage, or which are capable of healing the damaged or diseased tissue through the localized secretion of therapeutic peptides.

Given the activities modulated by full-length WF-HABP, it is readily apparent that a substantially altered (increased or decreased) level of expression of full-length WF-HABP in an individual compared to the standard or "normal" level produces pathological conditions such as those described above. It will also be appreciated by one of ordinary skill that the full-length WF-HABP agonists of the invention will exert modulating activities on any of its target cells. Therefore, it will be appreciated that conditions caused by a decrease in the standard or normal level of full-length WF-HABP mediated activity in an individual, can be treated by administration of full-length WF-HABP polypeptide or an agonist thereof.

Given the activities modulated by WF-HABP, it is readily apparent that a substantially altered (increased or decreased) level of expression of WF-HABP in an individual compared to the standard or "normal" level produces pathological conditions such as those described above. It will also be appreciated by one of ordinary skill that the WF-HABP agonists of the invention will exert modulating activities on any of its target cells. Therefore, it will be appreciated that conditions caused by a decrease in the standard or normal level of WF-HABP mediated activity in an individual, can be treated by administration of WF-HABP polypeptide or an agonist thereof.

Given the activities modulated by OE-HABP, it is readily apparent that a substantially altered (increased or decreased) level of expression of OE-HABP in an individual compared to the standard or "normal" level produces pathological conditions such as those described above. It will also be appreciated by one of ordinary skill that the OE-HABP agonists of the invention will exert modulating activities on any of its target cells. Therefore, it will be appreciated that conditions caused by a decrease in the standard or normal level of OE-HABP mediated activity in an individual, can be treated by administration of OE-HABP polypeptide or an agonist thereof.

Given the activities modulated by BM-HABP, it is readily apparent that a substantially altered (increased or decreased) level of expression of BM-HABP in an individual compared to the standard or "normal" level produces pathological conditions such as those described above. It will also be appreciated by one of ordinary skill that the BM-HABP agonists of the invention will exert modulating activities on any of its target cells. Therefore, it will be appreciated that conditions caused by a decrease in the standard or normal level of BM-HABP mediated activity in an individual, can be treated by administration of BM-HABP polypeptide or an agonist thereof.

Thus, in one embodiment, the present invention is directed to a method for enhancing (i.e., increasing) full-length WF-HABP mediated activity (e.g., cellular proliferation, cellular migration, cellular targeting, metastasis) which involves administering to an individual in need of an increased level of full-length WF-HABP mediated activity, a therapeutically effective amount of full-length WF-HABP polypeptide, fragment, variant, derivative, or analog, or an agonist capable of increasing full-length WF-HABP mediated activity. In specific embodiments, full-length WF-HABP mediated adhesion is increased to treat a disease or condition wherein decreased cell survival, secretion, proliferation, migration, and/or differentiation is exhibited.

Thus, in one embodiment, the present invention is directed to a method for enhancing (i.e., increasing) WF-HABP mediated activity (e.g., cellular proliferation, cellular migration, cellular targeting, metastasis) which involves administering to an individual in need of an increased level of WF-HABP mediated activity, a therapeutically effective amount of WF-HABP polypeptide, fragment, variant, derivative, or analog, or an agonist capable of increasing WF-HABP mediated activity. In specific embodiments, WF-HABP mediated adhesion is increased to treat a disease or condition wherein decreased cell survival, secretion, proliferation, migration, and/or differentiation is exhibited.

Thus, in one embodiment, the present invention is directed to a method for enhancing (i.e., increasing) OE-HABP mediated activity (e.g., cellular proliferation, cellular migration, cellular targeting, metastasis) which involves administering to an individual in need of an increased level of OE-HABP mediated activity, a therapeutically effective amount of OE-HABP polypeptide, fragment, variant, derivative, or analog, or an agonist capable of increasing OE-HABP mediated activity. In specific embodiments, OE-HABP mediated adhesion is increased to treat a disease or condition wherein decreased cell survival, secretion, proliferation, migration, and/or differentiation is exhibited.

Thus, in one embodiment, the present invention is directed to a method for enhancing (i.e., increasing) BM-HABP mediated activity (e.g., cellular proliferation, cellular migration, cellular targeting, metastasis) which involves administering to an individual in need of an increased level of BM-HABP mediated activity, a therapeutically effective amount of BM-HABP polypeptide, fragment, variant, derivative, or analog, or an agonist capable of increasing BM-HABP mediated activity. In specific embodiments, BM-HABP mediated adhesion is increased to treat a disease or condition wherein decreased cell survival, secretion, proliferation, migration, and/or differentiation is exhibited.

In another embodiment, the present invention is directed to a method for suppressing (i.e., decreasing) full-length WF-HABP mediated activity (e.g., adhesion, rheological properties, water homeostatsis, molecular exclusion), which involves administering to an individual in need of a decreased level of full-length WF-HABP mediated activity, a therapeutically effective amount of full-length WF-HABP polypeptide, fragment, variant, derivative, or analog or an antagonist capable of decreasing full-length WF-HABP mediated activity. In specific embodiments, full-length WF-HABP mediated adhesion is decreased to treat a disease or condition wherein increased cell survival, secretion, proliferation, migration and/or differentiation is exhibited.

In another embodiment, the present invention is directed to a method for suppressing (i.e., decreasing): WF-HABP mediated activity (e.g., adhesion, Theological properties, water homeostatsis, molecular exclusion), which involves administering to an individual in need of a decreased level of WF-HABP mediated activity, a therapeutically effective amount of WF-HABP polypeptide, fragment, variant, derivative, or analog or an antagonist capable of decreasing WF-HABP mediated activity. In specific embodiments, WF-HABP mediated adhesion is decreased to treat a disease or condition wherein increased cell survival, secretion, proliferation, migration and/or differentiation is exhibited.

In another embodiment, the present invention is directed to a method for suppressing (i.e., decreasing) OE-HABP mediated activity (e.g., adhesion, Theological properties, water homeostatsis, molecular exclusion), which involves administering to an individual in need of a decreased level of OE-HABP mediated activity, a therapeutically effective amount of OE-HABP polypeptide, fragment, variant, derivative, or analog or an antagonist capable of decreasing OE-HABP mediated activity. In specific embodiments, OE-HABP mediated adhesion is decreased to treat a disease or condition wherein increased cell survival, secretion, proliferation, migration and/or differentiation is exhibited.

In another embodiment, the present invention is directed to a method for suppressing (i.e., decreasing) BM-HABP mediated activity (e.g., adhesion, rheological properties, water homeostatsis, molecular exclusion), which involves administering to an individual in need of a decreased level of BM-HABP mediated activity, a therapeutically effective amount of BM-HABP polypeptide, fragment, variant, derivative, or analog or an antagonist capable of decreasing BM-HABP mediated activity. In specific embodiments, BM-HABP mediated adhesion is decreased to treat a disease or condition wherein increased cell survival, secretion, proliferation, migration and/or differentiation is exhibited.

In addition to treating diseases associated with elevated or decreased levels of full-length WF-HABP mediated activity, the invention encompasses methods of administering full-length WF-HABP agonists or antagonists to elevate or reduce full-length WF-HABP mediated biological activity, respectively.

In addition to treating diseases associated with elevated or decreased levels of WF-HABP mediated activity, the invention encompasses methods of administering WF-HABP agonists or antagonists to elevate or reduce WF-HABP mediated biological activity, respectively.

In addition to treating diseases associated with elevated or decreased levels of OE-HABP mediated activity, the invention encompasses methods of administering OE-HABP agonists or antagonists to elevate or reduce OE-HABP mediated biological activity, respectively.

In addition to treating diseases associated with elevated or decreased levels of BM-HABP mediated activity, the invention encompasses methods of administering BM-HABP agonists or antagonists to elevate or reduce BM-HABP mediated biological activity, respectively.

For example, any method which elevates full-length WF-HABP concentration and/or activity can be used to stimulate hematopoiesis. Using these methods, the full-length WF-HABP polypeptide and nucleotide sequences and full-length WF-HABP agonists as described herein may be used to stimulate hematopoiesis. In a specific embodiment, full-length WF-HABP polypeptides and polynucleotides and/or full-length WF-HABP agonists are used in erythropoietin therapy, which is directed toward supplementing the oxygen carrying capacity of blood. Full-length WF-HABP treatment within the scope of the invention includes, but is not limited, to patients generally requiring blood transfusions, such as, for example, trauma victims, surgical patients, dialysis patients, and patients with a variety of blood composition-affecting disorders, such as hemophilia, cystic fibrosis, pregnancy, menstrual disorders, early anemia of prematurity, spinal cord injury, space flight, aging, various neoplastic disease states, and the like. Examples of patient conditions that require supplementation of the oxygen carrying capacity of blood and which are within the scope of this invention, include but are not limited to: treatment of blood disorders characterized by low or defective red blood cell production, anemia associated with chronic renal failure, stimulation of reticulocyte response, development of ferrokinetic effects (such as plasma iron turnover effects and marrow transit time effects), erythrocyte mass changes, stimulation of hemoglobin C synthesis, and increasing levels of hematocrit in vertebrates. The invention also provides for treatment to enhance the oxygen-carrying capacity of an individual, such as for example, an individual encountering hypoxic environmental conditions.

For example, any method which elevates WF-HABP concentration and/or activity can be used to stimulate hematopoiesis. Using these methods, the WF-HABP polypeptide and nucleotide sequences and WF-HABP agonists as described herein may be used to stimulate hematopoiesis. In a specific embodiment, WF-HABP polypeptides and polynucleotides and/or WF-HABP agonists are used in erythropoietin therapy, which is directed toward supplementing the oxygen carrying capacity of blood. WF-HABP treatment within the scope of the invention includes, but is not limited, to patients generally requiring blood transfusions, such as, for example, trauma victims, surgical patients, dialysis patients, and patients with a variety of blood composition-affecting disorders, such as hemophilia, cystic fibrosis, pregnancy, menstrual disorders, early anemia of prematurity, spinal cord injury, space flight, aging, various neoplastic disease states, and the like. Examples of patient conditions that require supplementation of the oxygen carrying capacity of blood and which are within the scope of this invention, include but are not limited to: treatment of blood disorders characterized by low or defective red blood cell production, anemia associated with chronic renal failure, stimulation of reticulocyte response, development of ferrokinetic effects (such as plasma iron turnover effects and marrow transit time effects), erythrocyte mass changes, stimulation of hemoglobin C synthesis, and increasing levels of hematocrit in vertebrates. The invention also provides for treatment to enhance the oxygen-carrying capacity of an individual, such as for example, an individual encountering hypoxic environmental conditions.

For example, any method which elevates OE-HABP concentration and/or activity can be used to stimulate hematopoiesis. Using these methods, the OE-HABP polypeptide and nucleotide sequences and OE-HABP agonists as described herein may be used to stimulate hematopoiesis. In a specific embodiment, OE-HABP polypeptides and polynucleotides and/or OE-HABP agonists are used in erythropoietin therapy, which is directed toward supplementing the oxygen carrying capacity of blood. OE-HABP treatment within the scope of the invention includes, but is not limited, to patients generally requiring blood transfusions, such as, for example, trauma victims, surgical patients, dialysis patients, and patients with a variety of blood composition-affecting disorders, such as hemophilia, cystic fibrosis, pregnancy, menstrual disorders, early anemia of prematurity, spinal cord injury, space flight, aging, various neoplastic disease states, and the like. Examples of patient conditions that require supplementation of the oxygen carrying capacity of blood and which are within the scope of this invention, include but are not limited to: treatment of blood disorders characterized by low or defective red blood cell production, anemia associated with chronic renal failure, stimulation of reticulocyte response, development of ferrokinetic effects (such as plasma iron turnover effects and marrow transit time effects), erythrocyte mass changes, stimulation of hemoglobin C synthesis, and increasing levels of hematocrit in vertebrates. The invention also provides for treatment to enhance the oxygen-carrying capacity of an individual, such as for example, an individual encountering hypoxic environmental conditions.

For example, any method which elevates BM-HABP concentration and/or activity can be used to stimulate hematopoiesis. Using these methods, the BM-HABP polypeptide and nucleotide sequences and BM-HABP agonists as described herein may be used to stimulate hematopoiesis. In a specific embodiment, BM-HABP polypeptides and polynucleotides and/or BM-HABP agonists are used in erythropoietin therapy, which is directed toward supplementing the oxygen carrying capacity of blood. BM-HABP treatment within the scope of the invention includes, but is not limited, to patients generally requiring blood transfusions, such as, for example, trauma victims, surgical patients, dialysis patients, and patients with a variety of blood composition-affecting disorders, such as hemophilia, cystic fibrosis, pregnancy, menstrual disorders, early anemia of prematurity, spinal cord injury, space flight, aging, various neoplastic disease states, and the like. Examples of patient conditions that require supplementation of the oxygen carrying capacity of blood and which are within the scope of this invention, include but are not limited to: treatment of blood disorders characterized by low or defective red blood cell production, anemia associated with chronic renal failure, stimulation of reticulocyte response, development of ferrokinetic effects (such as plasma iron turnover effects and marrow transit time effects), erythrocyte mass changes, stimulation of hemoglobin C synthesis, and increasing levels of hematocrit in vertebrates. The invention also provides for treatment to enhance the oxygen-carrying capacity of an individual, such as for example, an individual encountering hypoxic environmental conditions.

The invention also encompasses combining the full-length WF-HABP polypeptides and polynucleotides and/or full-length WF-HABP agonists described herein with other proposed or conventional hematopoietic therapies. Thus, for example, full-length WF-HABP agonists can be combined with compounds that singly exhibit erythropoietic stimulatory effects, such as erythropoietin, testosterone, progenitor cell stimulators, insulin-like growth factor, prostaglandins, serotonin, cyclic AMP, prolactin, and triiodothyzonine. Also encompassed are combinations with compounds generally used to treat aplastic anemia, such as methenolene, stanozolol, and nandrolone; to treat iron-deficiency anemia, such as iron preparations; to treat malignant anemia, such as vitamin B12 and/or folic acid; and to treat hemolytic anemia, such as adrenocortical steroids, e.g., corticoids. See e.g., Resegotti et al., Panminerva Medica, 23:243–248 (1981); Kurtz, FEBS Letters, 14a:105–108 (1982); McGonigle et al., Kidney Int., 25:437–444 (1984); and Pavlovic-Kantera, Expt. Hematol., 8(supp. 8) 283–291 (1980).

The invention also encompasses combining the WF-HABP polypeptides and polynucleotides and/or WF-HABP agonists described herein with other proposed or conventional hematopoietic therapies. Thus, for example, WF-HABP agonists can be combined with compounds that singly exhibit erythropoietic stimulator effects, such as erythropoietin, testosterone, progenitor cell stimulators, insulin-like growth factor, prostaglandins, serotonin, cyclic AMP, prolactin, and triiodothyzonine. Also encompassed are combinations with compounds generally used to treat aplastic anemia, such as methenolene, stanozolol, and nandrolone; to treat iron-deficiency anemia, such as iron preparations; to treat malignant anemia, such as vitamin B12 and/or folic acid; and to treat hemolytic anemia, such as adrenocortical steroids, e.g., corticoids. See e.g., Resegotti et al., Panminerva Medica, 23:243–248 (1981); Kurtz, FEBS Letters, 14a:105–108 (1982); McGonigle et al., Kidney Int., 25:437–444 (1984); and Pavlovic-Kantera, Expt. Hematol., 8(supp. 8) 283–291 (1980).

The invention also encompasses combining the OE-HABP polypeptides and polynucleotides and/or OE-HABP agonists described herein with other proposed or conventional hematopoietic therapies. Thus, for example, OE-HABP agonists can be combined with compounds that singly exhibit erythropoietic stimulatory effects, such as erythropoietin, testosterone, progenitor cell stimulators, insulin-like growth factor, prostaglandins, serotonin, cyclic AMP, prolactin, and triiodothyzonine. Also encompassed are combinations with compounds generally used to treat aplastic anemia, such as methenolene, stanozolol, and nandrolone; to treat iron-deficiency anemia, such as iron preparations; to treat malignant anemia, such as vitamin B12 and/or folic acid; and to treat hemolytic anemia, such as adrenocortical steroids, e.g., corticoids. See e.g., Resegotti et al., Panminerva Medica, 23:243–248 (1981); Kurtz, FEBS Letters, 14a:105–108 (1982); McGonigle et al., Kidney Int., 25:437–444 (1984); and Pavlovic-Kantera, Expt. Hematol., 8(supp. 8) 283–291 (1980).

The invention also encompasses combining the BM-HABP polypeptides and polynucleotides and/or BM-HABP agonists described herein with other proposed or conventional hematopoietic therapies. Thus, for example, BM-HABP agonists can be combined with compounds that singly exhibit erythropoietic stimulatory effects, such as erythropoietin, testosterone, progenitor cell stimulators, insulin-like growth factor, prostaglandins, serotonin, cyclic AMP, prolactin, and triiodothyzonine. Also encompassed are combinations with compounds generally used to treat aplastic anemia, such as methenolene, stanozolol, and nandrolone; to treat iron-deficiency anemia, such as iron preparations; to treat malignant anemia, such as vitamin B12 and/or folic acid; and to treat hemolytic anemia, such as adrenocortical steroids, e.g., corticoids. See e.g., Resegotti et al., Panminerva Medica, 23:243–248 (1981); Kurtz, FEBS Letters, 14a:105–108 (1982); McGonigle et al., Kidney Int., 25:437444 (1984); and Pavlovic-Kantera, Expt. Hematol., 8(supp. 8) 283–291 (1980).

Methods for stimulating hematopoiesis comprise administering a hematopoietically effective amount (i.e, an amount which effects the formation of blood cells) of a pharmaceutical composition containing full-length WF-HABP or a full-length WF-HABP agonist to a patient. The full-length WF-HABP or full-length WF-HABP agonist is administered to the patient by any suitable technique, including but not limited to, parenteral, sublingual, topical, intrapulmonary and intranasal, and those techniques further discussed herein. The pharmaceutical composition optionally contains one or more members of the group consisting of erythropoietin, testosterone, progenitor cell stimulators, insulin-like growth factor, prostaglandins, serotonin, cyclic AMP, prolactin, triiodothyzonine, methenolene, stanozolol, and nandrolone, iron preparations, vitamin B12, folic acid and/or adrenocortical steroids. The full-length WF-HABP or full-length WF-HABP agonist and cotreatment drug(s) are suitably delivered by separate or by the same administration route, and at the same or at different times, depending, e.g., on dosing, the clinical condition of the patient, etc.

Methods for stimulating hematopoiesis comprise administering a hematopoietically effective amount (i.e, an amount which effects the formation of blood cells) of a pharmaceutical composition containing WF-HABP or a WF-HABP agonist to a patient. The WF-HABP or WF-HABP agonist is administered to the patient by any suitable technique, including but not limited to, parenteral, sublingual, topical, intrapulmonary and intranasal, and those techniques further discussed herein. The pharmaceutical composition optionally contains one or more members of the group consisting of erythropoietin, testosterone, progenitor cell stimulators, insulin-like growth factor, prostaglandins, serotonin, cyclic AMP, prolactin, triiodothyzonine, methenolene, stanozolol, and nandrolone, iron preparations, vitamin B12, folic acid and/or adrenocortical steroids. The WF-HAP or WF-HABP agonist and cotreatment drug(s) are suitably delivered by separate or by the same administration route, and at the same or at different times, depending, e.g., on dosing, the clinical condition of the patient, etc.

Methods for stimulating hematopoiesis comprise administering a hematopoietically effective amount (i.e, an amount which effects the formation of blood cells) of a pharmaceutical composition containing OE-HABP or a OE-HABP agonist to a patient. The OE-HABP or OE-HABP agonist is administered to the patient by any suitable technique, including but not limited to, parenteral, sublingual, topical, intrapulmonary and intranasal, and those techniques further discussed herein. The pharmaceutical composition optionally contains one or more members of the group consisting of erythropoietin, testosterone, progenitor cell stimulators, insulin-like growth factor, prostaglandins, serotonin, cyclic AMP, prolactin, triiodothyzonine, methenolene, stanozolol, and nandrolone, iron preparations, vitamin B12, folic acid and/or adrenocortical steroids. The OE-HABP or OE-HABP agonist and cotreatment drug(s) are suitably delivered by separate or by the same administration route, and at the same or at different times, depending, e.g., on dosing, the clinical condition of the patient, etc., Methods for stimulating hematopoiesis comprise administering a hematopoietically effective amount (i.e, an amount which effects the formation of blood cells) of a pharmaceutical composition containing BM-HABP or a BM-HABP agonist to a patient. The BM-HABP or BM-HABP agonist is administered to the patient by any suitable technique, including but not limited to, parenteral, sublingual, topical, intrapulmonary and intranasal, and those techniques further discussed herein. The pharmaceutical composition optionally contains one or more members of the group consisting of erythropoietin, testosterone, progenitor cell stimulators, insulin-like growth factor, prostaglandins, serotonin, cyclic AMP, prolactin, triiodothyzonine, methenolene, stanozolol, and nandrolone, iron preparations, vitamin B12, folic acid and/or adrenocortical steroids. The BM-HABP or BM-HABP agonist and cotreatment drug(s) are suitably delivered by separate or by the same administration route, and at the same or at different times, depending, e.g., on dosing, the clinical condition of the patient, etc.

For treating abnormal conditions related to an under-expression of full-length WF-HABP and its activity, or in which elevated or decreased levels of full-length WF-HABP are desired, several approaches are available. One approach comprises administering to an individual in need of an increased level of full-length WF-HABP mediated activity in the body, a therapeutically effective amount of an isolated full-length WF-HABP polypeptide, fragment, variant, derivative or analog of the invention, or a compound which activates full-length WF-HABP, i.e., an agonist as described above, optionally in combination with a pharmaceutically acceptable carrier. Alternatively, gene therapy may be employed to effect the endogenous production of full-length WF-HABP by the relevant cells in the subject. For example, a polynucleotide of the invention may be engineered for expression in a replication defective retroviral vector using techniques known in the art. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For an overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996).

For treating abnormal conditions related to an under-expression of OE-HABP and its activity, or in which elevated or decreased levels of OE-HABP are desired, several approaches are available. One approach comprises administering to an individual in need of an increased level of OE-HABP mediated activity in the body, a therapeutically effective amount of an isolated OE-HABP polypeptide, fragment, variant, derivative or analog of the invention, or a compound which activates OE-HABP, i.e., an agonist as described above, optionally in combination with a pharmaceutically acceptable carrier. Alternatively, gene therapy may be employed to effect the endogenous production of OE-HABP by the relevant cells in the subject. For example, a polynucleotide of the invention may be engineered for expression in a replication defective retroviral vector using techniques known in the art. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For an overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996).

For treating abnormal conditions related to an under-expression of BM-HABP and its activity, or in which elevated or decreased levels of BM-HABP are desired, several approaches are available. One approach comprises administering to an individual in need of an increased level of BM-HABP mediated activity in the body, a therapeutically effective amount of an isolated BM-HABP polypeptide, fragment, variant, derivative or analog of the invention, or a compound which activates BM-HABP, i.e., an agonist as described above, optionally in combination with a pharmaceutically acceptable carrier. Alternatively, gene therapy may be employed to effect the endogenous production of BM-HABP by the relevant cells in the subject. For example, a polynucleotide of the invention may be engineered for expression in a replication defective retroviral vector using techniques known in the art. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For an overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996).

Further, treatment can be administered, for example, in the form of gene replacement therapy. Specifically, one or more copies of a full-length WF-HABP nucleotide sequence of the invention that directs the production of a full-length WF-HABP gene product exhibiting normal function, may be inserted into the appropriate cells within a patient or animal subject, using vectors which include, but are not limited to, adenovirus, adeno-associated virus, retrovirus and herpesvirus vectors, in addition to other particles that introduce DNA into cells, such as liposomes and gene activated matrices. Because the full-length WF-HABP gene is expressed in hematopoietic tissue, lymph, bone, peripheral blood leukocytes etc, such gene replacement techniques should be capable of delivering full-length WF-HABP gene sequence to these cells within patients, or, alternatively, should involve direct administration of such full-length WF-HABP polynucleotide sequences to the site of the cells in which the full-length WF-HABP gene sequences are to be expressed. Alternatively, targeted homologous recombination can be utilized to correct the defective endogenous full-length WF-HABP gene and/or regulatory sequences thereof (e.g., promoter and enhancer sequences), or alternatively, to "turn on" other dormant full-length WF-HABP activity in the appropriate tissue or cell type.

Further, treatment can be administered, for example, in the form of gene replacement therapy. Specifically, one or more copies of a WF-HABP nucleotide sequence of the invention that directs the production of a WF-HABP gene product exhibiting normal function, may be inserted into the appropriate cells within a patient or animal subject, using vectors which include, but are not limited to, adenovirus, adeno-associated virus, retrovirus and herpesvirus vectors, in addition to other particles that introduce DNA into cells, such as liposomes and gene activated matrices. Because the WF-HABP gene is expressed in hematopoietic tissue, lymph, bone, peripheral blood leukocytes etc, such gene replacement techniques should be capable of delivering WF-HABP gene sequence to these cells within patients, or, alternatively, should involve direct administration of such WF-HABP polynucleotide sequences to the site of the cells in which the WF-HABP gene sequences are to be expressed. Alternatively, targeted homologous recombination can be utilized to correct the defective endogenous WF-HABP gene and/or regulatory sequences thereof (e.g., promoter and enhancer sequences), or alternatively, to "turn on" other dormant WF-HABP activity in the appropriate tissue or cell type.

Further, treatment can be administered, for example, in the form of gene replacement therapy. Specifically, one or more copies of a OE-HABP nucleotide sequence of the invention that directs the production of a OE-HABP gene product exhibiting normal function, may be inserted into the appropriate cells within a patient or animal subject, using vectors which include, but are not limited to, adenovirus, adeno-associated virus, retrovirus and herpesvirus vectors, in addition to other particles that introduce DNA into cells, such as liposomes and gene activated matrices. Because the OE-HABP gene is expressed in hematopoietic tissue, lymph, bone, peripheral blood leukocytes etc, such gene replacement techniques should be capable of delivering OE-HABP gene sequence to these cells within patients, or, alternatively, should involve direct administration of such OE-HABP polynucleotide sequences to the site of the cells in which the OE-HABP gene sequences are to be expressed. Alternatively, targeted homologous recombination can be utilized to correct the defective endogenous OE-HABP gene and/or regulatory sequences thereof (e.g., promoter and enhancer sequences), or alternatively, to "turn on" other dormant OE-HABP activity in the appropriate tissue or cell type.

Further, treatment can be administered, for example, in the form of gene replacement therapy. Specifically, one or more copies of a BM-HABP nucleotide sequence of the invention that directs the production of a BM-HABP gene product exhibiting normal function, may be inserted into the appropriate cells within a patient or animal subject, using vectors which include, but are not limited to, adenovirus, adeno-associated virus, retrovirus and herpesvirus vectors, in addition to other particles that introduce DNA into cells, such as liposomes and gene activated matrices. Because the BM-HABP gene is expressed in hematopoietic tissue, lymph, bone, peripheral blood leukocytes etc, such gene replacement techniques should be capable of delivering BM-HABP gene sequence to these cells within patients, or, alternatively, should involve direct administration of such BM-HABP polynuclcotide sequences to the site of the cells in which the BM-HABP gene sequences are to be expressed. Alternatively, targeted homologous recombination can be utilized to correct the defective endogenous BM-HABP gene and/or regulatory sequences thereof (e.g., promoter and enhancer sequences), or alternatively, to "turn on" other dormant BM-HABP activity in the appropriate tissue or cell type.

Additional methods which may be utilized to increase the overall level of full-length WF-HABP expression and/or full-length WF-HABP activity include the introduction of appropriate full-length WF-HABP-expressing cells, preferably autologous cells, into a patient at positions and in numbers which are sufficient to ameliorate the symptoms of abnormalities in cell growth regulation, cell signaling, and other full-length WF-HABP mediated activities. Such cells may be either recombinant or non-recombinant. Among the cells which can be administered to increase the overall level of full-length WF-HABP gene expression in a patient are normal cells, which express the full-length WF-HABP gene. Cell-based gene therapy techniques are well known to those skilled in the art, see, e.g., Anderson et al., U.S. Pat. No. 5,399,349; and Mulligan & Wilson, U.S. Pat. No. 5,460,959.

Additional methods which may be utilized to increase the overall level of WF-HABP expression and/or WF-HABP activity include the introduction of appropriate WF-HABP-expressing cells, preferably autologous cells, into a patient at positions and in numbers which are sufficient to ameliorate the symptoms of abnormalities in cell growth regulation cell signaling, and other WF-HABP mediated activities. Such cells may be either recombinant or non-recombinant. Among the cells which can be administered to increase the overall level of WF-HABP gene expression in a patient are normal cells, which express the WF-HABP gene. Cell-based gene therapy techniques are well known to those skilled in the art, see, e.g., Anderson et al., U.S. Pat. No. 5,399,349; and Mulligan & Wilson, U.S. Pat. No 5,460,959.

Additional methods which may be utilized to increase the overall level of OE-HABP expression and/or OE-HABP activity include the introduction of appropriate OE-HABP-expressing cells, preferably autologous cells, into a patient at positions and in numbers which are sufficient to ameliorate the symptoms of abnormalities in cell growth regulation, cell signaling, and other OE-HABP mediated activities. Such cells may be either recombinant or non-recombinant. Among the cells which can be administered to increase the overall level of OE-HABP gene expression in a patient are normal cells, which express the OE-HABP gene. Cell-based gene therapy techniques are well known to those skilled in the art, see, e.g., Anderson et al., U.S. Pat. No. 5,399,349; and Mulligan & Wilson, U.S. Pat. No. 5,460,959.

Additional methods which may be utilized to increase the overall level of BM-HABP expression and/or BM-HABP activity include the introduction of appropriate BM-HABP-expressing cells, preferably autologous cells, into a patient at positions and in numbers which are sufficient to ameliorate the symptoms of abnormalities in cell growth regulation, cell signaling, and other BM-HABP mediated activities. Such cells may be either recombinant or non-recombinant. Among the cells which can be administered to increase the overall level of BM-HABP gene expression in a patient are normal cells, which express the BM-HABP gene. Cell-based gene therapy techniques are well known to those skilled in the art, see, e.g., Anderson et al., U.S. Pat. No. 5,399,349; and Mulligan & Wilson, U.S. Pat. No. 5,460,959.

Thus, one embodiment of the invention comprises administering to in individual in need of an increased level of full-length WF-HABP mediated activity compound that stimulates full-length WF-HABP mediated activity (agonist), such as for example, an antibody or full-length WF-HABP fragment, variant, derivative or analog of the invention, along with a pharmaceutically acceptable carrier in an amount effective to enhance (i.e., increase) full-length WF-HABP mediated activity.

Thus, one embodiment of the invention comprises administering to in individual in need of an increased level of WF-HABP mediated activity compound that stimulates WF-HABP mediated activity (agonist), such as for example, an antibody or WF-HABP fragment, variant, derivative or analog of the invention, along with a pharmaceutically acceptable carrier in an amount effective to enhance (i.e., increase) WF-HABP mediated activity.

Thus, one embodiment of the invention comprises administering to in individual in need of an increased level of OE-HABP mediated activity compound that stimulates OE-HABP mediated activity (agonist), such as for example, an antibody or OE-HABP fragment, variant, derivative or analog of the invention, along with a pharmaceutically acceptable carrier in an amount effective to enhance (i.e., increase) OE-HABP mediated activity.

Thus, one embodiment of the invention comprises administering to in individual in need of an increased level of BM-HABP mediated activity compound that stimulates BM-HABP mediated activity (agonist), such as for example, an antibody or BM-HABP fragment, variant, derivative or analog of the invention, along with a pharmaceutically acceptable carrier in an amount effective to enhance (i.e., increase) BM-HABP mediated activity.

If the activity of full-length WF-HABP is in excess, several approaches are available to reduce or inhibit full-length WF-HABP activity using molecules derived from the polypeptide and polynucleotide sequences described above. Accordingly, a further aspect of the invention is related to a method for treating an individual in need of a decreased level of full-length WF-HABP mediated activity in the body comprising, administering to such an individual a composition comprising a therapeutically effective amount of a full-length WF-HABP polypeptide, fragment, variant, derivative or analog of the invention which acts as a full-length WF-HABP antagonist or full-length WF-HABP antagonist identified using the methods described herein, optionally, in combination with a pharmaceutically acceptable carrier. Preferably, full-length WF-HABP activity is decreased to treat a disease wherein increased cell survival, secretion, proliferation, migration, and/or differentiation is exhibited. Polypeptides, derivatives, variants and analogs of the invention and other compounds which function as antagonists of full-length WF-HABP can routinely be identified using the assays described infra and other techniques known in the art. Preferred antagonists for use in the present invention are full-length WF-HABP-specific antibodies.

If the activity of WF-HABP is in excess, several approaches are available to reduce or inhibit WF-HABP activity using molecules derived from the polypeptide and polynucleotide sequences described above. Accordingly, a further aspect of the invention is related to a method for treating an individual in need of a decreased level of WF-HABP mediated activity in the body comprising, administering to such an individual a composition comprising a therapeutically effective amount of a WF-HABP polypeptide, fragment, variant, derivative or analog of the invention which acts as a WF-HABP antagonist or WF-HABP antagonist identified using the methods described herein, optionally, in combination with a pharmaceutically acceptable carrier. Preferably, WF-HABP activity is decreased to treat a disease wherein increased cell survival, secretion, proliferation, migration, and/or differentiation is exhibited. Polypeptides, derivatives, variants and analogs of the invention and other compounds which function as antagonists of WF-HABP can routinely be identified using the assays described infra and other techniques known in the art. Preferred antagonists for use in the present invention are WF-HABP-specific antibodies.

If the activity of OE-HABP is in excess, several approaches are available to reduce or inhibit OE-HABP activity using molecules derived from the polypeptide and polynucleotide sequences described above. Accordingly, a further aspect of the invention is related to a method for treating an individual in need of a decreased level of OE-HABP mediated activity in the body comprising, administering to such an individual a composition comprising a therapeutically effective amount of a OE-HABP polypeptide, fragment, variant, derivative or analog of the invention which acts as a OE-HABP antagonist or OE-HABP antagonist identified using the methods described herein, optionally, in combination with a pharmaceutically acceptable carrier. Preferably, OE-HABP activity is decreased to treat a disease wherein increased cell survival, secretion, proliferation, migration, and/or differentiation is exhibited. Polypeptides, derivatives, variants and analogs of the invention and other compounds which function as antagonists of OE-HABP can routinely be identified using the assays described infra and other techniques known in the art. Preferred antagonists for use in the present invention are OE-HABP-specific antibodies.

If the activity of BM-HABP is in excess, several approaches are available to reduce or inhibit BM-HABP activity using molecules derived from the polypeptide and polynucleotide sequences described above. Accordingly, a further aspect of the invention is related to a method for treating an individual in need of a decreased level of BM-HABP mediated activity in the body comprising, administering to such an individual a composition comprising a therapeutically effective amount of a BM-HABP polypeptide, fragment, variant, derivative or analog of the invention which acts as a BM-HABP antagonist or BM-HABP antagonist identified using the methods described herein, optionally, in combination with a pharmaceutically acceptable carrier. Preferably, BM-HABP activity is decreased to treat a disease wherein increased cell survival, secretion, proliferation, migration, and/or differentiation is exhibited. Polypeptides, derivatives, variants and analogs of the invention and other compounds which function as antagonists of BM-HABP can routinely be identified using the assays described infra and other techniques known in the art. Preferred antagonists for use in the present invention are BM-HABP-specific antibodies.

In another approach, full-length WF-HABP activity can be reduced or inhibited by decreasing the level of full-length WF-HABP gene expression. In one embodiment, this is accomplished through the use of antisense sequences, either internally generated or separately administered (see, for example, O'Connor, J. Neurochem. (1991) 56:560 in Oligodeoxynucleotides as Antisense Inhibitors of Gene Expression, CRC Press, Boca Raton, Fla. (1988). Antisense technology can be used to control gene expression through antisense DNA or RNA or through triple-helix formation. Antisense techniques are discussed, for example, in Okano, J. Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1360 (1991). The methods are based on binding of a polynucleotide to a complementary DNA or RNA. For example, the 5' coding portion of a polynucleotide that encodes full-length WF-HABP polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the full-length WF-HABP polypeptide. The antisense RNA oligonucleotide hybridizes to the mRNA in vivo and blocks translation of the mRNA molecule into polypeptide.

In another approach, WF-HABP activity can be reduced or inhibited by decreasing the level of WF-HABP gene expression. In one embodiment, this is accomplished through the use of antisense sequences, either internally generated or separately administered (see, for example, O'Connor, J. Neurochem. (1991) 56:560 in Oligodeoxynucleotides as Antisense Inhibitors of Gene Expression, CRC Press, Boca Raton, Fla. (1988). Antisense technology can be used to control gene expression through antisense DNA or RNA or through triple-helix formation. Antisense techniques are discussed, for example, in Okano, J. Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1360 (1991). The methods are based on binding of a polynucleotide to a complementary DNA or RNA. For example, the 5' coding portion of a polynucleotide that encodes WF-HABP polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the WF-HABP polypeptide. The antisense RNA oligonucleotide hybridizes to the mRNA in vivo and blocks translation of the mRNA molecule into polypeptide.

In another approach, OE-HABP activity can be reduced or inhibited by decreasing the level of OE-HABP gene expression. In one embodiment, this is accomplished through the use of antisense sequences, either internally generated or separately administered (see, for example, O'Connor, J. Neurochem. (1991) 56:560 in Oligodeoxynucleotides as Antisense Inhibitors of Gene Expression, CRC Press, Boca Raton, Fla. (1988). Antisense technology can be used to control gene expression through antisense DNA or RNA or through triple-helix formation. Antisense Techniques are discussed for example, in Okano, J. Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1360 (1991). The methods are based on binding of a polynucleotide to a complementary DNA or RNA. For example, the 5' coding portion of a polynucleotide that encodes OE-HABP polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the OE-HABP polypeptide. The antisense RNA oligonucleotide hybridizes to the mRNA in vivo and blocks translation of the mRNA molecule into polypeptide.

In another approach, BM-HABP activity can be reduced or inhibited by decreasing the level of BM-HABP gene expression. In one embodiment, this is accomplished through the use of antisense sequences, either internally generated or separately administered (see, for example, O'Connor, J. Neurochem. (1991) 56:560 in Oligodeoxynucleotides as Antisense Inhibitors of Gene Expression, CRC Press, Boca Raton, Fla. (1988). Antisense technology can be used to control gene expression through antisense DNA or RNA or through triple-helix formation. Antisense techniques are discussed, for example, in Okano, J. Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1360 (1991). The methods are based on binding of a polynucleotide to a complementary DNA or RNA. For example, the 5' coding portion of a polynucleotide that encodes BM-HABP polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the BM-HABP polypeptide. The antisense RNA oligonucleotide hybridizes to the mRNA in vivo and blocks translation of the mRNA molecule into polypeptide.

In one embodiment, the full-length WF-HABP anti sense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the full-length WF-HABP antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding full-length WF-HABP, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304–310 (1981), the promoter contained in the 3' long terminal repeat of Rous sarcoma virus (Yamamoto et al., Cell 22:787–797 (1980)), the herpes thymidine promoter (Wagner et al., Proc. Natl. Acad. Sci. U.S.A. 78:1441–1445 (1981)), the regulatory sequences of the metallothionein gene (Brinster et al., Nature 296:39–42 (1982)), etc.

In one embodiment, the WF-HABP antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the WF-HABP antisense nucleic acid. Such a vector can remain episomal or become chromosomally integrated, as long as it can be transcribed to produce the desired antisense RNA. Such vectors can be constructed by recombinant DNA-technology methods standard in the art. Vectors can be plasmid, viral, or others know in the art, used for replication and expression in vertebrate cells. Expression of the sequence encoding WF-HABP, or fragments thereof, can be by any promoter known in the art to act in vertebrate, preferably human cells. Such promoters can be inducible or constitutive. Such promoters include, but are not limited to, the SV40 early promoter region (Bemoist and Chambon, Nature 29:304–310 (1981), the promoter contained in the 3' long terminal repeat of Rous sarcoma virus (Yamamoto et al., Cell 22:787–797 (1980)), the herpes thymidine promoter (Wagner et al., Proc. Natl. Acad. Sci. U.S.A. 78:1441–1445 (1981)), the regulatory sequences of the metallothionein gene (Brinster et al., Nature 296:39–42 (1982)), etc.

In one embodiment, the OE-HABP antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the OE-HABP antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding OE-HABP, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304–310 (1981), the promoter contained in the 3' long terminal repeat of Rous sarcoma virus (Yamamoto et al., Cell 22:787–797 (1980)), the herpes thymidine promoter (Wagner et al., Proc. Natl. Acad. Sci. U.S.A. 78:1441–1445 (1981)), the regulatory sequences of the metallothionein gene (Brinster et al., Nature 296:39–42 (1982)), etc.

In one embodiment, the BM-HABP antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the BM-HABP antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding BM-HABP, or fragments thereof, can be by any promoter known in the art to act in vertebrate, preferably human cells. Such promoters can be inducible or constitutive. Such promoters include, but are not limited to, the SV40 early promoter region (Bemoist and Chambon, Nature 29:304–310 (1981), the promoter contained in the 3' long terminal repeat of Rous sarcoma virus (Yamamoto et al., Cell 22:787–797 (1980)), the herpes thymidine promoter (Wagner et al., Proc. Natl. Acad. Sci. U.S.A. 78:1441–1445 (1981)), the regulatory sequences of the metallothionein gene (Brinster et al., Nature 296:39–42 (1982)), etc.

The antisense nucleic acids of the invention comprise a sequence complementary to at least a portion of an RNA transcript of a full-length WF-HABP gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded full-length WF-HABP antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a full-length WF-HABP RNA it may contain and still form a stable duplex (or triplex as the case may be). One skilled in the art can ascertain a tolerable degree of mismatch by use of standard procedures to determine the melting point of the hybridized complex.

The antisense nucleic acids of the invention comprise a sequence complementary to at least a portion of an RNA transcript of a WF-HABP gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded WF-HABP antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a WF-HABP RNA it may contain and still form a stable duplex (or triplex as the case may be). One skilled in the art can ascertain a tolerable degree of mismatch by use of standard procedures to determine the melting point of the hybridized complex.

The antisense nucleic acids of the invention comprise a sequence complementary to at least a portion of an RNA transcript of a OE-HABP gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded OE-HABP antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a OE-HABP RNA it may contain and still form a stable duplex (or triplex as the case may be). One skilled in the art can ascertain a tolerable degree of mismatch by use of standard procedures to determine the melting point of the hybridized complex.

The antisense nucleic acids of the invention comprise a sequence complementary to at least a portion of an RNA transcript of a BM-HABP gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded BM-HABP antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a BM-HABP RNA it may contain and still form a stable duplex (or triplex as the case may be). One skilled in the art can ascertain a tolerable degree of mismatch by use of standard procedures to determine the melting point of the hybridized complex.

Potential full-length WF-HABP antagonists according to the invention also include catalytic RNA, or a ribozyme (See, e.g., PCT International Publication WO 90/11364, published Oct. 4, 1990; Sarver et al., Science 247:1222–1225 (1990). While ribozymes that cleave mRNA at site specific recognition sequences can be used to destroy full-length WF-HABP RNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591 (1988). There are numerous potential hammerhead ribozyme cleavage sites within the nucleotide sequence of full-length WF-HABP (FIGS. 1A–P; SEQ ID NO:1). Preferably, the ribozyme is engineered so that the cleavage recognition site is located near the 5' end of the full-length WF-HABP mRNA; i.e., to increase efficiency and minimize the intracellular accumulation of non-functional mRNA transcripts. DNA constructs encoding the ribozyme may be introduced into the cell in the same manner as described above for the introduction of antisense encoding DNA. Since ribozymes, unlike antisense molecules are catalytic, a lower intracellular concentration is required for efficiency.

Potential WF-HABP antagonists according to the invention also include catalytic RNA, or a ribozyme (See, e.g., PCT International Publication WO 90/11364, published Oct. 4, 1990; Sarver et al., Science 247:1222–1225 (1990). While ribozymes that cleave mRNA at site specific recognition sequences can be used to destroy WF-HABP mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591 (1988). There are numerous potential hammerhead ribozyme cleavage sites within the nucleotide sequence of WF-HABP (FIGS. 2A–D; SEQ ID NO:4). Preferably, the ribozyme is engineered so that the cleavage recognition site is located near the 5' end of the WF-HABP mRNA; i.e., to increase efficiency and minimize the intracellular accumulation of non-functional mRNA transcripts. DNA constructs encoding the ribozyme may be introduced into the cell in the same manner as described above for the introduction of antisense encoding DNA. Since ribozymes, unlike antisense molecules are catalytic, a lower intracellular concentration is required for efficiency.

Potential OE-HABP antagonists according to the invention also include catalytic RNA, or a ribozyme (See, e.g., PCT International Publication WO 90/11364, published Oct. 4, 1990; Sarver et al., Science 247:1222–1225 (1990). While ribozymes that cleave mRNA at site specific recognition sequences can be used to destroy OE-HABP mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591 (1988). There are numerous potential hammerhead ribozyme cleavage sites within the nucleotide sequence of OE-HABP (FIGS. 3A–C; SEQ ID NO:7). Preferably, the ribozyme is engineered so that the cleavage recognition site is located near the 5' end of the OE-HABP mRNA; i.e., to increase efficiency and minimize the intracellular accumulation of non-functional mRNA transcripts. DNA constructs encoding the ribozyme may be introduced into the cell in the same manner as described above for the introduction of antisense encoding DNA. Since ribozymes, unlike antisense molecules are catalytic, a lower intracellular concentration is required for efficiency.

Potential BM-HABP antagonists according to the invention also include catalytic RNA, or a ribozyme (See, e.g., PCT International Publication WO 90/11364, published Oct. 4, 1990; Sarver et al., Science 247:1222–1225 (1990). While ribozymes that cleave mRNA at site specific recognition sequences can be used to destroy BM-HABP mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591 (1988). There are numerous potential hammerhead ribozyme cleavage sites within the nucleotide sequence of BM-HABP (FIGS. 4A–C; SEQ ID NO:10). Preferably, the ribozyme is engineered so that the cleavage recognition site is located near the 5' end of the BM-HABP mRNA; i.e., to increase efficiency and minimize the intracellular accumulation of non-functional mRNA transcripts. DNA constructs encoding the ribozyme may be introduced into the cell in the same manner as described above for the introduction of antisense encoding DNA. Since ribozymes, unlike antisense molecules are catalytic, a lower intracellular concentration is required for efficiency.

Endogenous full-length WF-HABP gene expression can also be reduced by inactivating or "knocking out" the full-length WF-HABP gene or its promoter using targeted homologous recombination (e.g., see Smithies et al., Nature 317:330–234 (1985); Thomas et al., Cell 51:503–512 (1987); Thompson et al., Cell 5:313–321 (1989); each of which is incorporated by reference herein in its entirety). Such approach can be adapted for use in humans provided the recombinant DNA constructs are directly administered or targeted to the required site in vivo using appropriate viral vectors.

Endogenous WF-HABP gene expression can also be reduced by inactivating or "knocking out" the WF-HABP gene or its promoter using targeted homologous recombination (e.g., see Smithies et al., Nature 317:330–234 (1985); Thomas et al., Cell 51:503–512 (1987); Thompson et al., Cell 5:313–321 (1989); each of which is incorporated by reference herein in its entirety). Such approach can be adapted for use in humans provided the recombinant DNA constructs are directly administered or targeted to the required site in vivo using appropriate viral vectors.

Endogenous OE-HABP gene expression can also be reduced by inactivating or "knocking out" the OE-HABP gene or its promoter using targeted homologous recombination (e.g., see Smithies et al., Nature 317:330–234 (1985); Thomas et al., Cell 51:503–512 (1987); Thompson et al., Cell 5:313–321 (1989); each of which is incorporated by reference herein in its entirety). Such approach can be adapted for use in humans provided the recombinant DNA constructs are directly administered or targeted to the required site in vivo using appropriate viral vectors.

Endogenous BM-HABP gene expression can also be reduced by inactivating or "knocking out" the BM-HABP gene or its promoter using targeted homologous recombination (e.g., see Smithies et al., Nature 317:330–234 (1985); Thomas et al., Cell 51:503–512 (1987); Thompson et al., Cell 5:313–321 (1989); each of which is incorporated by reference herein in its entirety). Such approach can be adapted for use in humans provided the recombinant DNA constructs are directly administered or targeted to the required site in vivo using appropriate viral vectors.

Alternatively, endogenous full-length WF-HABP gene expression can be reduced by targeted deoxyribonucleotide sequences complementary to the regulatory region of the full-length WF-HABP gene (i.e., the full-length WF-HABP promoter and/or enhancers) to form triple helical structures that prevent transcription of the full-length WF-HABP gene in target cells in the body, see generally, Helene et al., Ann, N.Y. Acad. Sci. 660:27–36 (1992); Helene, C., Anticancer Drug Des., 6(6):569–584 (1991); and Maher, L. J., Bioassays 14(12):807–815 (1992)).

Alternatively, endogenous WF-HABP gene expression can be reduced by targeted deoxyribonucleotide sequences complementary to the regulatory region of the WF-HABP gene (i.e., the WF-HABP promoter and/or enhancers) to form triple helical structures that prevent transcription of the WF-HABP gene in target cells in the body, see generally, Helene et al., Ann, N.Y. Acad. Sci. 660:27–36 (1992); Helene, C., Anticancer Drug Des., 6(6):569–584 (1991); and Maher, L. J., Bioassays 14(12):807–815 (1992)).

Alternatively, endogenous OE-HABP gene expression can be reduced by targeted deoxyribonucleotide sequences complementary to the regulatory region of the OE-HABP gene (i.e., the OE-HABP promoter and/or enhancers) to form triple helical structures that prevent transcription of the OE-HABP gene in target cells in the body, see generally, Helene et al., Ann, N.Y. Acad. Sci. 660:27–36 (1992); Helene, C., Anticancer Drug Des., 6(6):569–584 (1991); and Maher, L. J., Bioassays 14(12):807–815 (1992)).

Alternatively, endogenous BM-HABP gene expression can be reduced by targeted deoxyribonucleotide sequences complementary to the regulatory region of the BM-HABP gene (i.e., the BM-HABP promoter and/or enhancers) to form triple helical structures that prevent transcription of the BM-HABP gene in target cells in the body, see generally, Helene et al., Ann, N.Y. Acad. Sci. 660:27–36 (1992); Helene, C., Anticancer Drug Des., 6(6):569–584 (1991); and Maher, L. J., Bioassays 14(12):807–815 (1992)).

Thus, one embodiment of the invention comprises administering to an individual in need of a decreased level of full-length WF-HABP mediated activity, a full-length WF-HABP inhibitor compound (antagonist), such as for example, an antibody or full-length WF-HABP fragment, variant, derivative or analog of the invention, along with a pharmaceutically acceptable carrier in an amount effective to suppress (i.e., lower) full-length WF-HABP mediated activity.

Thus, one embodiment of the invention comprises administering to an individual in need of a decreased level of WF-HABP mediated activity, a WF-HABP inhibitor compound (antagonist), such as for example, an antibody or WF-HABP fragment, variant, derivative or analog of the invention, along with a pharmaceutically acceptable carrier in an amount effective to suppress (i.e., lower) WF-HABP mediated activity.

Thus, one embodiment of the invention comprises administering to an individual in need of a decreased level of OE-HABP mediated activity, a OE-HABP inhibitor compound (antagonist), such as for example, an antibody or OE-HABP fragment, variant, derivative or analog of the invention, along with a pharmaceutically acceptable carrier in an amount effective to suppress (i.e., lower) OE-HABP mediated activity.

Thus, one embodiment of the invention comprises administering to an individual in need of a decreased level of BM-HABP mediated activity, a BM-HABP inhibitor compound (antagonist), such as for example, an antibody or BM-HABP fragment, variant, derivative or analog of the invention, along with a pharmaceutically acceptable carrier in an amount effective to suppress (i.e., lower) BM-HABP mediated activity.

Formulation and Administration

It will be appreciated that conditions caused by a decrease in the standard or normal level of full-length WF-HABP mediated activity in an individual, can be treated by administration of full-length WF-HABP polypeptide or fragment, variant, derivative, or analog of the invention or an agonist thereof. Thus, the invention further provides a method of treating an individual in need of an increased level of full-length WF-HABP mediated activity comprising administering to such an individual a pharmaceutical composition comprising an effective amount of an isolated full-length WF-HABP polynucleotide or polypeptide; or fragment, variant, derivative, or analog of the invention, such as for example, the full length form of the full-length WF-HABP encoding polynucleotide, effective to increase the full-length WF-HABP mediated activity level in such an individual.

It will be appreciated that conditions caused by a decrease in the standard or normal level of WF-HABP mediated activity in an individual, can be treated by administration of WF-HABP polypeptide or fragment, variant, derivative, or analog of the invention or an agonist thereof. Thus, the invention further provides a method of treating an individual in need of an increased level of WF-HABP mediated activity comprising administering to such an individual a pharmaceutical composition comprising an effective amount of an isolated WF-HABP polynucleotide or polypeptide; or fragment, variant, derivative, or analog of the invention, such as for example, the full length form of the WF-HABP encoding polynucleotide, effective to increase the WF-HABP mediated activity level in such an individual.

It will be appreciated that conditions caused by a decrease in the standard or normal level of OE-HABP mediated activity in an individual, can be treated by administration of OE-HABP polypeptide or fragment, variant, derivative, or analog of the invention or an agonist thereof. Thus, the invention further provides a method of treating an individual in need of an increased level of OE-HABP mediated activity comprising administering to such an individual a pharmaceutical composition comprising an effective amount of an isolated OE-HABP polynucleotide or polypeptide; or fragment, variant, derivative, or analog of the invention, such as for example, the full length form of the OE-HABP encoding polynucleotide, effective to increase the OE-HABP mediated activity level in such an individual.

It will be appreciated that conditions caused by a decrease in the standard or normal level of BM-HABP mediated activity in an individual, can be treated by administration of BM-HABP polypeptide or fragment, variant, derivative, or analog of the invention or an agonist thereof. Thus, the invention further provides a method of treating an individual in need of an increased level of BM-HABP mediated activity comprising administering to such an individual a pharmaceutical composition comprising an effective amount of an isolated BM-HABP polynucleotide or polypeptide; or fragment, variant, derivative, or analog of the invention, such as for example, the full length form of the BM-HABP encoding polynucleotide, effective to increase the BM-HABP mediated activity level in such an individual.

The dosage range required depends on the choice of peptide, the route of administration, the nature of the formulation, the nature of the subject's condition, and the judgment of the attending practitioner. As a general proposition, the total pharmaceutically effective amount of full-length WF-HABP polypeptide administered parenterally per dose will be in the range of about 1 $\mu$g/kg/day to 10 mg/kg/day of patient body weight, although, as noted above, this will be subject to therapeutic discretion. More preferably, this dose is at least 0.01 mg/kg/day, and most preferably for humans this dose is in the range of 0.1–100 mg/kg of subject, or between about 0.01 and 1 mg/kg/day. If given continuously, the full-length WF-HABP polypeptide is typically administered at a dose rate of about 1 $\mu$g/kg/hour to about 50 $\mu$g/kg/hour, either by 1–4 injections per day or by continuous subcutaneous infusions, for example, using a mini-pump. An intravenous bag solution may also be employed. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

The dosage range required depends on the choice of peptide, the route of administration, the nature of the formulation, the nature of the subject's condition, and the judgment of the attending practitioner. As a general proposition, the total pharmaceutically effective amount of WF-HABP polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans this dose is in the range of 0.1–100 mg/kg of subject, or between about 0.01 and 1 mg/kg/day. If given continuously, the WF-HABP polypeptide is typically administered at a dose rate of about 1 µg/kg/hour to about 50 pg/kg/hour, either by 1–4 injections per day or by continuous subcutaneous infusions, for example, using a mini-pump. An intravenous bag solution may also be employed. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

The dosage range required depends on the choice of peptide, the route of administration, the nature of the formulation, the nature of the subject's condition, and the judgment of the attending practitioner. As a general proposition, the total pharmaceutically effective amount of OE-HABP polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans this dose is in the range of 0.1–100 mg/kg of subject, or between about 0.01 and 1 mg/kg/day. If given continuously, the OE-HABP polypeptide is typically administered at a dose rate of about 1 µg/kg/hour to about 50 pg/kg/hour, either by 1–4 injections per day or by continuous subcutaneous infusions, for example, using a mini-pump. An intravenous bag solution may also be employed. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

The dosage range required depends on the choice of peptide, the route of administration, the nature of the formulation, the nature of the subject's condition, and the judgment of the attending practitioner. As a general proposition, the total pharmaceutically effective amount of BM-HABP polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans this dose is in the range of 0.1–100 mg/kg of subject, or between about 0.01 and 1 mg/kg/day. If given continuously, the BM-HABP polypeptide is typically administered at a dose rate of about 1 µg/kg/hour to about 50 µg/kg/hour, either by 14 injections per day or by continuous subcutaneous infusions, for example, using a mini-pump. An intravenous bag solution may also be employed. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Pharmaceutical compositions containing the full-length WF-HABP polypeptides and polynucleotides of the invention (including fragments, variants, derivatives or analogs), and full-length WF-HABP agonists and antagonists may be routinely formulated in combination with a pharmaceutically acceptable carrier. By "pharmaceutically acceptable carrier" is meant a non-toxic solid, semisolid or liquid filler, diluent, encapsulating material or formulation auxiliary of any type. In a specific embodiment, "pharmaceutically acceptable" means approved by a regulatory agency of the federal or a state government or listed in the U.S. Pharmacopoeia or other generally recognized pharmacopoeia for use in animals, and more particularly humans. Nonlimiting examples of suitable pharmaceutical carriers according to this embodiment are provided in "Remington's Pharmaceutical Sciences" by E. W. Martin, and include sterile liquids, such as water, saline, buffered saline, glycerol, ethanol, and oils, including those of petroleum, animal, vegetable or synthetic origin, such as peanut oil, soybean oil, mineral oil, sesame oil and the like. Formulation should suit the mode of administration, and is well within the skill of the art. For example, water is a preferred carrier when the pharmaceutical composition is administered intravenously. Saline solutions and aqueous dextrose and glycerol solutions can be employed as liquid carriers, particularly for injectable solutions. The invention additionally relates to pharmaceutical packs and kits comprising one or more containers filled with one or more of the ingredients of the aforementioned compositions of the invention.

Pharmaceutical compositions containing the WF-HABP polypeptides and polynucleotides of the invention (including fragments, variants, derivatives or analogs), and WF-HABP agonists and antagonists may be routinely formulated in combination with a pharmaceutically acceptable carrier. By "pharmaceutically acceptable carrier" is meant a non-toxic solid, semisolid or liquid filler, diluent, encapsulating material or formulation auxiliary of any type. In a specific embodiment, "pharmaceutically acceptable" means approved by a regulatory agency of the federal or a state government or listed in the U.S. Pharmacopoeia or other generally recognized pharmacopoeia for use in animals, and more particularly humans. Nonlimiting examples of suitable pharmaceutical carriers according to this embodiment are provided in "Remington's Pharmaceutical Sciences" by E. W. Martin, and include sterile liquids, such as water, saline, buffered saline, glycerol, ethanol, and oils, including those of petroleum, animal, vegetable or synthetic origin, such as peanut oil, soybean oil, mineral oil, sesame oil and the like. Formulation should suit the mode of administration, and is well within the skill of the art. For example, water is a preferred carrier when the pharmaceutical composition is administered intravenously. Saline solutions and aqueous dextrose and glycerol solutions can be employed as liquid carriers, particularly for injectable solutions. The invention additionally relates to pharmaceutical packs and kits comprising one or more containers filled with one or more of the ingredients of the aforementioned compositions of the invention.

Pharmaceutical compositions containing the OE-HABP polypeptides and polynucleotides of the invention (including fragments, variants, derivatives or analogs), and OE-HABP agonists and antagonists may be routinely formulated in combination with a pharmaceutically acceptable carrier. By "pharmaceutically acceptable carrier" is meant a non-toxic solid, semisolid or liquid filler, diluent, encapsulating material or formulation auxiliary of any type. In a specific embodiment, "pharmaceutically acceptable" means approved by a regulatory agency of the federal or a state government or listed in the U.S. Pharmacopoeia or other generally recognized pharmacopoeia for use in animals, and more particularly humans. Nonlimiting examples of suitable pharmaceutical carriers according to this embodiment are provided in "Remington's Pharmaceutical Sciences" by E. W. Martin, and include sterile liquids, such as water, saline, buffered saline, glycerol, ethanol, and oils, including those of petroleum, animal, vegetable or synthetic origin, such as peanut oil, soybean oil, mineral oil, sesame oil and the like. Formulation should suit the mode of administration, and is well within the skill of the art. For example, water is a preferred carrier when the pharmaceutical composition is administered intravenously. Saline solutions and aqueous dextrose and glycerol solutions can be employed as liquid carriers, particularly for injectable solutions. The invention additionally relates to pharmaceutical packs and kits comprising one or more containers filled with one or more of the ingredients of the aforementioned compositions of the invention.

Pharmaceutical compositions containing the BM-HABP polypeptides and polynucleotides of the invention (including fragments, variants, derivatives or analogs), and BM-HABP agonists and antagonists may be routinely formulated in combination with a pharmaceutically acceptable carrier. By "pharmaceutically acceptable carrier" is meant a non-toxic solid, semisolid or liquid filler, diluent, encapsulating material or formulation auxiliary of any type. In a specific embodiment, "pharmaceutically acceptable" means approved by a regulatory agency of the federal or a state government or listed in the U.S. Pharmacopoeia or other generally recognized pharmacopoeia for use in animals, and more particularly humans. Nonlimiting examples of suitable pharmaceutical carriers according to this embodiment are provided in "Remington's Pharmaceutical Sciences" by E. W. Martin, and include sterile liquids, such as water, saline, buffered saline, glycerol, ethanol, and oils, including those of petroleum, animal, vegetable or synthetic origin, such as peanut oil, soybean oil, mineral oil, sesame oil and the like. Formulation should suit the mode of administration, and is well within the skill of the art. For example, water is a preferred carrier when the pharmaceutical composition is administered intravenously. Saline solutions and aqueous dextrose and glycerol solutions can be employed as liquid carriers, particularly for injectable solutions. The invention additionally relates to pharmaceutical packs and kits comprising one or more containers filled with one or more of the ingredients of the aforementioned compositions of the invention.

Polypeptides and other compounds of the present invention may be administered alone or in conjunction with other compounds, such as therapeutic compounds. The pharmaceutical composition of the invention may be administered orally, rectally, parenterally, intracisternally, intravaginally, intraperitoneally, topically (as by powders, ointments, drops or transdermal patch), bucally, or as an oral or nasal spray. Preferred forms of systemic administration of the pharmaceutical compositions include parenteral injection, typically by intravenous injection. Other injection routes, such as subcutaneous, intramuscular, intrasternal, intraarticular or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

Gene Mapping

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a full-length WF-HABP gene. This can be accomplished using a variety of well known techniques and libraries, which generally are available commercially. The genomic DNA then is used for in situ chromosome mapping using well known techniques for this purpose. The gene encoding the disclosed cDNA is believed to reside on chromosome 3. Accordingly, polynucleotides related to this invention are useful as a marker in linkage analysis for chromosome 3.

In certain preferred embodiments in this regard, the cDNA herein disclosed is used to clone genomic DNA of a WF-HABP gene. This can be accomplished using a variety of well known techniques and libraries, which generally are available commercially. The genomic DNA then is used for in situ chromosome mapping using well known techniques for this purpose. The gene encoding the disclosed cDNA is believed to reside on chromosome 3. Accordingly, polynucleotides related to this invention are useful as a marker in linkage analysis for chromosome 3.

In certain preferred embodiments in this regard, the cDNA herein disclosed is used to clone genomic DNA of a OE-HABP gene. This can be accomplished using a variety of well known techniques and libraries, which generally are available commercially. The genomic DNA then is used for in situ chromosome mapping using well known techniques for this purpose. The gene encoding the disclosed cDNA is believed to reside on chromosome 15. Accordingly, polynucleotides related to this invention are useful as a marker in linkage analysis for chromosome 15.

In certain preferred embodiments in this regard, the cDNA herein disclosed is used to clone genomic DNA of a BM-HABP gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al, Human Chromosomes: A Manual Of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance In Man, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting. Thus, the present invention is not to be limited in scope by the specific embodiments described herein, which are intended as single illustrations of individual aspects of the invention. Indeed, various modifications of the invention, in addition to those shown and described herein will become apparent to those skilled in the art from the foregoing description and accompanying drawings. Such modifications are intended to fall within the scope of the appended claims.

The entire disclosure of all publications (including patents, patent applications, journal articles, laboratory manuals, books, or other documents) cited herein are hereby incorporated by reference.

Further, the Sequence Listing submitted herewith in paper and computer readable form is herein incorporated by reference in their entireties.

EXAMPLES

Example 1

Isolation of the WF-HABP, OE-HARP or BM-HABP cDNA Clone from the Deposited Sample The cDNA for WF-HABP, OE-HABP, or BM-HABP, OE-HABP, or BM-HABP is inserted into the EcoRI and XhoI multiple cloning site of pbluescript (Stratagene). pBluescript contains an ampicillin resistance gene and may be transformed into *E. coli* strain DH10B, available from Life Technologies. (See, for instance, Gruber, C. E., et al., *Focus* 15:59 (1993).)

Two approaches can be used to isolate WF-HABP, OE-HABP, or BM-HABP from the deposited sample. First, a specific polynucleotide of SEQ ID NO:1, 4, 7, or 10 with 30–40 nucleotides is synthesized using an Applied Biosystems DNA synthesizer according to the sequence reported. The oligonucleotide is labeled, for instance, with $^{32}$P-g-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host (such as XLM-1 Blue (Stratagene)) using techniques known to those of skill in the art, such as those provided by the vector supplier or in related publications or patents. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:1, 4, 7, or 10 (i.e., within the region of SEQ ID NO:1, 4, 7, or 10 bounded by the 5' NT and the 3' NT of the clone) are synthesized and used to amplify the WF-HABP, OE-HABP, or BM-HABP cDNA using the deposited cDNA plasmid as a template. The polymerase chain reaction is carried out under routine conditions, for instance, in 25 ul of reaction mixture with 0.5 ug of the above cDNA template. A convenient reaction mixture is 1.5–5 MM $MgCl_2$, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94 degree C. for 1 min; annealing at 55 degree C. for 1 min; elongation at 72 degree C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of the WF-HABP, OE-HABP, or BM-HABP gene which may not be present in the deposited clone. These methods include but are not limited to filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7):1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the WF-HABP, OE-HABP, or BM-HABP gene of interest is used to PCR amplify the 5' portion of the WF-HABP, OE-HABP, or BM-HABP full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the WF-HABP, OE-HABP, or BM-HABP gene.

Example 2

Isolation of Full-length WF-HABP, WF-HABP, OE-HABP, or BM-HABP Genomic Clones

A human genomic P1 library (Genomic Systems, Inc.) is screened by PCR using primers selected for the cDNA sequence corresponding to SEQ ID NO:1, 4, 7, or 10, according to the method described in Example 1. (See also, Sambrook.)

Example 3

Chromosomal Mapping of Full-length WF-HABP, WF-HABP OE-HABP, or BM-HABP

An oligonucleotide primer set is designed according to the sequence at the 5' end of SEQ ID NO:1, 4, 7, or 10. This primer preferably spans about 100 nucleotides. This primer set is then used in a polymerase chain reaction under the following set of conditions: 30 seconds, 95 degree C.; 1 minute, 56 degree C.; 1 minute, 70 degree C. This cycle is repeated 32 times followed by one 5 minute cycle at 70 degree C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid. For example, the gene encoding the disclosed full-length WF-HABP cDNA is believed to reside on chromosome 3. Accordingly, polynucleotides related to this invention are useful as a marker in linkage analysis for chromosome 3. Moreover, the gene encoding the disclosed OE-HABP cDNA is believed to reside on chromosome 15. Accordingly, polynucleotides related to this invention are useful as a marker in linkage analysis for chromosome 15.

Example 4

Bacterial Expression of Full-length WF-HABP, WF-HABP, OE-HABP or BM-HABP Protein Full-length WF-HABP, WF-HABP, OE-HABP, or BM-HABP polynucleotide encoding a full-length WF-HABP, WF-HABP, OE-HABP, or BM-HABP polypeptide of the invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen Inc, Chatsworth, Calif.). This plasmid vector encodes antibiotic resistance (Amp'), a bacterial origin of replication (ori), an IPTG-regulatable promoter/operator (P/O), a ribosome binding site (RBS), a 6-histidine tag (6-His), and restriction enzyme cloning sites.

Specifically, to clone the full-length WF-HABP polypeptide in a bacterial vector, the 5' primer has the sequence 5' GCAGCA<u>GGATCC</u>ATGATGGACCAGGGCTGCCGGG AAATCCTTAC 3' (SEQ ID NO:13) containing the underlined EcoRI restriction site followed by a number of nucleotides of the amino terminal coding sequence of the full-length WF-HABP sequence in SEQ ID NO:1. One of ordinary skill in the art would appreciate, of course, that the point in the protein coding sequence where the 5' primer begins may be varied to amplify a DNA segment encoding any desired portion of the complete full-length WF-HABP protein shorter or longer than the full-length form of the protein. The 3' primer has the sequence 5' GCAGCA<u>TCTAGA</u>TCACTTGACTGTGAGGATCCTCTGGGTGT CAG 3' (SEQ ID NO:14) containing the underlined XhoI restriction site followed by a number nucleotides complementary to the 3' end of the coding sequence of the full-length WF-HABP polynucleotide sequence of SEQ ID NO:1.

Specifically, to clone the WF-HABP polypeptide in a bacterial vector, the 5' primer has the sequence 5' GCAGC A<u>GGATCC</u>ATGGTCACTTGTACCTGCCTGCCCGACT ACGAG 3' (SEQ ID NO:15) containing the underlined EcoRI restriction site followed by a number of nucleotides of the amino terminal coding sequence of the WF-HABP sequence in SEQ ID NO:4. One of ordinary skill in the art would appreciate, of course, that the point in the protein coding sequence where the 5' primer begins may be varied to amplify a DNA segment encoding any desired portion of the complete WF-HABP protein shorter or longer than the full-length form of the protein. The 3' primer has the sequence 5' GCAGCA<u>TCTAGA</u>TCACTTGACTGT GAG-GATCCTCTGGGTGTCAGG 3' (SEQ ID NO:16) containing the underlined XhoI restriction site followed by a number nucleotides complementary to the 3' end of the coding sequence of the WF-HABP polynucleotide sequence of SEQ ID NO:4.

Specifically, to clone the OE-HABP polypeptide in a bacterial vector, the 5' primer has the sequence 5' GCAGCA<u>GGATCC</u>ATGGGCCTGTTGCTCCTGGTCCCATTGCT CCTGCTG 3' (SEQ ID NO:17) containing the underlined EcoRI restriction site followed by a number of nucleotides of the amino terminal coding sequence of the OE-HABP sequence in SEQ ID NO:7. One of ordinary skill in the art would appreciate, of course, that the point in the protein coding sequence where the 5' primer begins may be varied to amplify a DNA segment encoding any desired portion of the complete OE-HABP protein shorter or longer than the full-length form of the protein. The 3' primer has the sequence 5' GCAGCA<u>TCTAGA</u>ATTTTT CTTGGCAG GCTTCCCTTGCTTNTGTCAG 3' (SEQ ID NO:18) containing the underlined XhoI restriction site followed by a number nucleotides complementary to the 3' end of the coding sequence of the OE-HABP polynucleotide sequence of SEQ ID NO:7.

Specifically, to clone the BM-HABP polypeptide in a bacterial vector, the 5' primer has the sequence 5' GCAGCA <u>GGATCC</u>ATGACAGGCCCGGGCAAGCACAAGTGT GAGTG 3' (SEQ ID NO:19) containing the underlined EcoRI restriction site followed by a number of nucleotides of the amino terminal coding sequence of the BM-HABP sequence in SEQ ID NO:10. One of ordinary skill in the art would appreciate, of course, that the point in the protein coding sequence where the 5' primer begins may be varied to amplify a DNA segment encoding any desired portion of the complete BM-HABP protein shorter or longer than the full-length form of the protein. The 3' primer has the sequence 5' GCAGCA<u>TCTAGA</u>TCAAAATGNT GGAAGCCGATTGTTTTCCGGTTTATCC 3' (SEQ ID NO:20) containing the underlined XhoI restriction site followed by a number nucleotides complementary to the 3' end of the coding sequence of the BM-HABP polynucleotide sequence of SEQ ID NO:10.

The PQE-9 vector is digested with BamHI and XbaI and the amplified fragment is ligated into the pBluescript vector maintaining the reading frame initiated at the bacterial RBS. The ligation mixture is then used to transform the *E. coli* strain M15/rep4 (Qiagen, Inc.) which contains multiple copies of the plasmid pREP4, which expresses the lacI repressor and also confers kanamycin resistance (Kan'). Transformants are identified by their ability to grow on LB plates and ampicillin/kanamycin resistant colonies are selected. Plasmid DNA is isolated and confirmed by restriction analysis.

Clones containing the desired constructs are grown overnight. (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG (Isopropyl-B-D-thiogalacto pyranoside) is then added to a final concentration of 1 mM. IPTG induces by inactivating the lad repressor, clearing the P/O leading to increased gene expression.

Cells are grown for an extra 3 to 4 hours. Cells are then harvested by centrifugation (20 mins at 6000×g).

In addition to the above expression vector, the present invention further includes an expression vector comprising phage operator and promoter elements operatively linked to a full-length WF-HABP, WF-HABP, OE-HABP, or BM-HABP polynucleotide, called pHE4a. (ATCC Accession Number 209645, deposited Feb. 25, 1998.) This vector contains: 1) a neomycinphosphotransferase gene as a selection marker, 2) an *E. coli* origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pIwEa by restricting the vector with NdeI and KpnI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 5

Cloning and Expression of Full-length WF-HABP, WF-HABP, OE-HABP, or BM-HABP in a Baculovirus Expression System In this example, the plasmid shuttle vector pA2 is used to insert full-length WF-HABP, WF-HABP, OE-HABP, or BM-HABP polynucleotide into a baculovirus to express insert full-length WF-HABP, WF-HABP, OE-HABP, or BM-HABP. This expression vector contains the strong polyhedrin promoter of the *Autographa californica* nuclear polyhedrosis virus (AcMNPV) followed by convenient restriction sites such as BamHI, XbaI and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedringene. The inserted genes are flanked on both sides by viral sequences for cell-mediated homologous recombination with wild-type viral DNA to generate a viable virus that express the cloned full-length WF-HABP, WF-HABP, OE-HABP, or BM-HABP polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame. AUG as required. Such vectors are described, for instance, in Luckow et al., Virology 170:31–39 (1989).

Specifically, the full-length WF-HABP, WF-HABP, OE-HABP, or BM-HABP cDNA sequence contained in the deposited clone, including the AUG initiation codon and any naturally associated leader sequence, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

More specifically, the cDNA sequence encoding the full-length. WF-HABP protein including the AUG initiation codon and the sequence shown in SEQ ID NO:1, is amplified using PCR oligonucleotide primers corresponding to the 5' and 3' sequences of the gene. The 5' primer has the sequence 5' GCAGCA<u>AGATCT</u>GCCATCATGA TGGAC-CAGGGCTGCCGGGAAATCCTT AC 3' (SEQ ID NO: 21) containing the BglII restriction enzyme site, an efficient signal for initiation of translation in eukaryotic cells (Kozak, M., *J. Mol. Biol.* 196:947–950 (1987)), followed by a number of nucleotides of the sequence of the complete full-length WF-HABP protein shown in FIGS. 1A–P (SEQ ID NO:1), beginning with the AUG initiation codon. The 3' primer has the sequence 5' GCAGCA <u>TCTAGA</u>TCACTTGACTGTGAGGATCCTCTGGGTGT CAGG 3' (SEQ ID NO: 22) containing the XbaI restriction site followed by a number of nucleotides complementary to the 3' noncoding sequence in FIGS. 1A–P (SEQ ID NO:1).

More specifically, the cDNA sequence encoding the WF-HABP protein of the deposited clone, including the AUG initiation codon and the sequence shown in SEQ ID NO:4, is amplified using PCR oligonucleotide primers corresponding to the 5' and 3' sequences of the gene. The 5' primer has the sequence 5' GCAGCA <u>AGATCT</u>GCCATCATGGTCACTTGTACCTGCCTGCCC GACTACG AG 3' (SEQ ID NO: 23) containing the BglII restriction enzyme site, an efficient signal for initiation of translation in eukaryotic cells (Kozak, M., *J. Mol. Biol.* 196:947–950 (1987)), followed by a number of nucleotides of the sequence of the complete WF-HABP protein shown in FIGS. 2A–D (SEQ ID NO:4), beginning with the AUG initiation codon. The 3' primer has the sequence 5' GCAGCA<u>TCTAGA</u>TCACTTGACTGTGAGGATCC TCTGGGTGTCAGG 3' (SEQ ID NO: 24) containing the XbaI restriction site followed by a number of nucleotides complementary to the 3' noncoding sequence in FIGS. 2A–D (SEQ ID NO:4).

More specifically, the cDNA sequence encoding the OE-HABP protein of the deposited clone, including the AUG initiation codon and the sequence shown in SEQ ID NO:7, is amplified using PCR oligonucleotide primers corresponding to the 5' and 3' sequences of the gene. The 5' primer has the sequence 5' GCAGCA<u>AGATCT</u>GCCATCATGGGCCTGTTGCTCCTGGTCCC ATTGCTCC TGCTG 3' (SEQ ID NO: 25) containing the BglII restriction enzyme site an efficient signal for initiation of translation in eukaryotic cells (Kozak, M., *J. Mol. Biol.* 196:947–950 (1987)), followed by a number of nucleotides of the sequence of the complete OE-HABP protein shown in FIGS. 3A–C (SEQ ID NO:7), beginning with the AUG initiation codon. The 3' primer has the sequence 5' GCAGCA<u>TCTAGA</u>ATTTTTCTTGGCAGGCTTCCC TTGCTTNTGTCAG 3' (SEQ ID NO: 26) containing the XbaI restriction site followed by a number of nucleotides complementary to the 3' noncoding sequence in FIGS. 3A–C (SEQ ID NO:7).

More specifically, the cDNA sequence encoding the BM-HABP protein of the deposited clone, including the AUG initiation codon and the sequence shown in SEQ ID NO:10, is amplified using PCR oligonucleotide primers corresponding to the 5' and 3' sequences of the gene. The 5' primer has the sequence 5' GCAGCA<u>AGATCT</u>GCCATCATGACAGGCCCGGGCAAGCAC AAGTGTGAGTG 3' (SEQ ID NO: 27) containing the BglII restriction enzyme site, an efficient signal for initiation of translation in eukaryotic cells (Kozak, M., *J. Mol. Biol.* 196:947–950 (1987)), followed by a number of nucleotides of the sequence of the complete BM-HABP protein shown in FIGS. 4A–C (SEQ ID NO:10), beginning with the AUG initiation codon. The 3' primer has the sequence 5' GCAGCA<u>TCTAGA</u>TCAAAATGNTGGAAGCCGATT GTTTTCCGGTTTATCC 3' (SEQ ID NO: 28) containing the XbaI restriction site followed by a number of nucleotides complementary to the 3' noncoding sequence in FIGS. 4A–C (SEQ ID NO:10).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transfected with 1.0 ug of a commercially available linearized baculovirus DNA ("BaculoGoldô baculovirus DNA", Pharmingen, San Diego, Calif.), using the lipofection method described by Felgner et al., Proc. Natl. Acad. Sci. USA 84:7413–7417 (1987). One ug of BaculoGoldô virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of $^{35}$S-methionine and 5 uCi $^{35}$S-cysteine (available from Amersham) are added. The cells are further incubated for 16 hours and then are harvested by centrifugation. The proteins are analyzed by SDS-PAGE followed by autoradiography (if radiolabeled).

Microsequencing of the amino acid sequence of the amino terminus of purified protein may be used to determine the amino terminal sequence of the produced full-length WF-HABP, WF-HABP, OE-HABP, or BM-HABP polypeptide.

Example 6

Expression of Full-length WF-HABP, WF-HABP, OE-HABP or BM-HABP in Mammalian Cells Full-length WF-HABP, WF-HABP, OE-HABP, or BM-HABP polypeptide can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing.

Highly efficient transcription is achieved with the early and late promoters from SV40, the long terminal repeats (LTRS) from Retroviruses, e.g. RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC-37152), pSV2DHFR (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C-127 cells, Cos 1, Cos 7 and CVI, quail QC1–3 cells, mouse L cells and Chinese hamster ovary (CHO) cells.

Alternatively, full-length WF-HABP, WF-HABP, OE-HABP, or BM-HABP polypeptide can be expressed in stable cell lines containing the full-length WF-HABP, WF-HABP, OE-HABP, or BM-HABP polynucleotide integrated into a chromosome. The co-transfection with a selectable marker such as DHFR, gpt, neomycin, hygromycin allows the identification and isolation of the transfected cells.

The transfected full-length WF-HABP, WF-HABP, OE-HABP, or BM-HABP gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-DHFR (ATCC Accession No. 37146), the expression vectors pC4 (ATCC Accession No. 209646) and pC6 (ATCC Accession No. 209647) contain the strong promoter (LTR) of the Rous Sarcoma Virus (Cullen et al., Molecular and Cellular Biology, 438447 (March, 1985)) plus a fragment of the CMV-enhancer (Boshart et al., Cell 41:521–530 (1985).) Multiple cloning sites, e.g., with the restriction enzyme cleavage sites BamHI, XbaI and Asp718, facilitate the cloning of WF-HABP, OE-HABP, or BM-HABP. The vectors also contain the 3' intron, the polyadenylation and termination signal of the rat preproinsulin gene, and the mouse DHFR gene under control of the SV40 early promoter.

Specifically, the plasmid pC4 is digested with BamHI and XbaI and then dephosphorylated using calf intestinal phosphates by procedures known in the art. The vector is then isolated from a 1% agarose gel.

The cDNA sequence encoding the full-length WF-HABP protein in the deposited clone is amplified using PCR oligonucleotide primers corresponding to the 5' and 3' sequences of the gene. The 5' primer has the sequence 5' GCAGCA<u>GGATCC</u>GCCATCATGATGGACCAGGGC TGCCGGGAAATCCTTAC 3' (SEQ ID NO:29) containing the BamHI restriction enzyme site, an efficient signal for initiation of translation in eukaryotic cells (Kozak, M., J. Mol. Biol. 196:947–950 (1987)), followed by a number of nucleotides of the sequence of the complete full-length WF-HABP protein shown in FIGS. 1A–P (SEQ ID NO:1), beginning with the AUG initiation codon. The 3' primer has the sequence 5' GCAGCA<u>TCTAGA</u> TCACTFGACTGT-GAGGATCCTCTGGGTGTCAG 3' (SEQ ID NO: 30) containing the XbaI restriction site followed by a number of nucleotides complementary to the 3' noncoding sequence in FIGS. 1A–P (SEQ ID NO:1).

The cDNA sequence encoding the WF-HABP protein in the deposited clone is amplified using PCR oligonucleotide primers corresponding to the 5' and 3' sequences of the gene. The 5' primer has the sequence 5' GCAGCA <u>AGATCT</u>GCCATCATGATGGTCACTTGTACCTGCCT GCCCGACTACGAG 3' (SEQ ID NO: 31) containing the BamHI restriction enzyme site, an efficient signal for initiation of translation in eukaryotic cells (Kozak, M., J. Mol Biol. 196:947–950 (1987)), followed by a number of nucleotides of the sequence of the complete WF-HABP protein shown in FIGS. 2A–D (SEQ ID NO:4), beginning with the AUG initiation codon. The 3' primer has the sequence 5' GCAGCA<u>TCTAGA</u>TCACTTGACTGTGAGGATCCTC TGGGTGTCAGG 3' (SEQ ID NO: 32) containing the XbaI restriction site followed by a number of nucleotides complementary to the 3' noncoding sequence in FIGS. 2A–D (SEQ ID NO:4).

The cDNA sequence encoding the OE-HABP protein in the deposited clone is amplified using PCR oligonucleotide primers corresponding to the 5' and 3' sequences of the gene. The 5' primer has the sequence 5' GCAGCA <u>AGATCT</u>GCCATCATGGGCCTGTTGCTCCTGGTCCC ATTGCTCCTGCTG 3' (SEQ ID NO: 33) containing the BamHI restriction enzyme site, an efficient signal for initiation of translation in eukaryotic cells (Kozak, M., J. Mol. Biol. 196:947–950 (1987)), followed by a number of nucleotides of the sequence of the complete OE-HABP protein shown in FIGS. 3A–C (SEQ ID NO:7), beginning with the AUG initiation codon. The 3' primer has the sequence 5' GCAGCA<u>TCTAGA</u>ATTTTTCTTGGCAGGCTTCCC TTGCTTNTGTCAG 3' (SEQ ID NO: 34) containing the XbaI restriction site followed by a number of nucleotides complementary to the 3' noncoding sequence in FIGS. 3A–C (SEQ ID NO:7).

The cDNA sequence encoding the BM-HABP protein in the deposited clone is amplified using PCR oligonucleotide primers corresponding to the 5' and 3' sequences of the gene. The 5' primer has the sequence 5' GCAGCA <u>AGATCT</u>GCCATCATGACAGGCCCGGGCAAGCACAA GTGTGAGTG 3' (SEQ ID NO: 35) containing the BamHI restriction enzyme site, an efficient signal for initiation of translation in eukaryotic cells (Kozak, M., J. Mol. Biol. 196:947–950 (1987)), followed by a number of nucleotides of the sequence of the complete OE-HABP protein shown in FIGS. 4A–C (SEQ ID NO:10), beginning with the AUG initiation codon. The 3' primer has the sequence 5' GCAGCA<u>TCTAGA</u>TCAAAATGNTGGAAGCCGATTG TTTTCCGGTTTATCC 3' (SEQ ID NO: 36) containing the XbaI restriction site followed by a number of nucleotides complementary to the 3' noncoding sequence in FIGS. 4A–C (SEQ ID NO:10).

If a naturally occurring signal sequence is used to produce a secreted protein, the vector does not need a second signal peptide. Alternatively, if a naturally occurring signal sequence is not used, the vector can be modified to include a heterologous signal sequence in an effort to secrete the protein from the cell. (See, e.g., WO 96/34891.) The amplified fragment is then digested with the BglII and XbaI and purified on a 1% agarose gel using a commercially available kit ("Geneclean," BIO 101 Inc., La Jolla, Calif.). The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene is used for transfection. Five µg of the expression plasmid pC4 is cotransfected with 0.5 ug of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100–200 uM. Expression of full-length WF-HABP, WF-HABP, OE-HABP, or BM-HABP is analyzed, for instance, by SDS-PAGE and Western blot or by reversed phase HPLC analysis.

Example 7

Construction of N-Terminal and/or C-Terminal Deletion Mutants

The following general approach may be used to clone a N-terminal or C-terminal deletion full-length WF-HABP, WF-HABP, OE-HABP, or BM-HABP deletion mutant. Generally, two oligonucleotide primers of about 15–25 nucleotides are derived from the desired 5' and 3' positions of a polynucleotide of SEQ ID NO:1, 4, 7, or 10. The 5' and 3' positions of the primers are determined based on the desired full-length WF-HABP, WF-HABP, OE-HABP, or BM-HABP polynucleotide fragment. An initiation and stop codon are added to the 5' and 3' primers respectively, if necessary, to express the full-length WF-HABP, WF-HABP, OE-HABP, or BM-HABP polypeptide fragment encoded by the polynucleotide fragment. Preferred full-length WF-HABP, WF-HABP, OE-HABP, or BM-HABP polynucleotide fragments are those encoding the N-terminal and C-terminal deletion mutants disclosed above in the "Polynucleotide and Polypeptide Fragments" section of the Specification.

Additional nucleotides containing restriction sites to facilitate cloning of the full-length WF-HABP, WF-HABP, OE-HABP, or BM-HABP polynucleotide fragment in a desired vector may also be added to the 5' and 3' primer sequences. The full-length WF-HABP, WF-HABP, OE-HABP, or BM-HABP polynucleotide fragment is amplified from genomic DNA or from the deposited cDNA clone using the appropriate PCR oligonucleotide primers and conditions discussed herein or known in the art. The full-length WF-HABP, WF-HABP, OE-HABP, or BM-HABP polypeptide fragments encoded by the full-length WF-HABP, WF-HABP, OE-HABP, or BM-HABP polynucleotide fragments of the present invention may be expressed and purified in the same general manner as the full length polypeptides, although routine modifications may be necessary due to the differences in chemical and physical properties between a particular fragment and full length polypeptide.

As a means of exemplifying but not limiting the present invention, the polynucleotide encoding the full-length WF-HABP, WF-HABP, OE-HABP, or BM-HABP polypeptide fragment L-39 to N-889 is amplified and cloned as follows: A 5' primer is generated comprising a restriction enzyme site followed by an initiation codon in frame with the polynucleotide sequence encoding the N-terminal portion of the polypeptide fragment beginning with L-39. A complementary 3' primer is generated comprising a restriction enzyme site followed by a stop codon in frame with the polynucleotide sequence encoding C-terminal portion of the full-length WF-HABP, WF-HABP, OE-HABP, or BM-HABP polypeptide fragment ending with N-889.

The amplified polynucleotide fragment and the expression vector are digested with restriction enzymes which recognize the sites in the primers. The digested polynucleotides are then ligated together. The full-length WF-HABP, WF-HABP, OE-HABP, or BM-HABP polynucleotide fragment is inserted into the restricted expression vector, preferably in a manner which places the full-length WF-HABP, WF-HABP, OE-HABP, or BM-HABP polypeptide fragment coding region downstream from the promoter. The ligation mixture is transformed into competent *E. coli* cells using standard procedures and as described in the Examples herein. Plasmid DNA is isolated from resistant colonies and the identity of the cloned DNA confirmed by restriction analysis, PCR and DNA sequencing.

Example 8

Protein Fusions of WF-HABP, OE-HABP, or BM-HABP

Full-length WF-HABP, WF-HABP, OE-HABP, or BM-HABP polypeptides are preferably fused to other proteins. These fusion proteins can be used for a variety of applications. For example, fusion of full-length WF-HABP, WF-HABP, OE-HABP, or BM-HABP polypeptides to His-tag, HA-tag, protein A, IgG domains, and maltose binding protein facilitates purification. (See Example 5; see also EP A 394,827; Traunecker, et al., Nature 331:84–86 (1988).) Similarly, fusion to IgG-1, IgG-3, and albumin increases the halflife time in vivo. Nuclear localization signals fused to full-length WF-HABP, WF-HABP, OE-HABP, or BM-HABP polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a manalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and full-length WF-HABP, WF-HABP, OE-HABP, or BM-HABP polynucleotide, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.) Human IgG Fc Region:
GGGATCCGGAGCCCAAATCTTCTGA-
CAAAACTCACACATGCCCACCGTGC CCAGCAC-
CTGAATTCGAGGGTGCACCGTCAGTCT-
TCCTCTTCCCCCCAAAACCCA
AGGACACCCTCATGATCTCCCGGACTC-
CTGAGGTCACATGCGTGGTGGTGGACGT AAGC-
CACGAAGACCCTGAGGTCAAGT-
TCAACTGGTACGTGGACGGCGTGGAGGT
GCATAATGCCAAGACAAAGCCGCGGGAG-
GAGCAGTACAACAGCACGTACCGTG TGGT-
CAGCGTCCTCACCGTCCTGCACCAG-
GACTGGCTGAATGGCAAbGAGTACA
AGTGCAAGGTCTCCAACAAAGCCCTC-
CCAACCCCCATCGAGAAAACCATCTCCA AAGC-
CAAAGGGCAGCCCCGAGAACCACAGGTG-
TACACCCTGCCCCCATCCCGGG
ATGAGCTGACCAAGAACCAGGTCAGCCT-
GACCTGCCTGGTCAAAGGCTTCTATC CAAGCGA-
CATCGCCGTGGAGTGGGAGAG-
CAATGGGCAGCCGGAGAACAACTAC
AAGACCACGCCTCCCGTGCTGGACTC-
CGACGGCTCCTTCTTCCTCTACAGCAAGC TCAC-
CGTGGACAAGAGCAGGTGGCAGCAGGG-
GAACGTCTTCTCATGCTCCGTGA
TGCATGAGGCTCTGCACAACCACTA-
CACGCAGAAGAGCCTCTCCCTGTCTCCGGG
TAAATGAGTGCGACGGCCGCGACTCTAGAGGAT (SEQ ID NO:37)

Example 9

Production of an Antibody

The antibodies of the present invention can be prepared by a variety of methods. (See, Current Protocols, Chapter 2.) For example, cells expressing full-length WF-HABP, WF-HABP, OE-HABP, or BM-HABP is administered to an animal to induce the production of sera containing polyclonal antibodies. In a preferred method, a preparation of full-length WF-HABP, WF-HABP, OE-HABP, or BM-HABP protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoima technology. (Kohler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with full-length WF-HABP, WF-HABP, OE-HABP, or BM-HABP polypeptide or, more preferably, with a secreted full-length WF-HABP, WF-HABP, OE-HABP, or BM-HABP polypeptide-expressing cell. Such cells may be cultured in any suitable tissue culture medium; however, it is preferable to culture cells in Earle's modified Eagle's medium supplemented with 10% fetal bovine serum (inactivated at about 56 degree C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the full-length WF-HABP, WF-HABP, OE-HABP, or BM-HABP polypeptide.

Alternatively, additional antibodies capable of binding to full-length WF-HABP, WF-HABP, OE-HABP, or BM-HABP polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the full-length WF-HABP, WF-HABP, OE-HABP, or BM-HABP specific antibody can be blocked by full-length WF-HABP, WF-HABP, OE-HABP, or BM-HABP. Such antibodies comprise anti-idiotypic antibodies to the full-length WF-HABP, WF-HABP, OE-HABP, or BM-HABP specific antibody and can be used to immunize an animal to induce formation of further full-length WF-HABP, WF-HABP, OE-HABP, or BM-HABP specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted full-length WF-HABP, WF-HABP, OE-HABP, or BM-HABP protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., BioTechniques 4:214 (1986); Cabilly et al., U.S. Pat. No. 4,816,567; Taniguchi et al., EP 11496; Morrison et al., EP 173494; Neuberger et al., WO 8601533; Robinson et al., WO 8702671; Boulianne et al., Nature 312:643 (1984); Neuberger et al., Nature 314:268 (1985).)

Example 10

Method of Detecting Abnormal Levels of full-length WF-HABP, WF-HABP, OE-HABP, or BM-HABP in a Biological Sample Full-length WF-HABP, WF-HABP, OE-HABP, or BM-HABP polypeptides can be detected in a biological sample, and if an increased or decreased level of full-length WF-HABP, WF-HABP, OE-HABP, or BM-HABP is detected, this polypeptide is a marker for a particular phenotype. Methods of detection are numerous, and thus, it is understood that one skilled in the art can modify the following assay to fit their particular needs.

For example, antibody-sandwich ELISAs are used to detect full-length WF-HABP, WF-HABP, OE-HABP, or BM-HABP in a sample, preferably a biological sample. Wells of a microtiter plate are coated with specific antibodies to full-length WF-HABP, WF-HABP, OE-HABP, or BM-HABP at a final concentration of 0.2 to 10 ug/ml. The antibodies are either monoclonal or polyclonal and are produced by the method described in Example 11. The wells are blocked so that non-specific binding of full-length WF-HABP, WF-HABP, OE-HABP, or BM-HABP to the well is reduced.

The coated wells are then incubated for >2 hours at RT with a sample containing full-length WF-HABP, WF-HABP, OE-HABP, or BM-HABP. Preferably, serial dilutions of the sample should be used to validate results. The plates are then washed three times with deionized or distilled water to remove unbounded full-length WF-HABP, WF-HABP, OE-HABP, or BM-HABP.

Next, 50 ul of specific antibody-alkaline phosphatase conjugate, at a concentration of 25400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot full-length WF-HABP, WF-HABP, OE-HABP, or BM-HABP polypeptide concentration on the X-axis (log scale) and fluorescence or absorbance of the Y-axis (linear scale). Interpolate the concentration of the full-length WF-HABP, WF-HABP, OE-HABP, or BM-HABP in the sample using the standard curve.

Example 11

Formulating a Polypeptide

The full-length WF-HABP, WF-HABP, OE-HABP, or BM-HABP composition will be formulated and dosed in a fashion consistent with good medical practice, taking into account the clinical condition of the individual patient (especially the side effects of treatment with the full-length WF-HABP, WF-HABP, OE-HABP, or BM-HABP polypeptide alone), the site of delivery, the method of administration, the scheduling of administration, and other factors known to practitioners. The "effective amount" for purposes herein is thus determined by such considerations.

As a general proposition, the total pharmaceutically effective amount of full-length WF-HABP, WF-HABP, OE-HABP, or BM-HABP administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, full-length WF-HABP, WF-HABP, OE-HABP, or BM-HABP is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing full-length WF-HABP, WF-HABP, OE-HABP, or BM-HABP are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

Full-length WF-HABP, WF-HABP, OE-HABP, or BM-HABP is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547–556 (1983)), poly(2-hydroxyethyl methacrylate) (R. Langer et al., J. Biomed. Mater. Res. 15:167–277 (1981), and R. Langer, Chem. Tech. 12:98–105 (1982)), ethylene vinyl acetate (R. Langer et al.) or poly-D-(-)-3-hydroxybutyric acid (EP 133,988). Sustained-release compositions also include liposomally entrapped full-length WF-HABP, WF-HABP, OE-HABP, or BM-HABP polypeptides. Liposomes containing the full-length WF-HABP, WF-HABP, OE-HABP, or BM-HABP are prepared by methods known per se: DE 3,218,121; Epstein et al., Proc. Natl. Acad. Sci. USA 82:3688–3692 (1985); Hwang et al., Proc. Natl. Acad. Sci. USA 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, full-length WF-HABP, WF-HABP, OE-HABP, or BM-HABP is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting full-length WF-HABP, WF-HABP, OE-HABP, or BM-HABP uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

Full-length WF-HABP, WF-HABP, OE-HABP, or BM-HABP is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Full-length WF-HABP, WF-HABP, OE-HABP, or BM-HABP used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

Full-length WF-HABP, WF-HABP, OE-HABP, or BM-HABP polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous full-length WF-HABP, WF-HABP, OE-HABP, or BM-HABP polypeptide solution, and the resulting mixture is lyophilized. The infusion solution is prepared by reconstituting the lyophilized full-length WF-HABP, WF-HABP, OE-HABP, or BM-HABP polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, full-length WF-HABP, WF-HABP, OE-HABP, or BM-HABP may be employed in conjunction with other therapeutic compounds.

Example 12

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) full-length WF-HABP, WF-HABP, OE-HABP, or BM-HABP sequences into an animal to increase or decrease the expression of the full-length WF-HABP, WF-HABP, OE-HABP, or BM-HABP polypeptide. The full-length WF-HABP, WF-HABP, OE-HABP, or BM-HABP polynucleotide may be operatively linked to a promoter or any other genetic elements necessary for the expression of the full-length WF-HABP, WF-HABP, OE-HABP, or BM-HABP polypeptide by the target tissue. Such gene therapy and delivery techniques and methods are known in the art, see, for example, WO90/11092, WO98/11779; U.S. Pat. NO. 5693622, 5705151, 5580859; Tabata H. et al. (1997) Cardiovasc. Res. 35(3):470479, Chao J et al. (1997) Pharmacol. Res. 35(6):517–522, Wolff J. A. (1997) Neuromuscul. Disord. 7(5):314–318, Schwartz B. et al. (1996) Gene Ther. 3(5):405–411, Tsurumi Y. et al. (1996) Circulation 94(12):3281–3290 (incorporated herein by reference).

The full-length WF-HABP, WF-HABP, OE-HABP, or BM-HABP polynucleotide constructs may be delivered by any method that delivers injectable materials to the cells of an animal, such as, injection into the interstitial space of tissues (heart, muscle, skin, lung, liver, intestine and the like). The full-length WF-HABP, WF-HABP, OE-HABP, or BM-HABP polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the full-length WF-HABP, WF-HABP, OE-HABP, or BM-HABP polynucleotides may also be delivered in liposome formulations (such as those taught in Felgner P. L. et al. (1995) Ann. NY Acad. Sci. 772:126–139 and Abdallah B. et al. (1995) Biol. Cell 85(1):1–7) which can be prepared by methods well known to those skilled in the art.

The full-length WF-HABP, WF-HABP, OE-HABP, or BM-HABP polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The full-length WF-HABP, WF-HABP, OE-HABP, or BM-HABP polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked full-length WF-HABP, WF-HABP, OE-HABP, or BM-HABP polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked full-length WF-HABP, WF-HABP, OE-HABP, or BM-HABP polynucleotide constructs can be delivered to arteries during angioplasty by the catheter used in the procedure.

The dose response effects of injected full-length WF-HABP, WF-HABP, OE-HABP, or BM-HABP polynucleotide in muscle in vivo is determined as follows. Suitable full-length WF-HABP, WF-HABP, OE-HABP, or BM-HABP template DNA for production of mRNA coding for full-length WF-HABP, WF-HABP, OE-HABP, or BM-HABP polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The full-length WF-HABP, WF-HABP, OE-HABP, or BM-HABP template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 urn cross-section of the individual quadriceps muscles is histochemically stained for full-length WF-HABP, WF-HABP, OE-HABP, or BM-HABP protein expression. A time course for full-length WF-HABP, WF-HABP, OE-HABP, or BM-HABP protein expression may be done in a similar fashion except that quadriceps from different mice are harvested at different times. Persistence of full-length WF-HABP, WF-HABP, OE-HABP, or BM-HABP DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using full-length WF-HABP, WF-HABP, OE-HABP, or BM-HABP naked DNA.

Example 13

WF-HABP, OE-HABP, and BM-HABP Expression in Human Tissues and Cells

As a first step toward characterizing the expression pattern of the gene encoding the novel WF-HABP protein, the WF-HABP mRNA expression levels in various human tissues and cells was examined by Northern blotting analysis. WF-HABP mRNA was detectable in all the human tissues examined with very low levels detected in the brain and kidney. The highest level of expression was observed in the heart, placenta and lung, with lower levels found in the liver, pancreas, and skeletal muscle. Four major transcripts of 9.5, 4.5, 3.0 and 2.4 Kb were detected. The 9.5 Kb band appeared to be the predominant mRNA and was especially prominent in the placenta and the heart. OE-HABP mRNA was detected in lung, placenta, and heart, with highest expression observed in the lung as a 2.2 Kb transcript. BM-HABP mRNA was apparent only in the liver and appeared as a smear between 5 and 2 Kb. The expression of BM-HABP was also analyzed in human fetal brain, lung, liver and kidney and found that a distinct 9.5 Kb mRNA was expressed at an elevated level in fetal liver with a low level of signal also observed the lung.

The expression pattern of WF-HABP, OE-HABP, and BM-HABP was also examined in human smooth muscle cells (SMCs), human fetal lung fibroblasts (ETL), human umbilical vein endothelial cells (HUVECs), as well as in HL-60 and U937 cells. WF-HABP mRNA expression was not detected in either uninduced or TPA-stimulated HL-60 cells. A minor 2.4 Kb band was detected in all of the other cell types examined. Induction of U937 cells with TPA resulted in a slight decrease of the signal. However, it is noteworthy that WF-HABP mRNAs of 9.5, 4.5 and 3.0 Kb were expressed exclusively by HUVECs.

The 2.2 Kb OE-HABP transcript identified supra was expressed by both HUVECs and SMCs, but not by ETLs, HL60 or U937 cells. Interestingly, U937 cells responded to stimulation with TPA by expressing a major new 4.3 Kb transcript and minor bands of 3.8, and 3 Kb. There was no detectable mRNA expression of BM-HABP in any of the above cell lines.

Given that endothelial cells express a unique set of WF-HABP mRNA transcripts the expression of this gene was analyzed in HUVECs in greater detail. We first examined whether short-term stimulation of endothelial cells with FGF-1, EL-1 and PNIA could alter mRNA expression of WF-HABP and found that HUVECs treated with these factors for up to four hours did not substantially alter the expression of this gene. However, growth-arrested HUVECs were consistently observed to express a high level of WF-HABP mRNA that decreased dramatically when the cells were induced to proliferate with FGF-1.

Conditions for culturing and preparing cells for the above Northern blotting experiments are described infra. BL-60 (human peripheral blood promyelocytic leukemia, ATCC CCL 240) and U937 (human histocytic lymphoma, ATCC CRL 1593) were obtained from the American Type Culture Collection (Rockville, Md.). Cells were grown in RPMI 1640, supplemented with 10% Fetal Bovine Serum (FBS). HFLI (human diploid fetal lung fibroblasts, ATCC CCL 153) were obtained from American Type Culture Collection (Rockville, Md.), and SMC (human saphenous vein smooth muscle Cells)7 were kindly provided by Dr. Peter Libby (Tufts University School of Medicine, Boston, Mass.). Cells were grown in DMEM and M-199 respectively, complemented with 10% FBS. HUVECs (human umbilical vein endothelial cells), strain H101, were a generous gift from Dr. Susan Garfinkel (Dept. of Molecular Biology, ARC, Rockville, NED). Cells were grown in M-199 containing 10% FBS, supplemented with FGFI/Heparin. BL-60 and U937 cells were grown under conditions as known by the skilled artisan for 2 days and then induced with 0.15 ug/ml of 12-O-tetradecanoylphorbol-13-acetate (TPA) for 72 hr to elicit a differentiation response. HUVECs were growth arrested for 48 hr in complete media with 10% serum without FGF-1/Heparin.

Conditions for Northern Blot hydridization are described infra. Total RNA were isolated from cultured cells by selective retention on a silica gel-based membrane with RNeasy Mini Kit (Qiagen Inc, Valencia, Calif.). Briefly, cells were lysed and homogenized under highly denaturing conditions in the presence of guanidinium isothiocyanate. Total RNA was separated from contaminating proteins and DNA by centrifugation and subsequently eluted from the column with water. Five micrograms of purified total RNA per lane were size-fractionated on a 1% agarose gel containing, 0.5M formaldehyde, transferred to Zetabind nylon membrane (AMF/Cuno, Inc., Meriden, Conn.) by electroblotting, and UV crosslinking. Immobilized RNA was hybridized at 55° C. overnight with 1 to $5 \times 10^6$ cpm/ml of a-$^{32}$P dCTP-labeled cDNA probes prepared by random primed DNA labeling (Boehringer Mannheim GmbH, Germany). Following hybridization, membranes were washed with increasing stringency at 55° C., 2×15 min in each of the following buffers. Wash Buffer A: 0.5% BSA, 5% SDS, 40 mM $NaH_2PO_4$, 1 mM EDTA; Wash Buffer B: 1% SDS, 40 mM $NaH_2PO_4$, 1 mM EDTA; 0.2×SSPE. Blots were air dried and exposed to Kodak X-Omat AR film (Eastman Kodak Company, Rochester, N.Y.) at −80° C. 800 bp human glyceraldehyde-3-phosphate dehydrogenase (GAPDH) cDNA was used as a control probe.

Blots, containing mRNA obtained from human heart, brain, placenta, lung, liver, skeletal muscle, kidney and pancreas, were aquired from Clontech (Palo Alto, Calif.). These blots were probed for the WF-HABP, OE-HABP, and BM-HABP message and also hybridized with GAPDH cDNA control probe.

Example 14

WF-HABP Expression In Vivo

Northern analysis revealed a high level of WF-HABP mRNA expression in vessel-rich human tissues including the heart and the placenta. Furthermore, in vitro analysis (Example 13, supra) revealed predominant expression of this message in cultured endothelial cells. Therefore, in situ hybridization was performed in the placenta to identify the cells that expressed WF-HABP mRNA. Hybridization signal was detected in cells lining fetal blood vessels and capillaries found inside terminal villi. Syncytial trophoblasts, composing the external layer of the terminal villi; were always negative. Using immunohistochemistry, this pattern was identical in sections stained for the endothelial specific antigen (CD31), suggesting that the major cell type in the placenta expressing WF-HABP are endothelial cells. We also examined the brain and found it expressed a very low level of WF-HABP mRNA when probed by Northern blotting. In situ hybridization generally confirmed a lack of WF-HABP positive cells in the brain with the exception of weak signals around small blood vessels and capillaries. CD31 staining revealed a similar, although more prominent, expression pattern.

The expression pattern of WF-HABP was examined in other vascular tissues including human aorta and atherectomy specimens. Positive RNA signal was apparently observed only in endothelial cells lining microvessels in the adventitia and in the medial layer of the aorta. No signal was detected in smooth muscle cells of the medial layer. Specificity was confirmed by the absence of the signal when hybridization was performed without probe or with a corresponding sense probe. We did observe non-specific staining of collagen fibers in the adventitia with both the sense and antisense probes, likely due to the binding of anti-digoxigenin antibody to collagen. To confirm that cells expressing WF-HABP mRNA were indeed endothelial cells, immunohistochemical analysis on adjacent sections of the same specimen was performed using an antibody that specifically recognizes CD31. The signal for CD31 antigen was found to be distributed in an analogous manner to that for WF-HABP.

The expression of WF-HABP mRNA in human atherosclerotic lesions was examined. A strong WF-HABP-specific signal was found in vessel-abundant regions of the specimens. Again, this signal co-localized with the distribution of EC-specific CD31 antigen. No signal was detected in SMC or in macrophage rich regions. However, sporadic appearance of positive stellate cells was observed in otherwise negative myxomatous tissue. In can be concluded from these studies that WF-HABP mRNA is expressed predominantly by endothelial cells in various tissues and its expression is especially prominent in diseased blood vessels.

The conditions for In situ hybridization are described infra. Non-radioactive In Situ hybridization was performed on paraffin-embedded human tissues and atherectomy specimens. WF-HABP mRNA probes (sense and antisense) were labeled with digoxigenin-11-uridine-5'-triphosphate (Boehringer Mannheim GmbH, Germany) via in vitro transcription (Dig RNA labeling kit, Boehringer Mannheim GmbH, Germany).

The tissues were cut into serial 5-um thick sections onto silanized double-positive glass slides (Fisher Scientific, Pittsburgh, Pa.). Tissue sections were deparaffinized for 60 min at 60° C., washed extensively in xylene and rehydrated in decreasing ethanol series. Endogenous peroxidase was quenched in PBS containing 3% $H_2O_2$ for 20 min. To facilitate probe penetration, tissue sections were deproteinized in 2mg/ml pepsin solution in 0.2N HCl (Nuovo). Sections were equilibrated, prehybridized and hybridized according to the SureSite II System Manual (Novagen, Inc., Madison, Wis.). Hybridization was carried out for 18 hrs in a humid chamber at 50° C.; probe concentration was 1 ng/ul.

After hybridization, sections were subjected to successively stringent washes as follows: 2×SSC 30 min at 50° C.; 2×SSC containing 0.02 ug/ml RNase A, 30 min at 37° C.; 2×SSC containing 50% foramide, 30 min. at 50° C.; 2 washes with 1×SSC containing 0.067% sodium paraphosphate, 30 min each at 50° C.

Signal amplification was carried out according to Tyranide Signal Amplification for chromogenic Situ hybridization (TSA-Indirect) protocol (NEN Life Science Products, Boston, Mass.). TNT wash buffer contained 0.05% TWEEN-20 in PBS, and TNB blocking buffer was comprised of 0.5% blocking reagent in PBS. Anti-digoxigenin antibody (sheep Fab fragments conjugated with horseradish peroxidase (POD), Boehringer Mannheim GmbH, Germany) was diluted 1–50 in TNB. Signal was visualized with DAB (diaminoberzidine) substrate kit (Vector Laboratories, Inc., Burlingame, Calif.). Myer's Hematoxylin was used to counterstain the sections.

To confirm reliability of the method, protamine antisense probe was hybridized to sections of mouse testes as a positive control in each experiment. Also, sense WF-HABP probe, as well as hybridization without any probe, were used as negative controls in each experiment.

Conditions for immunohistochemistry are described infra. Paraffin-embedded serial Sun-thin sections of the human tissues analyzed by Northern blotting and several atherectomy specimens (described in Example 13) were used. Endogenous peroxidase activity was quenched in methanol with 0.3% $H_2O_2$. The sections were reacted for 1 hr at room temperature with a monoclonal mouse anti-human CD31 antibody specific for endothelial cells (DAKO, Denmark). Antibodies were diluted 1–50 in PBS containing 10% normal horse serum and 1% bovine serum albumin. Primary antibody was detected by the indirect avidin-biotin-horseradish peroxidase method (ABC elite kit, Vector Laboratories, Inc., Burlingame, Calif.). Normal mouse IgG (1:1000) were used as negative controls. Myer's Hematoxylin was used to counterstain the sections.

Example 15

Identification and Characterization of Three Novel Hyaluronan-binding Protein Encoding Genes: Endothelial Cell-specific Expression of One Gene It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference.

Moreover, the sequence submitted herewith in paper and computer readable form are herein incorporated by reference in their entireties.

What is claimed is:

1. An isolated protein comprising amino acid residues 1 to 353 of SEQ ID NO:11.

2. The protein of claim 1 which comprises a heterologous polypeptide sequence.

3. A composition comprising the protein of claim 1 and a pharmaceutically acceptable carrier.

4. An isolated protein produced by the method comprising:
   (a) expressing the protein of claim 1 by a cell; and
   (b) recovering said protein.

5. An isolated protein comprising the amino acid sequence of the full-length polypeptide encoded by the cDNA contained in ATCC Deposit No. 203502.

6. The protein of claim 5 which comprises a heterologous polypeptide sequence.

7. A composition comprising the protein of claim 5 and a pharmaceutically acceptable carrier.

8. An isolated protein produced by the method comprising:
   (a) expressing the protein of claim 5 by a cell; and
   (b) recovering said protein.

9. An isolated protein comprising a first polypeptide at least 90% identical to a second polypeptide consisting of amino acid residues 1 to 353 of SEQ ID NO:11, wherein said first polypeptide binds hyaluronan.

10. The isolated protein of claim 9 wherein said first polypeptide is at least 95% identical to said second polypeptide.

11. The protein of claim 9 which comprises a heterologous polypeptide sequence.

12. A composition comprising the protein of claim 9 and a pharmaceutically acceptable carrier.

13. An isolated protein produced by the method comprising:
   (a) expressing the protein of claim 9 by a cell; and
   (b) recovering said protein.

14. An isolated protein comprising a first polypeptide at least 90% identical to a second polypeptide consisting of the amino acid sequence of the full-length polypeptide encoded by the cDNA contained in ATCC Deposit No. 203502, wherein said first polypeptide binds hyaluronan.

15. The isolated protein of claim 14 wherein said first polypeptide is at least 95% identical to said second polypeptide.

16. The protein of claim 14 which comprises a heterologous polypeptide sequence.

17. A composition comprising the protein of claim 14 and a pharmaceutically acceptable carrier.

18. An isolated protein produced by the method comprising:
   (a) expressing the protein of claim 14 by a cell; and
   (b) recovering said protein.

19. An isolated protein consisting of at least 10 contiguous amino acid residues of amino acid residues 1 to 353 of SEQ ID NO:11.

20. The isolated protein of claim 19 which consists of at least 20 contiguous amino acid residues of amino acid residues 1 to 353 of SEQ ID NO:11.

21. The isolated protein of claim 19 which consists of at least 30 contiguous amino acid residues of amino acid residues 1 to of SEQ ID NO:11.

22. The isolated protein of claim 19 which consists of at least 50 contiguous amino acid residues of amino acid residues 1 to 353 of SEQ ID NO:11.

23. The protein of claim 19 which comprises a heterologous polypeptide sequence.

24. A composition comprising the protein of claim 19 and a pharmaceutically acceptable carrier.

25. An isolated protein produced by the method comprising:
   (a) expressing the protein of claim 19 by a cell; and
   (b) recovering said protein.

26. An isolated protein consisting of at least 10 contiguous amino acid residues of the full-length polypeptide encoded by the cDNA contained in ATCC Deposit No. 203502.

27. The isolated protein of claim 26 which consists of at least 20 contiguous amino acid residues of the full-length polypeptide encoded by the cDNA contained in ATCC Deposit No. 203502.

28. The isolated protein of claim 26 which consists of at least 30 contiguous amino acid residues of the full-length polypeptide encoded by the cDNA contained in ATCC Deposit No. 203502.

29. The isolated protein of claim 26 which consists of at least 50 contiguous amino acid residues of the full-length polypeptide encoded by the cDNA contained in ATCC Deposit No. 203502.

30. The protein of claim 26 which comprises a heterologous polypeptide sequence.

31. A composition comprising the protein of claim 26 and pharmaceutically acceptable carrier.

32. An isolated protein produced by the method comprising:
   (a) expressing the protein of claim 26 by a cell; and
   (b) recovering said protein.

33. An isolated polypeptide consisting of a contiguous amino acid sequence selected from the group consisting of:
(a) amino acids 7 to 15 of SEQ ID NO:11;
(b) amino acids 22 to 30 of SEQ ID NO:11;
(c) amino acids 31 to 39 of SEQ ID NO:11;
(d) amino acids 61 to 69 of SEQ ID NO:11;
(e) amino acids 70 to 78 of SEQ ID NO:11;
(f) amino acids 93 to 101 of SEQ ID NO:11;
(g) amino acids 107 to 115 of SEQ ID NO:11;
(a) amino acids 7 to 15 of SEQ ID NO:11;
(b) amino acids 22 to 30 of SEQ ID NO:11;
(c) amino acids 31 to 39 of SEQ ID NO:11;
(d) amino acids 61 to 69 of SEQ ID NO:11;
(e) amino acids 70 to 78 of SEQ ID NO:11;
(f) amino acids 93 to 101 of SEQ ID NO:11;
(g) amino acids 107 to 115 of SEQ ID NO:11;
(h) amino acids 120 to 128 of SEQ ID NO:11;
(i) amino acids 135 to 143 of SEQ ID NO:11;
(j) amino acids 148 to 156 of SEQ ID NO:11;
(k) amino acids 193 to 201 of SEQ ID NO:11; and
(l) amino acids 229 to 237 of SEQ ID NO:11.

34. The polypeptide of claim 33 wherein said amino acid sequence is (a).

35. The polypeptide of claim 33 wherein said amino acid sequence is (b).

36. The polypeptide of claim 33 wherein said amino acid sequence is (c).

37. The polypeptide of claim 33 wherein said amino acid sequence is (d).

38. The polypeptide of claim 33 wherein said amino acid sequence is (e).

39. The polypeptide of claim 33 wherein said amino acid sequence is (f).

40. The polypeptide of claim 33 wherein said amino acid sequence is (g).

41. The polypeptide of claim 33 wherein said amino acid sequence is (h).

42. The polypeptide of claim 33 wherein said amino acid sequence is (i).

43. The polypeptide of claim 33 wherein said amino acid sequence is (j).

44. The polypeptide of claim 33 wherein said amino acid sequence is (k).

45. The polypeptide of claim 33 wherein said amino acid sequence is (l).

46. The polypeptide of claim 33 polypeptide is fused to a heterologous polypeptide sequence.

47. A composition comprising the polypeptide of claim 33 and a pharmaceutically acceptable carrier.

48. An isolated polypeptide produced by the method comprising:
(a) expressing the polypeptide of claim 33 by a cell; and
(b) recovering said polypeptide.

49. An isolated polypeptide consisting of a contiguous amino acid sequence selected from the group consisting of:
(a) amino acids 51 to 100 of SEQ ID NO:11;
(b) amino acids 105 to 150 of SEQ ID NO:11;
(c) amino acids 151 to 200 of SEQ ID NO:11; and
(d) amino acids 121 to 215 of SEQ ID NO:11.

50. The polypeptide of claim 49 wherein said amino acid sequence is (a).

51. The polypeptide of claim 49 wherein said amino acid sequence is (b).

52. The polypeptide of claim 49 wherein said amino acid sequence is (c).

53. The polypeptide of claim 49 wherein said amino acid sequence is (d).

54. The polypeptide of claim 49 wherein said polypeptide is fused to a heterologous polypeptide sequence.

55. A composition comprising the polypeptide of claim 49 and a pharmaceutically acceptable carrier.

56. An isolated polypeptide produced by the method comprising:
(a) expressing the polypeptide of claim 49 by a cell; and
(b) recovering said polypeptide.

* * * * *

UNITED STATES PATENT AND TRADEMARK OFFICE
CERTIFICATE OF CORRECTION

PATENT NO. : 6,872,546 B1
DATED : March 29, 2005
INVENTOR(S) : Hastings et al.

It is certified that error appears in the above-identified patent and that said Letters Patent is hereby corrected as shown below:

<u>Title page,</u>
Item [56], References Cited, OTHER PUBLICATIONS, fourth reference should read:
-- Lee et al., "A novel secretory Tumor Necrosis Factor-inducible Protein (TSG-6) is a member of the family of Hyaluronate Binding Proteins, closely related to the Adhesion Receptor CD44" Jan. 1992, vol. 116, No. 2, pp. 545-557.* --.

<u>Column 315,</u>
Starting at line 36, before claims, insert the attached sequence listing.

<u>Column 317,</u>
Lines 11-19, delete the second subsets (a)-(g).

<u>Column 318,</u>
Line 9, after "claim 33," insert -- wherein said --.

Signed and Sealed this

Fourth Day of April, 2006

JON W. DUDAS
*Director of the United States Patent and Trademark Office*

SEQUENCE LISTING

<160> NUMBER OF SEQ ID NOS: 37

<210> 1
<211> 6761
<212> DNA
<213> Homo sapiens

<220>
<221> CDS
<222> (170)..(6643)

<220>
<221> misc_feature
<222> (6342)
<223> n equals a, t, g or c

<220>
<221> misc_feature
<222> (6496)
<223> n equals a, t, g or c

<220>
<221> misc_feature
<222> (6529)
<223> n equals a, t, g or c

<220>
<221> misc_feature
<222> (6535)
<223> n equals a, t, g or c

<220>
<221> misc_feature
<222> (6537)
<223> n equals a, t, g or c

<220>
<221> misc_feature
<222> (6688)
<223> n equals a, t, g or c

<220>
<221> misc_feature
<222> (6724)
<223> n equals a, t, g or c

<220>
<221> misc_feature
<222> (6748)
<223> n equals a, t, g or c

```
<220>
<221> misc_feature
<222> (6749)
<223> n equals a, t, g or c

<220>
<221> misc_feature
<222> (6750)
<223> n equals a, t, g or c

<220>
<221> misc_feature
<222> (6753)
<223> n equals a, t, g or c

<400> 1
ctgcgaccgg tctgccactt gccaggtgac cgctgatggg aagaccagct gtgtgtgcag    60
ggaaagcgag gtgggggatg ggcgtgcctg ctacggacac ctgctccacg aggtgcagaa   120
ggccacgcag acaggccggg tgttcctgca gctgagggtc gccgtggcc atg atg gac   178
                                                      Met Met Asp
                                                        1 cag ggc tgc cgg gaa atc ctt acc aca gcg ggc cct ttc acc gtg ctg    226
Gln Gly Cys Arg Glu Ile Leu Thr Thr Ala Gly Pro Phe Thr Val Leu
    5               10                  15 gtg cca tcc gtc tcc tcc ttc tcc tcc agg acc atg aat gca tcc ctt    274
Val Pro Ser Val Ser Ser Phe Ser Ser Arg Thr Met Asn Ala Ser Leu
 20              25                  30                  35 gcc cag cag ctc tgt aga cag cac atc atc gca ggg cag cac atc ctg    322
Ala Gln Gln Leu Cys Arg Gln His Ile Ile Ala Gly Gln His Ile Leu
             40                  45                  50 gag gac aca agg acc caa caa aca cga agg tgg tgg acg ctg gcc ggg    370
Glu Asp Thr Arg Thr Gln Gln Thr Arg Arg Trp Trp Thr Leu Ala Gly
             55                  60                  65 cag gag atc acc gtc acc ttt aac caa ttc acg aaa tac tcc tac aag    418
Gln Glu Ile Thr Val Thr Phe Asn Gln Phe Thr Lys Tyr Ser Tyr Lys
             70                  75                  80
```

```
tac aaa gac cag ccc cag cag acg ttc aac atc tac aag gcc aac aac     466
Tyr Lys Asp Gln Pro Gln Gln Thr Phe Asn Ile Tyr Lys Ala Asn Asn
    85                  90                  95 ata gca gct aat ggc gtc ttc cac gtg gtc act ggc ctg cgg tgg cag     514
Ile Ala Ala Asn Gly Val Phe His Val Val Thr Gly Leu Arg Trp Gln
100             105                 110                 115 gcc ccc tct ggg acc cct ggg gat ccc aag aga act atc gga cag atc     562
Ala Pro Ser Gly Thr Pro Gly Asp Pro Lys Arg Thr Ile Gly Gln Ile
                120                 125                 130 ctc gcc tct acc gag gcc ttc agc cgc ttt gaa acc atc ctg gag aac     610
Leu Ala Ser Thr Glu Ala Phe Ser Arg Phe Glu Thr Ile Leu Glu Asn
                135                 140                 145 tgt ggg ctg ccc tcc atc ctg gac gga cct ggg ccc ttc aca gtc ttt     658
Cys Gly Leu Pro Ser Ile Leu Asp Gly Pro Gly Pro Phe Thr Val Phe
            150                 155                 160 gcc cca agc aat gag gct gtg gac agc ttg cgt gac ggc cgc ctg atc     706
Ala Pro Ser Asn Glu Ala Val Asp Ser Leu Arg Asp Gly Arg Leu Ile
            165                 170                 175 tac ctc ttc aca gcg ggt ctc tct aaa ctg cag gag ttg gtg cgg tac     754
Tyr Leu Phe Thr Ala Gly Leu Ser Lys Leu Gln Glu Leu Val Arg Tyr
180                 185                 190                 195 cac atc tac aac cac ggc cag ctg acc gtt gag aag ctc atc tcc aag     802
His Ile Tyr Asn His Gly Gln Leu Thr Val Glu Lys Leu Ile Ser Lys
                200                 205                 210 ggt cgg atc ctc acc atg gcg aac cag gtc ctg gct gtg aac att tct     850
Gly Arg Ile Leu Thr Met Ala Asn Gln Val Leu Ala Val Asn Ile Ser
                215                 220                 225 gag gag ggg cgc atc ctg ctg gga ccc gag ggg gtc ccg ctg cag agg     898
Glu Glu Gly Arg Ile Leu Leu Gly Pro Glu Gly Val Pro Leu Gln Arg
            230                 235                 240 gta gac gtg atg gcc gcc aat ggc gtg atc cac atg ctg gac ggc atc     946
Val Asp Val Met Ala Ala Asn Gly Val Ile His Met Leu Asp Gly Ile
            245                 250                 255
```

```
ctg ctg ccc ccg acc atc ctg ccc atc ctg ccc aag cac tgc agc gag    994
Leu Leu Pro Pro Thr Ile Leu Pro Ile Leu Pro Lys His Cys Ser Glu
260             265             270             275 gag cag cac aag att gtg gcg ggc tcc tgt gtg gac tgc caa gcc ctg   1042
Glu Gln His Lys Ile Val Ala Gly Ser Cys Val Asp Cys Gln Ala Leu
            280             285             290 aac acc agc acg tgt ccc ccc aac agt gtg aag ctg gac atc ttc ccc   1090
Asn Thr Ser Thr Cys Pro Pro Asn Ser Val Lys Leu Asp Ile Phe Pro
        295             300             305 aag gag tgt gtc tac atc cat gac cca acg ggg ctc aat gtg cta aag   1138
Lys Glu Cys Val Tyr Ile His Asp Pro Thr Gly Leu Asn Val Leu Lys
    310             315             320 aag ggc tgt gcc agc tac tgc aac caa acc atc atg gaa caa ggc tgc   1186
Lys Gly Cys Ala Ser Tyr Cys Asn Gln Thr Ile Met Glu Gln Gly Cys
    325             330             335 tgc aaa ggt ttt ttc ggg cct gac tgc acg cag tgt cct ggg ggc ttc   1234
Cys Lys Gly Phe Phe Gly Pro Asp Cys Thr Gln Cys Pro Gly Gly Phe
340             345             350             355 tcc aac ccc tgc tat ggc aaa ggc aat tgc agt gat ggg atc cag ggc   1282
Ser Asn Pro Cys Tyr Gly Lys Gly Asn Cys Ser Asp Gly Ile Gln Gly
            360             365             370 aat ggg gcc tgc ctc tgc ttc cca gac tac aag ggc atc gcc tgc cac   1330
Asn Gly Ala Cys Leu Cys Phe Pro Asp Tyr Lys Gly Ile Ala Cys His
        375             380             385 atc tgc tcg aac cca aac aag cat gga gag caa tgc cag gaa gac tgc   1378
Ile Cys Ser Asn Pro Asn Lys His Gly Glu Gln Cys Gln Glu Asp Cys
    390             395             400 ggc tgt gtc cat ggt ctc tgc gac aac cgc cca ggc agt ggg ggg gtg   1426
Gly Cys Val His Gly Leu Cys Asp Asn Arg Pro Gly Ser Gly Gly Val
    405             410             415
```

```
tgc cag cag ggc acg tgt gcc cct ggc ttc agt ggc cgg ttc tgc aac    1474
Cys Gln Gln Gly Thr Cys Ala Pro Gly Phe Ser Gly Arg Phe Cys Asn
420             425             430             435 gag tcc atg ggg gac tgt ggg ccc aca ggg ctg gcc cag cac tgc cac    1522
Glu Ser Met Gly Asp Cys Gly Pro Thr Gly Leu Ala Gln His Cys His
            440             445             450 ctg cat gcc cgc tgt gtt agc cag gag ggt gtt gcc aga tgt cgc tgt    1570
Leu His Ala Arg Cys Val Ser Gln Glu Gly Val Ala Arg Cys Arg Cys
            455             460             465 ctt gat ggc ttt gag ggt gat ggc ttc tcc tgc aca cct agc aac ccc    1618
Leu Asp Gly Phe Glu Gly Asp Gly Phe Ser Cys Thr Pro Ser Asn Pro
            470             475             480 tgc tcc cac ccg gac cgt gga ggc tgc tca gag aat gct gag tgt gtc    1666
Cys Ser His Pro Asp Arg Gly Gly Cys Ser Glu Asn Ala Glu Cys Val
            485             490             495 cct ggg tcc ctg ggc acc cac cac tgc aca tgc cac aaa ggc tgg agt    1714
Pro Gly Ser Leu Gly Thr His His Cys Thr Cys His Lys Gly Trp Ser
500             505             510             515 ggg gat ggc cgc gtc tgt gtg gct att gac gag tgt gag ctg gac gtg    1762
Gly Asp Gly Arg Val Cys Val Ala Ile Asp Glu Cys Glu Leu Asp Val
            520             525             530 aga ggt ggc tgc cac acc gat gcc ctc tgc agc tat gtg ggc ccc ggg    1810
Arg Gly Gly Cys His Thr Asp Ala Leu Cys Ser Tyr Val Gly Pro Gly
            535             540             545 cag agc cga tgc acc tgc aag ctg ggc ttt gcc ggg gat ggc tac cag    1858
Gln Ser Arg Cys Thr Cys Lys Leu Gly Phe Ala Gly Asp Gly Tyr Gln
            550             555             560 tgc agc ccc atc gac ccc tgc cgg gca ggc aat ggc ggc tgc cac ggc    1906
Cys Ser Pro Ile Asp Pro Cys Arg Ala Gly Asn Gly Gly Cys His Gly
            565             570             575
```

```
ctg gag ctg gag gca aat gcc cac ttc tcc atc ttc tac caa tgg ctt    1954
Leu Glu Leu Glu Ala Asn Ala His Phe Ser Ile Phe Tyr Gln Trp Leu
580             585                 590                 595 aag agt gcc ggc atc acg ctt cct gcc gac cgc cga gtc aca gcc ctg    2002
Lys Ser Ala Gly Ile Thr Leu Pro Ala Asp Arg Arg Val Thr Ala Leu
                600                 605                 610 gtg ccc tcc gag gct gca gtc cgt cag ctg agc ccc gag gac cga gct    2050
Val Pro Ser Glu Ala Ala Val Arg Gln Leu Ser Pro Glu Asp Arg Ala
            615                 620                 625 ttc tgg ctg cag cca agg acg ctg ccg aac ctg gtc agg gcc cat ttt    2098
Phe Trp Leu Gln Pro Arg Thr Leu Pro Asn Leu Val Arg Ala His Phe
        630                 635                 640 ctc cag ggt gcc ctc ttc gag gag gag ctg gcc cgg ctg ggt ggg cag    2146
Leu Gln Gly Ala Leu Phe Glu Glu Glu Leu Ala Arg Leu Gly Gly Gln
    645                 650                 655 gaa gtg gcc acc ctg aac ccc acc aca cgc tgg gag att cgc aac att    2194
Glu Val Ala Thr Leu Asn Pro Thr Thr Arg Trp Glu Ile Arg Asn Ile
660             665                 670                 675 agt ggg agg gtc tgg gtg cag aat gcc agc gtg gat gtg gct gac ctc    2242
Ser Gly Arg Val Trp Val Gln Asn Ala Ser Val Asp Val Ala Asp Leu
                680                 685                 690 ctt gcc acc aac ggt gtc cta cac atc ctc agc cag gtc tta ctg ccc    2290
Leu Ala Thr Asn Gly Val Leu His Ile Leu Ser Gln Val Leu Leu Pro
                695                 700                 705 ccc cga ggg gat gtg ccc ggt ggg cag ggg ttg ctg cag cag ctg gac    2338
Pro Arg Gly Asp Val Pro Gly Gly Gln Gly Leu Leu Gln Gln Leu Asp
            710                 715                 720 ttg gtg cct gcc ttc agc ctc ttc cgg gaa ttg ctg cag cac cat ggg    2386
Leu Val Pro Ala Phe Ser Leu Phe Arg Glu Leu Leu Gln His His Gly
    725                 730                 735
```

```
ttg gtg ccc cag att gag gct gcc act gcc tac acc atc ttt gtg ccc    2434
Leu Val Pro Gln Ile Glu Ala Ala Thr Ala Tyr Thr Ile Phe Val Pro
740                 745                 750                 755 acc aac cgc tcc ctg gag gcc cag ggc aac agc agt cac ctg gac gca    2482
Thr Asn Arg Ser Leu Glu Ala Gln Gly Asn Ser Ser His Leu Asp Ala
                760                 765                 770 gac aca gtg cgg cac cat gtg gtc ctg ggg gag gcc ctc tcc atg gaa    2530
Asp Thr Val Arg His His Val Val Leu Gly Glu Ala Leu Ser Met Glu
            775                 780                 785 acc ctg cgg aag ggt gga cac cgc aac tcc ctc ctg ggc cct gcc cac    2578
Thr Leu Arg Lys Gly Gly His Arg Asn Ser Leu Leu Gly Pro Ala His
        790                 795                 800 tgg atc gtc ttc tac aac cac agt ggc cag cct gag gtg aac cat gtg    2626
Trp Ile Val Phe Tyr Asn His Ser Gly Gln Pro Glu Val Asn His Val
805                 810                 815 cca ctg gaa ggc ccc atg ctg gag gcc cct ggc cgc tcg ctg att ggt    2674
Pro Leu Glu Gly Pro Met Leu Glu Ala Pro Gly Arg Ser Leu Ile Gly
820                 825                 830                 835 ctg tcg ggg gtc ctg acg gtg ggc tca agt cgc tgc ctg cat agc cac    2722
Leu Ser Gly Val Leu Thr Val Gly Ser Ser Arg Cys Leu His Ser His
                840                 845                 850 gct gag gcc ctg cgg gag aaa tgt gta aac tgc acc agg aga ttc cgc    2770
Ala Glu Ala Leu Arg Glu Lys Cys Val Asn Cys Thr Arg Arg Phe Arg
            855                 860                 865 tgc act cag ggc ttc cag ctg cag gac aca ccc agg aag agc tgt gtc    2818
Cys Thr Gln Gly Phe Gln Leu Gln Asp Thr Pro Arg Lys Ser Cys Val
        870                 875                 880 tac cga tct ggc ttc tcc ttc tcc cgg ggc tgc tct tac aca tgt gcc    2866
Tyr Arg Ser Gly Phe Ser Phe Ser Arg Gly Cys Ser Tyr Thr Cys Ala
    885                 890                 895
```

```
aag aag atc cag gtg ccg gac tgc tgc cct ggt ttc ttt ggc acg ctg    2914
Lys Lys Ile Gln Val Pro Asp Cys Cys Pro Gly Phe Phe Gly Thr Leu
900             905             910             915 tgt gag cca tgc cca ggg ggt cta ggg ggg gtg tgc tca ggc cat ggg    2962
Cys Glu Pro Cys Pro Gly Gly Leu Gly Gly Val Cys Ser Gly His Gly
        920             925             930 cag tgc cag gac agg ttc ctg ggc agc ggg gag tgc cac tgc cac gag    3010
Gln Cys Gln Asp Arg Phe Leu Gly Ser Gly Glu Cys His Cys His Glu
            935             940             945 ggc ttc cat gga acg gcc tgt gag gtg tgt gag ctg ggc cgc tac ggg    3058
Gly Phe His Gly Thr Ala Cys Glu Val Cys Glu Leu Gly Arg Tyr Gly
        950             955             960 ccc aac tgc acc gga gtg tgt gac tgt gcc cat ggg ctg tgc cag gag    3106
Pro Asn Cys Thr Gly Val Cys Asp Cys Ala His Gly Leu Cys Gln Glu
        965             970             975 ggg ctg caa ggg gac gga agc tgt gtc tgt aac gtg ggc tgg cag ggc    3154
Gly Leu Gln Gly Asp Gly Ser Cys Val Cys Asn Val Gly Trp Gln Gly
980             985             990             995 ctc cgc tgt gac cag aaa atc acc agc cct cag tgc cct agg aag tgc    3202
Leu Arg Cys Asp Gln Lys Ile Thr Ser Pro Gln Cys Pro Arg Lys Cys
            1000            1005            1010 gac ccc aat gcc aac tgc gtg cag gac tcg gcc gga gcc tcc acc tgc    3250
Asp Pro Asn Ala Asn Cys Val Gln Asp Ser Ala Gly Ala Ser Thr Cys
            1015            1020            1025 gcc tgt gct gcg gga tac tcc ggc aat ggc atc ttc tgt tca gag gtg    3298
Ala Cys Ala Ala Gly Tyr Ser Gly Asn Gly Ile Phe Cys Ser Glu Val
        1030            1035            1040 gac ccc tgc gcc cac ggc cat ggg ggc tgc tcc cct cat gcc aac tgt    3346
Asp Pro Cys Ala His Gly His Gly Gly Cys Ser Pro His Ala Asn Cys
    1045            1050            1055
```

```
acc aag gtg gca cct ggg cag cgg aca tgc acc tgc cag gat ggc tac    3394
Thr Lys Val Ala Pro Gly Gln Arg Thr Cys Thr Cys Gln Asp Gly Tyr
1060            1065            1070            1075 atg ggc gac ggg gag ctg tgc cag gaa att aac agc tgt ctc atc cac    3442
Met Gly Asp Gly Glu Leu Cys Gln Glu Ile Asn Ser Cys Leu Ile His
        1080            1085            1090 cac ggg ggc tgc cac att cac gcc gag tgc atc ccc act ggc ccc cag    3490
His Gly Gly Cys His Ile His Ala Glu Cys Ile Pro Thr Gly Pro Gln
        1095            1100            1105 cag gtc tcc tgc agc tgc cgt gag ggt tac agc ggg gat ggc atc cgg    3538
Gln Val Ser Cys Ser Cys Arg Glu Gly Tyr Ser Gly Asp Gly Ile Arg
        1110            1115            1120 acc tgc gag ctc ctg gac ccc tgc tct aag aac aat gga gga tgc agc    3586
Thr Cys Glu Leu Leu Asp Pro Cys Ser Lys Asn Asn Gly Gly Cys Ser
    1125            1130            1135 cca tat gcc acc tgc aaa agc aca ggg gat ggc cag agg aca tgt acc    3634
Pro Tyr Ala Thr Cys Lys Ser Thr Gly Asp Gly Gln Arg Thr Cys Thr
1140            1145            1150            1155 tgc gac aca gcc cac acc gtg ggg gac ggc ctc acc tgc cgt gcc cga    3682
Cys Asp Thr Ala His Thr Val Gly Asp Gly Leu Thr Cys Arg Ala Arg
            1160            1165            1170 gtc ggc ctg gag ctc ctg agg gat aag cat gcc tca ttc ttc agc ctc    3730
Val Gly Leu Glu Leu Leu Arg Asp Lys His Ala Ser Phe Phe Ser Leu
        1175            1180            1185 cgc ctc ctg gaa tat aag gag ctc aag ggc gat ggg cct ttc acc atc    3778
Arg Leu Leu Glu Tyr Lys Glu Leu Lys Gly Asp Gly Pro Phe Thr Ile
        1190            1195            1200 ttc gtg ccg cac gca gat cta atg agc aac ctg tcg cag gat gag ctg    3826
Phe Val Pro His Ala Asp Leu Met Ser Asn Leu Ser Gln Asp Glu Leu
    1205            1210            1215
```

```
gcc cgg att cgt gcg cat cgc cag ctg gtg ttt cgc tac cac gtg gtt     3874
Ala Arg Ile Arg Ala His Arg Gln Leu Val Phe Arg Tyr His Val Val
1220             1225                 1230                 1235 ggc tgt cgg cgg ctg cgg agc gag gac ctg ctg gag cag ggg tac gcc     3922
Gly Cys Arg Arg Leu Arg Ser Glu Asp Leu Leu Glu Gln Gly Tyr Ala
                 1240                 1245                 1250 acg gcc ctc tca ggg cac cca ctg cgc ttc agc gag agg gag ggc agc     3970
Thr Ala Leu Ser Gly His Pro Leu Arg Phe Ser Glu Arg Glu Gly Ser
             1255                 1260                 1265 ata tac ctc aat gac ttc gcg cgc gtg gtg agc agc gac cat gag gcc     4018
Ile Tyr Leu Asn Asp Phe Ala Arg Val Val Ser Ser Asp His Glu Ala
         1270                 1275                 1280 gtg aac ggc atc ctg cac ttc att gac cgt gtc ctg ctg ccc ccc gag     4066
Val Asn Gly Ile Leu His Phe Ile Asp Arg Val Leu Leu Pro Pro Glu
     1285                 1290                 1295 gcg ctg cac tgg gag cct gat gat gct ccc atc ccg agg aga aat gtc     4114
Ala Leu His Trp Glu Pro Asp Asp Ala Pro Ile Pro Arg Arg Asn Val
1300                 1305                 1310                 1315 acc gcc gcc gcc cag ggc ttc ggt tac aag atc ttc agc ggc ctc ctg     4162
Thr Ala Ala Ala Gln Gly Phe Gly Tyr Lys Ile Phe Ser Gly Leu Leu
                 1320                 1325                 1330 aag gtg gcc ggc ctc ctg ccc ctg ctt cga gag gca tcc cat agg ccc     4210
Lys Val Ala Gly Leu Leu Pro Leu Leu Arg Glu Ala Ser His Arg Pro
             1335                 1340                 1345 ttc aca atg ctg tgg ccc aca gac gcc gcc ttt cga gct ctg cct ccg     4258
Phe Thr Met Leu Trp Pro Thr Asp Ala Ala Phe Arg Ala Leu Pro Pro
         1350                 1355                 1360 gat cgc cag gcc tgg ctg tac cat gag gac cac cgt gac aag cta gca     4306
Asp Arg Gln Ala Trp Leu Tyr His Glu Asp His Arg Asp Lys Leu Ala
     1365                 1370                 1375
```

```
gcc att ctg cgg ggc cac atg att cgc aat gtc gag gcc ttg gca tct    4354
Ala Ile Leu Arg Gly His Met Ile Arg Asn Val Glu Ala Leu Ala Ser
1380            1385                1390                1395 gac ctg ccc aac ctg ggc cca ctt cga acc atg cat ggg acc ccc atc    4402
Asp Leu Pro Asn Leu Gly Pro Leu Arg Thr Met His Gly Thr Pro Ile
                1400                1405                1410 tct ttc tcc tgc agc cga acg cgg ccc ggt gag ctc atg gtg ggt gag    4450
Ser Phe Ser Cys Ser Arg Thr Arg Pro Gly Glu Leu Met Val Gly Glu
            1415                1420                1425 gat gat gct cgc att gtg cag cgg cac ttg ccc ttt gag ggt ggc ctg    4498
Asp Asp Ala Arg Ile Val Gln Arg His Leu Pro Phe Glu Gly Gly Leu
        1430                1435                1440 gcc tat ggc atc gac cag ctg ctg gag cca cct ggc ctt ggt gct cgc    4546
Ala Tyr Gly Ile Asp Gln Leu Leu Glu Pro Pro Gly Leu Gly Ala Arg
    1445                1450                1455 tgt gac cac ttt gag acc cgg ccc ctg cga ctg aac acc tgc agc atc    4594
Cys Asp His Phe Glu Thr Arg Pro Leu Arg Leu Asn Thr Cys Ser Ile
1460            1465                1470                1475 tgt ggg ctg gag cca ccc tgt cct gag ggg tca cag gag cag ggc agc    4642
Cys Gly Leu Glu Pro Pro Cys Pro Glu Gly Ser Gln Glu Gln Gly Ser
                1480                1485                1490 cct gag gcc tgc tgg cgc ttc tac ccg aag ttc tgg acg tcc cct ccg    4690
Pro Glu Ala Cys Trp Arg Phe Tyr Pro Lys Phe Trp Thr Ser Pro Pro
            1495                1500                1505 ctg cac tct ttg gga tta cgc agc gtc tgg gtc cac ccc agc ctt tgg    4738
Leu His Ser Leu Gly Leu Arg Ser Val Trp Val His Pro Ser Leu Trp
        1510                1515                1520 ggt agg ccc caa ggc ctg ggc agg ggc tgc cac cgc aat tgt gtc acc    4786
Gly Arg Pro Gln Gly Leu Gly Arg Gly Cys His Arg Asn Cys Val Thr
    1525                1530                1535
```

```
acc acc tgg aag ccc agc tgc tgc cct ggt cac tat ggc agt gag tgc    4834
Thr Thr Trp Lys Pro Ser Cys Cys Pro Gly His Tyr Gly Ser Glu Cys
1540            1545            1550            1555 caa gct tgc cct ggc ggc ccc agc agc cct tgt agt gac cgt ggc gtg    4882
Gln Ala Cys Pro Gly Gly Pro Ser Ser Pro Cys Ser Asp Arg Gly Val
        1560            1565            1570 tgc atg gac ggc atg agt ggc agt ggg cag tgt ctg tgc cgt tca ggt    4930
Cys Met Asp Gly Met Ser Gly Ser Gly Gln Cys Leu Cys Arg Ser Gly
            1575            1580            1585 ttt gct ggg aca gcc tgt gaa ctc tgt gct cct ggt gcc ttt ggg ccc    4978
Phe Ala Gly Thr Ala Cys Glu Leu Cys Ala Pro Gly Ala Phe Gly Pro
        1590            1595            1600 cat tgt caa gcc tgc cgc tgc act gtg cat ggc cgc tgt gat gag ggc    5026
His Cys Gln Ala Cys Arg Cys Thr Val His Gly Arg Cys Asp Glu Gly
        1605            1610            1615 ctt ggg ggc tct ggc tcc tgc ttc tgt gat gaa ggc tgg act ggg cca    5074
Leu Gly Gly Ser Gly Ser Cys Phe Cys Asp Glu Gly Trp Thr Gly Pro
1620            1625            1630            1635 cgc tgt gag gtg caa ctg gag ctg cag cct gtg tgt acc cca ccc tgt    5122
Arg Cys Glu Val Gln Leu Glu Leu Gln Pro Val Cys Thr Pro Pro Cys
                1640            1645            1650 gca ccc gag gct gtg tgc cgt gca ggc aac agc tgt gag tgc agc ctg    5170
Ala Pro Glu Ala Val Cys Arg Ala Gly Asn Ser Cys Glu Cys Ser Leu
            1655            1660            1665 ggc tat gaa ggg gat ggc cgt gtg tgt aca gtg gca gac ctg tgc cag    5218
Gly Tyr Glu Gly Asp Gly Arg Val Cys Thr Val Ala Asp Leu Cys Gln
        1670            1675            1680 gac ggg cat ggt ggc tgc agt gag cac gcc aac tgt agc cag gta gga    5266
Asp Gly His Gly Gly Cys Ser Glu His Ala Asn Cys Ser Gln Val Gly
        1685            1690            1695
```

```
aca atg gtc act tgt acc tgc ctg ccc gac tac gag ggt gat ggc tgg    5314
Thr Met Val Thr Cys Thr Cys Leu Pro Asp Tyr Glu Gly Asp Gly Trp
1700            1705                1710                1715 agc tgc cgg gcc cgc aac ccc tgc aca gat ggc cac cgc ggg ggc tgc    5362
Ser Cys Arg Ala Arg Asn Pro Cys Thr Asp Gly His Arg Gly Gly Cys
            1720                1725                1730 agc gag cac gcc aac tgc ttg agc acc ggc ctg aac aca cgg cgc tgt    5410
Ser Glu His Ala Asn Cys Leu Ser Thr Gly Leu Asn Thr Arg Arg Cys
        1735                1740                1745 gag tgc cac gca ggc tac gta ggc gat gga ctg cag tgt ctg gag gag    5458
Glu Cys His Ala Gly Tyr Val Gly Asp Gly Leu Gln Cys Leu Glu Glu
    1750                1755                1760 tcg gaa cca cct gtg gac cgc tgc ttg ggc cag cca ccg ccc tgc cac    5506
Ser Glu Pro Pro Val Asp Arg Cys Leu Gly Gln Pro Pro Pro Cys His
    1765                1770                1775 tca gat gcc atg tgc act gac ctg cac ttc cag gag aaa cgg gct ggc    5554
Ser Asp Ala Met Cys Thr Asp Leu His Phe Gln Glu Lys Arg Ala Gly
1780            1785                1790                1795 gtt ttc cac ctc cag gcc acc agc ggc cct tat ggt ctg aac ttt tcg    5602
Val Phe His Leu Gln Ala Thr Ser Gly Pro Tyr Gly Leu Asn Phe Ser
                1800                1805                1810 gag gct gag gcg gca tgc gaa gca cag gga gcc gtc ctt gct tca ttc    5650
Glu Ala Glu Ala Ala Cys Glu Ala Gln Gly Ala Val Leu Ala Ser Phe
            1815                1820                1825 cct cag ctc tct gct gcc cag cag ctg ggc ttc cac ctg tgc ctc atg    5698
Pro Gln Leu Ser Ala Ala Gln Gln Leu Gly Phe His Leu Cys Leu Met
        1830                1835                1840 ggc tgg ctg gcc aat ggc tcc act gcc cac cct gtg gtt ttc cct gtg    5746
Gly Trp Leu Ala Asn Gly Ser Thr Ala His Pro Val Val Phe Pro Val
    1845                1850                1855
```

```
gcg gac tgt ggc aat ggt cgg gtg ggc ata gtc agc ctg ggt gcc cgc    5794
Ala Asp Cys Gly Asn Gly Arg Val Gly Ile Val Ser Leu Gly Ala Arg
1860            1865                1870                1875 aag aac ctc tca gaa cgc tgg gat gcc tac tgc ttc cgt gtg caa gat    5842
Lys Asn Leu Ser Glu Arg Trp Asp Ala Tyr Cys Phe Arg Val Gln Asp
                1880                1885                1890 gtg gcc tgc cga tgc cga aat ggc ttc gtg ggt gac ggg atc agc acg    5890
Val Ala Cys Arg Cys Arg Asn Gly Phe Val Gly Asp Gly Ile Ser Thr
            1895                1900                1905 tgc aat ggg aag ctg ctg gat gtg ctg gct gcc act gcc aac ttc tcc    5938
Cys Asn Gly Lys Leu Leu Asp Val Leu Ala Ala Thr Ala Asn Phe Ser
        1910                1915                1920 acc ttc tat ggg atg cta ttg ggc tat gcc aat gcc acc cag cgg ggt    5986
Thr Phe Tyr Gly Met Leu Leu Gly Tyr Ala Asn Ala Thr Gln Arg Gly
    1925                1930                1935 ctc gac ttc ctg gac ttc ctg gat gat gag ctc acg tat aag aca ctc    6034
Leu Asp Phe Leu Asp Phe Leu Asp Asp Glu Leu Thr Tyr Lys Thr Leu
1940                1945                1950                1955 ttc gtc cct gtc aat gaa ggc ttt gtg gac aac atg acg ctg agt ggc    6082
Phe Val Pro Val Asn Glu Gly Phe Val Asp Asn Met Thr Leu Ser Gly
                1960                1965                1970 cca aac ttg gag ctg cat gcc tcc aac gcc acc ctc cta agt gcc aac    6130
Pro Asn Leu Glu Leu His Ala Ser Asn Ala Thr Leu Leu Ser Ala Asn
            1975                1980                1985 gcc agc cag ggg aag ttg ctt ccg gcc cac tca ggc ctc agc ctc atc    6178
Ala Ser Gln Gly Lys Leu Leu Pro Ala His Ser Gly Leu Ser Leu Ile
        1990                1995                2000 atc agt gac gca ggc cct gac aac agt tcc tgg gcc cct gtg gcc cca    6226
Ile Ser Asp Ala Gly Pro Asp Asn Ser Ser Trp Ala Pro Val Ala Pro
    2005                2010                2015
```

```
ggg aca gtt gtg gtt agc cgt atc att gtg tgg gac atc atg gcc ttc    6274
Gly Thr Val Val Val Ser Arg Ile Ile Val Trp Asp Ile Met Ala Phe
2020                2025                2030                2035 aat ggc atc atc cat gct ctg gcc agc ccc ctc ctg gca ccc cca cag    6322
Asn Gly Ile Ile His Ala Leu Ala Ser Pro Leu Leu Ala Pro Pro Gln
            2040                2045                2050 ccc cag gca gtg ctg gcg cnt gaa gcc cca cct gtg gcg gca ggc gtg    6370
Pro Gln Ala Val Leu Ala Xaa Glu Ala Pro Pro Val Ala Ala Gly Val
        2055                2060                2065 ggg gct gtg ctt gcc gct gga gca ctg ctt ggc ttg gtg gcc gga gct    6418
Gly Ala Val Leu Ala Ala Gly Ala Leu Leu Gly Leu Val Ala Gly Ala
    2070                2075                2080 ctc tac ctc cgt gcc cga ggc aag ccc atg ggc ttt ggc ttc tct gcc    6466
Leu Tyr Leu Arg Ala Arg Gly Lys Pro Met Gly Phe Gly Phe Ser Ala
2085                2090                2095 ttc cag gcg gaa gat gat gct gat gac gan ttc tca ccg tgg caa gaa    6514
Phe Gln Ala Glu Asp Asp Ala Asp Asp Xaa Phe Ser Pro Trp Gln Glu
2100                2105                2110                2115 ggg acc aac ccc acn ttg gtn tnt gtc ccc aac cct gtc ttt ggc agc    6562
Gly Thr Asn Pro Xaa Leu Xaa Xaa Val Pro Asn Pro Val Phe Gly Ser
            2120                2125                2130 gac acc ttt tgt gaa ccc ttc gat gac tca ctg ctg gag gag gac ttc    6610
Asp Thr Phe Cys Glu Pro Phe Asp Asp Ser Leu Leu Glu Glu Asp Phe
        2135                2140                2145 cct gac acc cag agg atc ctc aca gtc aag tga cgaggctggg gctgaaagca  6663
Pro Asp Thr Gln Arg Ile Leu Thr Val Lys
    2150                2155 gaagcatgca cagggaggag accanttta ttgcttgtct gggtggatgg ggcaggaggg   6723
nctgagggcc tgtcccagac aatannngtn ccctcgag                          6761
```

```
<210> 2
<211> 2157
<212> PRT
<213> Homo sapiens

<220>
<221> MISC_FEATURE
<222> (2058)
<223> Xaa equals any of the naturally occurring L-amino acids <220>
<221> MISC_FEATURE
<222> (2109)
<223> Xaa equals any of the naturally occurring L-amino acids <220>
<221> MISC_FEATURE
<222> (2120)
<223> Xaa equals any of the naturally occurring L-amino acids <220>
<221> MISC_FEATURE
<222> (2122)
<223> Xaa equals any of the naturally occurring L-amino acids <220>
<221> MISC_FEATURE
<222> (2123)
<223> Xaa equals any of the naturally occurring L-amino acids

<400> 2
```

| Met | Met | Asp | Gln | Gly | Cys | Arg | Glu | Ile | Leu | Thr | Thr | Ala | Gly | Pro | Phe |
|---|---|---|---|---|---|---|---|---|---|---|---|---|---|---|---|
| 1 | | | | 5 | | | | | 10 | | | | | 15 | |

| Thr | Val | Leu | Val | Pro | Ser | Val | Ser | Ser | Phe | Ser | Ser | Arg | Thr | Met | Asn |
|---|---|---|---|---|---|---|---|---|---|---|---|---|---|---|---|
| | | | 20 | | | | 25 | | | | | 30 | | | |

| Ala | Ser | Leu | Ala | Gln | Gln | Leu | Cys | Arg | Gln | His | Ile | Ala | Gly | Gln |
|---|---|---|---|---|---|---|---|---|---|---|---|---|---|---|
| | | 35 | | | | 40 | | | | | 45 | | | |

| His | Ile | Leu | Glu | Asp | Thr | Arg | Thr | Gln | Gln | Thr | Arg | Arg | Trp | Trp | Thr |
|---|---|---|---|---|---|---|---|---|---|---|---|---|---|---|---|
| | 50 | | | | | 55 | | | | | 60 | | | | |

```
Leu Ala Gly Gln Glu Ile Thr Val Thr Phe Asn Gln Phe Thr Lys Tyr
65                  70                  75                  80

Ser Tyr Lys Tyr Lys Asp Gln Pro Gln Gln Thr Phe Asn Ile Tyr Lys
                85                  90                  95

Ala Asn Asn Ile Ala Ala Asn Gly Val Phe His Val Val Thr Gly Leu
            100                 105                 110

Arg Trp Gln Ala Pro Ser Gly Thr Pro Gly Asp Pro Lys Arg Thr Ile
            115                 120                 125

Gly Gln Ile Leu Ala Ser Thr Glu Ala Phe Ser Arg Phe Glu Thr Ile
            130                 135                 140

Leu Glu Asn Cys Gly Leu Pro Ser Ile Leu Asp Gly Pro Gly Pro Phe
145                 150                 155                 160

Thr Val Phe Ala Pro Ser Asn Glu Ala Val Asp Ser Leu Arg Asp Gly
                165                 170                 175

Arg Leu Ile Tyr Leu Phe Thr Ala Gly Leu Ser Lys Leu Gln Glu Leu
                180                 185                 190

Val Arg Tyr His Ile Tyr Asn His Gly Gln Leu Thr Val Glu Lys Leu
        195                 200                 205

Ile Ser Lys Gly Arg Ile Leu Thr Met Ala Asn Gln Val Leu Ala Val
    210                 215                 220

Asn Ile Ser Glu Glu Gly Arg Ile Leu Leu Gly Pro Glu Gly Val Pro
225                 230                 235                 240

Leu Gln Arg Val Asp Val Met Ala Ala Asn Gly Val Ile His Met Leu
                245                 250                 255

Asp Gly Ile Leu Leu Pro Pro Thr Ile Leu Pro Ile Leu Pro Lys His
            260                 265                 270

Cys Ser Glu Glu Gln His Lys Ile Val Ala Gly Ser Cys Val Asp Cys
            275                 280                 285
```

```
Gln Ala Leu Asn Thr Ser Thr Cys Pro Pro Asn Ser Val Lys Leu Asp
    290                 295                 300
Ile Phe Pro Lys Glu Cys Val Tyr Ile His Asp Pro Thr Gly Leu Asn
305                 310                 315                 320
Val Leu Lys Lys Gly Cys Ala Ser Tyr Cys Asn Gln Thr Ile Met Glu
                325                 330                 335
Gln Gly Cys Cys Lys Gly Phe Phe Gly Pro Asp Cys Thr Gln Cys Pro
            340                 345                 350
Gly Gly Phe Ser Asn Pro Cys Tyr Gly Lys Gly Asn Cys Ser Asp Gly
        355                 360                 365
Ile Gln Gly Asn Gly Ala Cys Leu Cys Phe Pro Asp Tyr Lys Gly Ile
    370                 375                 380
Ala Cys His Ile Cys Ser Asn Pro Asn Lys His Gly Glu Gln Cys Gln
385                 390                 395                 400
Glu Asp Cys Gly Cys Val His Gly Leu Cys Asp Asn Arg Pro Gly Ser
                405                 410                 415
Gly Gly Val Cys Gln Gln Gly Thr Cys Ala Pro Gly Phe Ser Gly Arg
            420                 425                 430
Phe Cys Asn Glu Ser Met Gly Asp Cys Gly Pro Thr Gly Leu Ala Gln
        435                 440                 445
His Cys His Leu His Ala Arg Cys Val Ser Gln Glu Gly Val Ala Arg
    450                 455                 460
Cys Arg Cys Leu Asp Gly Phe Glu Gly Asp Gly Phe Ser Cys Thr Pro
465                 470                 475                 480
Ser Asn Pro Cys Ser His Pro Asp Arg Gly Gly Cys Ser Glu Asn Ala
                485                 490                 495
Glu Cys Val Pro Gly Ser Leu Gly Thr His His Cys Thr Cys His Lys
            500                 505                 510
```

```
Gly Trp Ser Gly Asp Gly Arg Val Cys Val Ala Ile Asp Glu Cys Glu
        515                 520                 525

Leu Asp Val Arg Gly Gly Cys His Thr Asp Ala Leu Cys Ser Tyr Val
    530                 535                 540

Gly Pro Gly Gln Ser Arg Cys Thr Cys Lys Leu Gly Phe Ala Gly Asp
545                 550                 555                 560

Gly Tyr Gln Cys Ser Pro Ile Asp Pro Cys Arg Ala Gly Asn Gly Gly
                565                 570                 575

Cys His Gly Leu Glu Leu Glu Ala Asn Ala His Phe Ser Ile Phe Tyr
            580                 585                 590

Gln Trp Leu Lys Ser Ala Gly Ile Thr Leu Pro Ala Asp Arg Arg Val
        595                 600                 605

Thr Ala Leu Val Pro Ser Glu Ala Ala Val Arg Gln Leu Ser Pro Glu
    610                 615                 620

Asp Arg Ala Phe Trp Leu Gln Pro Arg Thr Leu Pro Asn Leu Val Arg
625                 630                 635                 640

Ala His Phe Leu Gln Gly Ala Leu Phe Glu Glu Leu Ala Arg Leu
                645                 650                 655

Gly Gly Gln Glu Val Ala Thr Leu Asn Pro Thr Thr Arg Trp Glu Ile
            660                 665                 670

Arg Asn Ile Ser Gly Arg Val Trp Val Gln Asn Ala Ser Val Asp Val
        675                 680                 685

Ala Asp Leu Leu Ala Thr Asn Gly Val Leu His Ile Leu Ser Gln Val
    690                 695                 700

Leu Leu Pro Pro Arg Gly Asp Val Pro Gly Gly Gln Gly Leu Leu Gln
705                 710                 715                 720

Gln Leu Asp Leu Val Pro Ala Phe Ser Leu Phe Arg Glu Leu Leu Gln
                725                 730                 735
```

```
His His Gly Leu Val Pro Gln Ile Glu Ala Ala Thr Ala Tyr Thr Ile
            740             745             750

Phe Val Pro Thr Asn Arg Ser Leu Glu Ala Gln Gly Asn Ser Ser His
        755             760             765

Leu Asp Ala Asp Thr Val Arg His His Val Val Leu Gly Glu Ala Leu
    770             775             780

Ser Met Glu Thr Leu Arg Lys Gly Gly His Arg Asn Ser Leu Leu Gly
785             790             795             800

Pro Ala His Trp Ile Val Phe Tyr Asn His Ser Gly Gln Pro Glu Val
            805             810             815

Asn His Val Pro Leu Glu Gly Pro Met Leu Glu Ala Pro Gly Arg Ser
        820             825             830

Leu Ile Gly Leu Ser Gly Val Leu Thr Val Gly Ser Ser Arg Cys Leu
            835             840             845

His Ser His Ala Glu Ala Leu Arg Glu Lys Cys Val Asn Cys Thr Arg
        850             855             860

Arg Phe Arg Cys Thr Gln Gly Phe Gln Leu Gln Asp Thr Pro Arg Lys
865             870             875             880

Ser Cys Val Tyr Arg Ser Gly Phe Ser Phe Ser Arg Gly Cys Ser Tyr
            885             890             895

Thr Cys Ala Lys Lys Ile Gln Val Pro Asp Cys Cys Pro Gly Phe Phe
            900             905             910

Gly Thr Leu Cys Glu Pro Cys Pro Gly Gly Leu Gly Gly Val Cys Ser
            915             920             925

Gly His Gly Gln Cys Gln Asp Arg Phe Leu Gly Ser Gly Glu Cys His
            930             935             940

Cys His Glu Gly Phe His Gly Thr Ala Cys Glu Val Cys Glu Leu Gly
945             950             955             960
```

```
Arg Tyr Gly Pro Asn Cys Thr Gly Val Cys Asp Cys Ala His Gly Leu
            965                 970                 975

Cys Gln Glu Gly Leu Gln Gly Asp Gly Ser Cys Val Cys Asn Val Gly
            980                 985                 990

Trp Gln Gly Leu Arg Cys Asp Gln Lys Ile Thr Ser Pro Gln Cys Pro
        995                 1000                1005

Arg Lys Cys Asp Pro Asn Ala Asn Cys Val Gln Asp Ser Ala Gly Ala
        1010                1015                1020

Ser Thr Cys Ala Cys Ala Ala Gly Tyr Ser Gly Asn Gly Ile Phe Cys
1025                1030                1035                1040

Ser Glu Val Asp Pro Cys Ala His Gly His Gly Gly Cys Ser Pro His
                1045                1050                1055

Ala Asn Cys Thr Lys Val Ala Pro Gly Gln Arg Thr Cys Thr Cys Gln
            1060                1065                1070

Asp Gly Tyr Met Gly Asp Gly Glu Leu Cys Gln Glu Ile Asn Ser Cys
            1075                1080                1085

Leu Ile His His Gly Gly Cys His Ile His Ala Glu Cys Ile Pro Thr
        1090                1095                1100

Gly Pro Gln Gln Val Ser Cys Ser Cys Arg Glu Gly Tyr Ser Gly Asp
1105                1110                1115                1120

Gly Ile Arg Thr Cys Glu Leu Leu Asp Pro Cys Ser Lys Asn Asn Gly
                1125                1130                1135

Gly Cys Ser Pro Tyr Ala Thr Cys Lys Ser Thr Gly Asp Gly Gln Arg
            1140                1145                1150

Thr Cys Thr Cys Asp Thr Ala His Thr Val Gly Asp Gly Leu Thr Cys
        1155                1160                1165

Arg Ala Arg Val Gly Leu Glu Leu Leu Arg Asp Lys His Ala Ser Phe
        1170                1175                1180
```

```
Phe   Ser Leu Arg Leu  Leu   Glu Tyr Lys Glu  Leu   Lys Gly Asp Gly  Pro
1185                   1190                   1195                   1200

Phe Thr Ile Phe Val   Pro His Ala Asp Leu   Met Ser Asn Leu Ser   Gln
                1205                  1210                  1215

Asp Glu Leu Ala   Arg Ile Arg Ala His   Arg Gln Leu Val Phe   Arg Tyr
                1220                  1225                  1230

His Val Val   Gly Cys Arg Arg Leu   Arg Ser Glu Asp Leu   Leu Glu Gln
            1235                  1240                  1245

Gly Tyr   Ala Thr Ala Leu Ser   Gly His Pro Leu Arg   Phe Ser Glu Arg
        1250                  1255                  1260

Glu   Gly Ser Ile Tyr Leu   Asn Asp Phe Ala Arg   Val Val Ser Ser  Asp
1265                   1270                  1275                   1280

His Glu Ala Val Asn   Gly Ile Leu His Phe   Ile Asp Arg Val Leu   Leu
                1285                  1290                  1295

Pro Pro Glu Ala   Leu His Trp Glu Pro   Asp Ala Pro Ile   Pro Arg
                1300                  1305                1310

Arg Asn Val   Thr Ala Ala Ala Gln   Gly Phe Gly Tyr Lys   Ile Phe Ser
            1315                  1320                  1325

Gly Leu   Leu Lys Val Ala Gly   Leu Leu Pro Leu Leu   Arg Glu Ala Ser
        1330                  1335                  1340

His   Arg Pro Phe Thr Met   Leu Trp Pro Thr Asp   Ala Ala Phe Arg  Ala
1345                   1350                  1355                   1360

Leu Pro Pro Asp Arg   Gln Ala Trp Leu Tyr   His Glu Asp His Arg   Asp
                1365                  1370                  1375

Lys Leu Ala Ala   Ile Leu Arg Gly His   Met Ile Arg Asn Val   Glu Ala
                1380                  1385                  1390

Leu Ala Ser   Asp Leu Pro Asn Leu   Gly Pro Leu Arg Thr   Met His Gly
            1395                  1400                  1405
```

```
Thr Pro  Ile Ser Phe  Ser Cys  Ser Arg Thr  Arg Pro  Gly Glu Leu Met
    1410                  1415              1420

Val  Gly Glu Asp Asp  Ala  Arg Ile Val Gln  Arg  His Leu Pro Phe Glu
1425                  1430                  1435                  1440

Gly Gly Leu Ala Tyr  Gly Ile Asp Gln Leu  Leu Glu Pro Pro Gly  Leu
                1445                 1450                 1455

Gly Ala Arg Cys  Asp His Phe Glu Thr  Arg Pro Leu Arg Leu  Asn Thr
            1460                 1465                 1470

Cys Ser Ile  Cys Gly Leu Glu Pro  Pro Cys Pro Glu Gly  Ser Gln Glu
        1475              1480                 1485

Gln Gly  Ser Pro Glu Ala Cys  Trp Arg Phe Tyr Pro  Lys Phe Trp  Thr
    1490                 1495                 1500

Ser  Pro Pro Leu His Ser  Leu Gly Leu Arg Ser  Val Trp Val His  Pro
1505                 1510                 1515                  1520

Ser Leu Trp Gly Arg  Pro Gln Gly Leu Gly  Arg Gly Cys His Arg  Asn
                1525                1530                 1535

Cys Val Thr Thr  Thr Trp Lys Pro Ser  Cys Cys Pro Gly His  Tyr Gly
            1540                 1545                 1550

Ser Glu Cys  Gln Ala Cys Pro Gly  Gly Pro Ser Ser Pro  Cys Ser Asp
        1555                 1560                 1565

Arg Gly  Val Cys Met Asp Gly  Met Ser Gly Ser Gly  Gln Cys Leu Cys
    1570                 1575                 1580

Arg  Ser Gly Phe Ala Gly  Thr Ala Cys Glu Leu  Cys Ala Pro Gly Ala
1585                 1590                 1595                  1600

Phe Gly Pro His Cys  Gln Ala Cys Arg Cys  Thr Val His Gly Arg  Cys
                1605                 1610                 1615

Asp Glu Gly Leu  Gly Gly Ser Gly Ser  Cys Phe Cys Asp Glu  Gly Trp
            1620                 1625                 1630
```

```
Thr Gly Pro  Arg Cys Glu Val Gln  Leu Glu Leu Gln Pro  Val Cys Thr
        1635             1640             1645

Pro Pro  Cys Ala Pro Glu Ala  Val Cys Arg Ala Gly  Asn Ser Cys Glu
        1650             1655             1660

Cys  Ser Leu Gly Tyr Glu  Gly Asp Gly Arg Val  Cys Thr Val Ala Asp
1665             1670             1675             1680

Leu Cys Gln Asp Gly  His Gly Gly Cys Ser  Glu His Ala Asn Cys  Ser
            1685             1690             1695

Gln Val Gly Thr  Met Val Thr Cys Thr  Cys Leu Pro Asp Tyr  Glu Gly
            1700             1705             1710

Asp Gly Trp  Ser Cys Arg Ala Arg  Asn Pro Cys Thr Asp  Gly His Arg
        1715             1720             1725

Gly Gly  Cys Ser Glu His Ala  Asn Cys Leu Ser Thr  Gly Leu Asn Thr
        1730             1735             1740

Arg  Arg Cys Glu Cys His  Ala Gly Tyr Val Gly  Asp Gly Leu Gln Cys
1745             1750             1755             1760

Leu Glu Glu Ser Glu  Pro Pro Val Asp Arg  Cys Leu Gly Gln Pro  Pro
            1765             1770             1775

Pro Cys His Ser  Asp Ala Met Cys Thr  Asp Leu His Phe Gln  Glu Lys
            1780             1785             1790

Arg Ala Gly  Val Phe His Leu Gln  Ala Thr Ser Gly Pro  Tyr Gly Leu
        1795             1800             1805

Asn Phe  Ser Glu Ala Glu Ala  Ala Cys Glu Ala Gln  Gly Ala Val Leu
        1810             1815             1820

Ala  Ser Phe Pro Gln Leu  Ser Ala Ala Gln Leu  Gly Phe His Leu
1825             1830             1835             1840

Cys Leu Met Gly Trp  Leu Ala Asn Gly Ser  Thr Ala His Pro Val  Val
            1845             1850             1855
```

Phe Pro Val Ala Asp Cys Gly Asn Gly Arg Val Gly Ile Val Ser Leu
            1860                1865                    1870

Gly Ala Arg Lys Asn Leu Ser Glu Arg Trp Asp Ala Tyr Cys Phe Arg
            1875                1880                    1885

Val Gln Asp Val Ala Cys Arg Cys Arg Asn Gly Phe Val Gly Asp Gly
            1890                1895                    1900

Ile Ser Thr Cys Asn Gly Lys Leu Leu Asp Val Leu Ala Ala Thr Ala
1905                    1910                1915                1920

Asn Phe Ser Thr Phe Tyr Gly Met Leu Leu Gly Tyr Ala Asn Ala Thr
            1925                1930                    1935

Gln Arg Gly Leu Asp Phe Leu Asp Phe Leu Asp Asp Glu Leu Thr Tyr
            1940                1945                    1950

Lys Thr Leu Phe Val Pro Val Asn Glu Gly Phe Val Asp Asn Met Thr
            1955                1960                    1965

Leu Ser Gly Pro Asn Leu Glu Leu His Ala Ser Asn Ala Thr Leu Leu
            1970                1975                    1980

Ser Ala Asn Ala Ser Gln Gly Lys Leu Leu Pro Ala His Ser Gly Leu
1985                    1990                1995                2000

Ser Leu Ile Ile Ser Asp Ala Gly Pro Asp Asn Ser Ser Trp Ala Pro
            2005                2010                    2015

Val Ala Pro Gly Thr Val Val Val Ser Arg Ile Ile Val Trp Asp Ile
            2020                2025                    2030

Met Ala Phe Asn Gly Ile Ile His Ala Leu Ala Ser Pro Leu Leu Ala
            2035                2040                    2045

Pro Pro Gln Pro Gln Ala Val Leu Ala Xaa Glu Ala Pro Pro Val Ala
            2050                2055                    2060

Ala Gly Val Gly Ala Val Leu Ala Ala Gly Ala Leu Leu Gly Leu Val
2065                    2070                2075                2080

```
Ala Gly Ala Leu Tyr   Leu Arg Ala Arg Gly   Lys Pro Met Gly Phe   Gly
            2085                  2090                  2095

Phe Ser Ala Phe   Gln Ala Glu Asp Asp   Ala Asp Asp Xaa Phe   Ser Pro
            2100                  2105                  2110

Trp Gln Glu   Gly Thr Asn Pro Xaa   Leu Xaa Xaa Val Pro   Asn Pro Val
            2115                  2120                  2125

Phe Gly   Ser Asp Thr Phe Cys   Glu Pro Phe Asp Asp   Ser Leu Leu Glu
       2130                  2135                  2140

Glu   Asp Phe Pro Asp Thr   Gln Arg Ile Leu Thr   Val Lys
2145                  2150                  2155
```

<210> 3
<211> 193
<212> PRT
<213> Homo sapiens

<400> 3

```
Met Tyr Trp Asp Thr Gly Trp Gly Lys Asp Gly His Asn Ser Trp Arg
 1               5                  10                  15

Ala Ala Gly Val Tyr   His Arg Ala Arg Ser   Gly Lys Tyr Lys Thr   Tyr
            20                    25                  30

Ala Ala Lys Ala Val   Cys Gly Gly His Ala   Thr Tyr Lys Ala Ala   Arg
            35                    40                  45

Lys Gly His Val Cys   Ala Ala Gly Trp Met   Ala Lys Gly Arg Val   Gly
            50                    55                  60

Tyr Val Lys Gly Asn   Cys Gly Gly Lys Thr   Gly Asp Tyr Gly Arg   Asn
 65                    70                  75                    80

Arg Ser Arg Trp Asp   Ala Tyr Cys Tyr Asn   His Ala Lys Cys Gly   Gly
                85                    90                  95

Val Thr Asp Lys Arg   Lys Ser Gly Asn Tyr   Asp Asn Cys Tyr Trp   His
               100                  105                 110
```

```
Arg Lys Tyr Gly Arg His Ser Asp Asp Asp Gly Cys Ala Asp Tyr
        115                 120                 125

Val Tyr Asp Ser Tyr Asp Asp Val His Gly Val Gly Arg Tyr Cys Gly
        130                 135                 140

Asp Asp Asp Ser Thr Gly Asn Val Met Thr Lys Ser Asp Ala Ser Val
145                 150                 155                 160

Thr Ala Gly Gly Lys Tyr Val Ala Met Asp Val Ser Lys Ser Ser Gly
                165                 170                 175

Lys Asn Thr Ser Thr Thr Ser Thr Gly Asn Lys Asn Ala Gly Arg Ser
            180                 185                 190

His

<210> 4
<211> 1522
<212> DNA
<213> Homo sapiens

<220>
<221> CDS
<222> (31)..(1404)

<220>
<221> misc_feature
<222> (1103)
<223> n equals a, t, g or c

<220>
<221> misc_feature
<222> (1257)
<223> n equals a, t, g or c

<220>
<221> misc_feature
<222> (1290)
<223> n equals a, t, g or c
```

```
<220>
<221> misc_feature
<222> (1296)
<223> n equals a, t, g or c

<220>
<221> misc_feature
<222> (1298)
<223> n equals a, t, g or c

<220>
<221> misc_feature
<222> (1449)
<223> n equals a, t, g or c

<220>
<221> misc_feature
<222> (1485)
<223> n equals a, t, g or c

<220>
<221> misc_feature
<222> (1509)
<223> n equals a, t, g or c

<220>
<221> misc_feature
<222> (1511)
<223> n equals a, t, g or c

<220>
<221> misc_feature
<222> (1514)
<223> n equals a, t, g or c

<400> 4
gagcacgcca actgtagcca ggtaggaaca atg gtc act tgt acc tgc ctg ccc    54
                                 Met Val Thr Cys Thr Cys Leu Pro
                                  1               5
```

```
gac tac gag ggt gat ggc tgg agc tgc cgg gcc cgc aac ccc tgc aca      102
Asp Tyr Glu Gly Asp Gly Trp Ser Cys Arg Ala Arg Asn Pro Cys Thr
        10                  15                  20 gat ggc cac cgc ggg ggc tgc agc gag cac gcc aac tgc ttg agc acc      150
Asp Gly His Arg Gly Gly Cys Ser Glu His Ala Asn Cys Leu Ser Thr
25                  30                  35                  40 ggc ctg aac aca cgg cgc tgt gag tgc cac gca ggc tac gta ggc gat      198
Gly Leu Asn Thr Arg Arg Cys Glu Cys His Ala Gly Tyr Val Gly Asp
                45                  50                  55 gga ctg cag tgt ctg gag gag tcg gaa cca cct gtg gac cgc tgc ttg      246
Gly Leu Gln Cys Leu Glu Glu Ser Glu Pro Pro Val Asp Arg Cys Leu
            60                  65                  70 ggc cag cca ccg ccc tgc cac tca gat gcc atg tgc act gac ctg cac      294
Gly Gln Pro Pro Pro Cys His Ser Asp Ala Met Cys Thr Asp Leu His
            75                  80                  85 ttc cag gag aaa cgg gct ggc gtt ttc cac ctc cag gcc acc agc ggc      342
Phe Gln Glu Lys Arg Ala Gly Val Phe His Leu Gln Ala Thr Ser Gly
        90                  95                  100 cct tat ggt ctg aac ttt tcg gag gct gag gcg gca tgc gaa gca cag      390
Pro Tyr Gly Leu Asn Phe Ser Glu Ala Glu Ala Ala Cys Glu Ala Gln
105                 110                 115                 120 gga gcc gtc ctt gct tca ttc cct cag ctc tct gct gcc cag cag ctg      438
Gly Ala Val Leu Ala Ser Phe Pro Gln Leu Ser Ala Ala Gln Gln Leu
                125                 130                 135 ggc ttc cac ctg tgc ctc atg ggc tgg ctg gcc aat ggc tcc act gcc      486
Gly Phe His Leu Cys Leu Met Gly Trp Leu Ala Asn Gly Ser Thr Ala
            140                 145                 150 cac cct gtg gtt ttc cct gtg gcg gac tgt ggc aat ggt cgg gtg ggc      534
His Pro Val Val Phe Pro Val Ala Asp Cys Gly Asn Gly Arg Val Gly
            155                 160                 165
```

```
ata gtc agc ctg ggt gcc cgc aag aac ctc tca gaa cgc tgg gat gcc    582
Ile Val Ser Leu Gly Ala Arg Lys Asn Leu Ser Glu Arg Trp Asp Ala
    170             175                 180 tac tgc ttc cgt gtg caa gat gtg gcc tgc cga tgc cga aat ggc ttc    630
Tyr Cys Phe Arg Val Gln Asp Val Ala Cys Arg Cys Arg Asn Gly Phe
185             190                 195                 200 gtg ggt gac ggg atc agc acg tgc aat ggg aag ctg ctg gat gtg ctg    678
Val Gly Asp Gly Ile Ser Thr Cys Asn Gly Lys Leu Leu Asp Val Leu
                205                 210                 215 gct gcc act gcc aac ttc tcc acc ttc tat ggg atg cta ttg ggc tat    726
Ala Ala Thr Ala Asn Phe Ser Thr Phe Tyr Gly Met Leu Leu Gly Tyr
            220                 225                 230 gcc aat gcc acc cag cgg ggt ctc gac ttc ctg gac ttc ctg gat gat    774
Ala Asn Ala Thr Gln Arg Gly Leu Asp Phe Leu Asp Phe Leu Asp Asp
        235                 240                 245 gag ctc acg tat aag aca ctc ttc gtc cct gtc aat gaa ggc ttt gtg    822
Glu Leu Thr Tyr Lys Thr Leu Phe Val Pro Val Asn Glu Gly Phe Val
    250                 255                 260 gac aac atg acg ctg agt ggc cca aac ttg gag ctg cat gcc tcc aac    870
Asp Asn Met Thr Leu Ser Gly Pro Asn Leu Glu Leu His Ala Ser Asn
265                 270                 275                 280 gcc acc ctc cta agt gcc aac gcc agc cag ggg aag ttg ctt ccg gcc    918
Ala Thr Leu Leu Ser Ala Asn Ala Ser Gln Gly Lys Leu Leu Pro Ala
                285                 290                 295 cac tca ggc ctc agc ctc atc atc agt gac gca ggc cct gac aac agt    966
His Ser Gly Leu Ser Leu Ile Ile Ser Asp Ala Gly Pro Asp Asn Ser
            300                 305                 310 tcc tgg gcc cct gtg gcc cca ggg aca gtt gtg gtt agc cgt atc att   1014
Ser Trp Ala Pro Val Ala Pro Gly Thr Val Val Val Ser Arg Ile Ile
        315                 320                 325
```

```
gtg tgg gac atc atg gcc ttc aat ggc atc atc cat gct ctg gcc agc      1062
Val Trp Asp Ile Met Ala Phe Asn Gly Ile Ile His Ala Leu Ala Ser
    330                 335                 340 ccc ctc ctg gca ccc cca cag ccc cag gca gtg ctg gcg cnt gaa gcc      1110
Pro Leu Leu Ala Pro Pro Gln Pro Gln Ala Val Leu Ala Xaa Glu Ala
345                 350                 355                 360 cca cct gtg gcg gca ggc gtg ggg gct gtg ctt gcc gct gga gca ctg      1158
Pro Pro Val Ala Ala Gly Val Gly Ala Val Leu Ala Ala Gly Ala Leu
                365                 370                 375 ctt ggc ttg gtg gcc gga gct ctc tac ctc cgt gcc cga ggc aag ccc      1206
Leu Gly Leu Val Ala Gly Ala Leu Tyr Leu Arg Ala Arg Gly Lys Pro
            380                 385                 390 atg ggc ttt ggc ttc tct gcc ttc cag gcg gaa gat gat gct gat gac      1254
Met Gly Phe Gly Phe Ser Ala Phe Gln Ala Glu Asp Asp Ala Asp Asp
        395                 400                 405 gan ttc tca ccg tgg caa gaa ggg acc aac ccc acn tg gtn tnt gtc       1302
Xaa Phe Ser Pro Trp Gln Glu Gly Thr Asn Pro Xaa Leu Xaa Xaa Val
    410                 415                 420 ccc aac cct gtc ttt ggc agc gac acc ttt tgt gaa ccc ttc gat gac      1350
Pro Asn Pro Val Phe Gly Ser Asp Thr Phe Cys Glu Pro Phe Asp Asp
425                 430                 435                 440 tca ctg ctg gag gag gac ttc cct gac acc cag agg atc ctc aca gtc      1398
Ser Leu Leu Glu Glu Asp Phe Pro Asp Thr Gln Arg Ile Leu Thr Val
                445                 450                 455 aag tga cgaggctggg gctgaaagca gaagcatgca cagggaggag accantttta      1454
Lys ttgcttgtct gggtggatgg ggcaggaggg nctgagggcc tgtcccagac aatannngtn  1514
ccctcgag                                                             1522
```

```
<210> 5
<211> 457
<212> PRT
<213> Homo sapiens

<220>
<221> MISC_FEATURE
<222> (358)
<223> Xaa equals any of the naturally occurring L-amino acids <220>
<221> MISC_FEATURE
<222> (409)
<223> Xaa equals any of the naturally occurring L-amino acids <220>
<221> MISC_FEATURE
<222> (420)
<223> Xaa equals any of the naturally occurring L-amino acids <220>
<221> MISC_FEATURE
<222> (422)
<223> Xaa equals any of the naturally occurring L-amino acids <220>
<221> MISC_FEATURE
<222> (423)
<223> Xaa equals any of the naturally occurring L-amino acids

<400> 5
```

| Met | Val | Thr | Cys | Thr | Cys | Leu | Pro | Asp | Tyr | Glu | Gly | Asp | Gly | Trp | Ser |
|---|---|---|---|---|---|---|---|---|---|---|---|---|---|---|---|
| 1 | | | | 5 | | | | | 10 | | | | | 15 | |

| Cys | Arg | Ala | Arg | Asn | Pro | Cys | Thr | Asp | Gly | His | Arg | Gly | Gly | Cys | Ser |
|---|---|---|---|---|---|---|---|---|---|---|---|---|---|---|---|
| | | | 20 | | | | 25 | | | | | 30 | | | |

| Glu | His | Ala | Asn | Cys | Leu | Ser | Thr | Gly | Leu | Asn | Thr | Arg | Arg | Cys | Glu |
|---|---|---|---|---|---|---|---|---|---|---|---|---|---|---|---|
| | | | 35 | | | | 40 | | | | | 45 | | | |

| Cys | His | Ala | Gly | Tyr | Val | Gly | Asp | Gly | Leu | Gln | Cys | Leu | Glu | Glu | Ser |
|---|---|---|---|---|---|---|---|---|---|---|---|---|---|---|---|
| | 50 | | | | | 55 | | | | | 60 | | | | |

```
Glu Pro Pro Val Asp Arg Cys Leu Gly Gln Pro Pro Cys His Ser
65                  70              75                  80

Asp Ala Met Cys Thr Asp Leu His Phe Gln Glu Lys Arg Ala Gly Val
            85              90                  95

Phe His Leu Gln Ala Thr Ser Gly Pro Tyr Gly Leu Asn Phe Ser Glu
            100             105             110

Ala Glu Ala Ala Cys Glu Ala Gln Gly Ala Val Leu Ala Ser Phe Pro
        115             120             125

Gln Leu Ser Ala Ala Gln Gln Leu Gly Phe His Leu Cys Leu Met Gly
    130             135             140

Trp Leu Ala Asn Gly Ser Thr Ala His Pro Val Val Phe Pro Val Ala
145             150             155                 160

Asp Cys Gly Asn Gly Arg Val Gly Ile Val Ser Leu Gly Ala Arg Lys
            165             170             175

Asn Leu Ser Glu Arg Trp Asp Ala Tyr Cys Phe Arg Val Gln Asp Val
            180             185             190

Ala Cys Arg Cys Arg Asn Gly Phe Val Gly Asp Gly Ile Ser Thr Cys
        195             200             205

Asn Gly Lys Leu Leu Asp Val Leu Ala Ala Thr Ala Asn Phe Ser Thr
    210             215             220

Phe Tyr Gly Met Leu Leu Gly Tyr Ala Asn Ala Thr Gln Arg Gly Leu
225             230             235                 240

Asp Phe Leu Asp Phe Leu Asp Asp Glu Leu Thr Tyr Lys Thr Leu Phe
            245             250             255

Val Pro Val Asn Glu Gly Phe Val Asp Asn Met Thr Leu Ser Gly Pro
            260             265             270

Asn Leu Glu Leu His Ala Ser Asn Ala Thr Leu Leu Ser Ala Asn Ala
            275             280             285
```

```
Ser Gln Gly Lys Leu Leu Pro Ala His Ser Gly Leu Ser Leu Ile Ile
    290                 295                 300

Ser Asp Ala Gly Pro Asp Asn Ser Ser Trp Ala Pro Val Ala Pro Gly
305                 310                 315                 320

Thr Val Val Val Ser Arg Ile Ile Val Trp Asp Ile Met Ala Phe Asn
                325                 330                 335

Gly Ile Ile His Ala Leu Ala Ser Pro Leu Ala Pro Pro Gln Pro
            340                 345                 350

Gln Ala Val Leu Ala Xaa Glu Ala Pro Pro Val Ala Ala Gly Val Gly
        355                 360                 365

Ala Val Leu Ala Ala Gly Ala Leu Leu Gly Leu Val Ala Gly Ala Leu
        370                 375                 380

Tyr Leu Arg Ala Arg Gly Lys Pro Met Gly Phe Gly Phe Ser Ala Phe
385                 390                 395                 400

Gln Ala Glu Asp Asp Ala Asp Asp Xaa Phe Ser Pro Trp Gln Glu Gly
                405                 410                 415

Thr Asn Pro Xaa Leu Xaa Xaa Val Pro Asn Pro Val Phe Gly Ser Asp
                420                 425                 430

Thr Phe Cys Glu Pro Phe Asp Ser Leu Leu Glu Glu Asp Phe Pro
            435                 440                 445

Asp Thr Gln Arg Ile Leu Thr Val Lys
    450                 455

<210> 6
<211> 193
<212> PRT
<213> Homo sapiens

<400> 6
Met Tyr Trp Asp Thr Gly Trp Gly Lys Asp Gly His Asn Ser Trp Arg
  1               5                  10                  15
```

Ala Ala Gly Val Tyr His Arg Ala Arg Ser Gly Lys Tyr Lys Thr Tyr
            20                  25                  30

Ala Ala Lys Ala Val Cys Gly Gly His Ala Thr Tyr Lys Ala Ala Arg
            35                  40                  45

Lys Gly His Val Cys Ala Ala Gly Trp Met Ala Lys Gly Arg Val Gly
            50                  55                  60

Tyr Val Lys Gly Asn Cys Gly Gly Lys Thr Gly Asp Tyr Gly Arg Asn
 65                  70                  75                  80

Arg Ser Arg Trp Asp Ala Tyr Cys Tyr Asn His Ala Lys Cys Gly Gly
            85                  90                  95

Val Thr Asp Lys Arg Lys Ser Gly Asn Tyr Asp Asn Cys Tyr Trp His
            100                 105                 110

Arg Lys Tyr Gly Arg His Ser Asp Asp Asp Gly Cys Ala Asp Tyr
            115                 120                 125

Val Tyr Asp Ser Tyr Asp Asp Val His Gly Val Gly Arg Tyr Cys Gly
            130                 135                 140

Asp Asp Asp Ser Thr Gly Asn Val Met Thr Lys Ser Asp Ala Ser Val
145                 150                 155                 160

Thr Ala Gly Gly Lys Tyr Val Ala Met Asp Val Ser Lys Ser Ser Gly
            165                 170                 175

Lys Asn Thr Ser Thr Thr Ser Thr Gly Asn Lys Asn Ala Gly Arg Ser
            180                 185                 190

His

<210> 7
<211> 985
<212> DNA
<213> Homo sapiens

```
<220>
<221> CDS
<222> (118)..(984)

<220>
<221> misc_feature
<222> (36)
<223> n equals a, t, g or c

<220>
<221> misc_feature
<222> (51)
<223> n equals a, t, g or c

<220>
<221> misc_feature
<222> (248)
<223> n equals a, t, g or c

<220>
<221> misc_feature
<222> (508)
<223> n equals a, t, g or c

<220>
<221> misc_feature
<222> (521)
<223> n equals a, t, g or c

<220>
<221> misc_feature
<222> (564)
<223> n equals a, t, g or c

<220>
<221> misc_feature
<222> (933)
<223> n equals a, t, g or c
```

```
<220>
<221> misc_feature
<222> (945)
<223> n equals a, t, g or c

<220>
<221> misc_feature
<222> (951)
<223> n equals a, t, g or c

<220>
<221> misc_feature
<222> (958)
<223> n equals a, t, g or c

<400> 7
gcccacgcgt ccgaccggga cagctcgcgg ccccnagag ctctagccgt ngaggagctg    60
cctggggacg tttgccctgg ggccccagcc tggcccgggt caccctggca tgaggag    117 atg ggc ctg ttg ctc ctg gtc cca ttg ctc ctg ctg ccc ggc tcc tac    165
Met Gly Leu Leu Leu Leu Val Pro Leu Leu Leu Leu Pro Gly Ser Tyr
 1               5                  10                  15 gga ctg ccc ttc tac tac ggc ttc tac tac tcc aac agc gcc aac gac    213
Gly Leu Pro Phe Tyr Tyr Gly Phe Tyr Tyr Ser Asn Ser Ala Asn Asp
            20                  25                  30 cag aac cta ggc aac ggt cat ggc aaa gac cta cnt aat gga gtg aag    261
Gln Asn Leu Gly Asn Gly His Gly Lys Asp Leu Xaa Asn Gly Val Lys
        35                  40                  45 ctg gtg gtg gag aca ccc gag gag acc ctg ttc acc tac caa ggg gcc    309
Leu Val Val Glu Thr Pro Glu Glu Thr Leu Phe Thr Tyr Gln Gly Ala
    50                  55                  60 agt gtg atc ctg ccc tgc cgc tac cgc tac gag ccg gcc ctg gtc tcc    357
Ser Val Ile Leu Pro Cys Arg Tyr Arg Tyr Glu Pro Ala Leu Val Ser
65                  70                  75                  80
```

```
ccg cgg cgt gtg cgt gtc aaa tgg tgg aag ctg tcg gag aac ggg gcc    405
Pro Arg Arg Val Arg Val Lys Trp Trp Lys Leu Ser Glu Asn Gly Ala
            85                  90                  95 cca gag aag gac gtg ctg gtg gcc atc ggg ctg agg cac cgc tcc ttt    453
Pro Glu Lys Asp Val Leu Val Ala Ile Gly Leu Arg His Arg Ser Phe
            100                 105                 110 ggg gac tac caa ggc cgc gtg cac ctg cgg cag gac aaa gag cat gac    501
Gly Asp Tyr Gln Gly Arg Val His Leu Arg Gln Asp Lys Glu His Asp
            115                 120                 125 gtc tcg ntg gag atc cag gnt ctg cgg ctg gag gac tat ggg cgt tac    549
Val Ser Xaa Glu Ile Gln Xaa Leu Arg Leu Glu Asp Tyr Gly Arg Tyr
            130                 135                 140 cgc tgt gag gtc atn gac ggg ctg gag gat gaa agc ggt ctg gtg gag    597
Arg Cys Glu Val Xaa Asp Gly Leu Glu Asp Glu Ser Gly Leu Val Glu
145                 150                 155                 160 ctg gag ctg cgg ggt gtg gtc ttt cct tac cag tcc ccc aac ggg cgc    645
Leu Glu Leu Arg Gly Val Val Phe Pro Tyr Gln Ser Pro Asn Gly Arg
            165                 170                 175 tac cag ttc aac ttc cac gag ggc cag cag gtc tgt gca gag cag gct    693
Tyr Gln Phe Asn Phe His Glu Gly Gln Gln Val Cys Ala Glu Gln Ala
            180                 185                 190 gcg gtg gtg gcc tcc ttt gag cag ctc ttc cgg gcc tgg gag gag ggc    741
Ala Val Val Ala Ser Phe Glu Gln Leu Phe Arg Ala Trp Glu Glu Gly
            195                 200                 205 ctg gac tgg tgc aac gcg ggc tgg ctg cag gat gcc acg gtg cag tac    789
Leu Asp Trp Cys Asn Ala Gly Trp Leu Gln Asp Ala Thr Val Gln Tyr
            210                 215                 220 ccc atc atg ttg ccc cgg cag ccc tgc ggt ggc ccg gac ctg gca cct    837
Pro Ile Met Leu Pro Arg Gln Pro Cys Gly Gly Pro Asp Leu Ala Pro
225                 230                 235                 240
```

```
ggc gtg cga agc tac ggc ccc cgc cac cgc cgc ctg cac cgc tat gat        885
Gly Val Arg Ser Tyr Gly Pro Arg His Arg Arg Leu His Arg Tyr Asp
                245                 250                 255 gta ttc tgc ttc gct act gcc ctc arg ggg cgg gtg tac tac ctg gan        933
Val Phe Cys Phe Ala Thr Ala Leu Xaa Gly Arg Val Tyr Tyr Leu Xaa
                260                 265                 270 cac cct gag aan ctg acn ctg aca naa gca agg gaa gcc tgc caa gaa        981
His Pro Glu Xaa Leu Xaa Leu Thr Xaa Ala Arg Glu Ala Cys Gln Glu
                275                 280                 285 aaa t                                                                  985
Lys
```

<210> 8
<211> 289
<212> PRT
<213> Homo sapiens

<220>
<221> MISC_FEATURE
<222> (44)
<223> Xaa equals any of the naturally occurring L-amino acids <220>
<221> MISC_FEATURE
<222> (131)
<223> Xaa equals any of the naturally occurring L-amino acids <220>
<221> MISC_FEATURE
<222> (135)
<223> Xaa equals any of the naturally occurring L-amino acids <220>
<221> MISC_FEATURE
<222> (149)
<223> Xaa equals any of the naturally occurring L-amino acids

```
<220>
<221> MISC_FEATURE
<222> (265)
<223> Xaa equals any of the naturally occurring L-amino acids <220>
<221> MISC_FEATURE
<222> (272)
<223> Xaa equals any of the naturally occurring L-amino acids <220>
<221> MISC_FEATURE
<222> (276)
<223> Xaa equals any of the naturally occurring L-amino acids <220>
<221> MISC_FEATURE
<222> (278)
<223> Xaa equals any of the naturally occurring L-amino acids <220>
<221> MISC_FEATURE
<222> (281)
<223> Xaa equals any of the naturally occurring L-amino acids

<400> 8
```

| Met | Gly | Leu | Leu | Leu | Val | Pro | Leu | Leu | Leu | Pro | Gly | Ser | Tyr |
|---|---|---|---|---|---|---|---|---|---|---|---|---|---|
| 1 | | | | 5 | | | | | 10 | | | | 15 |

| Gly | Leu | Pro | Phe | Tyr | Tyr | Gly | Phe | Tyr | Tyr | Ser | Asn | Ser | Ala | Asn | Asp |
|---|---|---|---|---|---|---|---|---|---|---|---|---|---|---|---|
| | | | 20 | | | | | 25 | | | | | 30 | | |

| Gln | Asn | Leu | Gly | Asn | Gly | His | Gly | Lys | Asp | Leu | Xaa | Asn | Gly | Val | Lys |
|---|---|---|---|---|---|---|---|---|---|---|---|---|---|---|---|
| | | 35 | | | | | 40 | | | | | 45 | | | |

| Leu | Val | Val | Glu | Thr | Pro | Glu | Glu | Thr | Leu | Phe | Thr | Tyr | Gln | Gly | Ala |
|---|---|---|---|---|---|---|---|---|---|---|---|---|---|---|---|
| | 50 | | | | | 55 | | | | | 60 | | | | |

| Ser | Val | Ile | Leu | Pro | Cys | Arg | Tyr | Arg | Tyr | Glu | Pro | Ala | Leu | Val | Ser |
|---|---|---|---|---|---|---|---|---|---|---|---|---|---|---|---|
| 65 | | | | | 70 | | | | | 75 | | | | | 80 |

Pro Arg Arg Val Arg Val Lys Trp Trp Lys Leu Ser Glu Asn Gly Ala
                85                  90                  95

Pro Glu Lys Asp Val Leu Val Ala Ile Gly Leu Arg His Arg Ser Phe
            100                 105                 110

Gly Asp Tyr Gln Gly Arg Val His Leu Arg Gln Asp Lys Glu His Asp
            115                 120                 125

Val Ser Xaa Glu Ile Gln Xaa Leu Arg Leu Glu Asp Tyr Gly Arg Tyr
    130                 135                 140

Arg Cys Glu Val Xaa Asp Gly Leu Glu Asp Glu Ser Gly Leu Val Glu
145                 150                 155                 160

Leu Glu Leu Arg Gly Val Val Phe Pro Tyr Gln Ser Pro Asn Gly Arg
            165                 170                 175

Tyr Gln Phe Asn Phe His Glu Gly Gln Gln Val Cys Ala Glu Gln Ala
            180                 185                 190

Ala Val Val Ala Ser Phe Glu Gln Leu Phe Arg Ala Trp Glu Glu Gly
            195                 200                 205

Leu Asp Trp Cys Asn Ala Gly Trp Leu Gln Asp Ala Thr Val Gln Tyr
    210                 215                 220

Pro Ile Met Leu Pro Arg Gln Pro Cys Gly Gly Pro Asp Leu Ala Pro
225                 230                 235                 240

Gly Val Arg Ser Tyr Gly Pro Arg His Arg Arg Leu His Arg Tyr Asp
            245                 250                 255

Val Phe Cys Phe Ala Thr Ala Leu Xaa Gly Arg Val Tyr Tyr Leu Xaa
            260                 265                 270

His Pro Glu Xaa Leu Xaa Leu Thr Xaa Ala Arg Glu Ala Cys Gln Glu
            275                 280                 285

Lys

<210> 9
<211> 355
<212> PRT
<213> Homo sapiens

<400> 9

| | | | | | | | | | | | | | | |
|---|---|---|---|---|---|---|---|---|---|---|---|---|---|---|
| Met | Thr | Ser | Leu | Leu | Phe | Leu | Val | Leu | Ile | Ser | Val | Cys | Trp | Ala | Glu |
| 1 | | | | 5 | | | | | 10 | | | | | 15 |
| Pro | His | Pro | Asp | Asn | Ser | Ser | Leu | Glu | His | Glu | Arg | Ile | Ile | His | Ile |
| | | | 20 | | | | | 25 | | | | | 30 | | |
| Gln | Glu | Glu | Asn | Gly | Pro | Arg | Leu | Leu | Val | Val | Ala | Glu | Gln | Ala | Lys |
| | | 35 | | | | | 40 | | | | | 45 | | | |
| Ile | Phe | Ser | Gln | Arg | Gly | Gly | Asn | Val | Thr | Leu | Pro | Cys | Lys | Phe | Tyr |
| | 50 | | | | | 55 | | | | | 60 | | | | |
| His | Glu | His | Thr | Ser | Thr | Ala | Gly | Ser | Gly | Thr | His | Lys | Ile | Arg | Val |
| 65 | | | | 70 | | | | | 75 | | | | | 80 | |
| Lys | Trp | Thr | Lys | Leu | Thr | Ser | Asp | Tyr | Leu | Lys | Glu | Val | Asp | Val | Phe |
| | | | 85 | | | | | 90 | | | | | 95 | | |
| Val | Ala | Met | Gly | His | His | Arg | Lys | Ser | Tyr | Gly | Lys | Tyr | Gln | Gly | Arg |
| | | 100 | | | | | 105 | | | | | 110 | | | |
| Val | Phe | Leu | Arg | Glu | Ser | Ser | Glu | Asn | Asp | Ala | Ser | Leu | Ile | Ile | Thr |
| | 115 | | | | | 120 | | | | | 125 | | | | |
| Asn | Ile | Met | Leu | Glu | Asp | Tyr | Gly | Arg | Tyr | Lys | Cys | Glu | Val | Ile | Glu |
| 130 | | | | | 135 | | | | | 140 | | | | | |
| Gly | Leu | Glu | Asp | Asp | Thr | Ala | Val | Val | Ala | Leu | Asn | Leu | Glu | Gly | Val |
| 145 | | | | | 150 | | | | | 155 | | | | | 160 |
| Val | Phe | Pro | Tyr | Ser | Pro | Arg | Leu | Gly | Arg | Tyr | Asn | Leu | Asn | Phe | His |
| | | | 165 | | | | | 170 | | | | | 175 | | |
| Glu | Ala | Gln | Gln | Ala | Cys | Leu | Asp | Gln | Asp | Ser | Ile | Ile | Ala | Ser | Phe |
| | | | 180 | | | | | 185 | | | | | 190 | | |

Asp Gln Leu Tyr Glu Ala Trp Arg Ser Gly Leu Asp Trp Cys Asn Ala
        195                 200                 205

Gly Trp Leu Ser Asp Gly Ser Val Gln Tyr Pro Ile Thr Lys Pro Arg
    210                 215                 220

Glu Pro Cys Gly Gly Lys Asn Thr Val Pro Gly Val Arg Asn Tyr Gly
225                     230                 235                 240

Phe Trp Asp Lys Glu Arg Ser Arg Tyr Asp Val Phe Cys Phe Thr Ser
                245                 250                 255

Asn Phe Asn Gly Arg Phe Tyr Tyr Leu Ile His Pro Thr Lys Leu Thr
            260                 265                 270

Tyr Asp Glu Ala Val Gln Ala Cys Leu Lys Asp Gly Ala Gln Ile Ala
        275                 280                 285

Lys Val Gly Gln Ile Phe Ala Ala Trp Lys Leu Leu Gly Tyr Asp Arg
    290                 295                 300

Cys Asp Ala Gly Trp Leu Ala Asp Gly Ser Val Arg Tyr Pro Ile Ser
305                     310                 315                 320

Arg Pro Arg Lys Arg Cys Ser Pro Asn Glu Ala Ala Val Arg Phe Val
                325                 330                 335

Gly Phe Pro Asp Lys His Lys Leu Tyr Gly Val Tyr Cys Phe Arg
            340                 345                 350

Ala Tyr Asn
        355

<210> 10
<211> 1259
<212> DNA
<213> Homo sapiens

<220>
<221> CDS
<222> (199)..(1257)

```
<220>
<221> misc_feature
<222> (478)

<220>
<221> misc_feature
<222> (668)
<223> n equals a, t, g or c

<220>
<221> misc_feature
<222> (849)
<223> n equals a, t, g or c

<220>
<221> misc_feature
<222> (1138)
<223> n equals a, t, g or c

<220>
<221> misc_feature
<222> (1149)
<223> n equals a, t, g or c

<220>
<221> misc_feature
<222> (1157)
<223> n equals a, t, g or c

<220>
<221> misc_feature
<222> (1169)
<223> n equals a, t, g or c

<220>
<221> misc_feature
<222> (1172)
<223> n equals a, t, g or c
```

```
<220>
<221> misc_feature
<222> (1169)
<223> n equals a, t, g or c

<220>
<221> misc_feature
<222> (1172)
<223> n equals a, t, g or c

<220>
<221> misc_feature
<222> (1251)
<223> n equals a, t, g or c

<400> 10
ggaatcacat gcacagttgt ggatttytgc aaacaggaca acgggggctg tgcaaaggtg   60
gccagatgct cccagaaggg cacgaaggtc tcctgcagct gccagaaggg atacaaaggg  120
gacgggcaca gctgcacaga gatagacccc tgtgcagacg gccttaacgg agggtgtcac  180
gagcacgcca cctgtaag atg aca ggc ccg ggc aag cac aag tgt gag tgt    231
                    Met Thr Gly Pro Gly Lys His Lys Cys Glu Cys
                     1               5                      10 aaa agt cac tat gtc gga gat ggg ctg aac tgt gag ccg gag cag ctg    279
Lys Ser His Tyr Val Gly Asp Gly Leu Asn Cys Glu Pro Glu Gln Leu
             15                  20                  25 ccc att gac cgc tgc tta cag gac aat ggg cag tgc cat gca gac gcc    327
Pro Ile Asp Arg Cys Leu Gln Asp Asn Gly Gln Cys His Ala Asp Ala
         30                  35                  40 aaa tgt gtc gac ctc cac ttc cag gat acc act gtt ggg gtg ttc cat    375
Lys Cys Val Asp Leu His Phe Gln Asp Thr Thr Val Gly Val Phe His
     45                  50                  55
```

```
cta cgc tcc cca ctg ggc cag tat aag ctg acc ttt gac aaa gcc aga    423
Leu Arg Ser Pro Leu Gly Gln Tyr Lys Leu Thr Phe Asp Lys Ala Arg
 60              65                  70                  75 gag gcc tgt gcc aac gaa gct gcg acc atg gca acc tac aac cag ctc    471
Glu Ala Cys Ala Asn Glu Ala Ala Thr Met Ala Thr Tyr Asn Gln Leu
             80                  85                  90 tcc tat nnc cag aag gcc aag tac cac ctg tgc tca gca ggc tgg ctg    519
Ser Tyr Xaa Gln Lys Ala Lys Tyr His Leu Cys Ser Ala Gly Trp Leu
         95                 100                 105 gag acc ggg cgg gtt gcc tac ccc aca gcc ttc gcc tcc cag aac tgt    567
Glu Thr Gly Arg Val Ala Tyr Pro Thr Ala Phe Ala Ser Gln Asn Cys
        110                 115                 120 ggc tct ggt gtg gtt ggg ata gtg gac tat gga cct aga ccc aac aag    615
Gly Ser Gly Val Val Gly Ile Val Asp Tyr Gly Pro Arg Pro Asn Lys
        125                 130                 135 agt gaa atg tgg gat gtc ttc tgc tat cgg atg aaa gat gtg aac tgc    663
Ser Glu Met Trp Asp Val Phe Cys Tyr Arg Met Lys Asp Val Asn Cys
140                 145                 150                 155 acc tnc aag gtg ggc tat gtg gga gat ggc ttc tca tac agt ggg aac    711
Thr Xaa Lys Val Gly Tyr Val Gly Asp Gly Phe Ser Tyr Ser Gly Asn
                160                 165                 170 ctg ctg cag gtc ctg atg tcc ttc ccc tca ctc aca aac ttc ctg acg    759
Leu Leu Gln Val Leu Met Ser Phe Pro Ser Leu Thr Asn Phe Leu Thr
            175                 180                 185 gaa gtg ctg gcc tat tcc aac agc tca gct cga ggc cgt gca ttt cta    807
Glu Val Leu Ala Tyr Ser Asn Ser Ser Ala Arg Gly Arg Ala Phe Leu
        190                 195                 200 gaa cac ctg act gac ctg tcc atc cgc ggc acc ctc ttt gtn cca cag    855
Glu His Leu Thr Asp Leu Ser Ile Arg Gly Thr Leu Phe Val Pro Gln
        205                 210                 215
```

```
aac agt ggg ctg ggg gag aat gag acc ttg tct ggg cgg gac atc gag      903
Asn Ser Gly Leu Gly Glu Asn Glu Thr Leu Ser Gly Arg Asp Ile Glu
220             225                 230                 235 cac cac ctc gcc aat gtc agc atg ttt ttc tac aat gac ctt gtc aat      951
His His Leu Ala Asn Val Ser Met Phe Phe Tyr Asn Asp Leu Val Asn
                240                 245                 250 ggc acc acc ctg caa acg agg ctg gga agc aag ctc ctc atc act gac      999
Gly Thr Thr Leu Gln Thr Arg Leu Gly Ser Lys Leu Leu Ile Thr Asp
                255                 260             ·265 aga cag gac cca ctc cac ccg acg gag acc agg tgt gtt gat gga aga     1047
Arg Gln Asp Pro Leu His Pro Thr Glu Thr Arg Cys Val Asp Gly Arg
            270                 275                 280 gac act ctg gag tgg gac atc tgt gcc tcc aat ggg atc aca cat gtc     1095
Asp Thr Leu Glu Trp Asp Ile Cys Ala Ser Asn Gly Ile Thr His Val
        285                 290                 295 att tcc agg yct tta aaa gca ccc cct gcc ccc gtg acc ttg ncc cac     1143
Ile Ser Arg Xaa Leu Lys Ala Pro Pro Ala Pro Val Thr Leu Xaa His
300             305                 310                 315 act ggn ttg gga gna ggg atc ttc tnt gnc atc atc ctg gtg act ggg     1191
Thr Gly Leu Gly Xaa Gly Ile Phe Xaa Xaa Ile Ile Leu Val Thr Gly
                320                 325                 330 gct gtt gcc ttg gct gct tac tcc tac ttt cgg ata aac cgg aaa aca     1239
Ala Val Ala Leu Ala Ala Tyr Ser Tyr Phe Arg Ile Asn Arg Lys Thr
            335                 340                 345 atc ggc ttc can cat ttt ga                                          1259
Ile Gly Phe Xaa His Phe
            350

<210> 11
<211> 353
<212> PRT
<213> Homo sapiens
```

```
<220>
<221> MISC_FEATURE
<222> (94)
<223> Xaa equals any of the naturally occurring L-amino acids <220>
<221> MISC_FEATURE
<222> (157)
<223> Xaa equals any of the naturally occurring L-amino acids <220>
<221> MISC_FEATURE
<222> (303)
<223> Xaa equals any of the naturally occurring L-amino acids <220>
<221> MISC_FEATURE
<222> (314)
<223> Xaa equals any of the naturally occurring L-amino acids <220>
<221> MISC_FEATURE
<222> (320)
<223> Xaa equals any of the naturally occurring L-amino acids <220>
<221> MISC_FEATURE
<222> (324)
<223> Xaa equals any of the naturally occurring L-amino acids <220>
<221> MISC_FEATURE
<222> (325)
<223> Xaa equals any of the naturally occurring L-amino acids <220>
<221> MISC_FEATURE
<222> (351)
<223> Xaa equals any of the naturally occurring L-amino acids
```

<400> 11

| | | | | | | | | | | | | | | |
|---|---|---|---|---|---|---|---|---|---|---|---|---|---|---|
| Met | Thr | Gly | Pro | Gly | Lys | His | Lys | Cys | Glu | Cys | Lys | Ser | His | Tyr | Val |
| 1 | | | | 5 | | | | | 10 | | | | | 15 |
| Gly | Asp | Gly | Leu | Asn | Cys | Glu | Pro | Glu | Gln | Leu | Pro | Ile | Asp | Arg | Cys |
| | | | | 20 | | | | | 25 | | | | | 30 |
| Leu | Gln | Asp | Asn | Gly | Gln | Cys | His | Ala | Asp | Ala | Lys | Cys | Val | Asp | Leu |
| | | 35 | | | | | 40 | | | | | 45 | | | |
| His | Phe | Gln | Asp | Thr | Thr | Val | Gly | Val | Phe | His | Leu | Arg | Ser | Pro | Leu |
| | | 50 | | | | 55 | | | | | 60 | | | | |
| Gly | Gln | Tyr | Lys | Leu | Thr | Phe | Asp | Lys | Ala | Arg | Glu | Ala | Cys | Ala | Asn |
| 65 | | | | | 70 | | | | | 75 | | | | | 80 |
| Glu | Ala | Ala | Thr | Met | Ala | Thr | Tyr | Asn | Gln | Leu | Ser | Tyr | Xaa | Gln | Lys |
| | | | | 85 | | | | | 90 | | | | | 95 | |
| Ala | Lys | Tyr | His | Leu | Cys | Ser | Ala | Gly | Trp | Leu | Glu | Thr | Gly | Arg | Val |
| | | | 100 | | | | | 105 | | | | | 110 | | |
| Ala | Tyr | Pro | Thr | Ala | Phe | Ala | Ser | Gln | Asn | Cys | Gly | Ser | Gly | Val | Val |
| | | 115 | | | | | 120 | | | | | 125 | | | |
| Gly | Ile | Val | Asp | Tyr | Gly | Pro | Arg | Pro | Asn | Lys | Ser | Glu | Met | Trp | Asp |
| | 130 | | | | | 135 | | | | | 140 | | | | |
| Val | Phe | Cys | Tyr | Arg | Met | Lys | Asp | Val | Asn | Cys | Thr | Xaa | Lys | Val | Gly |
| 145 | | | | | 150 | | | | | 155 | | | | | 160 |
| Tyr | Val | Gly | Asp | Gly | Phe | Ser | Tyr | Ser | Gly | Asn | Leu | Leu | Gln | Val | Leu |
| | | | | 165 | | | | | 170 | | | | | 175 | |
| Met | Ser | Phe | Pro | Ser | Leu | Thr | Asn | Phe | Leu | Thr | Glu | Val | Leu | Ala | Tyr |
| | | | 180 | | | | | 185 | | | | | 190 | | |
| Ser | Asn | Ser | Ser | Ala | Arg | Gly | Arg | Ala | Phe | Leu | Glu | His | Leu | Thr | Asp |
| | | | 195 | | | | | 200 | | | | | 205 | | |
| Leu | Ser | Ile | Arg | Gly | Thr | Leu | Phe | Val | Pro | Gln | Asn | Ser | Gly | Leu | Gly |
| | | | 210 | | | | 215 | | | | | 220 | | | |

```
Glu Asn Glu Thr Leu Ser Gly Arg Asp Ile Glu His His Leu Ala Asn
225                 230                 235                 240

Val Ser Met Phe Phe Tyr Asn Asp Leu Val Asn Gly Thr Thr Leu Gln
                245                 250                 255

Thr Arg Leu Gly Ser Lys Leu Leu Ile Thr Asp Arg Gln Asp Pro Leu
                260                 265                 270

His Pro Thr Glu Thr Arg Cys Val Asp Gly Arg Asp Thr Leu Glu Trp
            275                 280                 285

Asp Ile Cys Ala Ser Asn Gly Ile Thr His Val Ile Ser Arg Xaa Leu
        290                 295                 300

Lys Ala Pro Pro Ala Pro Val Thr Leu Xaa His Thr Gly Leu Gly Xaa
305                 310                 315                 320

Gly Ile Phe Xaa Xaa Ile Ile Leu Val Thr Gly Ala Val Ala Leu Ala
                325                 330                 335

Ala Tyr Ser Tyr Phe Arg Ile Asn Arg Lys Thr Ile Gly Phe Xaa His
            340                 345                 350

Phe

<210> 12
<211> 275
<212> PRT
<213> Mus musculus

<400> 12
Met Val Val Leu Leu Cys Leu Cys Val Leu Leu Trp Glu Glu Ala His
 1               5                  10                  15

Gly Trp Gly Phe Lys Asn Gly Ile Phe His Asn Ser Ile Trp Leu Glu
                20                  25                  30

Gln Ala Ala Gly Val Tyr His Arg Glu Ala Arg Ala Gly Arg Tyr Lys
            35                  40                  45
```

```
Leu Thr Tyr Ala Glu Ala Lys Ala Val Cys Glu Phe Glu Gly Gly Arg
     50                  55                  60

Leu Ala Thr Tyr Lys Gln Leu Glu Ala Ala Arg Lys Ile Gly Phe His
 65                  70                  75                  80

Val Cys Ala Ala Gly Trp Met Ala Lys Gly Arg Val Gly Tyr Pro Ile
                 85                  90                  95

Val Lys Pro Gly Pro Asn Cys Gly Phe Gly Lys Thr Gly Ile Ile Asp
             100                 105                 110

Tyr Gly Ile Arg Leu Asn Arg Ser Glu Arg Trp Asp Ala Tyr Cys Tyr
         115                 120                 125

Asn Pro His Ala Lys Glu Cys Gly Gly Val Phe Thr Asp Pro Lys Arg
     130                 135                 140

Ile Phe Lys Ser Pro Gly Phe Pro Asn Glu Tyr Asp Asp Asn Gln Val
145                 150                 155                 160

Cys Tyr Trp His Ile Arg Leu Lys Tyr Gly Gln Arg Ile His Leu Ser
                 165                 170                 175

Phe Leu Asp Phe Asp Leu Glu His Asp Pro Gly Cys Leu Ala Asp Tyr
             180                 185                 190

Val Glu Ile Tyr Asp Ser Tyr Asp Val His Gly Phe Val Gly Arg
         195                 200                 205

Tyr Cys Gly Asp Glu Leu Pro Glu Asp Ile Ile Ser Thr Gly Asn Val
     210                 215                 220

Met Thr Leu Lys Phe Leu Ser Asp Ala Ser Val Thr Ala Gly Gly Phe
225                 230                 235                 240

Gln Ile Lys Tyr Val Thr Val Asp Pro Ala Ser Lys Ser Ser Gln Ala
             245                 250                 255

Lys Asn Thr Ser Thr Thr Gly Asn Lys Lys Phe Leu Pro Gly Arg Phe
             260                 265                 270
```

```
Ser His Leu
        275
```

`<210>` 13
`<211>` 44
`<212>` DNA
`<213>` artificial sequence

`<220>`
`<223>` contains an EcoRI restriction site

`<400>` 13
gcagcaggat ccatgatgga ccagggctgc cgggaaatcc ttac            44

`<210>` 14
`<211>` 44
`<212>` DNA
`<213>` artificial sequence

`<220>`
`<223>` contains a XhoI restriction site

`<400>` 14
gcagcatcta gatcacttga ctgtgaggat cctctgggtg tcag            44

`<210>` 15
`<211>` 45
`<212>` DNA
`<213>` artificial sequence

`<220>`
`<223>` contains an EcoRI restriction site

`<400>` 15
gcagcaggat ccatggtcac ttgtacctgc ctgcccgact acgag           45

`<210>` 16
`<211>` 45
`<212>` DNA
`<213>` artificial sequence

```
<220>
<223> contains a XhoI restriction site

<400> 16
gcagcaggat ccatggtcac ttgtacctgc ctgcccgact acgag          45

<210> 17
<211> 48
<212> DNA
<213> artificial sequence

<220>
<223> contains an EcoRI restriction site

<400> 17
gcagcaggat ccatgggcct gttgctcctg gtcccattgc tcctgctg       48

<210> 18
<211> 46
<212> DNA
<213> artificial sequence

<220>
<221> misc_feature
<222> (40)
<223> n equals a, t, g or c

<220>
<223> contains a XhoI restriction site

<400> 18
gcagcatcta gaatttttct tggcaggctt cccttgcttn tgtcag         46

<210> 19
<211> 44
<212> DNA
<213> artificial sequence

<220>
<223> contains an EcoRI restriction site
```

```
<400> 19
gcagcaggat ccatgacagg cccgggcaag cacaagtgtg agtg                    44

<210> 20
<211> 49
<212> DNA
<213> artificial sequence

<220>
<221> misc_feature
<222> (21)
<223> n equals a, t, g or c

<220>
<223> contains a XhoI restriction site

<400> 20
gcagcatcta gatcaaaatg ntggaagccg attgttttcc ggtttatcc              49

<210> 21
<211> 50
<212> DNA
<213> artificial sequence

<220>
<223> contains a BglII restriction site

<400> 21
gcagcaagat ctgccatcat gatggaccag ggctgccggg aaatccttac             50

<210> 22
<211> 45
<212> DNA
<213> artificial sequence

<220>
<223> contains a XbaI restriction site

<400> 22
gcagcatcta gatcacttga ctgtgaggat cctctgggtg tcagg                  45
```

<210> 23
<211> 51
<212> DNA
<213> artificial sequence

<220>
<223> contains a BglII restriction site

<400> 23
gcagcaagat ctgccatcat ggtcacttgt acctgcctgc ccgactacga g          51

<210> 24
<211> 45
<212> DNA
<213> artificial sequence

<220>
<223> contains an XbaI restriction site

<400> 24
gcagcatcta gatcacttga ctgtgaggat cctctgggtg tcagg                 45

<210> 25
<211> 54
<212> DNA
<213> artificial sequence

<220>
<223> contains a BglII restriction site

<400> 25
gcagcaagat ctgccatcat gggcctgttg ctcctggtcc cattgctcct gctg       54

<210> 26
<211> 46
<212> DNA
<213> artificial sequence

<220>
<221> misc_feature
<222> (40)
<223> n equals a, t, g or c

```
<220>
<223> contains an XbaI restriction site

<400> 26
gcagcatcta gaatttttct tggcaggctt cccttgcttn tgtcag                46

<210> 27
<211> 50
<212> DNA
<213> artificial sequence

<220>
<223> contains a BglII restriction site

<400> 27
gcagcaagat ctgccatcat gacaggcccg ggcaagcaca agtgtgagtg            50

<210> 28
<211> 49
<212> DNA
<213> artificial sequence

<220>
<221> misc_feature
<222> (21)
<223> n equals a,t,g, or c

<220>
<223> contains a XbaI restriction site

<400> 28
gcagcatcta gatcaaaatg ntggaagccg attgttttcc ggtttatcc             49

<210> 29
<211> 50
<212> DNA
<213> artificial sequence

<220>
<223> contains a BamHI restriction site
```

<400> 29
gcagcaagat ctgccatcat gatggaccag ggctgccggg aaatccttac					50

<210> 30
<211> 44
<212> DNA
<213> artificial sequence

<220>
<223> contains an XbaI restriction site

<400> 30
gcagcatcta gatcacttga ctgtgaggat cctctgggtg tcag					44

<210> 31
<211> 54
<212> DNA
<213> artificial sequence

<220>
<223> contains a BamHI restriction site

<400> 31
gcagcaagat ctgccatcat gatggtcact tgtacctgcc tgcccgacta cgag					54

<210> 32
<211> 45
<212> DNA
<213> artificial sequence

<220>
<223> contains an XbaI restriction site

<400> 32
gcagcatcta gatcacttga ctgtgaggat cctctgggtg tcagg					45

<210> 33
<211> 54
<212> DNA
<213> artificial sequence

<220>
<223> contains a BamHI restriction site

<400> 33
gcagcaagat ctgccatcat gggcctgttg ctcctggtcc cattgctcct gctg     54

<210> 34
<211> 46
<212> DNA
<213> artificial sequence

<220>
<221> misc_feature
<222> (40)
<223> n equals a, t, g or c

<220>
<223> contains an XbaI restriction site

<400> 34
gcagcatcta gaattttct tggcaggctt cccttgcttn tgtcag     46

<210> 35
<211> 50
<212> DNA
<213> artificial sequence

<220>
<223> contains a BamHI restriction site

<400> 35
gcagcaagat ctgccatcat gacaggcccg ggcaagcaca agtgtgagtg     50

<210> 36
<211> 49
<212> DNA
<213> artificial sequence

<220>
<221> misc_feature
<222> (21)
<223> n equals a, t, g or c

<220>
<223> contains an XbaI restriction site

<400> 36
gcagcatcta gatcaaaatg ntggaagccg attgttttcc ggtttatcc          49

<210> 37
<211> 733
<212> DNA
<213> Homo sapiens

<400> 37
gggatccgga gcccaaatct tctgacaaaa ctcacacatg cccaccgtgc ccagcacctg  60
aattcgaggg tgcaccgtca gtcttcctct tccccccaaa acccaaggac accctcatga 120
tctcccggac tcctgaggtc acatgcgtgg tggtggacgt aagccacgaa gaccctgagg 180
tcaagttcaa ctggtacgtg gacggcgtgg aggtgcataa tgccaagaca aagccgcggg 240
aggagcagta acagcacg taccgtgtgg tcagcgtcct caccgtcctg caccaggact 300
ggctgaatgg caaggagtac aagtgcaagg tctccaacaa agccctccca acccccatcg 360
agaaaaccat ctccaaagcc aaagggcagc ccgagaacc acaggtgtac accctgcccc 420
catcccggga tgagctgacc aagaaccagg tcagcctgac ctgcctggtc aaaggcttct 480
atccaagcga catcgccgtg gagtgggaga gcaatgggca gccggagaac aactacaaga 540
ccacgcctcc cgtgctggac tccgacggct ccttcttcct ctacagcaag ctcaccgtgg 600
acaagagcag gtggcagcag gggaacgtct tctcatgctc cgtgatgcat gaggctctgc 660
acaaccacta cacgcagaag agcctctccc tgtctccggg taaatgagtg cgacggccgc 720
gactctagag gat                                                   733